United States Patent
Sprott et al.

(10) Patent No.: US 10,519,135 B2
(45) Date of Patent: *Dec. 31, 2019

(54) INHIBITORS OF CYCLIN-DEPENDENT KINASE 7 (CDK7)

(71) Applicant: Syros Pharmaceuticals, Inc., Cambridge, MA (US)

(72) Inventors: Kevin Sprott, Needham, MA (US); Jason J. Marineau, Franklin, MA (US); Darby Schmidt, Arlington, MA (US); Michael Bradley, Allston, MA (US); Stephane Ciblat, Montreal (CA); M. Arshad Siddiqui, Newton, MA (US); Anzhelika Kabro, Montreal (CA); Melissa Leblanc, Laval (CA); Serge Leger, Notre-Dame-de-L'ile-Perrot (CA); Stephanie Roy, Lachine (CA); Dana K. Winter, Rigaud (CA); Tom Miller, Wakefield, MA (US); Amy Ripka, Reading, MA (US); Dansu Li, Warrington, PA (US)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/031,357

(22) Filed: Jul. 10, 2018

(65) Prior Publication Data

US 2018/0319772 A1    Nov. 8, 2018

Related U.S. Application Data

(63) Continuation of application No. 15/799,661, filed on Oct. 31, 2017, now Pat. No. 10,059,690, which is a continuation of application No. 15/301,815, filed as application No. PCT/US2015/024358 on Apr. 3, 2015, now Pat. No. 10,106,526.

(60) Provisional application No. 62/053,741, filed on Sep. 22, 2014, provisional application No. 61/975,457, filed on Apr. 4, 2014.

(51) Int. Cl.

| | |
|---|---|
| A61K 31/506 | (2006.01) |
| C07D 401/14 | (2006.01) |
| C07D 413/14 | (2006.01) |
| C07D 403/04 | (2006.01) |
| C07D 403/14 | (2006.01) |
| C07D 405/04 | (2006.01) |
| C07D 409/04 | (2006.01) |
| C07D 411/14 | (2006.01) |
| C07D 417/04 | (2006.01) |
| C07D 417/14 | (2006.01) |
| C07D 471/04 | (2006.01) |
| C07D 487/04 | (2006.01) |
| C07D 487/10 | (2006.01) |
| C07D 498/10 | (2006.01) |
| A61K 31/5377 | (2006.01) |
| A61K 31/551 | (2006.01) |
| A61K 45/06 | (2006.01) |
| C07D 451/04 | (2006.01) |
| C07D 471/10 | (2006.01) |
| A61P 35/00 | (2006.01) |

(52) U.S. Cl.
CPC .......... *C07D 401/14* (2013.01); *A61K 31/506* (2013.01); *A61K 31/5377* (2013.01); *A61K 31/551* (2013.01); *A61K 45/06* (2013.01); *A61P 35/00* (2018.01); *C07D 403/04* (2013.01); *C07D 403/14* (2013.01); *C07D 405/04* (2013.01); *C07D 409/04* (2013.01); *C07D 411/14* (2013.01); *C07D 413/14* (2013.01); *C07D 417/04* (2013.01); *C07D 417/14* (2013.01); *C07D 451/04* (2013.01); *C07D 471/04* (2013.01); *C07D 471/10* (2013.01); *C07D 487/04* (2013.01); *C07D 487/10* (2013.01); *C07D 498/10* (2013.01)

(58) Field of Classification Search
CPC ........................... A61K 31/506; C07D 401/14
USPC ........................................ 514/275; 544/331
See application file for complete search history.

(56) References Cited

U.S. PATENT DOCUMENTS

| | | | |
|---|---|---|---|
| 10,059,690 B2 * | 8/2018 | Ciblat | C07D 401/14 |
| 10,106,526 B2 * | 10/2018 | Sprott | C07D 401/14 |

* cited by examiner

*Primary Examiner* — Jeffrey H Murray
(74) *Attorney, Agent, or Firm* — Goodwin Procter LLP

(57) ABSTRACT

The present invention provides novel compounds of Formula (I) and Formula (II) and pharmaceutically acceptable salts, solvates, hydrates, tautomers, stereoisomers, isotopically labeled derivatives, and compositions thereof. Also provided are methods and kits involving the compounds or compositions for treating or preventing proliferative diseases (e.g., cancers (e.g., leukemia, melanoma, multiple myeloma), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of cyclin-dependent kinase 7 (CDK7), and therefore, induce cellular apoptosis and/or inhibit transcription in the subject.

18 Claims, 51 Drawing Sheets

FIG. 1A

| Patent Compound No. | Structure |
|---|---|
| 100 | 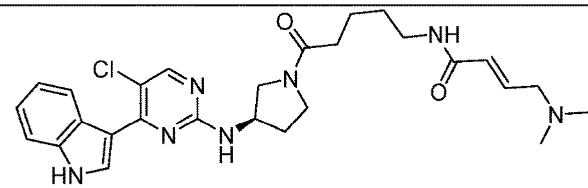 |
| 101 | 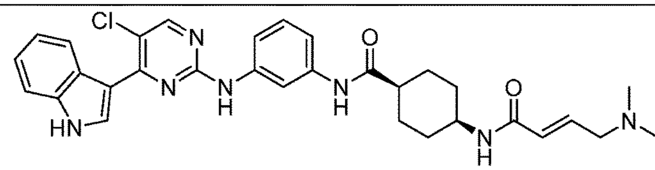 |
| 102 | 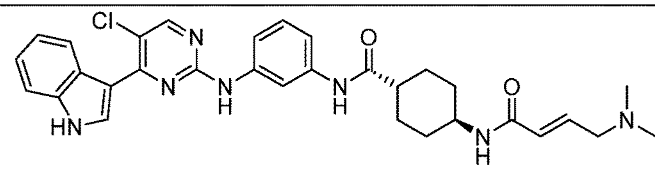 |
| 103 | 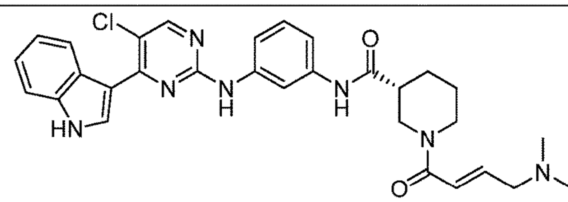 |
| 104 | 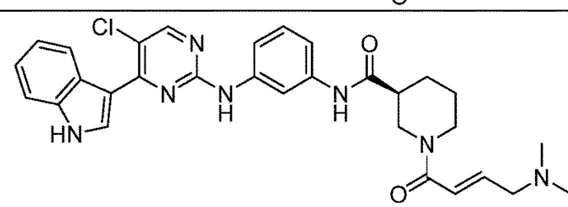 |
| 105 | 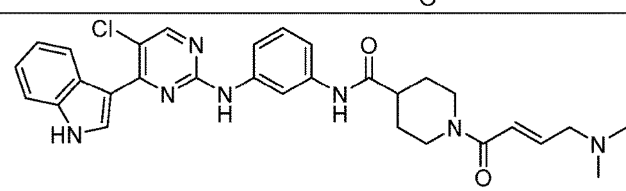 |
| 106 | 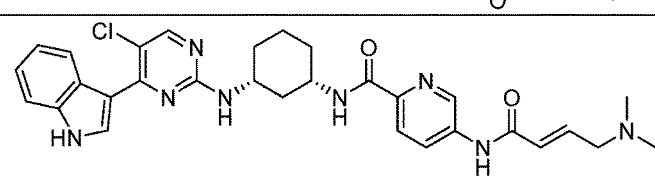 |
| 107 | 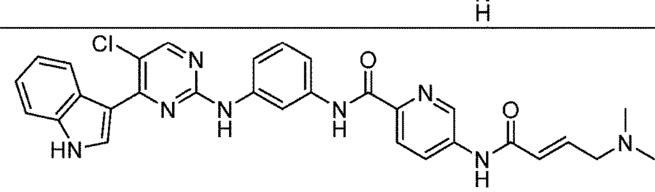 |

FIG. 1B

| Patent Compound No. | Structure |
|---|---|
| 108 | 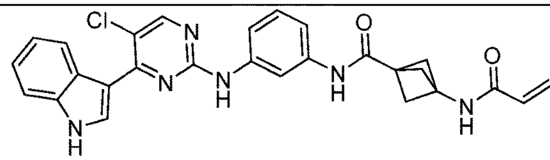 |
| 109 | 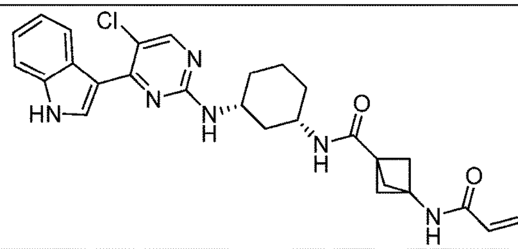 |
| 110 | 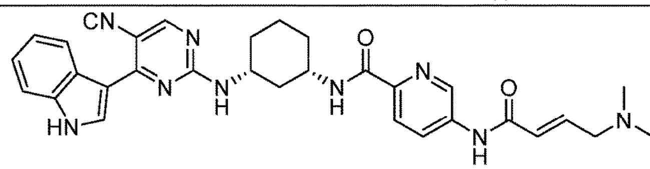 |
| 111 | 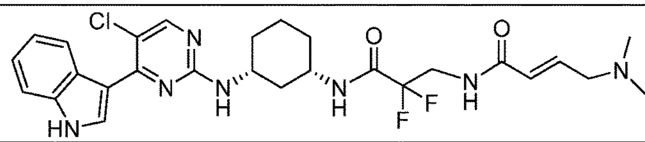 |
| 112 | 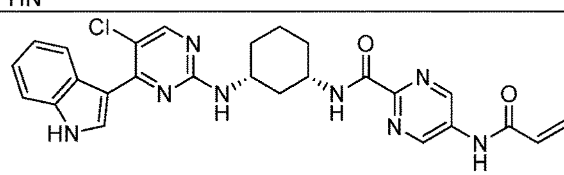 |
| 113 | 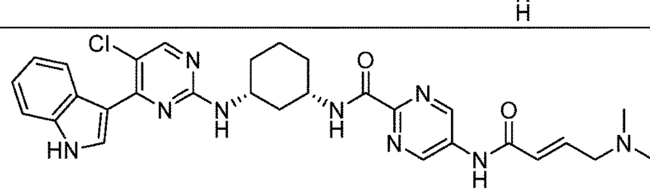 |
| 114 | 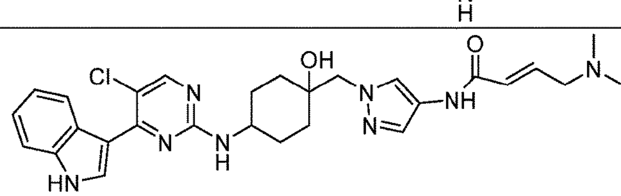 |
| 115 | 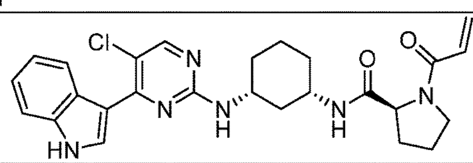 |

*FIG. 1C*

| Patent Compound No. | Structure |
|---|---|
| 116 | 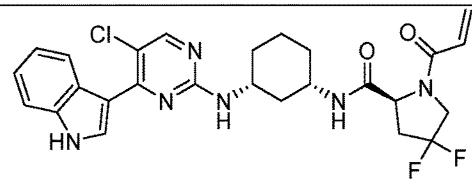 |
| 117 | 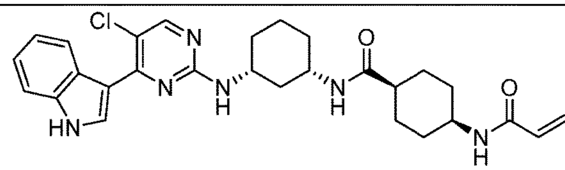 |
| 118 | 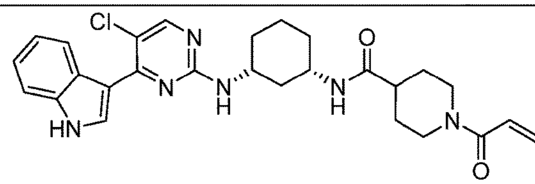 |
| 119 | 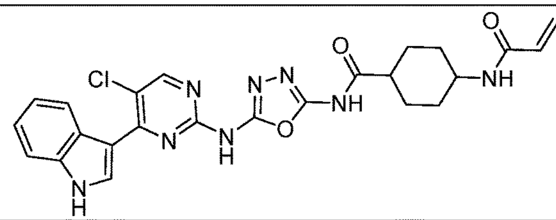 |
| 120 | 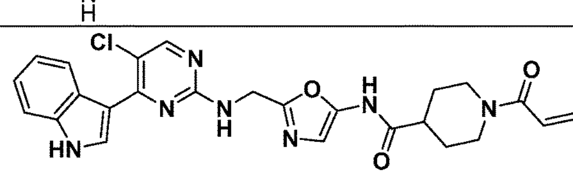 |
| 121 | 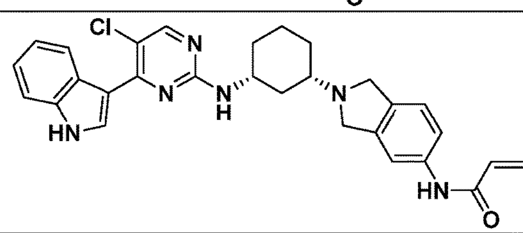 |
| 122 | 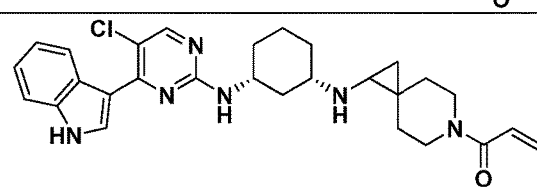 |
| 123 | 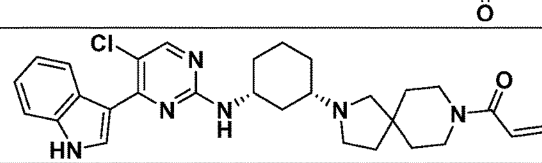 |

*FIG. 1D*
| Patent Compound No. | Structure |
|---|---|
| 124 | 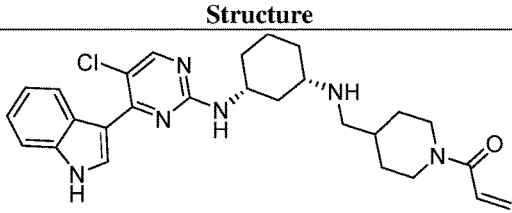 |
| 125 | 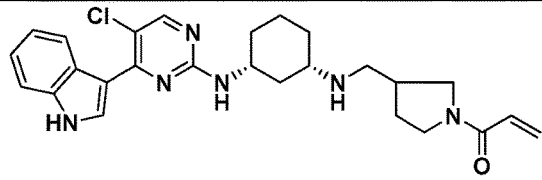 |
| 126 | 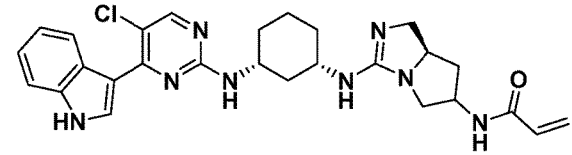 |
| 127 | 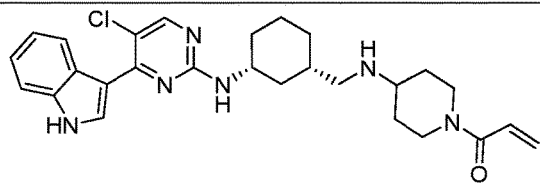 |
| 128 | 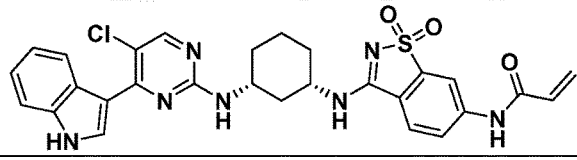 |
| 129 | 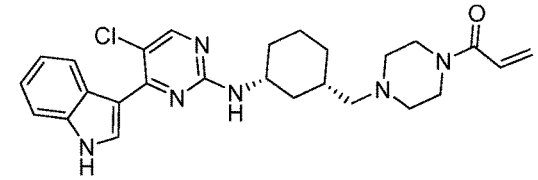 |
| 130 | 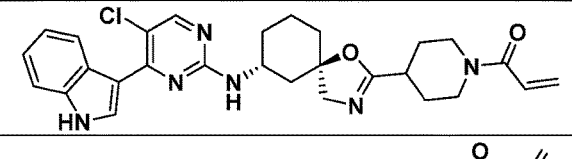 |
| 131 | 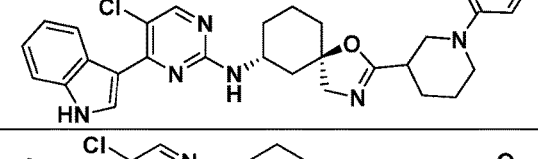 |
| 132 | 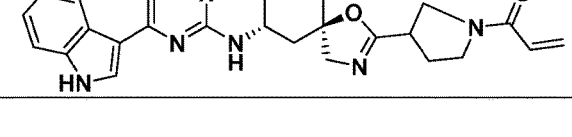 |

*FIG. 1E*

| Patent Compound No. | Structure |
|---|---|
| 133 | 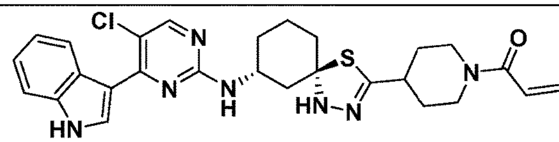 |
| 134 | 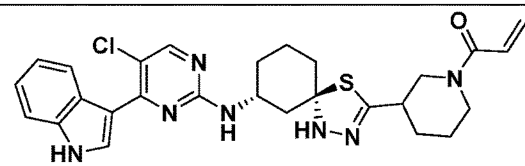 |
| 135 | 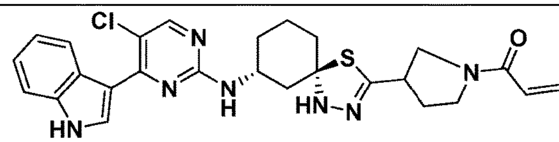 |
| 136 | 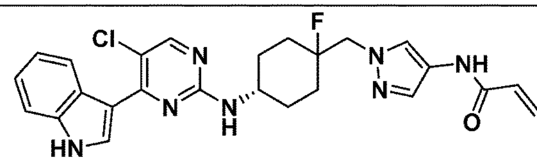 |
| 137 | 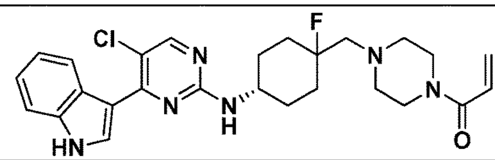 |
| 138 | 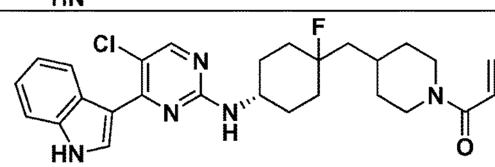 |
| 139 | 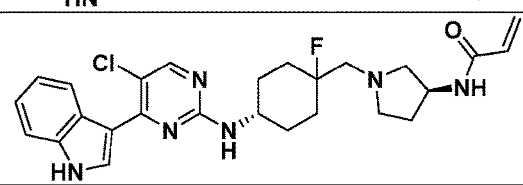 |
| 140 | 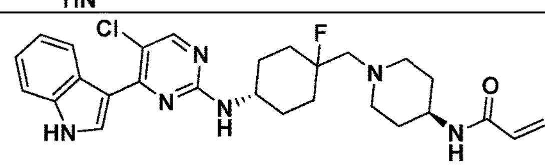 |
| 141 | 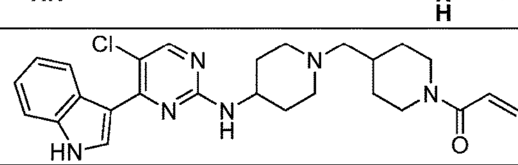 |

FIG. 1F

| Patent Compound No. | Structure |
|---|---|
| 142 | 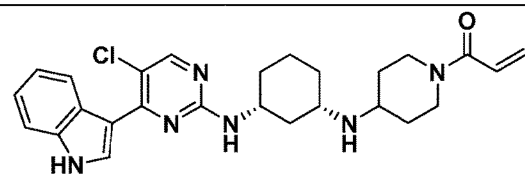 |
| 143 | 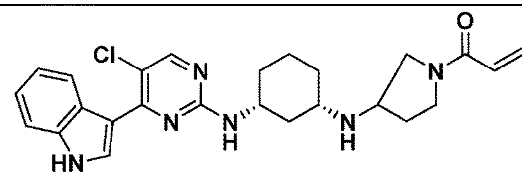 |
| 145 | 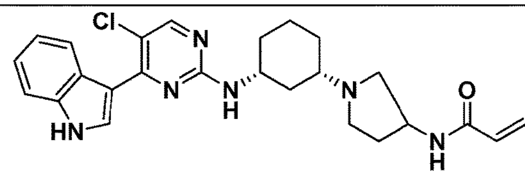 |
| 146 | 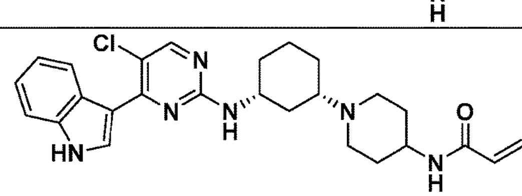 |
| 147 | 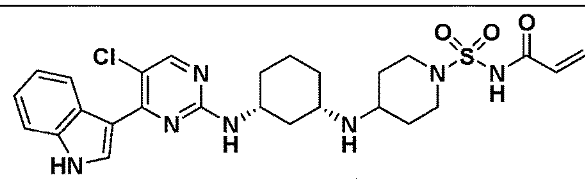 |
| 148 | 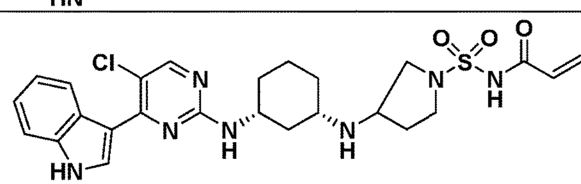 |
| 149 | 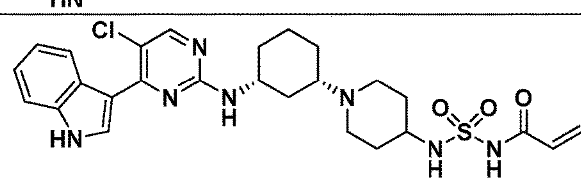 |
| 150 | 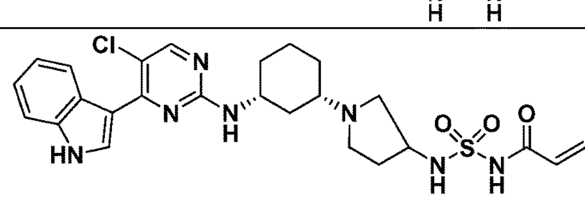 |

FIG. 1G
| Patent Compound No. | Structure |
|---|---|
| 151 | 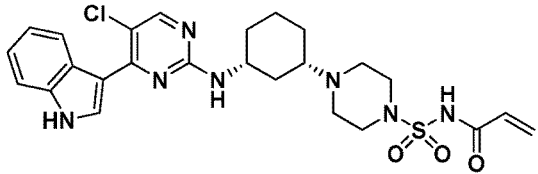 |
| 152 | 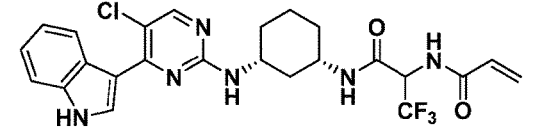 |
| 153 | 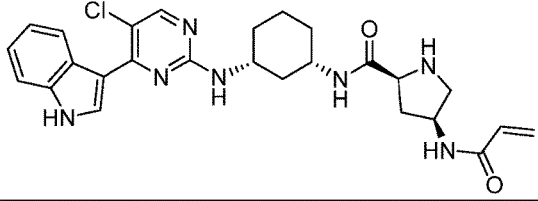 |
| 154 | 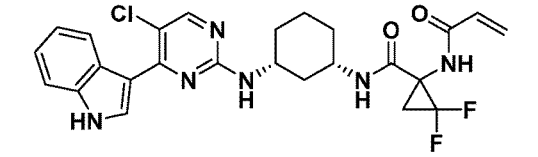 |
| 155 | 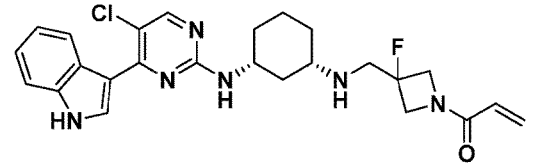 |
| 156 | 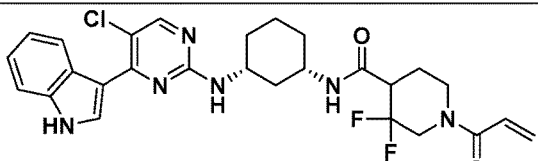 |
| 157 | 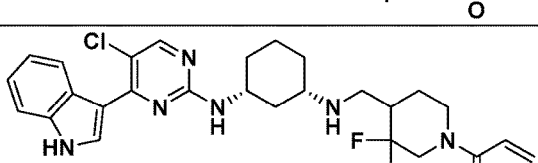 |
| 158 | 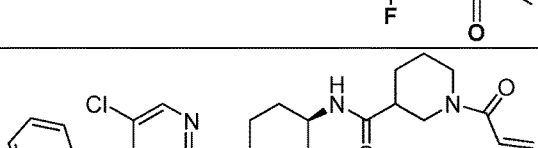 |

*FIG. 1H*

| Patent Compound No. | Structure |
|---|---|
| 159 | 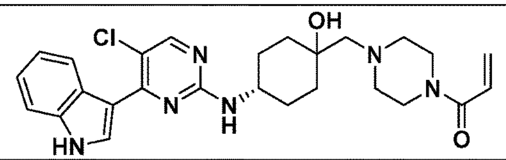 |
| 160 | 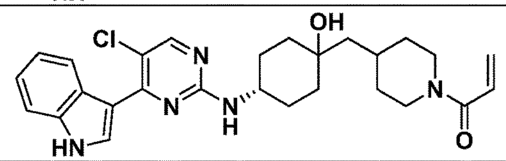 |
| 161 | 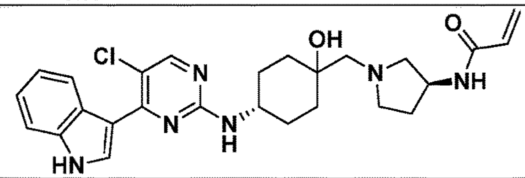 |
| 162 | 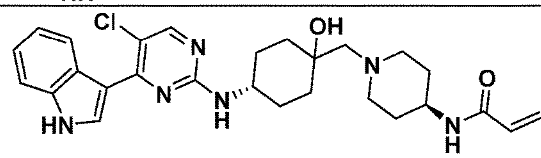 |
| 163 | 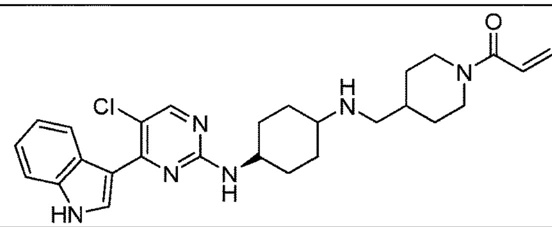 |
| 164 | 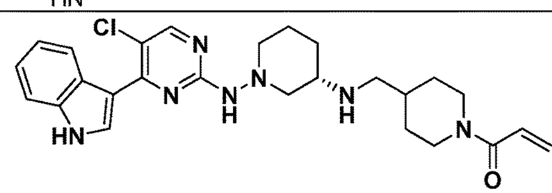 |
| 165 | 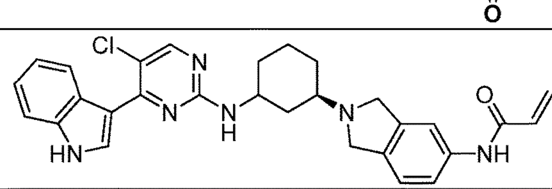 |
| 166 | 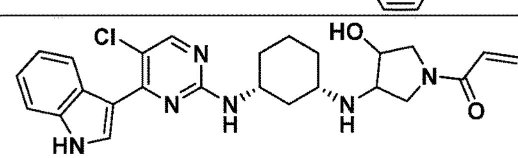 |

FIG. 11

| Patent Compound No. | Structure |
|---|---|
| 167 | 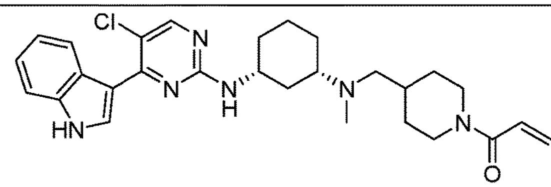 |
| 168 | 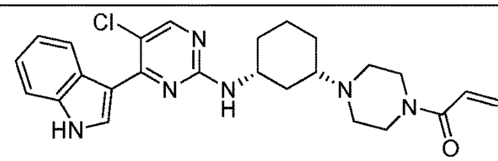 |
| 169 | 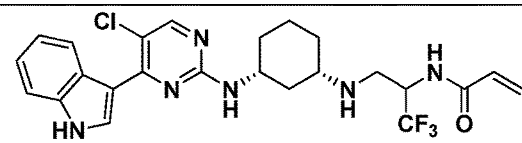 |
| 170 | 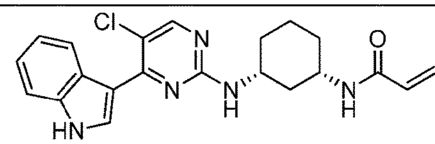 |
| 171 | 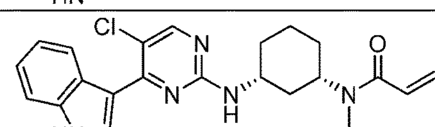 |
| 172 | 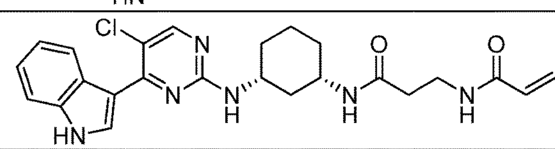 |
| 173 | 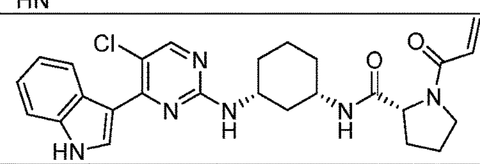 |
| 174 | 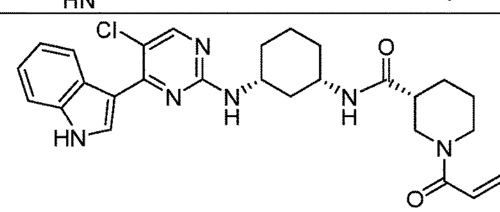 |
| 175 | 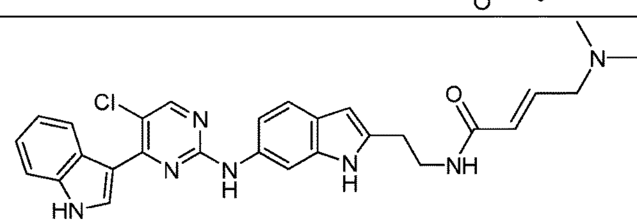 |

FIG. 1J

| Patent Compound No. | Structure |
|---|---|
| 176 | *(structure image)* |
| 177 | *(structure image)* |
| 178 | *(structure image)* |
| 179 | *(structure image)* |
| 180 | *(structure image)* |
| 181 | *(structure image)* |
| 182 | *(structure image)* |
| 183 | *(structure image)* |

FIG. 1K

| Patent Compound No. | Structure |
|---|---|
| 184 | 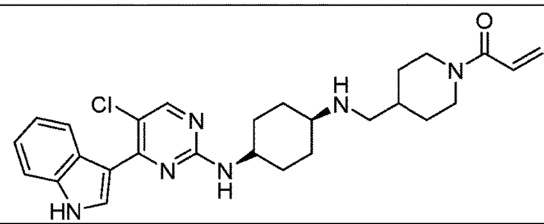 |
| 185 | 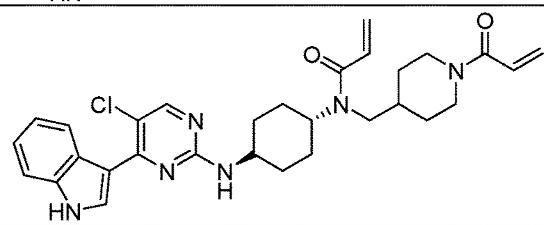 |
| 186 | 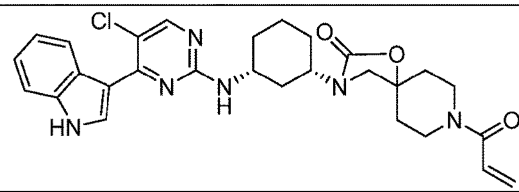 |
| 187 | 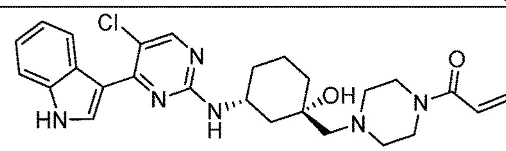 |
| 188 | 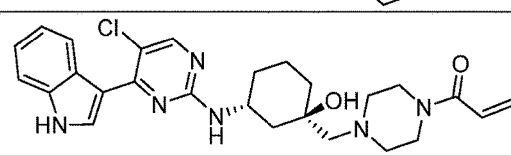 |
| 189 | 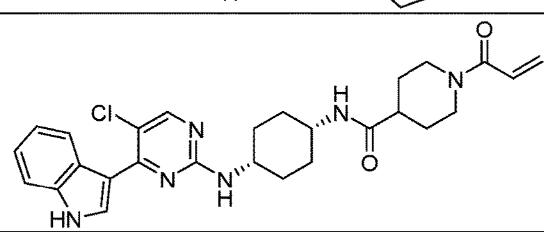 |
| 190 | 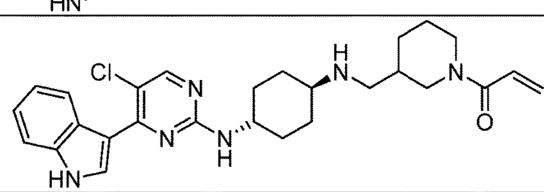 |

FIG. 1L

| Patent Compound No. | Structure |
|---|---|
| 191-1 | (structure) |
| 191-2 | (structure) |
| 192 | (structure) |
| 193 | (structure) |
| 194 | (structure) |
| 195 | (structure) |
| 196 | (structure) |

*FIG. 1M*

| Patent Compound No. | Structure |
|---|---|
| 197 | 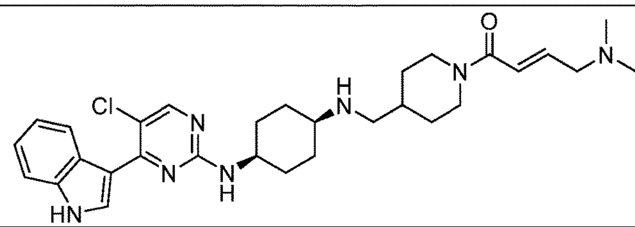 |
| 198 | 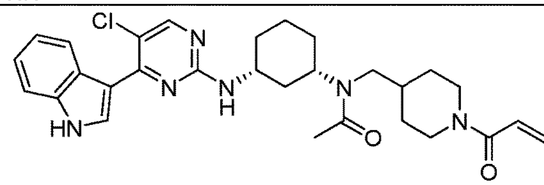 |
| 199 | 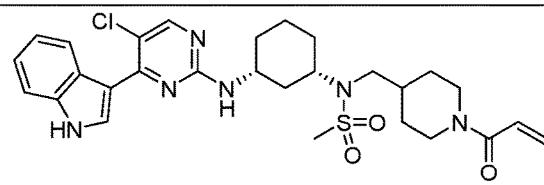 |
| 200 | 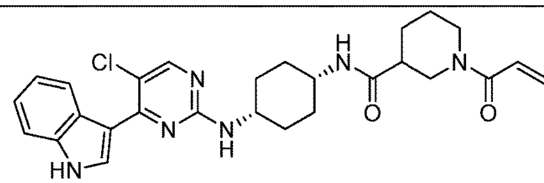 |
| 201 | 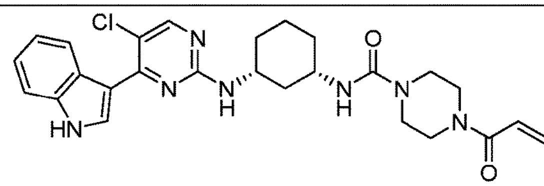 |
| 202-1 | 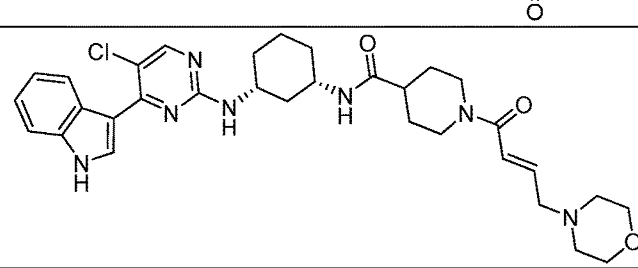 |
| 202-2 | 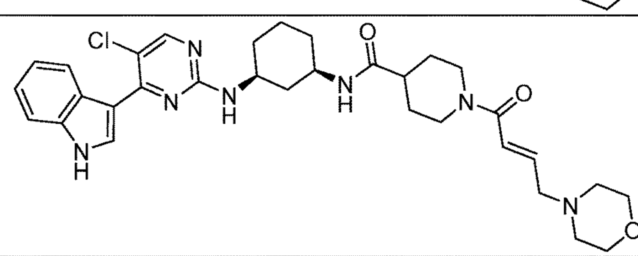 |

*FIG. 1N*

| Patent Compound No. | Structure |
|---|---|
| 203-1* | (structure) |
| 203-2* | (structure) |
| 203-3* | (structure) |
| 203-4* | (structure) |
| 203-5* | (structure) |
| 203-6* | (structure) |
| 203-7* | (structure) |
| 203-8* | (structure) |
| 204 | (structure) |

FIG. 1O
| Patent Compound No. | Structure |
|---|---|
| 205 | 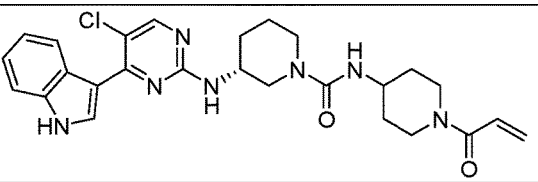 |
| 206 | 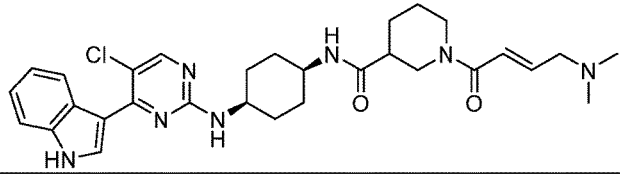 |
| 207 | 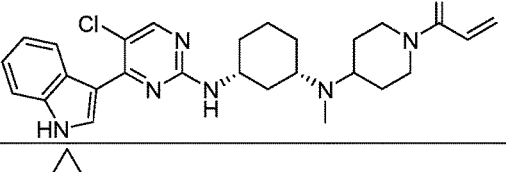 |
| 208 | 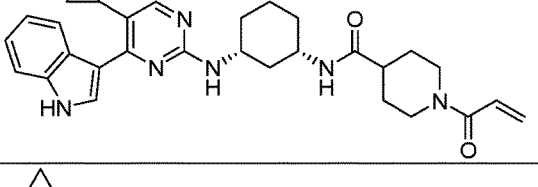 |
| 209 | 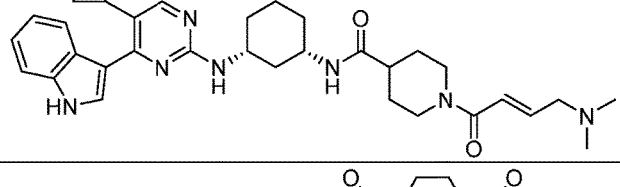 |
| 210 | 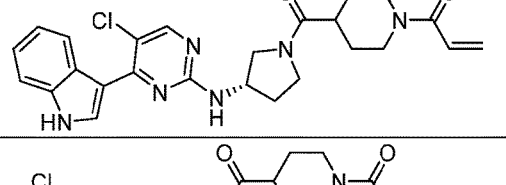 |
| 211 | 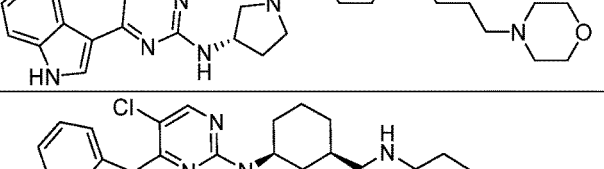 |
| 212 | 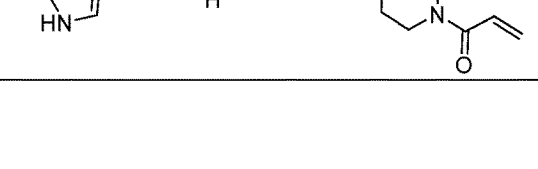 |

*FIG. 1P*

| Patent Compound No. | Structure |
|---|---|
| 213 | 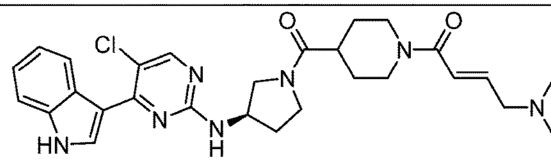 |
| 214 | 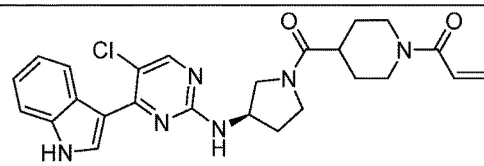 |
| 215 | 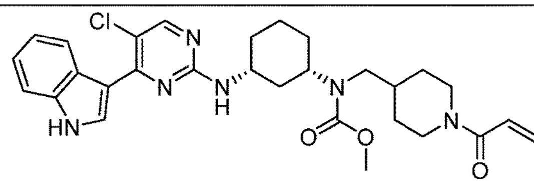 |
| 216 | 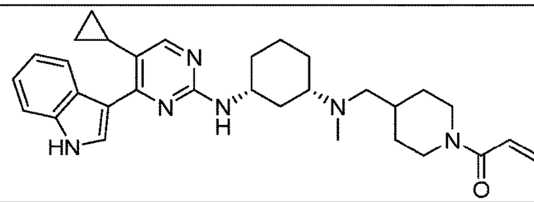 |
| 217 | 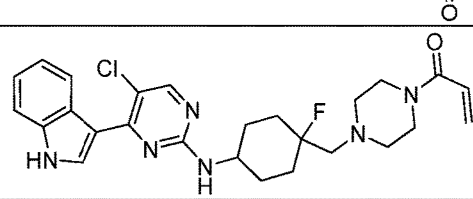 |
| 218 | 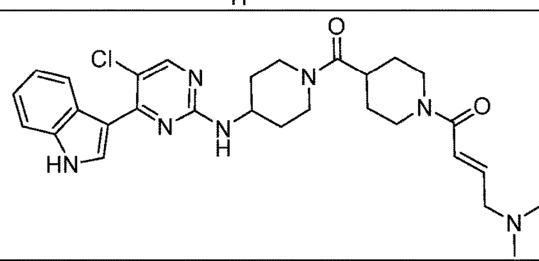 |
| 219 | 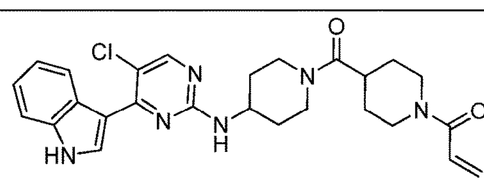 |

FIG. 1Q

| Patent Compound No. | Structure |
|---|---|
| 220 | 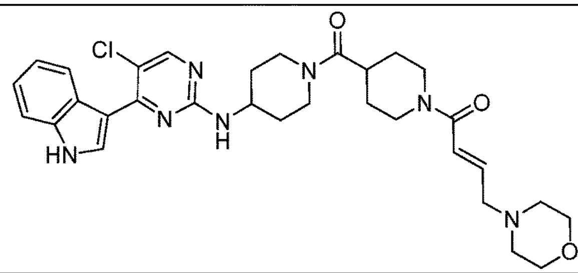 |
| 221 | 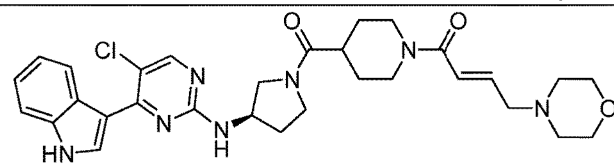 |
| 222 | 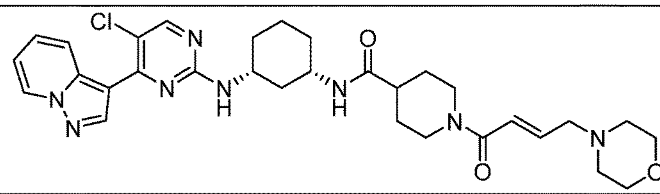 |
| 223 | 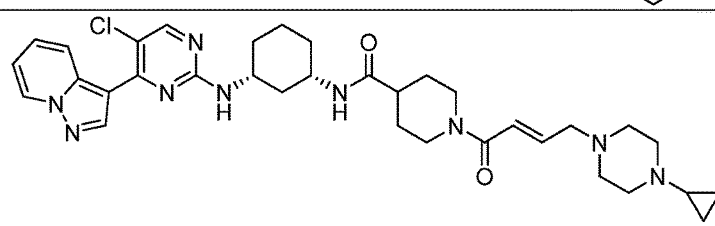 |
| 224 | 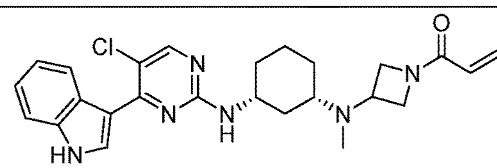 |
| 225 | 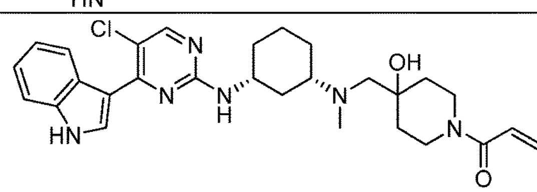 |
| 226 | 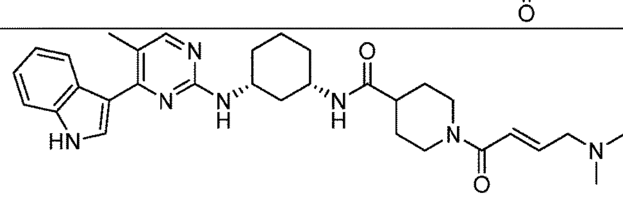 |

*FIG. 1R*

| Patent Compound No. | Structure |
|---|---|
| 227 | 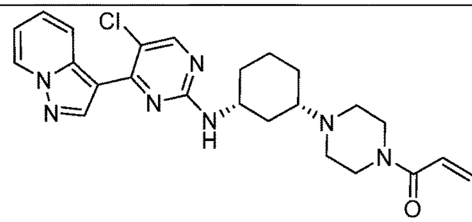 |
| 228 | 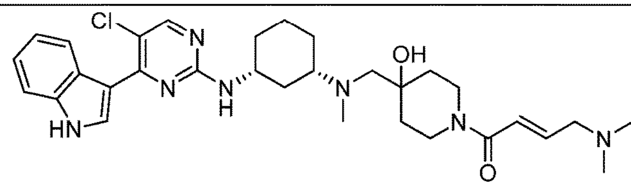 |
| 229 | 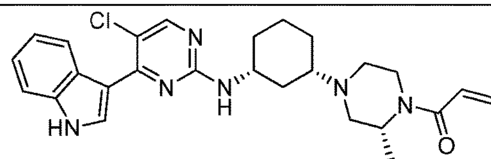 |
| 230 | 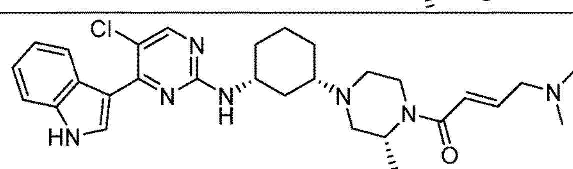 |
| 231 | 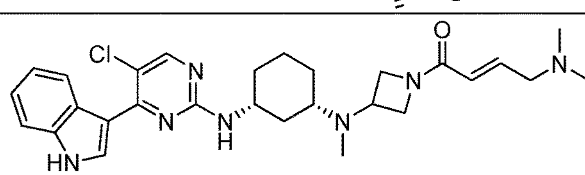 |
| 232 | 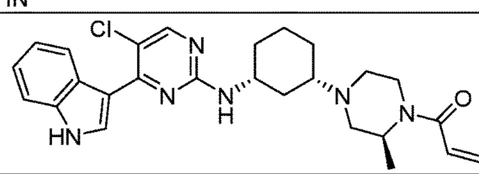 |
| 233 | 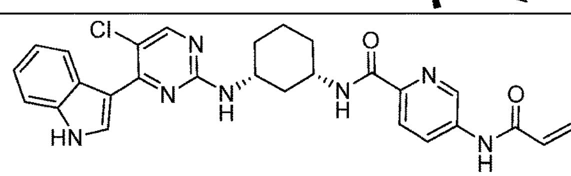 |
| 234 | 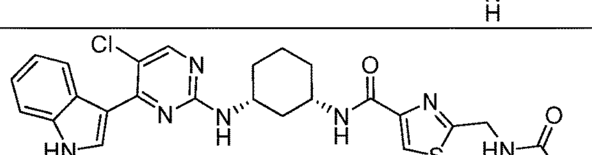 |

FIG. 1S
| Patent Compound No. | Structure |
|---|---|
| 235 | 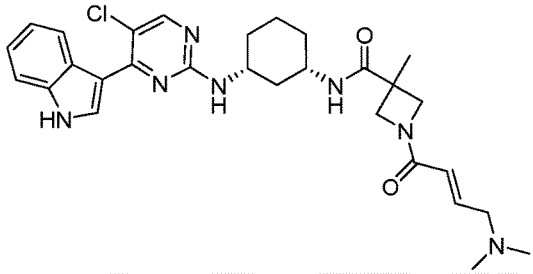 |
| 236 | 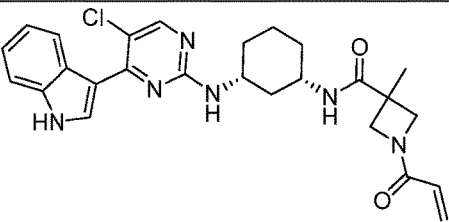 |
| 237 | 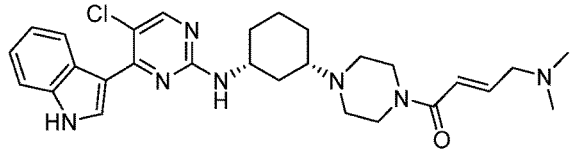 |
| 238 | 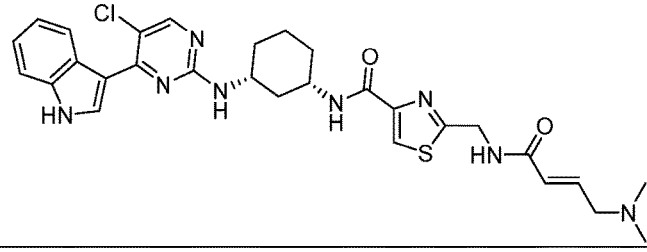 |
| 239 | 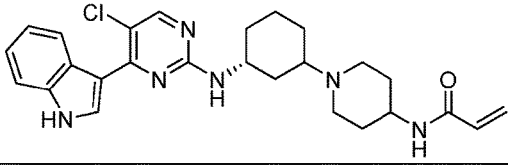 |
| 240 | 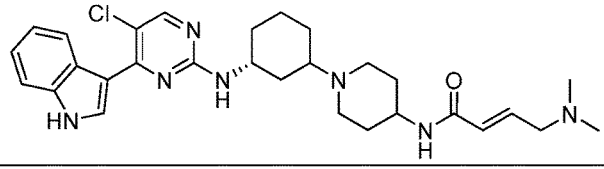 |
| 241 | 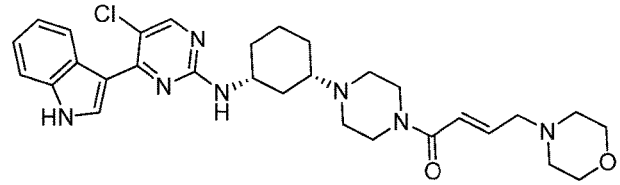 |

FIG. 1T
| Patent Compound No. | Structure |
|---|---|
| 242 | 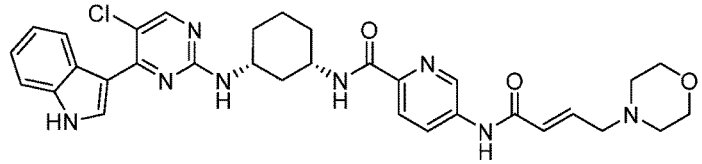 |
| 243 | 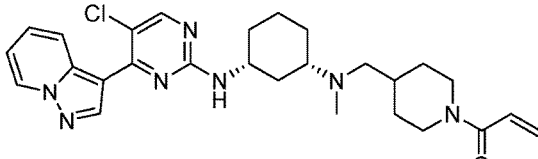 |
| 244 | 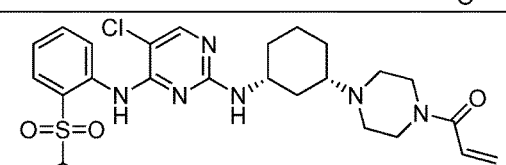 |
| 245 | 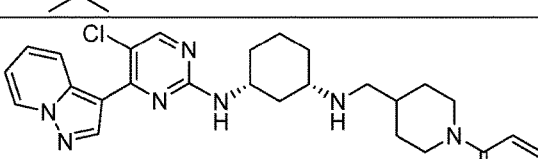 |
| 246 | 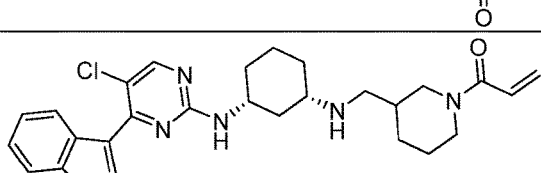 |
| 247 | 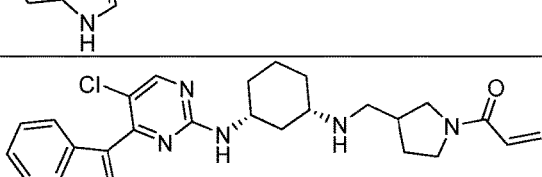 |
| 248 | 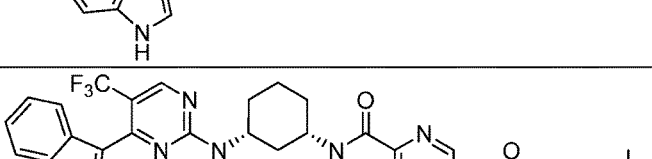 |
| 249 | 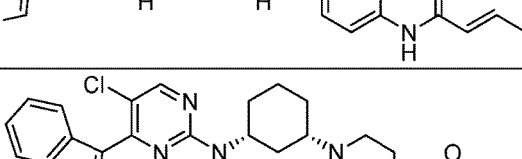 |

FIG. 1U

| Patent Compound No. | Structure |
|---|---|
| 250 | 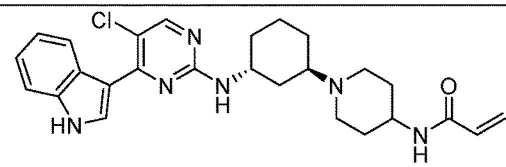 |
| 251 | 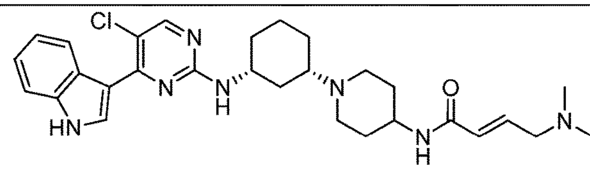 |
| 252 | 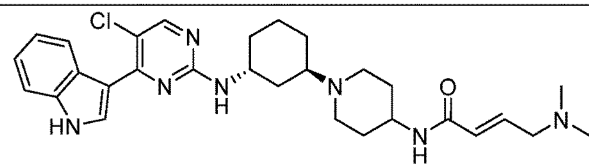 |
| 253 | 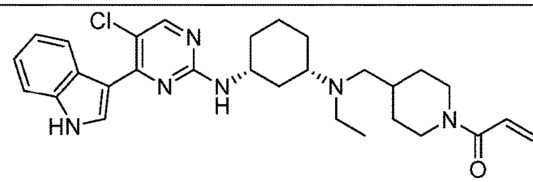 |
| 254 | 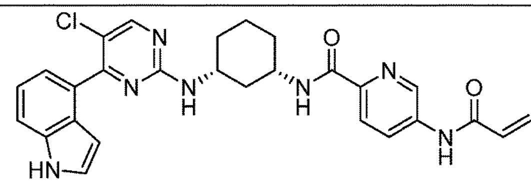 |
| 255 | 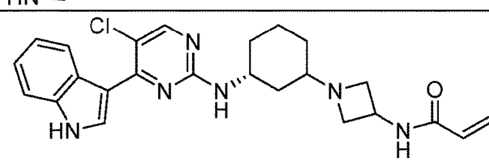 |
| 256 | 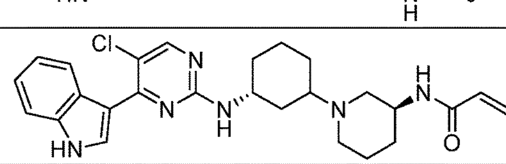 |
| 257 | 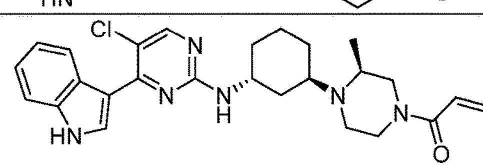 |
| 258 | 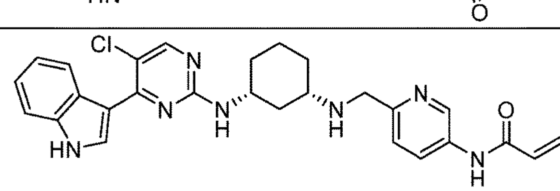 |

FIG. 1V

| Patent Compound No. | Structure |
|---|---|
| 259 | 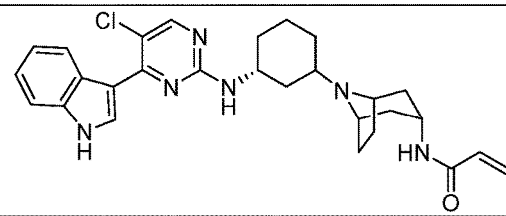 |
| 260 | 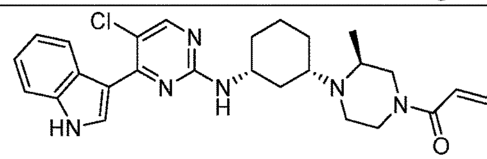 |
| 261 | 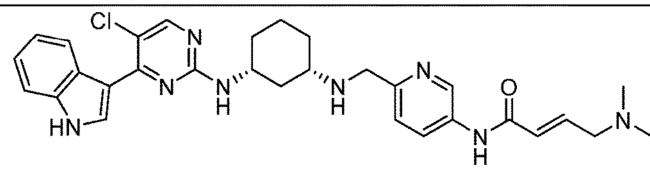 |
| 262 | 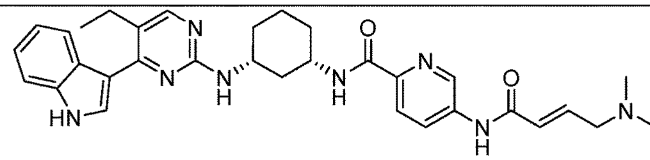 |
| 263 | 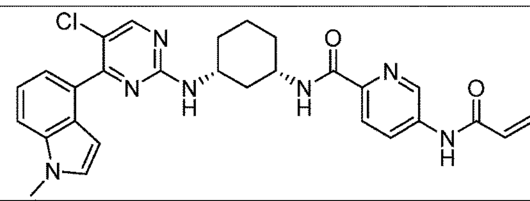 |
| 264 | 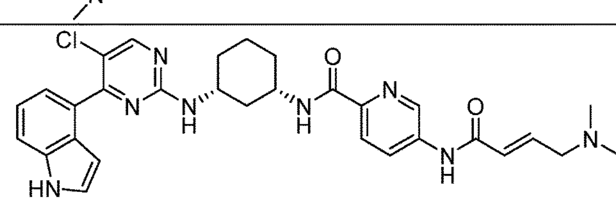 |
| 265 | 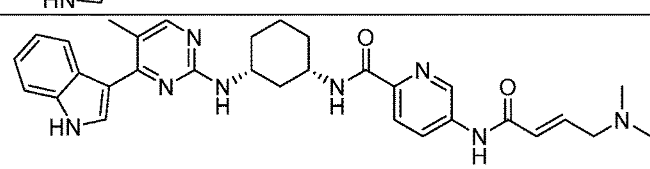 |
| 266 | 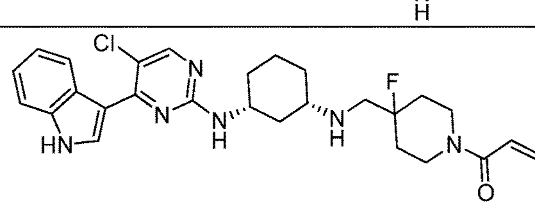 |

FIG. 1W

| Patent Compound No. | Structure |
|---|---|
| 267 | 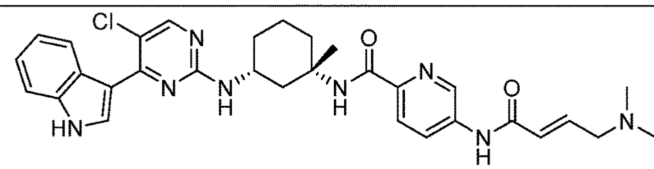 |
| 268 | 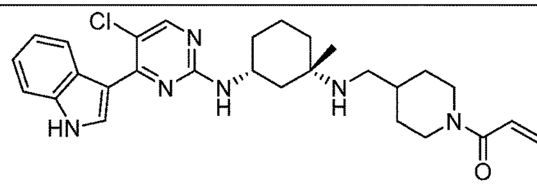 |
| 269 | 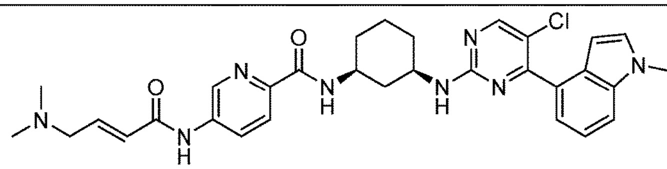 |
| 270 | 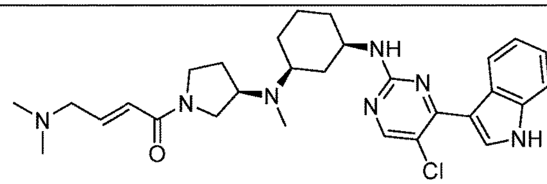 |
| 271 | 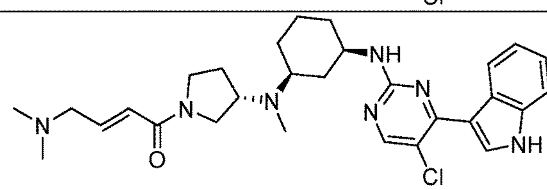 |
| 272 | 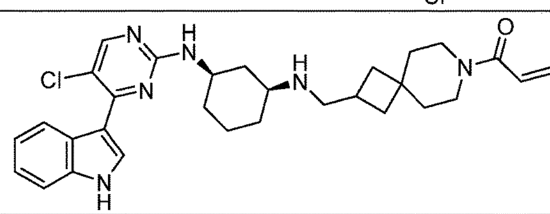 |
| 273 | 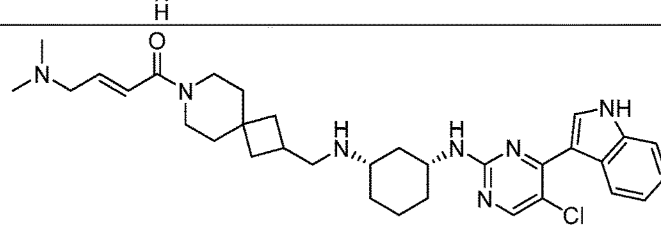 |
| 274 | 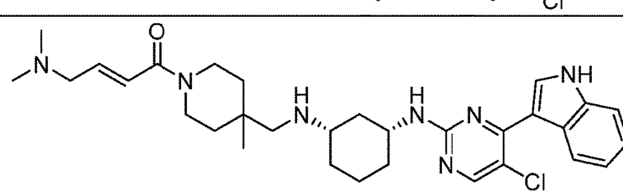 |

*FIG. 1X*

| Patent Compound No. | Structure |
|---|---|
| 275 | 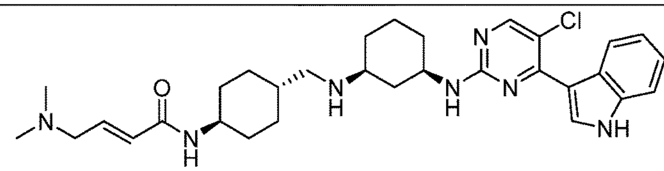 |
| 276† | 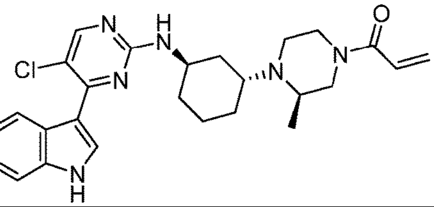 |
| 277† | 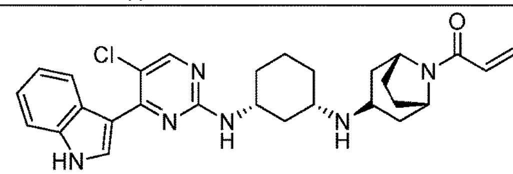 |
| 278 | 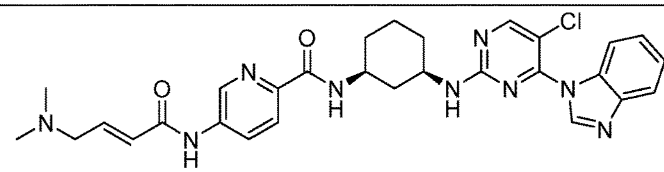 |
| 279 | 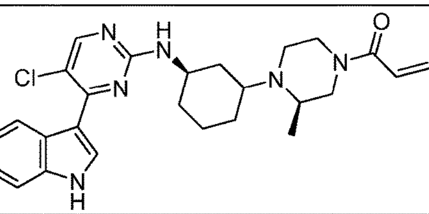 |
| 280 | 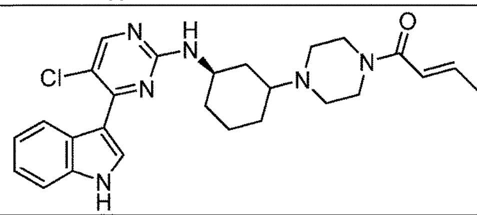 |
| 281 | 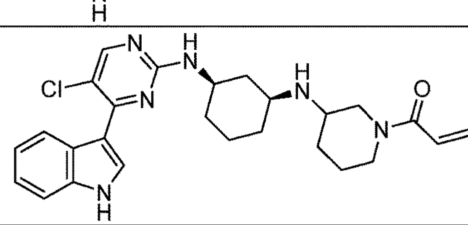 |

FIG. 1Y
| Patent Compound No. | Structure |
|---|---|
| 282 | 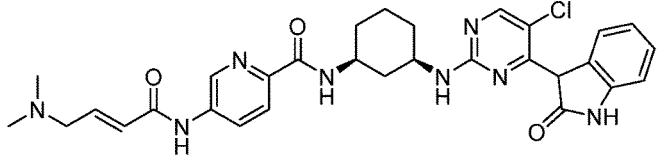 |
| 283 | 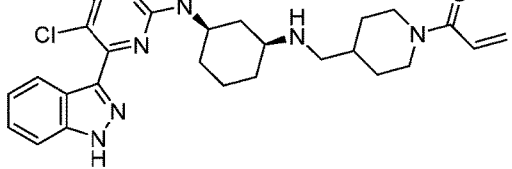 |
| 284 | 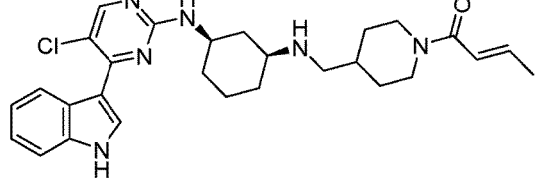 |
| 285 | 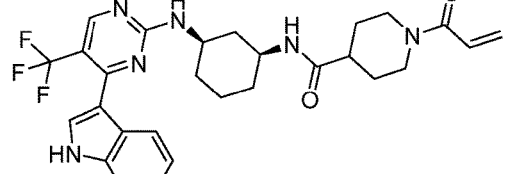 |
| 286 | 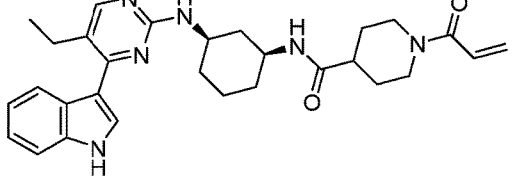 |
| 287 | 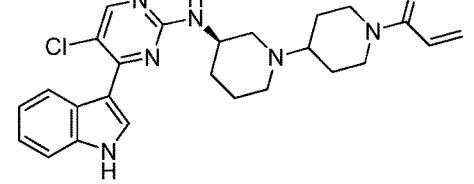 |
| 288 | 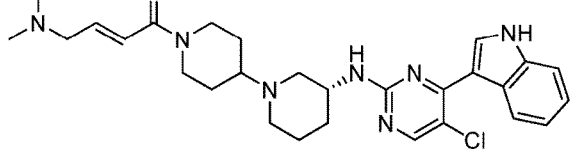 |

FIG. 1Z

| Patent Compound No. | Structure |
|---|---|
| 289 | 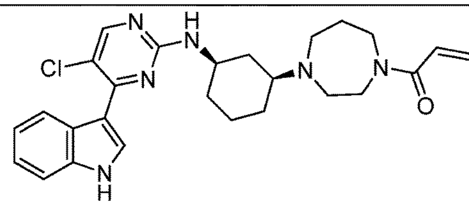 |
| 290 | 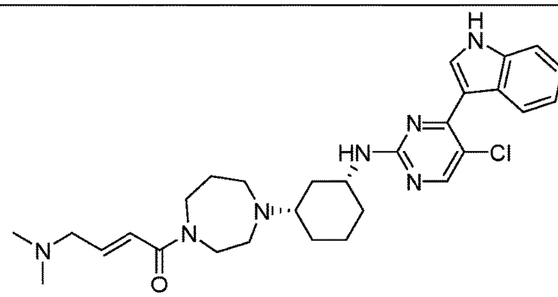 |
| 291 | 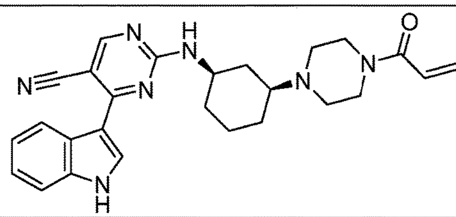 |
| 292 | 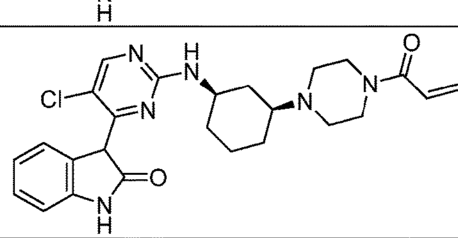 |
| 293 | 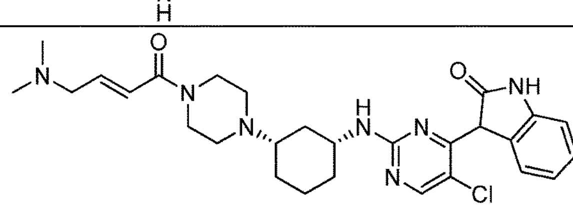 |
| 294 | 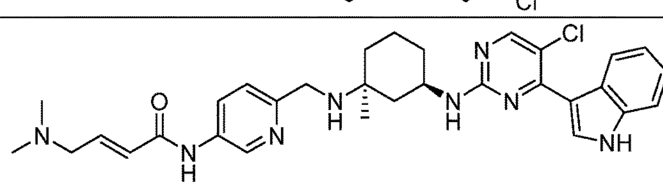 |

*FIG. 1AA*

| Patent Compound No. | Structure |
|---|---|
| 295 | 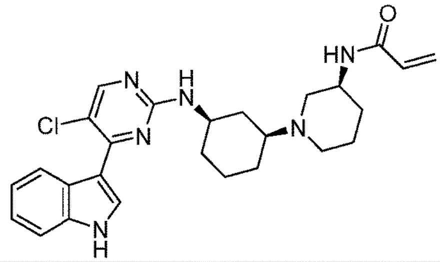 |
| 296 | 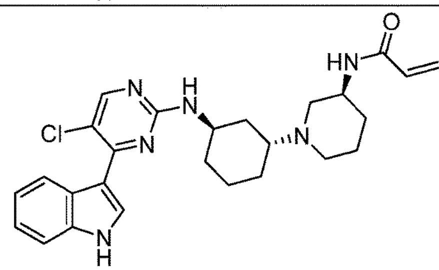 |
| 297 | 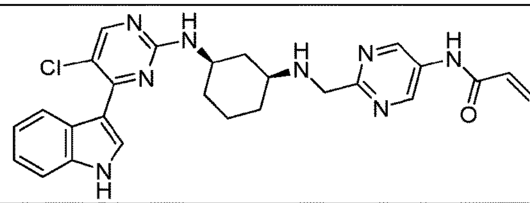 |
| 298 | 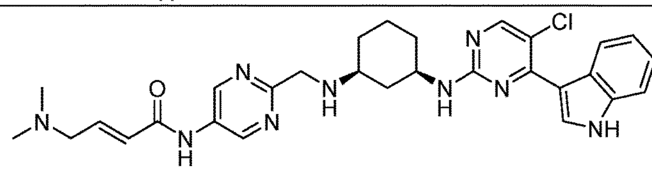 |
| 299 | 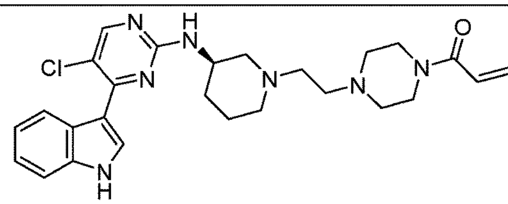 |
| 300 | 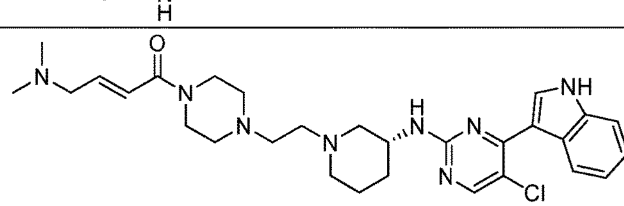 |
| 301 | 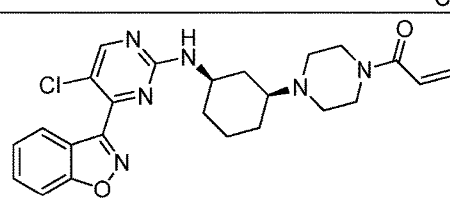 |

FIG. 1BB
| Patent Compound No. | Structure |
|---|---|
| 302 | 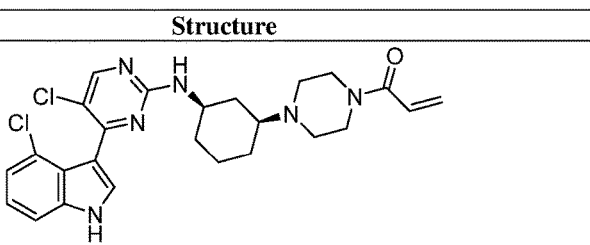 |
| 303 | 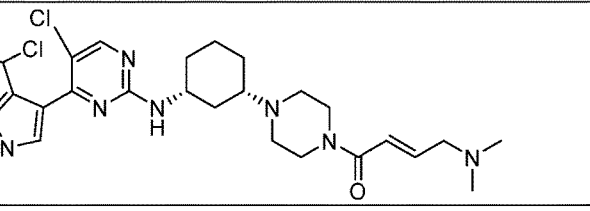 |
| 304 | 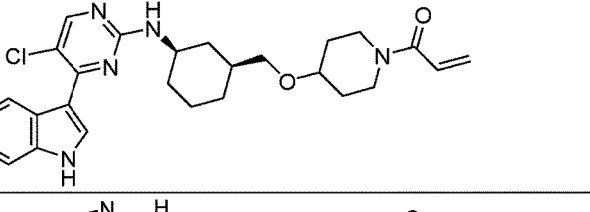 |
| 305 | 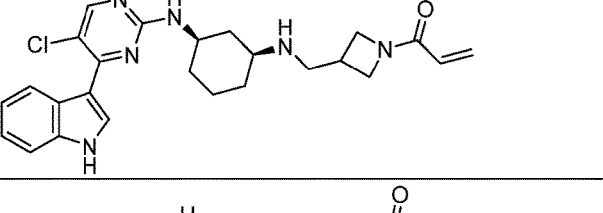 |
| 306 | 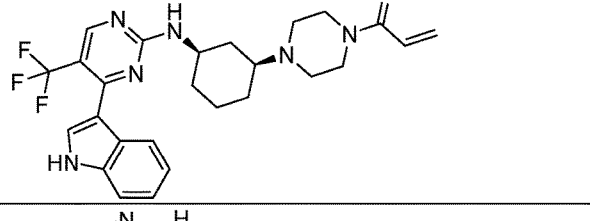 |
| 307 | 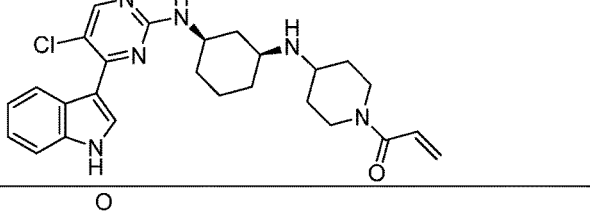 |
| 308 | 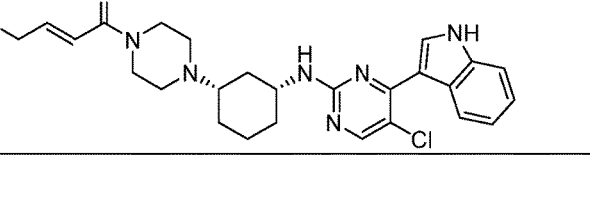 |

FIG. 1CC

| Patent Compound No. | Structure |
|---|---|
| 309 | 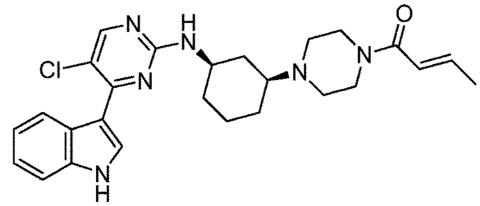 |
| 310 | 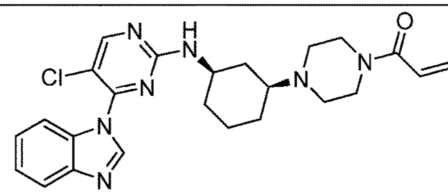 |
| 311 | 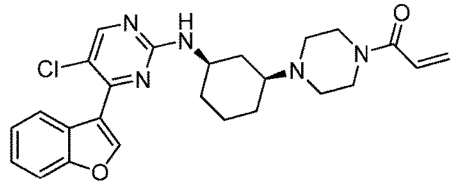 |
| 312 | 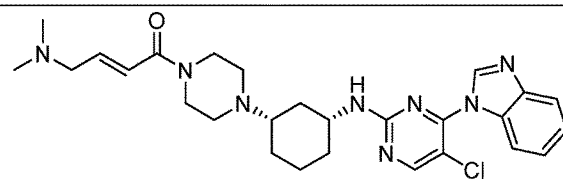 |
| 313 | 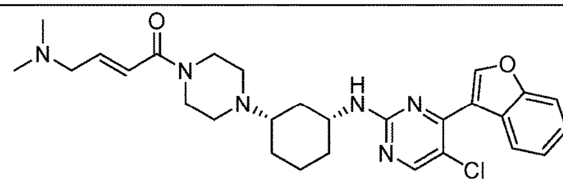 |
| 314 | 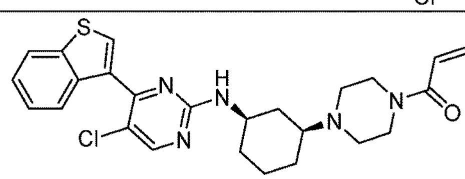 |
| 315 | 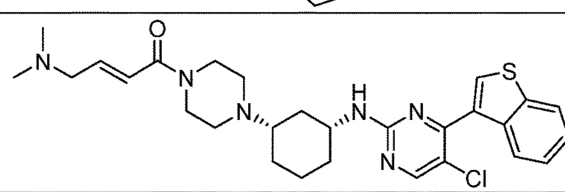 |
| 316 | 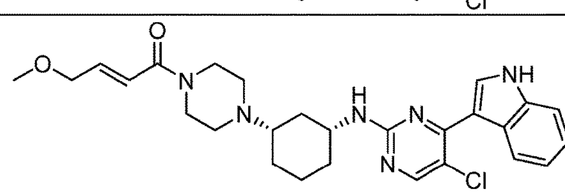 |

FIG. 1DD

| Patent Compound No. | Structure |
|---|---|
| 317 | 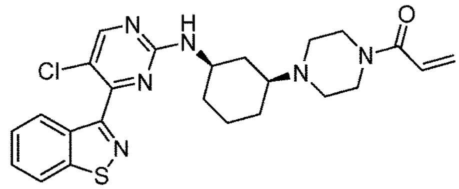 |
| 318 | 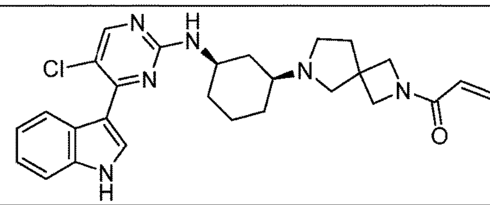 |
| 319 | 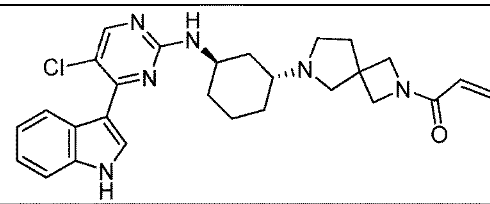 |
| 320 | 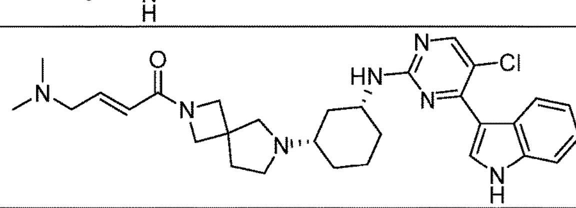 |
| 321 | 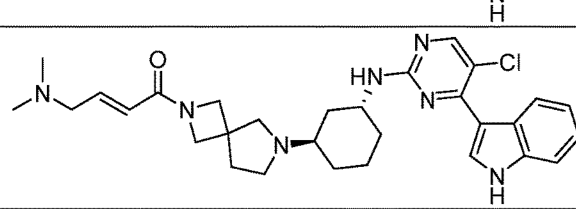 |
| 322 | 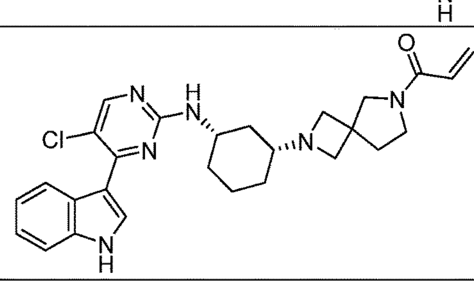 |
| 323 | 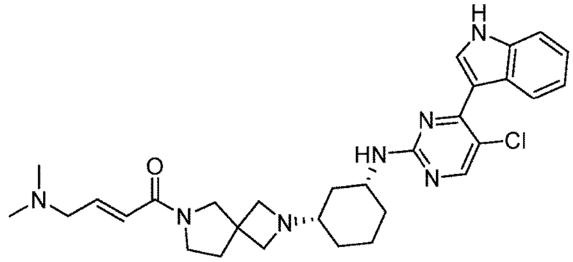 |

*FIG. 1EE*
| Patent Compound No. | Structure |
|---|---|
| 324 | 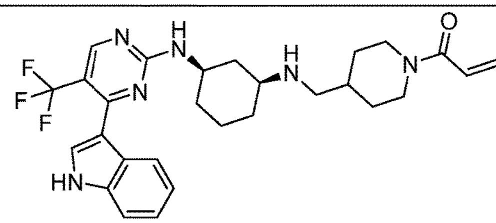 |
| 325 | 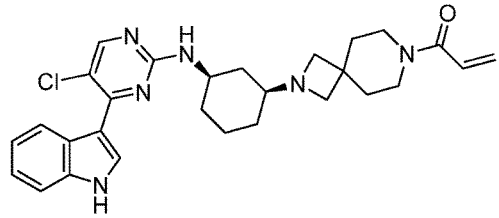 |
| 326 | 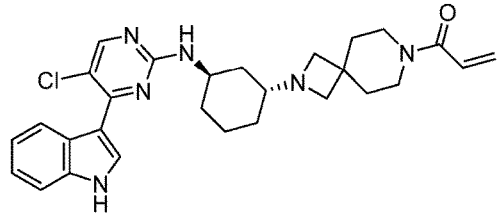 |
| 327 | 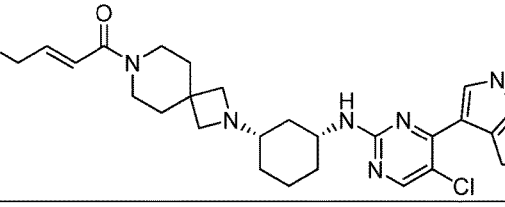 |
| 328 | 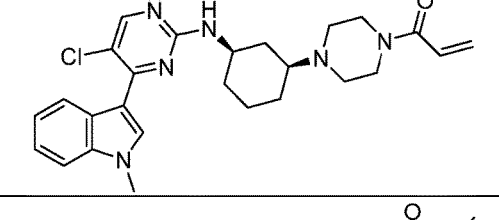 |
| 329 | 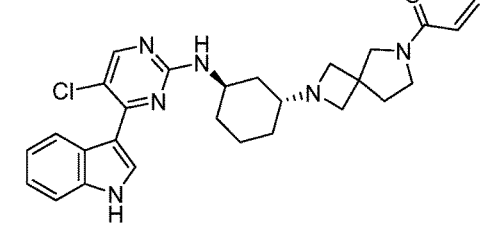 |

FIG. 1FF

| Patent Compound No. | Structure |
|---|---|
| 330 | 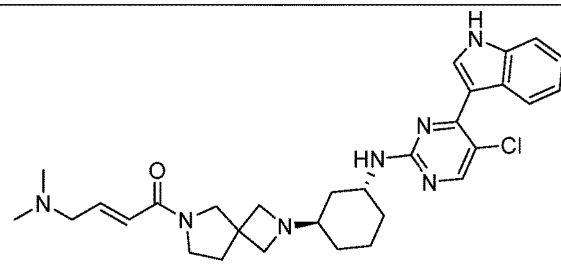 |
| 331 | 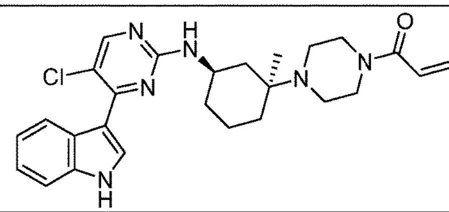 |
| 332 | 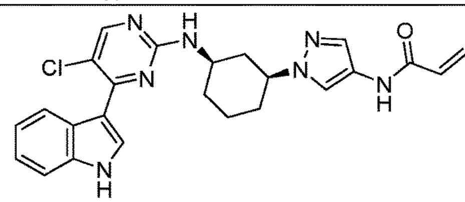 |
| 333 | 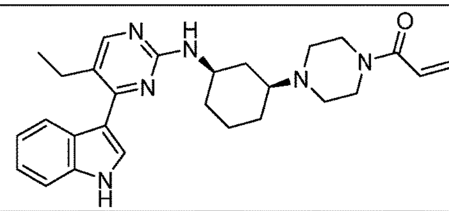 |
| 334 | 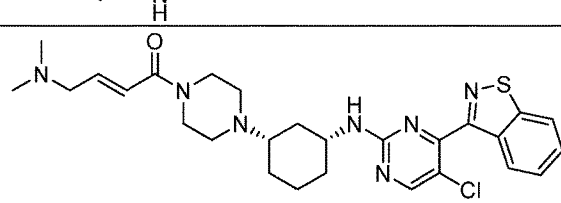 |
| 335 | 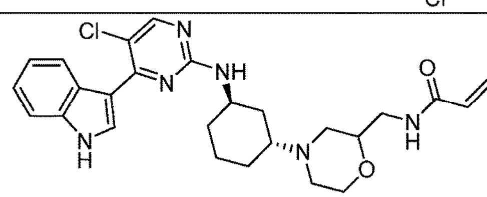 |
| 336 | 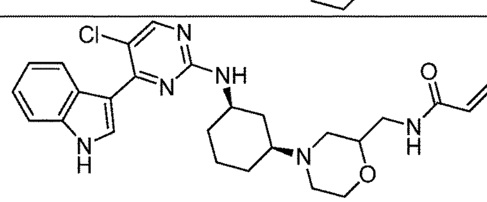 |

*FIG. 1GG*

| Patent Compound No. | Structure |
|---|---|
| 337 | 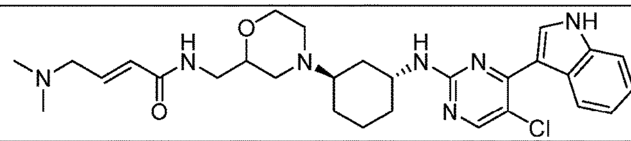 |
| 338 | 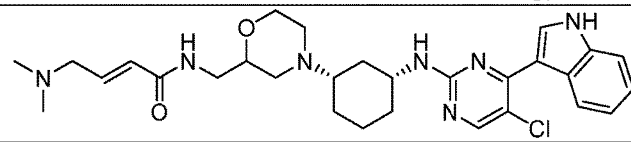 |
| 339 | 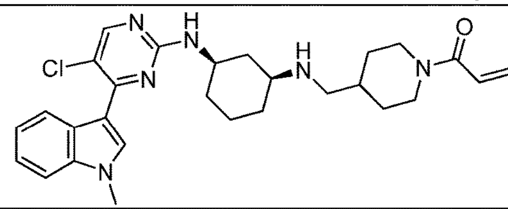 |
| 340 | 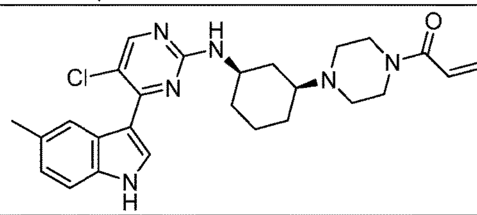 |
| 341 | 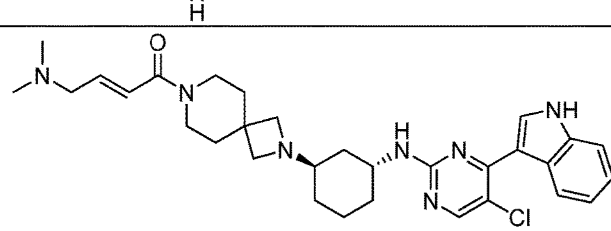 |
| 342 | 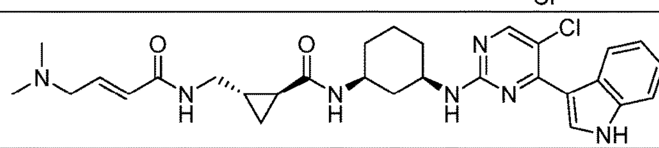 |
| 343 | 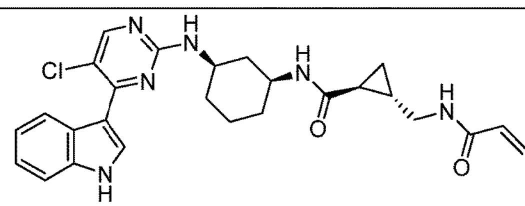 |
| 344 | 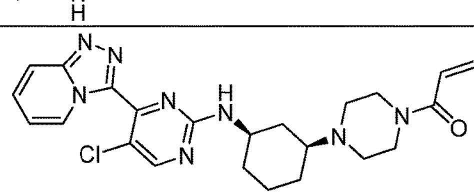 |

*FIG. 1HH*

| Patent Compound No. | Structure |
|---|---|
| 345 | 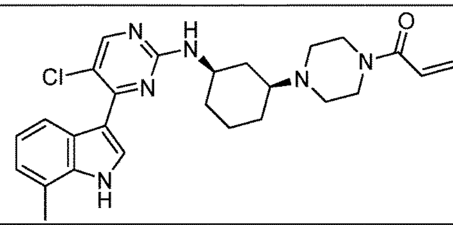 |
| 346 | 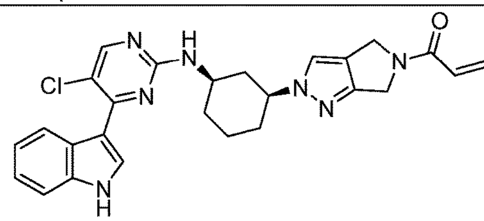 |
| 347 | 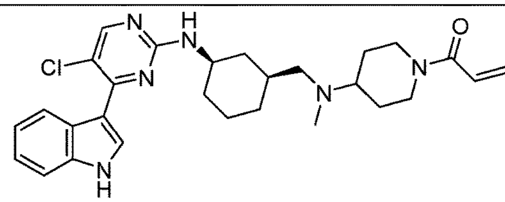 |
| 348 | 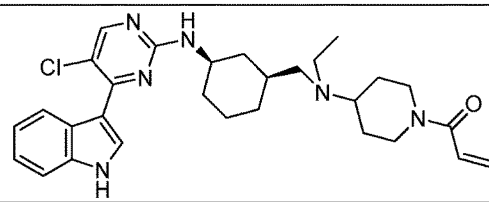 |
| 349 | 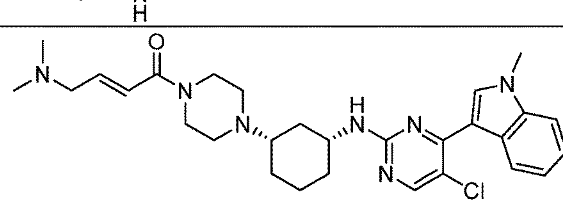 |
| 350 | 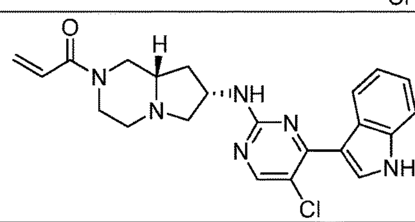 |
| 351 | 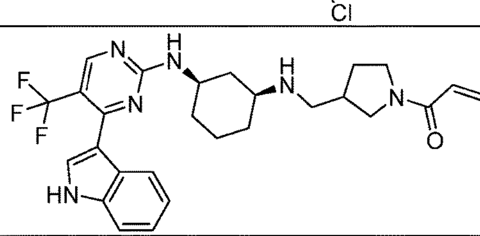 |

FIG. 1II

| Patent Compound No. | Structure |
|---|---|
| 352 | 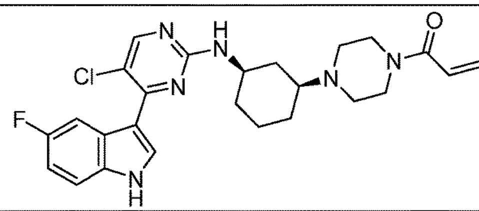 |
| 353 | 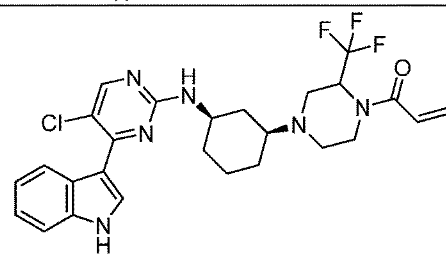 |
| 354 | 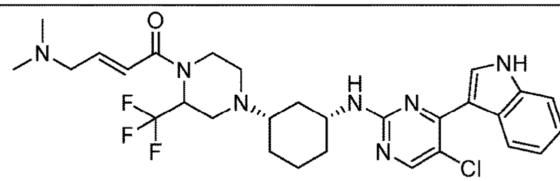 |
| 355 | 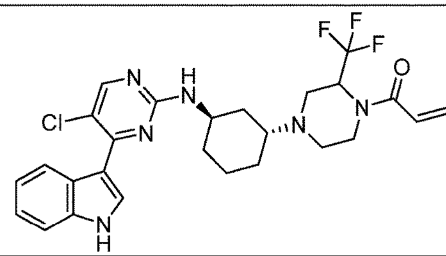 |
| 356 | 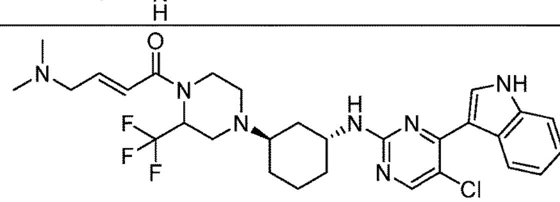 |
| 357 | 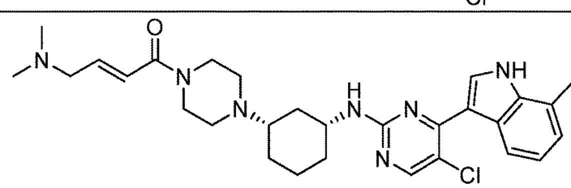 |
| 358 | 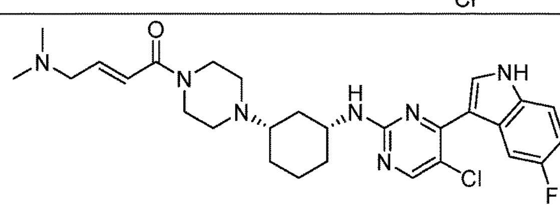 |

FIG. 1JJ
| Patent Compound No. | Structure |
|---|---|
| 359 | 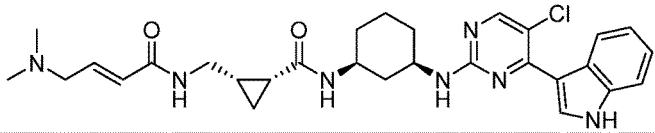 |
| 360 | 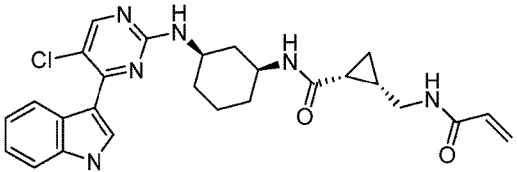 |
| 361 | 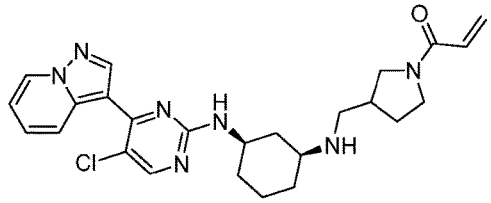 |
| 362 | 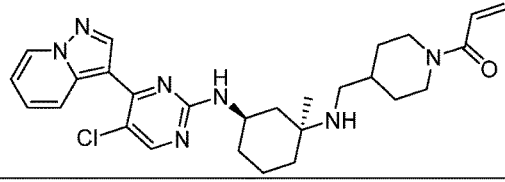 |
| 363 | 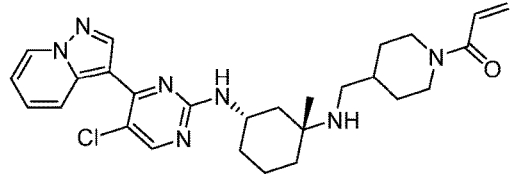 |
| 364 | 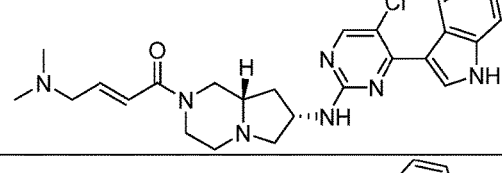 |
| 365 | 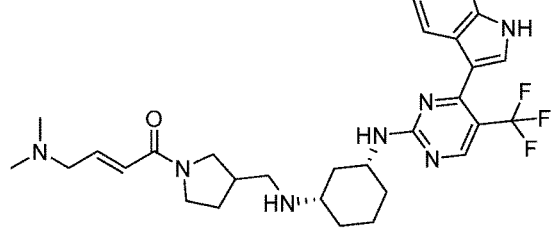 |

FIG. 1KK
| Patent Compound No. | Structure |
|---|---|
| 366 | 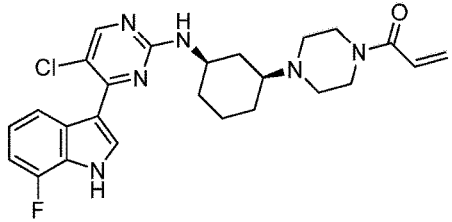 |
| 367 | 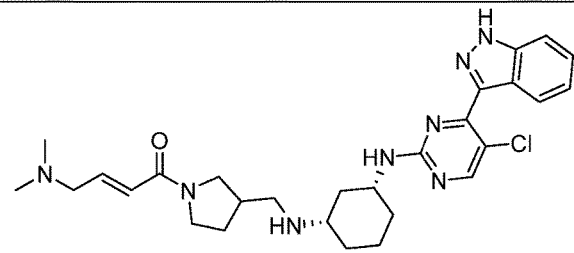 |
| 368 | 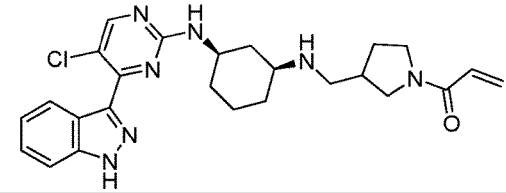 |
| 369† | 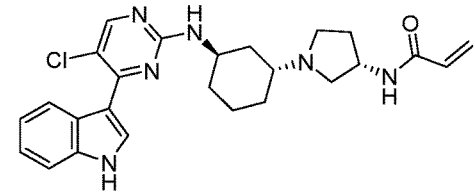 |
| 370 | 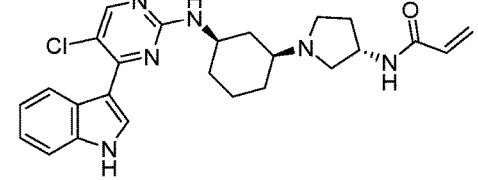 |
| 371 | 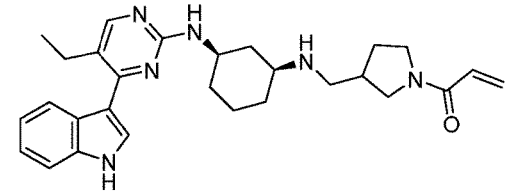 |

FIG. 1LL
| Patent Compound No. | Structure |
|---|---|
| 372 | 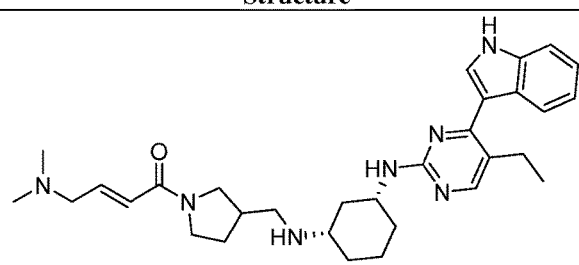 |
| 373 | 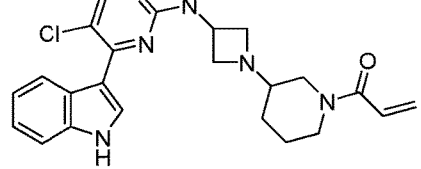 |
| 374 | 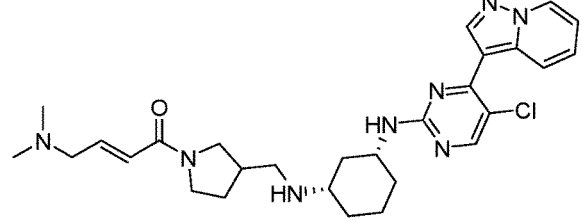 |
| 375 | 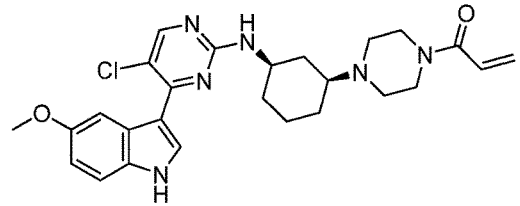 |
| 376 | 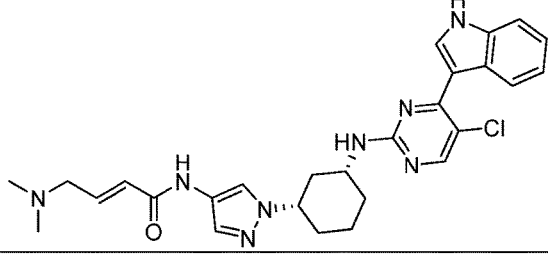 |
| 377 | 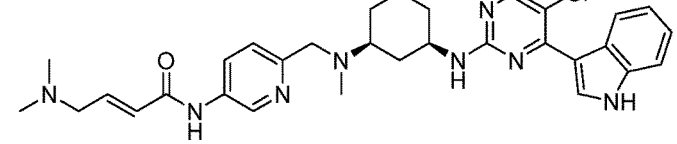 |

FIG. 1MM

| Patent Compound No. | Structure |
|---|---|
| 378 | 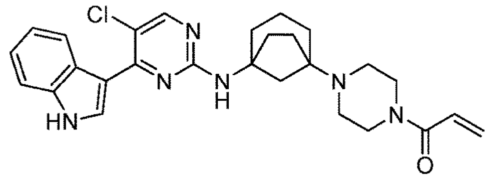 |
| 379† | 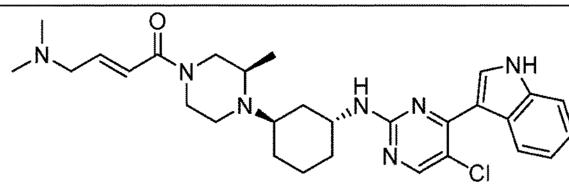 |
| 380† | 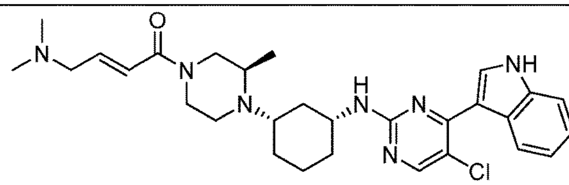 |
| 381 | 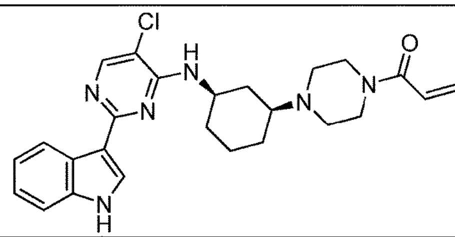 |
| 382 | 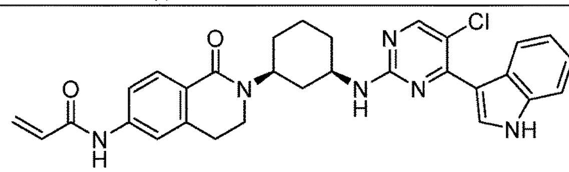 |
| 383 | 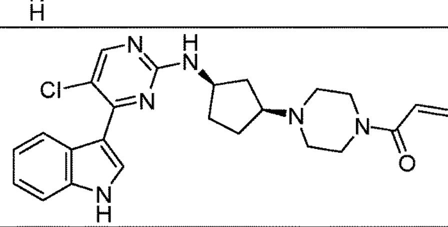 |
| 384 | 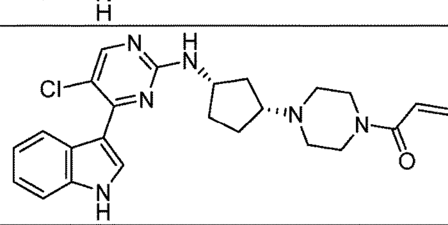 |

FIG. 1NN

| Patent Compound No. | Structure |
|---|---|
| 385 | 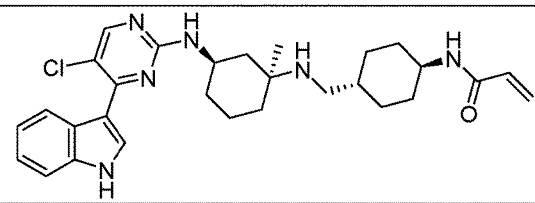 |
| 386 | 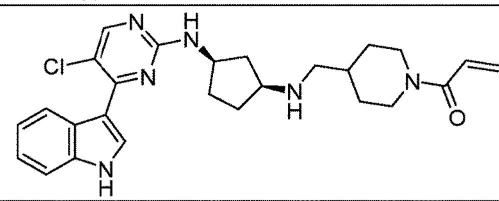 |
| 387 | 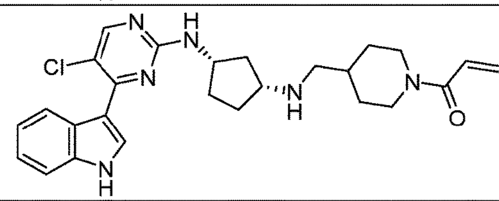 |
| 388 | 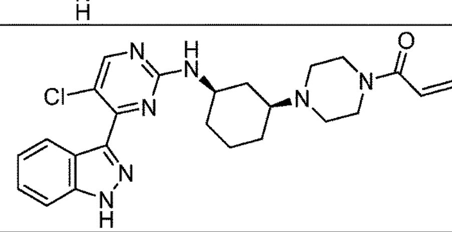 |
| 389 | 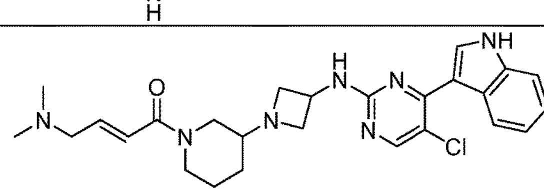 |
| 390 | 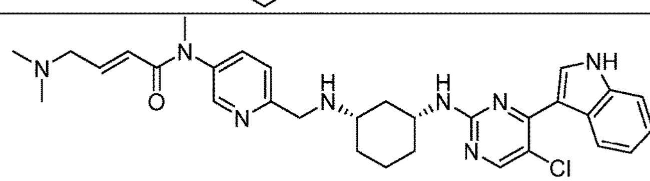 |
| 391 | 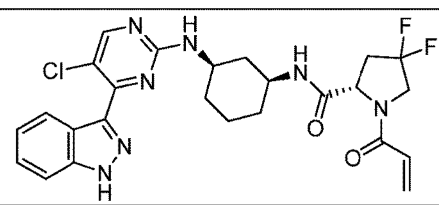 |

FIG. 100
| Patent Compound No. | Structure |
|---|---|
| 392 | 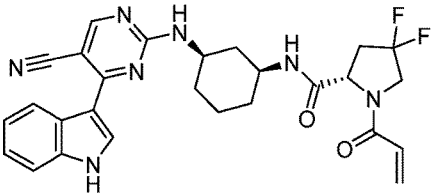 |
| 393 | 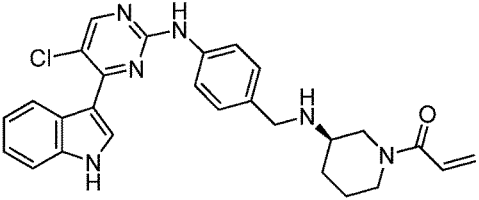 |
| 394 | 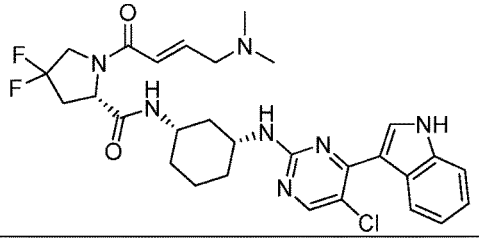 |
| 395 | 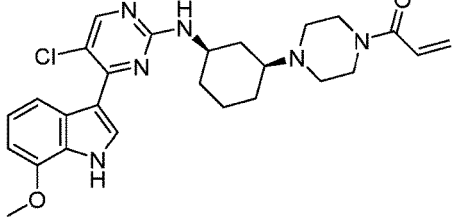 |
| 396 | 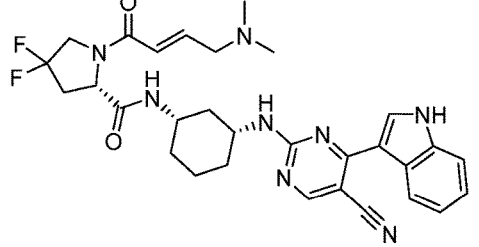 |
| 397 | 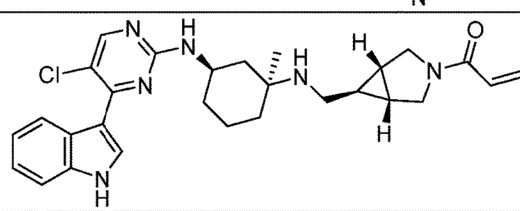 |

FIG. 1PP

| Patent Compound No. | Structure |
|---|---|
| 398 | 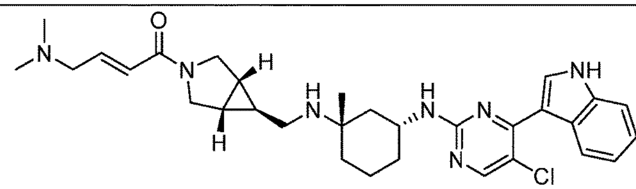 |
| 399 | 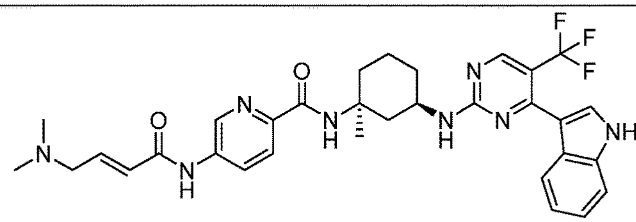 |
| 400 | 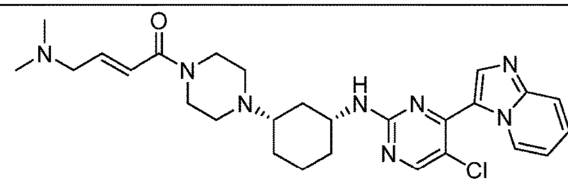 |
| 401 | 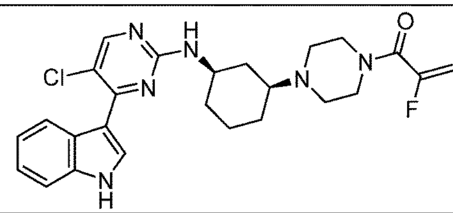 |
| 402 | 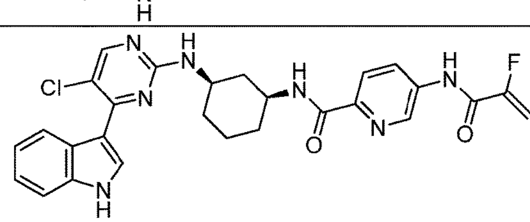 |
| 403 | 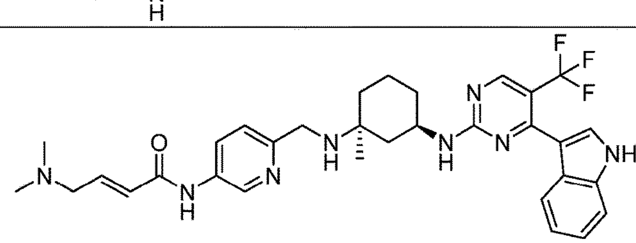 |
| 404 | 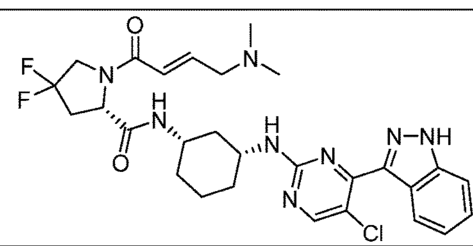 |

FIG. 1QQ
| Patent Compound No. | Structure |
|---|---|
| 405 | 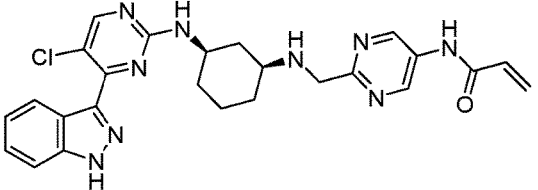 |
| 406 | 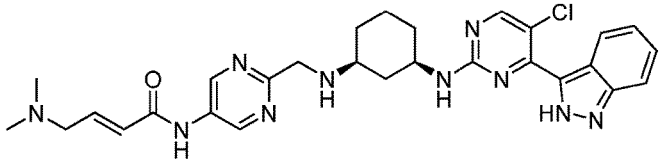 |
| 407 | 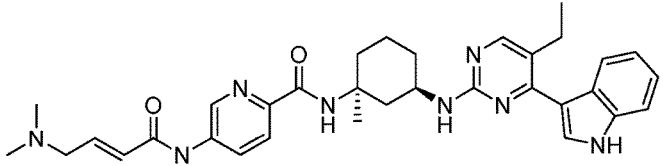 |
| 408 | 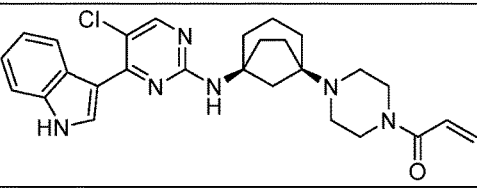 |
| 409 | 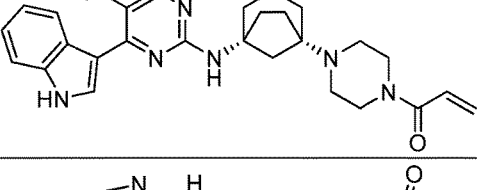 |
| 410 | 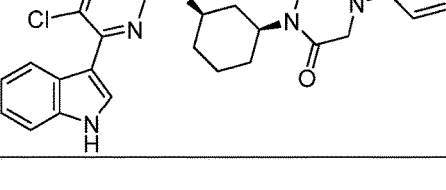 |
| 411 | 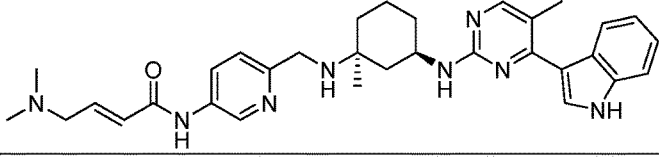 |

FIG. 1RR
| Patent Compound No. | Structure |
|---|---|
| 412 | 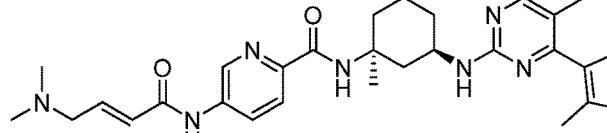 |
| 413 | 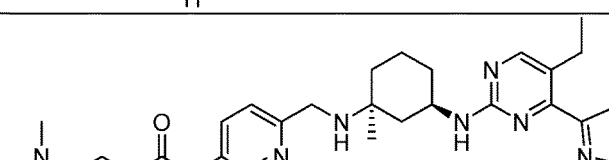 |
| 414 | 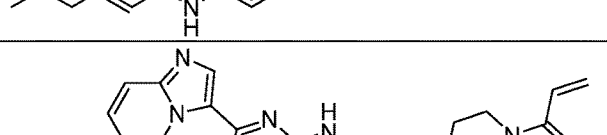 |
| 415 | 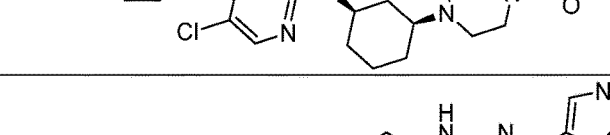 |

FIG 2A

| Patent Compound No. | Structure |
|---|---|
| 1000 | 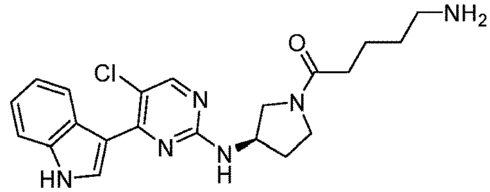 |
| 1001 | 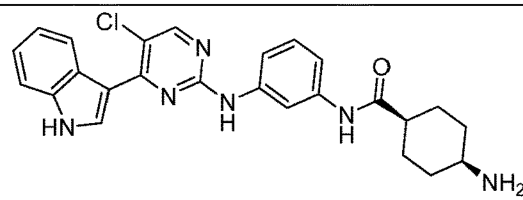 |
| 1002 | 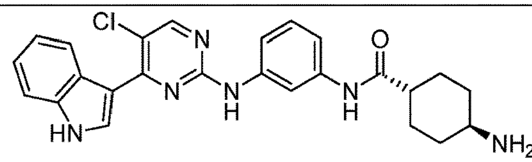 |
| 1003 | 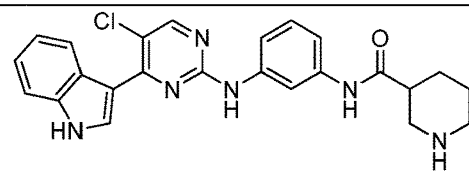 |
| 1004 | 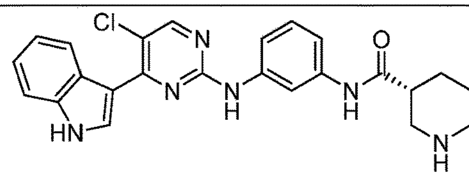 |
| 1005 | 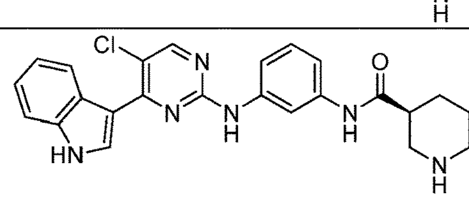 |
| 1006 | 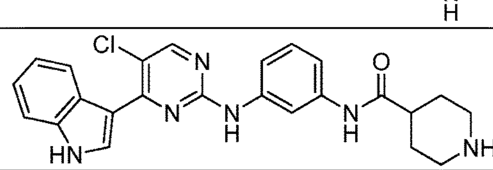 |
| 1007 | 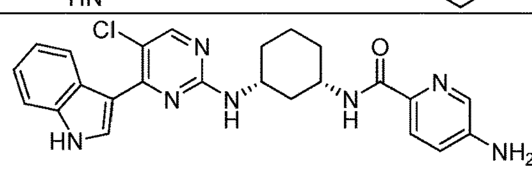 |
| 1008 | 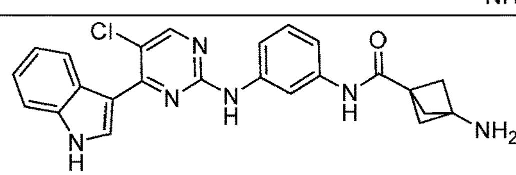 |

*FIG 2B*

| Patent Compound No. | Structure |
|---|---|
| 1009 | 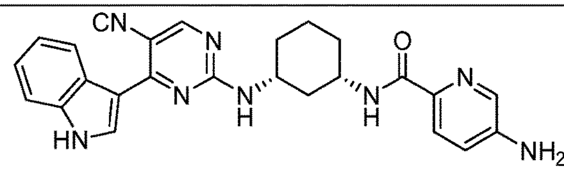 |
| 1010 | 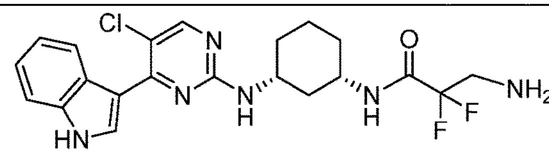 |
| 1011 | 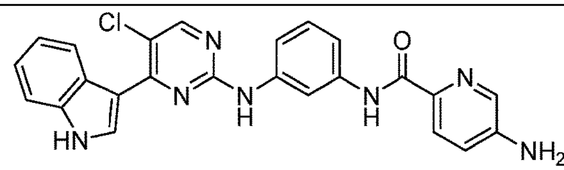 |
| 1023 | 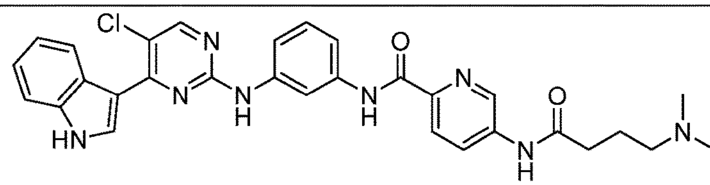 |
| 1024 | 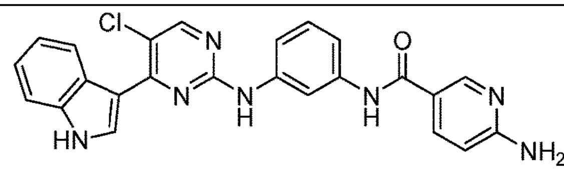 |
| 1025 | 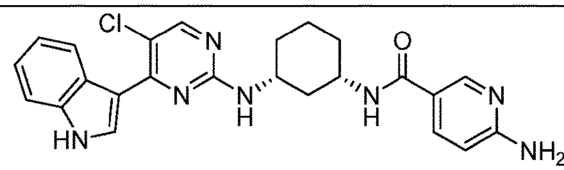 |
| 1026 | 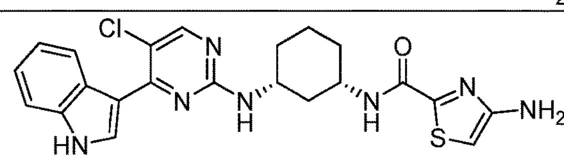 |
| 1027 | 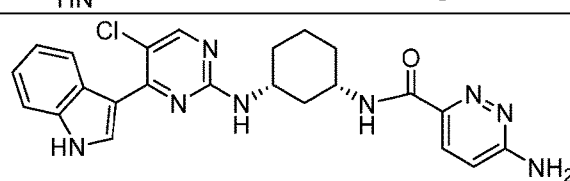 |
| 1028 | 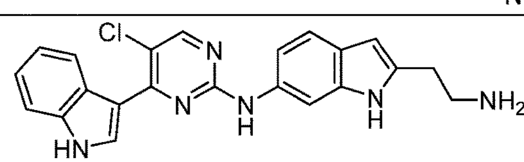 |

FIG 2C
| Patent Compound No. | Structure |
|---|---|
| 1029 | 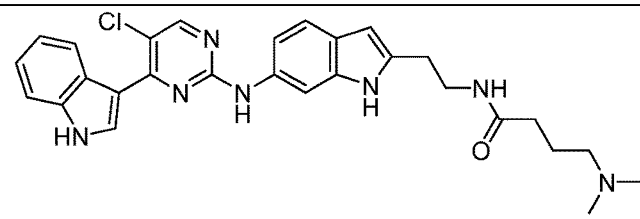 |
| 1030 | 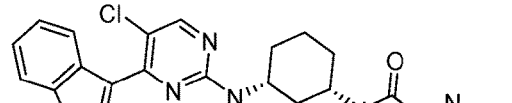 |
| 1031 | 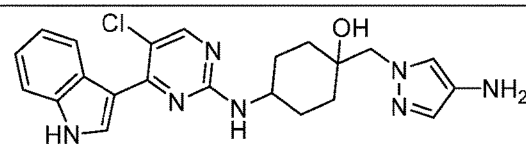 |
| 1032 | 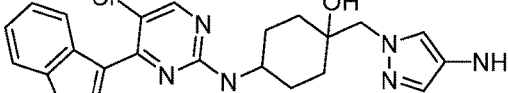 |
| 1033 | 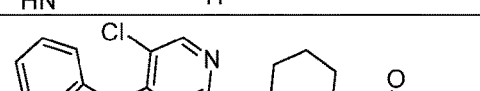 |
| 1034 | 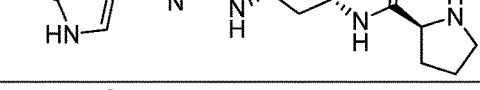 |
| 1035 | 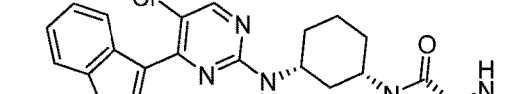 |
| 1036 | 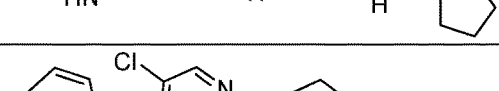 |

FIG 2D

| Patent Compound No. | Structure |
|---|---|
| 1037 | ![structure] |
| 1038 | ![structure] |
| 1039 | ![structure] |
| 1040 | ![structure] |
| 1041 | ![structure] |
| 1042 | ![structure] |
| 1043 | ![structure] |
| 1044 | ![structure] |
| 1045 | ![structure] |
| 1046 | ![structure] |

*FIG 2E*
| Patent Compound No. | Structure |
|---|---|
| 1047 | 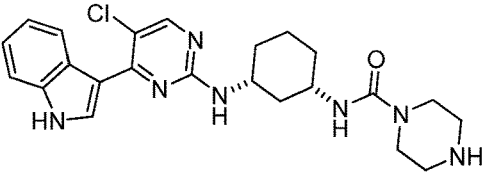 |
| 1048 | 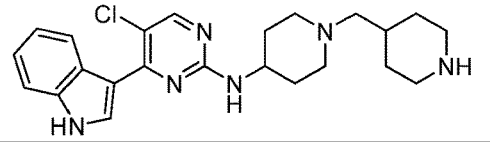 |
| 1049 | 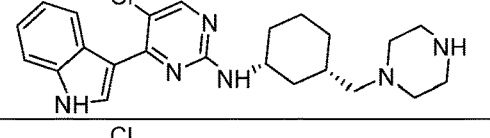 |
| 1050 | 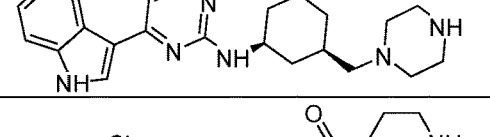 |
| 1051 | 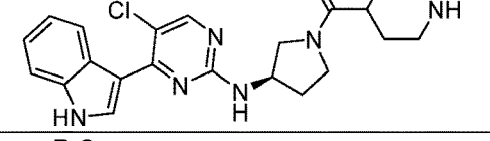 |
| 1052 | 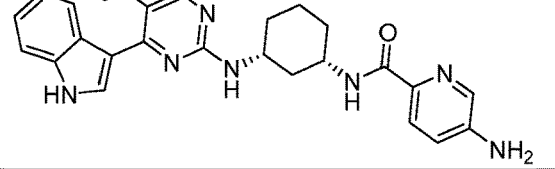 |
| 1053 | 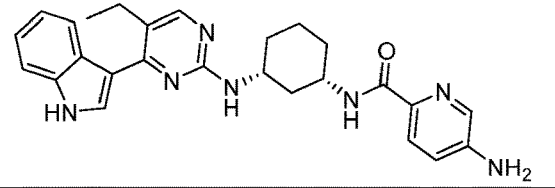 |
| 1054 | 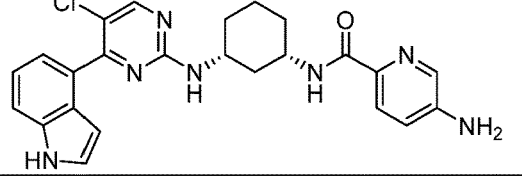 |
| 1055 | 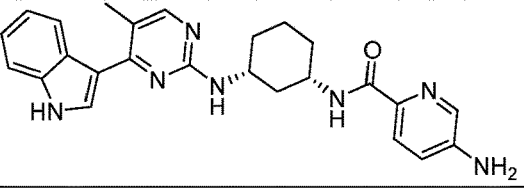 |

FIG 2F
| Patent Compound No. | Structure |
|---|---|
| 1056 | 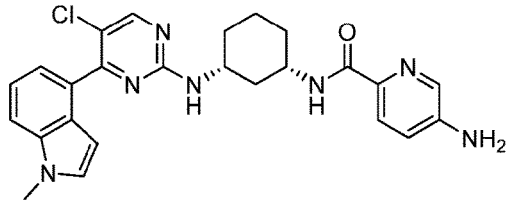 |
| 1057 | 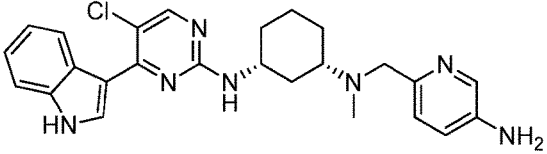 |
| 1058 | 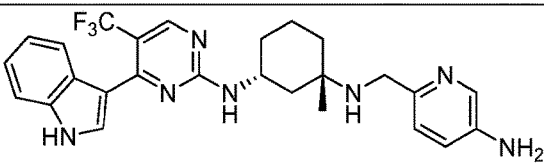 |
| 1059 | 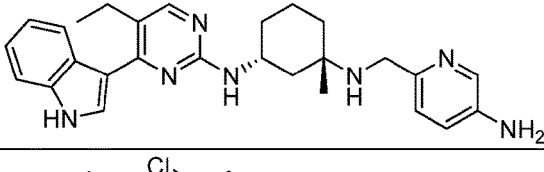 |
| 1060 | 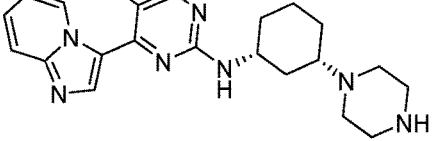 |
| 1061 | 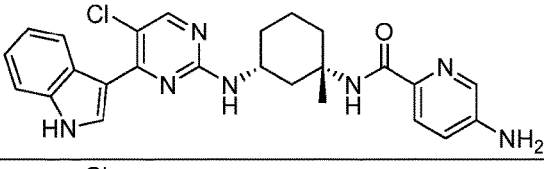 |
| 1062 | 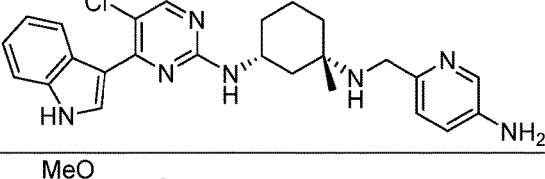 |
| 1063 | 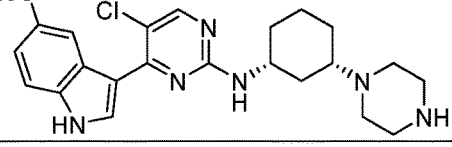 |
| 1064 | 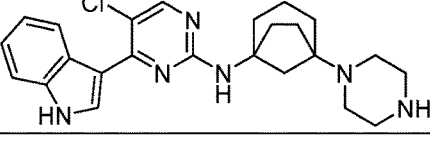 |

| Patent Compound No. | Structure |
|---|---|
| 1065 | 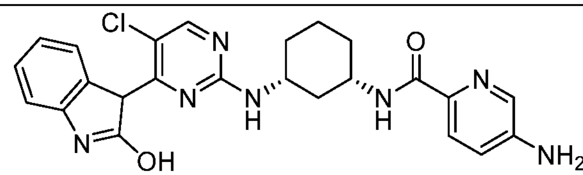 |

INHIBITORS OF CYCLIN-DEPENDENT KINASE 7 (CDK7)

CLAIM OF PRIORITY

The present application is a Continuation of U.S. patent application Ser. No. 15/799,661, filed Oct. 31, 2017, which is a Continuation of U.S. patent application Ser. No. 15/301,815, filed Oct. 4, 2016, which is a U.S. National Stage Application under 35 U.S.C. 371 of International Application No. PCT/US2015/024358, filed Apr. 3, 2015, and published on Oct. 8, 2015 as WO2015/154039, which claims priority under 35 U.S.C. 119(e) to U.S. Provisional Application No. 61/975,457, filed Apr. 4, 2014, and U.S. Provisional Application No. 62/053,741, filed Sep. 22, 2014. The entire contents of each of the foregoing applications are incorporated herein by reference.

BACKGROUND OF THE INVENTION

The members of the cyclin-dependent kinase (CDK) family play critical regulatory roles in proliferation. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression. In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation. Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family. Cancer cells have demonstrated ability to circumvent pro-cell death signaling through upregulation of BCL-2 family members. Therefore, inhibition of human CDK7 kinase activity is likely to result in anti-proliferative activity.

The discovery of selective inhibitors of CDK7 has been hampered by the high sequence and structural similarities of the kinase domain of CDK family members. Therefore, there is a need for the discovery and development of selective CDK7 inhibitors. Such CDK7 inhibitors hold promise as a therapeutic agent therapeutic agents for the treatment of CLL and other cancers.

BRIEF DESCRIPTION OF THE DRAWINGS

FIGS. 1A-1Z and 1AA-1RR are a table of exemplary compounds of Formula I. Compounds annotated with "*" refer to a single enantiomer in which the absolute stereochemistry of the highlighted bonds is undetermined. Compounds annotated with "†" refer to a single enantiomer in which the absolute stereochemistry of the bond between $R^3$ and Z is unknown.

FIGS. 2A-2G are a table of exemplary compounds of Formula II.

SUMMARY OF THE INVENTION

Figure 2G:
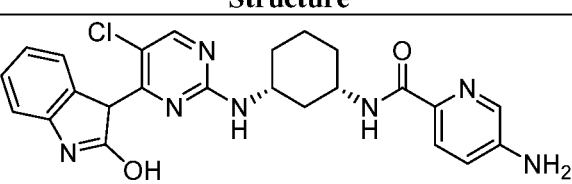

The present invention provides inhibitors of one or more of the family of CDK proteins. The present invention further provides CDK7 inhibitors, in particular selective CDK7 inhibitors of Formula (I) or Formula (II), and pharmaceutically acceptable salts, solvates, hydrates, tautomers, stereoisomers, isotopically labeled derivatives, and compositions thereof. The present invention additionally provides methods of using the compounds of the invention, and pharmaceutically acceptable salts, solvates, hydrates, tautomers, stereoisomers, isotopically labeled derivatives, and compositions thereof, to study the inhibition of CDK7 and CDK12 and/or CDK13 and as therapeutics for the prevention and/or treatment of diseases associated with overexpression and/or aberrant activity of CDK7 and/or CDK12 and/or CDK13. In certain embodiments, the inventive compounds are used for the prevention and/or treatment of proliferative diseases (e.g., cancers (e.g., leukemia, melanoma, multiple myeloma), benign neoplasms, angiogenesis, inflammatory diseases, autoinflammatory diseases, and autoimmune diseases) in a subject.

In one aspect, the present invention provides compounds of Formula (I):

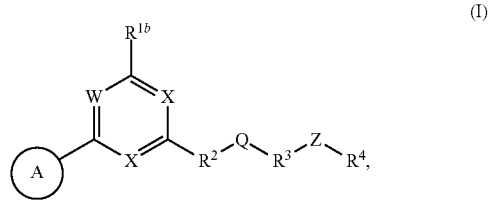

and pharmaceutically acceptable salts, solvates, hydrates, tautomers, stereoisomers, and isotopically labeled derivatives thereof, wherein Ring A, W, X, $R^{1b}$, $R^2$, Q, $R^3$, Z, $R^4$, and subvariables thereof are as defined herein.

In another aspect, the present invention provides compounds of Formula (II):

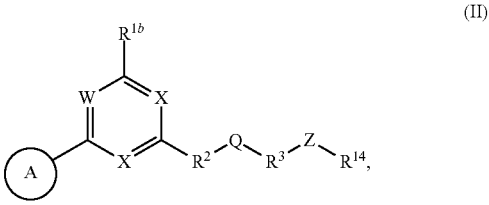

and pharmaceutically acceptable salts, solvates, hydrates, tautomers, stereoisomers, and isotopically labeled derivatives thereof, wherein Ring A, W, X, $R^{1b}$, $R^2$, Q, $R^3$, Z, $R^{14}$, and subvariables thereof are as defined herein.

In another aspect, the present invention provides pharmaceutical compositions comprising a compound of Formula (I) or Formula (II), or a pharmaceutically acceptable salt, solvate, hydrate, tautomer, stereoisomer, or isotopically labeled derivative thereof, and optionally a pharmaceutically acceptable excipient. In certain embodiments, the pharmaceutical compositions described herein include a therapeutically effective amount of a compound of Formula (I) or Formula (II), or a pharmaceutically acceptable salt, solvate, hydrate, tautomer, stereoisomer, or isotopically labeled derivative thereof. The pharmaceutical composition may be useful for treating and/or preventing a proliferative or infectious disease.

In another aspect, the present invention provides methods for treating and/or preventing proliferative diseases. Exemplary proliferative diseases include cancer (e.g., leukemia, melanoma, multiple myeloma), benign neoplasm, angiogenesis, inflammatory diseases, autoinflammatory diseases, and autoimmune diseases. In other embodiments, the present invention provides methods for treating and/or preventing an infectious disease (e.g., a viral infection).

In still another aspect, the present invention provides methods of down-regulating the expression of CDK7 in a biological sample or subject.

Another aspect of the invention relates to methods of inhibiting the activity of CDK7 in a biological sample or subject.

The present invention also provides methods of inhibiting cell growth in a biological sample or subject.

In still another aspect, the present invention provides methods of inducing apoptosis of a cell in a biological sample or a subject.

In yet another aspect, the present invention provides compounds of Formula (I) or Formula (II), and pharmaceutically acceptable salts, solvates, hydrates, tautomers, stereoisomers, isotopically labeled derivatives, and compositions thereof, for use in the treatment of a proliferative disease in a subject.

In yet another aspect, the present invention provides compounds of Formula (I) or Formula (II), and pharmaceutically acceptable salts, solvates, hydrates, tautomers, stereoisomers, isotopically labeled derivatives, and compositions thereof, for use in the treatment or prevention of an infectious disease in a subject. In certain embodiments, the infectious disease is a viral infection.

Another aspect of the present invention relates to kits comprising a container with a compound of Formula (I) or Formula (II), or a pharmaceutically acceptable salt, solvate, hydrate, tautomer, stereoisomer, or isotopically labeled derivative thereof, or a pharmaceutical composition thereof. In certain embodiments, the kits described herein further include instructions for administering the compound of Formula (I) or Formula (II), or the pharmaceutically acceptable salt, solvate, hydrate, tautomer, stereoisomer, or isotopically labeled derivative thereof, or the pharmaceutical composition thereof.

In still another aspect, the present invention provides methods of inhibiting other CDKs, specifically CDK12 and/or CDK13, with a compound of Formula (I) or Formula (II).

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spirofused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c] pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group (such as an alkyl, alkenyl, alkynyl, alkylene, alkenylene, alkynylene or the carbon atom of a carbocyclyl, aryl, heterocyclyl or heteroaryl) are independently deuterium; halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph (where "Ph" is phenyl), which may be substituted with R°; —(CH$_2$)$_{0-4}$O(CH$_2$)$_{0-1}$Ph which may be substituted with R°; —CH=CHPh, which may be substituted with —R°; —NO$_2$; —CN; —N$_3$; —(CH$_2$)$_{0-4}$N(R°)$_2$; —(CH$_2$)$_{0-4}$N(R°)C(O)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O) R°; —N(R°)N(R°)C(O)NR°$_2$; —N(R°)N(R°)C(O)OR°;

—(CH$_2$)$_{0-4}$C(O)R°; —C(S)R°; —(CH$_2$)$_{0-4}$C(O)OR°; —(CH$_2$)$_{0-4}$C(O)S R°; —(CH$_2$)$_{0-4}$C(O)OSiR°$_3$; —(CH$_2$)$_{0-4}$—C(O)—N(R)—S(O)$_2$—R°, —(CH$_2$)$_{0-4}$OC(O)R°; —OC(O)(CH$_2$)$_{0-4}$S R°—, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$ OC(O) NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$ SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched) alkylene)O—N(R°$_2$; or —(C$_{1-4}$ straight or branched) alkylene)C(O)O—N(R°$_2$, wherein each R° may be substituted as defined below and is independently hydrogen, deuterium, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently deuterium, halogen, —(CH$_2$)$_{0-2}$; R˙, -(haloR˙), —(CH$_2$)$_{0-2}$OH, —(CH$_2$)$_{0-2}$OR˙, —(CH$_2$)$_{0-2}$CH(OR˙)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR˙, —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include deuterium, halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently deuterium, halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

"Halo" or "halogen" refers to fluorine (fluoro, —F), chlorine (chloro, —Cl), bromine (bromo, —Br), or iodine (iodo, —I).

The term "one or more methylene units of the alkylene, alkenylene or alkynylene is optionally replaced with —O—, —S—, —S(=O)$_2$, or —NR$^X$—" as used herein means that none, one, more than one, or all of the methylene units present may be so replaced. Thus, for example, the moieties, —O—, —S—, and —NR$^X$— are included in this definition because in each case they represent a C$_1$ alkylene (i.e., methylene) replaced with —O—, —S—, or —NR$^X$—, respectively.

It should also be understood that reference to a variable or subvariable in Formula I or Formula II (e.g., R$^2$, R$^3$ or R$^4$) being "an optionally substituted C$_1$-C$_4$ alkylene, and an optionally substituted C$_2$-C$_4$ alkenylene or alkynylene, wherein one or more methylene units of the alkylene, alkenylene or alkynylene are optionally and independently replaced with —O—, —S—, or —N(R$^6$)—, or —S(O)$_2$—" is only intended to encompass chemically stable combinations of optionally substitutions and replacements.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, OTs), methanesulfonate (mesylate, OMs), p-bromobenzenesulfonyloxy (brosylate, OBs), or trifluoromethanesulfonate (triflate, OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or Formula (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" refer to compounds that are interchangeable forms of a particular compound structure, and that vary in the displacement of hydrogen atoms and electrons. Thus, two structures may be in equilibrium through the movement of $\pi$ electrons and an atom (usually H). For example, enols and ketones are tautomers because they are rapidly interconverted by treatment with either acid or base. Another example of tautomerism is the acid- and nitro-forms of phenylnitromethane that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A nonhuman animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) or Formula (II) refers to an amount sufficient to elicit the desired biological response, i.e., treating the condition. As will be appreciated by those of ordinary skill in this art, the effective amount of a compound of Formula (I) or Formula (II) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) or Formula (II) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) or Formula (II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endothelio sarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barr syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behget's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

DETAILED DESCRIPTION OF CERTAIN EMBODIMENTS OF THE INVENTION

Compounds

In one aspect of the present invention, provided are compounds of Formula (I):

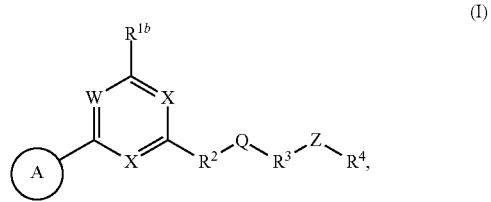

or a pharmaceutically acceptable salt, solvate, hydrate, tautomer, or stereoisomer thereof, wherein:

ring A is an optionally substituted heteroaryl ring of any one of the Formulae (i-1)-(i-6):

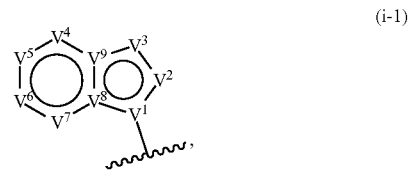

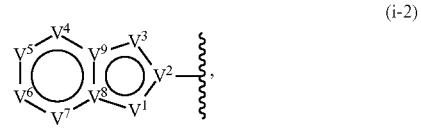

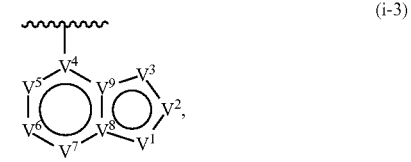

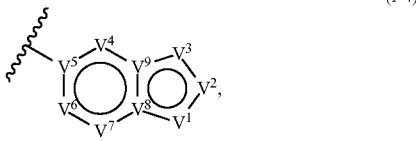

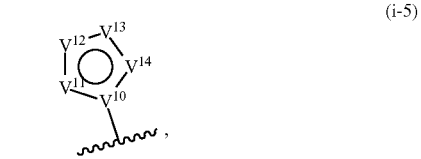

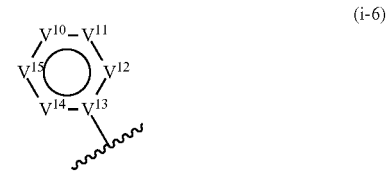

wherein:
each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V_{14}$ and $V^{15}$ is independently O, S, N, N($R^{41}$), C, or C($R^{42}$);

each instance of $R^{41}$ is independently selected from hydrogen, deuterium, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{42}$ is independently selected from hydrogen, deuterium, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A2a}$, —N—(R$^{A2a}$)$_2$, and —SR$^{A2a}$, wherein each occurrence of R$^{A2a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or any two R$^{A1}$, any two R$^{A2}$, or one R$^{A1}$ and one R$^{A2}$ are joined to form an optionally substituted carbocyclic, optionally substituted heterocyclic, optionally substituted aryl, or optionally substituted heteroaryl ring;

each X is independently selected from N and CH, wherein at least one X is N;

W is selected from N and C(R$^{1a}$);

each of R$^{1a}$, if present, and R$^{1b}$ is independently selected from hydrogen, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{B1a}$, —N(R$^{B1a}$)$_2$, and —SR$^{B1a}$, wherein each occurrence of R$^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or R$^{1a}$ and R$^{1b}$ are joined to form an optionally substituted carbocyclic, optionally substituted heterocyclic, optionally substituted aryl, or optionally substituted heteroaryl ring;

R$^2$ is an optionally substituted C$_1$-C$_4$ alkylene or an optionally substituted C$_2$-C$_4$ alkenylene or alkynylene, wherein one or more methylene units of the alkylene, alkenylene or alkynylene are optionally and independently replaced with —O—, —S—, or —N(R$^6$)—;

Q is selected from a bond, an optionally substituted divalent carbocyclyl, an optionally substituted divalent heterocyclyl, an optionally substituted divalent aryl, and an optionally substituted divalent heteroaryl;

R$^3$ is selected from a bond, an optionally substituted C$_1$-C$_4$ alkylene, and an optionally substituted C$_2$-C$_4$ alkenylene or alkynylene, wherein one or more methylene units of the alkylene, alkenylene or alkynylene is optionally and independently replaced with —O—, —S—, —N(R$^6$)—, or —S(O)$_2$—;

each R$^6$ is independently selected from hydrogen, and —C$_1$-C$_6$ alkyl;

Z is selected from a bond; a monocyclic or bicyclic heterocyclyl or heteroaryl comprising at least one ring nitrogen atom; and a cycloalkyl, wherein when Z is other than a bond, Z is optionally substituted;

R$^4$ is any one of the Formulae (ii-1)-(ii-19):

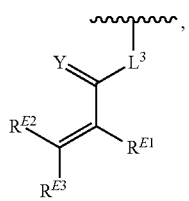

(ii-1)

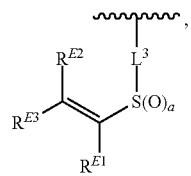

(ii-2)

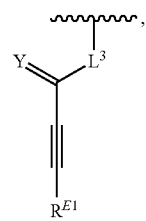

(ii-3)

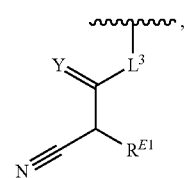

(ii-4)

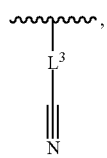

(ii-5)

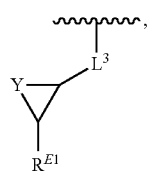

(ii-6)

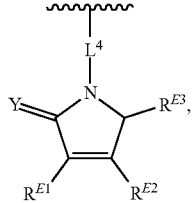

(ii-7)

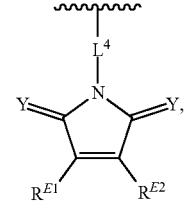

(ii-8)

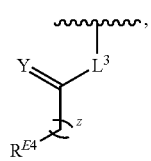

(ii-9)

-continued (ii-10)
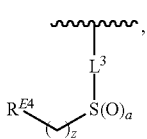

(ii-11)
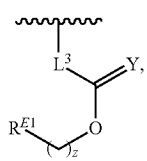

(ii-12)
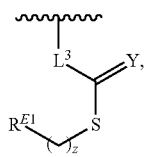

(ii-13)
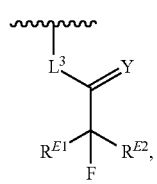

(ii-14)
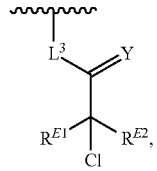

(ii-15)
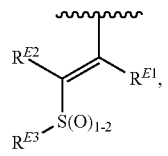

(ii-16)
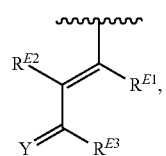

(ii-17)
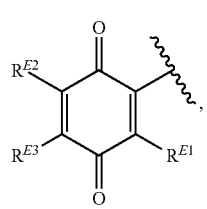

(ii-18)
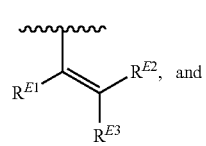

-continued (ii-19)
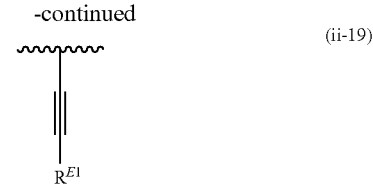

wherein:

$L^3$ is a bond, an optionally substituted $C_1$-$C_7$ alkylene, or an optionally substituted $C_2$-$C_7$ alkenylene or alkynylene, wherein one or more methylene units of the alkylene, alkenylene or alkynylene are optionally and independently replaced with —O—, —S—, —S(O)—, —S(O)$_2$, or —N(R$^6$)—;

$L^4$ is a bond, an optionally substituted $C_1$-$C_4$ alkylene, or an optionally substituted $C_2$-$C_4$ alkenylene or alkynylene;

each of $R^{E1}$, $R^{E2}$ and $R^{E3}$ is independently selected from hydrogen, deuterium, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^9$, —CH$_2$N(R$^9$)$_2$, —CH$_2$SR$^9$, —CN, —OR$^9$, —N(R$^9$)$_2$, and —SR$^9$, wherein each occurrence of R$^9$ is independently selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^9$ are taken together to form an optionally substituted heterocyclyl, or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

Y is O, S, or N(R$^6$); and z is 0, 1, 2, 3, 4, 5, or 6;

when Q is phenyl or a bond, Z is other than a bond; and no more than one of Q, R$^3$ and Z is a bond.

In certain embodiments, provided in the present invention are compounds of Formula (I), and pharmaceutically acceptable salts thereof.

In certain embodiments, no more than three of $V^1$, $V^2$, $V^3$, $V^4$, $V^5$, $V^6$, $V^7$, $V^8$, and $V^9$ are each independently selected from the group consisting of O, S, N, and N(R$^{41}$).

In certain embodiments, one of $V^{10}$, $V^{11}$, $V^{12}$, $V^{13}$, $V^{14}$, and $V^{15}$ is N and the others of $V^{10}$, $V^{11}$, $V^{12}$, $V^{13}$, $V^{14}$ and $V^{15}$ are independently C(R$^{42}$).

In certain embodiments, one or two of $V^1$, $V^2$, $V^3$, $V^4$, $V^5$, $V^6$, $V^7$, $V^8$, and $V^9$ are each independently selected from the group consisting of N and N(R$^{41}$); $V^1$, $V^2$, $V^3$, $V^4$, $V^5$, $V^6$, and $V^7$ are each independently C(R$^{42}$); and $V^8$ and $V^9$ are each independently C. In one aspect of these embodiments, ring A is

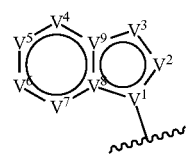

and $V^3$ is N(R$^{41}$). In a more specific aspect of these embodiments, $V^3$ is N(H), $V^4$ is selected from N and C(R$^{42}$); $V^1$, $V^2$, $V^5$, $V^6$, and $V^7$ are each independently C(R$^{42}$), and $V^8$ and $V^9$ are C. In another more specific aspect of these embodiments, $V^3$ is N(H), $V^4$ is selected from N and C(H); $V^1$, $V^2$, $V^5$, $V^6$, and $V^7$ are each independently C(H), and $V^8$ and $V^9$ are C.

In certain embodiments ring A is

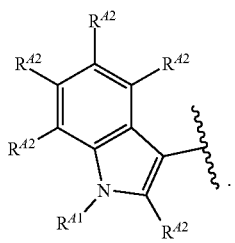

In one aspect of these embodiments, ring A is

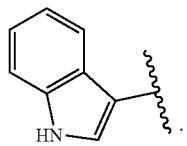 [SMILES: *c1c[nH]c2ccccc12]

In another aspect of these embodiments, ring A is

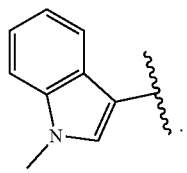 [SMILES: *c1cn(C)c2ccccc12]

In another aspect of these embodiments, ring A is additionally selected from:

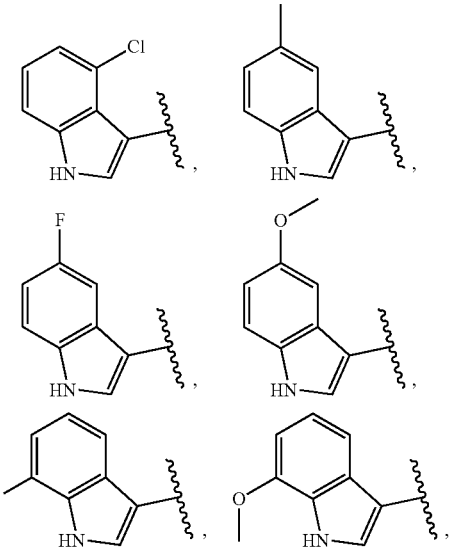

-continued

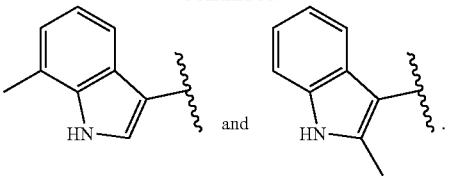

In certain embodiments ring A is

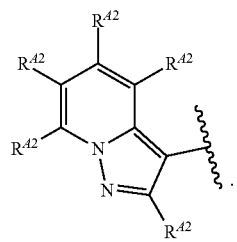

In one aspect of these embodiments, ring A is

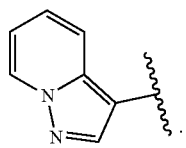 [SMILES: *c1cnn2ccccc12]

In certain embodiments ring A is

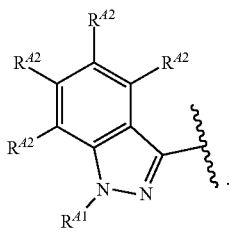

In one aspect of these embodiments, ring A is

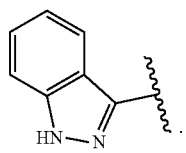 [SMILES: *c1n[nH]c2ccccc12]

In another aspect of these embodiments, ring A is

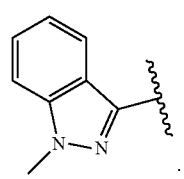 [SMILES: *c1nn(C)c2ccccc12]

In certain embodiments, ring A is additionally selected from:

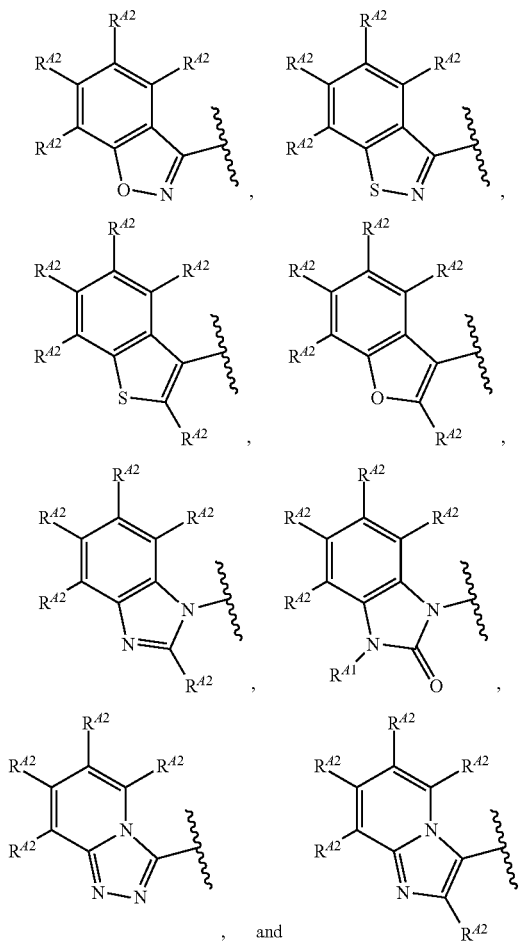

In some aspects of these embodiments, ring A is additionally selected from

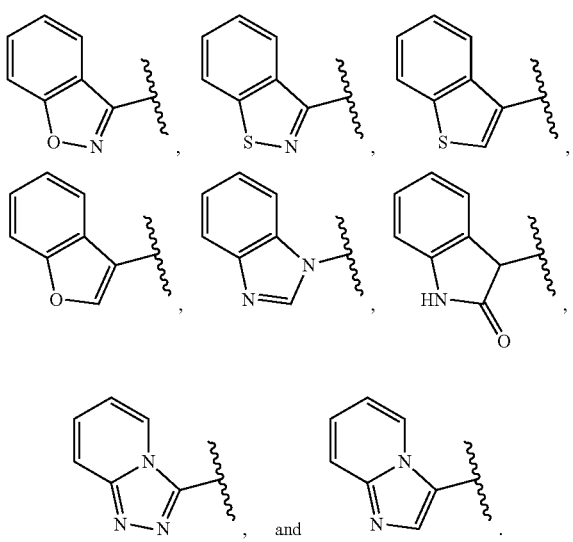

In certain embodiments, ring A is selected from:

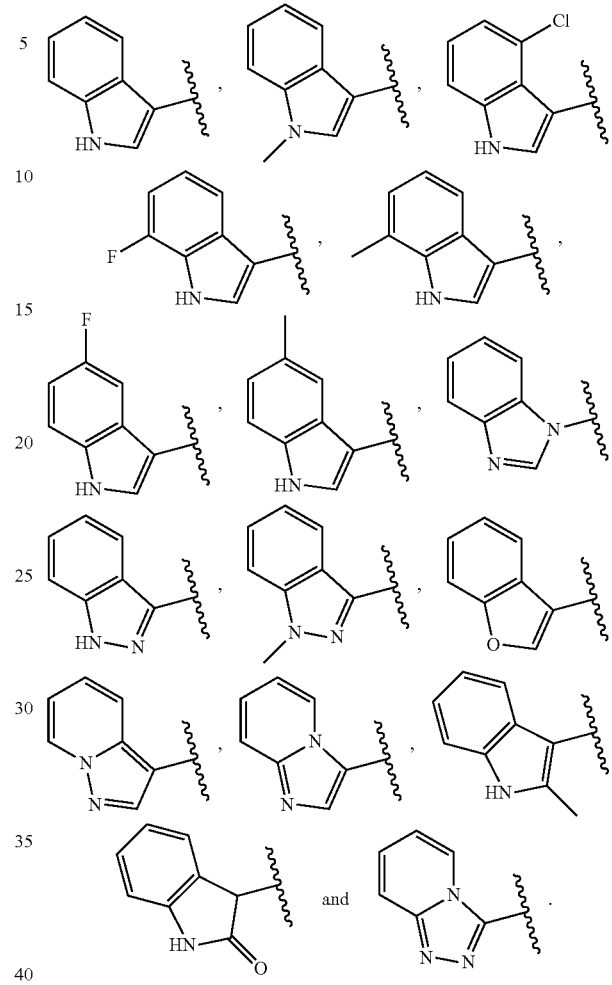

In certain embodiments, each $R^{A1}$ is independently selected from hydrogen or $C_{1-6}$ alkyl. In certain embodiments, all instances of $R^{A1}$ are hydrogen. In certain embodiments, one instance of $R^{A1}$ is methyl.

In certain embodiments, each $R^{A2}$ is independently selected from hydrogen, halogen, and optionally substituted $C_1$-$C_6$ alkyl. In certain embodiments, each $R^{A2}$ is additionally selected from hydroxy (or oxo as a tautomer), and —O—($C_{1-6}$ alkyl). In one aspect of these embodiments, all instances of $R^{A2}$ are hydrogen. In certain embodiments, one instance of $R^{A2}$ is additionally selected from fluoro, chloro, and —OCH$_3$.

In certain embodiments, each X is N.
In certain embodiments, W is N.
In certain embodiments, W is $C(R^{1a})$.
In certain embodiments, $R^{1a}$ is selected from selected from hydrogen, halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —NH$_2$, —NH($C_1$-$C_3$ alkyl), and —N($C_1$-$C_3$ alkyl)$_2$. In certain embodiments, $R^{1a}$ is additionally selected from $C_3$-$C_6$ cycloalkyl. In one aspect of these embodiments, $R^{1a}$ is other than hydrogen. In a specific aspect of these embodiments $R^{1a}$ is selected from halo, —CN, $C_1$-$C_3$ alkyl. In a more specific aspect of these embodiments, $R^{1a}$ is selected from chloro, methyl, ethyl, and —CN. In another more specific aspect of these embodiments, $R^{1a}$ is selected from halo, and —CN. In an even more specific aspect of these embodiments, $R^{1a}$ is selected from chloro, and —CN. In another more specific aspect of these embodiments, $R^{1a}$ is selected from chloro, —CN, —$CF_3$, methyl and ethyl.

In certain embodiments, $R^{1b}$ is selected from selected from hydrogen, halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —$NH_2$, —NH($C_1$-$C_3$ alkyl), and —N($C_1$-$C_3$ alkyl)$_2$. In one aspect of these embodiments, $R^{1b}$ is hydrogen.

In certain embodiments, $R^2$ is selected from —NH—; —N($C_1$-$C_3$ alkyl)-; —NH—$CH_2$—*; and $C_1$-$C_2$ alkylene optionally substituted with 1 to 4 substituents independently selected from halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —$NH_2$, —NH($C_1$-$C_3$ alkyl), —N($C_1$-$C_3$ alkyl)$_2$, wherein "*" represents a portion of $R^2$ bound to Q. In a more specific aspect of these embodiments, $R^2$ is selected from —NH— and —NH—$CH_2$—*. In an even more specific aspect of these embodiments, $R^2$ is —NH—.

In certain embodiments, Q is selected from divalent 1,3,4-oxadiazole, divalent 1-oxa-3-azaspiro[4.5]dec-2-ene, divalent cyclohexane, divalent 4-thia-1,2-diazaspiro[4.5]dec-2-ene, divalent oxazole, divalent benzene, divalent piperidine, and divalent pyrrolidine, wherein Q is optionally substituted with up to three independently selected substituents. In some embodiments, Q is additionally selected from divalent 1H-indole. In some embodiments, Q is additionally selected from divalent azetidine, divalent bicyclo[3.2.1]octane, divalent cyclopentane, and divalent benzene.

In some embodiments, Q is unsubstituted.

In alternate embodiments, Q is substituted by up to four substituents independently selected from deuterium, halo, hydroxyl, and $C_1$-$C_4$ alkyl. In one aspect of these embodiments, Q is substituted by one or two substituents independently selected from fluoro, hydroxyl and methyl.

In certain embodiments, Q is selected from 1,3,4-oxadiazol-2,5-diyl, 1-oxa-3-azaspiro[4.5]dec-2-en-7,2-diyl, 4-fluorocyclohex-1,4-diyl, 4-hydroxycyclohex-1,4-diyl, 4-thia-1,2-diazaspiro[4.5]dec-2-en-7,3-diyl, cyclohex-1,3-diyl, 3-methylcyclohex-1,3-diyl, cyclohex-1,4-diyl, oxazol-2,5-diyl, benzene-1,3-diyl, piperidin-1,3-diyl, piperidin-4,1-diyl and pyrrolidin-3,1-diyl. In some embodiments, Q is additionally selected from 1H-indol-6,2-diyl, 3-hydroxycyclohex-1,3-diyl, and piperidin-3,1-diyl. In some embodiments, Q is additionally selected from azetidin-3,1-diyl, bicyclo[3.2.1]octan-1,3-diyl, cyclopent-1,3-diyl, and benzene-1,4-diyl.

In a more specific aspect of these embodiments, Q is selected from 4-hydroxycyclohex-1,4-diyl, 4-fluorocyclohex-1,4-diyl, 3-hydroxycyclohex-1,3-diyl, cyclohex-1,4-diyl, cyclohex-1,3-diyl, benzene-1,3-diyl, pyrrolidin-3,1-diyl, piperidin-4,1-diyl and indol-6,2-diyl. In another more specific aspect of these embodiments, Q is additionally selected from 3-methylcyclohex-1,3-diyl, bicyclo[3.2.1]octan-1,5-diyl

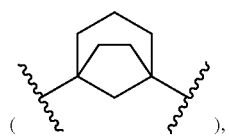 [SMILES: *C12CCCC(*)(CC1)C2]

benzene-1,4-diyl, piperidin-3,1-diyl, and cyclopent-1,3-diyl. In a further more specific aspect of these embodiments, Q is selected from cyclohex-1,3-diyl, and 3-methylcyclohex-1,3-diyl.

In the chemical names set forth above, the recitation ("—X,Y-diyl") is intended to indicate the orientation of Q, wherein "X" represents the ring atom of Q that is bound to $R^2$ and "Y" represents the ring atom of Q that is bound to $R^3$. For example, when Q is 1-oxa-3-azaspiro[4.5]dec-2-en-7,2-diyl, the structure of the $R^3$-Q-$R^4$ portion of the compound is:

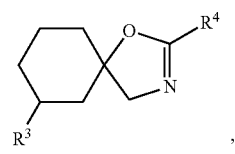

e.g., the 7-position carbon is bound to $R^2$ and the 2-position carbon is bound to $R^3$.

In certain embodiments, one or more methylene units in $R^3$ are optionally replaced with a moiety additionally selected from —N(C(O)—$C_2$-$C_4$ alkenyl)- and N(S($O_2$)—$C_1$-$C_4$ alkyl)-.

In certain embodiments, $R^3$ is selected from a bond, †-C(O)—($CH_2$)$_3$—, †-NH—C(O)—, †-NH—C(O)—$CF_2$—$CH_2$—, †-$CH_2$—, †-NH—, †-NH—$CH_2$—, †-$CH_2$—NH—, †-NH—C(O)—CH($CF_3$)—, †-N($CH_3$)—$CH_2$—, †-NH—C(O)—$CH_2$—$CH_2$—, †-N($CH_3$)— and †-NH—$CH_2$—CH($CF_3$)—, wherein "†" represents a portion of $R^3$ bound to Q. In certain embodiments, $R^3$ is additionally selected from †-$CH_2$—$CH_2$—, †-C(O)—NH, †-N(C(O)CH=$CH_2$)$CH_2$, †-N(C(O)$CH_3$)$CH_2$, †-N(C(O)O$CH_3$)$CH_2$, †-N(S($O_2$)$CH_3$)$CH_2$, †-N($CH_2CH_3$)$CH_2$—, and †-C(O)—. In certain embodiments, $R^3$ is additionally selected from †-$CH_2$N($CH_2CH_3$)—, †-$CH_2$N($CH_3$)—, †-$CH_2$—O—, and †-N($CH_3$)C(O)—. In a more specific aspect of these embodiments, $R^3$ is selected from a bond, †-$CH_2$—, †-$CH_2CH_2$—, †-$CH_2$NH—, †-C(O)—, †-C(O)—($CH_2$)$_3$—, †-N($CH_3$)—, †-N($CH_3$)$CH_2$—, †-N($CH_2CH_3$)$CH_2$—, †-N(C(O)$CH_3$)$CH_2$—, †-NH—, †-NH$CH_2$—, †-NHC(O)—, †-NHC(O)$CF_2CH_2$—, and †-NHC(O)$CH_2CH_2$—. In an even more specific aspect of these embodiments, $R^3$ is selected from †-NHC(O)— and †-N($CH_3$)C(O)—.

In certain embodiments, Z is selected from a bond,

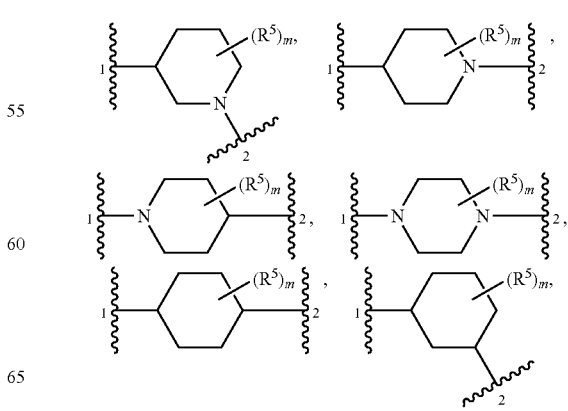

-continued

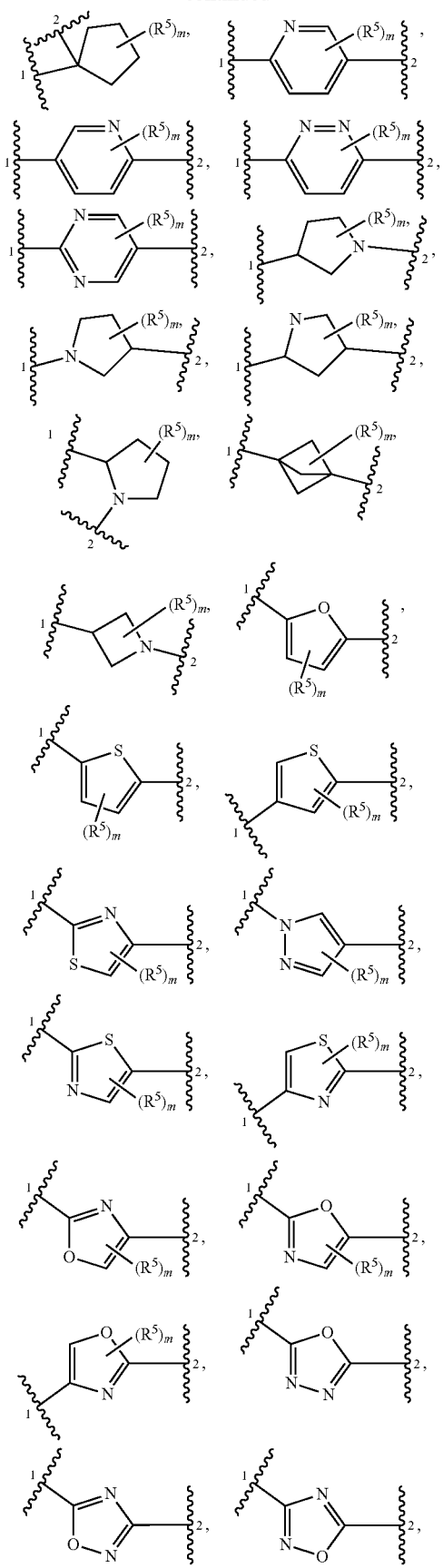

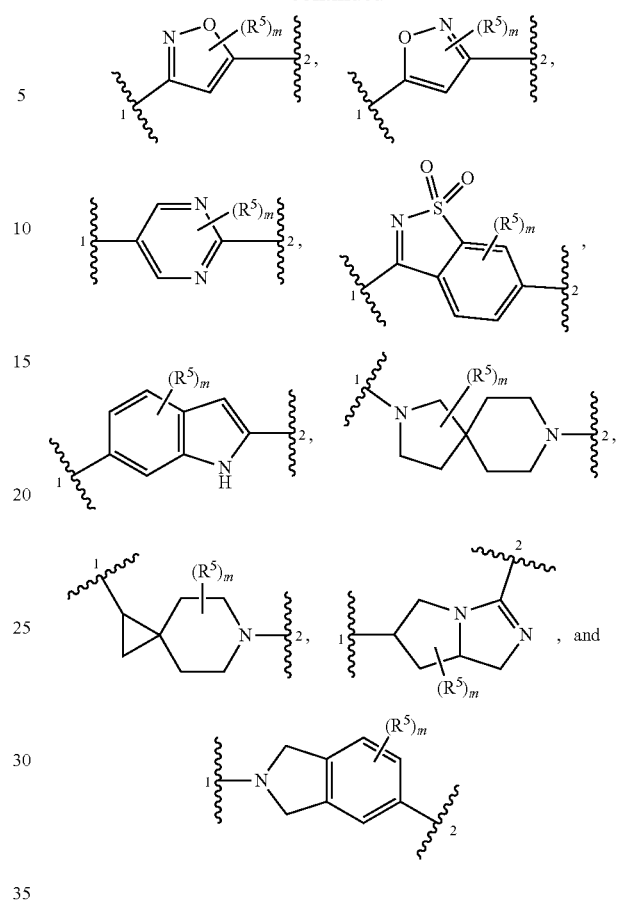

wherein:

"1" represents a portion of Z bound to R³;

"2" represents a portion of Z bound to R⁴;

each instance of R⁵, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)², and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, and optionally substituted aryl, optionally substituted heteroaryl; and m is 0, 1, 2, 3 or 4.

In one aspect of these embodiments, Z is additionally selected from

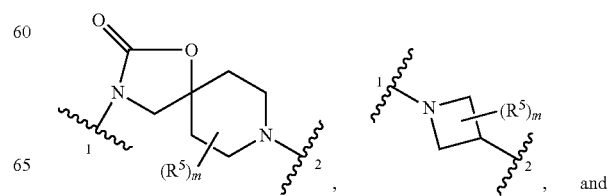

-continued
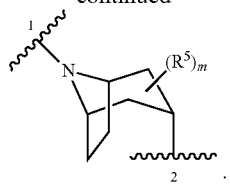
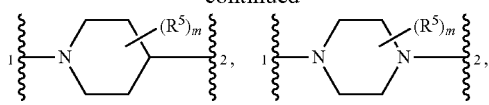
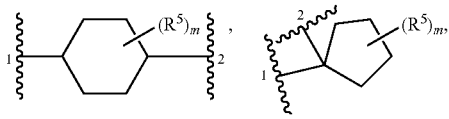
In another aspect of these embodiments, Z is additionally selected from:
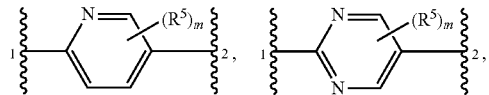
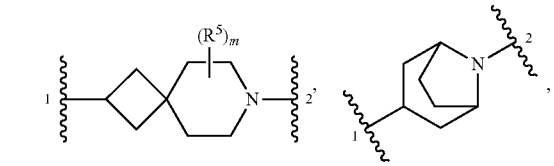
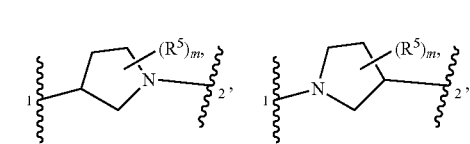
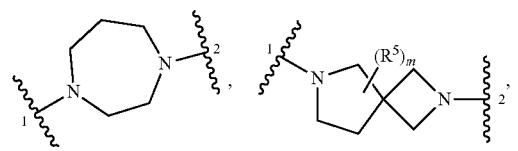
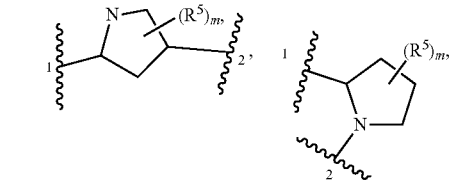
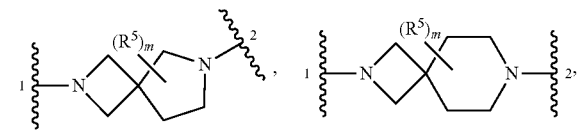
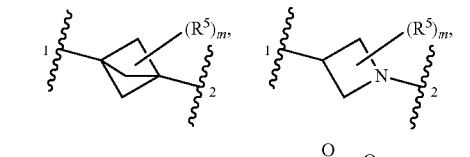
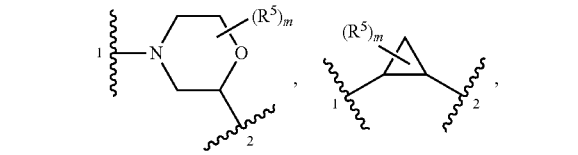
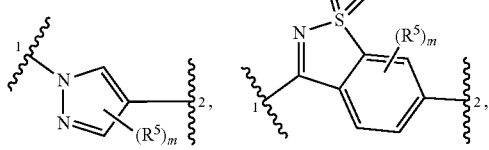
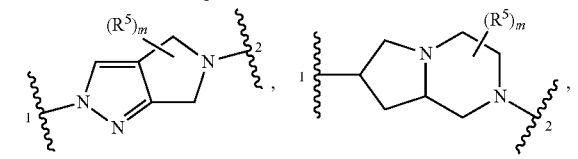
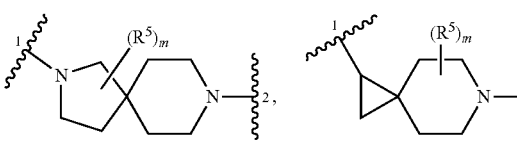
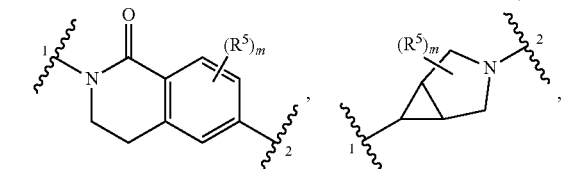
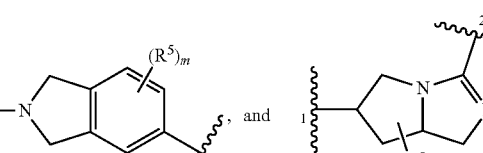
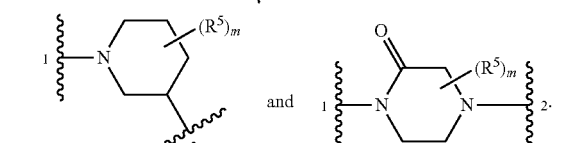
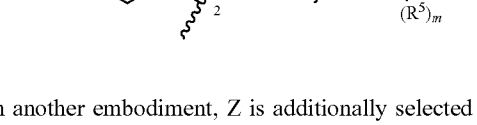, and
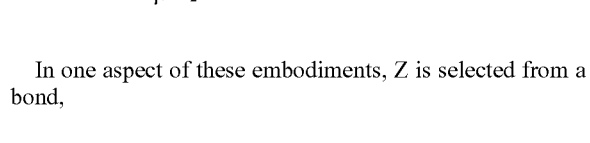
In one aspect of these embodiments, Z is selected from a bond,
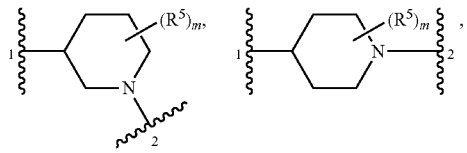
In another embodiment, Z is additionally selected from
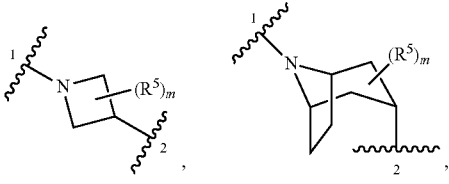

-continued

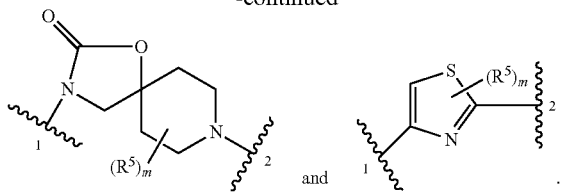
and

In a more specific aspect of these embodiments, Z is selected from a bond, cyclohex-1,4-diyl, piperidin-3,1-diyl, piperidin-4,1-diyl, pyridin-2,5-diyl, bicyclo[1.1.1]pent-1,3-diyl, pyrimidin-2,5-diyl, pyrazol-1,4-diyl, pyrrolidin-2,1-diyl, 4,4-difluoropyrrolidin-2,1-diyl, isoindolin-2,5-diyl, 6-azaspiro[2.5]octan-6,1-diyl, 2,8-diazaspiro[4.5]decan-2,8-diyl, pyrrolidin-3,1-diyl, 5,6,7,7a-tetrahydro-1H-pyrrolo[1,2-c]imidazol-3,6-diyl, 1,1-dioxobenzo[d]isothiazol-3,6-diyl, piperazin-1,4-diyl, pyrrolidin-1,3-diyl, piperidin-1,4-diyl, pyrrolidin-2,4-diyl, 2,2-difluorocyclopent-1,1-diyl, 3-fluoroazetidin-3,1-diyl, 3,3-difluoropiperidin-4,1-diyl, and 4-hydroxypyrrolidin-3,1-diyl.

In another more specific aspect of these embodiments, Z is additionally selected from 1-oxa-3,8-diazaspiro[4.5]decan-2-one-8,3-diyl, 3-methylazetidin-3,1-diyl, 3-methylpiperazin-1,4-diyl, 2-methylpiperazin-1,4-diyl, azetidin-3,1-diyl, azetidin-1,3-diyl, 8-azabicyclo[3.2.1]octan-8,3-diyl, 4-fluoropiperidin-4,1-diyl, 4-hydroxpiperidin-4,1-diyl and thiazol-4,2-diyl.

In another more specific aspect of these embodiments, Z is additionally selected from 1-oxo-3,4-dihydroisoquinolin-2,6-diyl, 2,4,5,6-tetrahydropyrrolo[3,4-c]pyrazol-2,5-diyl, 2,6-diazaspiro[3.4]octan-2,6-diyl, 2,6-diazaspiro[3.4]octan-6,2-diyl, 2,7-diazaspiro[3.5]nonan-2,7-diyl, 2-oxopiperazin-1,4-diyl, 3-azabicyclo[3.1.0]hexan-6,3-diyl, 3-trifluoromethylpiperazin-1,4-diyl, 4-methylpiperidin-4,1-diyl, 5-chloropyrimidin-2,6-diyl, 8-azabicyclo[3.2.1]octan-3,8-diyl, 7-azaspiro[3.5]nonan-2,7-diyl, cycloprop-1,2-diyl, diazepin-1,4-diyl, morpholin-4,2-diyl, octahydropyrrolo[1,2-a]pyrazin-7,2-diyl, and piperidin-1,3-diyl.

In an even more specific aspect of these embodiments, Z is selected from a bond, 1-oxa-3,8-diazaspiro[4.5]decan-2-one-8,3-diyl, 6-azaspiro[2.5]octan-6,1-diyl, cyclohex-1,4-diyl, isoindolin-2,5-diyl, piperazin-1,4-diyl, piperidin-3,1-diyl, piperidin-4,1-diyl, piperidin-1,4-diyl, pyrazol-1,4-diyl, pyridin-2,5-diyl, pyrimidin-2,5-diyl, pyrrolidin-2,1-diyl, 4,4-difluoropyrrolidin-2,1-diyl, thiazol-4,2-diyl, 3-methylazetidin-3,1-diyl, azetidin-3,1-diyl, 3-methylpiperazin-1,4-diyl, 4-hydroxpiperidin-4,1-diyl, 2-methylpiperazin-1,4-diyl, azetidin-1,3-diyl, 8-azabicyclo[3.2.1]octan-8,3-diyl, and pyrrolidin-2,4-diyl.

In an even more specific aspect of these embodiments, Z is additionally selected from 2,6-diazaspiro[3.4]octan-2,6-diyl, 2,6-diazaspiro[3.4]octan-6,2-diyl, 2,7-diazaspiro[3.5]nonan-2,7-diyl, 2-oxopiperazin-1,4-diyl, 3-azabicyclo[3.1.0]hexan-6,3-diyl, 3-trifluoromethylpiperazin-1,4-diyl, 4-methylpiperidin-4,1-diyl, 5-chloropyrimidin-2,6-diyl, 8-azabicyclo[3.2.1]octan-3,8-diyl, 7-azaspiro[3.5]nonan-2,7-diyl, cycloprop-1,2-diyl, diazepin-1,4-diyl, morpholin-4,2-diyl, piperidin-1,3-diyl, pyrrolidin-1,3-diyl, and pyrrolidin-3,1-diyl.

In the chemical names set forth above for Z, the recitation ("-A,B-diyl") is intended to indicate the orientation of Q, wherein "A" represents the ring atom of Z that is bound to $R^3$ and "B" represents the ring atom of Z that is bound to $R^4$. By way of example, the structure of $R^3$—Z—$R^4$, when Z is pyrrolidin-3,1-diyl is

whereas the structure of $R^3$—Z—$R^4$, when Z is pyrrolidin-1,3-diyl is

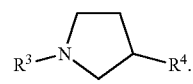

In certain embodiments, $R^4$ is

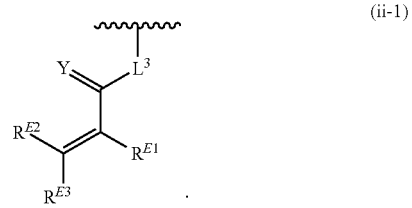

(ii-1)

In a more specific aspect of these embodiments, $L^3$ is selected from a bond, —NH—, —$CH_2$—NH—, —$S(O)_2$—NH—, and —NH—$S(O)_2$—NH—, wherein "" represents a portion of $L^3$ bound to —C(=Y)—. In an even more specific aspect of these embodiments, $R^4$ is selected from:
—$CH_2$—NH—C(O)—CH=CH—$CH_2$—$N(CH_3)_2$, —NH—C(O)—CH=CH—$CH_2$—$N(CH_3)_2$, —C(O)—CH=CH—$CH_2$—$N(CH_3)_2$, —NH—C(O)—CH=$CH_2$, —C(O)—CH=$CH_2$, —$S(O)_2$—NH—C(O)—CH=$CH_2$, and —NH—$S(O)_2$—NH—C(O)—CH=$CH_2$. In other embodiments, $R^4$ is additionally selected from —C(O)—$CH_2$—CH=$CH_2$, —$CH_2$—NH—C(O)—CH=$CH_2$,

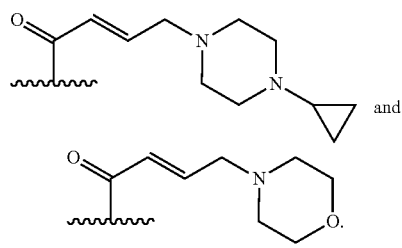

and

In still other embodiments, $R^4$ is additionally selected from —C(O)—CF=$CH_2$, —C(O)—CH=CH—$CH_2$—$N(CH_3)$—$OCH_3$, —C(O)—CH=CH—$CH_2$—O—$CH_3$, —C(O)—CH=CH—$CH_3$, —C(O)—NH=$CH_2$, —NH—C(O)—CF=$CH_2$, and —$N(CH_3)$—C(O)—CH=$CHCH_2$—$N(CH_3)_2$. In certain embodiments, $R^4$ is

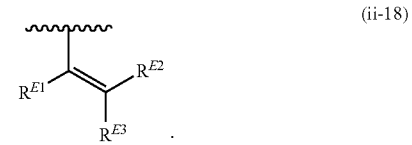

(ii-18)

In a more specific aspect of these embodiments $R^{E1}$ and $R^{E2}$ are hydrogen and $R^{E3}$ is an optionally substituted $C_1$-$C_4$ alkyl. In an even more specific aspect of these embodiments $R^{E3}$ is selected from —CH=CH—CH$_2$—N(CH$_3$)$_2$.

In another specific embodiment, $R^4$ is selected from —CH=CH—CH$_2$—N(CH$_3$)$_2$, —CH$_2$—NH—C(O)—CH=CH—CH$_2$—N(CH$_3$)$_2$, —C(O)—CH=CH$_2$, —C(O)—CH=CH—CH$_2$—N(CH$_3$)$_2$, —C(O)—CH$_2$—CH=CH$_2$, —NH—C(O)—CH=CH$_2$, —NH—C(O)—CH=CH—CH$_2$—N(CH$_3$)$_2$, —CH$_2$—NH—C(O)—CH=CH$_2$,

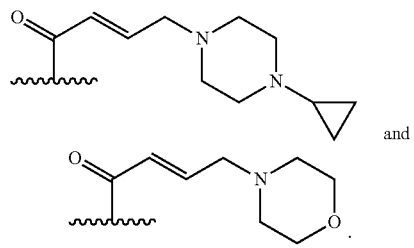

and

In another specific embodiment, $R^4$ is additionally selected from —C(O)—NH=CH$_2$, —N(CH$_3$)—C(O)—CH=CHCH$_2$—N(CH$_3$)$_2$, and —C(O)—CF=CH$_2$.

Although, as indicated above, various embodiments and aspects thereof for a variable in Formula (I) may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula (I) above, the invention encompasses all possible combinations of the different embodiments and aspects for each of the variables in Formula (I).

Thus, in certain embodiments, the compound of Formula (I) is of Formula (Ia):

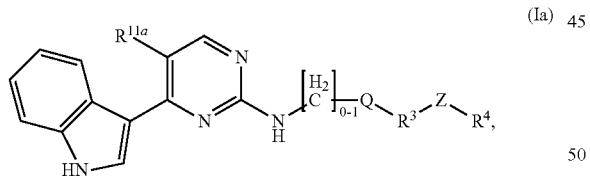

(Ia)

or a pharmaceutically acceptable salt, solvate, hydrate, tautomer, stereoisomer, or isotopically labeled derivative thereof, wherein:

$R^{11a}$ is selected from halo and —CN;

Q is selected from 1,3,4-oxadiazol-2,5-diyl, 1-oxa-3-azaspiro[4.5]dec-2-en-7,2-diyl, 4-fluorocyclohex-1,4-diyl, 4-hydroxycyclohex-1,4-diyl, 4-thia-1,2-diazaspiro[4.5]dec-2-en-7,3-diyl, cyclohex-1,3-diyl, cyclohex-1,4-diyl, oxazol-2,5-diyl, benzene-1,3-diyl, piperidin-1,3-diyl, piperidin-4,1-diyl and pyrrolidin-3,1-diyl;

$R^3$ is selected from a bond, †-C(O)—(CH$_2$)$_3$—, †-NH—C(O)—, †-NH—C(O)—CF$_2$—CH$_2$—, †-CH$_2$—, †—NH—, †-NH—CH$_2$—, †-CH$_2$—NH—, †-NH—C(O)—CH(CF$_3$)—, †-N(CH$_3$)—CH$_2$—, and †-NH—CH$_2$—CH(CF$_3$)—, wherein "†" represents a portion of $R^3$ bound to Q;

Z is selected from a bond, cyclohex-1,4-diyl, piperidin-3,1-diyl, piperidin-4,1-diyl, pyridin-2,5-diyl, bicyclo[1.1.1]pent-1,3-diyl, pyrimidin-2,5-diyl, pyrazol-1,4-diyl, pyrrolidin-2,1-diyl, 4,4-difluoropyrrolidin-2,1-diyl, isoindolin-2,5-diyl, 6-azaspiro[2.5]octan-6,1-diyl, 2,8-diazaspiro[4.5]decan-2,8-diyl, pyrrolidin-3,1-diyl, 5,6,7,7a-tetrahydro-1H-pyrrolo[1,2-c]imidazol-3,6-diyl, 1,1-dioxobenzo[d]isothiazol-3,6-diyl, piperazin-1,4-diyl, pyrrolidin-1,3-diyl, piperidin-1,4-diyl, pyrrolidin-2,4-diyl, 2,2-difluorocyclopent-1,1-diyl, 3-fluoroazetidin-3,1-diyl, 3,3-difluoropiperidin-4,1-diyl, and 4-hydroxypyrrolidin-3,1-diyl; and $R^4$ is selected from —CH$_2$—NH—C(O)—CH=CH—CH$_2$—N(CH$_3$)$_2$, —NH—C(O)—CH=CH—CH$_2$—N(CH$_3$)$_2$, —C(O)—CH=CH—CH$_2$—N(CH$_3$)$_2$, —NH—C(O)—CH=CH$_2$, —C(O)—CH=CH$_2$, —S(O)$_2$—NH—C(O)—CH=CH$_2$, and —NH—S(O)$_2$—NH—C(O)—CH=CH$_2$.

In certain embodiments, the compound of Formula (I) is of Formula (Ib):

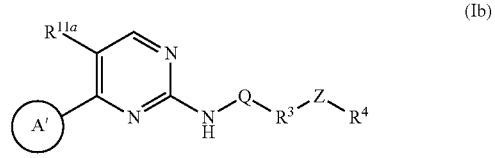

(Ib)

or a pharmaceutically acceptable salt, solvate, hydrate, tautomer, stereoisomer, or isotopically labeled derivative thereof, wherein:

Ring A' is selected from

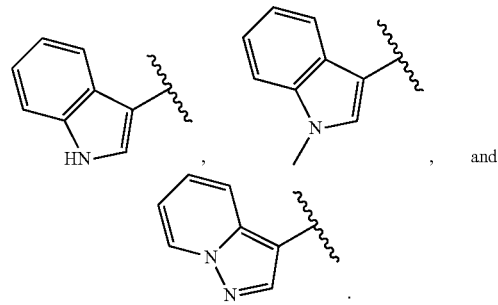

and $R^{11a}$ is selected from halo, $C_1$-$C_3$ alkyl, $C_1$-$C_3$ haloalkyl, cyclopropyl and —CN;

Q is selected from cyclohex-1,4-diyl, cyclohex-1,3-diyl, benzene-1,3-diyl, pyrrolidin-3,1-diyl, piperidin-4,1-diyl and indol-6,2-diyl, wherein Q is optionally substituted with one hydroxy, methyl or fluoro substituent;

$R^3$ is selected from a bond, †-CH$_2$—, †-CH$_2$—CH$_2$—, †-CH$_2$—NH—, †-C(O)—, †-C(O)—(CH$_2$)$_3$—, †-N(CH$_3$)—, †-N(CH$_3$)—CH$_2$—, †-N(CH$_2$CH$_3$)—CH$_2$—, †-N(C(O)CH$_3$)CH$_2$—, †-NH—, †-NH—CH$_2$—, †-NH—C(O)—, †-NH—C(O)—CF$_2$—CH$_2$—, —N(C(O)CH=CH$_2$)—CH$_2$—, †-N(C(O)OCH$_3$)—CH$_2$—, †-N(S(O)$_2$CH$_3$)CH$_2$, and †-NH—C(O)—(CH$_2$)$_2$—, wherein "†" represents a portion of $R^3$ bound to Q;

Z is selected from a bond, cyclohex-1,4-diyl, piperidin-3,1-diyl, piperidin-4,1-diyl, piperidin-1,4-diyl, piperazin-1,4-diyl, pyridin-2,5-diyl, pyrazol-1,4-diyl, pyrrolidin-2,1-diyl, pyrrolidin-2,4-diyl, isoindolin-2,5-diyl, 6-azaspiro[2.5]octan-6,1-diyl, 3,8-diazaspiro[4.5]decan-2-one-8,3-diyl, pyrimidin-2,5-diyl, thiazol-4,2-diyl, azetidin-3,1-diyl, azetidin-1,3-diyl, 8-azabicyclo[3.2.1]octan-8,3-diyl, and piperazin-1,4-diyl, wherein Z is optionally substituted up to two substituents independently selected from oxo, methyl, hydroxy or halo; and $R^4$ is selected
from —CH=CH—CH$_2$—N(CH$_3$)$_2$, —CH$_2$—NH—C(O)—CH=CH—CH$_2$—N(CH$_3$)$_2$, —C(O)—CH=CH$_2$, —C(O)—CH=CH—CH$_2$—N(CH$_3$)$_2$, —C(O)—CH$_2$—CH=CH$_2$, —NH—C(O)—CH=CH$_2$, —NH—C(O)—CH=CH—CH$_2$—N(CH$_3$)$_2$, —CH$_2$—NH—C(O)—CH=CH$_2$,

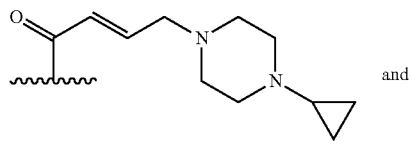

and

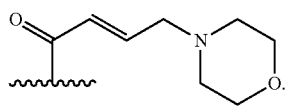

In certain embodiments of Formula (Ib), Ring A' is additionally selected from

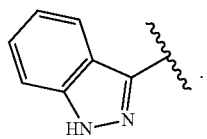 [SMILES: *c1n[nH]c2ccccc12]

In certain embodiments of Formula (Ib), $R^{11a}$ is selected from chloro, methyl, ethyl, and —CN. In certain embodiments of Formula (Ib), $R^{11a}$ is additionally selected from —CF$_3$. In one aspect of these embodiments, ring A' is

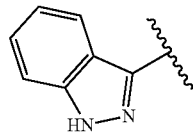 [SMILES: *c1n[nH]c2ccccc12]

and $R^{11a}$ is —CF$_3$.

In certain embodiments of Formula (Ib), Q is selected from 4-hydroxycyclohex-1,4-diyl, 4-fluorocyclohex-1,4-diyl, 3-hydroxycyclohex-1,3-diyl, cyclohex-1,4-diyl, cyclohex-1,3-diyl, benzene-1,3-diyl, pyrrolidin-3,1-diyl, piperidin-4,1-diyl and indol-6,2-diyl.

In certain embodiments of Formula (Ib), $R^3$ is selected from a bond, †-CH$_2$—, †-CH$_2$CH$_2$—, †-CH$_2$NH—, †-C(O)—, †-C(O)—(CH$_2$)$_3$—, †-N(CH$_3$)—, †-N(CH$_3$)CH$_2$—, †-N(CH$_2$CH$_3$)CH$_2$—, †-N(C(O)CH$_3$)CH$_2$—, †-NH—, †-NHCH$_2$—, †-NHC(O)—, †-NHC(O)CF$_2$CH$_2$—, and †-NHC(O)CH$_2$CH$_2$—.

In certain embodiments of Formula (Ib), Z is selected from a bond, 1-oxa-3,8-diazaspiro[4.5]decan-2-one-8,3-diyl, 6-azaspiro[2.5]octan-6,1-diyl, cyclohex-1,4-diyl, isoindolin-2,5-diyl, piperazin-1,4-diyl, piperidin-3,1-diyl, piperidin-4,1-diyl, piperidin-1,4-diyl, pyrazol-1,4-diyl, pyridin-2,5-diyl, pyrimidin-2,5-diyl, pyrrolidin-2,1-diyl, 4,4-difluoropyrrolidin-2,1-diyl, thiazol-4,2-diyl, 3-methylazetidin-3,1-diyl, azetidin-3,1-diyl, 3-methylpiperazin-1,4-diyl, 4-hydroxpiperidin-4,1-diyl 2-methylpiperazin-1,4-diyl, azetidin-1,3-diyl, 8-azabicyclo[3.2.1]octan-8,3-diyl, pyridin-2,5-diyl, and pyrrolidin-2,4-diyl.

In certain embodiments of Formula (I), (Ia), and (Ib), no ring nitrogen atom present in Q is bound to a nitrogen atom in $R^3$.

In certain embodiments of Formula (I), no ring nitrogen atom present in Q is bound to a nitrogen atom in $R^2$.

In certain embodiments of Formula (I), (Ia) and (Ib), no ring nitrogen atom present in Z is bound to a nitrogen atom in $R^3$ or $R^4$.

In some embodiments, the compound has structural Formula (Ic):

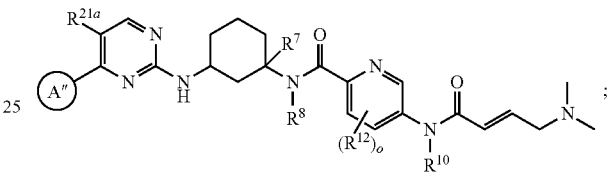

(Ic)

or a pharmaceutically acceptable salt thereof, solvate, hydrate, tautomer, stereoisomer, or isotopically labeled derivative thereof, wherein:

ring A" is selected from

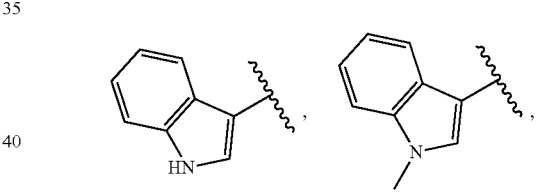

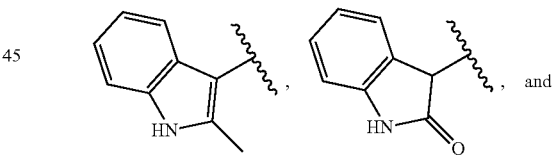

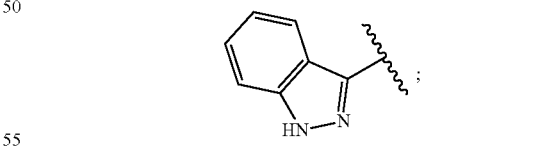

each of $R^7$, $R^8$ and $R^{10}$ is independently selected from hydrogen and methyl;

$R^{21a}$ is selected from —Cl, —CN, —CF$_3$, —CH$_3$, and —CH$_2$CH$_3$; and each $R^{12}$ if present is halo; and o is 0, 1, 2, or 3.

In some embodiments of Formula (Ic), the compound has the particular stereochemistry depicted in structural Formula (Ic)':

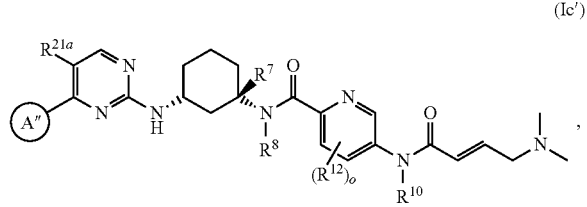

(Ic′)

wherein $R^7$, $R^8$, $R^{10}$, $R^{21a}$, $R^{12}$ and o are as defined above form Formula (Ic).

In some embodiments of Formula (Ic) or (Ic′), each $R^{12}$, if present, is fluoro.

In some embodiments of Formula (Ic) or (Ic′) o is 0.

In certain embodiments, the compound of Formula (I) is selected from the group consisting of any one of the compounds in FIGS. 1A-1Z and 1AA-1RR and pharmaceutically acceptable salts, solvates, hydrates, tautomers, stereoisomers, and isotopically labeled derivatives thereof.

In another embodiment, the invention provides a compound of Formula (II):

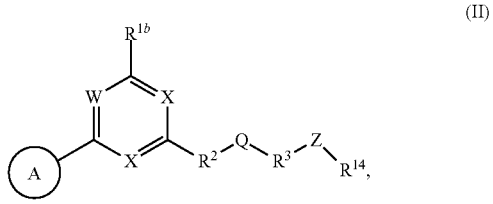

(II)

and pharmaceutically acceptable salts, solvates, hydrates, tautomers, stereoisomers, and isotopically labeled derivatives thereof, wherein Ring A, W, X, $R^{1b}$, $R^2$, Q, $R^3$, Z, and subvariables thereof are as defined herein for Formula I and embodiments and specific aspects thereof set forth above; and wherein $R^{14}$ is selected from hydrogen when bound to a nitrogen atom in Z or when Z is a bond, —$C_1$-$C_8$ alkyl, —O—$C_1$-$C_8$ alkyl, —$NH_2$, —NH($C_1$-$C_8$ alkyl), —N($C_1$-$C_8$ alkyl)$_2$, wherein each alkyl in $R^{14}$ is optionally and independently substituted.

In some embodiments of Formula (II), $R^{14}$ is selected from hydrogen, —($C_1$-$C_4$ alkyl), —C(O)—($C_1$-$C_4$ alkylene)-$NH_2$, —($C_1$-$C_4$ alkylene)-$NH_2$, —$NH_2$, —NH—C(O)—($C_1$-$C_4$ alkylene)-$NH_2$, —NH—C(O)—($C_1$-$C_4$ alkylene)-NH—($C_1$-$C_4$ alkyl), —NH—C(O)—($C_1$-$C_4$ alkylene)-N—($C_1$-$C_4$ alkyl)$_2$, —NH—C(O)—C(O)—($C_0$-$C_4$ alkylene)-$NH_2$, —NH—C(O)—C(O)—($C_0$-$C_4$ alkylene)-NH($C_1$-$C_4$ alkyl), —NH—C(O)—C(O)—($C_0$-$C_4$ alkylene)-N($C_1$-$C_4$ alkyl)$_2$, and —NH—C(O)—($C_1$-$C_4$ alkyl). In one aspect of these embodiments, $R^{14}$ is selected from hydrogen, —$CH_3$, —$NH_2$, —$CH_2$—$NH_2$, and —NH—C(O)—($CH_2$)$_3$—N($CH_3$)$_2$.

In some embodiments, of Formula II, ring A is selected from

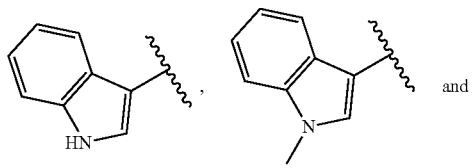

and

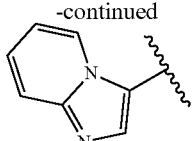

In some embodiments, of Formula II, ring A is selected from

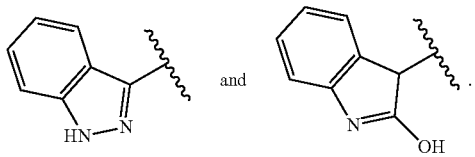 [SMILES: *c1n[nH]c2ccccc12 ; *C1C(O)=Nc2ccccc21]

and

Although, as indicated above, various embodiments and aspects thereof for a variable in Formula (II) may be selected from a group of chemical moieties set forth for the same variables in Formula (I), the invention also encompasses as further embodiments and aspects thereof situations where such variable in Formula (II) is: a) selected from any subset of chemical moieties in such a group; and b) any single member of such a group.

Although various embodiments and aspects thereof are set forth (or implied, as discussed in the preceding paragraphs) individually for each variable in Formula (II) above, the invention encompasses all possible combinations of the different embodiments and aspects for each of the variables in Formula (II).

Thus, in certain embodiments, the compound of Formula (II) is of Formula (IIa):

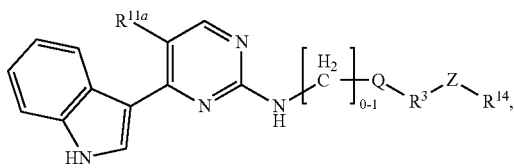

(IIa)

or a pharmaceutically acceptable salt, solvate, hydrate, tautomer, stereoisomer, or isotopically labeled derivative thereof, wherein:

$R^{11a}$ is selected from halo and —CN;

Q is selected from 1,3,4-oxadiazol-2,5-diyl, 1-oxa-3-azaspiro[4.5]dec-2-en-7,2-diyl, 4-fluorocyclohex-1,4-diyl, 4-hydroxycyclohex-1,4-diyl, 4-thia-1,2-diazaspiro[4.5]dec-2-en-7,3-diyl, cyclohex-1,3-diyl, cyclohex-1,4-diyl, oxazol-2,5-diyl, benzene-1,3-diyl, piperidin-1,3-diyl, piperidin-4,1-diyl, pyrrolidin-3,1-diyl, and 1H-indol-6,2-diyl;

$R^3$ is selected from a bond, †-C(O)—($CH_2$)$_3$—, †-NH—C(O)—($CH_2$)$_2$—, †-NH—C(O)—, †-NH—C(O)—$CF_2$—$CH_2$—, †-$CH_2$—, †-$CH_2$—$CH_2$—, †-NH—, †-NH—$CH_2$—, †-$CH_2$—NH—, †-NH—C(O)—CH($CF_3$)—, †-N($CH_3$)—$CH_2$—, and †-NH—$CH_2$—CH($CF_3$)—, wherein "†" represents a portion of $R^3$ bound to Q;

Z is selected from a bond, cyclohex-1,4-diyl, piperidin-3,1-diyl, piperidin-4,1-diyl, pyridin-2,5-diyl, bicyclo[1.1.1]pent-1,3-diyl, pyrimidin-2,5-diyl, pyrazol-1,4-diyl, pyrrolidin-2,1-diyl, 4,4-difluoropyrrolidin-2,1-diyl, isoindolin-2,5-diyl, 6-azaspiro[2.5]octan-6,1-diyl, 2,8-diazaspiro[4.5]decan-2,8-diyl, pyrrolidin-3,1-diyl, 5,6,7,7a-tetrahydro-1H- pyrrolo[1,2-c]imidazol-3,6-diyl, 1,1-dioxobenzo[d]isothiazol-3,6-diyl, piperazin-1,4-diyl, pyrrolidin-1,3-diyl, piperidin-1,4-diyl, pyrrolidin-2,4-diyl, 2,2-difluorocyclopent-1,1-diyl, 3-fluoroazetidin-3,1-diyl, 3,3-difluoropiperidin-4,1-diyl, and 4-hydroxypyrrolidin-3,1-diyl; and $R^{14}$ is selected from hydrogen, —NH$_2$, —CH$_3$, —CH$_2$—NH$_2$, and —NH—C(O)—(CH$_2$)$_3$—N(CH$_3$)$_2$.

In certain embodiments of Formula II and Formula IIa, Q is additionally selected from 3-methylcyclohex-1,3-diyl and

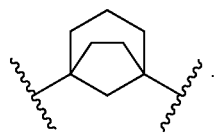 [SMILES: *C12CCCC(*)(CC1)C2]

In certain embodiments of Formula II and Formula IIa, $R^{11a}$ is additionally selected from methyl, ethyl and —CF$_3$.

In certain embodiments of Formula II and Formula IIa, no ring nitrogen atom present in Q is bound to a nitrogen atom in $R^2$ or $R^3$.

In certain embodiments of Formula II and Formula IIa, no ring nitrogen atom present in Z is bound to a nitrogen atom in $R^3$ or $R^{14}$.

In certain embodiments, the compound of Formula (II) is selected from the group consisting of any one of the compounds in the table in FIGS. 2A-2G and pharmaceutically acceptable salts, solvates, hydrates, tautomers, stereoisomers, and isotopically labeled derivatives thereof.

Pharmaceutical Compositions, Kits, and Administration

The present invention provides pharmaceutical compositions comprising a compound of Formula (I) or Formula (II), e.g., a compound of Formula (I) or Formula (II), or a pharmaceutically acceptable salt, solvate, hydrate, tautomer, stereoisomer, or isotopically labeled derivative thereof, as described herein, and optionally a pharmaceutically acceptable excipient. In certain embodiments, the pharmaceutical composition of the invention comprises a compound of Formula (I) or Formula (II), or a pharmaceutically acceptable salt thereof, and optionally a pharmaceutically acceptable excipient. In certain embodiments, the compound of Formula (I) or Formula (II), or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) or Formula (II) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) or Formula (II) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, tautomer, stereoisomer, and isotopically labeled derivative, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, tautomer, stereoisomer, isotopically and labeled derivative thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of Formula (I) or Formula (II), or a pharmaceutically acceptable salt, solvate, hydrate, tautomer, stereoisomer, or isotopically labeled derivative thereof, or a pharmaceutical composition thereof. In certain embodiments, the methods described herein include administering to a subject an effective amount of a compound of Formula (I) or Formula (II), or a pharmaceutically acceptable salt thereof, or a pharmaceutical composition thereof.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I) or Formula (II) will typically be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of Formula (I) or Formula (II), and pharmaceutically acceptable salts, solvates, hydrates, tautomers, stereoisomers, isotopically labeled derivatives, and compositions thereof, may inhibit the activity of CDK7 and be useful in treating and/or preventing proliferative diseases.

In other embodiments, the proliferative disease to be treated or prevented using the compounds of Formula (I) or Formula (II) will typically be associated with aberrant activity of CDK12 and/or CDK13. Aberrant activity of CDK12 and/or CDK13 may be an elevated and/or an inappropriate (e.g., abnormal) activity of CDK12 and/or CDK13. In certain embodiments, CDK12 and/or CDK13 is not overexpressed, and the activity of CDK12 and/or CDK13 is elevated and/or inappropriate. In certain other embodiments, CDK12 and/or CDK13 is overexpressed, and the activity of CDK12 and/or CDK13 is elevated and/or inappropriate. The compounds of Formula (I) or Formula (II), and pharmaceutically acceptable salts, solvates, hydrates, tautomers, stereoisomers, isotopically labeled derivatives, and compositions thereof, may inhibit the activity of CDK12 and/or CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of CDK7 is expected to cause cytotoxicity via induction of apoptosis. The compounds of Formula (I) or Formula (II), and pharmaceutically acceptable salts, solvates, hydrates, tautomers, stereoisomers, isotopically labeled derivatives, and compositions thereof, may induce apoptosis, and therefore, be useful in treating and/or preventing proliferative diseases.

In certain embodiments, the proliferative disease to be treated or prevented using the compounds of Formula (I) or Formula (II) is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is lymphoma. In certain embodiments, the proliferative disease is melanoma. In certain embodiments, the proliferative disease is multiple myeloma. In certain embodiments, the proliferative disease is a bone cancer. In certain embodiments, the proliferative disease is osteosarcoma. In some embodiments, the proliferative disease is Ewing's sarcoma. In some embodiments, the proliferative disease is triple-negative breast cancer (TNBC). In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is large cell lung cancer. In some embodiments, the proliferative disease is a benign neoplasm. All types of benign neoplasms disclosed herein or known in the art are contemplated as being within the scope of the invention.

In some embodiments, the proliferative disease is associated with angiogenesis. All types of angiogenesis disclosed herein or known in the art are contemplated as being within the scope of the invention.

In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of CDK7 in a biological sample or subject.

In certain embodiments, the methods described herein comprise the additional step of administering one or more additional pharmaceutical agents in combination with the compound of Formula (I) or Formula (II), a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 or CDK12 and/or CDK13 induced by the inventive compounds or compositions of this invention in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In yet another aspect, the present invention provides the compounds of Formula (I) or Formula (II), and pharmaceutically acceptable salts, solvates, hydrates, tautomers, stereoisomers, isotopically labeled derivatives, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., Protecting Groups in Organic Synthesis, Second Edition, Wiley, New York, 1991, and references cited therein.

| ABBREVIATIONS | |
|---|---|
| Ac | acetyl |
| ACN | acetonitrile |
| aq. | aqueous |
| atm | atmospheres |
| Boc | tert-butoxy carbonyl |
| $Boc_2O$ | Di-t-butyl dicarbonate |
| CDI | 1,1'-Carbonyldiimidazole |
| DBU | 1-8-Diazabicyclo[5.4.0]undec-7-ene |
| DCC | N, N'-Dicyclohexylcarbodiimide |
| DCM | Dichloromethane |
| DIAD | Diisopropyl azodicarboxylate |
| DIPEA | N,N-Diisopropyl ethylamine |
| DMA | Dimethyl adipate |

ABBREVIATIONS

| | |
|---|---|
| DMF | Dimethylformamide |
| DMSO | Dimethylsulfoxide |
| DPPA | Diphenoxyphosphoryl azide |
| EDTA | Ethylenediamine tetraacetic acid |
| eq(s). | equivalent(s) |
| EtOAc | Ethyl acetate |
| Et | Ethyl |
| EtOH | Ethanol |
| Et$_3$N | Triethylamine |
| g | gram(s) |
| h | hour(s) |
| HATU | (Dimethylamino)-N,N-dimethyl(3H-[1,2,3]triazolo[4,5-b]pyridin-3-yloxy)methaniminium hexafluorophosphate |
| HBTU | O-Benzotriazole-N,N,N',N'-tetramethyl-uronium-hexafluoro-phosphate |
| Hex | Hexanes |
| HOBt | 1-Hydroxybenzotriazole |
| HPLC | High pressure liquid chromatography |
| IPA | Isopropanol |
| LCMS; LC-MS | liquid chromatography mass spectrometry |
| MeOH | Methanol |
| mg | milligram(s) |
| min | Minute(s) |
| mL; ml | milliliter(s) |
| MS | mass spectrometry |
| MTBE | Methyl tert-butyl ether |
| mW | megawatt |
| NMe | N-methyl |
| NMP | N-Methyl-2-pyrrolidone |
| NMR | Nuclear magnetic resonance |
| Pd$_2$dba$_3$ | Tris(dibenzylideneacetone) dipalladium(0) |
| Ph | phenyl |
| r.t.; rt; RT | Room temperature |
| S., sat. | saturated |
| TEA | Triethylamine |
| TFA | Trifluoroacetic acid |
| THF | Tetrahydrofuran |
| TLC | Thin layer chromatography |
| TMSI | Trimethylsilyl iodide |
| X-Phos | 2-Dicyclohexylphosphino-2',4',6'-triisopropylbiphenyl |

Example 1. Synthesis of (E)-N-(3-(5-chloro-4-(1H-indol-3-yl)pyrimidin-2-ylamino)phenyl)-5-(4-(dimethylamino)but-2-enamido)picolinamide (Compound 107)

N1-(5-chloro-4-(1-(phenylsulfonyl)-1H-indol-3-yl)pyrimidin-2-yl)benzene-1,3-diamine

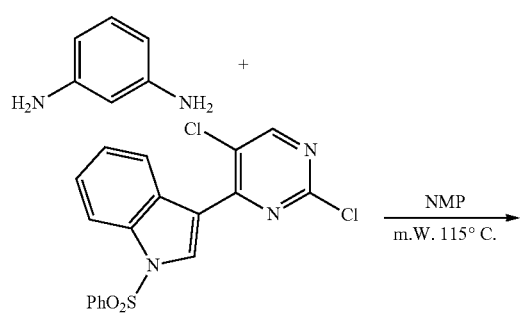

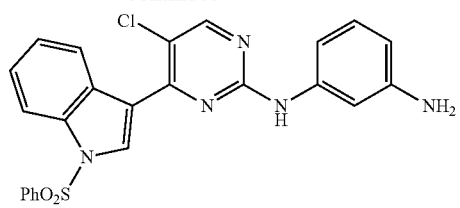

A solution of 3-(2,5-dichloropyrimidin-4-yl)-1-(phenylsulfonyl)-1H-indole (1.5 g, 3.70 mmol) and m-phenylenediamine (400 mg, 3.70 mmol) in NMP (15 mL) was heated 15 min at 175° C. (mW). The cooled mixture was diluted with EtOAc (100 mL) and water (50 mL). The layers were separated and the aqueous layer was extracted with EtOAc (3×50 mL). The combined organics were washed with brine (50 mL) dried (MgSO$_4$), filtered and evaporated to dryness. The mixture was purified by SiO$_2$ column (DCM/EtOAc 0 to 30% gradient) and afforded the title compound (606 mg, 1.27 mmol, 34%) as a pale brown solid.

5-amino-N-(3-(5-chloro-4-(1-(phenylsulfonyl)-1H-indol-3-yl)pyrimidin-2-ylamino)phenyl)picolinamide

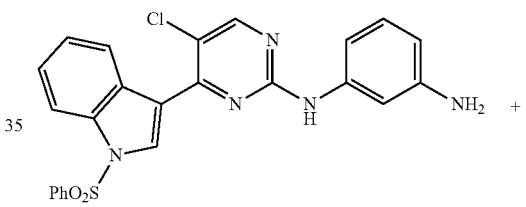

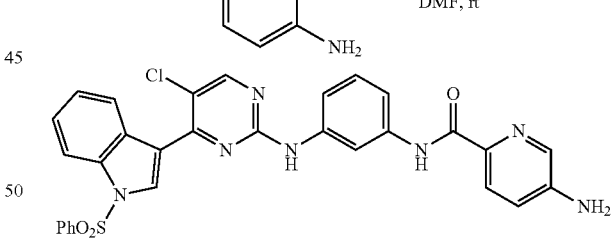

To a solution of N1-(5-chloro-4-(1-(phenylsulfonyl)-1H-indol-3-yl)pyrimidin-2-yl)benzene-1,3-diamine (125 mg, 0.263 mmol), 5-amino-2-pyridinecarboxylic acid (44 mg, 0.315 mmol) and Et$_3$N (110 µL, 0.788 mmol) in DMF (5 mL) was added, followed by HBTU (150 mg, 0.394 mmol). The mixture was stirred 24 h at rt. The mixture was diluted with EtOAc (30 mL) and washed with sat. NaHCO$_3$ (10 mL), brine (10 mL), and dried (MgSO$_4$), then filtered and evaporated to dryness. The mixture was purified by SiO$_2$ chromatography (DCM/EtOAc 20 to 100% gradient) and afforded the title compound (131 mg, 0.220 mmol, 84%) as pale, creamy solid.

(E)-N-(3-(5-chloro-4-(1-(phenylsulfonyl)-1H-indol-3-yl)pyrimidin-2-ylamino)phenyl)-5-(4-(dimethylamino)but-2-enamido)picolinamide

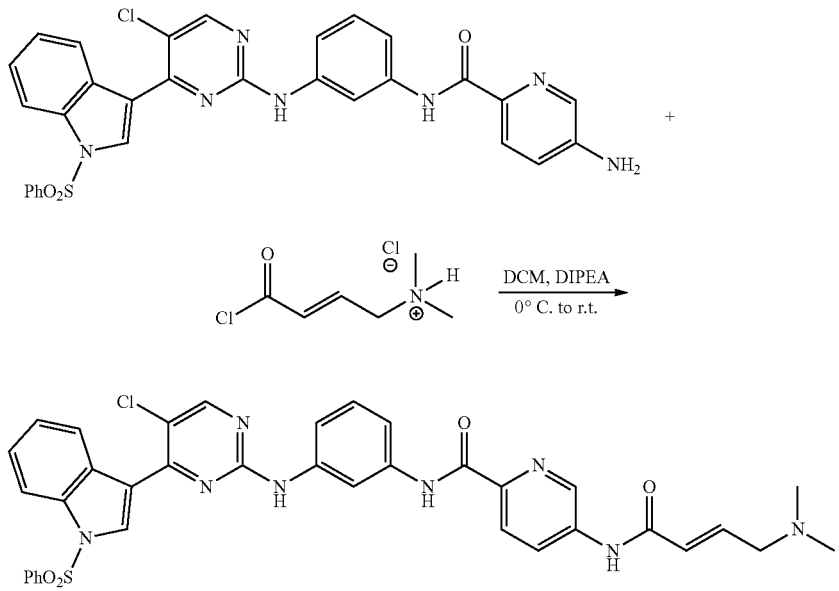

To a 0° C. solution of 5-amino-N-(3-(5-chloro-4-(1-(phenylsulfonyl)-1H-indol-3-yl)pyrimidin-2-ylamino)phenyl)picolinamide (48 mg, 0.080 mmol) and DIPEA (43 µL, 0.241 mmol) in DCM (1 mL) was slowly added a solution of 54 mg/mL (E)-4-chloro-N,N-dimethyl-4-oxobut-2-en-1-aminium chloride (0.6 mL, 0.080 mmol). The mixture was stirred at RT for 2 h, before being diluted with CHCl₃ (10 mL) and washed with sat. NaHCO₃ (5 mL). The organic layer was dried (MgSO₄), filtered, and evaporated to dryness and afforded the title compound (52.3 mg, 0.074 mmol, 92%), which was used without further purification.

(E)-N-(3-(5-chloro-4-(1H-indol-3-yl)pyrimidin-2-ylamino)phenyl)-5-(4-(dimethylamino)but-2-enamido)picolinamide A solution of (E)-N-(3-(5-chloro-4-(1-(phenylsulfonyl)-1H-indol-3-yl)pyrimidin-2-ylamino)phenyl)-5-(4-(dimethylamino)but-2-enamido)picolinamide (52.3 mg, 0.074 mmol) in dioxane (1.5 mL) and NaOH 5M (148 µL) was stirred for 3 h at 50° C. The cooled solution was diluted with DCM (5 mL) and H₂O (3 mL). The layers were separated and the aqueous layer was extracted with DCM (4×5 mL). The combined organic layers were dried (MgSO₄), filtered, and evaporated to dryness. The residue was purified by preparative HPLC (0.1% (NH₄)₂CO₃, H₂O/ACN 10 to 90% gradient). The title compound was obtained as a white solid (1.57 mg, 0.003 mmol, 4%) after lyophilisation. ¹H NMR (500 MHz, DMSO-d6) δ 11.92 (s, 1H), 10.64 (s, 1H), 10.31 (s, 1H), 9.69 (s, 1H), 8.95 (d, J=2.4 Hz, 1H), 8.63 (d, J=8.5 Hz, 1H), 8.52 (d, J=2.6 Hz, 1H), 8.48 (s, 1H), 8.36 (s, 1H), 8.31 (dd, J=8.6, 2.4 Hz, 1H), 8.26 (t, J=1.9 Hz, 1H), 8.13 (d, J=8.8 Hz, 1H), 7.56-7.41 (m, 2H), 7.28 (t, J=8.1 Hz, 1H), 7.16 (t, J=7.5 Hz, 1H), 7.09 (t, J=7.1 Hz, 1H), 6.84 (dt, J=15.4, 5.7 Hz, 1H), 6.33 (d, J=15.4 Hz, 1H), 3.10 (d, J=4.2 Hz, 2H), 2.20 (s, 3H); MS (m/z): 567.61 [M+1]⁺.

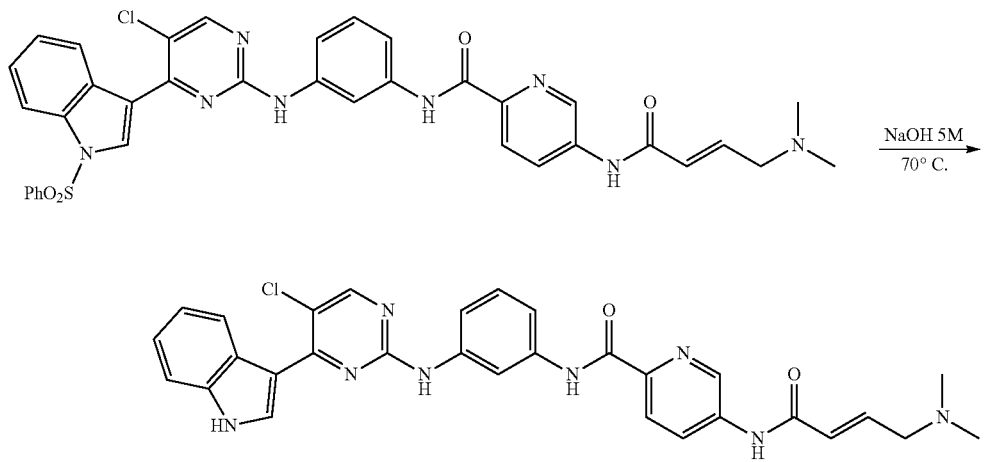

Example 2. Synthesis of (E)-N-(3-(5-chloro-4-(1H-indol-3-yl)pyrimidin-2-ylamino)phenyl)-1-(4-(dimethylamino)but-2-enoyl)piperidine-4-carboxamide (Compound 105)

tert-butyl 4-(3-(5-chloro-4-(1-(phenylsulfonyl)-1H-indol-3-yl)pyrimidin-2-ylamino)phenylcarbamoyl)piperidine-1-carboxylate

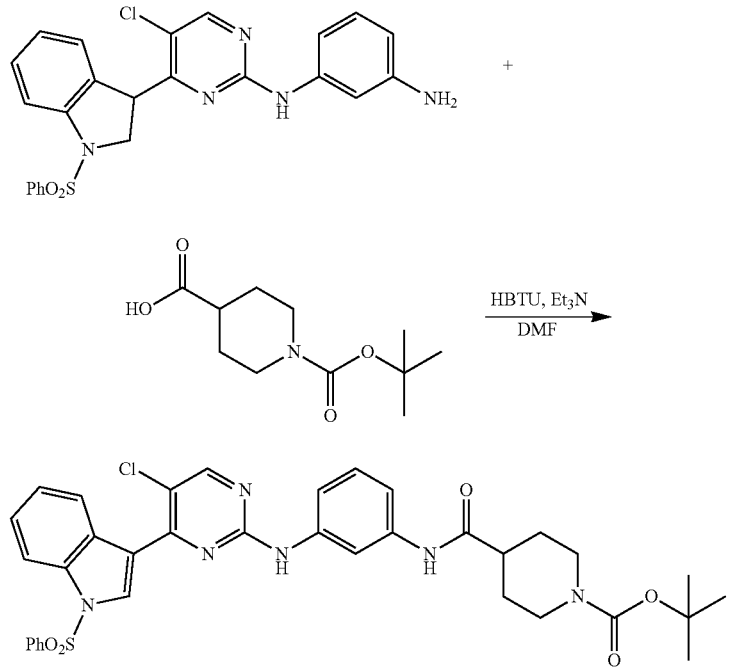

To a solution N1-(5-chloro-4-(1-(phenylsulfonyl)-1H-indol-3-yl)pyrimidin-2-yl)benzene-1,3-diamine prepared as in Example 1 (150 mg, 0.315 mmol), N-Boc-isonipecotic acid (87 mg, 0.378 mmol) and Et₃N (132 μL, 0.945 mmol) in DMF (3 mL) was added, followed by HBTU (179 mg, 0.473 mmol). The mixture was stirred overnight at room temperature, diluted with EtOAc (20 mL), washed with sat. NaHCO₃ (3×5 mL), brine (2×5 mL), and dried (MgSO₄), then filtered and evaporated to dryness. The residue was purified by SiO₂ chromatography (DCM/EtOAc 0 to 100% gradient) and afforded the title compound (210 mg, 0.306 mmol, 97%) as a pale cream solid.

tert-butyl 4-(3-(5-chloro-4-(1H-indol-3-yl)pyrmidin-2-ylamino)phenylcarbamoyl)piperidine-1-carboxylate

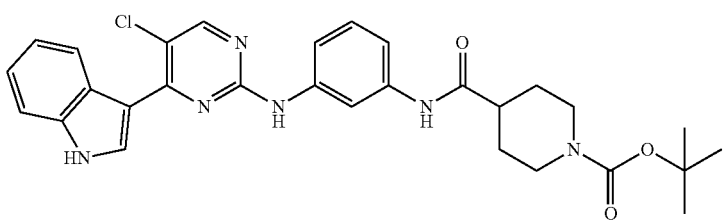

A solution of tert-butyl 4-(3-(5-chloro-4-(1-(phenylsulfonyl)-1H-indol-3-yl)pyrimidin-2-ylamino)phenylcarbamoyl)piperidine-1-carboxylate (210 mg, 0.311 mmol), NaOH 1M (5.3 mL, 5.29 mmol) in dioxane (5 mL) was stirred 1 h. The mixture was diluted with DCM (20 mL) and sat. NH$_4$Cl (5 mL). The layers were separated and the aqueous layer was extracted with DCM (3×10 mL), dried (phase cartridge separator) and evaporated to dryness. The residue was purified by SiO$_2$ chromatography (DCM/EtOAc 10 to 100% gradient) and afforded the title compound (135 mg, 0.252 mmol, 81%) as a pale creamy solid.

N-(3-(5-chloro-4-(1H-indol-3-yl)pyrimidin-2-ylamino)phenyl)piperidine-4-carboxamide (Compound 1006)

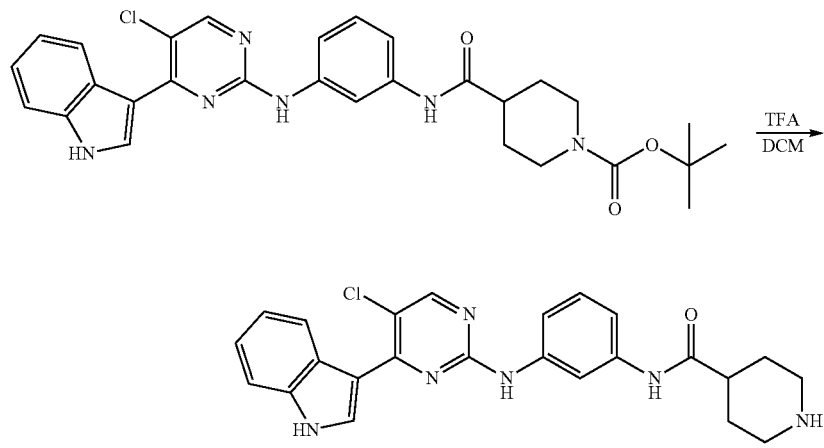 [SMILES: CC(C)(C)OC(=O)N1CCC(C(=O)Nc2cccc(Nc3ncc(Cl)c(-c4c[nH]c5ccccc45)n3)c2)CC1 ; O=C(Nc1cccc(Nc2ncc(Cl)c(-c3c[nH]c4ccccc34)n2)c1)C1CCNCC1]

A solution of tert-butyl 4-(3-(5-chloro-4-(1H-indol-3-yl)pyrimidin-2-ylamino)phenylcarbamoyl)piperidine-1-carboxylate (135 mg, 0.252 mmol) in DCM (2.5 mL) was treated with TFA (200 μL) for 3 h at rt. The mixture was diluted with DCM (10 mL) and washed with sat. NaHCO$_3$, dried (phase cartridge separator), and evaporated to dryness to afford the title compound (64 mg, 0.143 mmol, 57%) as a beige solid.

(E)-N-(3-(5-chloro-4-(1H-indol-3-yl)pyrimidin-2-ylamino)phenyl)-1-(4-(dimethylamino)but-2-enoyl)piperidine-4-carboxamide To a −60° C. solution of N-(3-(5-chloro-4-(1H-indol-3-yl)pyrimidin-2-ylamino)phenyl)piperidine-4-carboxamide (35 mg, 0.078 mmol) and DIPEA (41 μL, 0.235 mmol) in DMF (0.4 mL) was added a 1M solution of (E)-4-bromobut-2-enoyl chloride (78 μL, 0.078 mmol). The resulting mixture was stirred for 90 min at −60° C. before addition of a 2M solution of dimethylamine in THF (390 μL, 0.78 mmol). The resulting mixture was stirred for 3 h at rt before being evaporated to dryness. The residue was purified by reverse phase chromatography (C18, water/ACN 15 to 60% gradient) and afforded the title compound (8.0 mg, 0.014 mmol, 18%) as a white solid after lyophilisation. $^1$H NMR (500 MHz, DMSO-d6) δ 11.90 (s, 1H), 9.87 (s, 1H), 9.60 (s, 1H), 8.61 (d, J=7.7 Hz, 1H), 8.52 (d, J=3.1 Hz, 1H), 8.44 (s, 1H), 7.95 (s, 1H), 7.50 (d, J=8.1 Hz, 1H), 7.46 (d, J=9.0 Hz, 1H), 7.27 (d, J=8.7 Hz, 1H), 7.25-7.16 (m, 1H), 7.10 (t, J=7.5 Hz, 1H), 6.87 (d, J=16.1 Hz, 1H), 6.67-6.52 (m, 1H), 4.48-4.41 (2H), 4.24-3.96 (m, 2H), 3.89-3.58 (m, 2H), 3.21-2.98 (m, 2H), 2.85-2.55 (m, 6H), 1.93-1.71 (m, 2H), 1.71-1.39 (m, 2H); MS (m/z): 558.66 [M+1]$^+$.

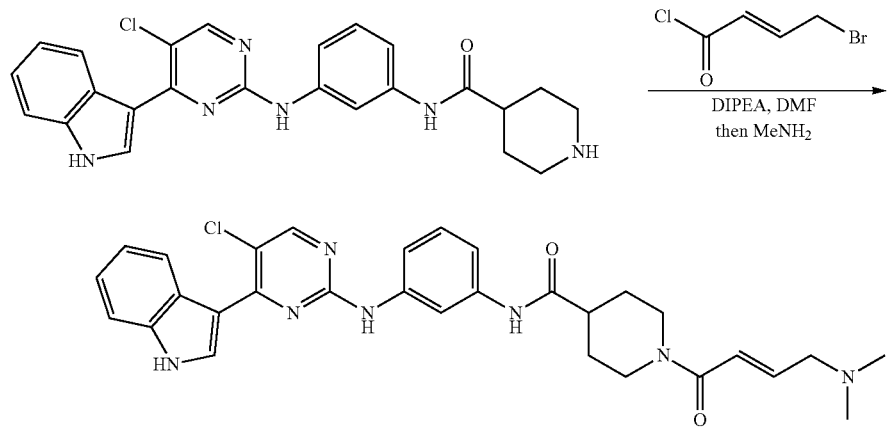

Example 3. Synthesis of (E)-N-(5-((R)-3-(5-chloro-4-(1H-indol-3-yl)pyrimidin-2-ylamino)pyrrolidin-1-yl)-5-oxopentyl)-4-(dimethylamino)but-2-enamide (Compound 100)

(3R)-tert-butyl 3-(5-chloro-4-(1-(phenylsulfonyl)-1H-indol-3-yl)pyrimidin-2-ylamino)pyrolidine-1-carboxylate

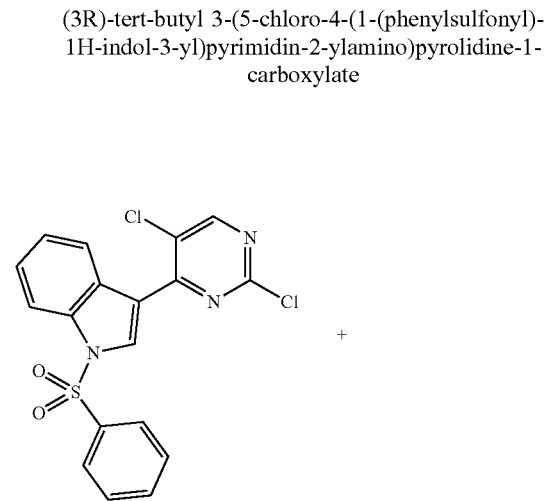

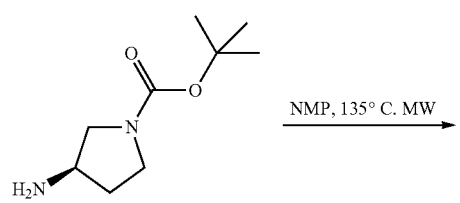

NMP, 135° C. MW

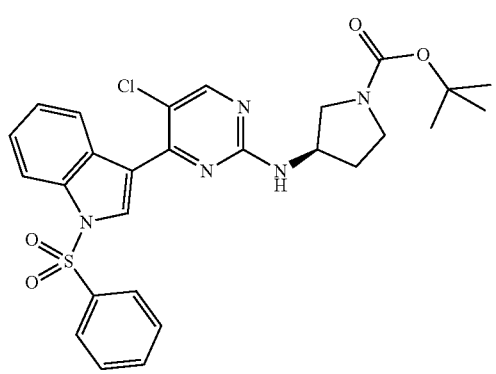

A solution of 3-(2,5-dichloropyrimidin-4-yl)-1-(phenylsulfonyl)-1H-indole (2.50 g, 6.18 mmol), (R)-tert-butyl 3-aminopyrrolidine-1-carboxylate (1.209 g, 6.49 mmol) and diisopropylethylamine (1.08 mL, 6.18 mmol) in NMP (16 mL) was heated for 15 min at 135° C. The mixture was diluted with EtOAc (50 mL), washed with water (10 mL), brine (10 mL), dried (MgSO₄), then filtered and evaporated to dryness. The residue was purified by SiO₂ chromatography (DCM/EtOAc 0 to 40% gradient) and afforded the title compound (2.378 g, 4.29 mmol, 69%) as a white solid.

5-chloro-4-(1-(phenylsulfonyl)-1H-indol-3-yl)-N—((R)-pyrolidin-3-yl)pyrimidin-2-amine

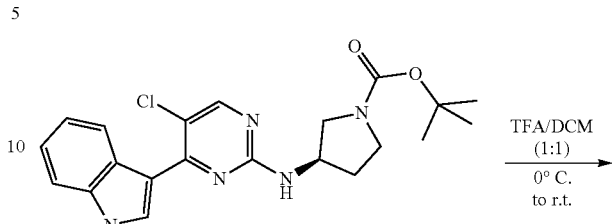

TFA/DCM (1:1) 0° C. to r.t.

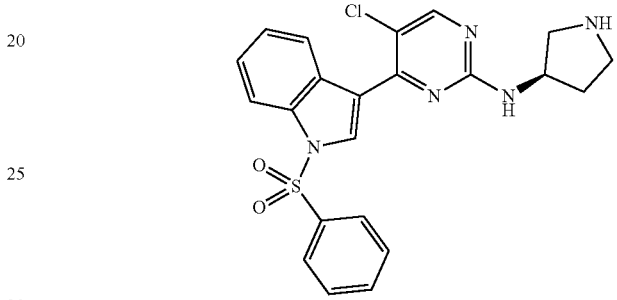

Trifluoroacetic acid (7 mL, 85.8 mmol) was added to a stirring solution of (3R)-tert-butyl 3-(5-chloro-4-(1-(phenylsulfonyl)-1H-indol-3-yl)pyrimidin-2-ylamino)pyrrolidine-1-carboxylate (2.378 g, 4.292 mmoL) in DCM (7 mL) at 0° C. The resulting solution was stirred 2 h at rt, evaporated to dryness, then diluted with DCM (100 mL) and sat NaHCO₃ (15 mL). The phases were separated and aqueous extracted DCM (2×75 mL). The combined organic layers were dried (MgSO₄), filtered, evaporated to dryness to afford the title compound (1.95 g, 4.29 mmol, 100%) as a yellow foam which was used in the next step without further purification.

tert-butyl 5-((R)-3-(5-chloro-4-(1-(phenylsulfonyl)-1H-indol-3-yl)pyrimidin-2-ylamino)pyrolidin-1-yl)-5-oxopentylcarbamate

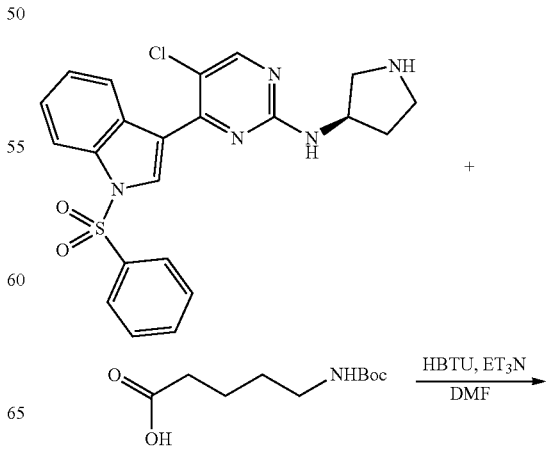

HBTU, ET₃N
DMF

-continued

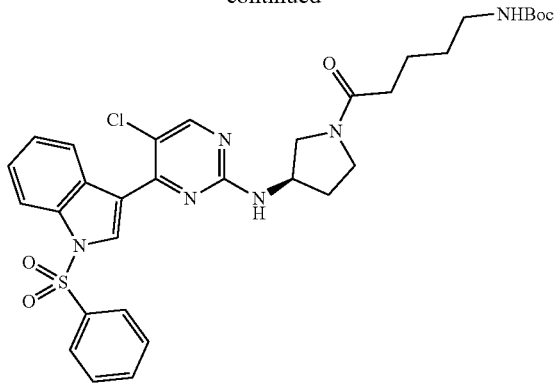

To a solution of 5-chloro-4-(1-(phenylsulfonyl)-1H-indol-3-yl)-N—((R)-pyrrolidin-3-yl)pyrimidin-2-amine (200 mg, 0.441 mmol), 5-(Boc-amino)valeric acid (115 mg, 0.529 mmol) and Et₃N (184 µL, 1.32 mmol) in DMF (3 mL) was added, followed by HBTU (251 mg, 0.661 mmol). The mixture was stirred 4 h at rt, diluted with EtOAc (15 mL), washed with sat. NaHCO₃ (5 mL), brine (2×5 mL), dried (MgSO₄), then filtered and evaporated to dryness. The residue was purified by SiO₂ chromatography (DCM/EtOAc 10 to 100% gradient) and afforded the title compound (265 mg, 0.406 mmol, 92%) as a pale cream foam.

tert-butyl 5-((R)-3-(5-chloro-4-(1H-indol-3-yl)pyrimidin-2-ylamino)pyrolidin-1-yl)-5-oxopentylcarbamate

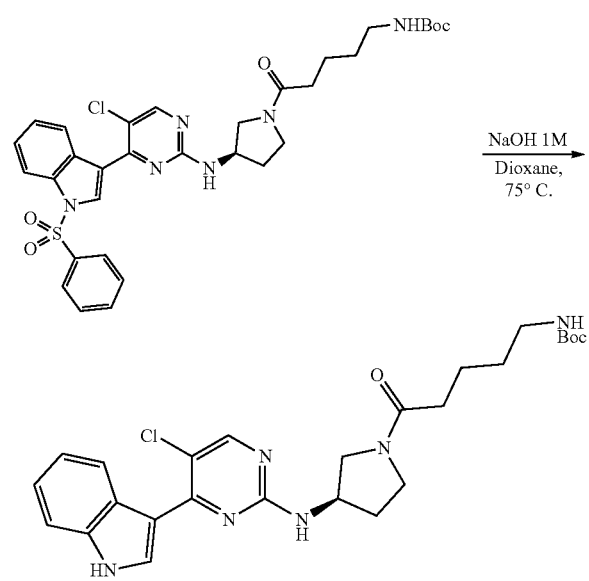

A solution of tert-butyl 5-((R)-3-(5-chloro-4-(1-(phenylsulfonyl)-1H-indol-3-yl)pyrimidin-2-ylamino)pyrrolidin-1-yl)-5-oxopentylcarbamate (265 mg, 0.406 mmol) and NaOH 1M (1.2 mL, 6.08 mmol) in dioxane (7 mL) was heated 2.5 h at 75° C. The cooled mixture was diluted with DCM (10 mL) and sat. NH₄Cl (5 mL). The aqueous layer was extracted with DCM (3×5 mL) and the combined organic layers were dried (MgSO₄), filtered and evaporated to dryness. The residue was purified by SiO₂ chromatography (DCM/EtOAc 10 to 100% gradient) and afforded the title compound (208 mg, 0.406 mmol, 100%) as a pale cream solid.

5-(R)-3-(5-chloro-4-(1H-indol-3-yl)pyrimidin-2-ylamino)pyrolidin-1-yl)-5-oxopentan-1-aminium chloride (Compound 1000)

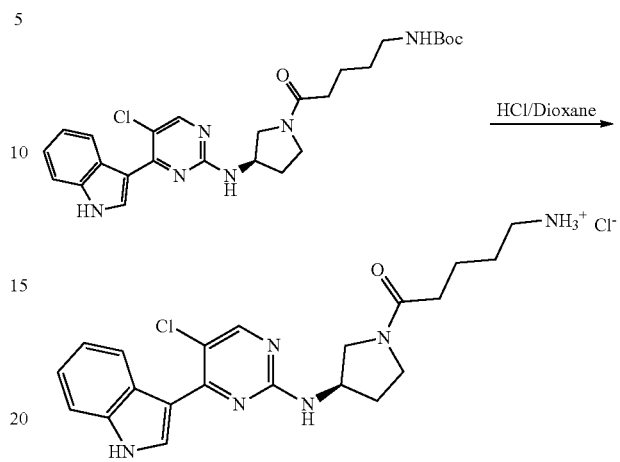

To a solution of tert-butyl 5-((R)-3-(5-chloro-4-(1H-indol-3-yl)pyrimidin-2-ylamino)pyrrolidin-1-yl)-5-oxopentylcarbamate (260 mg, 0.507 mmol) in DCM (2.5 mL) was added a 4N solution of HCl in dioxane (1.90 mL, 7.60 mmol). The resulting mixture was stirred 3 h at rt and the resulting solid was filtered, washed with DCM (3×2 mL), evaporated to dryness and afforded the title compound (183 mg, 0.408 mmol, 81%) as an orange solid.

(E)-N-(5-((R)-3-(5-chloro-4-(1H-indol-3-yl)pyrimidin-2-ylamino)pyrolidin-1-yl)-5-oxopentyl)-4-(dimethylamino)but-2-enamide

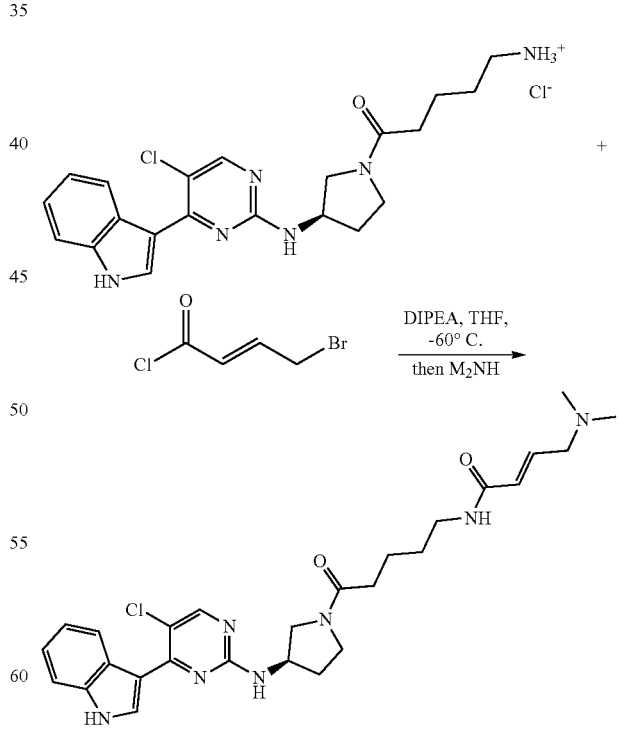

To a −60° C. solution of 5-((R)-3-(5-chloro-4-(1H-indol-3-yl)pyrimidin-2-ylamino)pyrrolidin-1-yl)-5-oxopentan-1-aminium chloride (60 mg, 0.134 mmol) and DIPEA (93 µL, 0.535 mmol) in THF (1.34 mL) and DMF (0.5 mL) was slowly added a 45 mg/mL solution of (E)-4-bromobut-2- enoyl chloride in THF (366 µL, 0.134 mmol). The reaction was stirred 30 min at −60° C., then 1 h at −20° C. before addition of a 2M solution of dimethylamine (134 µL, 0.268 mmol). The resulting mixture was stirred overnight at 0° C. and evaporated to dryness. The residue was purified by reverse phase chromatography (C18, water/ACN 15 to 100% gradient) and afforded the title compound (16 mg, 0.031 mmol, 23%) as a pale yellow solid after lyophilisation. $^1$H NMR (500 MHz, DMSO d6) δ 11.87 (s, 1H), 9.88 (s, 1H), 8.59 (s, 1H), 8.47 (d, J=3.0 Hz, 1H), 8.34-8.19 (m, 2H), 7.55 (dd, J=23.5, 6.3 Hz, 1H), 7.49 (d, J=8.0 Hz, 1H), 7.21 (t, J=7.4 Hz, 1H), 7.15 (ddt, J=8.1, 7.1, 1.1 Hz, 1H), 6.56 (dtd, J=11.6, 7.2, 4.2 Hz, 1H), 6.23 (dd, J=15.3, 5.6 Hz, 1H), 4.48 (ddd, J=52.5, 28.1, 15.1 Hz, 1H), 3.91-3.74 (m, 1H), 3.73-3.59 (m, 1H), 3.58-3.43 (m, 1H), 3.34-3.21 (m, 2H), 3.13 (dt, J=20.8, 6.3 Hz, 2H), 3.06-3.00 (m, 1H), 2.74 (s, 3H), 2.50 (s, 3H), 2.32-2.19 (m, 2H), 2.18-2.09 (m, 1H), 2.01 (ddd, J=20.5, 12.5, 7.1 Hz, 1H), 1.60-1.37 (m, 3H); MS (m/z): 524.70 [M+1]$^+$.

Example 4. Synthesis of (Cis,E)-N-(3-(5-chloro-4-(1H-indol-3-yl)pyrimidin-2-ylamino)phenyl)-4-(4-(dimethylamino)but-2-enamido)cyclohexanecarboxamide (Compound 101)

tert-butyl cis-4-(3-(5-chloro-4-(1-(phenylsulfonyl)-1H-indol-3-yl)pyrimidin-2-ylamino)phenylcarbamoyl)cyclohexylcarbamate

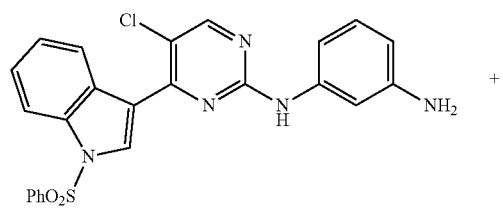

+

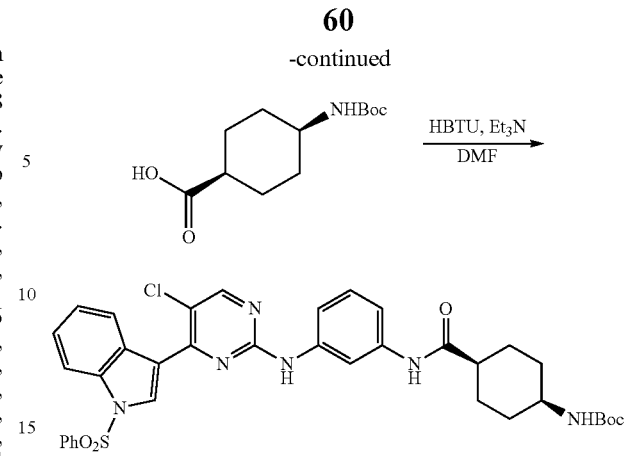

To a solution of N1-(5-chloro-4-(1-(phenylsulfonyl)-1H-indol-3-yl)pyrimidin-2-yl)benzene-1,3-diamine prepared as in Example 1 (123 mg, 0.258 mmol), cis-4-(tert-butoxycarbonylamino) cyclohexanecarboxylic acid (75 mg, 0.31 mmol) and Et$_3$N (108 µL, 0.775 mmol) in DMF (1.7 mL) was added, followed by HBTU (147 mg, 0.388 mmol). The mixture was stirred overnight at rt, diluted with EtOAc (20 mL), washed with sat. NaHCO$_3$ (5 mL), brine (2×5 mL), dried (MgSO$_4$), filtered and evaporated to dryness. The residue was purified by SiO$_2$ chromatography (DCM/EtOAc 10 to 50% gradient) and afforded the title compound (85 mg, 0.121 mmol, 47%) as a white solid.

tert-butyl cis-4-(3-(5-chloro-4-(1H-indol-3-yl)pyrimidin-2-ylamino)phenylcarbamoyl)cyclohexylcarbamate

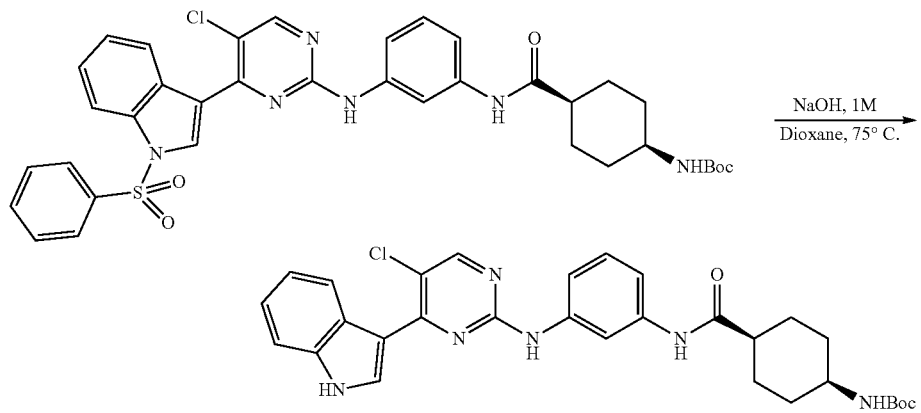

A solution of tert-butyl cis-4-(3-(5-chloro-4-(1-(phenylsulfonyl)-1H-indol-3-yl)pyrimidin-2-ylamino)phenylcarbamoyl)cyclohexylcarbamate (85 mg, 0.121 mmol) and NaOH 5M (0.36 mL, 1.81 mmol) in dioxane (2 mL) was stirred 2.5 h at 75° C. The cooled mixture was concentrated and diluted with DCM (15 mL) and water (10 mL). The aqueous layer was extracted with DCM (3×10 mL), dried (MgSO$_4$), filtered, and evaporated to dryness to afford the title compound (57 mg, 0.102 mmol, 84%) as a white solid which was used in the next step without further purification.

Cis-4-amino-N-(3-(5-chloro-4-(1H-indol-3-yl)pyrimidin-2-ylamino)phenyl) cyclohexanecarboxamide.HCl (Compound 1001)

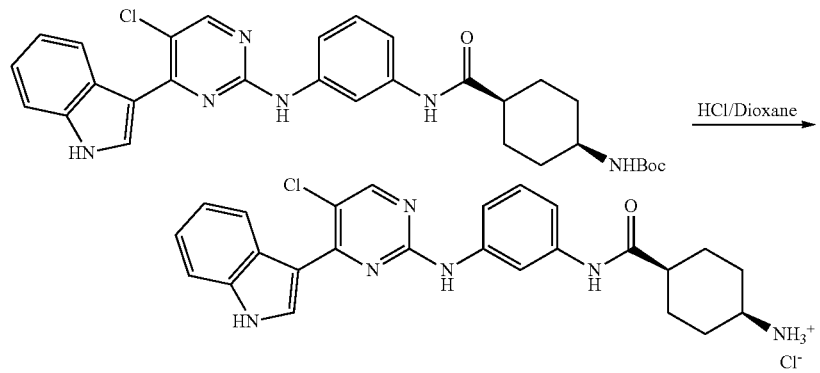

A solution of tert-butyl cis-4-(3-(5-chloro-4-(1H-indol-3-yl)pyrimidin-2-ylamino)phenylcarbamoyl)cyclohexylcarbamate (57 mg, 0.102 mmol) in DCM (0.5 mL) was treated with a 4N solution of HCl in dioxane (0.38 mL, 1.52 mmol). The mixture was stirred 3 h at rt and the resulting solid was filtered and washed several times with DCM to afford the title compound (36 mg, 0.072 mmol, 72%) as a white solid which was used in the next step without further purification.

(Cis,E)-N-(3-(5-chloro-4-(1H-indol-3-yl)pyrimidin-2-ylamino)phenyl)-4-(4-(dimethylamino)but-2-enamido)cyclohexanecarboxamide To a −60° C. solution of cis-4-amino-N-(3-(5-chloro-4-(1H-indol-3-yl)pyrimidin-2-ylamino)phenyl)cyclohexanecarboxamide.HCl (35 mg, 0.070 mmol) and DIPEA (49 μL, 0.281 mmol) in DMF (0.7 mL) was slowly added a 52 mg/mL of (E)-4-bromobut-2-enoyl chloride in THF (0.245 mL, 0.070 mmol). The mixture was stirred 1 h at −60° C. and 1 h at −20° for 1 h before addition of a 2M solution of dimethylamine in THF (280 μL, 0.56 mmol). The mixture was stirred overnight at rt and evaporated to dryness. The residue was purified by reverse phase chromatography (C18, water/ACN 15 to 60% gradient) and afforded the title compound (19 mg, 0.033 mmol, 47%) as a white solid after lyophilisation. $^1$H NMR (500 MHz, DMSO-d6) δ 11.91 (d, J=2.6 Hz, 1H), 9.77 (s, 1H), 9.59 (s, 1H), 8.61 (d, J=7.9 Hz, 1H), 8.52 (d, J=3.1 Hz, 1H), 8.43 (s, 1H), 8.21 (d, J=7.2 Hz, 1H), 7.92 (t, J=1.9 Hz, 1H), 7.49 (d, J=8.1 Hz, 1H), 7.43 (dd, J=8.1, 1.1 Hz, 1H), 7.31 (d, J=8.8 Hz, 1H), 7.24-7.15 (m, 2H), 7.09 (dd, J=11.1, 4.0 Hz, 1H), 6.56 (ddd, J=14.8, 7.7 Hz, 1H), 6.38 (d, J=15.4 Hz, 1H), 3.91 (s, 1H), 3.77 (d, J=5.8 Hz, 2H), 2.71 (s, 3H), 2.49 (s, 4H), 2.46-2.38 (m, 1H), 1.88-1.69 (m, 4H), 1.67-1.52 (m, 3H).

Example 5. Synthesis of (3R,E)-N-(3-(5-chloro-4-(1H-indol-3-yl)pyrimidin-2-ylamino)phenyl)-1-(4-(dimethylamino)but-2-enoyl)piperidine-3-carboxamide (Compound 103)

(3R)-tert-butyl 3-(3-(5-chloro-4-(1-(phenylsulfonyl)-1H-indol-3-yl)pyrimidin-2-ylamino)phenylcarbamoyl)piperidine-1-carboxylate

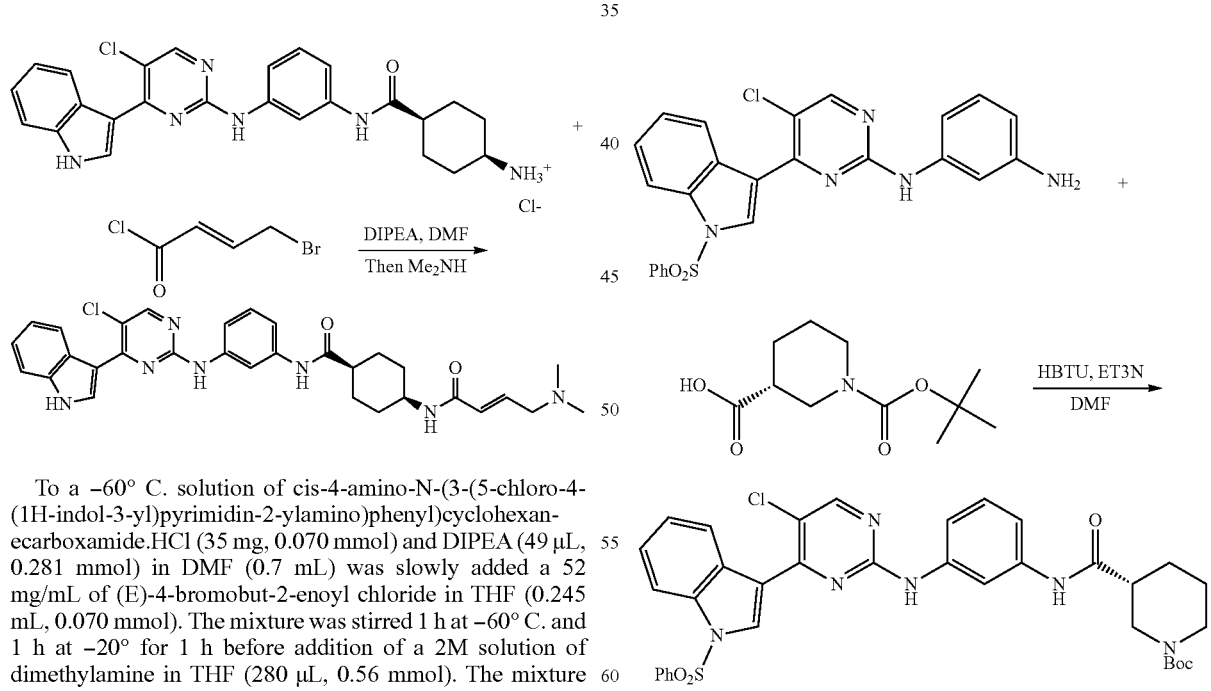

A solution of N1-(5-chloro-4-(1-(phenylsulfonyl)-1H-indol-3-yl)pyrimidin-2-yl)benzene-1,3-diamine prepared as in Example 1 (150 mg, 0.315 mmol), (R)-1-Boc-piperidine 3-carboxylic acid (87 mg, 0.378 mmol), Et$_3$N (132 μL, 0.945 mmol) and HBTU (179 mg, 0.473 mmol) in DMF (2.1 mL)

was stirred overnight at rt. The mixture was diluted with EtOAc (20 mL), washed with sat. NaHCO₃ (5 ml) and brine (2×5 mL), dried (MgSO₄), then filtered and evaporated to dryness. The residue was purified by SiO₂ chromatography (DCM/EtOAc 0 to 45% gradient) and afforded the title compound (184 mg, 0.268 mmol, 85%) as a white solid.

(3R)-tert-butyl 3-(3-(5-chloro-4-(1H-indol-3-yl)py-rimidin-2-ylamino)phenylcarbamoyl)piperidine-1-carboxylate A solution of (3R)-tert-butyl 3-(3-(5-chloro-4-(1-(phenylsulfonyl)-1H-indol-3-yl)pyrimidin-2-ylamino)phenylcarbamoyl)piperidine-1-carboxylate (184 mg, 0.268 mmol) and NaOH 5M (4.02 mmol) in dioxane (4.5 mL) was heated for 1.5 h at 75° C. The cooled mixture was diluted with DCM (20 mL) and sat. NH₄Cl (5 mL). The aqueous layer was extracted with DCM (3×5 mL), dried (phase cartridge separator), and evaporated to dryness. The residue was purified by SiO₂ chromatography (DCM/EtOAc 0 to 60%) and afforded the title compound (114 mg, 0.208 mmol, 78%) as a cream foam.

(3R)—N-(3-(5-chloro-4-(1H-indol-3-yl)pyrmidin-2-ylamino)phenyl)piperidine-3-carboxamide (Compound 1004)

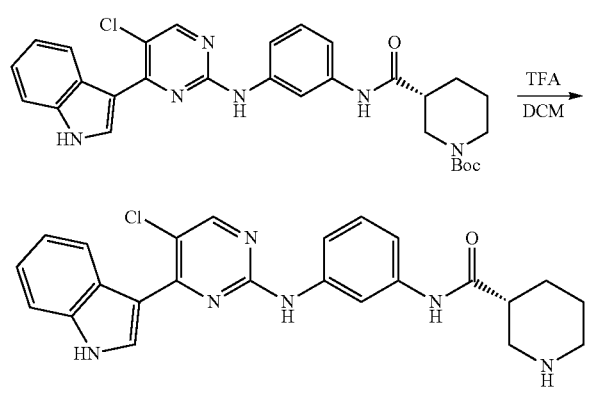

A solution of (3R)-tert-butyl 3-(3-(5-chloro-4-(1H-indol-3-yl)pyrimidin-2-ylamino)phenylcarbamoyl)piperidine-1-carboxylate (114 mg, 0.208 mmol) in DCM (2.1 mL) was treated with TFA (239 μL, 3.13 mmol). The mixture was stirred 3 h at rt before careful addition of sat. NaHCO₃ (10 mL). The aqueous layer was extracted with CHCl₃/IPA 4/1 (3×10 mL), dried (MgSO₄), filtered, then evaporated to dryness to afford the title compound (93 mg, 0.208 mmol, 100%) as a white solid.

(3R,E)-N-(3-(5-chloro-4-(1H-indol-3-yl)pyrimidin-2-ylamino)phenyl)-1-(4-(dimethylamino)but-2-enoyl)piperidine-3-carboxamide

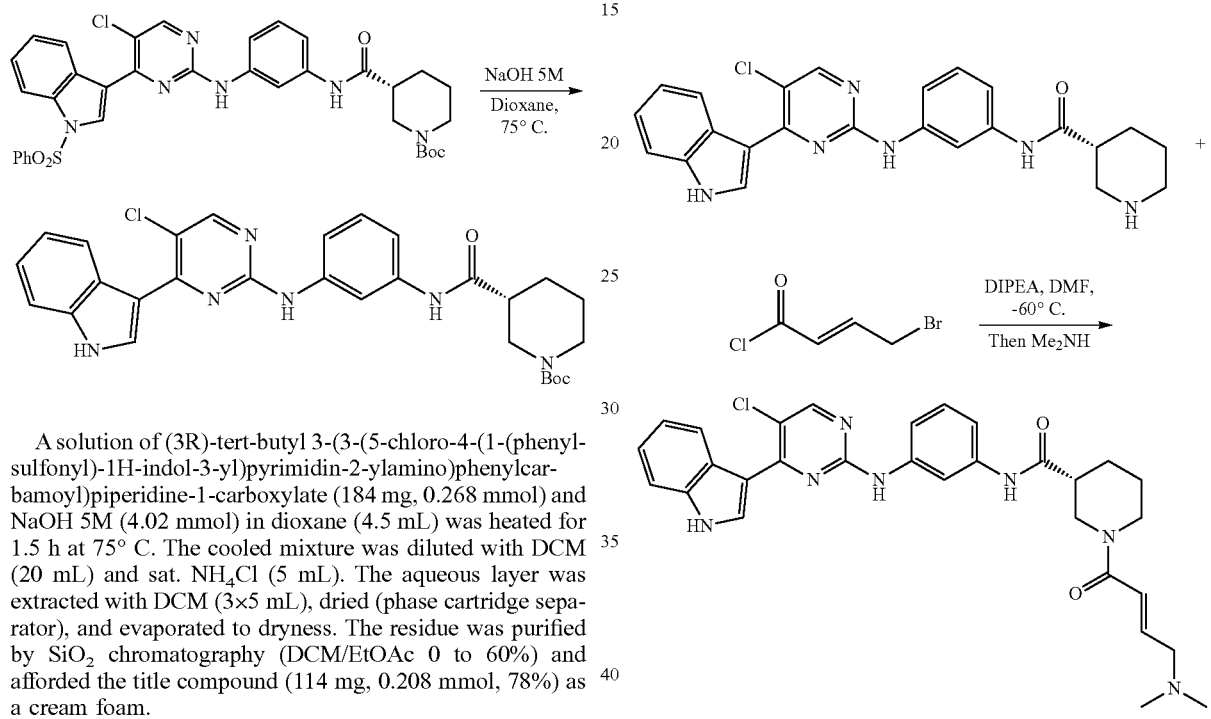

To a −60° C. solution of (3R)—N-(3-(5-chloro-4-(1H-indol-3-yl)pyrimidin-2-ylamino)phenyl)piperidine-3-carboxamide (71 mg, 0.154 mmol) and DIPEA (81 μL, 0.462 mmol) in THF (1 mL) was slowly added a 62 mg/mL solution of (E)-4-bromobut-2-enoyl chloride in THF (0.455 mL, 0.154 mmol). The reaction was stirred 1.5 h at −60° C. before addition of a 2M solution of dimethylamine in THF (462 μL, 0.924 mmol). The mixture was warmed to rt, concentrated under reduced pressure and diluted with CHCl₃/IPA 4/1 (5 mL) and water (5 mL). The aqueous layer was extracted with CHCl₃/IPA 4/1 (3×5 mL), dried (MgSO₄), filtered, and evaporated to dryness to afford the title compound (84 mg, 0.151 mmol, 98%) as a white solid after lyophilization. ¹H NMR (500 MHz, DMSO d6) δ 11.92 (s, 1H), 9.95 (s, 1H), 9.61 (s, 1H), 8.61 (d, J=8.0 Hz, 1H), 8.52 (d, J=2.8 Hz, 1H), 8.44 (s, 1H), 7.95 (s, 1H), 7.50 (d, J=8.1 Hz, 1H), 7.47 (s, 1H), 7.34-7.15 (m, 3H), 7.10 (t, J=7.3 Hz, 1H), 6.70-6.50 (m, 2H), 4.48 (dd, J=19.7, 7.7 Hz, 1H), 4.26 (dd, J=17.2, 8.0 Hz, 1H), 4.15-3.89 (m, 1H), 3.29-3.22 (m, 2H), 3.10-2.95 (m, 2H), 2.74 (dt, J=15.7, 13.1 Hz, 1H), 2.15 (s, 3H), 2.12 (s, 3H) 2.03-1.86 (m, 1H), 1.71 (tdd, J=17.7, 14.4, 5.8 Hz, 2H); MS (m/z): 558.66 [M+1]⁺.

Example 6. Synthesis of (3S,E)-N-(3-(5-chloro-4-(1H-indol-3-yl)pyrimidin-2-ylamino)phenyl)-1-(4-(dimethylamino)but-2-enoyl)piperidine-3-carboxamide (Compound 104)

(3S)-tert-butyl 3-(3-(5-chloro-4-(1-(phenylsulfonyl)-1H-indol-3-yl)pyrimidin-2-ylamino)phenylcarbamoyl)piperidine-1-carboxylate

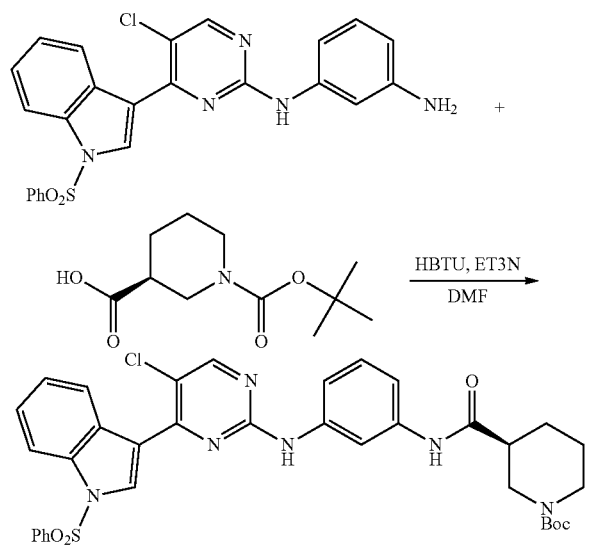

To a solution of N1-(5-chloro-4-(1-(phenylsulfonyl)-1H-indol-3-yl)pyrimidin-2-yl)benzene-1,3-diamine prepared as in Example 1 (193 mg, 0.315 mmol), (S)-1-Boc-piperidine 3-carboxylic acid (86.7 mg, 0.378 mmol) and Et₃N (131 µL, 0.945 mmol) in DMF (2.1 mL) was added, followed by HBTU (179 mg, 0.473 mmol). The mixture was stirred overnight at rt, diluted with EtOAc (20 mL), washed with sat. NaHCO₃ (5 mL) and brine (2×5 mL), dried (MgSO₄), then filtered and evaporated to dryness. The residue was purified by SiO₂ chromatography (DCM/EtOAc 0 to 50% gradient) and afforded the title compound (216 mg, 0.315 mmol, 100%) as a white solid.

(3S)-tert-butyl 3-(3-(5-chloro-4-(1H-indol-3-yl)pyrimidin-2-ylamino)phenylcarbamoyl)piperidine-1-carboxylate A solution of (3S)-tert-butyl 3-(3-(5-chloro-4-(1-(phenylsulfonyl)-1H-indol-3-yl)pyrimidin-2-ylamino)phenylcarbamoyl)piperidine-1-carboxylate (215 mg, 0.312 mmol) and NaOH 5M (939 µL, 4.69 mmol) in dioxane (5.2 mL) was heated 1.5 h at 75° C. The cooled mixture was diluted with DCM (15 mL) and sat. NH₄Cl (5 mL); the aqueous layer was extracted with DCM (3×5 mL) and the combined organic layers were dried (phase cartridge separator) and evaporated to dryness. The residue was purified by SiO₂ chromatography (DCM/EtOAc 0 to 60% gradient) and afforded the title compound (130 mg, 0.238 mmol, 76%) as a cream foam.

(3S)—N-(3-(5-chloro-4-(1H-indol-3-yl)pyrmidin-2-ylamino)phenyl)piperidine-3-carboxamide (Compound 1005)

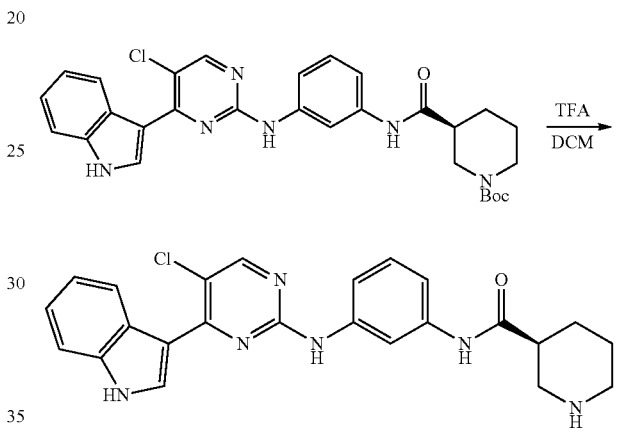

A solution of (3S)-tert-butyl 3-(3-(5-chloro-4-(1H-indol-3-yl)pyrimidin-2-ylamino)phenylcarbamoyl)piperidine-1-carboxylate (130 mg, 0.238 mmol) in DCM (2.4 mL) was treated with TFA (272 µL, 3.56 mmol). The mixture was stirred 3 h at rt before careful addition of sat. NaHCO₃ (10 mL). The aqueous layer was extracted with CHCl₃/IPA 4/1 (3×10 mL), dried (MgSO₄), filtered, then evaporated to dryness to afford the title compound (105 mg, 0.235 mmol, 99%) as a white solid.

(3S,E)-N-(3-(5-chloro-4-(1H-indol-3-yl)pyrmidin-2-ylamino)phenyl)-1-(4-(dimethylamino)but-2-enoyl)piperidine-3-carboxamide

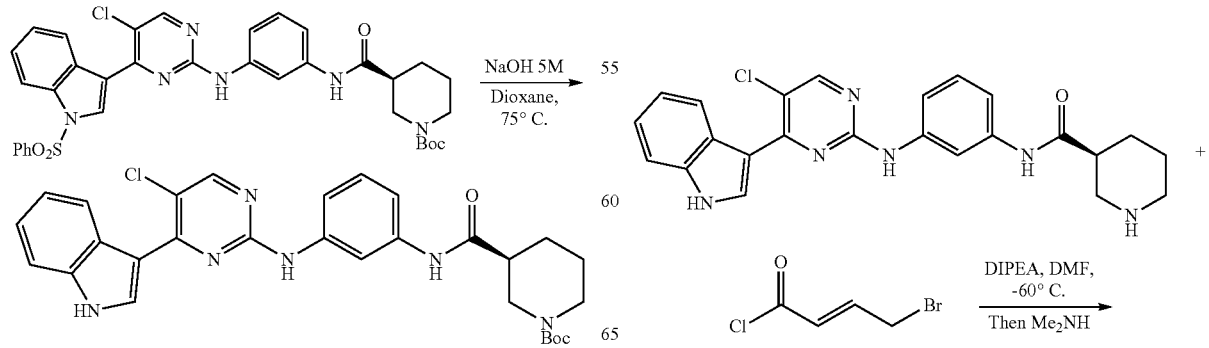

-continued

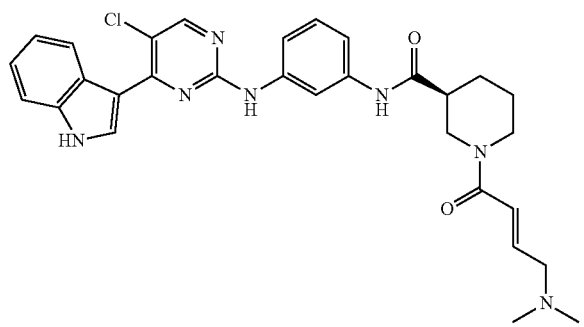

To a −60° C. solution of (3S)—N-(3-(5-chloro-4-(1H-indol-3-yl)pyrimidin-2-ylamino)phenyl)piperidine-3-carboxamide (88 mg, 0.191 mmol) and DIPEA (100 µL, 0.572 mmol) in THF (1 mL) was slowly added a 56 mg/mL solution of (E)-4-bromobut-2-enoyl chloride in THF (0.624 mL, 0.191 mmol). The reaction was stirred 1.5 h at −60° C. before addition of a 2M solution of dimethylamine in THF (573 µL, 1.145 mmol). The mixture was stirred 1 h at rt then concentrated under reduced pressure. The residue was suspended in water, sonicated, then filtered. The solid was washed several times with water and afforded the title compound (73 mg, 0.131 mmol, 69%) as white solid after lyophilization. $^1$H NMR (500 MHz, DMSO d6) δ 11.90 (s, 1H), 9.93 (d, J=9.3 Hz, 1H), 9.61 (s, 1H), 8.61 (d, J=8.2 Hz, 1H), 8.52 (d, J=3.0 Hz, 1H), 8.44 (s, 1H), 7.95 (s, 1H), 7.49 (d, J=8.1 Hz, 1H), 7.47 (d, J=6.6 Hz, 1H), 7.27 (d, J=7.7 Hz, 1H), 7.21 (dt, J=8.0, 4.5 Hz, 1H), 7.10 (t, J=7.4 Hz, 1H), 6.72-6.53 (m, 2H), 4.48 (d, J=13.4 Hz, 1H), 4.26 (d, J=12.5 Hz, 1H), 4.02 (dd, J=25.6, 14.0 Hz, 1H), 3.16-2.98 (m, 2H), 2.84-2.63 (m, 1H), 2.19 (s, 3H), 2.18 (s, 3H), 2.08-1.86 (m, 1H), 1.71 (dt, J=29.0, 14.1 Hz, 1H), 1.50-1.28 (m, 1H); MS (m/z): 558.66 [M+1]$^+$.

Example 7. Synthesis of (trans,E)-N-(3-(5-chloro-4-(1H-indol-3-yl)pyrimidin-2-ylamino)phenyl)-4-(4-(dimethylamino)but-2-enamido)cyclohexanecarboxamide (Compound 102)

tert-butyl trans −4-(3-(5-chloro-4-(1-(phenylsulfonyl)-1H-indol-3-yl)pyrimidin-2-ylamino)phenylcarbamoyl)cyclohexylcarbamate

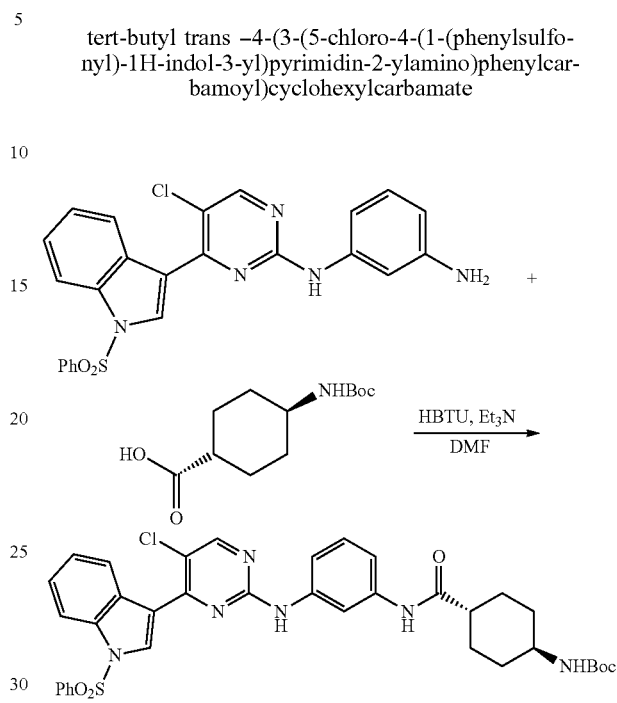

To a solution of N1-(5-chloro-4-(1-(phenylsulfonyl)-1H-indol-3-yl)pyrimidin-2-yl)benzene-1,3-diamine prepared as in Example 1 (123 mg, 0.258 mmol), trans-4-(tert-butoxycarbonylamino) cyclohexanecarboxylic acid (75 mg, 0.31 mmol) and Et$_3$N (108 µL, 0.775 mmol) in DMF (1.7 mL) was added, followed by HBTU (147 mg, 0.388 mmol). The mixture was stirred overnight at rt, diluted with EtOAc (20 mL), washed with sat. NaHCO$_3$ (5 mL) and brine (2×5 mL), dried (MgSO$_4$), then filtered and evaporated to dryness. The residue was purified by SiO$_2$ chromatography (DCM/EtOAc 10 to 50% gradient) and afforded the title compound (85 mg, 0.121 mmol, 47%) as a white solid.

tert-butyl trans-4-(3-(5-chloro-4-(1H-indol-3-yl)pyrimidin-2-ylamino)phenylcarbamoyl) cyclohexylcarbamate

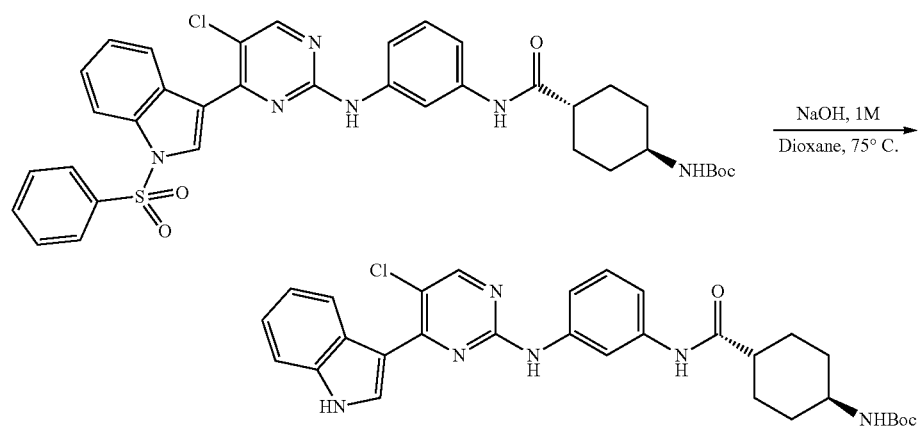

A solution of tert-butyl trans-4-(3-(5-chloro-4-(1-(phenyl-sulfonyl)-1H-indol-3-yl)pyrimidin-2-ylamino)phenylcarbamoyl)cyclohexylcarbamate (85 mg, 0.121 mmol) and NaOH 5M (0.36 mL, 1.81 mmol) in dioxane (2 mL) was stirred 2.5 h at 75° C. The cooled mixture was concentrated, then diluted with DCM (15 mL) and water (10 mL). The aqueous layer was extracted with DCM (3×10 mL), dried (MgSO$_4$), filtered, evaporated to dryness and afforded the title compound (57 mg, 0.102 mmol, 84%) as a white solid which was used in the next step without further purification.

trans-4-amino-N-(3-(5-chloro-4-(1H-indol-3-yl)pyrimidin-2-ylamino)phenyl) cyclohexanecarboxamide.HCl (Compound 1002)

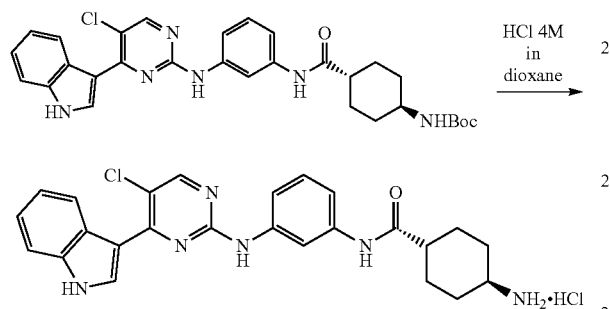

A solution of tert-butyl trans-4-(3-(5-chloro-4-(1H-indol-3-yl)pyrimidin-2-ylamino)phenylcarbamoyl)cyclohexylcarbamate (57 mg, 0.102 mmol) in DCM (0.5 mL) was treated with a 4N solution of HCl in dioxane (0.38 mL, 1.52 mmol). The mixture was stirred 3 h at rt and the resulting solid was filtered and washed several times with DCM to afford the title compound (36 mg, 0.072 mmol, 72%) as a white solid which was used in the next step without further purification.

(trans,E)-N-(3-(5-chloro-4-(1H-indol-3-yl)pyrimidin-2-ylamino)phenyl)-4-(4-(dimethylamino)but-2-enamido)cyclohexanecarboxamide

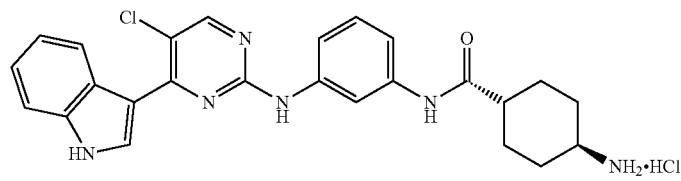

To a −60° C. solution of trans-4-amino-N-(3-(5-chloro-4-(1H-indol-3-yl)pyrimidin-2-ylamino)phenyl)cyclohexanecarboxamide.HCl (35 mg, 0.070 mmol) and DIPEA (49 µL, 0.281 mmol) in DMF (0.7 mL) was slowly added a 52 mg/mL of (E)-4-bromobut-2-enoyl chloride in THF (0.245 mL, 0.070 mmol). The mixture was stirred 1 h at −60° C. and 1 h at −20° for 1 h before addition of a 2M solution of dimethylamine in THF (280 µL, 0.56 mmol). The mixture was stirred overnight at rt and evaporated to dryness. The residue was purified by reverse phase chromatography (C18, water/ACN 15 to 60% gradient) and afforded the title compound (19 mg, 0.033 mmol, 47%) as a white solid after lyophilisation. MS (m/z): 572.59 [M+1]$^+$.

Example 8. Synthesis of N-((1S,3R)-3-(5-chloro-4-(1H-indol-3-yl)pyrimidin-2-ylamino)cyclohexyl)-5-((E)-4-(dimethylamino)but-2-enamido)picolinamide (Compound 106)

(1S,3R)-3-(Benzyloxycarbonylamino)cyclohexylamino 2,2-dimethylpropionate

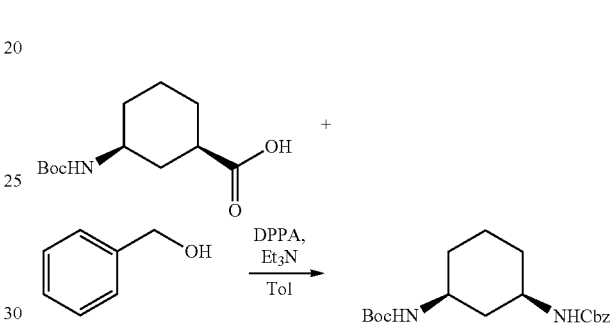

To a solution of (1R,3S)-3-(tert-butoxycarbonylamino) cyclohexanecarboxylic acid (prepared following Tetrahedron: *Asymmetry* 2010 (21), 864-866) (8.77 g, 36.1 mmol) was added Et$_3$N (5.53 mL, 39.7 mmol) and DPPA (7.7 mL, 36.1 mmol). The resulting solution was stirred 2 h at 110° C. then cooled to 80° C. Benzyl alcohol (4.66 mL, 45.1 mmol) and triethylamine (5.53 mL, 39.7 mmol) were added and the mixture was stirred for 20 h at 80° C. The cooled solution was diluted with EtOAc (100 mL) and water (50 mL). The layers were separated and the aqueous layer was extracted with EtOAc (2×50 mL). The combined organics were dried (MgSO$_4$), filtered, and evaporated to dryness. The residue was purified by SiO$_2$ chromatography (Hex/EtOAc 1 to 100% gradient), and afforded the title compound (9.89 g, 28.4 mmol, 79%) as a white solid.

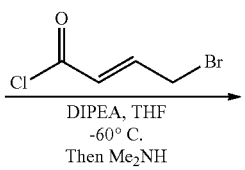
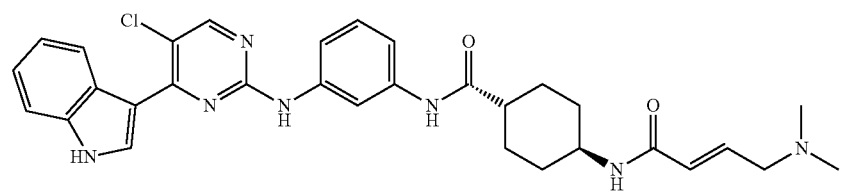

71 tert-butyl(1S,3R)-3-aminocyclohexylcarbamate

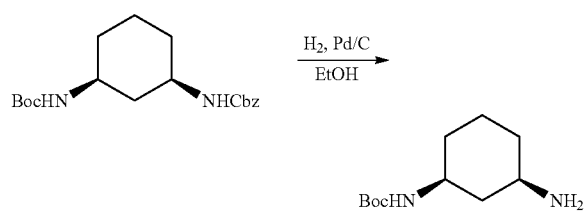

To a degassed solution of (1S,3R)-3-(Benzyloxycarbonylamino)cyclohexylamino 2,2-dimethylpropionate (10 g, 28.4 mmol) in EtOH (473 mL) was added 10% w/w Pd/C (450 mg). The reaction mixture was stirred 5 h under H₂ (1 atm). The reaction mixture was filtered through a pad of celite (EtOH), then the filtrate was evaporated to dryness to afford the title compound (6.08 g, 28.4 mmol, 100%) as a white solid.

tert-butyl (1S,3R)-3-(5-chloro-4-(1-(phenylsulfonyl)-1H-indol-3-yl)pyrimidin-2-ylamino)cyclohexylcarbamate

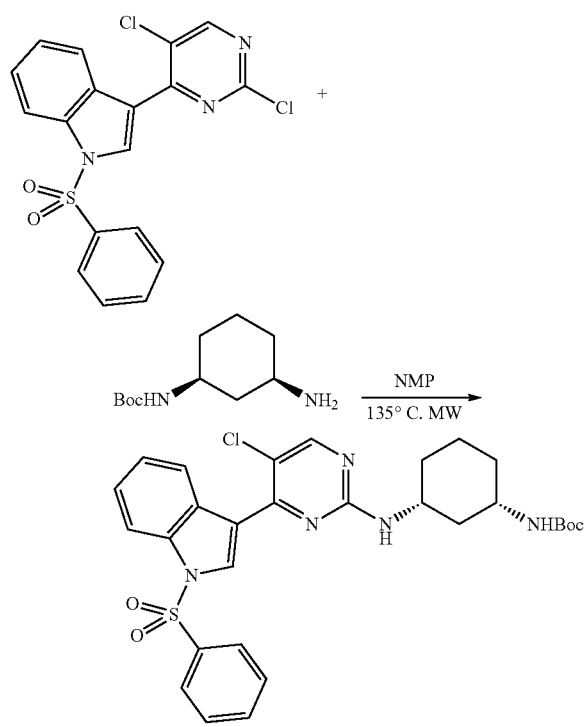

A solution of 3-(2,5-dichloropyrimidin-4-yl)-1-(phenylsulfonyl)-1H-indole (2.91 g, 7.20 mmol), tert-butyl (1S,3R)-3-aminocyclohexylcarbamate (1.24 g, 5.76 mmol) and diisopropylethylamine (1.05 mL, 6.05 mmol) in NMP (14.5 mL) was heated 1.5 h at 135° C. (mW). The mixture was diluted with EtOAc (200 mL), washed with water (50 mL), brine (50 mL), dried (MgSO₄), then filtered and evaporated to dryness. The residue was purified by SiO₂ chromatography (DCM/EtOAc 0 to 30% gradient) and afforded the title compound (1.88 g, 3.23 mmol, 56%) as a light yellow foam.

72

(1R,3S)—N1-(5-chloro-4-(1-(phenylsulfonyl)-1H-indol-3-yl)pyrimidin-2-yl)cyclohexane-1,3-diamine.HCl

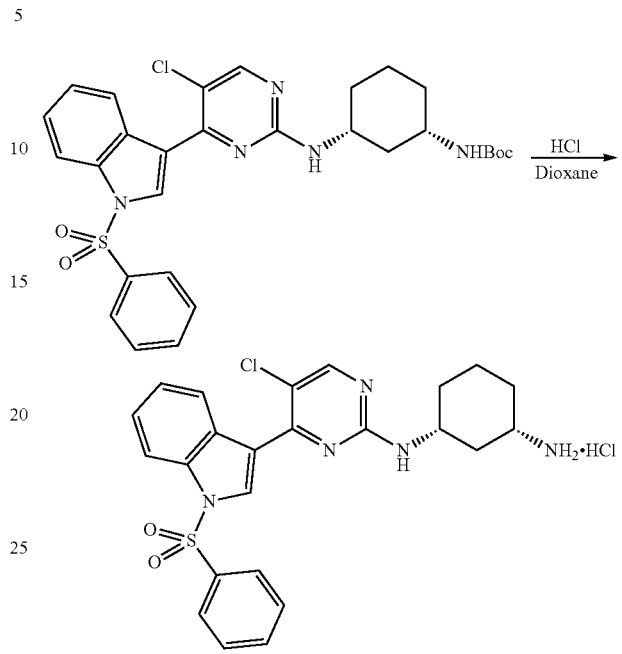

To a solution of tert-butyl (1S,3R)-3-(5-chloro-4-(1-(phenylsulfonyl)-1H-indol-3-yl)pyrimidin-2-ylamino)cyclohexylcarbamate (1.88 g, 3.23 mmol) in DCM (16.1 mL) was added a solution of 4 N HCl in dioxane (12.11 mL, 48.44 mmol). The resulting mixture was stirred 1.5 h at rt before being evaporated to dryness and afforded the title compound (1.72 g, 3.10 mmol, 96%) as a light yellow solid which was used in the next step without further purification.

5-amino-N-((1S,3R)-3-(5-chloro-4-(1-(phenylsulfonyl)-1H-indol-3-yl)pyrimidin-2-ylamino)cyclohexyl)picolinamide

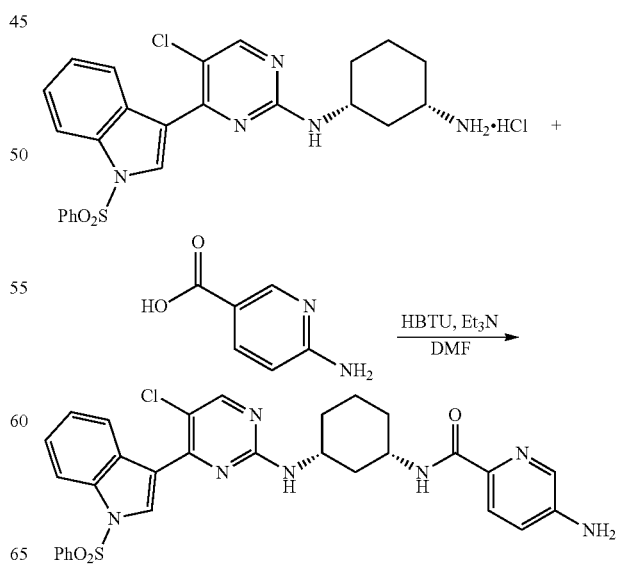

To a solution of (1R,3S)—N1-(5-chloro-4-(1-(phenylsulfonyl)-1H-indol-3-yl)pyrimidin-2-yl)cyclohexane-1,3-diamine.HCl (300 mg, 0.579 mmol) in DMF (4 mL) was added Et₃N (322 µL, 2.315 mmol), 5-amino-2-pyridinecarboxylic acid (96 mg, 0.694 mmol), and HBTU (329 mg, 0.868 mmol). The mixture was stirred overnight at rt and then diluted with EtOAc (20 mL). The mixture was then washed twice with a saturated solution of NaHCO₃ (10 mL) followed by brine (5 mL), then dried (MgSO₄), filtered, and evaporated to dryness. The residue was triturated with MTBE and filtered, and the filtrate was evaporated to dryness which afforded the title compound (282 mg, 0.468 mmol, 81%) as a yellow solid.

5-amino-N-((1S,3R)-3-(5-chloro-4-(1H-indol-3-yl)pyrmidin-2-ylamino)cyclohexyl)picolinamide (Compound 1007)

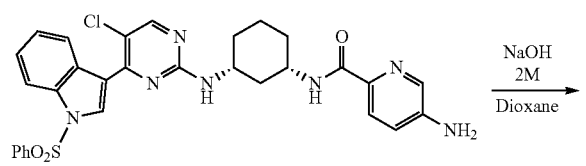

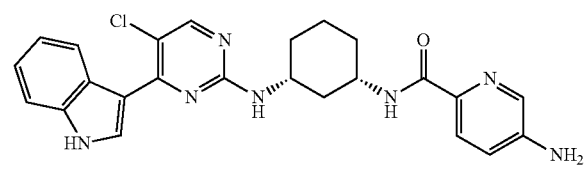

A solution of 5-amino-N-((1S,3R)-3-(5-chloro-4-(1-(phenylsulfonyl)-1H-indol-3-yl)pyrimidin-2-ylamino)cyclohexyl)picolinamide in dioxane (5 mL) was treated with a 2M solution of NaOH (3.5 mL, 7.02 mmol) and heated at 75° C. for 3 h and overnight at rt. The formed solid was filtered and washed several times with water. The solid was dissolved in THF (10 mL) and the resulting solution was evaporated to dryness which afforded the title compound (188 mg, 0.407 mmol, 87%) as a white solid which was used in the next step without further purification.

N-((1S,3R)-3-(5-chloro-4-(1H-indol-3-yl)pyrmidin-2-ylamino)cyclohexyl)-5-((E)-4-(dimethylamino)but-2-enamido)picolinamide

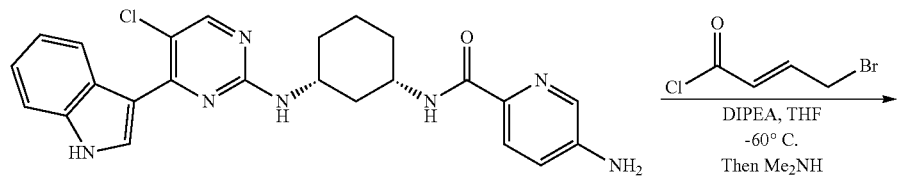

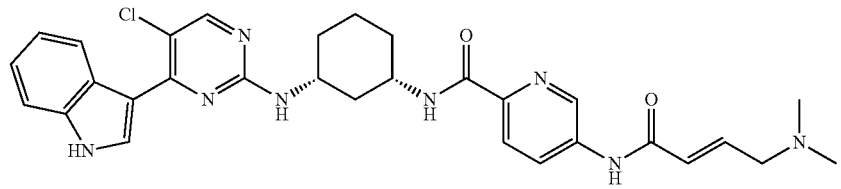

To a −60° C. solution of 5-amino-N-((1S,3R)-3-(5-chloro-4-(1H-indol-3-yl)pyrimidin-2-ylamino)cyclohexyl) picolinamide (188 mg, 0.407 mmol) and DIPEA (212 µL, 1.22 mmol) in 3/1 THF/NMP (3.7 mL) was slowly added a 54 mg/mL of (E)-4-bromobut-2-enoyl chloride in THF (1.37 mL, 0.407 mmol). The mixture was stirred 1 h at −60° C. and 1 h at −20° for 1 h before addition of a 2M solution of dimethylamine in THF (814 µL, 1.63 mmol). The mixture was stirred 2 h at rt and evaporated to dryness. The residue was purified by reverse phase chromatography (C18, water/ACN 0 to 50% gradient) and afforded the title compound (60 mg, 0.105 mmol, 25%) as a white solid after lyophilisation. ¹H NMR (500 MHz, DMSO) δ 11.82 (s, 1H), 10.54 (s, 1H), 8.87 (d, J=2.1 Hz, 1H), 8.61 (bs, 1H), 8.53-8.40 (m, 2H), 8.32-8.14 (m, 2H), 8.01 (d, J=8.6 Hz, 1H), 7.48 (d, J=8.6 Hz, 1H), 7.39-7.08 (m, 3H), 6.80 (dt, J=15.4, 5.8 Hz, 1H), 6.29 (d, J=15.4 Hz, 1H), 3.94 (s, 2H), 3.08 (d, J=5.1 Hz, 2H), 2.18 (s, 6H), 2.10-1.69 (m, 3H), 1.69-1.35 (m, 3H), 1.35-1.18 (m, 1H).

Example 9. Synthesis of N-((1S,3R)-3-(5-cyano-4-(1H-indol-3-yl)pyrimidin-2-ylamino)cyclohexyl)-5-((E)-4-(dimethylamino)but-2-enamido)picolinamide (Compound 110)

tert-butyl(1S,3R)-3-(5-cyano-4-(1-(phenylsulfonyl)-1H-indol-3-yl)pyrimidin-2-ylamino)cyclohexylcarbamate

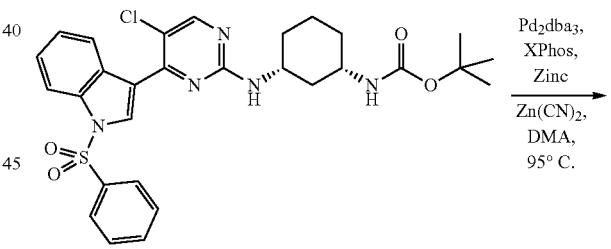

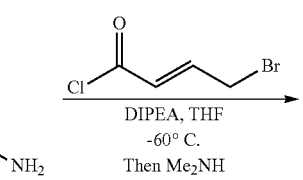

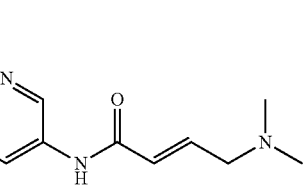

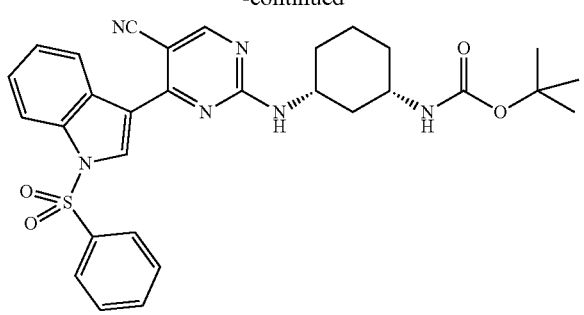

A degassed solution of tert-butyl (1S,3R)-3-(5-chloro-4-(1-(phenylsulfonyl)-1H-indol-3-yl)pyrimidin-2-ylamino)cyclohexylcarbamate prepared as in Example 8 (250 mg, 0.429 mmol), Zn (2.8 mg, 0.04 mmol), $Pd_2dba_3$ (39.3 mg, 0.04 mmol), X-Phos (41 mg, 0.09 mmol) and $Zn(CN)_2$ (30.3 mg, 0.26 mmol) in DMA (8.6 mL) was heated at 95° C. for 18 h. The cooled solution was diluted with EtOAc (20 mL) and washed with water (3×5 mL), brine (5 mL), dried ($MgSO_4$) and evaporated to dryness. The residue was purified by $SiO_2$ chromatography (DCM/EtOAc 0 to 70% gradient) and afforded the title compound (180 mg, 0.314 mmol, 73%) as a bright yellow foam.

2-((1R,3S)-3-aminocyclohexylamino)-4-(1-(phenylsulfonyl)-1H-indol-3-yl)pyrimidine-5-carbonitrile.HCl

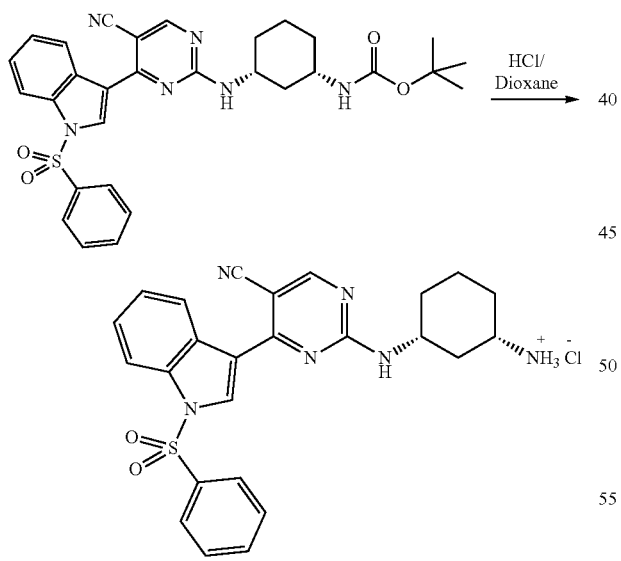

To a solution of tert-butyl (1S,3R)-3-(5-cyano-4-(1-(phenylsulfonyl)-1H-indol-3-yl)pyrimidin-2-ylamino)cyclohexylcarbamate (180 mg, 0.314 mmol) in DCM (3.1 mL) was added a 4M solution of HCl in dioxane (0.79 mL, 3.14 mmol). The mixture was stirred 3 h at rt and evaporated to dryness to afford the title compound (160 mg, 0.314 mmol, 100%) as a white solid which was used in the next step without further purification.

5-amino-N-((1S,3R)-3-(5-cyano-4-(1-(phenylsulfonyl)-1H-indol-3-yl)pyrimidin-2-ylamino)cyclohexyl)picolinamide

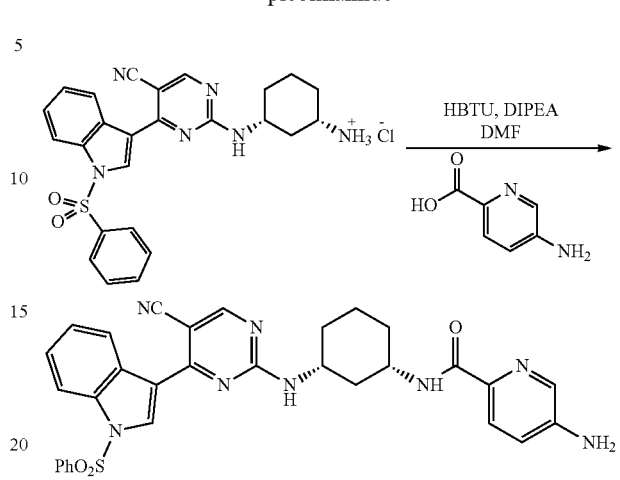

To a solution of 2-((1R,3S)-3-aminocyclohexylamino)-4-(1-(phenylsulfonyl)-1H-indol-3-yl)pyrimidine-5-carbonitrile.HCl (160 mg, 0.338 mmol), 5-amino-2-pyridinecarboxylic acid (56 mg, 0.406 mmol) and DIPEA (236 µL, 1.35 mmol) in DMF (3.4 mL) was added, followed by HBTU (174 mg, 1.352 mmol). The mixture was stirred 16 h at rt then diluted with EtOAc (30 mL) and a saturated solution of $NaHCO_3$ (5 mL). The layers were separated and the aqueous layer was extracted with EtOAc (2×10 ML). The combined organic layers were dried ($MgSO_4$), filtered, and evaporated to dryness. The residue was purified by $SiO_2$ chromatography (EtOAc/DCM 1 to 100% gradient) and afforded the title compound (123 mg, 0.207 mmol, 61%) as a white solid.

5-amino-N-((1S,3R)-3-(5-cyano-4-(1H-indol-3-yl)pyrmidin-2-ylamino)cyclohexyl)picolinamide (Compound 1009)

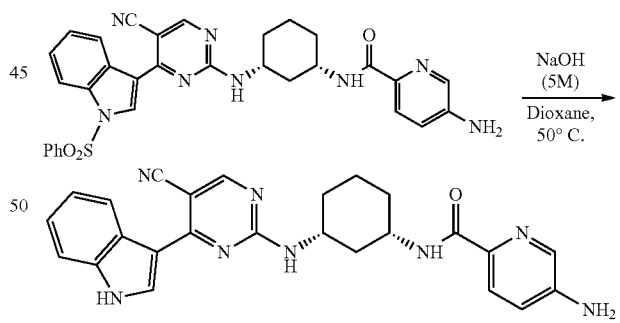

A solution of 5-amino-N-((1S,3R)-3-(5-cyano-4-(1-(phenylsulfonyl)-1H-indol-3-yl)pyrimidin-2-ylamino)cyclohexyl)picolinamide (123 mg, 0.208 mmol) in dioxane (4 mL) was treated with a 5M solution of NaOH (0.210 mL, 1.04 mmol) and heated at 50° C. for 7 h. The cooled solution was diluted with water (5 mL) and the aqueous layer was extracted with methyl-THF (3×10 mL). The combined organic layers were dried ($MgSO_4$), filtered and evaporated to dryness. The residue was purified by reverse phase chromatography (C18, water/ACN 0 to 100% gradient) and afforded the title compound (54 mg, 0.119 mmol, 58%) as a white solid.

N-((1S,3R)-3-(5-cyano-4-(1H-indol-3-yl)pyrmidin-2-ylamino)cyclohexyl)-5-((E)-4-(dimethylamino)but-2-enamido)picolinamide

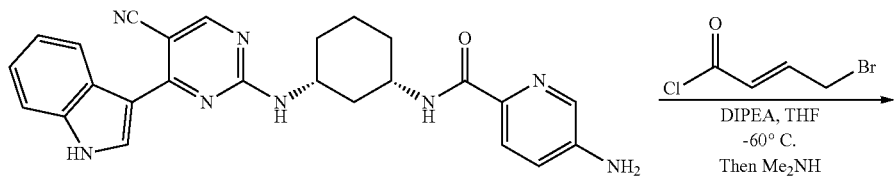

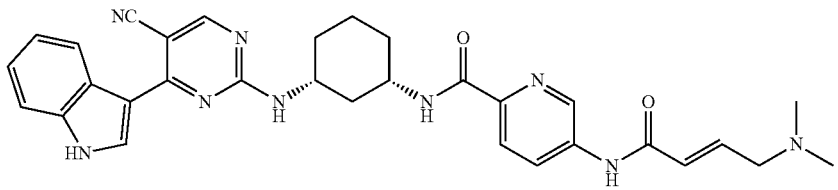

To a −60° C. solution of 5-amino-N-((1S,3R)-3-(5-cyano-4-(1H-indol-3-yl)pyrimidin-2-ylamino)cyclohexyl)picolinamide (50 mg, 0.111 mmol) and DIPEA (58 µL, 0.334 mmol) in 3/1 THF/NMP (4.0 mL) was slowly added a 54 mg/mL of (E)-4-bromobut-2-enoyl chloride in THF (239 µL, 0.117 mmol). The mixture was stirred 4 h at −60° C. h before addition of a 2M solution of dimethylamine in THF (333 µL, 0.667 mmol). The mixture was stirred 2 h at rt and evaporated to dryness. The residue was purified by reverse phase chromatography (C18, water/ACN+0.1% $HCO_2H$ 0 to 100% gradient) and afforded the title compound (35 mg, 0.062 mmol, 56%) as a white solid after lyophilisation. $^1H$ NMR (500 MHz, DMSO) indicated the presence of rotamers. Rotamer 1: δ 12.00 (s, 1H), 10.53 (s, 1H), 8.88 (dd, J=8.6, 2.4 Hz, 1H), 8.57 (s, 1H) 8.57-8.42 (m, 2H), 8.20 (ddd, J=20.8, 8.4, 3.3 Hz, 2H), 8.01 (d, J=8.7 Hz, 1H), 7.52 (dd, J=14.0, 8.0 Hz, 1H), 7.31 (t, J=7.3 Hz, 1H), 7.24 (m, 1H), 6.80 (dt, J=15.4, 5.8 Hz, 1H), 6.29 (d, J=15.5 Hz, 1H), 4.10-3.87 (m, 2H), 3.07 (d, J=5.8 Hz, 2H), 2.27-2.06 (m, 2H), 2.18 (s, 6H), 2.04 (d, J=8.2 Hz, 1H), 1.94-1.79 (m, 2H), 1.64-1.28 (m, 3H). Rotamer 2: δ 11.95 (s, 1H), 10.54 (s, 2H), 8.72 (d, J=7.7 Hz, 1H), 8.65 (s, 1H), 8.57-8.42 (m, 2H), 8.20 (ddd, J=20.8, 8.4, 3.3 Hz, 2H), 8.01 (d, J=8.7 Hz, 2H), 7.52 (dd, J=14.0, 8.0 Hz, 1H), 7.31 (t, J=7.3 Hz, 1H), 7.24 (m, 1H), 6.80 (dt, J=15.4, 5.8 Hz, 1H), 6.29 (d, J=15.5 Hz, 1H), 4.10-3.87 (m, 2H), 3.07 (d, J=5.8 Hz, 2H), 2.27-2.06 (m, 2H), 2.18 (s, 6H), 2.04 (d, J=8.2 Hz, 1H), 1.94-1.79 (m, 2H), 1.64-1.28 (m, 3H); MS (m/z): 563.64 $[M+1]^+$.

Example 10. (E)-N-(3-((1S,3R)-3-(5-chloro-4-(1H-indol-3-yl)pyrimidin-2-ylamino)cyclohexylamino)-2,2-difluoro-3-oxopropyl)-4-(dimethylamino)but-2-enamide (Compound 111)

Ethyl 3-(tert-butoxycarbonylamino)-2,2-difluoropropanoate

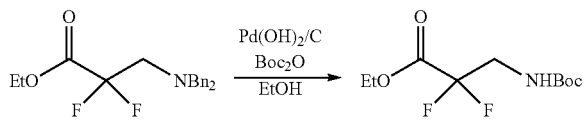

To a degassed solution of ethyl 3-(tert-butoxycarbonylamino)-2,2-difluoropropanoate prepared as described in WO2007062308 (1.463 g, 4.39 mmol) and $Boc_2O$ (2 g, 8.78 mmol) in EtOH (10 mL) was added 20% w/w $Pd(OH)_2/C$ (150 mg) and 10% w/w Pd/C (50 mg). The mixture was stirred overnight under $H_2$ (1 atm.) and filtered over a pad of celite (EtOH). The filtrate was evaporated to dryness and afforded the title compound (1.11 g, 4.39 mmol, 100%) as a light yellow oil which was used in the next step without further purification.

3-(tert-butoxycarbonylamino)-2,2-difluoropropanoic acid

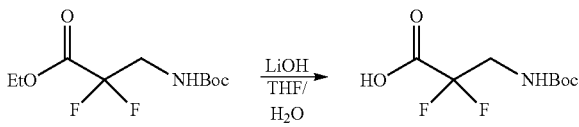 [SMILES: CCOC(=O)C(F)(F)CNC(=O)OC(C)(C)C ; "LiOH" ; "THF/H2O" ; CC(C)(C)OC(=O)NCC(F)(F)C(=O)O]

To a solution of ethyl 3-(tert-butoxycarbonylamino)-2,2-difluoropropanoate (355 mg, 1.40 mmol) in THF (10 mL) was treated with a 2M solution of $LiOH.H_2O$ (2.1 mL, 4.20 mmol). The mixture was stirred overnight at rt and the volatiles were evaporated. A 1M solution of NaOH (5 mL) was added and the mixture was washed with $Et_2O$ (2×5 mL). The aqueous layer was acidified with a 1M aqueous solution of HCl until pH=4 and extracted with EtOAc (4×50 mL). The combined organic layers were dried ($Na_2SO_4$), filtered, and evaporated to dryness affording the title compound (84 mg, 0.373 mmol, 54%) as a colorless oil.

tert-butyl 3-(1S,3R)-3-(5-chloro-4-(1-(phenylsulfo-nyl)-1H-indol-3-yl)pyrmidin-2-ylamino)cyclohexy-lamino)-2,2-difluoro-3-oxopropylcarbamate

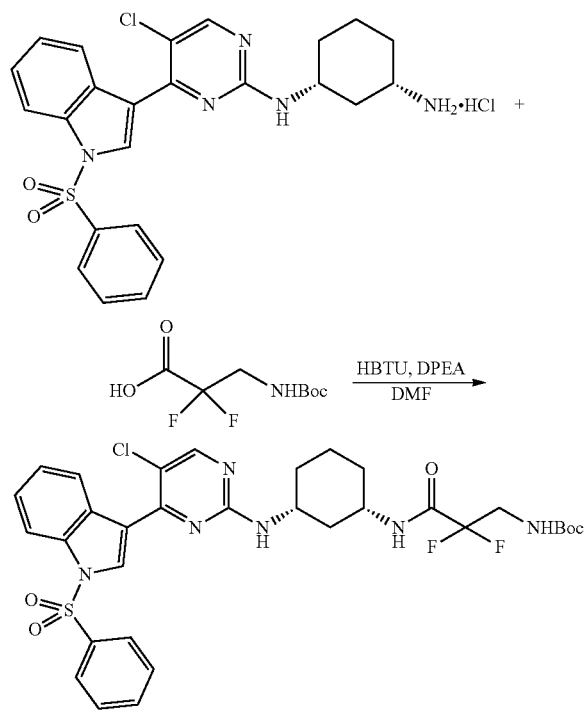

To a solution of 2-((1R,3S)-3-aminocyclohexylamino)-4-(1-(phenylsulfonyl)-1H-indol-3-yl)pyrimidine-5-carboni-trile.HCl prepared as in Example 8 (161 mg, 0.310 mmol), 3-(tert-butoxycarbonylamino)-2,2-difluoropropanoic acid (84 mg, 0.373 mmol) and DIPEA (216 µL, 1.24 mmol) in DMF (3.1 mL) was added, followed by HBTU (177 mg, 0.465 mmol). The mixture was stirred 16 h at rt, then diluted with EtOAc (30 mL) and a saturated solution of NaHCO₃ (5 mL). The layers were separated and the aqueous layer was extracted with EtOAc (2×10 ML). The combined organic layers were dried (MgSO₄), filtered, and evaporated to dryness. The residue was purified by SiO₂ chromatography (DCM/MeOH 0 to 20% gradient) and afforded the title compound (200 mg, 0.290 mmol, 94%) as a white solid.

3-amino-N-((1S,3R)-3-(5-chloro-4-(1-(phenylsulfo-nyl)-1H-indol-3-yl)pyrmidin-2-ylamino)cyclohexyl)-2,2-difluoropropanamide.HCl

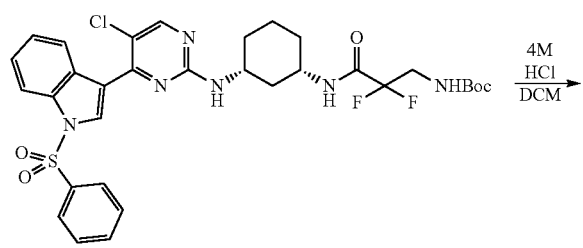

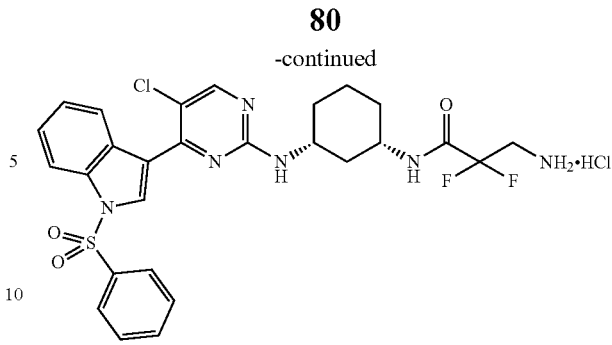

To a solution of tert-butyl 3-((1S,3R)-3-(5-chloro-4-(1-(phenylsulfonyl)-1H-indol-3-yl)pyrimidin-2-ylamino)cy-clohexylamino)-2,2-difluoro-3-oxopropylcarbamate (210 mg, 0.30 mmol) in DCM (3.0 mL) was added a solution of 4 N HCl in dioxane (1.2 mL, 4.57 mmol). The resulting mixture was stirred 2 h at rt before being evaporated to dryness to afford the title compound (188 mg, 0.30 mmol, 100%) as a brown glue which was used in the next step without further purification.

3-amino-N-((1S,3R)-3-(5-chloro-4-(1H-indol-3-yl)pyrimidin-2-ylamino)cyclohexyl)-2,2-difluoropro-panamide (Compound 1010)

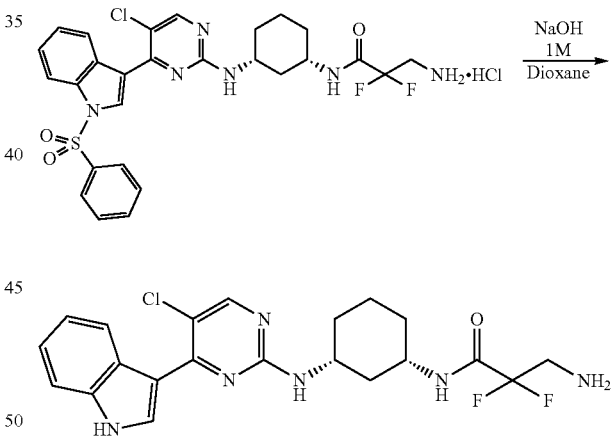

A solution of 3-amino-N-((1S,3R)-3-(5-chloro-4-(1-(phe-nylsulfonyl)-1H-indol-3-yl)pyrimidin-2-ylamino)cyclo-hexyl)-2,2-difluoropropanamide.HCl (188 mg, 0.30 mmol) in dioxane (10 mL) was treated with a 1M solution of NaOH (4.5 mL, 4.5 mmol) and heated at 70° C. for 1 h. The cooled solution was diluted with water (5 mL) and brine (5 mL) and the aqueous layer was extracted with methyl-THF (20 mL). The organic layer was dried (MgSO₄), filtered, and evaporated to dryness. The residue was purified by reverse phase chromatography (C18, water/ACN+0.1% HCO₂H 0 to 100% gradient) and afforded the title compound (41 mg, 0.091 mmol, 30%) as a white solid.

(E)-N-(3-((1S,3R)-3-(5-chloro-4-(1H-indol-3-yl)pyrimidin-2-ylamino)cyclohexylamino)-2,2-difluoro-3-oxopropyl)-4-(dimethylamino)but-2-enamide

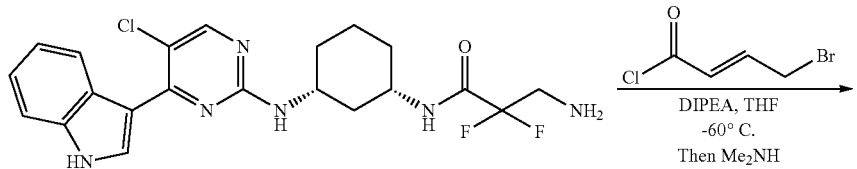

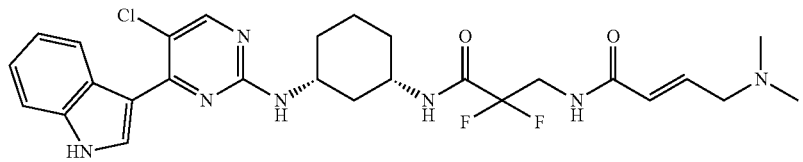

To a −60° C. solution of 3-amino-N-((1S,3R)-3-(5-chloro-4-(1H-indol-3-yl)pyrimidin-2-ylamino)cyclohexyl)-2,2-difluoropropanamide (36 mg, 0.081 mmol) and DIPEA (42 μL, 0.242 mmol) in 3/1 THF/NMP (5.0 mL) was slowly added a 54 mg/mL of (E)-4-bromobut-2-enoyl chloride in THF (273 mL, 0.081 mmol). The mixture was stirred 1 h at −60° C. h before addition of a 2M solution of dimethylamine in THF (242 μL, 0.484 mmol). The mixture was stirred 1 h at rt and evaporated to dryness. The residue was purified by reverse phase chromatography (C18, water/ACN+0.1% HCO₂H 0 to 60% gradient) and afforded the title compound (19 mg, 0.034 mmol, 42%) as a white solid after lyophilisation. $^1$H NMR (500 MHz, DMSO) δ 11.83 (brs, 1H), 8.73 (d, J=7.2 Hz, 1H), 8.54 (brs, 1H), 8.47 (d, J=2.9 Hz, 1H), 8.32 (t, J=6.1 Hz, 1H), 8.23 (s, 1H), 7.49 (d, J=8.7 Hz, 1H), 7.28 (d, J=8.1 Hz, 1H), 7.23-7.10 (m, 2H), 6.58 (dt, J=15.5, 6.1 Hz, 1H), 6.09 (d, J=15.5 Hz, 1H), 3.88-3.72 (m, 4H), 2.95 (dd, J=6.1, 1.2 Hz, 2H), 2.11 (s, 7H), 1.98 (brs, 1H), 1.79 (brs, 2H), 1.48-1.18 (m, 4H); MS (m/z): 560.61 [M+1]⁺.

Example 11. 5-acrylamido-N-((1S,3R)-3-(5-chloro-4-(1H-indol-3-yl)pyrimidin-2-ylamino)cyclohexyl)pyrimidine-2-carboxamide (Compound 112)

5-amino-N-((1S,3R)-3-(5-chloro-4-(1-(phenylsulfonyl)-1H-indol-3-yl)pyrimidin-2-ylamino)cyclohexyl)pyrimidine-2-carboxamide

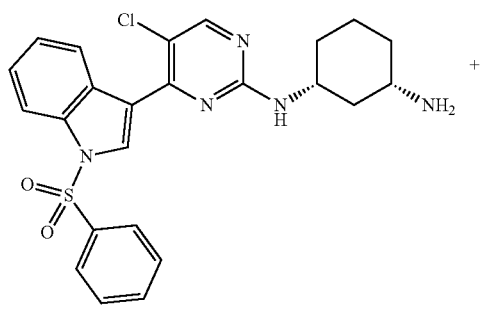

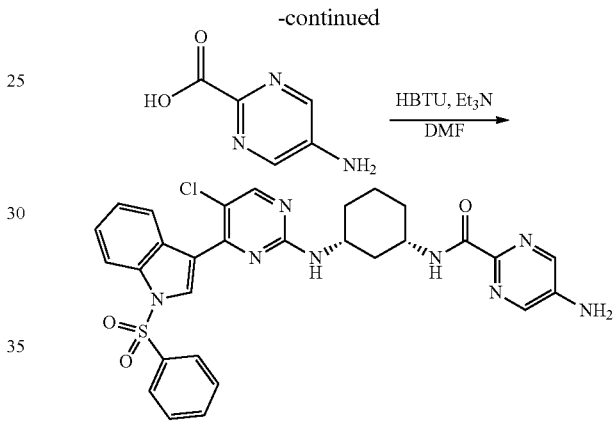

To a solution of 2-(1R,3S)-3-aminocyclohexylamino)-4-(1-(phenylsulfonyl)-1H-indol-3-yl)pyrimidine-5-carbonitrile.HCl prepared as in Example 8 (100 mg, 0.207 mmol), 2-aminopyrimidine-5-carboxylic acid (34 mg, 0.249 mmol) and Et₃N (87 μL, 0.622 mmol) in DMF (1.0 mL) was added, followed by HBTU (118 mg, 0.311 mmol). The mixture was stirred overnight at rt, then diluted with EtOAc (30 mL) and a saturated solution of NaHCO₃ (5 mL). The layers were separated and the organic layer was washed with brine (5 mL), dried (MgSO₄), filtered, and evaporated to dryness affording the title compound (125 mg, 0.207 mmol, 100%) as a pale yellow solid which was used in the next step without further purification.

5-amino-N-((1S,3R)-3-(5-chloro-4-(1H-indol-3-yl)pyrimidin-2-ylamino)cyclohexyl)pyrimidine-2-carboxamide (Compound 1030)

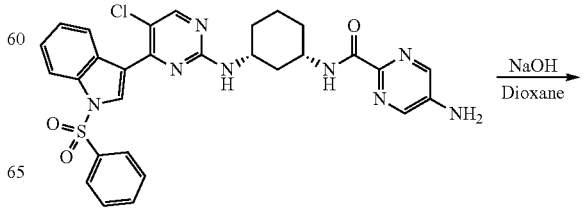

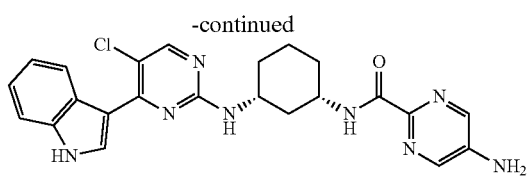

A solution of 5-amino-N-((1S,3R)-3-(5-chloro-4-(1-(phenylsulfonyl)-1H-indol-3-yl)pyrimidin-2-ylamino)cyclohexyl)pyrimidine-2-carboxamide (125 mg, 0.175 mmol) in dioxane (10 mL) was treated with a 2M solution of NaOH (1.31 mL, 2.62 mmol) and heated at 60° C. for 3 h. The cooled solution was diluted with water (5 mL) and the aqueous layer was extracted with methyl-THF (3×20 mL). The combined organic layers were dried (MgSO$_4$), filtered, and evaporated to dryness affording the title compound (81 mg, 0.175 mmol, 100%) as a pale yellow solid which was used in the next step without further purification.

5-acrylamido-N-((1S,3R)-3-(5-chloro-4-(1H-indol-3-yl)pyrimidin-2-ylamino)cyclohexyl)pyrimidine-2-carboxamide

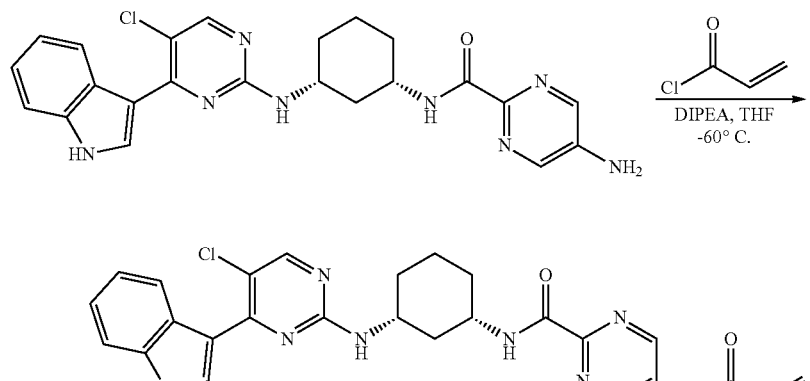

To a −60° C. solution of 5-amino-N-((1S,3R)-3-(5-chloro-4-(1H-indol-3-yl)pyrimidin-2-ylamino)cyclohexyl)pyrimidine-2-carboxamide (14.6 mg, 0.032 mmol) and DIPEA (17 µL, 0.095 mmol) in 3/1 THF/NMP (1.0 mL) was added acryloyl chloride (2.7 µL, 0.033 mmol). The mixture was stirred 1 h at −60° C. and then warmed to rt. The mixture was evaporated to dryness and the residue was purified by reverse phase chromatography (C18, water/ACN+0.1% HCO$_2$H 0 to 70% gradient) to afford the title compound (2.8 mg, 0.0054 mmol, 17%) as a yellow solid after lyophilisation. $^1$H NMR (500 MHz, DMSO) δ 11.83 (s, 1H), 10.80 (s, 1H), 9.17 (s, 2H), 8.70 (s, 2H), 8.47 (d, J=3.0 Hz, 1H), 8.25 (s, 1H), 7.49 (d, J=8.6 Hz, 1H), 7.31 (d, J=3.6 Hz, 1H), 7.26-7.18 (m, 1H), 6.46 (dd, J=17.0, 10.1 Hz, 1H), 6.36 (dd, J=17.0, 1.9 Hz, 1H), 5.90 (dd, J=10.0, 1.9 Hz, 1H), 3.97-3.82 (m, 2H), 2.21 (s, 1H), 1.93-1.79 (m, 2H), 1.61-1.37 (m, 3H); MS (m/z): 517.58 [M+1]$^+$.

Example 12. N-((1S,3R)-3-(5-chloro-4-(1H-indol-3-yl)pyrimidin-2-ylamino)cyclohexyl)-5-((E)-4-(dimethylamino)but-2-enamido)pyrimidine-2-carboxamide (Compound 113)

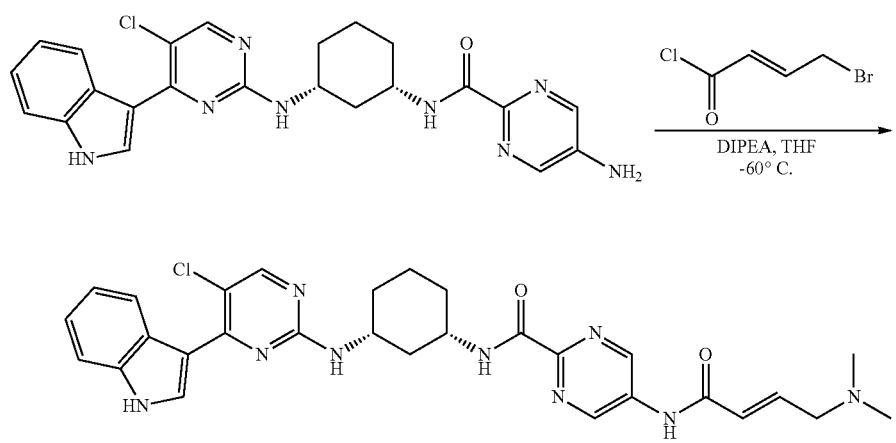

To a −60° C. solution of 5-amino-N-((1S,3R)-3-(5-chloro-4-(1H-indol-3-yl)pyrimidin-2-ylamino)cyclohexyl)pyrimidine-2-carboxamide prepared as in Example 11 (28 mg, 0.060 mmol) and DIPEA (32 μL, 0.181 mmol) in 3/1 THF/NMP (1.5 mL) was slowly added a 54 mg/mL of (E)-4-bromobut-2-enoyl chloride in THF (203 μL, 0.060 mmol). The mixture was stirred 1 h at −60° C. h before addition of a 2M solution of dimethylamine in THF (33 μL, 0.067 mmol). The mixture was stirred 1 h at rt and evaporated to dryness. The residue was purified by reverse phase chromatography (C18, water/ACN+0.1% HCO$_2$H 0 to 70% gradient) and afforded the title compound (3.85 mg, 0.007 mmol, 11%) as a light yellow solid after lyophilisation. MS (m/z): 574.64 [M+1]$^+$.

Example 13. (E)-N-(1-((4-(5-chloro-4-(1H-indol-3-yl)pyrimidin-2-ylamino)-1-hydroxycyclohexyl)methyl)-1H-pyrazol-4-yl)-4-(dimethylamino)but-2-enamide (Compound 114)

tert-butyl 1-oxaspiro[2.5]octan-6-ylcarbamate

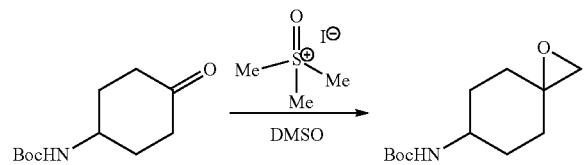 [SMILES: CC(C)(C)OC(=O)NC1CCC(=O)CC1 ; C[S+](C)(C)=O ; [I-] ; CC(C)(C)OC(=O)NC1CCC2(CC1)CO2]

A solution of Me$_3$SOI (2.47 g, 11.25 mmol) in DMSO (15.6 mL) was treated with a 60% suspension of NaH in oil (413 mg, 10.31 mmol) and stirred 1 h at rt, at which point N-Boc-4-aminocyclohexanone (1.00 g, 4.689 mmol) was added. The resulting mixture was stirred overnight at rt before addition of water (50 mL) and hexanes (50 mL). The layers were separated and the aqueous layer was extracted with hexanes (2×50 mL). The combined organic layers were dried (MgSO$_4$), filtered, and evaporated to dryness leaving the title compound (453 mg, 2.00 mmol, 43%) as a white solid which was used in the next step without further purification.

tert-butyl 4-hydroxy-4-((4-nitro-1H-pyrazol-1-yl)methyl)cyclohexylcarbamate

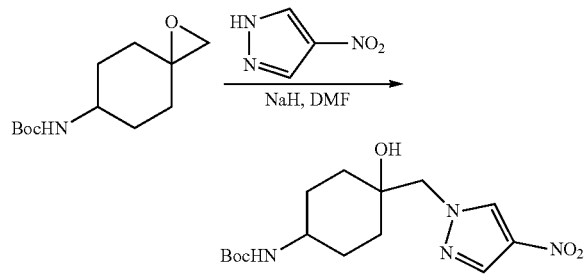

A cooled (0° C.) solution of 4-nitro-1H-pyrazole (1.13 g, 9.96 mmol) in DMF (10 mL) was treated with a 60% suspension of NaH in oil (199 mg, 4.98 mmol) and stirred 20 min at 0° C. before addition of tert-butyl 4-methylenecyclohexylcarbamate oxide (453 mg, 1.99 mmol). The resulting mixture was stirred at 60° C. overnight. The cooled mixture was diluted with water (20 mL) and DCM (20 mL). The layers were separated and the aqueous layer was extracted with DCM (2×20 mL). The combined organic layers were dried (MgSO$_4$), filtered and evaporated to dryness. The residue was purified by SiO$_2$ chromatography (Hex/EtOAc 0 to 80% gradient) and afforded the title compound (360 mg, 0.0.531 mmol, 53%) as a colorless oil.

4-amino-1-((4-nitro-1H-pyrazol-1-yl)methyl)cyclohexanol.HCl

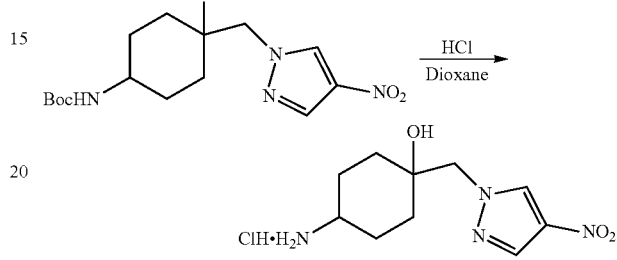

A solution of tert-butyl 4-hydroxy-4-((4-nitro-1H-pyrazol-1-yl)methyl)cyclohexylcarbamate (360 mg, 1.06 mmol) in DCM (5.3 mL) was treated with a 4M HCl solution in dioxane (2.6 mL, 10.58 mmol) and stirred 2 h at rt. The mixture was evaporated to dryness and afforded the title compound (294 mg, 1.06 mmol, 100%) as a white solid which was used in the next step without further purification.

4-(5-chloro-4-(1-(phenylsulfonyl)-1H-indol-3-yl)pyrimidin-2-ylamino)-1-((4-nitro-1H-pyrazol-1-yl)methyl)cyclohexanol

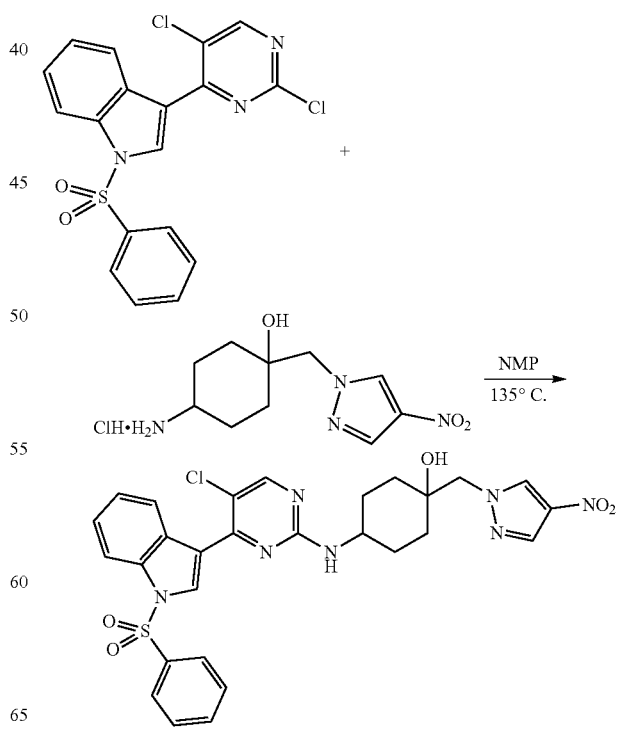

A solution of 3-(2,5-dichloropyrimidin-4-yl)-1-(phenylsulfonyl)-1H-indole (460 mg, 1.14 mmol), 4-amino-1-((4-nitro-1H-pyrazol-1-yl)methyl)cyclohexanol.HCl (287 mg, 1.20 mmol) and DIPEA (0.60 µL, 3.42 mmol) in NMP (12 mL) was heated at 135° C. (microwave) for 50 min. The cooled mixture was diluted with EtOAc (40 mL), washed with water (10 mL), brine (10 mL), dried (MgSO₄), then filtered and evaporated to dryness. The residue was purified by SiO₂ chromatography (DCM/EtOAc 0 to 50% gradient) and afforded the title compound (187 mg, 0.308 mmol, 27%) as a light yellow oil.

1-((4-amino-1H-pyrazol-1-yl)methyl)-4-(5-chloro-4-(1-(phenylsulfonyl)-1H-indol-3-yl)pyrimidin-2-ylamino)cyclohexanol

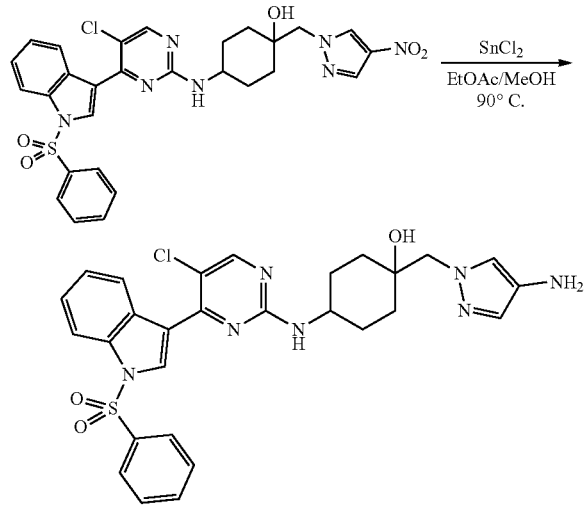

A solution of 4-(5-chloro-4-(1-(phenylsulfonyl)-1H-indol-3-yl)pyrimidin-2-ylamino)-1-((4-nitro-1H-pyrazol-1-yl)methyl)cyclohexanol (187 mg, 0.308 mmol) in 5/1 EtOAc/IPA (6 mL) was treated with SnCl₂.2H₂O (173 mg, 0.769 mmol) and heated at 70° C. overnight. The cooled mixture was diluted with methyl-THF (20 mL) and a saturated solution of NaHCO₃ (10 mL). The mixture was stirred 30 min at rt and the layers were separated. The aqueous layer was extracted with methyl-THF (3×20 mL) and the combined organic layers were dried (MgSO₄), filtered and evaporated to dryness. The residue was purified by SiO₂ chromatography (DCM/MeOH 0 to 15% gradient) and afforded the title compound (97 mg, 0.168 mmol, 55%) as a 1/1 bright orange mixture with the IPA adduct.

1-((4-amino-1H-pyrazol-1-yl)methyl)-4-(5-chloro-4-(1H-indol-3-yl)pyrimidin-2-ylamino)cyclohexanol (Compound 1031)

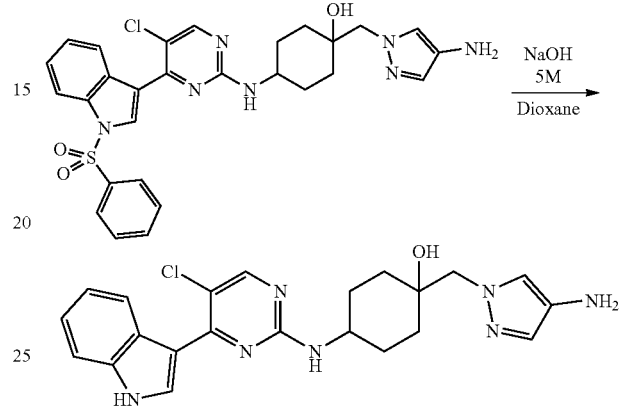

A solution of 1-((4-amino-1H-pyrazol-1-yl)methyl)-4-(5-chloro-4-(1-(phenylsulfonyl)-1H-indol-3-yl)pyrimidin-2-ylamino)cyclohexanol (97 mg, 0.153 mmol) in dioxane (5 mL) was treated with a 5M solution of NaOH (0.31 mL, 1.52 mmol) and heated at 70° C. for 5 h. The cooled solution was diluted with water (10 mL) and the aqueous layer was extracted with methyl-THF (3×25 mL). The combined organic layers were dried (MgSO₄), filtered, and evaporated to dryness. The residue was purified by reverse phase chromatography (C18, water/ACN+0.1% HCO₂H 0 to 100% gradient) and afforded the title compound (15 mg, 0.034 mmol, 23%) as a white solid.

(E)-N-(1-((4-(5-chloro-4-(1H-indol-3-yl)pyrimidin-2-ylamino)-1-hydroxycyclohexyl)methyl)-1H-pyrazol-4-yl)-4-(dimethylamino)but-2-enamide

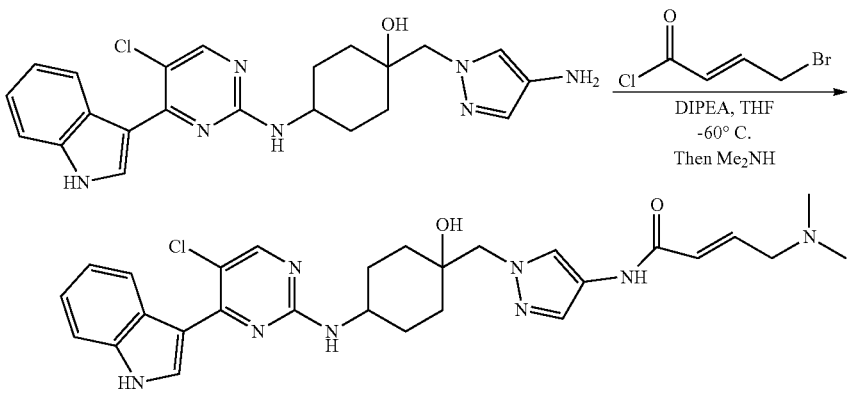

To a −60° C. solution of 1-((4-amino-1H-pyrazol-1-yl)methyl)-4-(5-chloro-4-(1H-indol-3-yl)pyrimidin-2-ylamino)cyclohexanol (13 mg, 0.0297 mmol) and DIPEA (16 µL, 0.0891 mmol) in 2/1 THF/NMP (1.5 mL) was slowly added a 54 mg/mL of (E)-4-bromobut-2-enoyl chloride in THF (105 mL, 0.0312 mmol). The mixture was stirred 1 h at −60° C. h before addition of a 2M solution of dimethylamine in THF (178 µL, 0.356 mmol). The mixture was stirred 1 h at rt and evaporated to dryness. The residue was purified by reverse phase chromatography (C18, water/ACN+0.1% HCO₂H 0 to 70% gradient) and afforded the title compound (12.1 mg, 0.022 mmol, 74%) as a white solid after lyophilisation. ¹H NMR (500 MHz, DMSO) δ 11.81 (s, 1H), 10.15 (s, 1H), 8.51 (br s, 1H), 8.47 (s, 1H), 8.20 (s, 1H), 7.98 (s, 1H), 7.47-7.45 (m, 2H), 7.22-7.05 (m, 3H), 6.66 (ddd, J=15.4, 12.7, 6.6 Hz, 1H), 6.16 (t, J=15.0 Hz, 1H), 4.55 (br s, 1H), 4.06 (d, J=29.3 Hz, 2H), 3.67 (br s, 1H), 3.17 (s, 3H), 3.03 (dd, J=13.6, 6.3 Hz, 2H), 2.17 (s, 3H), 1.90-1.61 (m, 8H); MS (m/z): 549.64 [M+1]⁺.

Example 14. (S)-1-acryloyl-N-((1S,3R)-3-(5-chloro-4-(1H-indol-3-yl)pyrimidin-2-ylamino)cyclohexyl)pyrrolidine-2-carboxamide (Compound 115)

(S)-tert-butyl 2-((1S,3R)-3-(5-chloro-4-(1-phenyl-sulfonyl)-1H-indol-3-yl)pyrimidin-2-ylamino)cyclo-hexylcarbamoyl)pyrrolidine-1-carboxylate

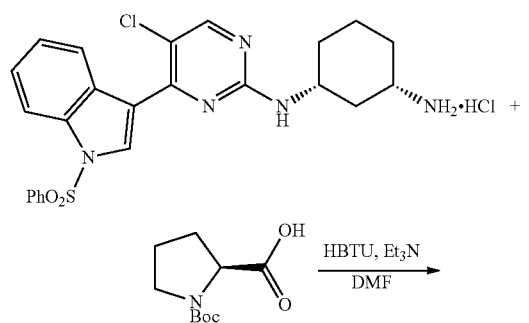

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), N-tert-butyoxycarbonyl-L-proline (74 mg, 0.347 mmol) and Et₃N (121 µL, 0.868 mmol) in DMF (2.0 mL) was added, followed by HBTU (165 mg, 0.434 mmol). The mixture was stirred 2 h at rt, then diluted with EtOAc (30 mL) and a saturated solution of NaHCO₃ (5 mL). The layers were separated and the organic layer was washed with brine (2×5 mL), dried (MgSO₄), then filtered and evaporated to dryness. The residue was purified by SiO₂ chromatography (DCM/EtOAc 0 to 50% gradient) and afforded the title compound (145 mg, 0.214 mmol, 74%) as a yellow solid.

(S)-tert-butyl 2-((1S,3R)-3-(5-chloro-4-(1H-indol-3-yl)pyrimidin-2-ylamino)cyclohexylcarbamoyl)pyrolidine-1-carboxylate

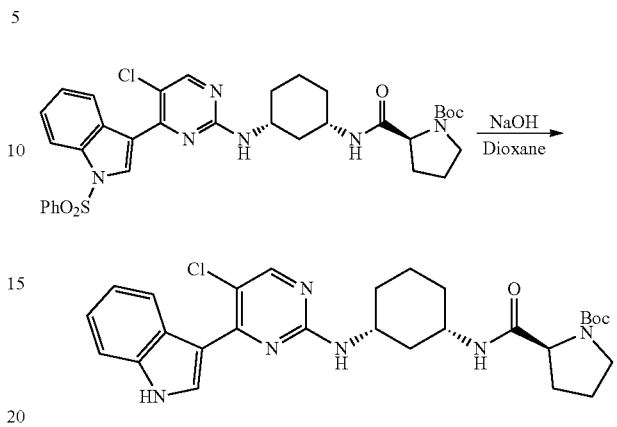

A solution of (S)-tert-butyl 2-((1S,3R)-3-(5-chloro-4-(1-(phenylsulfonyl)-1H-indol-3-yl)pyrimidin-2-ylamino)cy-clohexylcarbamoyl)pyrrolidine-1-carboxylate (145 mg, 0.214 mmol) in dioxane (2.0 mL) was treated with a 2M solution of NaOH (1.60 mL, 3.20 mmol) and heated at 70° C. for 3 h. The cooled solution was diluted with water (5 mL) and the aqueous layer was extracted with methyl-THF (3×20 mL). The combined organic layers were dried (MgSO₄), filtered and evaporated to dryness affording the title compound (99 mg, 0.184 mmol, 86%) as a pale yellow solid which was used in the next step without further purification.

(S)—N-((1S,3R)-3-(5-chloro-4-(1H-indol-3-yl)pyr-midin-2-ylamino)cyclohexyl)pyrrolidine-2-carbox-amide.HCl (Compound 1032)

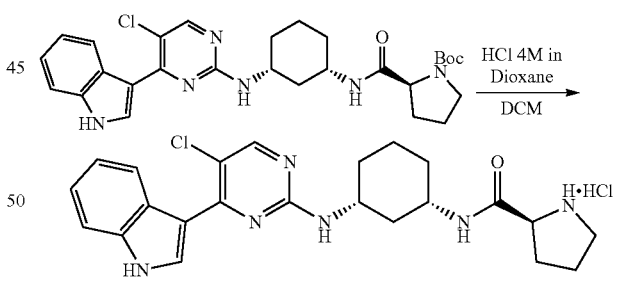

To a solution of (S)-tert-butyl 2-((1S,3R)-3-(5-chloro-4-(1H-indol-3-yl)pyrimidin-2-ylamino)cyclohexylcarbamoyl)pyrrolidine-1-carboxylate (101 mg, 0.187 mmol) in DCM (2.0 mL) was added a solution of 4 N HCl HCl in dioxane (0.703 mL, 2.81 mmol). The resulting mixture was stirred overnight at rt before being evaporated to dryness and afforded the title compound (89 mg, 0.187 mmol, 100%) as a yellow solid which was used in the next step without further purification.

(S)-1-acryloyl-N-((1S,3R)-3-(5-chloro-4-(1H-indol-3-yl)pyrimidin-2-ylamino)cyclohexyl)pyrolidine-2-carboxamide

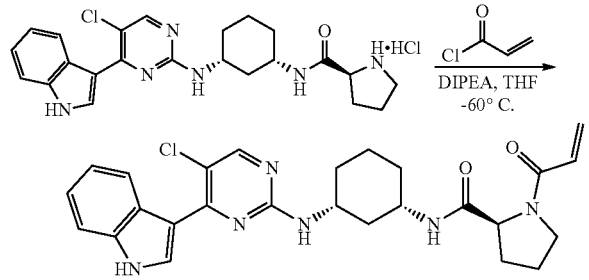

To a −60° C. solution of (S)—N-((1S,3R)-3-(5-chloro-4-(1H-indol-3-yl)pyrimidin-2-ylamino)cyclohexyl)pyrrolidine-2-carboxamide.HCl (90 mg, 0.189 mmol) and DIPEA (132 µL, 0.757 mmol) in 5/1 THF/NMP (4.5 mL) was added acryloyl chloride (16.2 µL, 0.199 mmol). The mixture was stirred 2 h at −20° C. and then warmed to rt. The mixture was evaporated to dryness and the residue was purified by reverse phase chromatography (C18, water/ACN+0.1% HCO₂H 0 to 100% gradient) and afforded the title compound (45 mg, 0.091 mmol, 49%) as a yellow solid after lyophilisation. MS (m/z): 493.58 [M+1]⁺.

Example 15. (R)-1-acryloyl-N-((1S,3R)-3-(5-chloro-4-(1H-indol-3-yl)pyrimidin-2-ylamino)cyclohexyl)pyrrolidine-2-carboxamide (Compound 173)

(R)-tert-butyl 2-((1S,3R)-3-(5-chloro-4-(1-(phenylsulfonyl)-1H-indol-3-yl)pyrimidin-2-ylamino)cyclohexylcarbamoyl)pyrrolidine-1-carboxylate

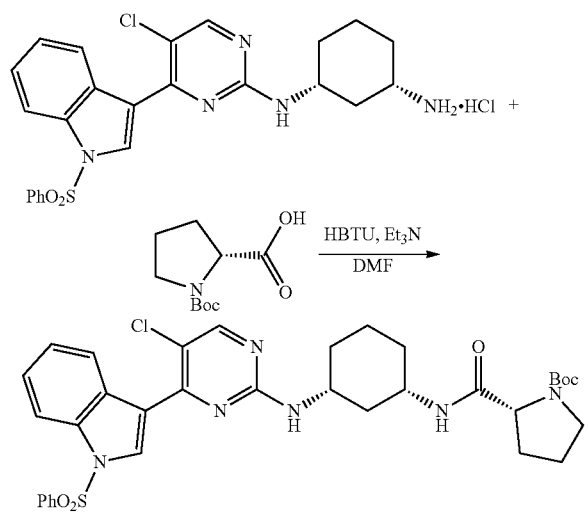

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), N-tert-butyoxycarbonyl-D-proline (74 mg, 0.347 mmol) and Et₃N (121 µL, 0.868 mmol) in DMF (2.0 mL) was added, followed by HBTU (165 mg, 0.434 mmol). The mixture was stirred 2 h at rt, then diluted with EtOAc (30 mL) and a saturated solution of NaHCO₃ (5 mL). The layers were separated and the organic layer was washed with brine (2×5 mL), dried (MgSO₄), filtered and evaporated to dryness. The residue was purified by SiO₂ chromatography (DCM/EtOAc 0 to 50% gradient) and afforded the title compound (113 mg, 0.166 mmol, 58%) as a pale yellow solid.

(R)-tert-butyl 2-((1S,3R)-3-(5-chloro-4-(1H-indol-3-yl)pyrimidin-2-ylamino)cyclohexylcarbamoyl)pyrrolidine-1-carboxylate

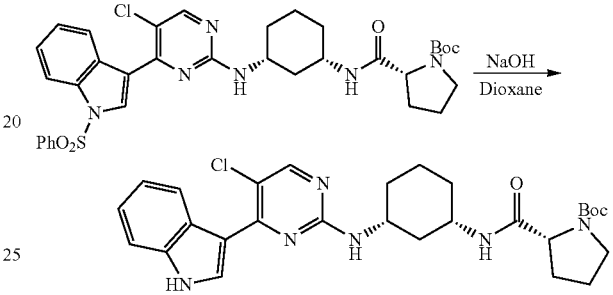

A solution of (R)-tert-butyl 2-((1S,3R)-3-(5-chloro-4-(1-(phenylsulfonyl)-1H-indol-3-yl)pyrimidin-2-ylamino)cyclohexylcarbamoyl)pyrrolidine-1-carboxylate (113 mg, 0.166 mmol) in dioxane (2.0 mL) was treated with a 2M solution of NaOH (1.25 mL, 2.49 mmol) and heated at 70° C. for 3 h. The cooled solution was diluted with water (5 mL) and the aqueous layer was extracted with DCM (3×20 mL). The combined organic layers were dried (MgSO₄), filtered and evaporated to dryness affording the title compound (85 mg, 0.158 mmol, 95%) as a pale yellow solid which was used in the next step without further purification.

(R)—N-((1S,3R)-3-(5-chloro-4-(1H-indol-3-yl)pyrimidin-2-ylamino)cyclohexyl)pyrrolidine-2-carboxamide.HCl (Compound 1033)

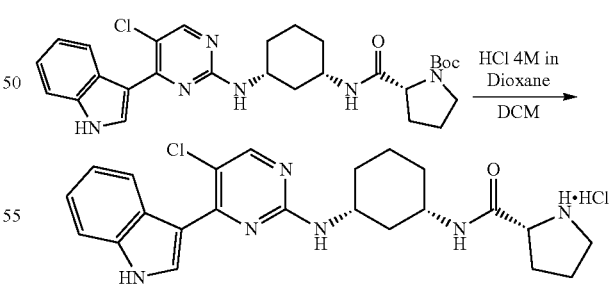

To a solution of (R)-tert-butyl 2-((1S,3R)-3-(5-chloro-4-(1H-indol-3-yl)pyrimidin-2-ylamino)cyclohexylcarbamoyl)pyrrolidine-1-carboxylate (60 mg, 0.166 mmol) in DCM (1.6 mL) was added a solution of 4 N HCl in dioxane (0.624 mL, 2.50 mmol). The resulting mixture was stirred 4 h at rt before being evaporated to dryness and afforded the title compound (78 mg, 0.164 mmol, 99%) as a yellow solid which was used in the next step without further purification.

(R)-1-acryloyl-N-((1S,3R)-3-(5-chloro-4-(1H-indol-3-yl)pyrimidin-2-ylamino)cyclohexyl)pyrolidine-2-carboxamide

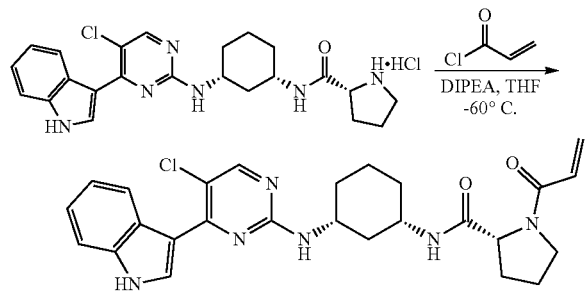

To a –60° C. solution of (R)—N-((1S,3R)-3-(5-chloro-4-(1H-indol-3-yl)pyrimidin-2-ylamino)cyclohexyl)pyrrolidine-2-carboxamide.HCl (79 mg, 0.166 mmol) and DIPEA (116 µL, 0.665 mmol) in 5/1 THF/NMP (3.8 mL) was added acryloyl chloride (14.2 µL, 0.175 mmol). The mixture was stirred 1 h at –20° C. and then warmed to rt. The mixture was evaporated to dryness and the residue was purified by reverse phase chromatography (C18, water/ACN+0.1% HCO₂H 0 to 100% gradient) and afforded the title compound (43 mg, 0.087 mmol, 52%) as a yellow solid after lyophilisation. MS (m/z): 493.58 [M+1]⁺.

Example 16. (S)-1-acryloyl-N-((1S,3R)-3-(5-chloro-4-(1H-indol-3-yl)pyrimidin-2-ylamino)cyclohexyl)-4,4-difluoropyrrolidine-2-carboxamide (Compound 116)

(S)-tert-butyl 2-((1S,3R)-3-(5-chloro-4-(1-(phenylsulfonyl)-1H-indol-3-yl)pyrimidin-2-ylamino)cyclohexylcarbamoyl)-4,4-difluoropyrrolidine-1-carboxylate

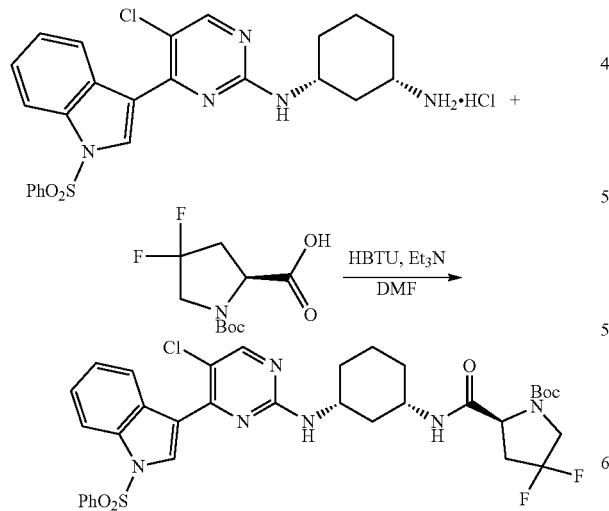

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), Boc-4,4-difluoro-L-proline (87 mg, 0.347 mmol) and Et₃N (121 µL, 0.868 mmol) in DMF (2.0 mL) was added, followed by HBTU (165 mg, 0.434 mmol). The mixture was stirred overnight at rt, then diluted with EtOAc (30 mL) and a saturated solution of NaHCO₃ (5 mL). The layers were separated and the organic layer was washed with brine (2×5 mL), dried (MgSO₄), filtered and evaporated to dryness. The residue was purified by SiO₂ chromatography (DCM/EtOAc 0 to 50% gradient) and afforded the title compound (170 mg, 0.238 mmol, 82%) as a pale yellow solid.

(S)-tert-butyl 2-((1S,3R)-3-(5-chloro-4-(1H-indol-3-yl)pyrimidin-2-ylamino)cyclohexylcarbamoyl)-4,4-difluoropyrrolidine-1-carboxylate

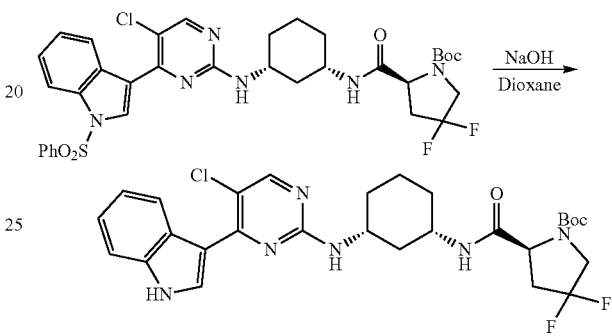

A solution of (S)-tert-butyl 2-((1S,3R)-3-(5-chloro-4-(1-(phenylsulfonyl)-1H-indol-3-yl)pyrimidin-2-ylamino)cyclohexylcarbamoyl)-4,4-difluoropyrrolidine-1-carboxylate (170 mg, 0.238 mmol) in dioxane (2.4 mL) was treated with a 2M solution of NaOH (1.78 mL, 3.57 mmol) and heated at 70° C. for 3 h. The cooled solution was diluted with water (5 mL) and the aqueous layer was extracted with methyl THF (3×20 mL). The combined organic layers were dried (MgSO₄), filtered and evaporated to dryness affording the title compound (123 mg, 0.214 mmol, 90%) as a pale yellow solid which was used in the next step without further purification.

(R)—N-((1S,3R)-3-(5-chloro-4-(1H-indol-3-yl)pyrimidin-2-ylamino)cyclohexyl)-4,4-difluoropyrrolidine-2-carboxamide.HCl (Compound 1034)

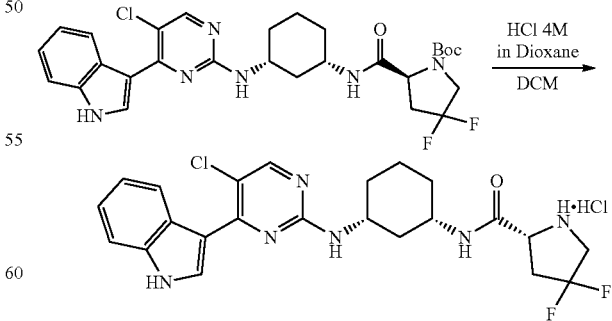

To a solution of (S)-tert-butyl 2-((1S,3R)-3-(5-chloro-4-(1H-indol-3-yl)pyrimidin-2-ylamino)cyclohexylcarbamoyl)-4,4-difluoropyrrolidine-1-carboxylate (123 mg, 0.214 mmol) in DCM (2.2 mL) was added a solution of 4 N HCl in dioxane (0.802 mL, 3.21 mmol). The resulting mixture was stirred 3 h at rt before being evaporated to dryness and afforded the title compound (109 mg, 0.214 mmol, 100%) as a yellow solid which was used in the next step without further purification.

(S)-1-acryloyl-N-((1S,3R)-3-(5-chloro-4-(1H-indol-3-yl)pyrimidin-2-ylamino)cyclohexyl)-4,4-difluoro-pyrrolidine-2-carboxamide

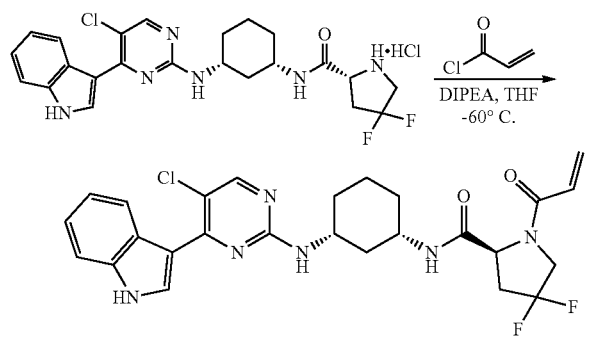

To a −60° C. solution of (R)—N-((1S,3R)-3-(5-chloro-4-(1H-indol-3-yl)pyrimidin-2-ylamino)cyclohexyl)-4,4-difluoropyrrolidine-2-carboxamide.HCl (109 mg, 0.213 mmol) and DIPEA (149 µL, 0.853 mmol) in 5/1 THF/NMP (5.0 mL) was added acryloyl chloride (18.2 µL, 0.224 mmol). The mixture was stirred 2 h at −20° C. and then warmed to rt. The mixture was evaporated to dryness and the residue was purified by reverse phase chromatography (C18, water/ACN+0.1% HCO₂H, 0 to 100% gradient) to afford the title compound (61 mg, 0.115 mmol, 54%) as a yellow solid after lyophilisation. $^1$H NMR (500 MHz, DMSO) δ 11.82 (s, 1H), 8.85-8.49 (m, 1H), 8.46 (d, J=2.6 Hz, 1H), 8.25 (s, 1H), 8.09 (dd, J=121.6, 8.2 Hz, 1H), 7.48 (d, J=8.4 Hz, 1H), 7.40-7.00 (m, 3H), 6.74-6.25 (m, 1H), 6.21-6.08 (m, 1H), 5.74 (dd, J=10.4, 2.1 Hz, 1H), 4.62 (ddd, J=14.5, 9.2, 4.5 Hz, 1H), 4.35-3.57 (m, 4H), 3.08-2.65 (m, 1H), 2.40-1.58 (m, 5H), 1.57-1.03 (m, 4H); MS (m/z): 529.56 [M+1]⁺.

Example 17. 4-trans-acrylamido-N-((1S,3R)-3-(5-chloro-4-(1H-indol-3-yl)pyrimidin-2-ylamino)cyclohexyl)cyclohexanecarboxamide (Compound 117)

tert-butyl (1S,3R)-3-(5-chloro-4-(1H-indol-3-yl)pyrimidin-2-ylamino)cyclohexylcarbamate

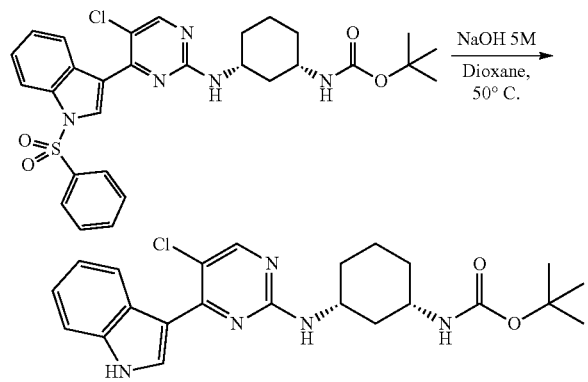

A solution of tert-butyl (1S,3R)-3-(5-chloro-4-(1-(phenylsulfonyl)-1H-indol-3-yl)pyrimidin-2-ylamino)cyclohexylcarbamate prepared as in Example 8 (400 mg, 0.687 mmol) in dioxane (13.7 mL) was treated with a 5M solution of NaOH (1.37 mL, 6.87 mmol) and heated at 70° C. for 4 h. The cooled solution was diluted with water (5 mL) and the aqueous layer was extracted with methyl THF (3×40 mL). The combined organic layers were dried (MgSO₄), filtered, and evaporated to dryness affording the title compound (304 mg, 0.687 mmol, 100%) as a pale yellow solid which was used in the next step without further purification.

(1R,3S)—N1-(5-chloro-4-(1H-indol-3-yl)pyrimidin-2-yl)cyclohexane-1,3-diamine.HCl

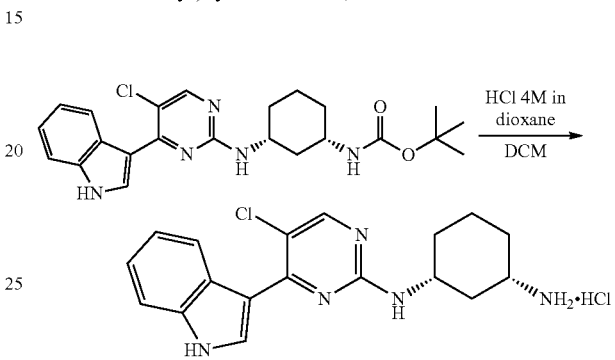

To a solution of tert-butyl (1S,3R)-3-(5-chloro-4-(1H-indol-3-yl)pyrimidin-2-ylamino)cyclohexylcarbamate (220 mg, 0.498 mmol) in DCM (5.0 mL) was added a solution of 4 N HCl in dioxane (2.49 mL, 9.96 mmol). The resulting mixture was stirred 72 h at rt before being evaporated to dryness and afforded the title compound (188 mg, 0.498 mmol, 100%) as a pale yellow solid which was used in the next step without further purification.

tert-butyl-cis-4-(((1S,3R)-3-(5-chloro-4-(1H-indol-3-yl)pyrmidin-2-ylamino)cyclohexylcarbamoyl) cyclohexylcarbamate

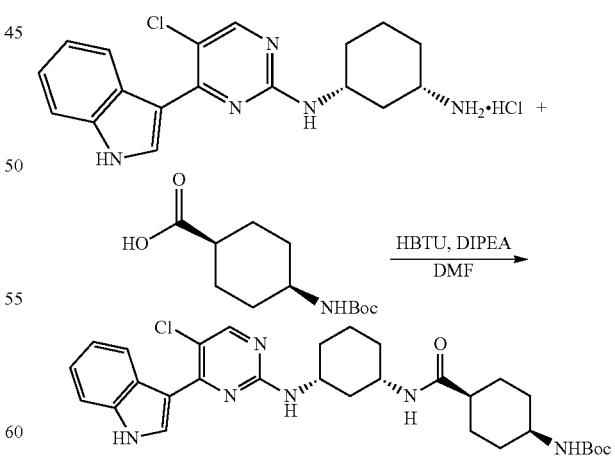

To a solution of (1R,3S)—N1-(5-chloro-4-(1H-indol-3-yl)pyrimidin-2-yl)cyclohexane-1,3-diamine.HCl (89 mg, 0.260 mmol), cis-4-(tert-butoxycarbonylamino)cyclohexanecarboxylic acid (148 mg, 0.286 mmol) and DIPEA (227 µL, 1.302 mmol) in DMF (2.6 mL) was added, followed by HBTU (148 mg, 0.391 mmol). The mixture was stirred overnight at rt, diluted with methyl THF (30 mL) and a saturated solution of NaHCO$_3$ (5 mL). The layers were separated and the organic layer was washed with brine (2×5 mL), dried (MgSO$_4$), filtered and evaporated to dryness. The residue was purified by SiO$_2$ chromatography (DCM/THF 0 to 50% gradient) and afforded the title compound (99 mg, 0.174 mmol, 67%) as a pale yellow oil.

cis-4-amino-N-((1S,3R)-3-(5-chloro-4-(1H-indol-3-yl)pyrimidin-2-ylamino)cyclohexyl) cyclohexanecarboxamide.HCl (Compound 1035)

To a −60° C. solution of cis-4-amino-N-((1S,3R)-3-(5-chloro-4-(1H-indol-3-yl)pyrimidin-2-ylamino)cyclohexyl) cyclohexanecarboxamide.HCl (87 mg, 0.173 mmol) and DIPEA (151 µL, 0.864 mmol) in 5/1 THF/NMP (6.5 mL) was added acryloyl chloride (15.0 µL, 0.181 mmol). The mixture was stirred 1 h at −20° C. and then warmed up to rt. The mixture was evaporated to dryness and the residue was purified by reverse phase chromatography (C18, water/ACN+0.1% HCO$_2$H 0 to 100% gradient) and afforded the title compound (38 mg, 0.073 mmol, 42%) as a yellow solid

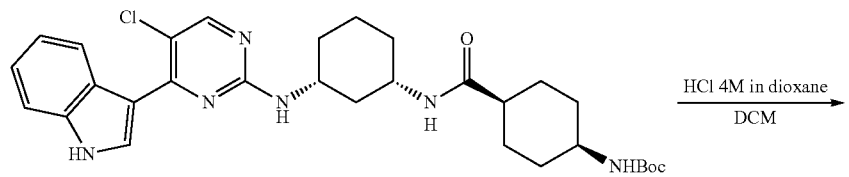

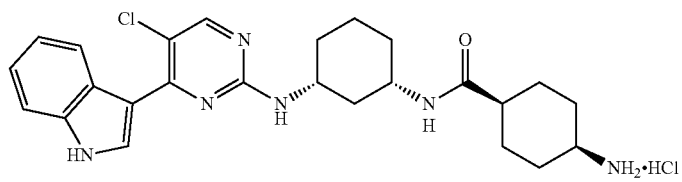

To a solution of tert-butyl-cis-4-((1S,3R)-3-(5-chloro-4-(1H-indol-3-yl)pyrimidin-2-ylamino)cyclohexylcarbamoyl) cyclohexylcarbamate (99 mg, 0.174 mmol) in DCM (1.7 mL) was added a solution of 4 N HCl in dioxane (0.870 mL, 3.49 mmol). The resulting mixture was stirred 1 h at rt before being evaporated to dryness and afforded the title compound (88 mg, 0.174 mmol, 100%) as a yellow solid which was used in the next step without further purification.

4-cis-acrylamido-N-((1S,3R)-3-(5-chloro-4-(1H-indol-3-yl)pyrimidin-2-ylamino)cyclohexyl) cyclohexanecarboxamide after lyophilisation. $^1$H NMR (500 MHz, DMSO) δ 11.82 (s, 1H), 8.57 (br s, 1H), 8.46 (d, J=2.8 Hz, 1H), 8.24 (d, J=3.5 Hz, 1H), 7.97 (d, J=7.3 Hz, 1H), 7.65 (d, J=7.9 Hz, 1H), 7.48 (d, J=8.8 Hz, 1H), 7.24 (d, J=8.1 Hz, 1H), 7.23-7.12 (m, 2H), 6.34 (dd, J=17.1, 10.2 Hz, 1H), 6.05 (dd, J=17.1, 2.3 Hz, 1H), 5.53 (dd, J=10.2, 2.3 Hz, 1H), 3.84 (br s, 2H), 3.71 (br s, 1H), 2.16-2.07 (m, 2H), 1.94 (br s, 1H), 1.83-1.70 (m, 3H), 1.68-1.59 (m, 2H), 1.54-1.42 (m, 4H), 1.37-1.16 (m, 4H), 1.14-1.03 (m, 1H); MS (m/z): 521.63 [M+1]$^+$.

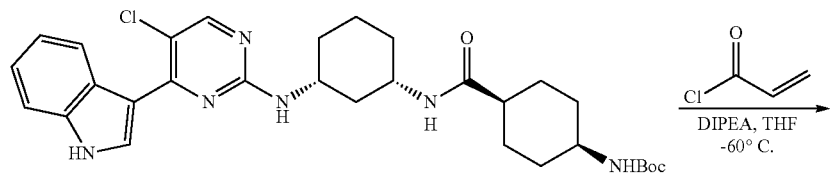

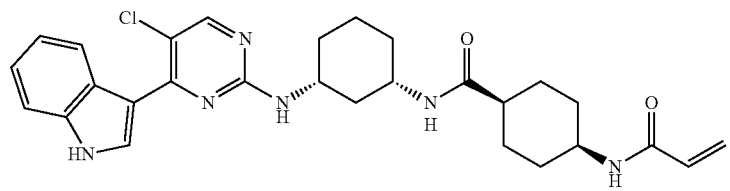

Example 18. 1-acryloyl-N-((1S,3R)-3-(5-chloro-4-(1H-indol-3-yl)pyrimidin-2-ylamino)cyclohexyl)piperidine-4-carboxamide (Compound 118)

tert-butyl 4-((1S,3R)-3-(5-chloro-4-(1-(phenylsulfonyl)-1H-indol-3-yl)pyrimidin-2-ylamino)cyclohexylcarbamoyl)piperidine-1-carboxylate

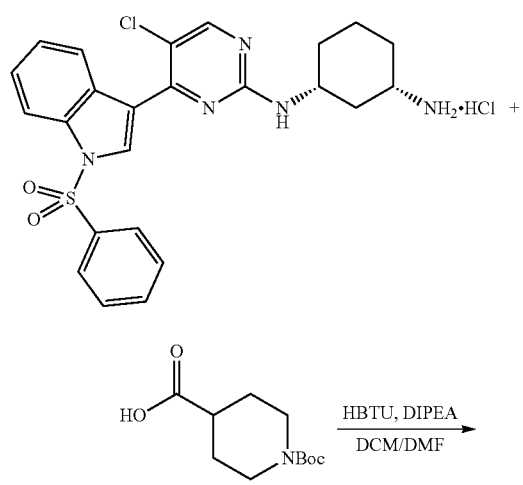

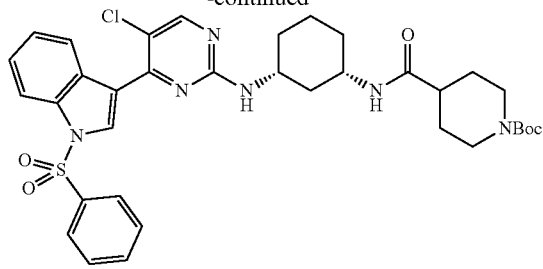

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), 1-Boc-piperidine-4-carboxylic acid (66 mg, 0.290 mmol) and DIPEA (150 µL, 0.868 mmol) in 1/1 DCM/DMF (2.0 mL) was added, followed by HBTU (219 mg, 0.580 mmol). The mixture was stirred overnight at rt, diluted with methyl THF (20 mL) and a saturated solution of NaHCO$_3$ (5 mL). The layers were separated and the aqueous layer was extracted with methyl THF (4×10 mL). The combined organic layers were washed with brine (2×5 mL), dried (MgSO$_4$), then filtered and evaporated to dryness which afforded the title compound (200 mg, 0.289 mmol, 100%) as a pale orange solid that was used in the next step without further purification.

N-((1S,3R)-3-(5-chloro-4-(1H-indol-3-yl)pyrmidin-2-ylamino)cyclohexyl)piperidine-4-carboxamide (Compound 1036)

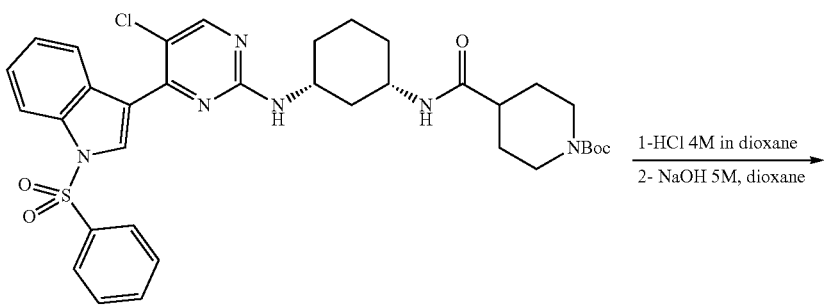

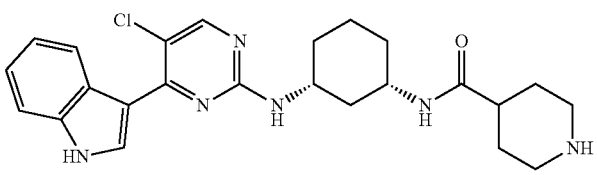

To a solution of tert-butyl 4-((1S,3R)-3-(5-chloro-4-(1-(phenylsulfonyl)-1H-indol-3-yl)pyrimidin-2-ylamino)cyclohexylcarbamoyl)piperidine-1-carboxylate (200 mg, 0.289 mmol) in DCM (2.0 mL) was added a solution of 4 N HCl in dioxane (1.09 mL, 4.35 mmol). The resulting mixture was stirred 2 h at rt before being evaporated to dryness. The residue was suspended in dioxane (2 mL), treated with a 5M solution of NaOH (0.87 mL, 4.35 mmol) and heated at 70° C. for 90 min. The volatiles were evaporated and the residue was purified by reverse phase chromatography (C18, water/ACN+0.1% HCO$_2$H 0 to 90% gradient) and afforded the title compound (126 mg, 0.278 mmol, 96%) as a pale yellow solid.

1-acryloyl-N-((1S,3R)-3-(5-chloro-4-(1H-indol-3-yl)pyrimidin-2-ylamino)cyclohexyl)piperidine-4-carboxamide

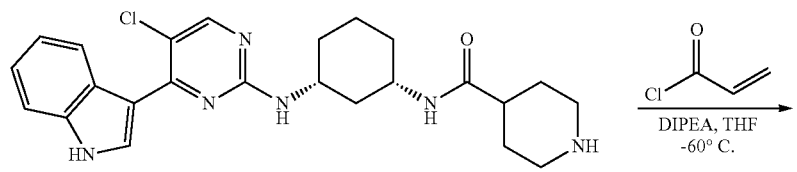

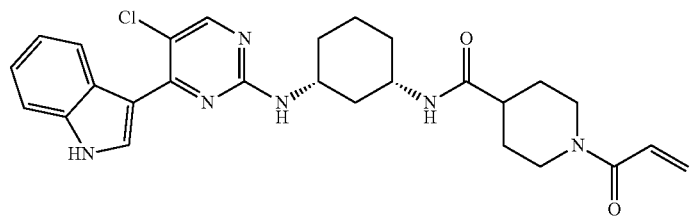

To a −60° C. solution of N-((1S,3R)-3-(5-chloro-4-(1H-indol-3-yl)pyrimidin-2-ylamino)cyclohexyl)piperidine-4-carboxamide (80 mg, 0.177 mmol) and DIPEA (92 µL, 0.530 mmol) in 5/2 THF/NMP (1.8 mL) was added acryloyl chloride (14.6 µL, 0.180 mmol). The mixture was stirred 1 h at −20° C. and then warmed to rt. The mixture was evaporated to dryness and the residue was purified by reverse phase chromatography (C18, water/ACN+0.1% HCO₂H 0 to 100% gradient) and afforded the title compound (19 mg, 0.037 mmol, 21%) as a light yellow solid after lyophilisation. ¹H NMR (500 MHz, DMSO) δ 11.83 (s, 1H), 8.70-8.49 (m, 1H), 8.46 (d, J=2.8 Hz, 1H), 8.24 (s, 1H), 7.78 (d, J=7.8 Hz, 1H), 7.48 (d, J=8.5 Hz, 1H), 7.30-7.06 (m, 3H), 6.78 (dd, J=15.7, 11.0 Hz, 1H), 6.07 (dd, J=16.7, 2.4 Hz, 1H), 5.64 (d, J=10.6 Hz, 1H), 4.37 (t, J=11.3 Hz, 1H), 4.09-3.96 (m, 1H), 3.93-3.75 (m, 1H), 3.75-3.62 (m, 1H), 3.03 (t, J=14.6 Hz, 1H), 2.64 (t, J=13.1 Hz, 1H), 2.34 (tt, J=11.3, 3.8 Hz, 1H), 2.19-2.05 (m, 1H), 2.04-1.86 (m, 1H), 1.78 (d, J=11.3 Hz, 2H), 1.67 (t, J=11.9 Hz, 2H), 1.52-1.31 (m, 3H), 1.24 (t, J=12.0 Hz, 2H), 1.10 (dt, J=12.2, 9.0 Hz, 1H); MS (m/z): 507.61 [M+1]⁺.

Example 19. (R)-1-acryloyl-N-((1S,3R)-3-(5-chloro-4-(1H-indol-3-yl)pyrimidin-2-ylamino)cyclohexyl)piperidine-3-carboxamide (Compound 174)

(R)-tert-butyl 3-((1S,3R)-3-(5-chloro-4-(1-(phenylsulfonyl)-1H-indol-3-yl)pyrimidin-2-ylamino)cyclohexylcarbamoyl)piperidine-1-carboxylate

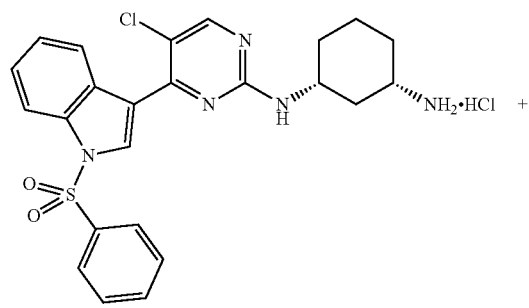

-continued

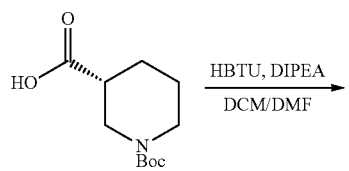

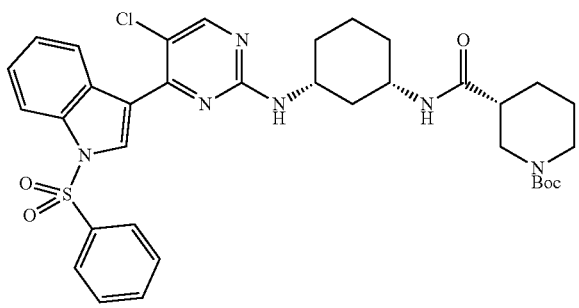

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), 1-Boc-D-nipecotic acid (73 mg, 0.320 mmol) and DIPEA (101 µL, 0.580 mmol) in DCM/DMF (2.0 mL) was added, followed by HBTU (167 mg, 0.440 mmol). The mixture was stirred overnight at rt, then diluted with EtOAc (20 mL) and a saturated solution of NaHCO₃ (5 mL). The layers were separated and the aqueous layer was extracted with EtOAc (4×10 mL). The combined organic layers were washed with brine (5 mL), dried (MgSO₄), filtered and evaporated to dryness. The residue was purified by SiO₂ chromatography (DCM/MeOH 0 to 10% gradient) and afforded the title compound (200 mg, 0.289 mmol, 100%) as a pale yellow oil.

(R)—N-((1S,3R)-3-(5-chloro-4-(1H-indol-3-yl)pyrimidin-2-ylamino)cyclohexyl)piperidine-3-carboxamide.HCl (Compound 1037)

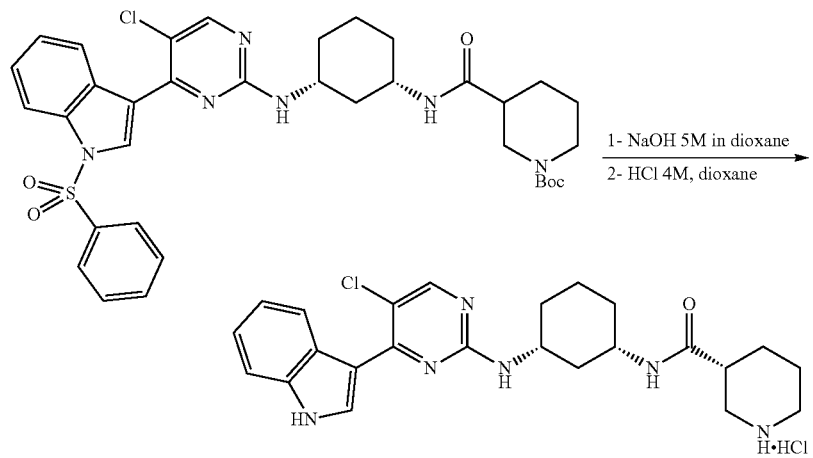

A solution of (R)-tert-butyl 3-((1S,3R)-3-(5-chloro-4-(1-(phenylsulfonyl)-1H-indol-3-yl)pyrimidin-2-ylamino)cyclohexylcarbamoyl)piperidine-1-carboxylate (200 mg, 0.290 mmol) in dioxane (3.0 mL) was treated with a 2M solution of NaOH (2.2 mL, 4.35 mmol) and heated at 70° C. for 2 h. The cooled solution was diluted with water (5 mL) and the aqueous layer was extracted with methyl THF (3×20 mL). The combined organic layers were dried (MgSO$_4$), filtered, and evaporated to dryness. The residue was dissolved in DCM (3.0 mL) and treated with a 4M solution of HCl in dioxane (1.10 mL, 4.35 mmol). The residue was stirred 2 h at rt and evaporated to dryness which afforded the title compound (141 mg, 0.288 mmol, 99%) as a yellow solid which was used in the next step without further purification.

(R)-1-acryloyl-N-((1S,3R)-3-(5-chloro-4-(1H-indol-3-yl)pyrimidin-2-ylamino)cyclohexyl)piperidine-3-carboxamide

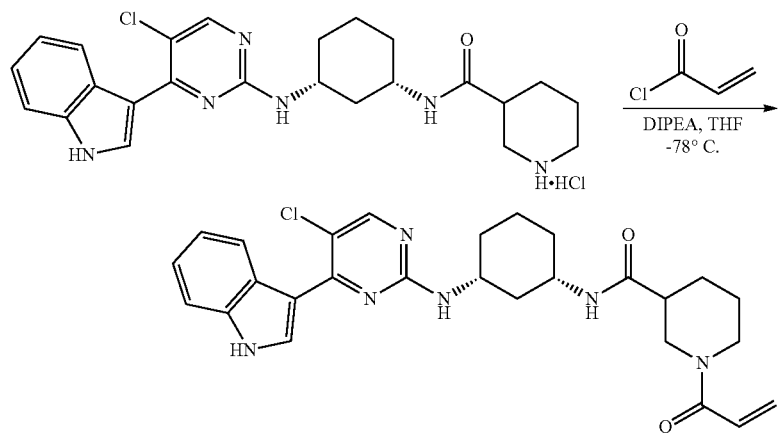

To a −60° C. solution of (R)—N-((1S,3R)-3-(5-chloro-4-(1H-indol-3-yl)pyrimidin-2-ylamino)cyclohexyl)piperidine-3-carboxamide.HCl (71 mg, 0.150 mmol) and DIPEA (105 µL, 0.600 mmol) in 5/1 THF/NMP (3.6 mL) was added acryloyl chloride (12 µL, 0.143 mmol). The mixture was stirred 1 h at −20° C. and then warmed to rt. The mixture was evaporated to dryness and the residue was purified by reverse phase chromatography (C18, water/ACN+0.1% HCO$_2$H 0 to 60% gradient) and afforded the title compound (28 mg, 0.055 mmol, 37%) as a light yellow solid after lyophilisation. MS (m/z): 507.3 [M+1]$^+$.

Example 20. N-((1S,3R)-3-(5-chloro-4-(1H-indol-3-yl)pyrimidin-2-ylamino)cyclohexyl)acrylamide (Compound 170)

N-((1S,3R)-3-(5-chloro-4-(1-(phenylsulfonyl)-1H-indol-3-yl)pyrimidin-2-ylamino)cyclohexyl) acrylamide

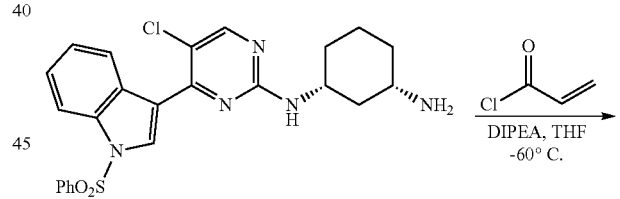

-continued

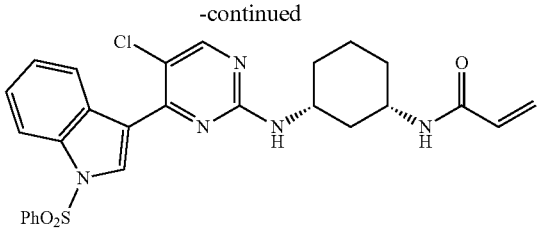

To a −60° C. solution of 2-((1R,3S)-3-aminocyclohexylamino)-4-(1-(phenylsulfonyl)-1H-indol-3-yl)pyrimidine-5-carbonitrile.HCl prepared as in Example 8 (75 mg, 0.145 mmol) and DIPEA (126 μL, 0.723 mmol) in THF (2.9 mL) was added acryloyl chloride (13 μL, 0.159 mmol). The mixture was stirred 90 min at −20° C. and then warmed to rt. The mixture was evaporated to dryness and the residue was purified by SiO$_2$ chromatography (DCM/THF 0 to 25% gradient) and afforded the title compound (58 mg, 0.108 mmol, 75%) as a pale yellow oil.

N-((1S,3R)-3-(5-chloro-4-(1H-indol-3-yl)pyrimidin-2-ylamino)cyclohexybacrylamide

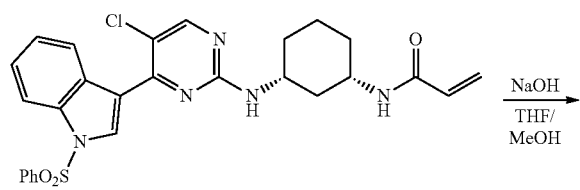

A solution of N-((1S,3R)-3-(5-chloro-4-(1-(phenylsulfonyl)-1H-indol-3-yl)pyrimidin-2-ylamino)cyclohexyl)acrylamide (21 mg, 0.039 mmol) in 3/1 THF/MeOH (1.5 mL) was treated with a 5M solution of NaOH (0.51 mL, 2.55 mmol) and stirred 1 h at rt. The volatiles were evaporated and the residue was purified by reverse phase chromatography (C18, water/ACN+0.1% HCO$_2$H 0 to 100% gradient) to afford the title compound (14 mg, 0.035 mmol, 90%) as a light yellow solid after lyophilisation. $^1$H NMR (500 MHz, DMSO) δ 11.83 (s, 1H), 8.57 (br s, 1H), 8.46 (d, J=2.5 Hz, 1H), 8.25 (s, 1H), 8.06 (d, J=7.9 Hz, 1H), 7.49 (d, J=8.7 Hz, 1H), 7.26 (d, J=8.1 Hz, 1H), 7.24-7.12 (m, 2H), 6.19 (dd, J=17.1, 10.1 Hz, 1H), 6.07 (dd, J=17.1, 2.3 Hz, 1H), 5.56 (dd, J=10.1, 2.3 Hz, 1H), 3.93-3.75 (m, 2H), 2.16 (br s, 1H), 1.99 (br s, 1H), 1.80 (d, J=12.9 Hz, 2H), 1.46-1.06 (m, 4H); MS (m/z): 396.56 [M+1]$^+$.

Example 21. N-((1S,3R)-3-(5-chloro-4-(1H-indol-3-yl)pyrimidin-2-ylamino)cyclohexyl)-N-methylacrylamide (Compound 171)

N-((1S,3R)-3-(5-chloro-4-(1-(phenylsulfonyl)-1H-indol-3-yl)pyrimidin-2-ylamino)cyclohexyl)-2,2,2-trifluoroacetamide

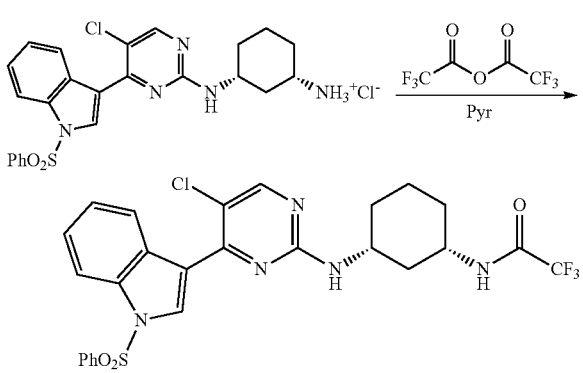

To a solution of 2-((1R,3S)-3-aminocyclohexylamino)-4-(1-(phenylsulfonyl)-1H-indol-3-yl)pyrimidine-5-carbonitrile.HCl prepared as in Example 8 (500 mg, 0.967 mmol) and pyridine (0.16 mL, 1.93 mmol) in DCM (4.8 mL) was added trifluoroacetic anhydride (77 μL, 0.556 mmol). The mixture was stirred overnight at rt and diluted with DCM (20 mL) and a saturated solution of NaHCO$_3$ (10 mL). The layers were separated and the organic layer was dried (MgSO$_4$), filtered, and evaporated to dryness. The residue was purified by SiO$_2$ chromatography (DCM/EtOAc 0 to 30% gradient) and afforded the title compound (252 mg, 0.906 mmol, 45%) as a pale yellow solid.

N-((1S,3R)-3-(5-chloro-4-(1-(phenylsulfonyl)-1H-indol-3-yl)pyrimidin-2-ylamino)cyclohexyl)-2,2,2-trifluoro-N-methylacetamide

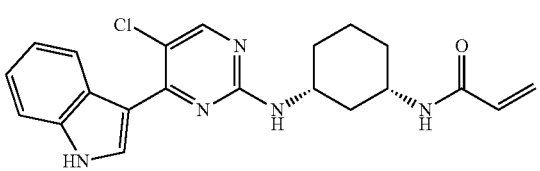

A cooled (0° C.) solution of N-((1S,3R)-3-(5-chloro-4-(1-(phenylsulfonyl)-1H-indol-3-yl)pyrimidin-2-ylamino)cyclohexyl)-2,2,2-trifluoroacetamide (252 mg, 0.436 mmol) in DMF (4.4 mL) was treated with a 60% suspension of NaH in oil (21 mg, 0.523 mmol). After 15 min at rt, MeI (28 μL, 0.458 mmol) was added and the mixture was stirred for 3 h at rt. The mixture was diluted with water (5 mL) and EtOAc (30 mL). The layers were separated and the organic layer was washed with water (2×5 mL), dried (MgSO$_4$), filtered and evaporated to dryness. The residue was purified by SiO$_2$ chromatography (DCM/EtOAc 0 to 50% gradient) and afforded the title compound (190 mg, 0.321 mmol, 74%) as a pale yellow oil.

(1R,3S)—N1-(5-chloro-4-(1H-indol-3-yl)pyrimidin-2-yl)-N3-methylcyclohexane-1,3-diamine

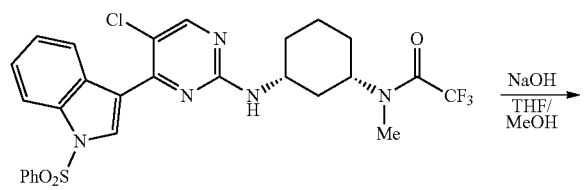

A solution of N-((1S,3R)-3-(5-chloro-4-(1-(phenylsulfonyl)-1H-indol-3-yl)pyrimidin-2-ylamino)cyclohexyl)-2,2,2-trifluoro-N-methylacetamide (265 mg, 0.448 mmol) in 3/1 THF/MeOH (3.0 mL) was treated with a 5M solution of NaOH (1.25 mL, 6.27 mmol) and stirred 1 h at rt. The volatiles were evaporated and the residue was purified by reverse phase chromatography (C18, water/ACN+0.1% HCO$_2$H 0 to 100% gradient) and afforded the title compound (157 mg, 0.441 mmol, 99%) as a bright yellow foam.

N-((1S,3R)-3-(5-chloro-4-(1H-indol-3-yl)pyrimidin-2-ylamino)cyclohexyl)-N-methylacrylamide

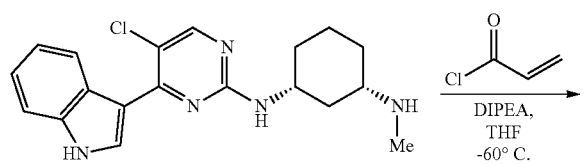

To a −60° C. solution of (1R,3S)—N1-(5-chloro-4-(1H-indol-3-yl)pyrimidin-2-yl)-N3-methylcyclohexane-1,3-diamine (77 mg, 0.167 mmol) and DIPEA (87 μL, 0.501 mmol) in 5/1 THF/NMP (6.0 mL) was added acryloyl chloride (14 μL, 0.175 mmol). The mixture was stirred 1 h at −20° C. and then warmed to rt. The mixture was evaporated to dryness and the residue was purified by reverse phase chromatography (C18, water/ACN+0.1% HCO$_2$H 0 to 60% gradient) and afforded the title compound (18 mg, 0.043 mmol, 26%) as a white solid after lyophilisation.

$^1$H NMR (500 MHz, DMSO) δ 11.83 (s, 1H), 8.55 (br s, 1H), 8.47 (d, J=2.7 Hz, 1H), 8.25 (s, 1H), 7.49 (d, J=8.0 Hz, 1H), 7.24-7.11 (m, 3H), 6.72 (dd, J=16.6, 10.6 Hz, 1H), 6.09 (d, J=16.7 Hz, 1H), 5.65 (d, J=10.3 Hz, 1H), 4.48 (br s, 1H), 3.95 (br s, 1H), 2.90 (s, 3H), 1.90-1.80 (m, 2H), 1.70-1.16 (m, 5H); MS (m/z): 410.53 [M+1]$^+$.

Example 22. N-(3-((1S,3R)-3-(5-chloro-4-(1H-indol-3-yl)pyrimidin-2-ylamino)cyclohexylamino)-3-oxopropyl)acrylamide (Compound 172)

tert-butyl 3-((1S,3R)-3-(5-chloro-4-(1-(phenylsulfonyl)-1H-indol-3-yl)pyrimidin-2-ylamino)cyclohexylamino)-3-oxopropylcarbamate

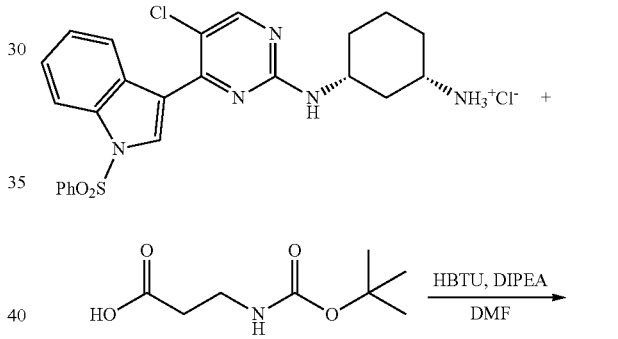

To a solution of 2-((1R,3S)-3-aminocyclohexylamino)-4-(1-(phenylsulfonyl)-1H-indol-3-yl)pyrimidine-5-carbonitrile.HCl prepared as in Example 8 (416 mg, 0.802 mmol), Boc-β-alanine-OH (167 mg, 0.883 mmol) and DIPEA (700 μL, 4.01 mmol) in DMF (8.0 mL) was added, followed by HBTU (456 mg, 1.204 mmol). The mixture was stirred overnight at rt, then diluted with EtOAc (50 mL) and a saturated solution of NaHCO$_3$ (20 mL). The layers were separated and the aqueous layer was extracted with EtOAc (4×20 mL). The combined organic layers were washed with brine (20 mL), dried (MgSO$_4$), filtered and evaporated to dryness. The residue was purified by SiO$_2$ chromatography (DCM/THF 0 to 40% gradient) and afforded the title compound (458 mg, 0.701 mmol, 87%) as a pale orange oil.

tert-butyl 3-((1S,3R)-3-(5-chloro-4-(1H-indol-3-yl)
pyrmidin-2-ylamino)cyclohexylamino)-3-oxopropyl-
carbamate

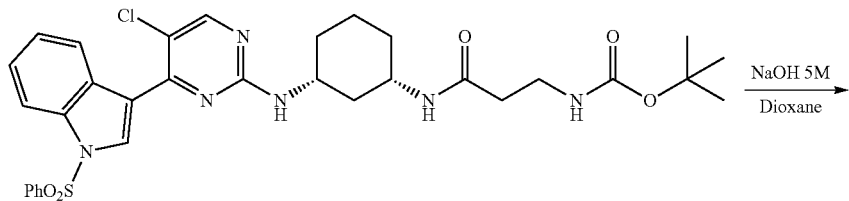

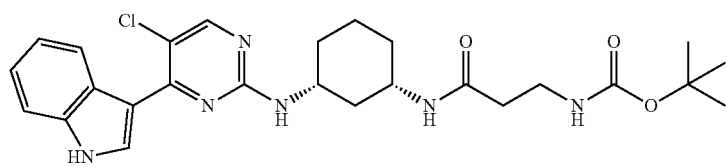

A solution of tert-butyl 3-((1S,3R)-3-(5-chloro-4-(1-(phe-nylsulfonyl)-1H-indol-3-yl)pyrimidin-2-ylamino)cyclo-hexylamino)-3-oxopropylcarbamate (176 mg, 0.269 mmol) in dioxane (5.4 mL) was treated with a 5M solution of NaOH (1.08 mL, 5.39 mmol) and heated at 70° C. for 5 h. The cooled solution was diluted with water (10 mL) and the aqueous layer was extracted with methyl THF (3×50 mL). The combined organic layers were dried (MgSO₄), filtered and evaporated to dryness affording the title compound (138 mg, 0.269 mmol, 100%) as a pale yellow solid which was used in the next step without further purification.

3-amino-N-((1S,3R)-3-(5-chloro-4-(1H-indol-3-yl)
pyrmidin-2-ylamino)cyclohexyl)propanamide.HCl
(Compound 1038)

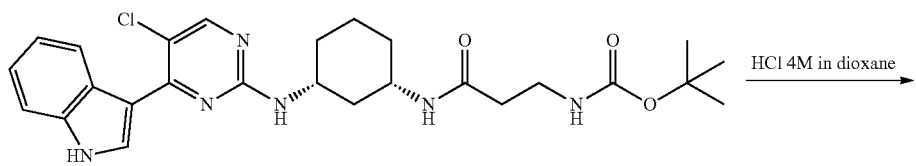

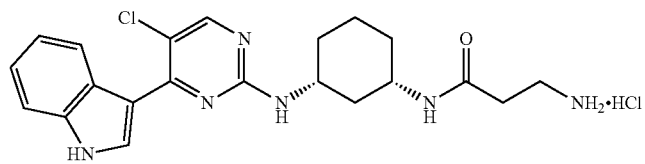

To a solution of tert-butyl 3-((1S,3R)-3-(5-chloro-4-(1H-indol-3-yl)pyrimidin-2-ylamino)cyclohexylamino)-3-oxo-propylcarbamate (138 mg, 0.269 mmol) in DCM (2.7 mL) was added a solution of 4 N HCl in dioxane (1.34 mL, 5.38 mmol). The resulting mixture was stirred 16 h at rt before being evaporated to dryness and afforded the title compound (121 mg, 0.269 mmol, 100%) as a yellow solid which was used in the next step without further purification.

N-(3-((1S,3R)-3-(5-chloro-4-(1H-indol-3-yl)pyrimidin-2-ylamino)cyclohexylamino)-3-oxopropyl)acrylamide

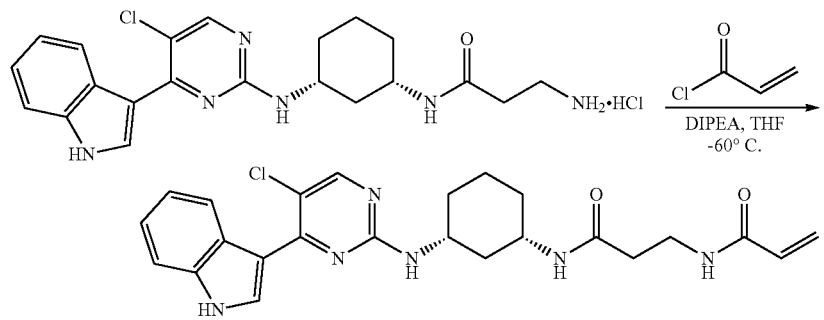

To a −60° C. solution of (3-amino-N-((1S,3R)-3-(5-chloro-4-(1H-indol-3-yl)pyrimidin-2-ylamino)cyclohexyl)propanamide.HCl (121 mg, 0.269 mmol) and DIPEA (153 μL, 0.879 mmol) in 5/1 THF/NMP (7.0 mL) was added acryloyl chloride (25 μL, 0.308 mmol). The mixture was stirred 1 h at −20° C. and then warmed to rt. The mixture was evaporated to dryness and the residue was purified by reverse phase chromatography (C18, water/ACN+0.1% HCO$_2$H 0 to 60% gradient) and afforded the title compound (64 mg, 0.137 mmol, 51%) as a light yellow solid after lyophilisation. $^1$H NMR (500 MHz, DMSO) δ 11.82 (s, 1H), 8.55 (br s, 1H), 8.46 (d, J=2.9 Hz, 1H), 8.11 (t, J=5.2 Hz, 1H), 7.86 (d, J=7.7 Hz, 1H), 7.49 (d, J=8.2 Hz, 1H), 7.28-7.13 (m, 3H), 6.19 (dd, J=17.1, 10.2 Hz, 1H), 6.05 (dd, J=17.1, 2.2 Hz, 1H), 5.54 (dd, J=10.1, 2.2 Hz, 1H), 3.85 (br s, 1H), 3.70 (br s, 1H), 3.30 (t, J=7.0 Hz, 2H), 2.24 (t, J=7.0 Hz, 2H), 2.12 (br s, 1H), 1.97 (br s, 1H), 1.79 (br s, 2H), 1.38-1.00 (m, 4H); MS (m/z): 467.55 [M+1]$^+$.

Example 23. (2S,4S)-4-acrylamido-N-((1S,3R)-3-(5-chloro-4-(1H-indol-3-yl)pyrimidin-2-ylamino)cyclohexyl)pyrrolidine-2-carboxamide (Compound 153)

(2S,4R)-tert-butyl 2-((1S,3R)-3-(5-chloro-4-(1-(phenylsulfonyl)-1H-indol-3-yl)pyrimidin-2-ylamino)cyclohexylcarbamoyl)-4-hydroxypyrrolidine-1-carboxylate

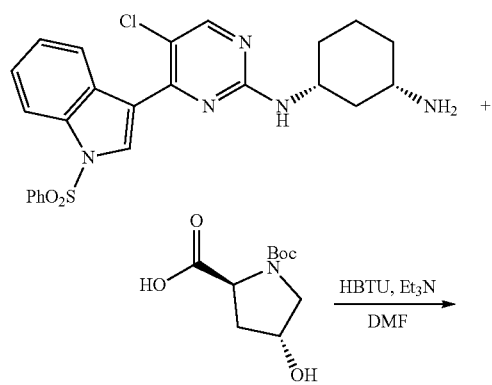

-continued

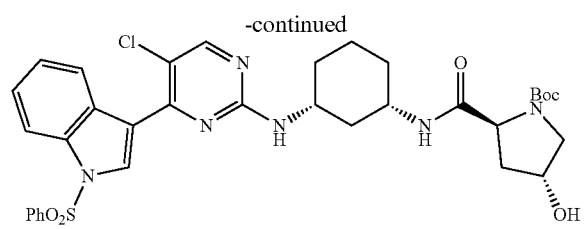

To a solution of 2-((1R,3S)-3-aminocyclohexylamino)-4-(1-(phenylsulfonyl)-1H-indol-3-yl)pyrimidine-5-carbonitrile.HCl prepared as in Example 8 (150 mg, 0.289 mmol), trans-hydroxy-L-proline (80 mg, 0.347 mmol) and Et$_3$N (121 μL, 0.868 mmol) in DMF (2.0 mL) was added, followed by HBTU (165 mg, 0.434 mmol). The mixture was stirred overnight at rt, then diluted with EtOAc (30 mL) and a saturated solution of NaHCO$_3$ (10 mL). The layers were separated and the aqueous layer was extracted with EtOAc (3×20 mL). The combined organic layers were washed with brine (10 mL), dried (MgSO$_4$), filtered and evaporated to dryness. The residue was purified by SiO$_2$ chromatography (DCM/EtOAc 0 to 100% gradient) and afforded the title compound (139 mg, 0.200 mmol, 69%) as a pale yellow solid.

(2S,4S)-tert-butyl 2-((1S,3R)-3-(5-chloro-4-(1-(phenylsulfonyl)-1H-indol-3-yl)pyrimidin-2-ylamino)cyclohexylcarbamoyl)-4-(1,3-dioxoisoindolin-2-yl)pyrrolidine-1-carboxylate

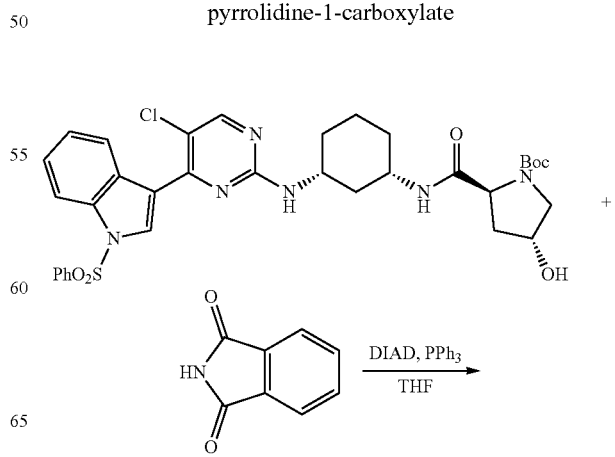

-continued

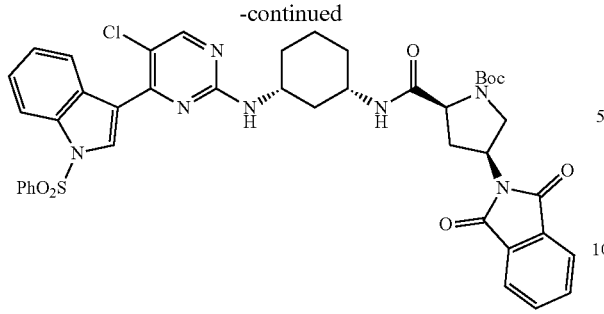

To a cooled (0° C.) solution of PPh₃ (65 mg, 0.249 mmol) in THF (1.9 mL) was added DIAD (49 µL, 0.249 mmol) followed by phthalimide (37 mg, 0.249 mmol) and a solution of (2S,4R)-tert-butyl 2-((1S,3R)-3-(5-chloro-4-(1-(phenylsulfonyl)-1H-indol-3-yl)pyrimidin-2-ylamino)cyclohexylcarbamoyl)-4-hydroxypyrrolidine-1-carboxylate (133 mg, 0.191 mmol) in THF (1.4 mL). The resulting mixture was stirred 4 h at rt and 2 h at 45° C. The cooled mixture was evaporated to dryness and the residue was purified by SiO₂ chromatography (DCM/MeOH 0 to 20% gradient) and afforded the title compound (157 mg, 0.191 mmol, 100%) as a white solid polluted with some triphenylphosphine oxide.

(2S,4S)-tert-butyl 4-amino-2-((1S,3R)-3-(5-chloro-4-(1-(phenylsulfonyl)-1H-indol-3-yl)pyrimidin-2-ylamino)cyclohexylcarbamoyl)pyrolidine-1-carboxylate

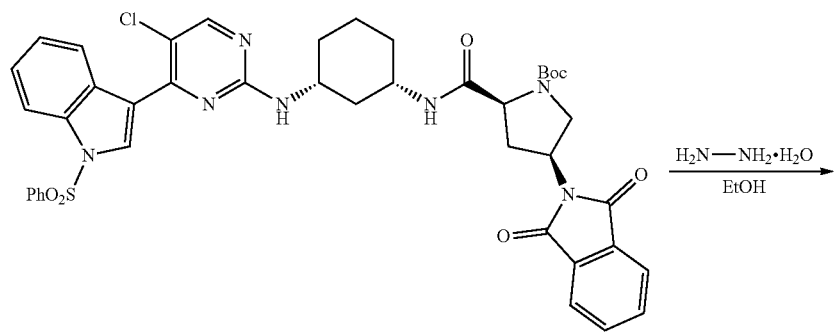

A solution of (2S,4S)-tert-butyl 2-((1S,3R)-3-(5-chloro-4-(1-(phenylsulfonyl)-1H-indol-3-yl)pyrimidin-2-ylamino)cyclohexylcarbamoyl)-4-(1,3-dioxoisoindolin-2-yl)pyrrolidine-1-carboxylate (157 mg, 0.190 mmol) in 8/1 THF/EtOH (2.1 mL) was treated with hydrazine hydrate (200 µL, 2.85 mmol) and stirred 5 h at rt. The mixture was evaporated to dryness and the residue was purified by reverse phase chromatography (C18, water/ACN+0.1% HCO₂H 35 to 75% gradient) and afforded the title compound (64 mg, 0.116 mmol, 60%) as a white solid.

(2S,4S)-tert-butyl 4-amino-2-((1S,3R)-3-(5-chloro-4-(1H-indol-3-yl)pyrimidin-2-ylamino)cyclohexylcarbamoyl)pyrolidine-1-carboxylate

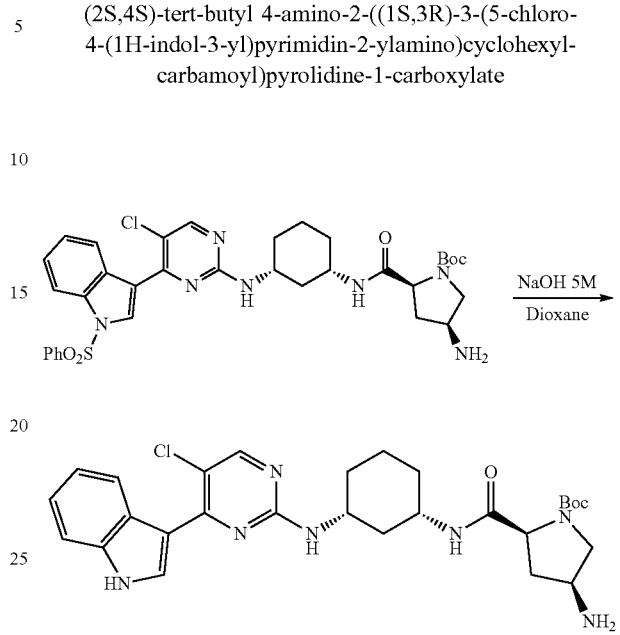

A solution of (2S,4S)-tert-butyl 4-amino-2-((1S,3R)-3-(5-chloro-4-(1-(phenylsulfonyl)-1H-indol-3-yl)pyrimidin-2-ylamino)cyclohexylcarbamoyl)pyrrolidine-1-carboxylate (64 mg, 0.092 mmol) in dioxane (1.8 mL) was treated with a 5M solution of NaOH (0.180 mL, 0.915 mmol) and heated at 50° C. for 18 h. The cooled solution was evaporated to dryness and the residue was purified by reverse phase chromatography (C18, water/ACN+0.1% HCO₂H 30 to 100% gradient) and afforded the title compound (42 mg, 0.076 mmol, 84%) as a beige solid.

115

(4S)-tert-butyl 4-acrylamido-2-((1S,3R)-3-(5-chloro-4-(1H-indol-3-yl)pyrimidin-2-ylamino)cyclohexyl-carbamoyl)pyrrolidine-1-carboxylate

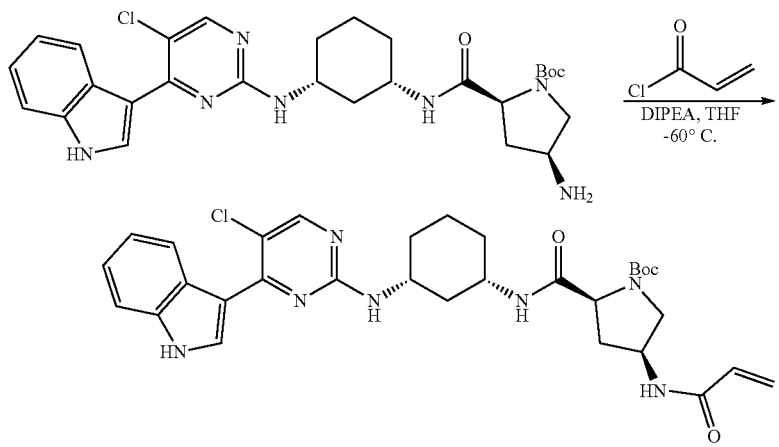

To a −78° C. solution of (2S,4S)-tert-butyl 4-amino-2-((1S,3R)-3-(5-chloro-4-(1H-indol-3-yl)pyrimidin-2-ylamino)cyclohexylcarbamoyl)pyrrolidine-1-carboxylate (61 mg, 0.110 mmol) and DIPEA (96 μL, 0.551 mmol) in 5/1 THF/NMP (4.4 mL) was added acryloyl chloride (9 μL, 0.116 mmol). The mixture was stirred 1 h at −20° C. and then warmed to rt. The mixture was evaporated to dryness and the residue was purified by reverse phase chromatography (C18, water/ACN+0.1% HCO$_2$H 0 to 60% gradient) and afforded the title compound (17.6 mg, 0.029 mmol, 26%) as a light yellow solid after lyophilisation.

(2S,4S)-4-acrylamido-N-((1S,3R)-3-(5-chloro-4-(1H-indol-3-yl)pyrimidin-2-ylamino)cyclohexyl) pyrolidine-2-carboxamide

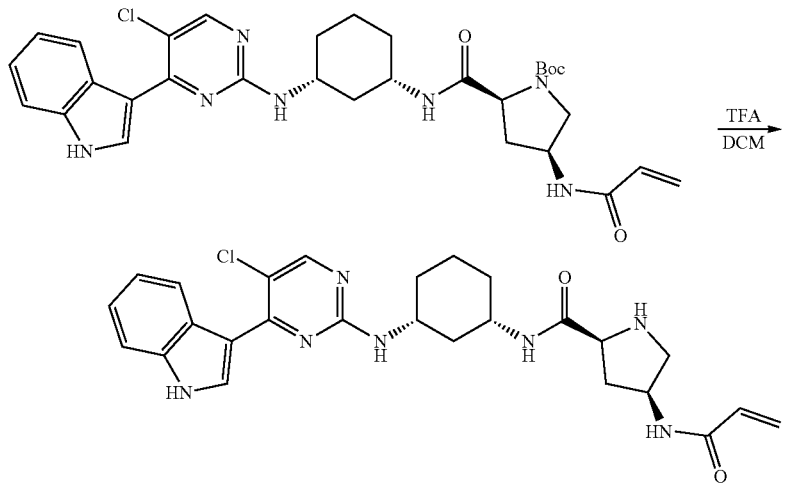

116

A cooled (0° C.) solution of (4S)-tert-butyl 4-acrylamido-2-((1S,3R)-3-(5-chloro-4-(1H-indol-3-yl)pyrimidin-2-ylamino)cyclohexylcarbamoyl)pyrrolidine-1-carboxylate (11 mg, 0.018 mmol) in DCM (1.0 mL) was treated with TFA (400 μL). The mixture was stirred 2 h at rt and the mixture was evaporated to dryness. The residue was purified by reverse phase chromatography (C18, water/ACN+0.1% HCO$_2$H 0 to 100% gradient) and afforded the title compound (5.7 mg, 0.011 mmol, 64%) as a light yellow solid after lyophilisation. $^1$H NMR (500 MHz, DMSO) δ 11.84 (s, 1H), 9.28 (s, 1H), 8.76 (s, 1H), 8.55-8.40 (m, 2H), 8.35-8.27 (m, 1H), 8.25 (s, 1H), 7.49 (d, J=6.5 Hz, 1H), 7.36-7.24 (m, 1H), 7.23-7.12 (m, 2H), 6.20-6.03 (m, 2H), 5.59 (dd, J=8.8, 3.4 Hz, 1H), 4.47-4.32 (m, 1H), 4.20-4.05 (m, 1H), 4.03-3.65 (m, 2H), 3.12-2.97 (m, 1H), 2.20-2.10 (m, 1H), 2.08-1.55 (m, 3H), 1.50-1.32 (m, 1H), 1.33-1.04 (m, 4H); MS (m/z): 508.65 [M+1]$^+$.

Example 24. 1-acryloyl-N-((1r,4r)-4-(5-chloro-4-(1H-indol-3-yl)pyrimidin-2-ylamino)cyclohexyl) piperidine-3-carboxamide (Compound 158)

Trans-N1-(5-chloro-4-(1-(phenylsulfonyl)-1H-indol-3-yl)pyrimidin-2-yl)cyclohexane-1,4-diamine

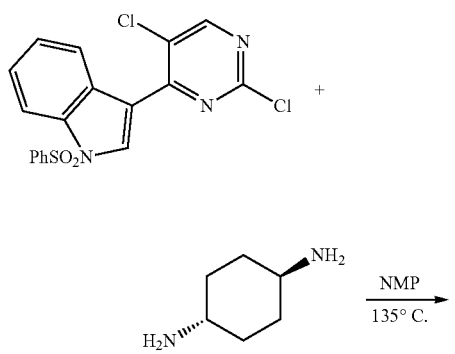

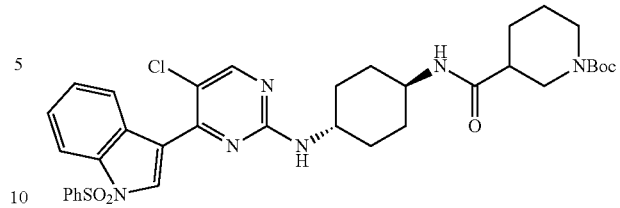

To a solution of trans-N1-(5-chloro-4-(1-(phenylsulfonyl)-1H-indol-3-yl)pyrimidin-2-yl)cyclohexane-1,4-diamine (100 mg, 0.207 mmol), (DL)-1-Boc-piperidine-3-carboxylic acid (52 mg, 0.228 mmol) and DIPEA (54 μL, 0.311 mmol) in DMF (2.0 mL) was added, followed by HBTU (118 mg, 0.311 mmol). The mixture was stirred overnight at rt, diluted with EtOAc (20 mL) and a saturated solution of NaHCO₃ (10 mL). The layers were separated and the aqueous layer was extracted with EtOAc (3×20 mL). The combined organic layers were washed with brine (10 mL), dried (MgSO₄), then filtered and evaporated to dryness which afforded and afforded the title compound (143 mg, 0.207 mmol, 100%) as a pale yellow solid which was used in the next step without further purification.

tert-butyl 3-(trans-4-(5-chloro-4-(1H-indol-3-yl)pyrimidin-2-ylamino)cyclohexylcarbamoyl)piperidine-1-carboxylate A solution of 3-(2,5-dichloropyrimidin-4-yl)-1-(phenylsulfonyl)-1H-indole (609 mg, 1.51 mmol), trans-1,4-diaminocyclohexane (206 mg, 1.81 mmol) and diisopropylethylamine (315 μL, 1.81 mmol) in NMP (15 mL) was heated 45 min at 135° C. (microwave). The mixture was diluted with EtOAc (50 mL), washed with water (100 mL), brine (100 mL), dried (MgSO₄), then filtered and evaporated to dryness. The residue was purified by SiO₂ chromatography (DCM/MeOH 0 to 10% gradient), and afforded the title compound (313 g, 0.649 mmol, 43%) as a yellow solid.

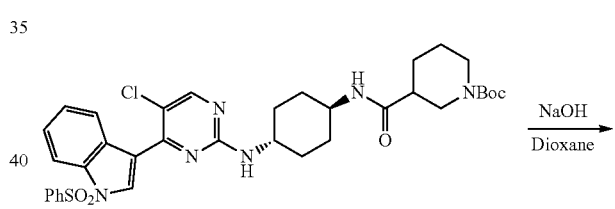

tert-butyl 3-(trans-4-(5-chloro-4-(1-(phenylsulfonyl)-1H-indol-3-yl)pyrimidin-2-ylamino)cyclohexylcarbamoyl)piperidine-1-carboxylate

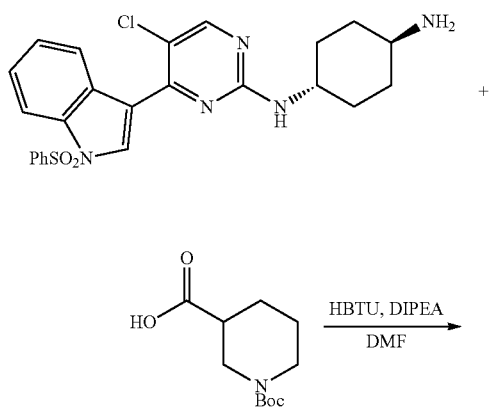

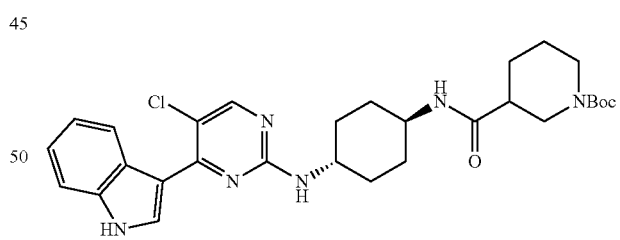

A solution of tert-butyl 3-(trans-4-(5-chloro-4-(1-(phenylsulfonyl)-1H-indol-3-yl)pyrimidin-2-ylamino)cyclohexylcarbamoyl)piperidine-1-carboxylate (144 mg, 0.207 mmol) in dioxane (2.0 mL) was treated with a 2M solution of NaOH (1.5 mL, 3.00 mmol) and heated at 70° C. for 1 h. The cooled solution was diluted with methyl THF (20 mL) and water (10 mL). The layers were separated and the aqueous layer was extracted with methyl THF (4×10 mL). The combined organic layers were dried (MgSO₄), filtered and evaporated to dryness which afforded the title compound (115 mg, 0.207 mmol, 100%) as a yellow solid which was used in the next step without further purification.

N-(trans-4-(5-chloro-4-(1H-indol-3-yl)pyrmidin-2-ylamino)cyclohexyl)piperidine-3-carboxamide.HCl (Compound 1039)

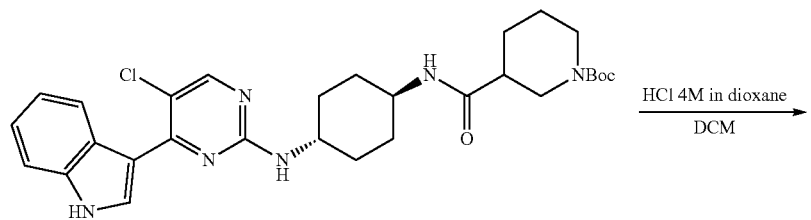

To a solution of tert-butyl 3-(trans-4-(5-chloro-4-(1H-indol-3-yl)pyrimidin-2-ylamino)cyclohexylcarbamoyl)piperidine-1-carboxylate (115 mg, 0.208 mmol) in DCM (2.0 mL) was added a solution of 4 N HCl in dioxane (800 µL, 3.12 mmol). The resulting mixture was stirred 1 h at rt before being evaporated to dryness and afforded the title compound (101 mg, 0.208 mmol, 100%) as a yellow solid which was used in the next step without further purification.

1-acryloyl-N-((1R,4R)-4-(5-chloro-4-(1H-indol-3-yl)pyrmidin-2-ylamino)cyclohexyl)piperidine-3-carboxamide

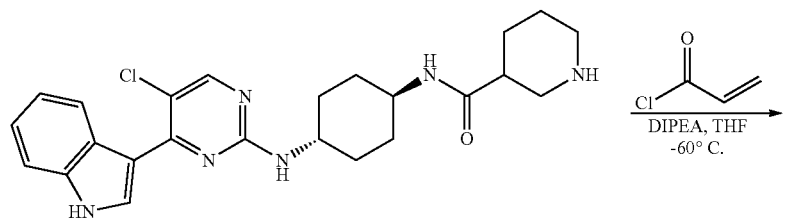

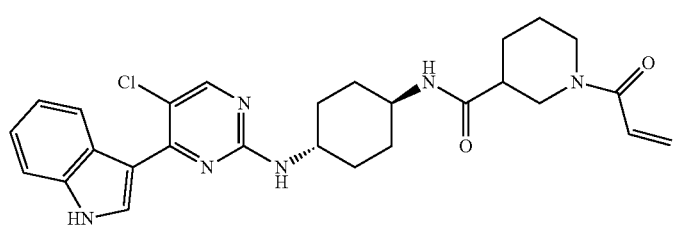

To a −78° C. solution of N-(trans-4-(5-chloro-4-(1H-indol-3-yl)pyrimidin-2-ylamino)cyclohexyl)piperidine-3-carboxamide.HCl (105 mg, 0.215 mmol) and DIPEA (150 µL, 0.860 mmol) in 5/1 THF/NMP (5.0 mL) was added acryloyl chloride (17 µL, 1.11 mmol). The mixture was stirred 1 h at −20° C. and then warmed to rt. The mixture was evaporated to dryness and the residue was purified by reverse phase chromatography (C18, water/ACN+0.1% $HCO_2H$ 0 to 60% gradient) and afforded the title compound (50 mg, 0.099 mmol, 46%) as a light yellow solid after lyophilisation. LCMS: $(M+H^+)$: 507.2@2.375 min (10-80% ACN in $H_2O$, 4.5 min).

$^1$H NMR (400 MHz, MeOD) δ 1.49-1.68 (m, 4H), 1.85 (d, J=11.04 Hz, 2H), 1.93-2.16 (m, 3H), 2.20-2.47 (m, 3H), 2.84-3.05 (m, 1H), 3.23 (d, J=12.30 Hz, 1H), 3.38-3.48 (m, 1H), 3.77 (br. s., 1H), 4.07 (br. s., 2H), 4.34-4.52 (m, 1H), 5.77 (d, J=10.29 Hz, 1H), 6.23 (d, J=15.81 Hz, 1H), 6.76-6.90 (m, 1H), 7.39 (br. s., 2H), 7.59 (br. s., 1H), 8.19-8.33 (m, 1H), 8.67 (br. s., 1H), 9.04 (br. s., 1H).

Example 25. Synthesis of N-[(±)-3-{[5-chloro-4-(1H-indol-3-yl)pyrimidin-2-yl]amino}cyclohexyl]-3-(prop-2-enamido)bicyclo[1.1.1]pentane-1-carboxamide (Compound 109)

tert-butyl (3-(((±)-3-((5-chloro-4-(1-(phenylsulfonyl)-1H-indol-3-yl)pyrimidin-2-yl)amino)cyclohexyl)carbamoyl)bicyclo[1.1.1]pentan-1-yl)carbamate

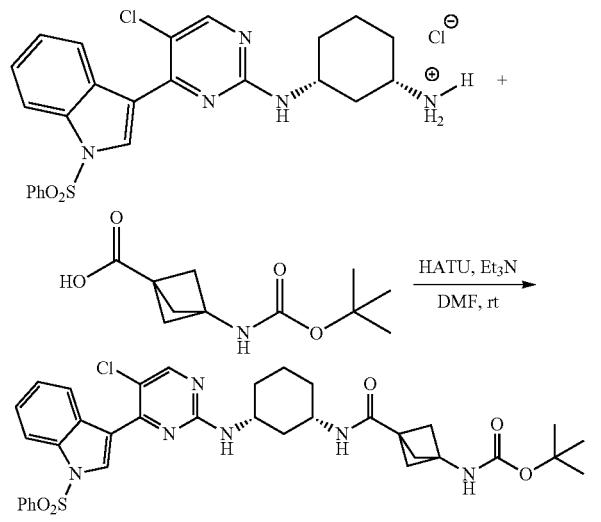

To a solution of (±)-N1-(5-chloro-4-(1-(phenylsulfonyl)-1H-indol-3-yl)pyrimidin-2-yl)cyclohexane-1,3-diamine.HCl (80 mg, 0.155 mmol) in DMF (1.1 mL) was added Et₃N (65 μL, 0.466 mmol,), 3-((tert-butoxycarbonyl)amino)bicyclo[1.1.1]pentane-1-carboxylic acid (53 mg, 0.233 mmol) and HATU (88 mg, 0.233 mmol). The mixture was stirred for 2 h at rt, then diluted with dichloromethane (5 mL) and extracted twice with water. Organic portion was washed with brine (5 mL), then dried over sodium sulfate, filtered and concentrated. The crude residue was purified by SiO₂ chromatography (0-100% EtOAc/DCM gradient) to afford the title compound (45 mg, 0.065 mmol, 42%) as an off-white solid.

3-amino-N-[(±)-3-((5-chloro-4-(1H-indol-3-yl)pyrimidin-2-yl)amino)cyclohexyl)bicyclo[1.1.1]pentane-1-carboxamide (Compound 1040)

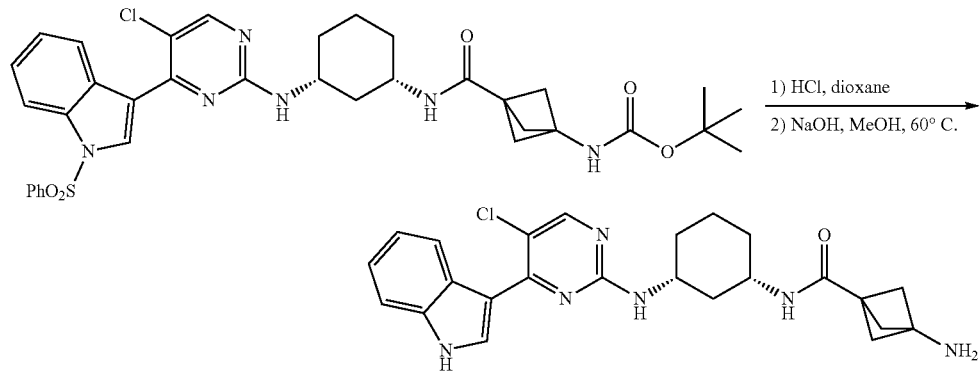

tert-butyl (3-(((±)-3-((5-chloro-4-(1-(phenylsulfonyl)-1H-indol-3-yl)pyrimidin-2-yl)amino)cyclohexyl)carbamoyl)bicyclo[1.1.1]pentan-1-yl)carbamate (45 mg, 0.065 mmol) was dissolved in a 4M solution of HCl in dioxane (650 μL). The mixture was stirred for 2 h at rt and evaporated to dryness and used directly without further purification.

3-amino-N-((±)-3-((5-chloro-4-(1-(phenylsulfonyl)-1H-indol-3-yl)pyrimidin-2-yl)amino)cyclohexyl)bicyclo[1.1.1]pentane-1-carboxamide was dissolved in methanol (650 μL) and a 1M solution of aqueous NaOH was added (975 μL, 0.975 mmol). The mixture was heated to 60° C. for 3 h, cooled and concentrated to ¼ volume. Mixture was diluted with DCM (5 mL) and extracted with saturated aqueous NH₄Cl (5 mL). Organics were washed with brine (5 mL) and then dried over sodium sulfate, filtered and concentrated. Crude residue was purified by SiO₂ chromatography (MeOH/DCM, 0-20% gradient) to afford the title compound (23 mg, 0.051 mmol, 78%) as a white solid.

N-[(±)-3-{[5-chloro-4-(1H-indol-3-yl)pyrimidin-2-yl]amino}cyclohexyl]-3-(prop-2-enamido)bicyclo[1.1.1]pentane-1-carboxamide

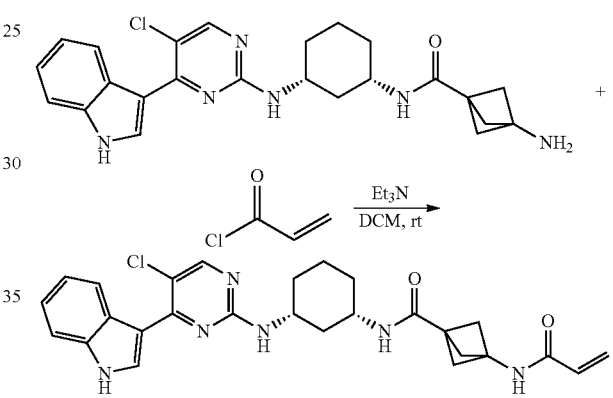

3-amino-N-[(±)-3-{[5-chloro-4-(1H-indol-3-yl)pyrimidin-2-yl]amino}cyclohexyl]bicyclo[1.1.1]pentane-1-carboxamide (23 mg, 0.051 mmol) was dissolved in DCM (1 mL) and Et₃N (14.2 μL, 0.102 mmol) was added followed by acryloyl chloride (6.2 μL, 0.076 mmol). The mixture was stirred for 1 hour at rt, diluted with DCM (5 mL) and quenched by saturated aqueous NaHCO₃. The aqueous layer was extracted with DCM (2×5 mL) and combined organics were washed with brine (10 mL), dried over sodium sulfate, filtered and concentrated. Crude residue was purified by SiO$_2$ chromatography (MeOH/DCM gradient 0-20%) to afford the title compound (4 mg, 0.0079 mmol, 16%) as a white solid. MS (m/z): 505.60 [M+1]$^+$.

Example 26. Synthesis of N-(3-{[5-chloro-4-(1H-indol-3-yl)pyrimidin-2-yl]amino}phenyl)-3-(prop-2-enamido)bicyclo[1.1.1]pentane-1-carboxamide (Compound 108)

tert-butyl(3-((3-((5-chloro-4-(1-(phenylsulfonyl)-1H-indol-3-yl)pyrimidin-2-yl)amino)phenyl)carbamoyl)bicyclo[1.1.1]pentan-1-yl)carbamate

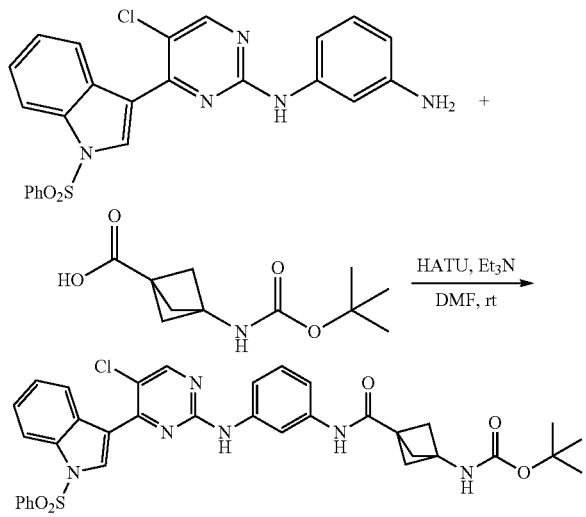

To a solution N1-(5-chloro-4-(1-(phenylsulfonyl)-1H-indol-3-yl)pyrimidin-2-yl)benzene-1,3-diamine (17.8 mg, 0.0374 mmol) in DMF (748 μL) was added Et$_3$N (18 μL, 0.123 mmol), 3-((tert-butoxycarbonyl)amino)bicyclo[1.1.1]pentane-1-carboxylic acid (18.7 mg, 0.0411 mmol) and HATU (15.6 mg, 0.0411 mmol). The mixture was stirred for 3 h at rt, then diluted with dichloromethane (5 mL) and extracted twice with water. The organic portion was washed with brine (5 mL), then dried over sodium sulfate, filtered and concentrated. The crude residue was purified by SiO$_2$ chromatography (0-20% MeOH/DCM gradient) to afford the title compound (12.8 mg, 0.00934 mmol, 50%) as an off-white solid.

3-amino-N-(3-{[5-chloro-4-(1H-indol-3-yl)pyrimidin-2-yl]amino}phenyl)bicyclo[1.1.1]pentane-1-carboxamide (Compound 1008)

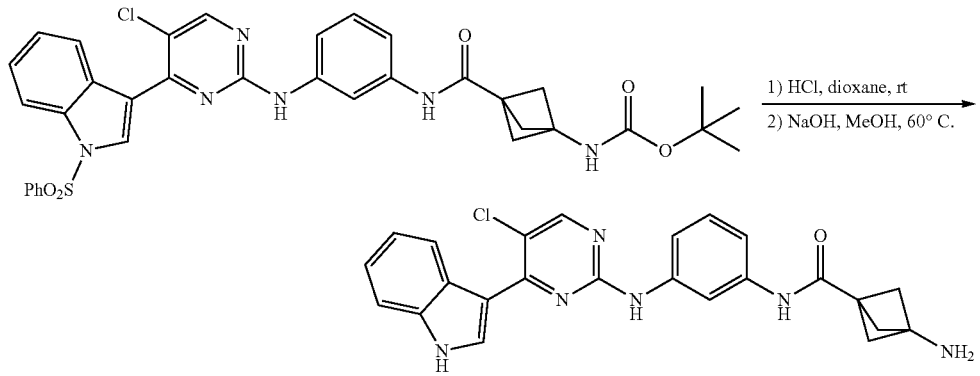

tert-butyl (3-((3-((5-chloro-4-(1-(phenylsulfonyl)-1H-indol-3-yl)pyrimidin-2-yl)amino)phenyl)carbamoyl)bicyclo[1.1.1]pentan-1-yl)carbamate (12.8 mg, 0.0187 mmol) was dissolved in a 4M solution of HCl in dioxane (200 μL). The mixture was stirred for 2 h at rt and evaporated to dryness and used directly without further purification.

3-amino-N-(3-((5-chloro-4-(1-(phenylsulfonyl)-1H-indol-3-yl)pyrimidin-2-yl)amino)phenyl)bicyclo[1.1.1]pentane-1-carboxamide was dissolved in methanol (200 μL) and a 1M solution of aqueous NaOH was added (281 μL, 0.281 mmol). The mixture was heated to 60° C. for 3 h, cooled and concentrated to ¼ volume. Mixture was diluted with DCM (5 mL) and extracted with saturated aqueous NH$_4$Cl (5 mL). Organics were washed with brine (5 mL) and then dried over sodium sulfate, filtered and concentrated. Crude residue was purified by SiO$_2$ chromatography (MeOH/DCM, 0-20% gradient) to afford the title compound (6.4 mg, 0.0144 mmol, 77%) as a white solid.

N-[(±)-3-{[5-chloro-4-(1H-indol-3-yl)pyrimidin-2-yl]amino}cyclohexyl]-3-(prop-2-enamido)bicyclo[1.1.1]pentane-1-carboxamide

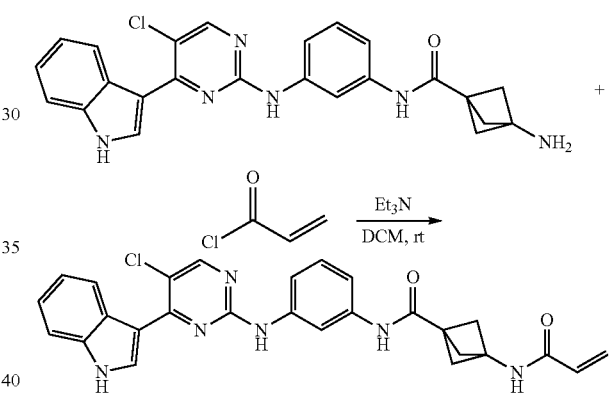

3-amino-N-(3-{[5-chloro-4-(1H-indol-3-yl)pyrimidin-2-yl]amino}phenyl)bicyclo[1.1.1]pentane-1-carboxamide (6.4 mg, 0.0144 mmol) was dissolved in DCM (500 μL) and Et$_3$N (4 μL, 0.0286 mmol) was added followed by acryloyl chloride (1.7 μL, 0.0215 mmol). The mixture was stirred for 2 h at rt diluted with DCM (5 mL) and quenched by saturated aqueous NaHCO$_3$. The aqueous layer was extracted with DCM (2×5 mL) and combined organics were washed with brine (10 mL), dried over sodium sulfate, filtered and concentrated. Crude residue was purified by SiO₂ chromatography (MeOH/DCM gradient 0-20%) to afford the title compound (3.1 mg, 0.00621 mmol, 44%) as a clear film. MS (m/z): 499.56 [M+1]⁺.

Example 27. Synthesis of (E)-N-(2-(6-(5-chloro-4-(1H-indol-3-yl)pyrimidin-2-ylamino)-1H-indol-2-yl)ethyl)-4-(dimethylamino)but-2-enamide (Compound 175)

tert-butyl 4-(2-amino-4-nitrophenyl)but-3-ynylcarbamate

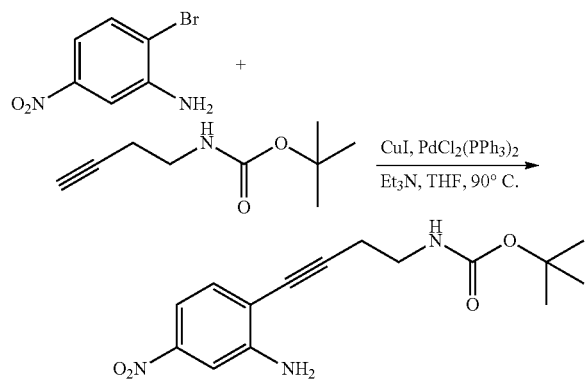

A degassed solution of 2-bromo-5-nitroaniline (1 g, 4.63 mmol), tert-butyl but-3-ynylcarbamate (0.78 g, 4.63 mmol), Et₃N (1.93 mL, 13.9 mmol), CuI (88 mg, 0.46 mmol) Pd(PPh₃)₂Cl₂ (323 mg, 0.46 mmol) in THF (15 mL) was heated 12 h at 75° C. The cooled mixture was diluted with EtOAc (50 mL), washed with saturated NaHCO₃ (10 mL), brine (10 mL), then dried over MgSO₄, filtered and evaporated to dryness. The residue was purified SiO₂ chromatography (Hex/EtOAc 10 to 70% gradient) and afforded the title compound (1 g, 3.28 mmol, 71%) as an orange solid.

tert-butyl 2-(6-nitro-1H-indol-2-yl)ethylcarbamate

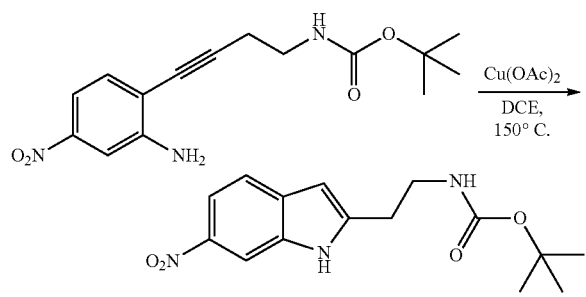

A solution of tert-butyl 4-(2-amino-4-nitrophenyl)but-3-ynylcarbamate (975 mg, 3.20 mmol) and Cu(OAc)₂ (872 mg, 4.80 mmol) in DCE (10 mL) was heated 15 min at 150° C. The cooled mixture was filtered over celite (DCM) and the filtrate was evaporated to dryness. The residue was purified by SiO₂ chromatography (Hex/EtOAc 10 to 45% gradient) and afforded the title compound (570 mg, 1.87 mmol, 58%) as a brown oil.

tert-butyl 2-(6-amino-1H-indol-2-yl)ethylcarbamate

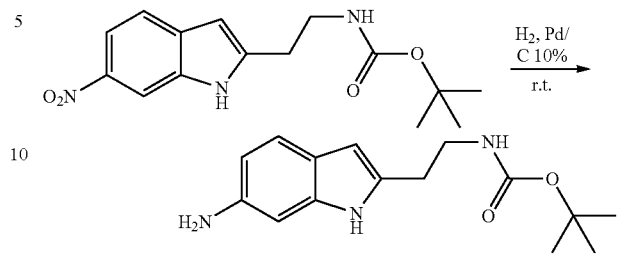

A degassed solution of tert-butyl 2-(6-nitro-1H-indol-2-yl)ethylcarbamate (54 mg, 0.177 mmol) in MeOH (3 mL) was treated with 10% Pd/C (15 mg). The mixture was stirred 5 h under H₂ (1 atm), filtered over celite (MeOH) and the filtrate was evaporated to dryness affording the title compound (49 mg, 0.177 mmol, 100%) as a pale yellow solid.

tert-butyl 2-(6-(5-chloro-4-(1-(phenylsulfonyl)-1H-indol-3-yl)pyrimidin-2-ylamino)-1H-indol-2-yl)ethylcarbamate

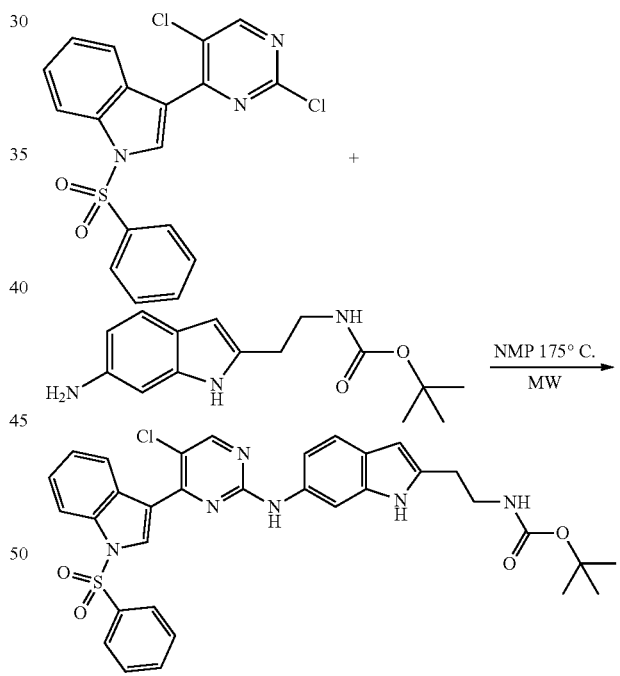

A suspension of 3-(2,5-dichloropyrimidin-4-yl)-1-(phenylsulfonyl)-1H-indole (73 mg, 0.181 mmol), tert-butyl 2-(6-amino-1H-indol-2-yl)ethylcarbamate (50 mg, 0.181 mmol) and DIPEA (63 µL, 0.36 mmol) in NMP (3 mL) was heated 20 min at 175° C. (microwave). The cooled mixture was diluted with EtOAc (10 mL), washed with saturated NaHCO₃ (3 mL), brine (3 mL), then dried over MgSO₄, filtered and evaporated to dryness. The residue was purified by SiO₂ chromatography (DCM/MeOH 0 to 10%, gradient) and afforded the title compound (45 mg, 0.070 mmol, 39%) as a pale beige solid.

2-(2-aminoethyl)-N-(5-chloro-4-(1H-indol-3-yl)pyr-
midin-2-yl)-1H-indol-6-amine.HCl (Compound
1028)

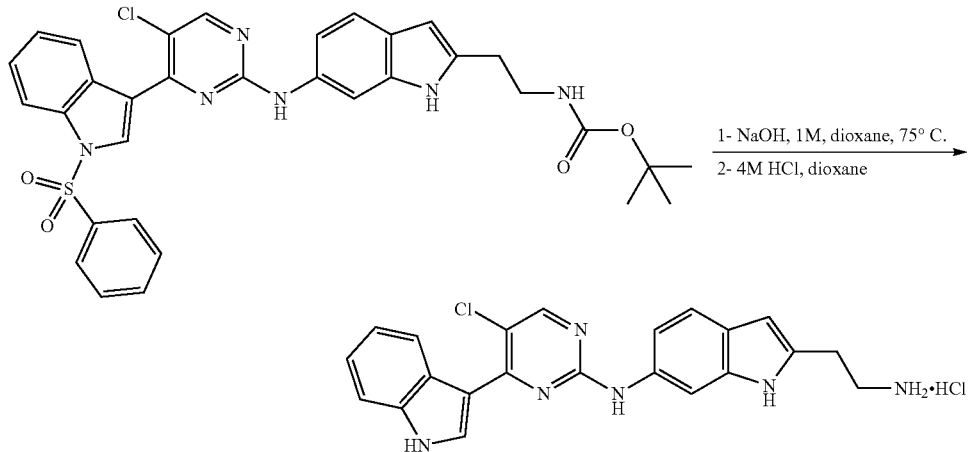

A suspension of tert-butyl 2-(6-(5-chloro-4-(1-(phenyl-sulfonyl)-1H-indol-3-yl)pyrimidin-2-ylamino)-1H-indol-2-yl)ethylcarbamate (150 mg, 0.233 mmol) and 1M NaOH (2 mL, 0.467 mmol) in dioxane (2 mL) was heated 30 min at 75° C. The cooled mixture was diluted with DCM (25 mL) and H$_2$O (25 mL); the aqueous layer was extracted DCM (3×10 mL) and the combined organic layers were dried over MgSO$_4$, filtered and evaporated to dryness. The residue was dissolved in DCM (2 mL) and treated dropwise with 4M HCl dioxane (2 mL). The resulting suspension was stirred for 30 min before addition of Et$_2$O (25 mL). The resulting suspension was filtered and afforded the title compound (90 mg, 0.205 mmol, 88%) as a brown solid which was used in the next step without further purification. $^1$H NMR (500 MHz, DMSO) δ 11.83 (s, 1H), 10.86 (s, 1H), 9.40 (s, 1H), 8.55 (s, 1H), 8.44 (d, J=3.0 Hz, 1H), 8.39-8.27 (m, 1H), 7.81 (d, J=20.4 Hz, 3H), 7.43 (d, J=8.1 Hz, 1H), 7.30 (d, J=8.5 Hz, 1H), 7.22 (dd, J=8.5, 1.9 Hz, 1H), 7.14 (t, J=7.1 Hz, 1H), 6.98 (s, 1H), 6.15 (s, 1H), 3.18-3.05 (m, 2H), 2.95 (t, J=7.7 Hz, 2H);
MS (m/z): 403.57 [M+1]$^+$.

(E)-N-(2-(6-(5-chloro-4-(1H-indol-3-yl)pyrimidin-2-
ylamino)-1H-indol-2-yl)ethyl)-4-(dimethylamino)
but-2-enamide To a solution of 2-(2-aminoethyl)-N-(5-chloro-4-(1H-indol-3-yl)pyrimidin-2-yl)-1H-indol-6-amine.HCl (37 mg, 0.084 mmol), (E)-4-(dimethylamino)but-2-enoic acid (13 mg, 0.100 mmol) and Et$_3$N (51 μL, 0.51 mmol) in DMF (2 mL) was added, followed by HBTU (48 mg, 0.127 mmol). The mixture was stirred 3 h at rt, purified on a reverse phase chromatography column (C18, water/ACN 15 to 70% gradient) and afforded the title compound (3.7 mg, 0.007 mmol, 9%) as a white solid after lyophilisation. $^1$H NMR (500 MHz, DMSO) δ 11.79 (s, 1H), 10.77 (s, 1H), 9.34 (s, 1H), 8.58-8.49 (m, 1H), 8.43 (d, J=3.1 Hz, 1H), 8.33 (s, 1H), 8.26-8.19 (m, 1H), 7.72 (s, 1H), 7.41 (d, J=8.1 Hz, 1H), 7.25 (d, J=8.5 Hz, 1H), 7.18 (dd, J=8.5, 1.9 Hz, 1H), 7.15-7.10 (m, 1H), 6.97 (s, 1H), 6.48 (dd, J=21.1, 14.2 Hz, 2H), 6.08 (d, J=18.7 Hz, 2H), 3.49-3.36 (m, 4H), 2.81 (t, J=7.2 Hz, 2H), 1.62-1.33 (m, 4H); MS (m/z): 514.65 [M+1]$^+$.

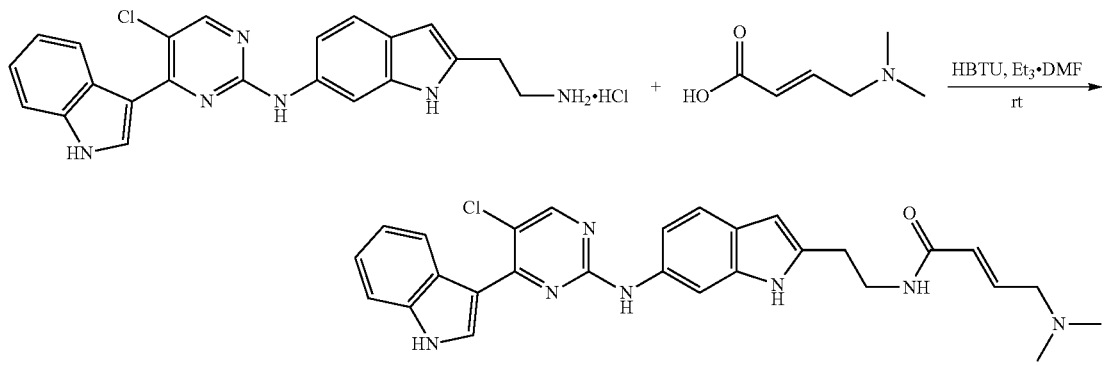

Example 28. Synthesis of N-(2-(6-(5-chloro-4-(1H-indol-3-yl)pyrimidin-2-ylamino)-1H-indol-2-yl)ethyl)-4-(dimethylamino)butanamide (Compound 1029)

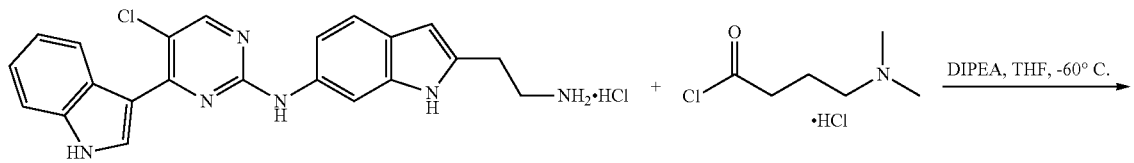

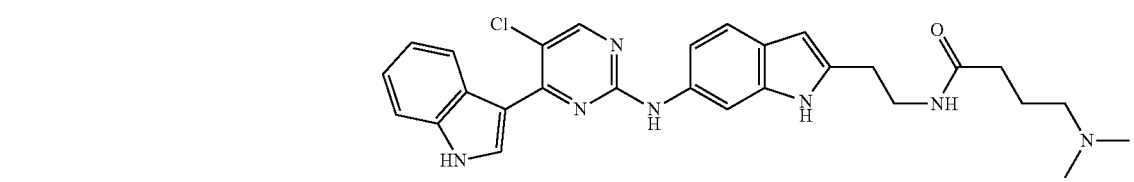

A cooled (−30° C.) solution of 2-(2-aminoethyl)-N-(5-chloro-4-(1H-indol-3-yl)pyrimidin-2-yl)-1H-indol-6-amine.HCl (Compound 1028; 37 mg, 0.084 mmol) and DIPEA (44 µL, 0.25 mmol) in DMF (2 mL) was treated with a 45 mg/mL solution of 4-(dimethylamino)butanoyl chloride.HCl in THF (288 µL, 0.084 mmol). The mixture was stirred 30 min at rt and concentrated under reduced pressure. The residue was purified by reverse phase chromatography ($C_{18}$, $H_2O$/ACN+0.1% $HCO_2H$ 15 to 60% gradient) and afforded the title compound (43 mg, 0.083 mmol, 99%) as a white solid after lyophilisation. MS (ES+)=516.66 $[M+1]^+$.

Example 29. Synthesis of 6-amino-N-(3-(5-chloro-4-(1H-indol-3-yl)pyrimidin-2-ylamino)phenyl)nicotinamide (Compound 1024)

N1-(5-chloro-4-(1-(phenylsulfonyl)-1H-indol-3-yl)pyrimidin-2-yl)benzene-1,3-diamine

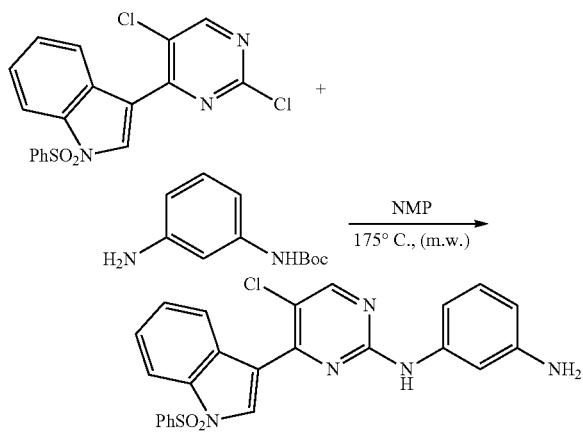

A solution of 3-(2,5-dichloropyrimidin-4-yl)-1-(phenylsulfonyl)-1H-indole (971 mg, 2.40 mmol), tert-butyl 3-aminophenylcarbamate prepared following WO2006136005 (500 mg. 2.40 mmol) in NMP (10 mL) was heated at 175° C. (microwave) for 15 min. The cooled mixture was diluted with EtOAc (50 mL), washed with $H_2O$ (15 mL), brine (15 mL), dried over $MgSO_4$, filtered and evaporated to dryness. The residue was purified by $SiO_2$ chromatography (Hex/EtOAc 10 to 70%, gradient) and afforded the title compound (363 mg, 0.763 mmol, 32%) as a pale yellow solid.

6-amino-N-(3-(5-chloro-4-(1-(phenylsulfonyl)-1H-indol-3-yl)pyrimidin-2-ylamino)phenyl)nicotinamide

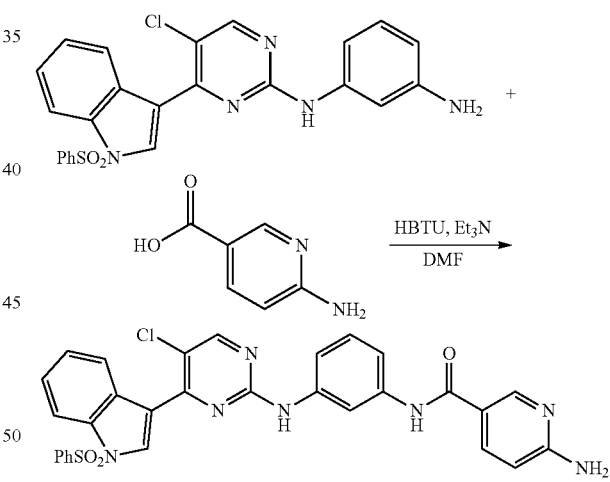

A solution of N1-(5-chloro-4-(1-(phenylsulfonyl)-1H-indol-3-yl)pyrimidin-2-yl)benzene-1,3-diamine (80 mg, 0.168 mmol) and 6-aminonicotinic acid (28 mg, 0.202 mmol) in DMF (1.1 mL) was treated with HBTU (96 mg, 0.252 mmol) and $Et_3N$ (70 µL, 0.504 mmol). The resulting mixture was stirred 24 h at rt and diluted with EtOAc (20 mL) and saturated $H_2O$ (10 mL). The layers were separated and the aqueous layer was extracted with EtOAc (3×10 mL). The combined organic layers were washed with brine (10 mL), dried over $MgSO_4$, filtered and evaporated to dryness. The residue was purified by $SiO_2$ chromatography (Hex/EtOAc 30 to 100% gradient) and afforded the title compound (52 mg, 0.087 mmol, 52%) as a creamy solid.

6-amino-N-(3-(5-chloro-4-(1H-indol-3-yl)pyrmidin-2-ylamino)phenyl)nicotinamide (Compound 1024)

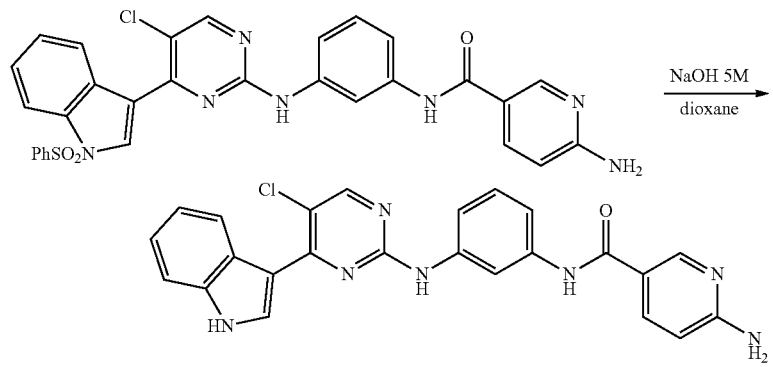

A solution of 6-amino-N-(3-(5-chloro-4-(1-(phenylsulfonyl)-1H-indol-3-yl)pyrimidin-2-ylamino)phenyl)nicotinamide (40 mg, 0.067 mmol) in dioxane (0.67 mL) was treated with a 5M solution of NaOH in H₂O (134 µL, 0.671 mmol) and heated at 50° C. for 3 h. The cooled mixture was diluted with a saturated solution of NH₄Cl (500 µL) and DMSO (500 µL) and directly purified by reverse phase chromatography (C₁₈, H₂O/ACN+0.1% HCO₂H 25 to 100% gradient) to afford the title compound (5.2 mg, 0.011 mmol, 17%) as a yellow solid after lyophilisation.

MS (m/z): 456.59 [M+1]⁺.

Example 30. Synthesis of 6-amino-N-((1S,3R)-3-(5-chloro-4-(1H-indol-3-yl)pyrimidin-2-ylamino)cyclohexyl)nicotinamide (Compound 1025)

(1S,3R)-3-(Benzyloxycarbonylamino)cyclohexylamino 2,2-dimethylpropionate

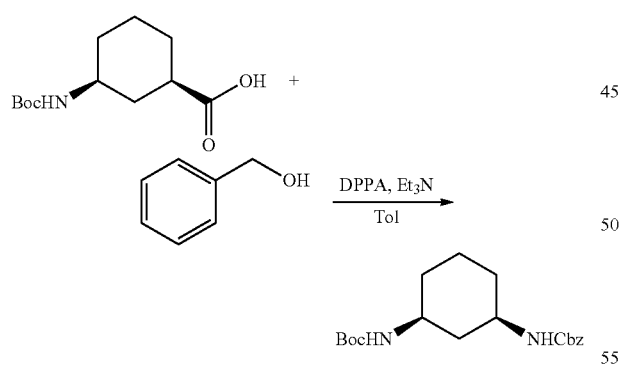

To a solution of (1R,3S)-3-(tert-butoxycarbonylamino)cyclohexanecarboxylic acid (prepared following Tetrahedron: *Asymmetry* 2010 (21), 864-866) (8.77 g, 36.1 mmol) was added Et₃N (5.53 mL, 39.7 mmol) and DPPA (7.7 mL, 36.1 mmol). The resulting solution was stirred 2 h at 110° C. then cooled down to 80° C. Benzyl alcohol (4.66 mL, 45.1 mmol) and triethylamine (5.53 mL, 39.7 mmol) were added and the mixture was stirred 20 h at 80° C. The cooled solution was diluted with EtOAc (100 mL) and H₂O (50 mL). The layers were separated and the aqueous layer was extracted with EtOAc (2×50 mL). The combined organics were dried (MgSO₄), filtered and evaporated to dryness. The residue was purified by SiO₂ chromatography (Hex/EtOAc 1 to 100% gradient) and afforded the title compound (9.89 g, 28.4 mmol, 79%) as a white solid.

tert-butyl(1S,3R)-3-aminocyclohexylcarbamate

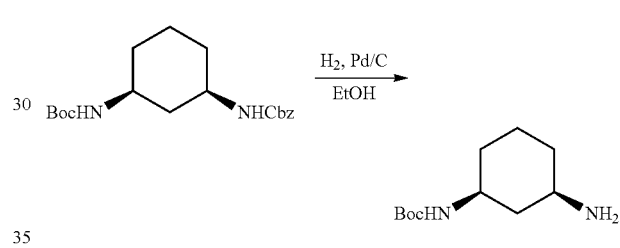

To a degassed solution of (1S,3R)-3-(Benzyloxycarbonylamino)cyclohexylamino 2,2-dimethylpropionate (10 g, 28.4 mmol) in EtOH (473 mL) was added 10% w/w Pd/C (450 mg). The reaction mixture was stirred 5 h under H₂ (1 atm). The reaction mixture was filtered through a pad of celite (EtOH), then the filtrate was evaporated to dryness to afford the title compound (6.08 g, 28.4 mmol, 100%) as a white solid.

tert-butyl(1S,3R)-3-(5-chloro-4-(1-(phenylsulfonyl)-1H-indol-3-yl)pyrimidin-2-ylamino)cyclohexylcarbamate

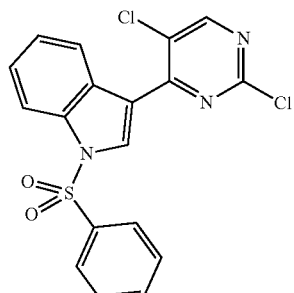

+

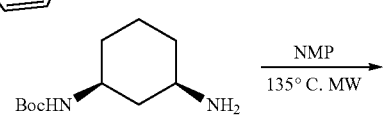

133

-continued

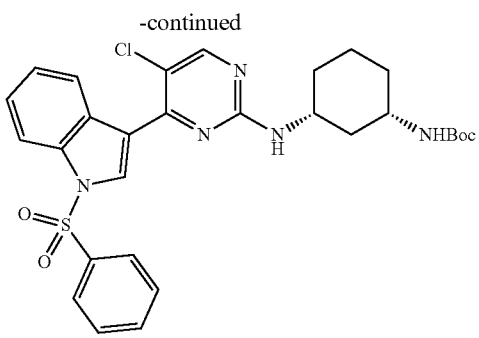

A solution of 3-(2,5-dichloropyrimidin-4-yl)-1-(phenylsulfonyl)-1H-indole (2.91 g, 7.20 mmol), tert-butyl (1S,3R)-3-aminocyclohexylcarbamate (1.24 g, 5.76 mmol) and diisopropylethylamine (1.05 mL, 6.05 mmol) in NMP (14.5 mL) was heated 1 h 30 at 135° C. The mixture was diluted with EtOAc (200 mL), washed with H$_2$O (50 mL), brine (50 mL), then dried (MgSO$_4$), filtered and evaporated to dryness. The residue was purified by SiO$_2$ chromatography (DCM/EtOAc 0 to 30% gradient), and afforded the title compound (1.88 g, 3.23 mmol, 56%) as a light yellow foam.

(1R,3S)—N$^1$-(5-chloro-4-(1-(phenylsulfonyl)-1H-indol-3-yl)pyrimidin-2-yl)cyclohexane-1,3-diamine.HCl

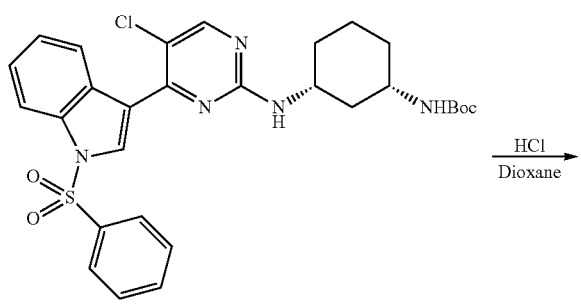

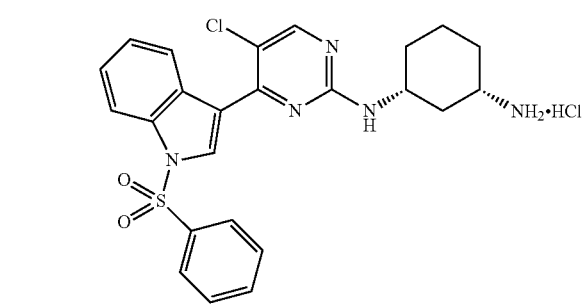

To a solution of tert-butyl (1S,3R)-3-(5-chloro-4-(1-(phenylsulfonyl)-1H-indol-3-yl)pyrimidin-2-ylamino)cyclohexylcarbamate (1.88 g, 3.23 mmol) in DCM (16.1 mL) was added a solution of 4 N HCl in dioxane (12.11 mL, 48.44 mmol). The resulting mixture was stirred 1.5 h at rt before being evaporated to dryness and afforded the title compound (1.72 g, 3.10 mmol, 96%) as a light yellow solid which was used in the next step without further purification.

134

6-amino-N-((1S,3R)-3-(5-chloro-4-(1-(phenylsulfonyl)-1H-indol-3-yl)pyrimidin-2-ylamino)cyclohexyl)nicotinamide

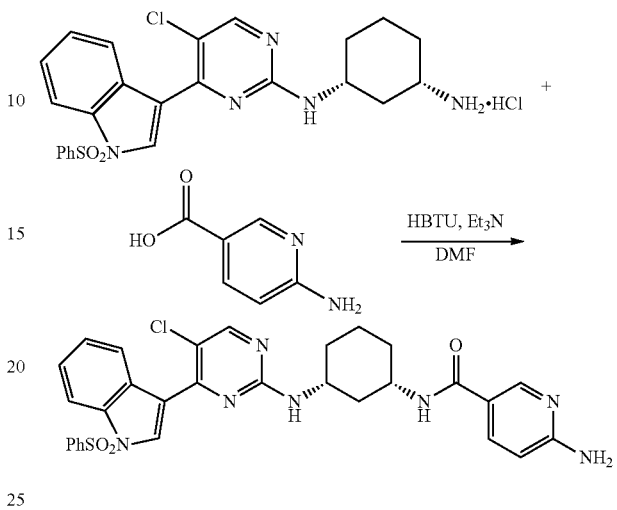

A solution of (1R,3S)—N$^1$-(5-chloro-4-(1-(phenylsulfonyl)-1H-indol-3-yl)pyrimidin-2-yl)cyclohexane-1,3-diamine.HCl (107 mg, 0.207 mmol) and 6-aminonicotinic acid (34 mg, 0.249 mmol) in DMF (1.4 mL) was treated with HBTU (118 mg, 0.311 mmol) and Et$_3$N (87 μL, 0.622 mmol). The resulting mixture was stirred 24 h at rt and diluted with EtOAc (20 mL) and H$_2$O (10 mL). The layers were separated and the aqueous layer was extracted with EtOAc (3×10 mL). The combined organic layers were washed with brine (10 mL), dried over MgSO$_4$, filtered and evaporated to dryness. The residue was purified by SiO$_2$ chromatography (Hex/EtOAc 20 to 100% gradient) and afforded the title compound (44 mg, 0.073 mmol, 35%) as a creamy solid.

6-amino-N-((1S,3R)-3-(5-chloro-4-(1H-indol-3-yl)pyrimidin-2-ylamino)cyclohexyl)nicotinamide

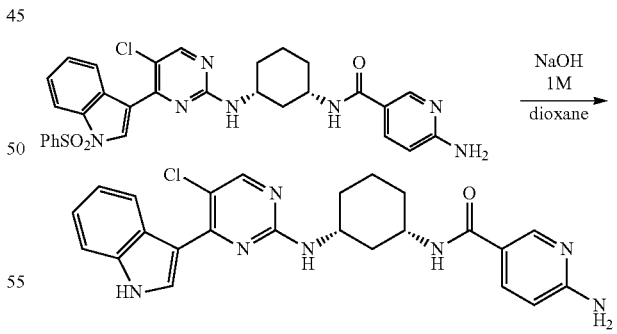

A solution of 6-amino-N-((1S,3R)-3-(5-chloro-4-(1-(phenylsulfonyl)-1H-indol-3-yl)pyrimidin-2-ylamino)cyclohexyl)nicotinamide (44 mg, 0.073 mmol) in dioxane (0.73 mL) was treated with a 1M solution of NaOH in H$_2$O (1.10 mL, 1.096 mmol) and heated at 50° C. for 5 h. The cooled mixture was diluted with a 4M solution of HCl in H$_2$O (274 μL, 1.096 mmol) and the residue was evaporated to dryness. The residue was purified by reverse phase chromatography (C$_{18}$, H$_2$O/ACN+0.1% HCO$_2$H 0 to 60% gradient) and afforded the title compound (18 mg, 0.039 mmol, 54%) as a yellow solid after lyophilisation. $^1$H NMR (500 MHz, DMSO) δ 11.82 (s, 1H), 8.59 (s, 1H), 8.50-8.37 (m, 2H), 8.25 (s, 1H), 7.98 (d, J=8.0 Hz, 1H), 7.80 (dd, J=8.7, 2.4 Hz, 1H), 7.55-7.43 (m, 1H), 7.28 (d, J=8.0 Hz, 1H), 7.21 (s, 2H), 6.52-6.27 (m, 3H), 3.92 (s, 2H), 2.18 (s, 1H), 2.00 (s, 1H), 1.82 (d, J=12.3 Hz, 2H), 1.57-1.33 (m, J=47.8 Hz, 2H), 1.36-1.19 (m, J=16.4, 8.1 Hz, 2H); MS (m/z): 462.58 [M+1]$^+$.

Example 31. Synthesis of 2-amino-N-((1S,3R)-3-(5-chloro-4-(1H-indol-3-yl)pyrimidin-2-ylamino)cyclohexyl)thiazole-4-carboxamide (Compound 1026)

tert-butyl 4-((1S,3R)-3-(5-chloro-4-(1-(phenylsulfonyl)-1H-indol-3-yl)pyrimidin-2-ylamino)cyclohexylcarbamoyl)thiazol-2-ylcarbamate

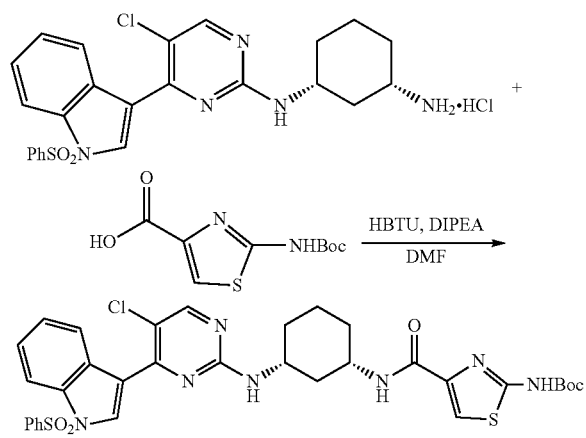

and afforded the title compound (95 mg, 0.134 mmol, 58%) as a pale yellow foam.

2-amino-N-((1S,3R)-3-(5-chloro-4-(1-(phenylsulfonyl)-1H-indol-3-yl)pyrmidin-2-ylamino)cyclohexyl)thiazole-4-carboxamide.HCl

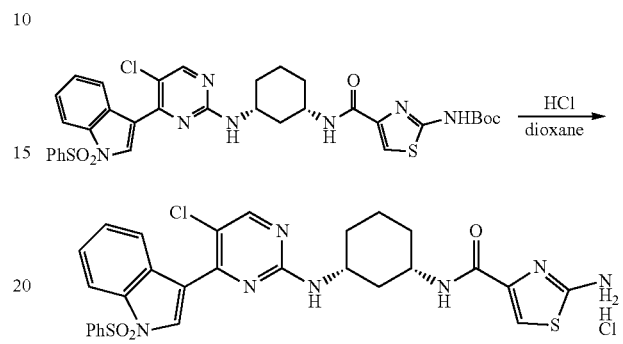

A solution of tert-butyl 4-((1S,3R)-3-(5-chloro-4-(1-(phenylsulfonyl)-1H-indol-3-yl)pyrimidin-2-ylamino)cyclohexylcarbamoyl)thiazol-2-ylcarbamate (94 mg, 0.133 mmol) in DCM (700 µL) was treated with a 4M solution of HCl in dioxane (500 µL, 1.99 mmol) and stirred 90 min at rt. The resulting mixture was evaporated to dryness and afforded the title compound (77 mg, 0.126 mmol, 95%) as a white solid which was used in the next step without further purification.

2-amino-N-((1S,3R)-3-(5-chloro-4-(1H-indol-3-yl)pyrmidin-2-ylamino)cyclohexyl)thiazole-4-carboxamide (Compound 1026)

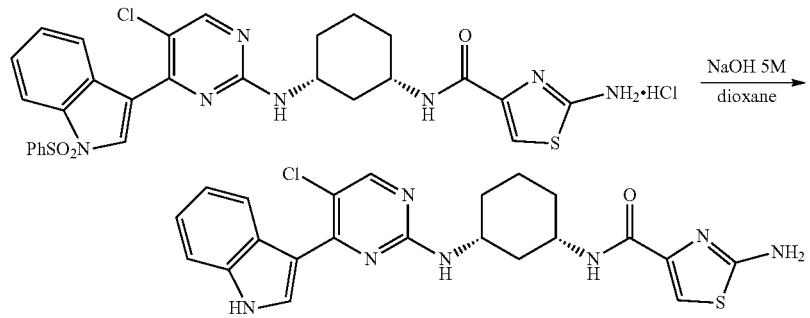

A solution of (1R,3S)—N$^1$-(5-chloro-4-(1-(phenylsulfonyl)-1H-indol-3-yl)pyrimidin-2-yl)cyclohexane-1,3-diamine.HCl prepared as in Example 30 (119 mg, 0.230 mmol) and 2-(tert-butoxycarbonylamino)thiazole-4-carboxylic acid (68 mg, 0.276 mmol) in DMF (2.3 mL) was treated with HBTU (131 mg, 0.276 mmol) and DIPEA (114 µL, 0.691 mmol). The resulting mixture was stirred 16 h at rt and diluted with EtOAc (30 mL) and saturated NaHCO$_3$ (10 mL). The layers were separated and the aqueous layer was extracted with EtOAc (3×10 mL). The combined organic layers were washed with brine (10 mL), dried over MgSO$_4$, filtered and evaporated to dryness. The residue was purified by SiO$_2$ chromatography (DCM/EtOAc 0 to 60% gradient)

A solution of 2-amino-N-((1S,3R)-3-(5-chloro-4-(1-(phenylsulfonyl)-1H-indol-3-yl)pyrimidin-2-ylamino)cyclohexyl)thiazole-4-carboxamide.HCl (60 mg, 0.093 mmol) in dioxane (1.9 mL) was treated with a 5M solution of NaOH in H$_2$O (90 µL, 0.466 mmol) and heated at 50° C. for 4 h. The cooled mixture was treated with a 1M solution of HCl in H$_2$O until pH reached 7.0 and diluted with EtOAc (20 mL). The layers were separated and the aqueous layer was washed with EtOAc (3×10 mL). The aqeuous layer was evaporated to dryness and the residue was purified by reverse phase chromatography (C$_{18}$, H$_2$O/ACN+0.1% HCO$_2$H 10 to 70% gradient) and afforded the title compound (37 mg, 0.079 mmol, 85%) as a white solid after lyophilization. $^1$H NMR (500 MHz, DMSO) δ 11.82 (s, 1H), 8.59 (br s, 1H), 8.47 (d, J=2.5 Hz, 1H), 8.25 (s, 1H), 7.56-7.41 (m, 2H), 7.26 (d, J=7.9 Hz, 1H), 7.23-7.18 (m, 2H), 7.18 (s, 1H), 7.07 (s, 2H), 4.04-3.75 (m, 2H), 2.24-2.12 (m, 1H), 2.06-1.94 (m, 1H), 1.87-1.76 (m, 2H), 1.48-1.34 (m, 2H), 1.32-1.18 (m, 2H); MS (m/z): 468.57 [M+1]+.

Example 32. Synthesis of 6-amino-N-((1S,3R)-3-(5-chloro-4-(1H-indol-3-yl)pyrimidin-2-ylamino)cyclohexyl)pyridazine-3-carboxamide (Compound 1027)

6-amino-N-((1S,3R)-3-(5-chloro-4-(1-(phenylsulfonyl)-1H-indol-3-yl)pyrimidin-2-ylamino)cyclohexyl)pyridazine-3-carboxamide

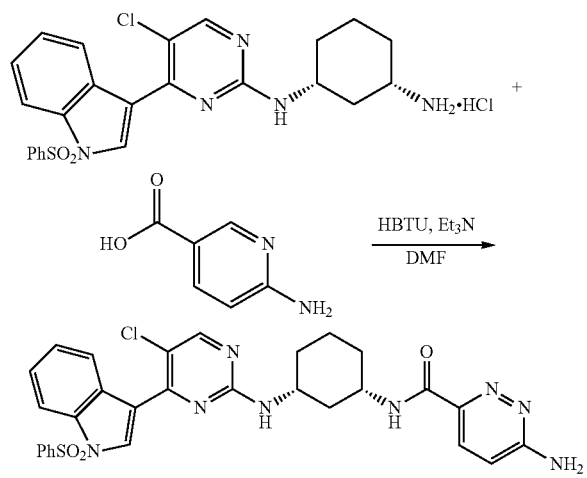

A solution of (1R,3S)—N[1]-(5-chloro-4-(1-(phenylsulfonyl)-1H-indol-3-yl)pyrimidin-2-yl)cyclohexane-1,3-diamine.HCl prepared as in Example 4 (113 mg, 0.218 mmol) and 6-aminopyridazine-3-carboxylic acid (36 mg, 0.262 mmol) in DMF (2.5 mL) was treated with HBTU (124 mg, 0.327 mmol) and DIPEA (152 μL, 0.872 mmol). The resulting mixture was stirred 16 h at rt and diluted with EtOAc (30 mL) and saturated NaHCO₃ (10 mL). The layers were separated and the aqueous layer was extracted with EtOAc (3×10 mL). The combined organic layers were washed with brine (10 mL), dried over MgSO₄, filtered and evaporated to dryness. The residue was purified by SiO₂ chromatography (DCM/MeOH 0 to 10% gradient) and afforded the title compound (78 mg, 0.129 mmol, 59%) as a pale yellow solid.

6-amino-N-((1S,3R)-3-(5-chloro-4-(1H-indol-3-yl)pyrmidin-2-ylamino)cyclohexyl)pyridazine-3-carboxamide (Compound 1027)

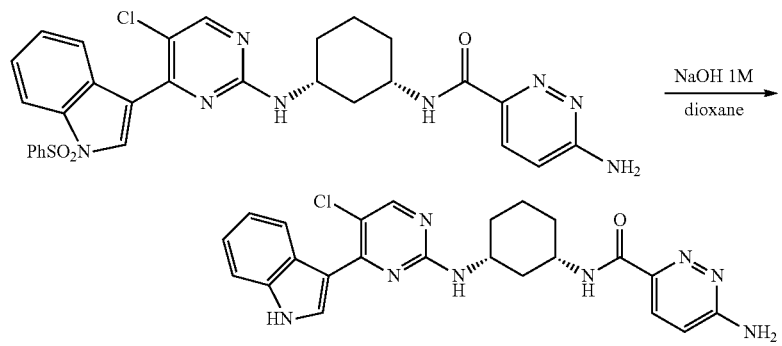

A solution of 6-amino-N-((1S,3R)-3-(5-chloro-4-(1-(phenylsulfonyl)-1H-indol-3-yl)pyrimidin-2-ylamino)cyclohexyl)pyridazine-3-carboxamide (78 mg, 0.129 mmol) in dioxane (3.0 mL) was treated with a 1M solution of NaOH in H₂O (1.29 mL, 1.29 mmol) and heated at 75° C. for 3 h. The cooled mixture was treated with a 1M solution of HCl in H₂O until the pH reached 7. The resulting solid was filtered, washed with H₂O and the residue was purified by reverse phase chromatography (C₁₈, H₂O/ACN+0.1% HCO₂H 10 to 70% gradient) and afforded the title compound (40 mg, 0.086 mmol, 67%) as a yellow solid after lyophilisation. $^1$H NMR (500 MHz, DMSO) δ 11.75 (brs, 1H), 8.60 (brs, 1H), 8.50 (d, J=8.6 Hz, 1H), 8.40 (d, J=2.2 Hz, 1H), 8.18 (brs, 1H), 7.69 (d, J=9.2 Hz, 1H), 7.42 (d, J=8.9 Hz, 1H), 7.22 (d, J=8.0 Hz, 1H), 7.18-7.10 (m, 2H), 6.84 (s, 2H), 6.76 (d, J=9.2 Hz, 1H), 3.88 (brs, 2H), 2.11 (brs, 1H), 1.93 (brs, 1H), 1.75 (brs, 2H), 1.48 (brs, 1H), 1.37 (brs, 2H), 1.21 (brs, 1H); MS (m/z): 463.56 [M+1]+.

Example 33. Synthesis of 1-(4-((1S,3R)-3-(5-chloro-4-(1H-indol-3-yl)pyrimidin-2-ylamino)cyclohexyl)piperazin-1-yl)prop-2-en-1-one tert-Butyl (1R,3S)-3-(hydroxymethyl)cyclohexylcarbamate

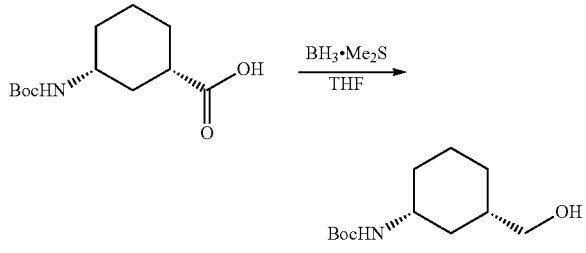

A cooled (0° C.) solution of (1S,3R)-3-(tert-butoxycarbonylamino)cyclohexanecarboxylic acid (prepared following *Tetrahedron: Asymmetry* 2010 (21), 864-866) (1.24 g, 5.09 mmol) in THF (34 mL) was treated with a 2M solution of BH₃Me₂S in THF (3.7 mL, 7.38 mmol) and stirred overnight at rt. The resulting solution was treated with a 1M solution of HCl in H₂O (20 mL) and extracted with EtOAc (3×20 mL). The combined organic layers were dried over MgSO₄, filtered and evaporated to dryness affording the title compound (1.17 g, 5.09 mmol, 100%) as a colorless oil which was used in the next step without further purification.

(R)-tert-butyl 3-methylenecyclohexylcarbamate

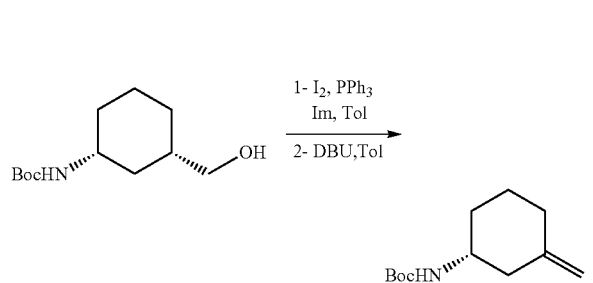

A cooled (0° C.) solution of tert-butyl (1R,3S)-3-(hydroxymethyl)cyclohexylcarbamate (200 mg, 0.87 mmol) in toluene (6 mL) was sequentially treated with imidazole (148 mg, 2.18 mmol), PPh$_3$ (572 mg, 2.18 mmol), and I$_2$ (288 mg, 1.13 mmol). The resulting mixture was stirred overnight at rt before being diluted with a saturated solution of NaHCO$_3$ (10 mL), a 5% solution of Na$_2$S$_2$O$_3$ (10 mL) and DCM (30 mL). The layers were separated and the aqueous layer was extracted with DCM (2×30 mL). The combined organic layers were dried over MgSO$_4$, filtered and evaporated to dryness. The residue was taken back in toluene (10 mL), treated with DBU (261 mL, 1.74 mmol) and heated overnight at 80° C. The cooled mixture was diluted with a saturated solution of NH$_4$Cl (10 mL) and EtOAc (20 mL). The layers were separated and the aqueous layer was extracted with EtOAc (3×20 mL). The combined organic layers were dried over MgSO$_4$, filtered and evaporated to dryness. The residue was purified by SiO$_2$ chromatography (Hex/EtOAc 5 to 30% gradient) and afforded the title compound (72 mg, 0.341 mmol, 39%) as a white solid.

(R)-tert-butyl 3-oxocyclohexylcarbamate

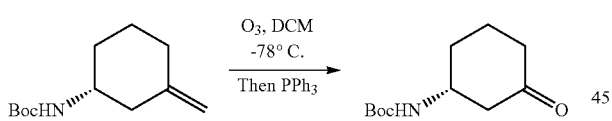

O$_3$ was bubbled into a cooled (−78° C.) solution of (R)-tert-butyl 3-methylenecyclohexylcarbamate (424 mg, 2.01 mmol) in DCM (40 mL) for 30 min, at which point PPh$_3$ (917 mg, 6.02 mmol) was added. The resulting mixture was warmed up to rt and evaporated to dryness. The residue was purified by SiO$_2$ chromatography (Hex/EtOAc 0 to 60% gradient) and afforded the title compound (415 mg, 1.95 mmol, 97%) as a white solid.

Benzyl 4-((3R)-3-(tert-butoxycarbonylamino)cyclohexyl)piperazine-1-carboxylate

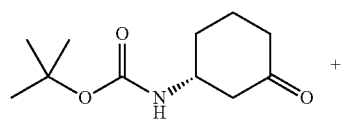

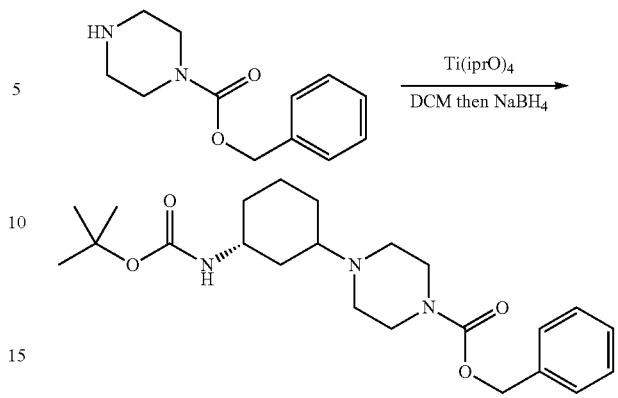

Titanium isopropoxyde (1.04 mL, 3.52 mmol) was added to a stirring solution of (R)-tert-butyl 3-oxocyclohexylcarbamate (150 mg, 0.703 mmol) and 1-Z-piperazine (203 µL, 1.06 mmol) at room temperature. The reaction mixture was allowed to stir for 18 h at room temperature. NaBH$_4$ (160 mg, 4.22 mmol) was then added and the reaction mixture was cooled to −78° C. where upon MeOH (2 mL) was added dropwise. The reaction mixture was then allowed to warm to rt, diluted with DCM (150 mL) and NaHCO$_3$ (sat) (30 mL) and filtered through celite. The phases were then separated, dried with MgSO$_4$, filtered and concentrated under reduced pressure to a yellow oil (267 mg). The residue was purified by SiO$_2$ chromatography (DCM/EtOAc 0 to 100% gradient) and afforded the title compounds as 2 diastereoisomers D1 (trans) as a yellow oil (109 mg, 0.26 mmol, 37%) and D2 (cis) as a yellow oil (92 mg, 0.22 mmol, 31%) with a diastereoisomer ratio 3:2 for the reaction.

Benzyl 4-((1S,3R)-3-aminocyclohexyl)piperazine-1-carboxylate hydrochloride

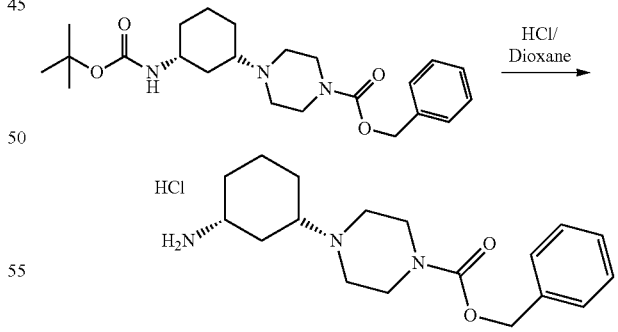

To a solution of benzyl 4-((3R)-3-(tert-butoxycarbonylamino)cyclohexyl)piperazine-1-carboxylate (92 mg, 0.22 mmol) in DCM (2.2 mL) is added 4 N HCl in dioxane (0.3 mL, 1.1 mmol). The reaction was stirred at room temperature for 18 h. The reaction mixture was then concentrated, azeotroped three times with DCM and dried on vacuum pump to afford the title compound as a yellow oil (70 mg, 0.22 mmol, 100%).

Benzyl 4-((1S,3R)-3-(5-chloro-4-(1-(phenylsulfonyl)-1H-indol-3-yl)pyrimidin-2-ylamino)cyclohexyl)piperazine-1-carboxylate

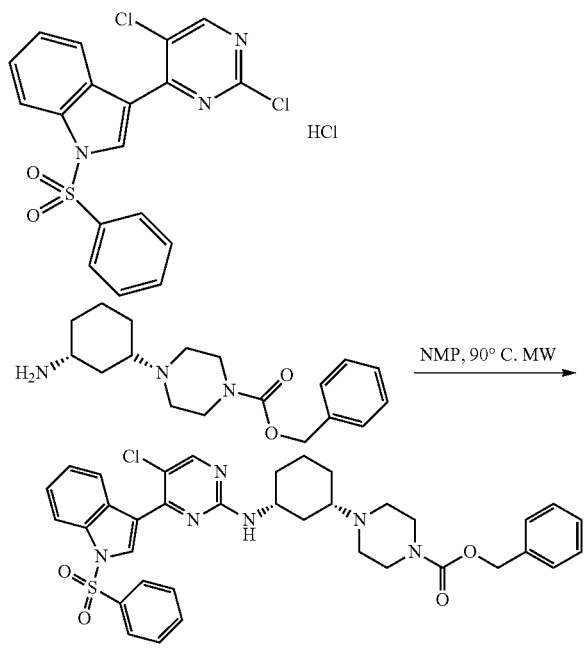

3-(2,5-dichloropyrimidin-4-yl)-1-(phenylsulfonyl)-1H-indole (94 mg, 0.23 mmol), benzyl 4-((1S,3R)-3-aminocyclohexyl)piperazine-1-carboxylate hydrochloride (70 mg, 0.22 mmol) and diisopropylethylamine (0.12 mL, 0.66 mmol) were dissolved in NMP (2.2 mL) in a microwave vial. The vial was heated to 135° C. under microwave irradiation and stirred for 45 min. The reactions mixture was then diluted with EtOAc and the organic phase washed with water and brine, dried with MgSO₄, filtered and concentrated under reduced pressure to yield a light orange oil. The residue was purified by SiO₂ chromatography (DCM/THF 0 to 70% gradient) to yield the title compound as a light yellow foam (88 mg, 0.13 mmol, 58%).

5-Chloro-4-(1-(phenylsulfonyl)-1H-indol-3-yl)-N-((1R,3S)-3-(piperazin-1-yl)cyclohexyl)pyrimidin-2-amine

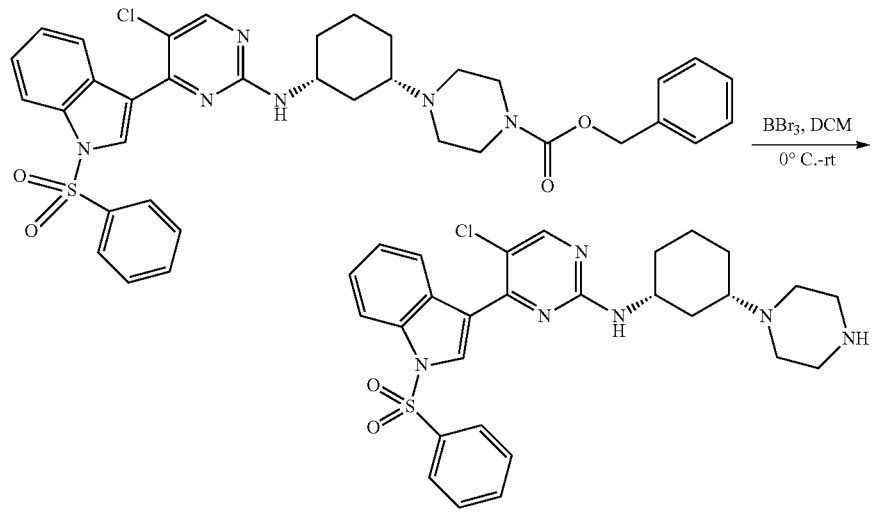

A solution of 1M BBr₃ (0.38 mL, 0.38 mmol) was added to a stirring solution of benzyl 4-((1S,3R)-3-(5-chloro-4-(1-(phenylsulfonyl)-1H-indol-3-yl)pyrimidin-2-ylamino)cyclohexyl)piperazine-1-carboxylate (88 mg, 0.128 mmol) at 0° C. The reaction mixture was allowed to stir 30 min at this temperature and then allowed to stir for 3 h at room temperature. The reaction mixture was cooled to 0° C. and quenched with MeOH (5 mL). The solution was allowed to stir 30 min and was then concentrated under reduced pressure to a light yellow oil. The oil was purified by reverse phase column reverse phase (MeCN—H₂O-0.1% HCOOH, 0 to 70% gradient) to yield after direct lyophilisation the title compound as a white solid (30 mg, 0.054 mmol, 42%).

5-Chloro-4-(1H-indol-3-yl)-N-((1R,3S)-3-(piperazin-1-yl)cyclohexyl)pyrimidin-2-amine (Compound 1045)

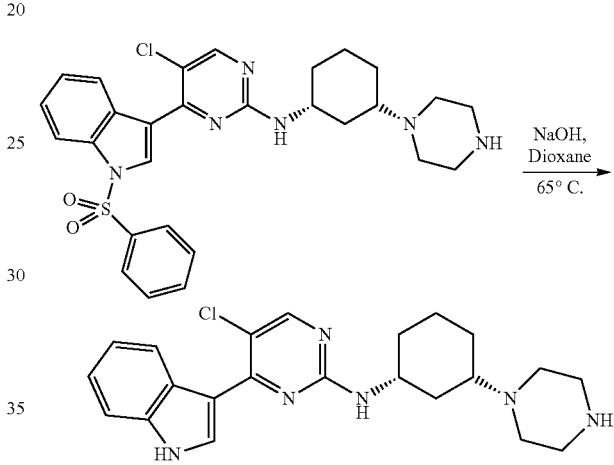

NaOH (0.22 mL, 1.63 mmol) was added to a stirring solution of 5-chloro-4-(1-(phenylsulfonyl)-1H-indol-3-yl)-N-((1R,3S)-3-(piperazin-1-yl)cyclohexyl)pyrimidin-2-amine (30 mg, 0.054 mmol) in dioxane (1.1 mL). The resulting solution was heated for 5 h at 65° C. The solution was diluted with H₂O and extracted 3× into methyl THF (30 mL). The organics were combined, dried over MgSO₄, filtered and concentrated to afford the title compound as a light yellowish white solid (22, 0.054 mmol, 100%).

1-((4-(1S,3R)-3-(5-chloro-4-(1H-indol-3-yl)pyrimidin-2-ylamino)cyclohexyl)piperazin-1-yl)prop-2-en-1-one (Compound 168)

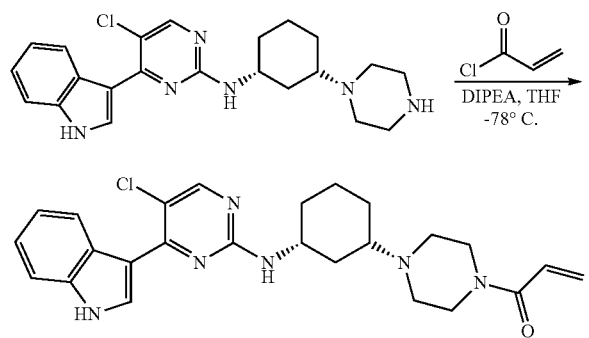

To a −78° C. solution of 5-chloro-4-(1H-indol-3-yl)-N-(1R,3S)-3-(piperazin-1-yl)cyclohexyl)pyrimidin-2-amine (22 mg, 0.054 mmol) and DIPEA (29 µL, 0.16 mmol) in THF/NMP (1.8 mL/0.5 mL) was added slowly a solution of acryloyl chloride (5 µL, 0.057 mmol). After 2 h at this temperature the reaction was allowed to warm up to room temperature and then concentrated under reduced pressure to an orange oil. The oil was purified on a reverse phase HPLC column (MeCN—H$_2$O-0.1% HCOOH, 0 to 60% gradient). The fractions containing product were directly lyophilized without concentration to yield the title compound as a light yellow solid (12.7 mg, 0.027 mmol, 50%).

Example 34. Synthesis of 3-(2,5-Dichloropyrimidin-4-yl)pyrazolo[1,5-a]pyridine (E)-4-(2-Butoxyvinyl)-2,5-dichloropyrimidine

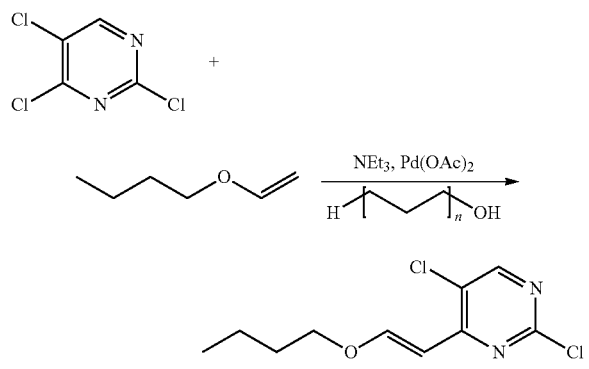

To a degassed solution of 2,4,5-trichloropyrimidine (15.0 g, 81.8 mmol) in PEG 300 (91 mL) at room temperature under nitrogen atmosphere was added triethylamine (12.0 mL, 85.8 mmol), butyl vinyl ether (13.5 mL, 98.1 mmol) and palladium acetate (0.73 g, 3.3 mmol). The reaction mixture was stirred for 1.5 h at 80° C. under nitrogen atmosphere. The reaction was cooled to room temperature, Et$_2$O (250 mL) was added, and the layers were separated. The dark glycol layer was extracted with Et$_2$O (4×90 mL). The combined Et$_2$O layers were washed with water (4×90 mL), then dried over MgSO$_4$, filtered and concentrated to yield an orange oil. The residue was purified by SiO$_2$ chromatography (Hex/Et$_2$O 0 to 30% gradient) and afforded the title compound as an orange oil (10.70 g, 43.2 mmol, 53%).

3-(2,5-Dichloropyrimidin-4-yl)pyrazolo[1,5-a]pyridine

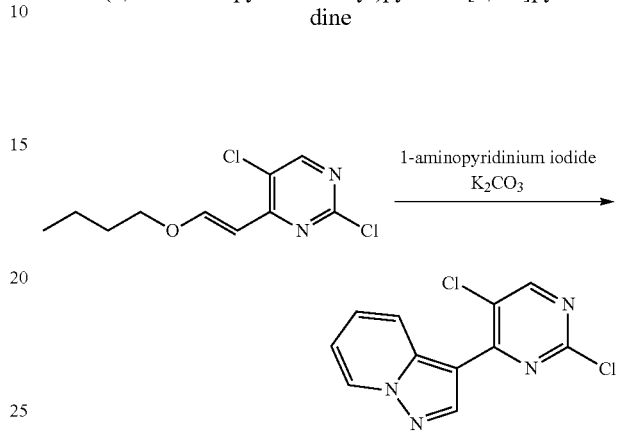

To a solution of (E)-4-(2-butoxyvinyl)-2,5-dichloropyrimidine (6.70 g, 27.1 mmol) in DMA (85 mL) were added 1-aminopyridinium iodide (6.00 g, 27.1 mmol), followed by freshly ground K$_2$CO$_3$ (9.36 g, 67.8 mmol). The mixture was stirred at 110° C. for 5 h and the reaction was allowed to cool to room temperature. The mixture was diluted with EtOAc (200 mL). The organic phase was washed with water (3×100 mL). The combined aqueous layers were extracted twice more with EtOAc. The organics were combined, washed with brine, dried over MgSO$_4$, filtered and concentrated to give a dark solid. The residue was purified by SiO$_2$ chromatography (DCM/EtOAc 0 to 50% gradient) and yielded a yellow solid. Trituration in Et$_2$O and filtration yielded the product as white solid (1.95 g, 7.35 mmol, 27%).

Example 35. Synthesis of tert-Butyl-4-((((1S,3R)-3-(5-chloro-4-(1H-indol-3-yl)pyrimidin-2-ylamino)cyclohexylamino)methyl)-4-azaspiro-piperidine-1-carboxylate tert-Butyl-4-((((1S,3R)-3-(5-chloro-4-(1H-indol-3-yl)pyrimidin-2-ylamino)cyclohexylamino)methyl)-4-hydroxypiperidine-1-carboxylate

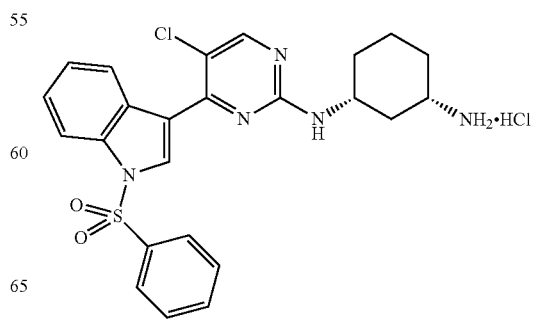

+

-continued

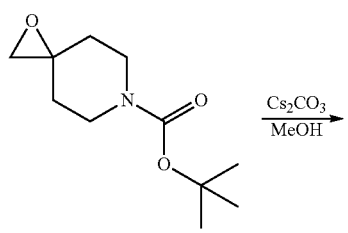

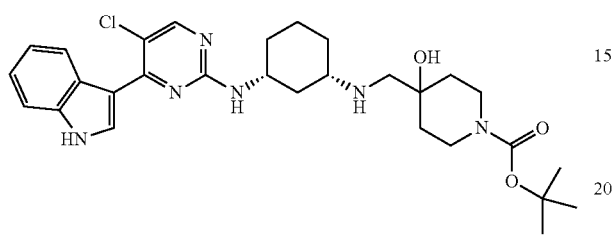

Cesium carbonate (364 mg, 1.12 mmol) was added to a stirring solution of (1R,3S)—N1-(5-chloro-4-(1-(phenylsulfonyl)-1H-indol-3-yl)pyrimidin-2-yl)cyclohexane-1,3-diamine hydrochloride (193 mg, 0.372 mmol) in MeOH at room temperature. To this the tert-Butyl-1-oxa-6-azaspiro[2.5]octane-6-carboxylate (119 mg, 0.56 mmol) was added and the solution stirred at room temperature for 2 h. The solution was then heated at 50° C. for 18 h. The reaction mixture was concentrated under reduced pressure and was purified by reverse phase (MeCN—H₂O-0.1% HCOOH, 0 to 60% gradient). Fractions containing product were concentrated under reduced pressure to afford the title compound as a yellow oil (90 mg, 0.16 mmol, 44%).

tert-Butyl-4-(((1S,3R)-3-(5-chloro-4-(1H-indol-3-yl)pyrimidin-2-ylamino)cyclohexylamino)methyl)-4-azaspiro-piperidine-1-carboxylate DBU (138 µL, 0.916 mmol) was added to a stirring solution of tert-Butyl-4-(((1S,3R)-3-(5-chloro-4-(1H-indol-3-yl)pyrimidin-2-ylamino)cyclohexylamino)methyl)-4-hydroxypiperidine-1-carboxylate (56 mg, 0.101 mmol) and CDI (63 mg, 0.390 mmol) in ACN (2.0 mL) at room temperature. The resulting solution was stirred at 80° C. for 18 h. The reaction mixture was then concentrated under reduced pressure and purified by SiO₂ chromatography (DCM/EtOAc 0 to 60% gradient) to yield the title compound as a bright yellow oil (25 mg, 0.043 mmol, 42% yield).

Example 36. Synthesis of 1-(4-(((3R)-3-(5-chloro-4-(1H-indol-3-yl)pyrimidin-2-ylamino)-1-hydroxycyclohexyl)methyl)piperazin-1-yl)prop-2-en-1-one (R)-3-Methylenecyclohexanamine 2,2,2-trifluoroacetate

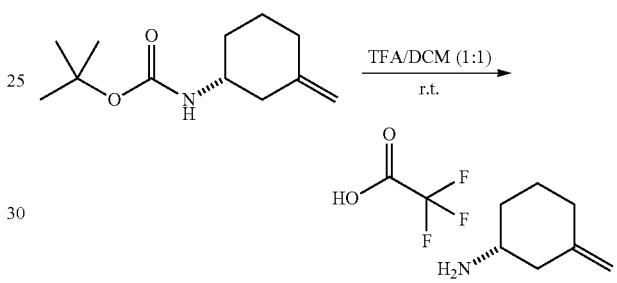

Trifluoroacetic acid (0.76 mL, 9.88 mmol) was added to a stirring solution of (R)-tert-butyl 3-methylenecyclohexylcarbamate (145 mg, 0.686 mmoL) in DCM (1.4 mL) at 0° C. The resulting solution was then allowed to stir at room temperature for 1 h. The resulting solution was then concentrated under reduced pressure and azeotroped 3 times with DCM and toluene to yield the title compound as a yellow oil (565 mg, 0.686 mmol, quantitative yield).

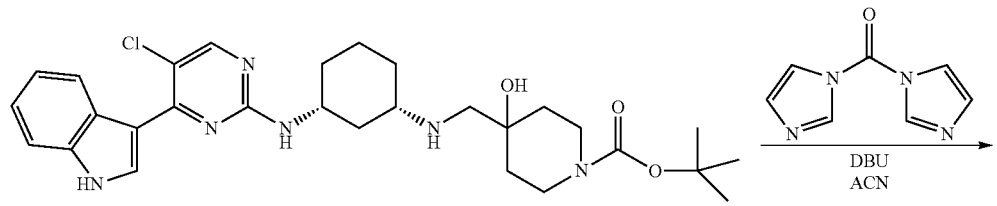

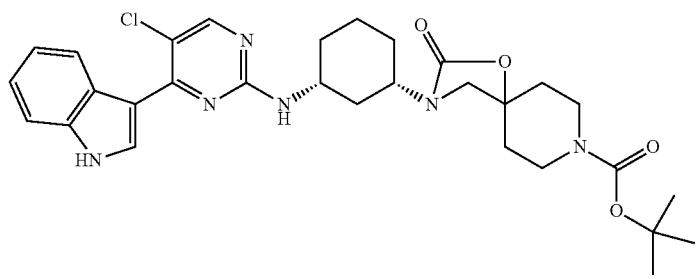

147

5-Chloro-N—((R)-3-methylenecyclohexyl)-4-(1-(phenylsulfonyl)-1H-indol-3-yl)pyrimidin-2-amine

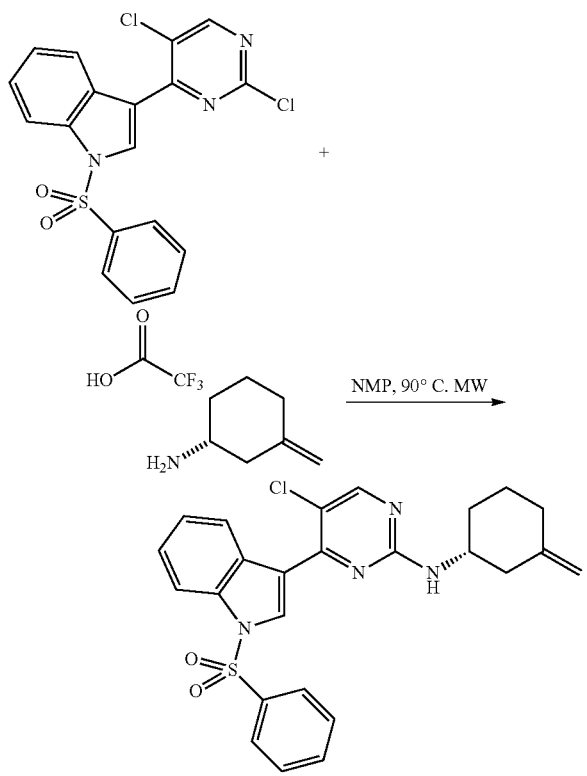

3-(2,5-dichloropyrimidin-4-yl)-1-(phenylsulfonyl)-1H-indole (1.06 g, 2.63 mmol), amine (R)-3-methylenecyclohexanamine 2,2,2-trifluoroacetate (565 mg, 2.51 mmol) and diisopropylethylamine (1.31 mL, 7.53 mmol) were dissolved in NMP (10 mL) in a microwave vial. The vial was heated to 155° C. under microwave irradiation and stirred for 60 min two times. The reaction mixture was then diluted with EtOAc and the organic phase washed with water and brine, dried with MgSO$_4$, filtered and concentrated under reduced pressure to yield a brown oil. The residue was purified by SiO$_2$ chromatography (DCM/EtOAc 0 to 15% gradient) to yield the title compound as a white foam (343 mg, 0.716 mmol, 28%).

5-Chloro-N-(3-oxirane-cyclohexyl)-4-(1-(phenylsulfonyl)-1H-indol-3-yl)pyrimidin-2-amine

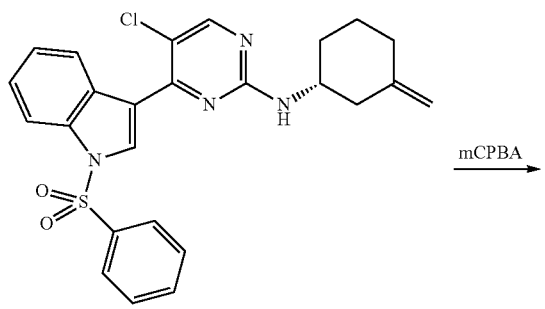

148

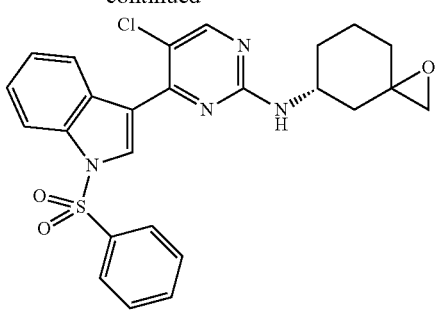

mCPBA (84 mg, 0.37 mmol, 77%) was added to a stirring solution of 5-chloro-N—((R)-3-methylenecyclohexyl)-4-(1-(phenylsulfonyl)-1H-indol-3-yl)pyrimidin-2-amine (170 mg, 0.084 mmol) in DCM at room temperature. The reaction was allowed to stir overnight at room temperature. The solution was then diluted with EtOAc (30 mL) and washed with NaHCO$_3$ (sat). The aqueous was extracted twice more with EtOAc, the organics were then combined, washed with Na$_2$S$_2$O$_4$ (sat), dried over MgSO$_4$, filtered and concentrated to a yellow oil (198 mg). The residue was purified by SiO$_2$ chromatography (DCM/EtOAc 0 to 40% gradient) to yield the title compound as a light yellow oil (70 mg, 0.343 mmol, 40%).

tert-Butyl 4-(((3R)-3-(5-chloro-4-(1-(phenylsulfonyl)-1H-indol-3-yl)pyrimidin-2-ylamino)-1-hydroxycyclohexyl) methyl) piperazine-1-carboxylate

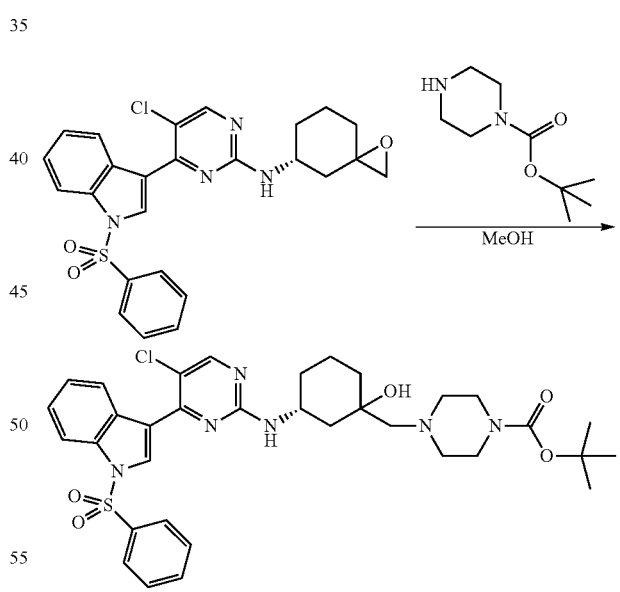

1-Boc piperazine (35 μL, 0.212 mmol) was added to a stirring solution of 5-chloro-N-(3-oxirane-cyclohexyl)-4-(1-(phenylsulfonyl)-1H-indol-3-yl)pyrimidin-2-amine (70 mg, 0.141 mmol) at room temperature. The reaction was then heated at 50° C. for 62 h. The reaction mixture was concentrated under reduced pressure and was purified by SiO$_2$ chromatography (DCM/EtOAc 0 to 100% gradient) to yield the title compound as a light yellow oil (61 mg, 0.896 mmol, 64%).

tert-Butyl 4-(((3R)-3-(5-chloro-4-(1H-indol-3-yl)
pyrimidin-2-ylamino)-1-hydroxycyclohexyl)methyl)
piperazine-1-carboxylate

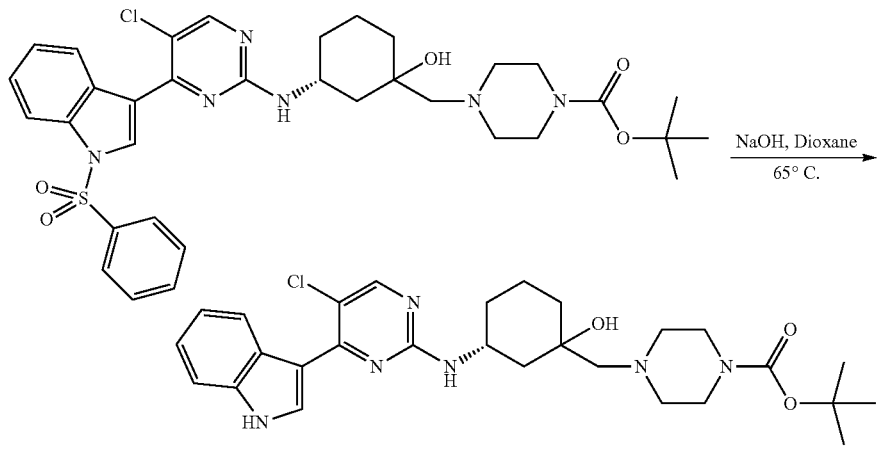

NaOH (0.36 mL, 1.79 mmol) was added to a stirring solution of tert-butyl 4-(((3R)-3-(5-chloro-4-(1-(phenylsulfonyl)-1H-indol-3-yl)pyrimidin-2-ylamino)-1-hydroxycyclohexyl) methyl) piperazine-1-carboxylate (61 mg, 0.090 mmol) in dioxane (1.8 mL). The resulting solution was heated for 2 h at 65° C. A second portion of NaOH (0.36 mL, 1.791 mmol) was added and stirred for an additional 24 h. The solution was diluted with H₂O and extracted 3 times into MeTHF (30 mL). The organics were combined, dried over MgSO₄, filtered and concentrated to light yellowish oil. The residue was purified by SiO₂ chromatography (DCM/THF 0 to 50% gradient) and afforded the title compound as a light yellow oil (48 mg, 0.090 mmol, 100%).

(3R)-3-(5-chloro-4-(1H-indol-3-yl)pyrimidin-2-
ylamino)-1-(piperazin-1-ylmethyl)cyclohexanol 2,2,
2-trifluoroacetate (Compound 1046, 2,2,2-trifluoro-
acetate salt)

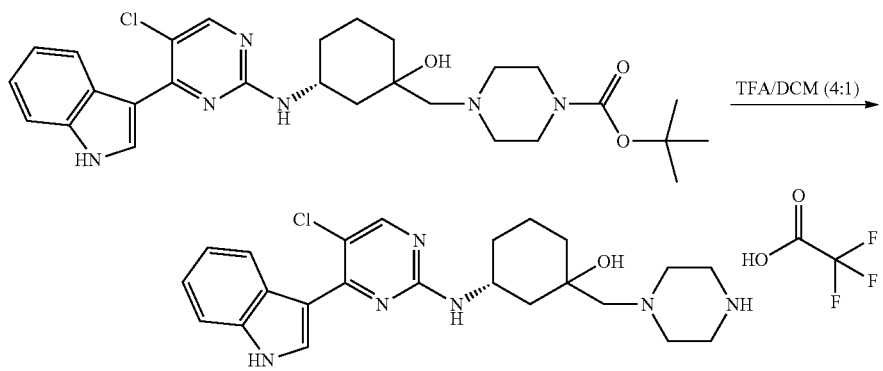

Trifluoroacetic acid (0.54 mL, 7.10 mmol) was added to a stirring solution of tert-butyl 4-(((3R)-3-(5-chloro-4-(1H-indol-3-yl)pyrimidin-2-ylamino)-1-hydroxycyclohexyl) methyl)-piperazine-1-carboxylate (48 mg, 0.089 mmoL) in DCM (1.2 mL) at 0° C. The resulting solution was then allowed to stir at room temperature for 1 h. The resulting solution was then concentrated under reduced pressure and azeotroped DCM 3 times to yield the title compound as a yellow foam (49 mg, 0.089 mmol, 100%).

1-(4-(((3R)-3-(5-chloro-4-(1H-indol-3-yl)pyrimidin-2-ylamino)-1-hydroxycyclohexyl)methyl)piperazin-1-yl)prop-2-en-1-one (Compounds 187 and 188)

to dryness and afforded the title compound (1.23 g, 4.31 mmol, 100%) as a white solid which was used in the next step without further purification.

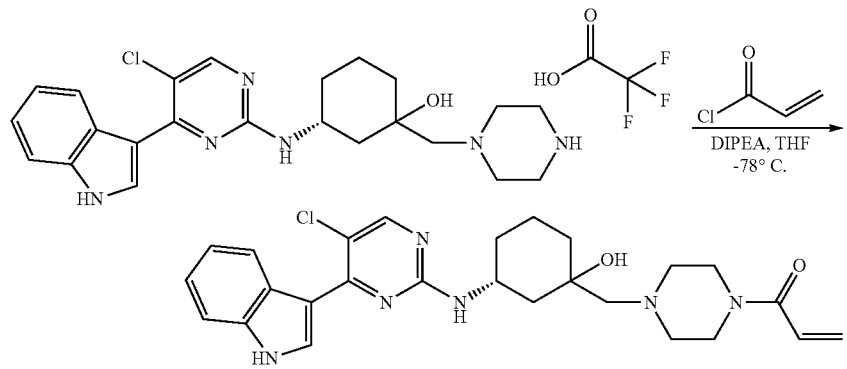

To a −78° C. solution of (3R)-3-(5-chloro-4-(1H-indol-3-yl)pyrimidin-2-ylamino)-1-(piperazin-1-ylmethyl)cyclohexanol 2,2,2-trifluoroacetate (49 mg, 0.088 mmol) and DIPEA (77 μL, 0.44 mmol) in THF/NMP (2.9 mL/0.5 mL) was added slowly acryloyl chloride (8 μL, 0.093 mmol). After 3 h at this temperature the reaction was complete. The reaction mixture was then allowed to warm to room temperature and was concentrated under reduced pressure to an orange oil. The oil was purified by reverse phase flash column (MeCN—H$_2$O-0.1% HCOOH, 0 to 55% gradient). The fractions containing product were directly lyophilized without concentration to yield the title compound as a light yellow solid (26.0 mg, 0.053 mmol, 53% yield) which contains a 2:1 diastereoisomeric ratio (determined by chiral pak IA 10% MeOH: 10% DCM in hexanes isocratic). The compound was separated using ChiralPak IA 90 Hex: 5MeOH: 5 DCM Prep UV 15 mL/min to yield Compound 187 as an off white solid (9.2 mg, 0.019 mmol, 21% yield) and Compound 188 as a white solid (5.3 mg, 0.011 mmol, 12%).

Example 37. Synthesis of 1-(4-(((1S,3R)-3-(5-chloro-4-(1H-indol-3-yl)pyrimidin-2-ylamino)cyclohexylamino)methyl)piperidin-1-yl)prop-2-en-1-one Benzyl (1S,3R)-3-aminocyclohexylcarbamate.HCl

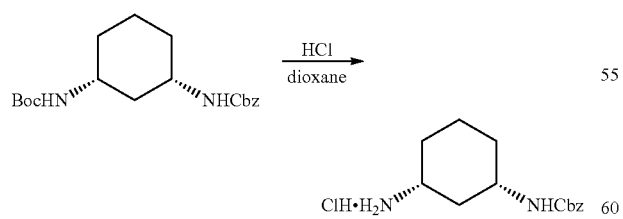

A solution of (1R,3S)-3-(Benzyloxycarbonylamino)cyclohexylamino 2,2-dimethylpropionate prepared similarly to Example 3 (1.50 g, 4.31 mmol) in DCM (43 mL) was treated with a 4M solution of HCl in dioxane (16 mL, 64.6 mmol) and stirred 2 h at rt. The resulting solution was evaporated Benzyl(1S,3R)-3-(5-chloro-4-(1-(phenylsulfonyl)-1H-indol-3-yl)pyrimidin-2-ylamino)cyclohexylcarbamate

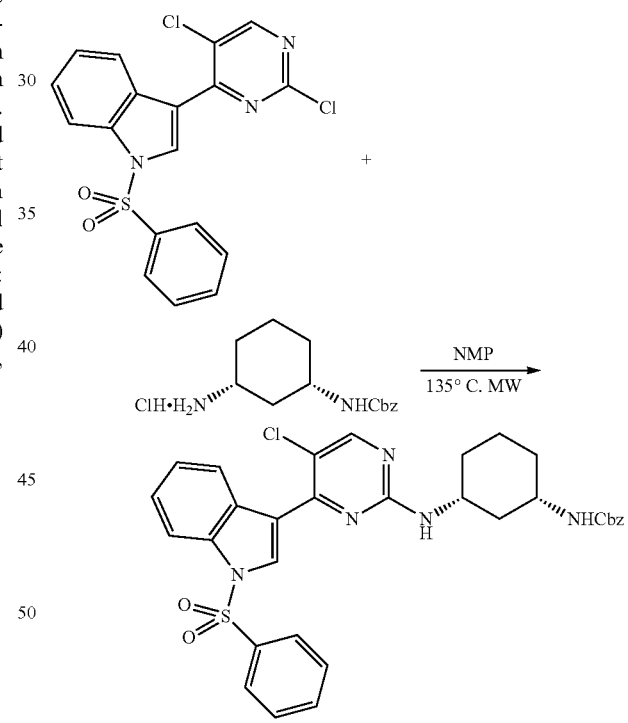

A solution of 3-(2,5-dichloropyrimidin-4-yl)-1-(phenylsulfonyl)-1H-indole (791 mg, 1.96 mmol), benzyl (1S,3R)-3-aminocyclohexylcarbamate (613 mg, 2.15 mmol) and diisopropylethylamine (0.75 mL, 4.31 mmol) in NMP (20.0 mL) was heated 30 min at 135° C. (microwave). The mixture was diluted with EtOAc (100 mL), washed with H$_2$O (50 mL), brine (50 mL), then dried (MgSO$_4$), filtered and evaporated to dryness. The residue was purified by SiO$_2$ chromatography (Hex/EtOAc 5 to 70% gradient), and afforded the title compound (1.04 g, 1.69 mmol, 40%) as a yellow solid.

(1R,3S)—N-(5-chloro-4-(1-(phenylsulfonyl)-1H-indol-3-yl)pyrimidin-2-yl)cyclohexane-1,3-diamine

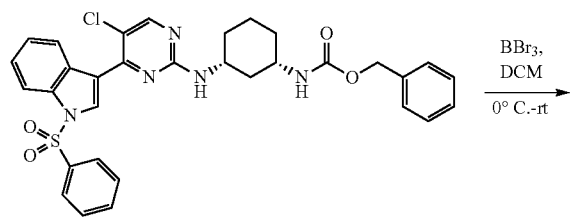

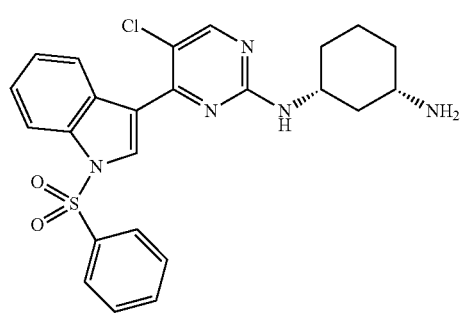

A solution of 1M BBr₃ (1.97 mL, 1.97 mmol) was added to a stirring solution of benzyl (1S,3R)-3-(5-chloro-4-(1-(phenylsulfonyl)-1H-indol-3-yl)pyrimidin-2-ylamino)cyclohexylcarbamate (971 mg, 1.58 mmol) at 0° C. The reaction mixture was allowed to stir 30 min at this temperature and then allowed to stir at room temperature overnight. The solution was then recooled to 0° C. and quenched with MeOH (10 mL). The solution was allowed to stir 30 min and was then concentrated under reduced pressure to a light yellow oil. The oil was purified by reverse phase column (MeCN/H₂O/0.1% HCOOH 5 to 100% gradient), to yield the title compound as a light yellow solid (762 mg, 1.58 mmol, 100%).

Piperidin-4-ylmethanol hydrochloride

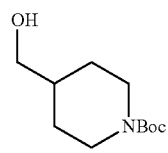

HCl 4M in 1,4-dioxane (23 mL, 93 mmol) was added to a stirring solution of N-Boc-4-piperidinemethanol (2.0 g, 9.29 mmol) in 1,4-dioxane (37 mL) at room temperature. The resulting solution was allowed to stir for 3 h at room temperature. The solution was concentrated to dryness and coevaporated 3 times with DCM to give the title compound as a white solid (1412 mg, 9.29 mmol, quantitative yield).

2,2,2-Trichloroethyl 4-(hydroxymethyl)piperidine-1-carboxylate

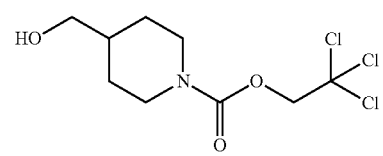

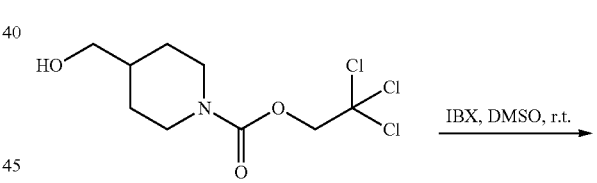

Piperidin-4-ylmethanol hydrochloride (715 mg, 4.72 mmol), was dissolved in a 1:1 mixture of DCM and water (31.4 mL) along with sodium carbonate (1 g, 9.43 mmol) and the solution was cooled to 0° C. Then, 2,2,2-trichloroethyl chloroformate (682 µL, 4.95 mmol) was added and the reaction mixture stirred at 0° C. for 5 h. The solution was then quenched with sat. NaHCO₃ and extracted 3 times into DCM. The organic layers were combined, washed with brine, dried over MgSO₄, filtered and concentrated to give the title compound as a clear oil (1.45 g, 5.1 mmol, 108%). Used without further purification.

2,2,2-Trichloroethyl 4-formylpiperidine-1-carboxylate

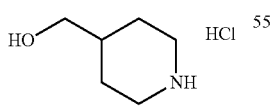

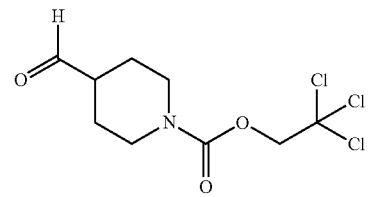

2,2,2-trichloroethyl 4-(hydroxymethyl)piperidine-1-carboxylate (1341 mg, 4.72 mmol) was dissolved in DMSO (9.4 mL) and IBX (45% w., 3.52 g, 5.66 mmol) was added in one portion. The reaction mixture was stirred overnight at room temperature. The solution was then quenched with sat. NaHCO₃ and extracted 3 times into EtOAc. The organic layers were combined, washed with water (2 times) and brine, dried over MgSO₄, filtered and concentrated. The crude residue was purified by SiO₂ chromatography (Hex/EtOAc, 0 to 60% gradient) to afford the title compound as a clear oil (846 mg, 2.93 mmol, 62% over 3 steps).

2,2,2-Trichloroethyl 4-(((1S,3R)-3-(5-chloro-4-(1-(phenylsulfonyl)-1H-indol-3-yl)pyrimidin-2-ylamino)cyclohexylamino) methyl)piperidine-1-carboxylate

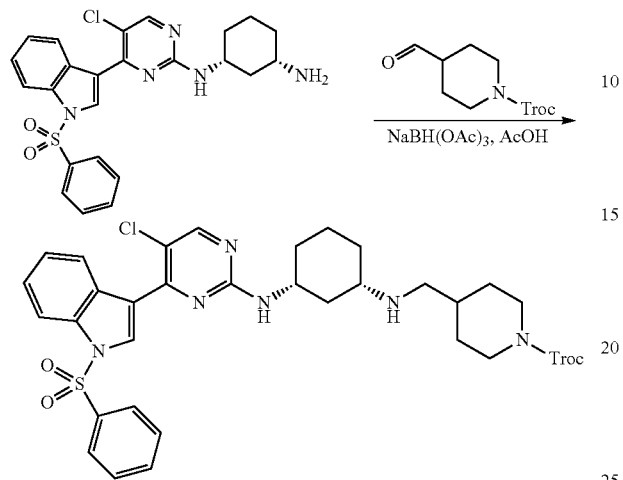

To a DCE solution of (1R,3S)—N-(5-chloro-4-(1-(phenylsulfonyl)-1H-indol-3-yl)pyrimidin-2-yl)cyclohexane-1,3-diamine (200 mg, 0.41 mmol) was added acetic acid (12 µL, 0.21 mmol) followed by the addition of the 2,2,2-trichloroethyl 4-formylpiperidine-1-carboxylate (126 mg, 0.44 mmol). Mixture was stirred at r.t. for 15 minutes. NaBH(OAc)₃ (176 mg, 0.83 mmol) was then added in one portion and the resulting mixture was stirred at room temperature overnight. The reaction was then diluted with DCM before washing with NaHCO₃ sat. and brine. The organic layer was dried (MgSO₄), filtered and concentrated in vacuo leaving a pale yellow solid (315 mg, 0.41 mmol, 101% crude yield), was used crude for next step.

2,2,2-Trichloroethyl 4-((tert-butoxycarbonyl((1S,3R)-3-(5-chloro-4-(1-(phenylsulfonyl)-1H-indol-3-yl)pyrimidin-2-ylamino)cyclohexylamino)methyl)piperidine-1-carboxylate

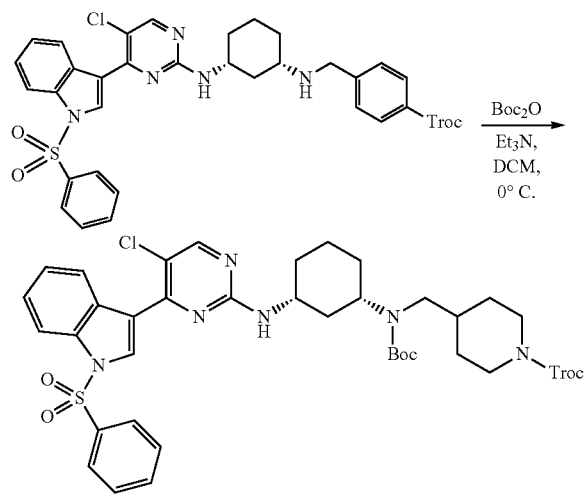

2,2,2-Trichloroethyl-4-(((1S,3R)-3-(5-chloro-4-(1-(phenylsulfonyl)-1H-indol-3-yl)pyrimidin-2-ylamino)cyclohexylamino)methyl) piperidine-1-carboxylate (313 mg, 0.41 mmol), was dissolved in DCM (10.4 mL) along with triethylamine (116 µL, 0.83 mmol) and the solution was cooled to 0° C. Then, Boc-anhydride (118 mg, 0.54 mmol) was added and the reaction mixture stirred from 0° C. to room temperature overnight. The solution was quenched with sat. NaHCO₃ and extracted 3 times with DCM. The organic layers were combined, washed with brine, dried over MgSO₄, filtered and concentrated to afford the title compound as a light yellow foamy solid. (355 mg, 0.415 mmol, 100%).

2,2,2-Trichloroethyl 4-((tert-butoxycarbonyl((1S,3R)-3-(5-chloro-4-(1H-indol-3-yl)pyrimidin-2-ylamino)cyclohexyl)amino)methyl)piperidine-1-carboxylate

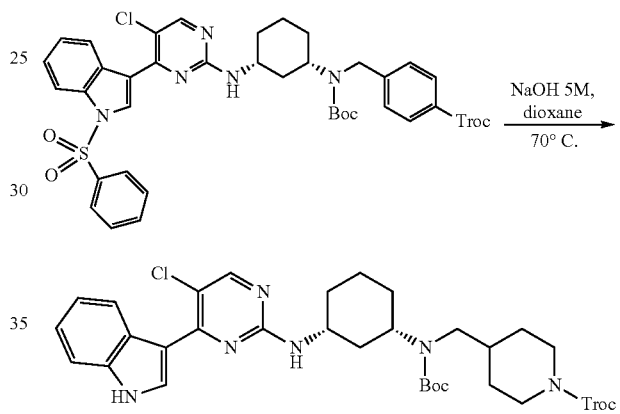

2,2,2-Trichloroethyl-4-((tert-butoxycarbonyl((1S,3R)-3-(5-chloro-4-(1-(phenylsulfonyl)-1H-indol-3-yl)pyrimidin-2-ylamino)cyclohexyl)amino)methyl)piperidine-1-carboxylate (349 mg, 0.41 mmol) was dissolved in 1,4-dioxane (3 mL, 0.15 M) and 5M NaOH (0.82 mL, 4.1 mmol) was added. The reaction mixture was stirred at 70° C. overnight. The reaction mixture was diluted with water and extracted 3 times with EtOAc. Organics were combined, washed with brine, dried over MgSO₄, filtered and concentrated under reduced pressure. The crude residue was used directly for next step without further purification and afforded the title compound as a pale yellow solid (302 mg, 0.423 mmol, 103%).

tert-Butyl (1S,3R)-3-(5-chloro-4-(1H-indol-3-yl)pyrimidin-2-ylamino)cyclohexyl(piperidin-4-ylmethyl)carbamate

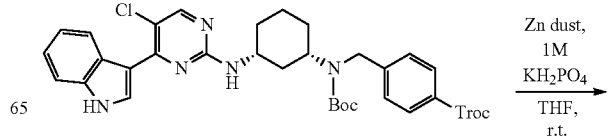

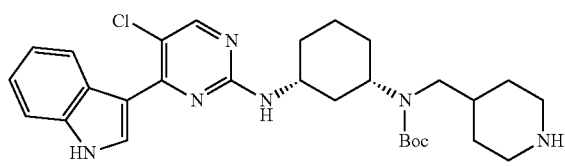

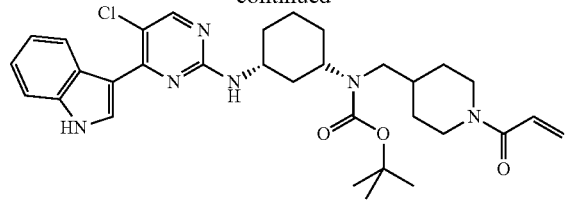

2,2,2-Trichloroethyl-4-((tert-butoxycarbonyl((1S,3R)-3-(5-chloro-4-(1H-indol-3-yl)pyrimidin-2-ylamino)cyclohexyl)amino)methyl) piperidine-1-carboxylate (302 mg, 0.423 mmol), was dissolved in THF (8.5 mL) and potassium phosphate monobasic (1M in H₂O, 4.2 mL, 4.2 mmol) was added followed by zinc dust (691 mg, 10.6 mmol). The reaction mixture was stirred at room temperature for 45 min. Acetic acid (24 µL, 0.423 mmol) was added to the suspension along with zinc dust (200 mg, 3.1 mmol) and the suspension was placed in a sonic bath for 1 h then stirred at rt for 3 h. The reaction mixture was filtered through a C₁₈ pad which was rinsed with THF and ACN. Organics were concentrated and the residual solid was purified by reverse phase flash chromatography (MeCN—H₂O-0.1% HCOOH, 5 to 100% gradient). Pure fractions were concentrated under reduced pressure to remove acetonitrile and to the residual water was added NaHCO₃. Water was then extracted with methyl THF (3 times), organics combined, dried, filtered and concentrated. The title compound was produced as a pale yellow solid (136 mg, 0.252 mmol, 60%).

tert-Butyl (1-acryloylpiperidin-4-yl)methyl((1S,3R)-3-(5-chloro-4-(1H-indol-3-yl)pyrimidin-2-ylamino) cyclohexyl) carbamate

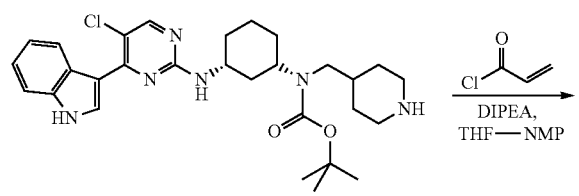

tert-Butyl-(1S,3R)-3-(5-chloro-4-(1H-indol-3-yl)pyrimidin-2-ylamino)cyclohexyl(piperidin-4-ylmethyl)carbamate (136 mg, 0.25 mmol), was dissolved in anhydrous THF (3.0 mL) and NMP (1.2 mL) along with diisopropylethylamine (132 µL, 0.76 mmol) under inert atmosphere and the solution was cooled to −78° C. Then, the acryloyl chloride (20.5 µL, 0.25 mmol) was added and the reaction mixture stirred at −78° C. for 35 min. The reaction mixture was concentrated to remove THF. The residual solution was diluted in MeTHF and washed with water (2 times). The aqueous layers were extracted with MeTHF (2 times). Organics were all combined, washed with brine, dried over MgSO₄, filtered and concentrated to afford the title compound as a pale yellow solid (151 mg, 0.255 mmol, 101%), which was sed directly without further purification.

1-(4-((((1S,3R)-3-(5-chloro-4-(1H-indol-3-yl)pyrimidin-2-ylamino)cyclohexylamino)methyl)piperidin-1-yl)prop-2-en-1-one (Compound 124)

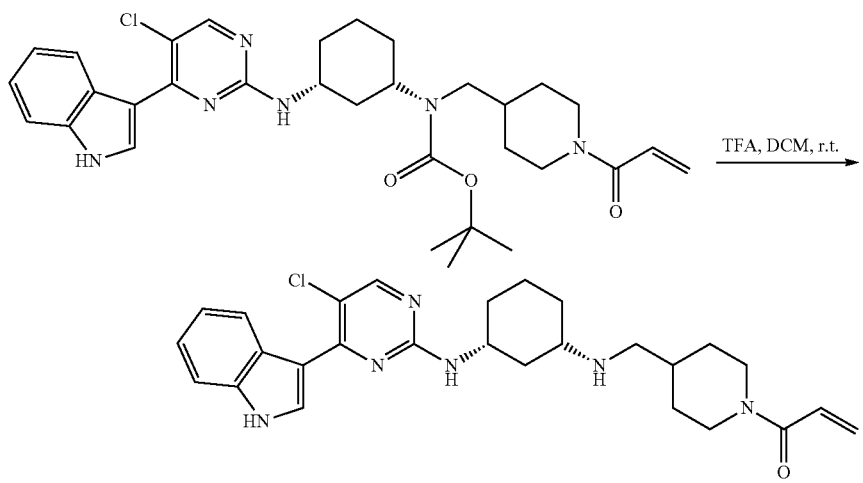

tert-Butyl (1-acryloylpiperidin-4-yl)methyl((1S,3R)-3-(5-chloro-4-(1H-indol-3-yl)pyrimidin-2-ylamino)cyclohexyl) carbamate (150 mg, 0.25 mmol) was dissolved in DCM (1.7 mL) and trifluoroacetic acid (290 µL, 3.79 mmol) was added. The reaction mixture was stirred at room temperature for 5 h. The reaction mixture was concentrated to remove DCM and excess TFA. Excess triethylamine was added and the residual oil was directly purified by reverse phase flash chromatography (MeCN—H₂O-0.1% HCOOH, 5 to 65% gradient). Pure fractions were directly lyophilized and afforded the title compound as a pale yellow solid (64.8 mg, 0.131 mmol, 52%).

Example 38. Synthesis of tert-Butyl 4-((((1S,3R)-3-(5-chloro-4-(1-(phenylsulfonyl)-1H-indol-3-yl)pyrimidin-2-ylamino)cyclohexyl)(methyl)amino)methyl)piperidine-1-carboxylate

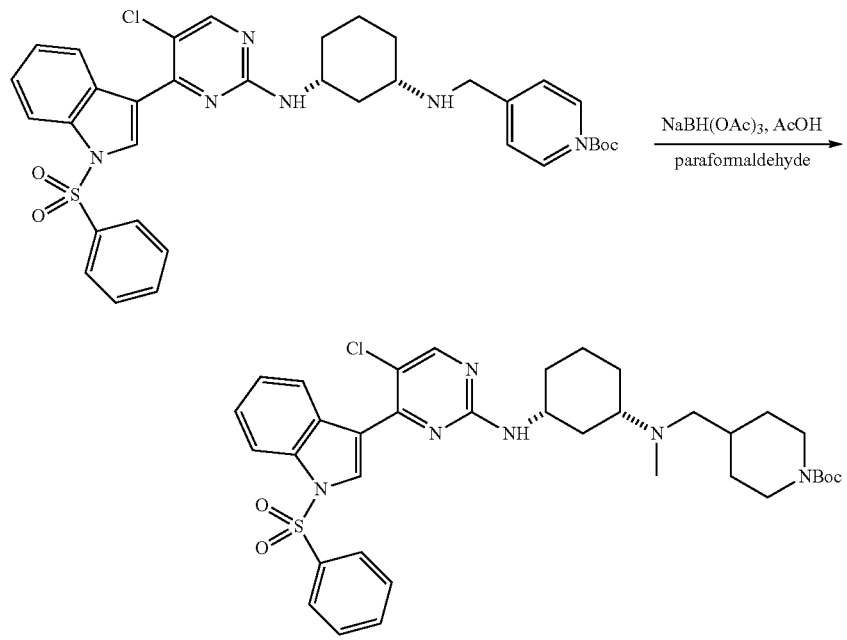

To a DCE solution of tert-butyl 4-(((1S,3R)-3-(5-chloro-4-(1-(phenylsulfonyl)-1H-indol-3-yl)pyrimidin-2-ylamino)cyclohexylamino)methyl) piperidine-1-carboxylate (200 mg, 0.29 mmol) was added acetic acid (8 µL, 0.15 mmol) followed by the addition of the paraformaldehyde (10 mg, 0.32 mmol). Mixture was stirred at rt for 30 minutes. NaBH(OAc)₃ (112 mg, 0.53 mmol) was then added in one portion and the resulting mixture was stirred at room temperature for 48 hours. The reaction was then diluted with DCM before washing with NaHCO₃ sat. and brine. The organic layer was dried (MgSO₄), filtered and concentrated under reduced pressure to yield the title compound as a pale yellow solid (208 mg, 0.207 mmol, 101%), which was used crude for next step.

Example 39. Synthesis of tert-butyl 4-((N-((1S,3R)-3-(5-chloro-4-(1-(phenylsulfonyl)-1H-indol-3-yl)pyrimidin-2-ylamino)cyclohexyl)acetamido)-methyl)piperidine-1-carboxylate

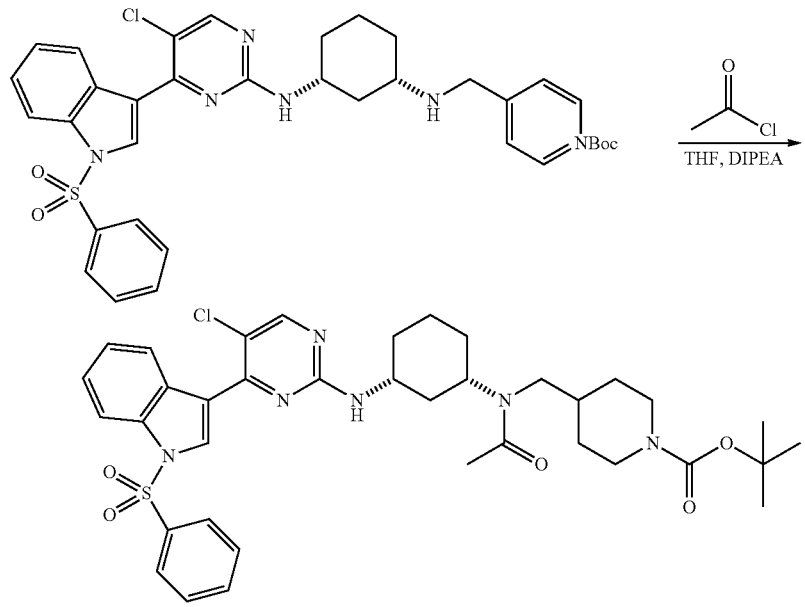

tert-Butyl 4-(((1S,3R)-3-(5-chloro-4-(1-(phenylsulfonyl)-1H-indol-3-yl)pyrimidin-2-ylamino)cyclohexylamino)methyl)piperidine-1-carboxylate (60 mg, 0.088 mmol) was dissolved in anhydrous THF (1.8 mL) along with diisopropylethylamine (31 µL, 0.177 mmol) under inert atmosphere and the solution was cooled to −78° C. Then, acetyl chloride (7.2 µL, 0.102 mmol) was added and the reaction mixture stirred at this temperature for 35 minutes. The solution was then quenched with sat. NaHCO₃ and extracted 3 times into EtOAc. The organic layers were combined, washed with brine, dried over MgSO₄, filtered and concentrated to yield the title compound as a beige solid (76 mg, 0.105 mmol, 119%). The crude product was used without further purification.

Example 40. Synthesis of 4-acryloyl-N-((1S,3R)-3-(5-chloro-4-(1H-indol-3-yl)pyrimidin-2-ylamino)cyclohexyl)piperazine-1-carboxamide (1S,3R)-Methyl 3-(tert-butoxycarbonylamino)cyclohexanecarboxylate

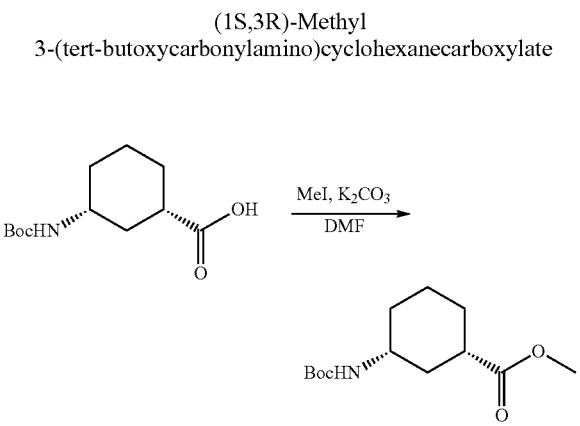

A solution of (1R,3S)-3-(tert-butoxycarbonylamino)cyclohexanecarboxylic acid (prepared following *Tetrahedron: Asymmetry* 2010 (21), 864-866) (1.0 g, 4.11 mmol), K₂CO₃ (474 mg, 3.43 mmol) and MeI (0.21 mL, 3.43 mmol) in DMF (8 mL) was stirred 72 h at rt. The resulting mixture was diluted with H₂O (30 mL) and EtOAc (100 mL). The layers were separated and the aqueous layer was extracted into EtOAc (3×50 mL). The combined organic layers were dried over MgSO₄, filtered and evaporated to dryness leaving the title compound as a light orange solid (1.35 g, 4.11 mmol, 100%) which was used in the next step without further purification.

(1S,3R)-Methyl 3-aminocyclohexanecarboxylate.HCl

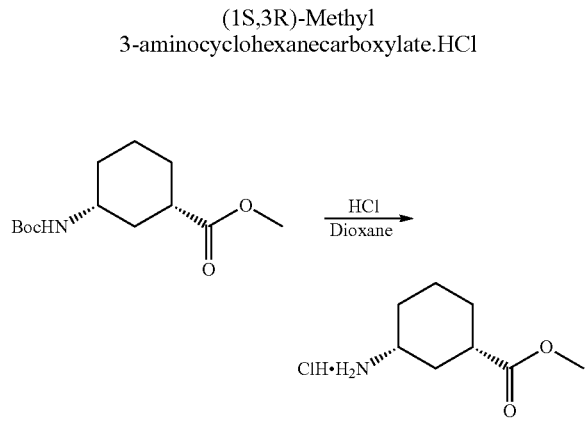

A solution of (1S,3R)-methyl 3-(tert-butoxycarbonylamino)cyclohexanecarboxylate (1.06 g, 4.11 mmol) in DCM (21 mL) was treated with a 4M solution of HCl in dioxane (10.3 mL, 10.3 mmol) and stirred for 16 h. The mixture was concentrated to dryness leaving the title compound as a light yellow solid (739 mg, 3.81 mmol, 93%) which was used in the next step without further purification.

(1S,3R)-Methyl 3-(5-chloro-4-(1-(phenylsulfonyl)-1H-indol-3-yl)pyrimidin-2-ylamino)cyclohexanecarboxylate

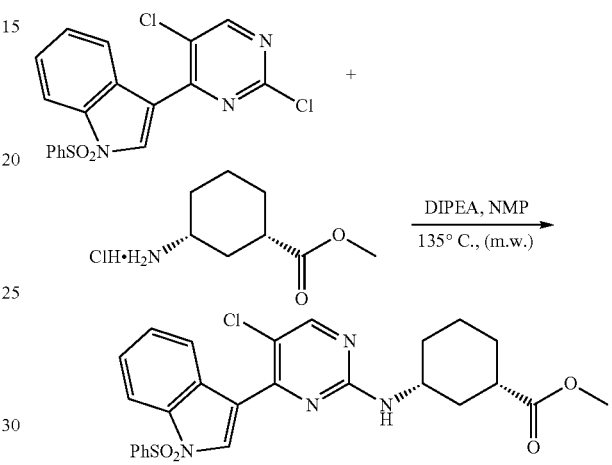

A solution of 3-(2,5-dichloropyrimidin-4-yl)-1-(phenylsulfonyl)-1H-indole (1.40 g, 3.46 mmol), (1S,3R)-methyl 3-aminocyclohexanecarboxylate.HCl (639 mg, 3.30 mmol) and DIPEA (1.7 mL, 9.90 mmol) in NMP (13 mL) was heated at 135° C. (microwave) for 25 min. The cooled mixture was diluted with EtOAc (50 mL), washed with H₂O (15 mL), brine (15 mL), dried over MgSO₄, filtered and evaporated to dryness. The residue was purified by SiO₂ chromatography (DCM/EtOAc 0 to 10% gradient) and afforded the title compound as a white foam (900 mg, 1.71 mmol, 52%).

(1S,3R)-3-(5-chloro-4-(1-(phenylsulfonyl)-1H-indol-3-yl)pyrimidin-2-ylamino)cyclohexanecarboxylic acid

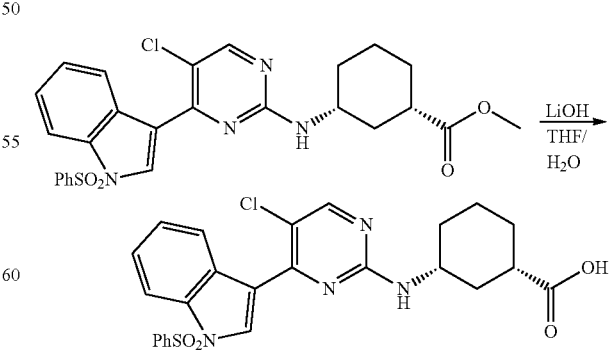

A solution of (1S,3R)-methyl 3-(5-chloro-4-(1-(phenylsulfonyl)-1H-indol-3-yl)pyrimidin-2-ylamino)cyclohexanecarboxylate (200 mg, 0.38 mmol) in THF was treated with a 0.55M solution of LiOH H₂O in H₂O (0.8 mL, 0.4 mmol) and stirred over 48 h at rt. The mixture was diluted with EtOAc (20 mL) and acidified with 1M HCl until the pH reached 2-3. The layers were separated and the aqueous layer was extracted with EtOAc (3×10 mL), dried over MgSO₄, filtered and evaporated to dryness leaving the title compound (108 mg, 0.211 mmol, 56%) as a white solid which was used in the next step without further purification.

tert-Butyl 4-((1S,3R)-3-(5-chloro-4-(1-(phenylsulfonyl)-1H-indol-3-yl)pyrimidin-2-ylamino)cyclohexyl-carbamoyl) piperazine-1-carboxylate

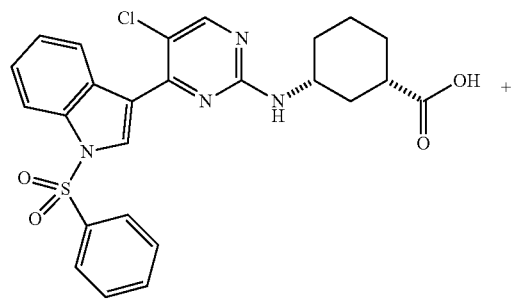

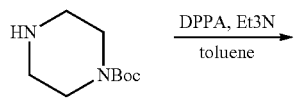

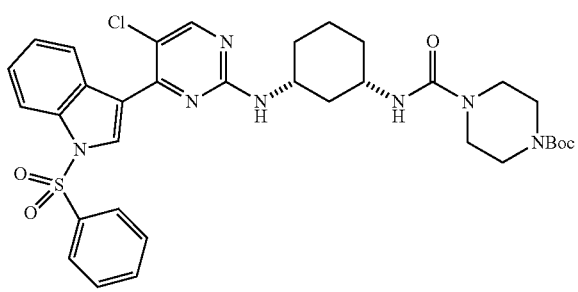

Et₃N (50 μL, 0.36 mmol) and DPPA (70 μL, 0.33 mmol) were added to a stirring solution of (1S,3R)-3-(5-chloro-4-(1-(phenylsulfonyl)-1H-indol-3-yl)pyrimidin-2-ylamino)cyclohexanecarboxylic acid (167 mg, 0.33 mmol) in toluene (3.3 mL). The resulting solution was then stirred at 110° C. for 2 h. The solution was cooled down to 80° C. and triethylamine (50 μL, 0.36 mmol), titanium isopropoxide (121 μL, 0.41 mmol) and 1-Boc-piperazine (76 mg, 0.41 mmol) were added. The resulting solution was stirred at 80° C. for 20 h. The reaction mixture was then allowed to cool to room temperature, poured in water/EtOAc, and the phases were separated. The aqueous was extracted twice more with methyl THF and the organics were combined washed twice with brine, dried over MgSO₄, filtered and concentrated. The crude product was purified on by flash silica column (Hex/EtOAc, 10-100% gradient) to yield the title compound as a white solid (35 mg, 0.05 mmol, 15%).

tert-Butyl 4-((1S,3R)-3-(5-chloro-4-(1H-indol-3-yl)pyrimidin-2-ylamino)cyclohexylcarbamoyl)piperazine-1-carboxylate

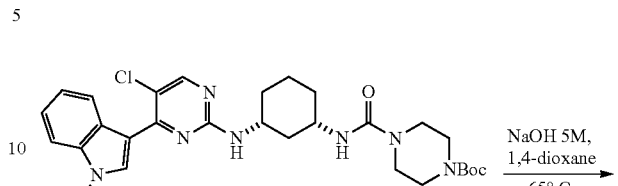

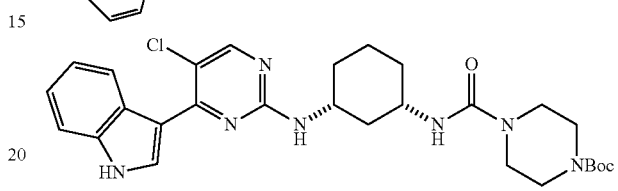

tert-butyl 4-((1S,3R)-3-(5-chloro-4-(1-(phenylsulfonyl)-1H-indol-3-yl)pyrimidin-2-ylamino)cyclohexylcarbamoyl) piperazine-1-carboxylate (35 mg, 0.05 mmol) was dissolved in 1,4-dioxane (340 μL, 0.15 M) and 5M NaOH (100 μL, 0.5 mmol) was added. The reaction mixture was stirred at 65° C. for 5 h and at rt overnight. The reaction was monitored by LCMS. The reaction mixture was then concentrated under reduced pressure and coevaporated 3 times with EtOH and DCM to afford the title compound as a beige solid (25 mg, 0.045 mmol, 90%), which was used directly for next step without further purification.

N-((1S,3R)-3-(5-chloro-4-(1H-indol-3-yl)pyrimidin-2-ylamino)cyclohexyl)piperazine-1-carboxamide (Compound 1047)

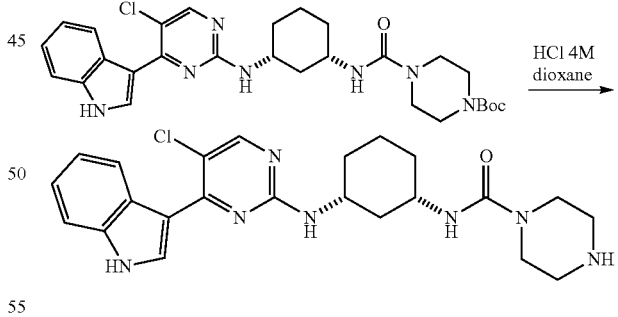

tert-Butyl 4-((1S,3R)-3-(5-chloro-4-(1H-indol-3-yl)pyrimidin-2-ylamino)cyclohexyl-carbamoyl)piperazine-1-carboxylate (25 mg, 0.045 mmol) was dissolved in 1,4-dioxane (100 μL) and 4M HCl in 1,4-dioxane (110 μL, 0.45 mmol) was added. The reaction mixture was stirred at rt for 3 h. The reaction mixture was concentrated under reduced pressure and coevaporated with DCM 3 times. The residual solid was stirred with excess triethylamine and then purified by reverse phase chromatography (MeCN—H2O-0.1% HCOOH, 5 to 70% gradient) to afford an off-white solid (10.1 mg, 0.022 mmol, 49%).

4-Acryloyl-N-((1S,3R)-3-(5-chloro-4-(1H-indol-3-yl)pyrimidin-2-ylamino)cyclohexyl)piperazine-1-carboxamide (Compound 201)

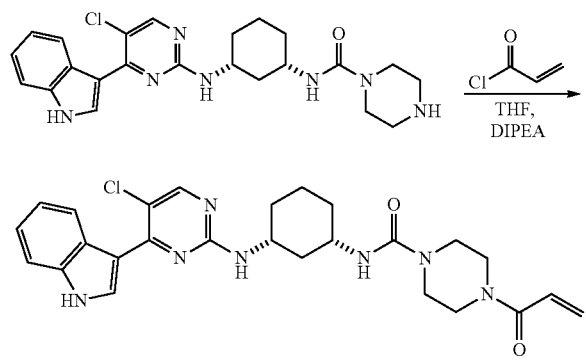

N-((1S,3R)-3-(5-chloro-4-(1H-indol-3-yl)pyrimidin-2-ylamino)cyclohexyl)piperazine-1-carboxamide (10.1 mg, 0.022 mmol) was dissolved in anhydrous THF (1.5 mL) and NMP (0.7 mL) along with diisopropylethylamine (12 µL, 0.067 mmol) under inert atmosphere and the solution was cooled to −78° C. Then, the acryloyl chloride (2 µL, 0.022 mmol) was added and the reaction mixture stirred at −78° C. for 20 min. The reaction mixture was then concentrated under reduced pressure and directly purified by reverse phase flash chromatography (MeCN—H₂O-0.1% HCOOH, 5 to 100% gradient) to afford the title compound as a pale yellow solid (2.0 mg, 0.0038 mmol, 18%).

Example 41. Synthesis of tert-Butyl 4-((R)-3-(5-chloro-4-(1-(phenylsulfonyl)-1H-indol-3-yl)pyrimidin-2-ylamino)piperidine-1-carboxamido)piperidine-1-carboxylate

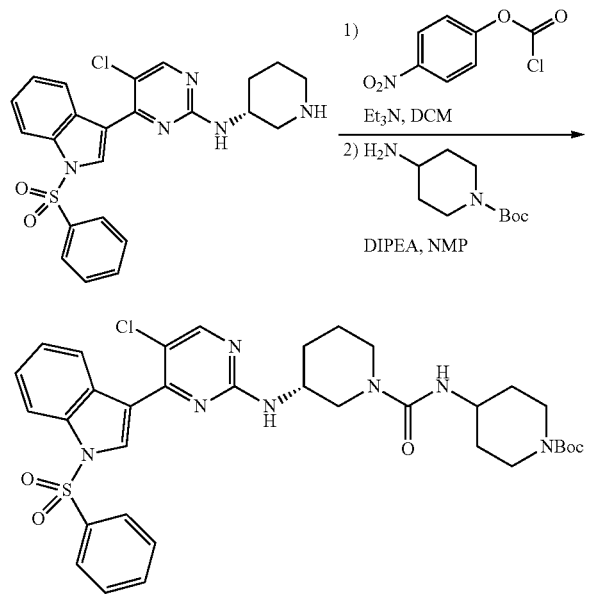

Triethylamine (0.13 mL, 0.90 mmol) and 4-nitrochloroformate (86 mg, 0.43 mmol) were added to a stirring solution of 5-chloro-4-(1-(phenylsulfonyl)-1H-indol-3-yl)-N—((R)-piperidin-3-yl)pyrimidin-2-amine (200 mg, 0.43 mmol), prepared as in Example 8 starting from (R)-tert-butyl piperidin-3-ylcarbamate, in DCM (5 mL) at 0° C. The resulting solution was allowed to stir at rt for 1 h. Water was added and the reaction mixture extracted 3× into DCM. The organics were then combined, dried over MgSO₄, filtered and concentrated to a yellow oil. The oil was then dissolved in NMP (1 mL) and the solution cooled to 0° C. DIPEA (0.10 mL, 0.60 mmol) and 4-amino-1-Boc-piperidine (120 mg, 0.60 mmol) were added to the reaction mixture and heated at 95° C. overnight. The reaction mixture was diluted with water and extracted with EtOAc (100 mL) and washed with H₂O (3×50 mL). The organic layer was dried over MgSO₄, filtered and concentrated to a light orange oil. The crude product was purified on a flash silica column (hex/MeOH, 0-10% gradient) to yield the title compound as an orange solid (216 mg, 0.311 mmol, 73%).

Example 42. Synthesis of (1R,3S)—N1-(5-cyclopropyl-4-(1-(phenylsulfonyl)-1H-indol-3-yl)pyrimidin-2-yl)cyclohexane-1,3-diamine Benzyl (1S,3R)-3-(5-cyclopropyl-4-(1-(phenylsulfonyl)-1H-indol-3-yl)pyrimidin-2-ylamino)cyclohexylcarbamate

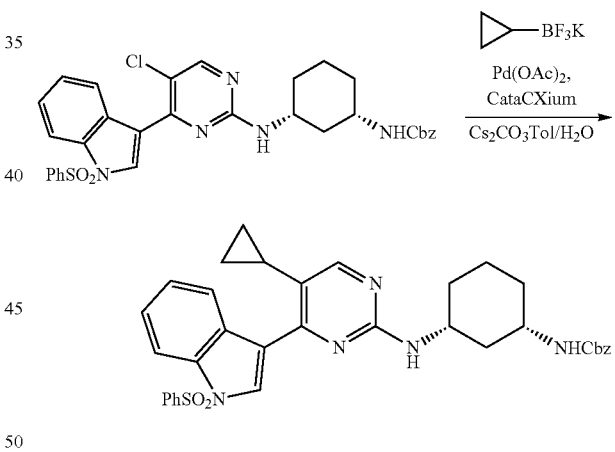

A degas sed solution of benzyl (1S,3R)-3-(5-chloro-4-(1-(phenylsulfonyl)-1H-indol-3-yl)pyrimidin-2-ylamino)cyclohexylcarbamate (500 mg, 0.812 mmol), Cs₂CO₃ (794 mg, 2.435 mmol) and potassium cyclopropyltrifluoroborate (360 mg, 2.435 mmol) in 1.4/1 tol/H₂O (12 mL) was treated with a premixed solution of Pd(OAc)₂ (9 mg, 0.04 mmol) and butyldi-1-adamantylphosphine (29 mg, 0.08 mmol) in degassed tol (3 mL) and heated at 140° C. (microwave) for 2 h. The cooled mixture was diluted with EtOAc (50 mL) and saturated NaHCO₃ (20 mL). The layers were separated and the aqueous layer was extracted with EtOAc (2×20 mL). The combined organic layers were dried over Na₂SO₄, filtered and evaporated to dryness. The residue was purified by SiO₂ chromatography (Hex/EtOAc 0 to 70% gradient) and afforded the title compound (324 mg, 0.521 mmol, 64%) as a yellow solid.

(1R,3S)—N1-(5-cyclopropyl-4-(1-(phenylsulfonyl)-1H-indol-3-yl)pyrimidin-2-yl)cyclohexane-1,3-diamine

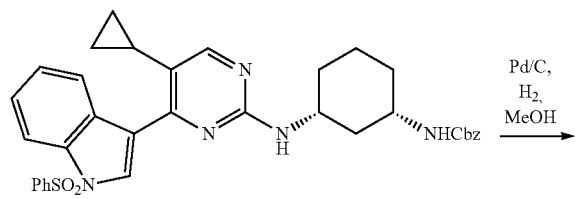

To a solution of benzyl (1S,3R)-3-(5-cyclopropyl-4-(1-(phenylsulfonyl)-1H-indol-3-yl)pyrimidin-2-ylamino)cyclohexylcarbamate (800 mg, 1.287 mmol) in MeOH (100 mL) was added Pd/C, activated, 10% (80 mg) and reaction mixture was stirred under hydrogen atm for 16 h at rt. The reaction mixture was filtered though a celite pad, washed with MeOH and EtOAc, and concentrated providing the title compound (480 mg, 0.984 mmol, 77% yield) as a pale yellow solid that was used for the next step without purification.

Example 43. Synthesis of 3-(2,5-dichloropyrimidin-4-yl)-1-methyl-1H-indole 3-(2,5-dichloropyrimidin-4-yl)-1H-indole

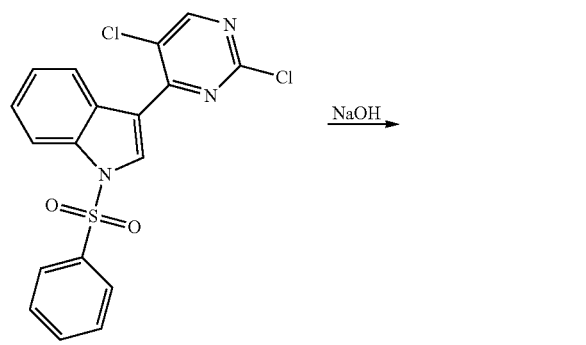

To a suspension of 3-(2,5-dichloropyrimidin-4-yl)-1-(phenylsulfonyl)-1H-indole (1.50 g, 3.71 mmol) in water/1,4-dioxane (62 mL/19 mL) is added an aqueous solution of NaOH (11 mL, 5M, 55 mmol). The suspension is stirred at 75° C. for 3 h. The reaction was then cooled to room temperature, concentrated under reduced pressure and extracted into DCM (100 mL). The DCM layer was dried over MgSO$_4$, filtered and concentrated to afford the title compound as a light yellow oil (0.734 g, 2.78 mmol, 75%), which was used without any further purification.

3-(2,5-dichloropyrimidin-4-yl)-1-methyl-1H-indole

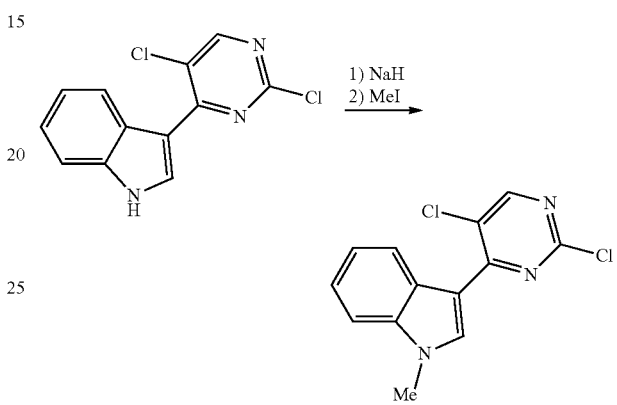

To a suspension of 3-(2,5-dichloropyrimidin-4-yl)-1H-indole (970 mg, 3.67 mmol) in DMF (18.4 mL) at 0° C., sodium hydride in mineral oil (0.220 g, 5.51 mmol, 60% w/w) was added. The reaction was warmed to room temperature and stirred for 0.5 h. The reaction was cooled to 0° C., and methyl iodide (0.834 g, 5.88 mmol) was added. The reaction was warmed to room temperature and stirred for 12 h, then diluted with ice-water (200 mL) and extracted with EtOAc (2×50 mL). The organic layer was washed with brine and directly concentrated to dryness. The crude product was then stirred in MTBE (100 mL) for 1 h, and filtered to afford the title compound as a white-yellow powder (0.500 g, 1.798 mmol, 49%).

Example 43A. Synthesis of Additional Intermediates and Compounds of the Invention Additional compounds of the invention were synthesized using modification or one or more of the foregoing examples. In the table below the specific examples and modifications are indicated for each compound. In addition, the table below contains the $^1$NMR, as well as the calculated and LCMS-found masses of certain of the exemplified compounds of the invention. Compound numbers ("Cmpd #") correspond to the compound numbers in FIGS. 1A-1Z and 1AA-1RR.

| Cmpd # | How Synthesized | $^1$H NMR | Calcd. Mass | Found Mass (MH$^+$) |
|---|---|---|---|---|
| 124 | See Example 37 above | 1H NMR (500 MHz, DMSO) δ 11.85 (s, 1H), 8.74-8.50 (m, 1H), 8.47 (s, 1H), 8.29 (s, 1H), 8.24 (s, 1H), 7.49 (d, J = 7.9 Hz, 1H), 7.28 (br s, 1H), 7.24-7.18 (m, 1H), | 493.04 | 493.29 |

-continued

| Cmpd # | How Synthesized | ¹H NMR | Calcd. Mass | Found Mass (MH⁺) |
|---|---|---|---|---|
| | | 7.18-7.10 (m, 1H), 6.76 (dd, J = 16.7, 10.5 Hz, 1H), 6.05 (dd, J = 16.7, 2.4 Hz, 1H), 5.63 (dd, J = 10.5, 2.4 Hz, 1H), 4.36 (br d, J = 11.1 Hz, 1H), 3.99 (br d, J = 12.2 Hz, 1H), 3.95-3.72 (m, 2H), 3.03-2.91 (m, 1H), 2.76 (br t, J = 11.1 Hz, 1H), 2.67-2.52 (m, 3H), 2.39-2.19 (m, 1H), 2.03-1.88 (m, 2H), 1.81 (br d, J = 11.1 Hz, 1H), 1.76-1.65 (m, 2H), 1.44-1.31 (m, 1H), 1.31-1.15 (m, 2H), 1.10 (ddd, J = 13.3, 12.6, 3.0 Hz, 1H), 1.05-0.90 (m, 2H). | | |
| 165 | Starting from (R)-tert-butyl 3-oxo cyclohexylcarbamate and 5-nitroisoindoline following Example 33 and reduction of nitro as intermediate 278 in Example 13 | | 513.03 | 513.62 |
| 167 | Starting from (1R,3S)-N-(5-chloro-4-(1-(phenylsulfonyl)-1H-indol-3-yl)pyrimidin-2-yl)cyclohexane-1,3-diamine and tert-butyl 4-formylpiperidine-1-carboxylate following Example 37 and Example 38 | 1H NMR (500 MHz, DMSO) δ 11.83 (br s, 1H), 8.75-8.51 (m, 1H), 8.47 (s, 1H), 8.23 (br s, J = 8.7 Hz, 1H), 7.49 (d, J = 7.9 Hz, 1H), 7.20 (dd, J = 11.1, 4.0 Hz, 1H), 7.18-7.15 (m, 1H), 7.16-7.12 (m, 1H), 6.76 (dd, J = 16.6, 10.5 Hz, 1H), 6.05 (dd, J = 16.7, 2.4 Hz, 1H), 5.62 (d, J = 10.4 Hz, 1H), 4.41-4.27 (m, 1H), 4.03-3.92 (m, 1H), 3.91-3.60 (m, 2H), 3.04-2.92 (m, 1H), 2.63-2.53 (m, 1H), 2.21 (d, J = 6.9 Hz, 2H), 2.19 (s, 3H), 2.16-2.08 (m, 1H), 2.00-1.90 (m, 1H), 1.87-1.76 (m, 1H), 1.76-1.59 (m, 4H), 1.35-1.13 (m, 4H), 0.96-0.81 (m, 2H). | 507.07 | 507.63 |
| 168 | See Example 33 above | ¹H NMR (500 MHz, DMSO) δ 11.83 (s, 1H), 8.55 (s, 1H), 8.47 (s, 1H), 8.23 (s, 1H), 7.49 (d, J = 7.7 Hz, 1H), 7.21 (dd, J = 11.1, 4.0 Hz, 2H), 7.16-7.10 (m, 1H), 6.76 (dd, J = 16.7, 10.5 Hz, 1H), 6.07 (dd, J = 16.7, 2.3 Hz, 1H), 5.64 (dd, J = 10.5, 2.2 Hz, 1H), 3.85 (br s, 2H), 3.51-3.46 (m, 8H), 2.23-2.17 (m, 1H), 1.99-1.92 (m, 1H), 1.80 (br s, 2H), 1.40-1.09 (m, 4H). | 464.99 | 465.65 |
| 176 | Starting from 5-chloro-4-(1-(phenylsulfonyl)-1H-indol-3-yl)-N-((R)-pyrrolidin-3-yl)pyrimidin-2-amine using the final step following Example 3 | ¹H NMR (500 MHz, DMSO) δ 11.87 (s, 1H), 8.61 (s(br), 1H), 8.48 (d, J = 3.1 Hz, 1H), 8.31 (d, J = 3.2 Hz, 1H), 7.60 (dd, J = 29.8, 6.2 Hz, 1H), 7.50 (d, J = 8.0 Hz, 1H), 7.21 (ddd, J = 8.2, 7.1, 1.3 Hz, 1H), 7.16 (ddd, J = 8.1, 7.1, 1.1 Hz, 1H), 6.71-6.53 (m, 2H), 4.58-4.41 (m, 1H), 3.97-3.88 (m, 1H), 3.81-3.60 (m, 3H), 3.59-3.45 (m, 2H), 2.70-2.56 (m, 6H), 2.33-2.14 (m, 1H), 2.14-1.99 (m, 1H). | 424.93 | 425.58 |
| 177 | Starting from Benzyl (1S,3R)-3-amino cyclohexylcarbamate. HCl, following Example 33 and Example 8 | ¹H NMR (500 MHz, DMSO) δ 11.89 (s, 1H), 8.74-8.51 (m, 1H), 8.47 (s, 1H), 8.33 (br s, 1H), 8.24 (s, 1H), 7.49 (d, J = 7.9 Hz, 1H), 7.27 (br s, 1H), 7.21 (t, J = 7.5 Hz, 1H), 7.18-7.11 (m, 1H), 6.57-6.52 (m, 1H), 4.43-4.27 (m, 1H), 4.04-3.93 (m, 1H), 3.92-3.79 (m, 2H), 3.17 (d, J = 10.7 Hz, 2H), 3.05-2.91 (m, 3H), 2.80-2.66 (m, 2H), 2.57 (br s, 1H), 2.35-2.23 (m, 1H), 2.13 (s, 4H), 2.01-1.89 (m, 2H), 1.85-1.75 (m, 2H), 1.75-1.63 (m, 2H), 1.41-1.30 (m, 1H), 1.30-1.17 (m, 3H), 1.15-0.92 (m, 3H). | 550.14 | 550.69 |
| 178 | Starting from Benzyl (1S,3R)-3-amino cyclohexylcarbamate. HCl following Example 37 (TcBoc as piperidine protecting group) | | 507.07 | 507.65 |
| 179 | Starting from tert-butyl (1S,3R)-3-aminocyclohexylcarbamate | ¹H NMR (500 MHz, DMSO) δ 11.76 (s, 1H), 8.66-8.42 (m, 1H), 8.39 (d, J = 2.9 Hz, 1H), 8.18 (br s, 1H), 7.72 (d, J = 8.1 | 564.12 | 564.68 |

-continued

| Cmpd # | How Synthesized | ¹H NMR | Calcd. Mass | Found Mass (MH⁺) |
|---|---|---|---|---|
| | using the same synthetic sequence as Example 18 and Example 8 | Hz, 1H), 7.42 (d, J = 8.6 Hz, 1H), 7.23-7.03 (m, 3H), 6.52-6.46 (m, 2H), 4.38-4.23 (m, 1H), 4.07-3.88 (m, 2H), 3.86-3.71 (m, 2H), 3.69-3.54 (m, 2H), 2.97-2.90 (m, 2H), 2.27 (ddt, J = 11.7, 7.5, 3.1 Hz, 1H), 2.06 (s, 6H), 1.97-1.80 (m, 1H), 1.78-1.66 (m, 2H), 1.60 (br t, J = 12.9 Hz, 2H), 1.43-1.24 (m, 3H), 1.23-1.10 (m, 2H), 1.08-0.96 (m, 1H). | | |
| 180 | Starting from trans-benzyl 4-((3R)-3-(tert-butoxycarbonylamino) cyclohexyl)piperazine-1-carboxylate using the same synthetic sequence as Example 33 | ¹H NMR (500 MHz, DMSO) δ 11.81 (s, 1H), 8.59 (s, 1H), 8.44 (d, J = 3.0 Hz, 1H), 8.25 (s, 1H), 7.48 (d, J = 7.9 Hz, 1H), 7.20 (dd, J = 11.1, 4.1 Hz, 1H), 7.17-7.07 (m, 2H), 6.81-6.67 (m, 1H), 6.07 (d, J = 15.7 Hz, 1H), 5.65 (d, J = 12.8 Hz, 1H), 4.31 (br s 1H), 3.55-3.43 (m, 4H), 2.57 (br s, 1H), 2.49-2.38 (m, 4H), 1.92-1.81 (m, 1H), 1.82-1.63 (m, 3H), 1.62-1.48 (m, 4H). | 464.99 | 465.66 |
| 181 | Starting from 3-(2,5-dichloropyrimidin-4-yl)pyrazolo[1,5-a]pyridine from Example 34 using the same synthetic sequence as Example 11 | | 508.02 | 508.61 |
| 182 | Starting from 3-(2,5-dichloropyrimidin-4-yl)pyrazolo[1,5-a]pyridine from Example 34 using the same synthetic sequence as Example 8 | | 565.11 | 565.72 |
| 183 | Starting from (1R,3S)-N-(5-chloro-4-(1-(phenylsulfonyl)-1H-indol-3-yl)pyrimidin-2-yl)cyclohexane-1,3-diamine and tert-butyl 4-formylpiperidine-1-carboxylate following Example 37 and Example 39 | | | |
| 186 | Starting from tert-Butyl-1-oxa-6-azaspiro[2.5]octane-6-carboxylate and using a similar synthetic sequence as Example 35 and Example 36 | | 535.04 | 535.63 |
| 187 | See Example 36 above | | 495.02 | 495.63 |
| 188 | See Example 36 above | | 495.02 | 495.63 |
| 189 | Starting from cis-1,4-diaminocyclohexane using the same synthetic sequence as Example 24 and Example 11 | ¹H NMR (500 MHz, DMSO) δ 11.83 (s, 1H), 8.62 (s, 1H), 8.47 (d, J = 2.8 Hz, 1H), 8.25 (s, 1H), 7.69(d, J = 6.8 Hz, 1H), 7.49 (d, J = 8.0 Hz, 1H, 7.25-7.19 (m, 1H), 7.17-7.11 (m, 1H), 7.06(d, J = 6.7 Hz, 1H), 6.79 (dd, J = 16.7, 10.5 Hz, 1H), 6.08 (dd, J = 16.7, 2.4 Hz, 1H), 5.65 (dd, J = 10.5, 2.4 Hz, 1H), 4.40 (d, J = 12.8 Hz, 1H), 4.06(d, J = 12.9 Hz, 1H), 3.94-3.79 (m, 1H), 3.79-3.67 (m, 1H), 3.04(t, J = 12.0 Hz, 1H), 2.71-2.59 (m, 1H), 2.46(dt, J = 11.5, 3.9 Hz, 1H), 1.87-1.63 (m, 8H), 1.63-1.52 (m, 2H), 1.43(ddd, J = 16.3, 12.4, 2.9 Hz, 2H). | 507.03 | 507.58 |
| 192 | Starting from trans-1,4-diaminocyclohexane using the same synthetic sequence as Example 24 and Example 8 | ¹H NMR (500 MHz, DMSO) δ 11.84 (s, 1H), 8.75-8.54 (m, 1H), 8.47 (s, 1H), 8.24 (s, 1H), 8.19 (s, 1H), 7.92-7.80(m, 1H), 7.57-7.44 (m, 1H), 7.28-7.09 (m, 3H), 6.67-6.46 (m, 1H), 4.40-4.16 (m, 1H), 3.99-3.85 (m, 1H), 3.03 (d, J = 5.0 Hz, 2H), 2.75-2.65 (m, 1H), 2.33-2.13 (m, 1H), 2.15 (s, 6H), 2.09-1.95 (m, 1H), | 564.12 | 564.67 |

-continued

| Cmpd # | How Synthesized | ¹H NMR | Calcd. Mass | Found Mass (MH⁺) |
|---|---|---|---|---|
| | | 1.90-1.77 (m, 4H), 1.70-1.58 (m, 2H), 1.48-1.21 (m, 6H). | | |
| 198 | Starting from (1R,3S)-N-(5-chloro-4-(1-(phenylsulfonyl)-1H-indol-3-yl)pyrimidin-2-yl)cyclohexane-1,3-diamine and tert-butyl 4-formylpiperidine-1-carboxylate following Example 37 and Example 39 | 1H NMR (500 MHz, DMSO) δ 11.84 (s, 1H), 8.75-8.52 (m, 1H), 8.46 (d, J = 3.0 Hz, 1H), 8.24 (d, J = 6.5 Hz, 1H), 7.49 (d, J = 7.5 Hz, 1H), 7.28-7.08 (m, 3H), 6.77 (dd, J = 16.7, 10.5 Hz, 1H), 6.06 (dd, J = 16.7, 2.3 Hz, 1H), 5.63 (dt, J = 5.2, 2.8 Hz, 1H), 4.38 (br d, J = 12.3 Hz, 1H), 4.01 (br d, J = 12.8 Hz, 1H), 3.96-3.86 (m, 1H), 3.86-3.77 (m, 1H), 3.73 (td, J = 11.0, 2.6 Hz, 1H), 3.18-3.00 (m, 2H), 2.99-2.88 (m, 1H), 2.19-1.75 (m, 7H), 1.76-1.51 (m, 4H), 1.52-1.29 (m, 2H), 1.30-1.12 (m, 1H), 1.12-0.91 (m, 2H). | 535.08 | 535.66 |
| 199 | Starting from (1R,3S)-N-(5-chloro-4-(1-(phenylsulfonyl)-1H-indol-3-yl)pyrimidin-2-yl)cyclohexane-1,3-diamine and tert-butyl 4-formylpiperidine-1-carboxylate following Example 37 and Example 39 | | 571.13 | 571.62 |
| 200 | Starting from cis-1,4-diaminocyclohexane using the same synthetic sequence as Example 24 | ¹H NMR (500 MHz, DMSO) δ 11.83 (s, 1H), 8.68-8.57 (m, 1H), 8.47 (d, J = 2.9 Hz, 1H), 8.25 (s, 1H), 7.85-7.73 (m, 1H), 7.49 (d, J = 8.0 Hz, 1H), 7.25-7.18 (m, 1H), 7.16 (dd, J = 11.0, 4.0 Hz, 1H), 7.09 (d, J = 6.7 Hz, 1H), 6.89-6.73 (m, 1H), 6.08 (dd, J = 16.7, 2.4 Hz, 1H), 5.66 (dd, J = 10.5, 2.4 Hz, 1H), 4.38-4.25 (m, 1H), 4.01-3.92(m, 1H), 3.91-3.81 (m, 1H), 3.74 (br s, 1H), 3.20-2.97 (m, 1H), 2.76-2.62 (m, 1H), 2.42-2.24 (m, 1H), 1.92-1.48 (m, 11H), 1.31 (m, 1H). | 507.03 | 507.62 |
| 201 | See Example 40 | 1H NMR (500 MHz, DMSO) δ 11.82 (s, 1H), 8.58 (br s, 1H), 8.46 (d, J = 2.4 Hz, 1H), 8.24 (s, 1H), 7.48 (d, J = 8.6 Hz, 1H), 7.21 (dd, J = 17.1, 8.0 Hz, 2H), 6.79 (dd, J = 16.7, 10.5 Hz, 1H), 6.63 (br s, 1H), 6.40 (d, J = 7.7 Hz, 1H), 6.10 (dd, J = 16.7, 2.3 Hz, 1H), 5.68 (dd, J = 10.5, 2.3 Hz, 1H), 3.99-3.74 (m, 2H), 3.67-3.55 (m, 2H), 3.55-3.47 (m, 4H), 3.36-3.24 (m, 4H), 2.20-2.07 (m, 1H), 2.06-1.89 (m, 1H), 1.88-1.63 (m, 2H), 1.40-1.27 (m, 1H), 1.24-1.11 (m, 1H). | 508.02 | 508.58 |
| 205 | Starting from (R)-tert-butyl piperidin-3-ylcarbamate using the same synthetic sequence as Example 8 and Example 41 | ¹H NMR (500 MHz, DMSO) δ 11.83 (br s, 1H), 8.65 (s, 1H), 8.45 (d, J = 2.8 Hz, 1H), 8.26 (s, 1H), 7.48 (d, J = 8.1 Hz, 1H), 7.20 (t, J = 7.3 Hz, 1H), 7.11 (br s, 1H), 6.78 (dd, J = 16.0, 10.7 Hz, 1H), 6.60 (s, 1H), 6.22 (d, J = 7.7 Hz, 1H), 6.06 (dd, J = 16.7, 2.4 Hz, 1H), 5.64 (dd, J = 10.5, 2.4 Hz, 1H), 4.29 (d, J = 12.8 Hz, 1H), 4.09-3.75 (m, 4H), 3.68 (s, 1H), 3.14-2.90 (m, 1H), 2.72-2.68 (m, 3H), 2.03 (s, 1H), 1.79-1.69 (m, 3H), 1.57-1.33 (m, 2H), 1.30-1.15 (m, 2H). | 508.02 | 508.28 |
| 206 | Starting from cis-1,4-diaminocyclohexane using the same synthetic sequence as Example 24 and Example 8 | ¹H NMR (500 MHz, DMSO) δ 11.84 (s, 11H), 8.70-8.56 (m, 1H), 8.47 (d, J = 2.7 Hz, 1H), 8.25 (s, 1H), 7.91 (d, J = 7.7 Hz, 0.25H), 7.78 (d, J = 6.1 Hz, 0.75H), 7.49 (d, J = 8.1 Hz, 1H), 7.20 (dd, J = 11.5, 4.6 Hz, 1H), 7.18-7.12 (m, 1H), 7.14-7.11 (m, 1H), 6.64-6.52 (m, 2H), 4.38-4.22(m, 1H), 4.01-3.82 (m, 2H), 3.78-3.70 (m, 1H), 3.01 (t, J = 4.3 Hz, 2H), 2.75-2.59 (m, 1H), 2.44-2.28(m, 1H), 2.13 (s, 6H), 1.90-1.52 (m, 12H), 1.49-1.39 (m, 1H), 1.36-1.25 (m, 1H). | 564.12 | 564.37 |
| 207 | Starting from 4-amino-1-N-cbz- | ¹H NMR (500 MHz, DMSO) δ 11.83 (s, 1H), 8.57 (br s, 1H), 8.47 (s, 1H), 8.23 (d, | 493.04 | 493.30 |

| Cmpd # | How Synthesized | ¹H NMR | Calcd. Mass | Found Mass (MH⁺) |
|---|---|---|---|---|
| | piperidine using the same synthetic sequence as Example 33 and Example 38 | J = 6.3 Hz, 1H), 7.49 (d, J = 8.3 Hz, 1H), 7.18 (dt, J = 15.1, 7.0 Hz, 3H), 6.75 (br s, 1H), 6.05 (d, J = 16.6 Hz, 1H), 5.63 (d, J = 12.8 Hz, 1H), 4.39-4.23 (m, 2H), 4.13-3.69 (m, 4H), 2.92-2.81 (m, 1H), 2.78-2.64 (m, 2H), 2.16 (s, 3H), 2.01-1.89 (m, 1H), 1.85-1.58 (m, 4H), 1.45-1.15 (m, 5H). | | |
| 208 | Example 42 above, then using the same synthetic sequence as Example 11 | ¹H NMR (500 MHz, DMSO) δ 11.63 (s, 1H), 8.64 (brs, 1H), 8.29 (d, J = 2.9 Hz, 1H), 8.04 (s, 1H), 7.76 (d, J = 7.9 Hz, 1H), 7.45 (d, J = 8.2 Hz, 1H), 7.18-7.11 (m, 2H), 6.80-6.74 (m, 2H), 6.07 (dd, J = 16.7, 2.4 Hz, 1H), 5.64 (d, J = 10.3 Hz, 1H), 4.37 (brs, 1H), 4.03 (brs, 1H), 3.86 (brs, 1H), 3.66 (brs, 1H), 3.02 (brs, 1H), 2.63 (brs, 1H), 2.39-2.28 (m, 1H), 2.10 (brs, 1H), 1.95-1.93 (m, 2H), 1.77 (d, J = 10.9 Hz, 2H), 1.67 (t, J = 12.4 Hz, 2H), 1.53-1.30 (m, 3H), 1.28-1.03 (m, 3H), 1.02-0.90 (m, 2H), 0.58 (brs, 2H). | 512.65 | 513.32 |
| 209 | Following Example 42 above and Example 8 | ¹H NMR (500 MHz, DMSO) δ 11.64 (s, 1H), 8.63 (brs, 1H), 8.29 (d, J = 2.9 Hz, 1H), 8.04 (s, 1H), 7.76 (d, J = 8.0 Hz, 1H), 7.45 (d, J = 8.2 Hz, 1H), 7.21-7.08 (m, 2H), 6.75 (d, J = 8.1 Hz, 1H), 6.55 (brs, 2H), 4.36 (brs, 1H), 4.01 (brs, 1H), 3.85 (brs, 1H), 3.65 (brs, 2H), 3.00 (brs, 3H), 2.63 (brs, 1H), 2.40-2.28 (m, 1H), 2.13 (s, 6H), 1.96-1.90 (m, 2H), 1.77 (d, J = 10.5 Hz, 2H), 1.66 (brs, 2H), 1.50-1.30 (m, 3H), 1.23-1.08 (m, 3H), 0.96-0.94 (m, 2H), 0.57 (brs, 2H). | 569.74 | 570.37 |
| 215 | Starting from (1R,3S)-N-(5-chloro-4-(1-(phenylsulfonyl)-1H-indol-3-yl)pyrimidm-2-yl)cyclohexane-1,3-diamine and tert-butyl 4-formylpiperidine-1-carboxylate following Example 37 and Example 39 | ¹H NMR (500 MHz, DMSO) δ 11.87 (s, 1H), 8.77-8.51 (m, 1H), 8.24 (s, 1H), 7.49 (d, J = 7.9 Hz, 1H), 7.29-7.11 (m, 3H), 6.76 (dd, J = 15.5, 11.2 Hz, 1H), 6.06 (dd, J = 16.7, 2.4 Hz, 1H), 5.63 (dd, J = 10.6, 1.8 Hz, 1H), 4.36 (br s, 1H), 4.08-3.75 (m, 2H), 3.74-3.62 (m, 1H), 3.55 (s 3H) 3.05 (d, J = 6.9 Hz, 2H), 2.98-2.76 (m, 1H), 2.65-2.33 (m, 1H), 2.14-1.91 (m, 2H), 1.89-1.76 (m, 2H), 1.76-1.49 (m, 5H), 1.47-1.31 (m, 1H), 1.30-1.13 (m, 1H), 1.08-0.86 (m, 2H). | 551.08 | 551.28 |
| 216 | Starting from (1R,3S)-N1-(5-cyclopropyl-4-(1-(phenylsulfonyl)-1H-indol-3-yl)pyrimidin-2-yl)cyclohexane-1,3-diamine (Example 42) and tert-butyl 4-formylpiperidine-1-carboxylate following Example 37 and Example 38. | ¹H NMR (500 MHz, DMSO) δ 11.64 (s, 1H), 8.67 (s, 1H), 8.41 (s, 1H), 8.30 (d, J = 2.8 Hz, 1H), 8.03 (s, 1H), 7.46 (d, J = 8.2 Hz, 1H), 7.17 (t, J = 7.3 Hz, 1H), 7.10 (t, J = 7.0 Hz, 1H), 6.76 (dd, J = 16.8, 10.5 Hz, 1H), 6.05 (dd, J = 16.8, 2.3 Hz, 1H), 5.62 (d, J = 11.4 Hz, 1H), 4.34 (brs, 1H), 3.99 (brs, 1H), 3.82-3.60 (m, 4H), 2.99 (brs, 1H), 2.22-2.19 (m, 4H), 1.92 (t, 2H), 1.85-1.65 (m, 5H), 1.24-1.15 (m, 5H), 0.97-0.82 (m, 4H), 0.59-0.56 (m, 2H). | 512.69 | 513.39 |
| 222 | Starting from 3-(2,5-dichloropyrimidin-4-yl)pyrazolo[1,5-a]pyridine from Example 34 using the same synthetic sequence as Example 8 using morpholine in the final step. | ¹H NMR (500 MHz, DMSO) δ 8.92 (s, 1H), 8.85 (d, J = 6.9 Hz, 1H), 8.70-8.44 (m, 1H), 8.30 (s, 1H), 7.79 (d, J = 5.7 Hz, 1H), 7.59 (s, 1H), 7.38 (d, J = 7.9 Hz, 1H), 7.15 (td, J = 6.9, 1.3 Hz, 1H), 6.69-6.47 (m, 2H), 4.36 (s, 1H), 4.01 (s, 1H), 3.74 (d, J = 29.2 Hz, 2H), 3.63-3.51 (m, 4H), 3.05 (t, J = 13.5 Hz, 3H), 2.63 (dd, J = 6.4, 4.6 Hz, 1H), 2.32 (dd, J = 15.3, 3.7 Hz, 5H), 2.14 (s, 1H), 1.99-1.88 (m, 1H), 1.71 (d, J = 44.7 Hz, 4H), 1.40 (dd, J = 24.6, 11.9 Hz, 3H), 1.28-1.05 (m, 3H). | 606.28 | 607.35 |
| 223 | Starting from 3-(2,5-dichloropyrimidin-4-yl)pyrazolo[1,5-a]pyridine from Example 34 using the same synthetic sequence as Example | | 645.33 | 646.39 |

-continued

| Cmpd # | How Synthesized | ¹H NMR | Calcd. Mass | Found Mass (MH⁺) |
|---|---|---|---|---|
| | 8 using cyclopropylpiperazine in the final step. | | | |
| 224 | Starting from (1R,3S)-N-(5-chloro-4-(1-(phenyl sulfonyl)-1H-indol-3-yl)pyrimidin-2-yl)cyclohexane-1,3-diamine and tert-butyl-3-oxoazetidine-1-carboxylate following Example 37. | ¹H NMR (500 MHz, DMSO) δ 11.83 (s, 1H), 8.55 (br s, 1H), 8.47 (s, 1H), 8.23 (s, 1H), 7.49 (d, J = 7.7 Hz, 1H), 7.26-7.09 (m, 3H), 6.26 (br s, 1H), 6.06 (d, J = 17.0 Hz, 1H), 5.64 (dd, J = 10.3, 2.0 Hz, 1H), 4.23-4.13 (m, 1H), 4.10-3.98 (m, 1H), 3.93-3.79 (m, 2H), 3.79-3.72 (m, 1H), 3.72-3.63 (m, 1H), 2.61-2.46 (m, 1H), 2.15 (s, 3H), 2.09-1.87 (m, 2H), 1.81 (br s, 1H), 1.63 (br s, 1H), 1.39-1.10 (m, 4H). | 464.99 | 465.31 |
| 225 | Starting from N-Boc-1-oxa-6-azaspiro[2,5-octane], following Example 36 and then Examples 38 and 37. | ¹H NMR (500 MHz, DMSO) δ 11.84 (brs, 1H), 8.57 (brs, 1H), 8.48 (s, 1H), 8.23 (s, 1H), 7.49 (d, J = 7.7 Hz, 1H), 7.22-7.13 (m, 3H), 6.81-6.78 (m, 1H), 6.08-6.05 (m, 1H), 5.67-5.60 (m, 1H), 4.11 (brs, 1H), 3.90-3.60 (m, 3H), 2.96-2.93 (m, 1H), 2.31 (s, 5H), 2.16-1.73 (m, 5H), 1.49-1.11 (m, 8H). | 523.07 | 523.36 |
| 226 | Starting from benzyl (1S,3R)-3-(5-chloro-4-(1-(phenylsulfonyl)-1H-indol-3-yl)pyrimidin-2-ylamino)cyclohexyl-carbamate following Example 42 using potassium methyltrifluoroborate for the methylation and Example 8. | | 543.7 | 544.45 |
| 228 | Starting from N-Boc-1-oxa-6-azaspiro[2,5-octane], following Example 36 and then Examples 38 and 8. | ¹H NMR (500 MHz, DMSO) δ 11.85 (brs, 1H), 8.56 (brs, 1H), 8.48 (s, 1H), 8.24 (s, 1H), 8.20 (s, 1H), 7.49 (d, J = 7.9 Hz, 1H), 7.25-7.10 (m, 3H), 6.63-6.49 (m, 2H), 4.11 (s, 1H), 3.90-3.70 (m, 2H), 3.32-3.29 (m, 2H), 3.07-2.99 (m, 3H), 2.35-2.33 (m, 5H), 2.16 (d, 6H), 1.96 (brs, 2H), 1.80-1.76 (m, 2H), 1.47-1.15 (m, 8H). | 580.16 | 580.39 |
| 229 | Starting from (R)-1-N-Cbz-2-methylpiperazine using the same synthetic sequence as Example 33. | ¹H NMR (500 MHz, DMSO) δ 11.83 (brs, 1H), 8.56 (brs, 1H), 8.47 (s, 1H), 8.24 (s, 1H), 7.49 (d, J = 8.0 Hz, 1H), 7.28-7.03 (m, 3H), 6.82-6.67 (m, 1H), 6.06 (d, J = 16.6 Hz, 1H), 5.63 (d, J = 10.7 Hz, 1H), 4.56 (brs, 1H), 4.23 (brs, 1H), 3.86 (brs, 2H), 2.93-2.60 (m, 3H), 2.37-2.05 (m, 3H), 2.03-1.66 (m, 4H), 1.34 (s, 1H), 1.27-1.09 (m, 5H). | 479.02 | 479.29 |
| 230 | Starting from (R)-1-N-Cbz-2-methylpiperazine using the same synthetic sequence as Example 33 and final step following Example 8. | ¹H NMR (500 MHz, DMSO) δ 11.77 (brs, 1H), 8.49 (brs, 1H), 8.41 (s, 1H), 8.17 (s, 1H), 7.42 (d, J = 7.6 Hz, 1H), 7.16-7.06 (m, 3H), 6.47 (brs, 2H), 4.49 (brs, 1H), 4.12 (brs, 1H), 3.79 (brs, 2H), 2.94 (d, J = 4.5 Hz, 2H), 2.75-2.66 (m, 3H), 2.24 (brs, 1H), 2.06 (s, 6H), 1.86 (brs, 2H), 1.74 (brs, 2H), 1.30-1.01 (m, 8H). | 536.11 | 536.34 |
| 231 | Starting from (1R,3S)-N-(5-chloro-4-(1-(phenyl sulfonyl)-1H-indol-3-yl)pyrimidin-2-yl)cyclohexane-1,3-diamine and tert-butyl-3-oxoazetidine-1-carboxylate following Example 37. | ¹H NMR (500 MHz, DMSO) δ 11.83 (s, 1H), 8.53 (d, J = 30.3 Hz, 1H), 8.47 (s, 1H), 8.23 (s, 1H), 7.49 (d, J = 7.8 Hz, 1H), 7.19 (dt, J = 15.6, 7.0 Hz, 3H), 6.54 (dt, J = 15.3, 6.1 Hz, 1H), 6.07 (d, J = 14.0 Hz, 1H), 4.15 (1H), 4.02 (s, 1H), 3.86 (s, 2H), 3.68 (dd, J = 22.2, 16.3 Hz, 2H), 3.01 (d, J = 5.7 Hz, 2H), 2.54 (t, J = 10.0 Hz, 1H), 2.22-2.00 (m, 9H), 2.04-1.91 (m, 2H), 1.80 (s, 1H), 1.63 (s, 1H), 1.36-1.13 (m, 4H). | | |
| 232 | Starting from (S)-benzyl 2-methylpiperazine-1-carboxylate using the same synthetic | ¹H NMR (500 MHz, DMSO) δ 11.83 (s, 1H), 8.55 (br s, 1H), 8.47 (s, 1H), 8.24 (s, 1H), 7.49 (d, J = 8.2 Hz, 1H), 7.21 (t, J = 7.2 Hz, 2H), 7.14 (t, J = 7.4 Hz, 1H), 6.80-6.67 (m, 1H), 6.07 (d, J = 16.2 Hz, 1H), | 479.02 | 479.29 |

-continued

| Cmpd # | How Synthesized | ¹H NMR | Calcd. Mass | Found Mass (MH⁺) |
|---|---|---|---|---|
| | sequence as Example 33 and Example 8. | 5.64 (d, J = 11.9 Hz, 1H), 4.62-4.47 (m, 1H), 4.31-4.11 (m, 1H), 3.95-3.74 (m, 2H), 2.89-2.84 (m, 1H), 2.74-2.67 (m, 1H), 2.41 (s, 3H), 2.41-2.23 (m, 1H), 2.22-2.08 (m, 2H), 2.02-1.88 (m, 1H), 1.84-1.69 (m, 2H), 1.46-1.01 (m, 5H). | | |
| 237 | See Example 33 above and final step following Example 8. | ¹H NMR (500 MHz, DMSO) δ 11.84 (brs, 1H), 8.62 (brs, 1H), 8.47 (s, 1H), 8.24 (s, 1H), 7.49 (d, J = 7.9 Hz, 1H), 7.25-7.18 (m, 2H), 7.17-7.11 (m, 1H), 6.60-6.49 (m, 2H), 3.90-3.49 (m, 10H), 3.00 (d, J = 4.0 Hz, 2H), 2.13 (s, 6H), 1.98 (brs, 1H), 1.81 (brs, 2H), 1.43-1.10 (m, 5H). | 522.08 | 522.30 |
| 255 | Starting from benzyl-1,3-diazetidine-1-carboxylate using the same synthetic sequence as Example 33. | ¹H NMR (500 MHz, DMSO) δ 11.81 (s, 1H), 8.63 (br s, 1H), 8.53-8.37 (m, 2H), 8.23 (s, 1H), 7.49 (d, J = 7.5 Hz, 1H), 7.19 (dt, J = 25.3, 12.0 Hz, 2H), 7.04 (d, J = 8.0 Hz, 1H), 6.19 (dt, J = 19.8, 9.9 Hz, 1H), 6.07 (d, J = 17.0 Hz, 1H), 5.58 (d, J = 10.0 Hz, 1H), 4.34-4.23 (m, 1H), 3.56-3.46 (m, 2H), 2.88-2.77 (m, 1H), 2.76-2.71 (m, 1H), 2.16-2.01 (m, 1H), 2.01-1.82 (m, 1H), 1.80-1.62 (m, 2H), 1.56-1.41 (m, 2H), 1.38-1.18 (m, 2H), 1.17-1.01 (m, 1H), 0.94-0.79 (m, 1H). | 451.2 | 451.29 |
| 256 | Starting from (3S)-3-benzyloxycarbonyl-aminopiperidine using the same synthetic sequence as Example 33. | ¹H NMR (500 MHz, DMSO) δ 11.81 (s, 1H), 8.60 (br s, 1H), 8.45 (dd, J = 8.3, 3.0 Hz, 1H), 8.23 (s, 1H), 7.88 (d, J = 8.0 Hz, 1H), 7.48 (d, J = 8.1 Hz, 1H), 7.22-7.06 (m, 3H), 6.30-6.15 (m, 1H), 6.06 (dd, J = 17.1, 2.3 Hz, 1H), 5.54 (dd, J = 10.2, 1.7 Hz, 1H), 4.48-4.16 (m, 1H), 3.90-3.64 (m, 2H), 2.99-2.81 (m, 1H), 2.79-2.65 (m, 2H), 2.25-2.10 (m, 1H), 2.08-2.01 (m, 1H), 2.02-1.89 (m, 1H), 1.86-1.54 (m, 6H), 1.53-1.38 (m, 1H), 1.36-1.09 (m, 3H). | 479.02 | 479.30 |
| 257 | Starting from (S)-benzyl 3-methylpiperazine-1-carboxylate using the same synthetic sequence as Example 33. | ¹H NMR (500 MHz, DMSO) δ 11.81 (brs, 1H), 8.56 (brs, 1H), 8.42 (brs, 1H), 8.25 (brs, 1H), 7.48 (d, J = 7.9 Hz, 1H), 7.21-7.12 (m, 3H), 6.82-6.71 (m, 1H), 6.06 (d, J = 16.3 Hz, 1H), 5.68-5.58 (m, 1H), 4.26 (brs, 2H), 3.63 (brs, 1H), 3.30-3.20 (m, 4H), 3.00-2.82 (m, 2H), 2.47-2.39 (m, 1H), 1.82-1.45 (s, 7H), 1.23 (s, 1H), 0.87-0.71 (m, 2H). | 479.02 | 479.35 |
| 258 | Starting from benzyl 6-formylpyridin-3-ylcarbamate using the same synthetic sequence as Example 37. | ¹H NMR (500 MHz, DMSO) δ 11.82 (brs, 1H), 10.35 (brs, 1H), 8.76 (brs, 1H), 8.59-8.51 (m, 1H), 8.47 (d, J = 2.7 Hz, 1H), 8.24 (s, 1H), 8.06 (d, J = 6.2 Hz, 1H), 7.48 (d, J = 8.2 Hz, 1H), 7.45-7.40 (m, 1H), 7.27 (brs, 1H), 7.19 (brs, 1H), 7.15-6.96 (m, 2H), 6.44 (dd, J = 17.0, 10.2 Hz, 1H), 6.29 (dd, J = 17.0, 1.9 Hz, 1H), 5.80 (dd, J = 10.1, 1.9 Hz, 1H), 3.95 (brs, 3H), 2.76 (brs, 1H), 2.30 (brs, 1H), 1.99 (brs, 2H), 1.80 (brs, 1H), 1.40-1.04 (m, 4H). | 502.01 | 502.30 |
| 259 | Starting from endo-benzyl 8-azabicyclo[3.2.1]oct-3-ylcarbamate using the same synthetic sequence as Example 33. | ¹H NMR (500 MHz, DMSO) δ 11.82 (s, 1H), 8.60 (s, 1H), 8.45 (s, 1H), 8.22 (d, J = 8.9 Hz, 1H), 7.48 (d, J = 7.9 Hz, 1H), 7.27-7.03 (m, 3H), 6.38-6.12 (m, 2H), 6.11-5.99 (m, 1H), 5.59-5.48 (m, 1H), 4.17-4.02 (m, 1H), 3.95-3.72 (m, 2H), 3.74-3.55 (m, 1H), 2.98-2.75 (m, 2H), 2.34-1.59 (m, 8H), 1.60-1.20 (m, 4H), 1.17-0.79 (m, 3H). | 505.05 | 505.36 |
| 260 | Starting from (S)-benzyl 3-methylpiperazine-1-carboxylate using the same synthetic sequence as Example 33. | ¹H NMR (500 MHz, DMSO) δ 11.83 (brs, 1H), 8.72-8.38 (m, 2H), 8.26 (brs, 1H), 7.49 (d, J = 7.8 Hz, 1H), 7.25-7.11 (m, 3H), 6.78 (brs, 1H), 6.12 (brs, 1H), 5.75-5.60 (m, 1H), 3.30-3.20 (m, 4H), 3.05-2.70 (m, 4H), 2.01-1.63 (m, 5H), 1.58-0.75 (m, 7H). | 479.02 | 479.31 |
| 261 | Starting from benzyl 6-formylpyridin-3- | ¹H NMR (500 MHz, DMSO) δ 11.83 (brs, 1H), 10.26 (s, 1H), 8.74 (brs, 1H), 8.55 | 559.1 | 559.37 |

| Cmpd # | How Synthesized | ¹H NMR | Calcd. Mass | Found Mass (MH⁺) |
|---|---|---|---|---|
| | ylcarbamate using the same synthetic sequence as Example 37 and Example 8. | (brs, 1H), 8.47 (d, J = 2.8 Hz, 1H), 8.24 (s, 1H), 8.19 (s, 1H), 8.04 (d, J = 6.7 Hz, 1H), 7.48 (d, J = 8.2 Hz, 1H), 7.40 (d, J = 9.0 Hz, 1H), 7.26 (s, 1H), 7.18 (t, J = 7.4 Hz, 1H), 7.05 (brs, 1H), 6.76 (dt, J = 15.4, 5.9 Hz, 1H), 6.27 (dt, J = 15.4, 1.6 Hz, 1H), 3.93 (brs, 3H), 3.07 (dd, J = 5.9, 1.5 Hz, 2H), 2.73 (brs, 1H), 2.35 (brs, 1H), 2.18 (s, 6H), 2.01 (brs, 2H), 1.79 (brs, 1H), 1.40-1.20 (m, 3H), 1.15-1.05 (m, 1H). | | |
| 267 | Starting from (R)-benzyl-3-(5-chloro-4-(1-(phenylsulfonyl)-1H-indol-3-yl)pyrimidin-2-ylamino)-1-methylcyclohexyl-carbamate (4, Prov B) and 5-aminopicolinic acid using the same synthetic sequence as Example 8. | ¹H NMR (500 MHz, DMSO) δ 11.84 (s, 1H), 10.54 (s, 1H), 8.82 (d, J = 2.3 Hz, 1H), 8.64 (s, 1H), 8.47 (s, 1H), 8.25 (dd, J = 8.6, 2.4 Hz, 2H), 7.98 (d, J = 8.9 Hz, 2H), 7.50 (d, J = 7.7 Hz, 1H), 7.25-7.07 (m, 3H), 6.81 (dt, J = 15.5, 5.8 Hz, 1H), 6.29 (d, J = 15.4 Hz, 1H), 4.23-4.08 (m, 1H), 3.08 (dd, J = 5.7, 1.1 Hz, 2H), 2.46-2.37 (m, 1H), 2.18 (s, 6H), 2.04-1.95 (m, 2H), 1.87-1.70 (m, 3H), 1.63-1.46 (m, 4H), 1.39-1.26 (m, 1H). | 587.12 | 587.39 |
| 268 | Starting from (R)-benzyl-3-(5-chloro-4-(1-(phenylsulfonyl)-1H-indol-3-yl)pyrimidin-2-ylamino)-1-methylcyclohexyl-carbamate (4, Prov B) and tert-butyl 4-formylpiperidine-1-carboxylate using the same synthetic sequence as Example 37 without protection of the central amine. | ¹H NMR (500 MHz, DMSO) δ 11.84 (s, 1H), 8.57 (s, 1H), 8.45 (s, 1H), 8.24 (s, 2H), 7.49 (d, J = 7.9 Hz, 1H), 7.37 (s, 1H), 7.21 (dd, J = 11.1, 4.1 Hz, 1H), 7.12 (t, J = 7.0 Hz, 1H), 6.83-6.55 (m, 1H), 6.05 (d, J = 16.9 Hz, 1H), 5.62 (d, J = 10.2 Hz, 1H), 4.44-4.26 (m, 1H), 4.18-4.13 (m, 1H), 4.07-3.91 (m, 1H), 3.11-2.92 (m, 3H), 2.61-2.55 (m, 1H), 1.91-1.68 (m, 5H), 1.66-1.58 (m, 1H), 1.55-1.25 (m, 5H), 1.25-0.93 (m, 5H). | 507.07 | 507.39 |

Example 44. Synthesis of 1-[3-[[[4-[[5-chloro-4-(1H-indol-3-yl)pyrimidin-2-yl]amino]cyclohexyl]amino]methyl]-1-piperidyl]prop-2-en-1-one (Compound 190)

tert-butyl N-[4-[[4-[1-(benzenesulfonyl)indol-3-yl]-5-chloro-pyrimidin-2-yl]amino]cyclohexyl]carboxylate

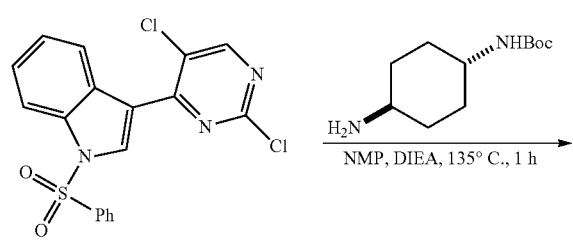

A solution of trans tert-butyl N-(4-aminocyclohexyl)carbamate (1 g, 4.67 mmol), 1-(benzenesulfonyl)-3-(2,5-dichloropyrimidin-4-yl)indole (2.27 g, 5.60 mmol) and DIEA (3.02 g, 23.35 mmol) in NMP (5 mL) was degassed with N₂, heated to 135° C., and stirred for 1 h by microwave. The mixture was poured into water, extracted with EA, and the organic phase was concentrated under vacuum. The residue was purified by silica gel to afford tert-butyl N-[4-[[4-[1-(benzenesulfonyl)indol-3-yl]-5-chloro-pyrimidin-2-yl]amino]cyclohexyl]carbamate (1.30 g, 47.8%) as a yellow solid.

N4-[4-[1-(benzenesulfonyl)indol-3-yl]-5-chloro-pyrimidin-2-yl]cyclohexane-1,4-diamine

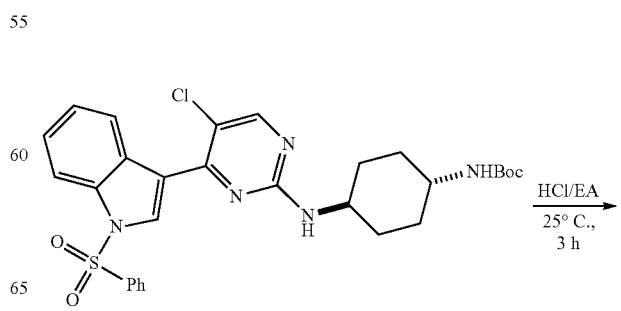

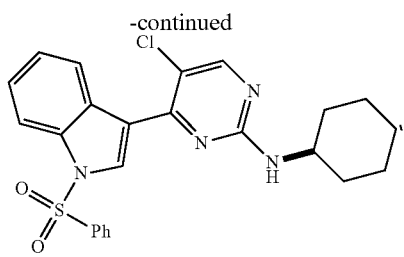

A solution of tert-butyl-N-[4-[[4-[1-(benzenesulfonyl)indol-3-yl]-5-chloro-pyrimidin-2-yl]amino]cyclohexyl]carbamate (2.5 g, 4.29 mmol) in HCl/EA (50 mL) was stirred at 25° C. for 3 h. The mixture was concentrated to give N4-[4-[1-(benzenesulfonyl)indol-3-yl]-5-chloro-pyrimidin-2-yl]cyclohexane-1,4-diamine (1.8 g, 87%) as a yellow solid.

tert-butyl 3-[[[4-[[4-[1-(benzenesulfonyl)indol-3-yl]-5-chloro-pyrimidin-2-yl]amino]cyclohexyl]amino]methyl]piperidine-1-carboxylate

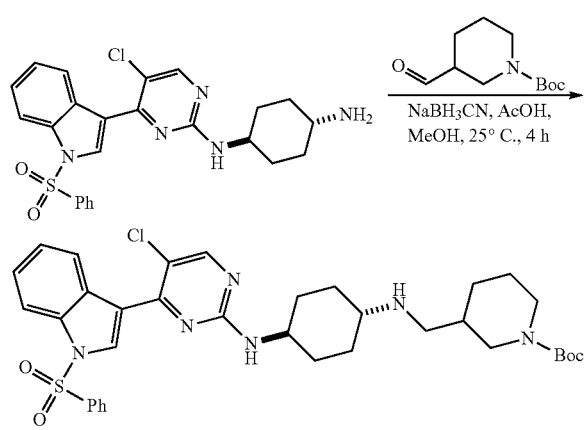

To a solution of N4-[4-[1-(benzenesulfonyl)indol-3-yl]-5-chloro-pyrimidin-2-yl] cyclohexane-1,4-diamine (500 mg, 1.04 mmol) and tert-butyl-3-formylpiperidine-1-carboxylate (266 mg, 1.25 mmol) in MeOH (15 mL) was added AcOH (0.5 mL) at 25° C. and the mixture was stirred for 1 h. Then NaBH$_3$CN (98 mg, 1.56 mmol) was added and the mixture was stirred for another 3 h. The mixture was concentrated under vacuum and the residue was purified by column to afford tert-butyl 3-[[[4-[[4-[1-(benzenesulfonyl)indol-3-yl]-5-chloro-pyrimidin-2-yl]amino]cyclohexyl]amino]methyl]piperidine-1-carboxylate (400 mg, 56.6%) as a yellow solid.

tert-butyl3-[[[4-[[5-chloro-4-(1H-indol-3-yl)pyrimidin-2-yl]amino]cyclohexyl]amino]methyl]piperidine-1-carboxylate

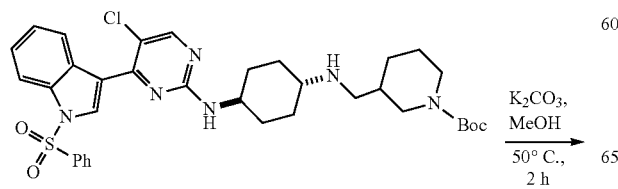

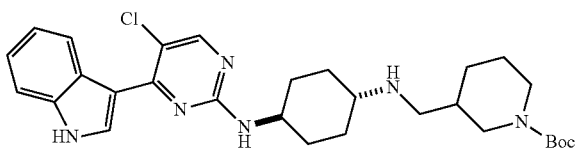

To a solution of tert-butyl 3-[[[4-[[4-[1-(benzenesulfonyl)indol-3-yl]-5-chloro-pyrimidin-2-yl]amino]cyclohexyl]amino]methyl]piperidine-1-carboxylate (700 mg, 1.03 mmol) in MeOH (20 mL) was added K$_2$CO$_3$ (285 mg, 2.06 mmol) and the mixture was heated to 50° C. and stirred for 2 h. The mixture was poured into water, extracted with EA, and the organic phase was concentrated under vacuum to afford tert-butyl3-[[[4-[[5-chloro-4-(1H-indol-3-yl)pyrimidin-2-yl]amino]cyclohexyl]amino]methyl]piperidine-1-carboxylate (450 mg, 81%) as a yellow solid.

N4-[5-chloro-4-(1H-indol-3-yl)pyrimidin-2-yl]-N1-(3-piperidylmethyl)cyclohexane-1,4-diamine hydrochloride (Compound 1041 HCl salt)

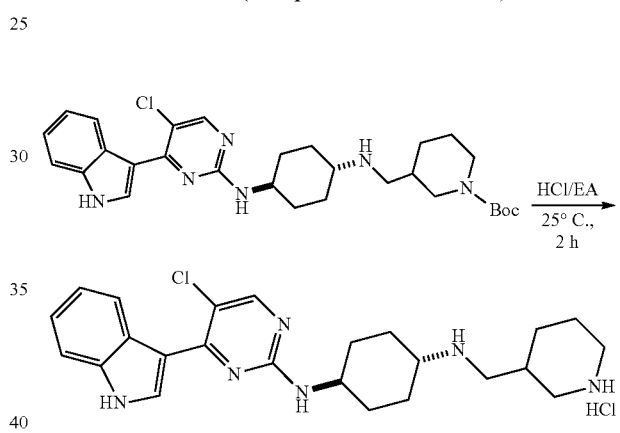

A solution of tert-butyl 3-[[[4-[[5-chloro-4-(1H-indol-3-yl)pyrimidin-2-yl]amino]cyclohexyl]amino]methyl]piperidine-1-carboxylate (250 mg, 0.46 mmol) in HCl/EA (50 mL) was stirred at 25° C. for 2 h. The mixture was concentrated under vacuum to afford N4-[5-chloro-4-(1H-indol-3-yl)pyrimidin-2-yl]-N1-(3-piperidylmethyl)cyclohexane-1,4-diamine; hydrochloride (200 mg, 90.7%) as a yellow solid.

1-[3-[[[4-[[5-chloro-4-(1H-indol-3-yl)pyrimidin-2-yl]amino]cyclohexyl]amino]methyl]-1-piperidyl] prop-2-en-1-one (Compound 190) and N-[4-[[5-chloro-4-(1H-indol-3-yl)pyrimidin-2-yl]amino] cyclohexyl]-N-[(1-prop-2-enoyl-3-piperidyl)methyl] prop-2-enamide (Compound 191)

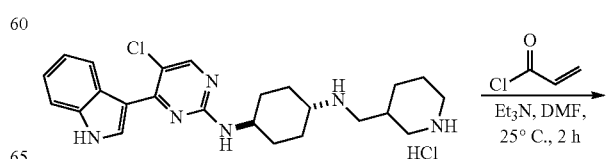

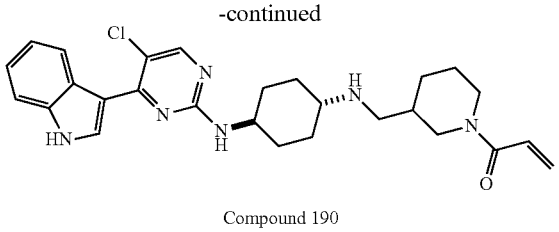

Compound 190

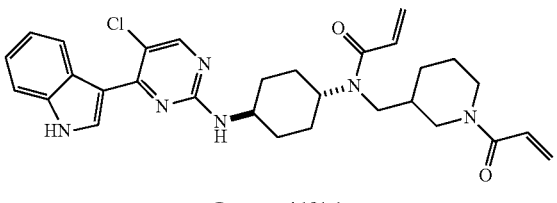

Compound 191-1

A solution of N4-[5-chloro-4-(1H-indol-3-yl)pyrimidin-2-yl]-N1-(3-piperidylmethyl) cyclohexane-1,4-diamine hydrochloride (200 mg, 0.42 mmol) and Et₃N (128 mg, 1.26 mmol) in DMF (10 mL) was added a solution of prop-2-enoyl chloride (31 mg, 0.34 mmol) in DCM (2 mL) at 25° C. and the mixture was stirred for 2 h. The mixture was concentrated under vacuum and residue was purified by pre-HPLC to afford 1-[3-[[[4-[[5-chloro-4-(1H-indol-3-yl)pyrimidin-2-yl]amino]cyclohexyl]amino]methyl]-1-piperidyl]prop-2-en-1-one (Compound 190; 20 mg, 9%) and N-[4-[[5-chloro-4-(1H-indol-3-yl)pyrimidin-2-yl]amino]cyclohexyl]-N-[(1-prop-2-enoyl-3-piperidyl)methyl]prop-2-enamide (Compound 191-1; 25 mg, 10%) as a side product. Both of them were yellow solids.

Compound 190: LCMS: M+H⁺: 493.2@2.190 min (10-80% ACN in H₂O, 4.5 min)

¹H NMR: (MeOD, 400 MHz) δ 1.41-2.06 (μ, 10H), 2.30 (βρ. σ., 3H), 3.01 (8, J=6.78 Hz, 3H), 3.14-3.22 (m, 1H), 3.35 (d, J=12.55 Hz, 1H), 3.82-4.40 (m, 3H), 5.74 (d, J=10.54 Hz, 1H), 6.20 (d, J=16.56 Hz, 1H), 6.67-6.96 (m, 1H), 7.27-7.54 (m, 3H), 8.18 (br. s., 1H), 8.53 (br. s., 1H), 8.94 (br.s., 1H), 12.19 (br. s., 1H).

Compound 191-1: LCMS: M+H⁺: 547.2@2.536 min (10-80% ACN in H₂O, 4.5 min).

¹H NMR: ET285-136-1 (MeOD, 400 MHz): δ 1.29-1.79 (μ, 4H), 1.94 (δ, J=13.55 Hz, 6H), 2.29 (br. s., 3H), 2.60-3.19 (m, 2H), 3.42 (br. s., 2H), 3.76-4.23 (m, 3H), 4.52 (br. s., 1H), 5.78 (br. s., 2H), 6.08-6.35 (m, 2H), 6.70-7.04 (m, 2H), 7.23-7.45 (m, 2H), 7.57 (br. s., 1H), 8.20 (d, J=15.56 Hz, 1H), 8.59 (br.s., 1H), 8.99 (br. s., 1H), 12.25 (br. s., 1H).

Following essentially the procedure described for Compound 190, the following compounds were prepared:

| Compound No. | ¹H NMR | Calcd. Mass | Found Mass (M + H⁺) |
|---|---|---|---|
| 184 | (MeOD, 400 MHz) δ1.17-1.35 (μ, 2 H), 1.83-2.32 (μ, 12 H), 2.76 (τ, J = 12.42 Hz, 1 H), 3.02 (d, J = 7.03 Hz, 2 H), 3.10-3.24 (m, 1H), 4.17 (d, J = 15.31 Hz, 1 H), 4.42-4.68 (m, 2 H), 5.73 (dd, J = 10.67, 1.88 Hz, 1 H), 6.17 (dd, J = 16.69, 1.88 Hz, 1 H), 6.76 (dd, J = 16.81, 10.79 Hz, 1 H) 7.32(dt, J = 13.93, 6.84 Hz, 2 H), 7.55 (d, J = 8.28 Hz, 1 H), 8.30 (s, 1 H), 8.56 (br. s., 1 H), 9.00 (br. s., 1 H), 12.23 (br. s., 1 H). | 493.2 | 493.2 |
| 191-2† | (MeOD, 400 MHz) δ 1.24 (d, J = 11.04 Hz, 2 H), 1.67-2.35 (m, 11 H), 2.70 (br. s., 1 H), 3.10 (br. s., 1 H), 3.38 (br. s., 2 H), 3.88-4.20(m, 2 H), 4.54 (br. s., 2 H), 5.72 (br. s., 2 H), 6.11-6.27 (m, 2 H), 6.68-6.93 (m, 2 H), 7.27-7.39 (m, 2 H), 7.55 (d, J = 8.28 Hz, 1 H), 8.31 (s, 1 H), 8.59 (br. s., 1H), 9.00 (br. s., 1 H), 12.22 (br. s., 1 H) | 547.2 | 547.2 |
| 195† | (MeOD, 400 MHz) δ 1.33-1.63 (μ, 2 H), 1.76-2.24 (μ, 11 H), 2.91-3.18 (μ, 3 H), 3.42 (βρ. σ, 2 H), 3.76-4.52 (μ, 3 H), 5.76 (δ, J = 10.04 Hz, 1 H), 6.22 (d, J = 16.31 Hz, 1 H), 6.72-6.96 (m, 1 H), 7.26-7.40 (m, 2 H), 7.54 (d, J = 7.53 Hz, 1 H), 8.27 (s, 1 H), 8.54 (br. s., 1 H), 8.98 (br. s., 1 H), 12.23 (br. s., 1H). | 493.2 | 493.2 |
| 163 | (MeOD, 400 MHz) δ 1.15-1.31 (m, 2 H), 1.51-1.65 (m, 2 H), 1.65-1.79 (m, 2 H), 1.90(br. s., 2 H), 1.97-2.20 (m, 2 H), 2.31 (d, J = 10.29 Hz, 4 H), 2.74 (t, J = 12.30 Hz, 1 H), 2.99 (d, J = 6.53 Hz, 2 H), 3.09-3.24 (m, 2 H), 4.15 (d, J = 13.55 Hz, 1 H), 4.58 (d, J = 14.05 Hz, 1 H), 5.71 (d, J = 10.79 Hz, 1 H), 6.15 (d, J = 16.56 Hz, 1 H), 6.75 (dd, J = 16.81, 10.79 Hz, 1 H), 7.25-7.44 (m, 2 H), 7.53 (d, J = 8.03 Hz, 1 H), 8.20 (s, 1 H), 8.57 (br. s., 1 H), 8.96 (br. s., 1 H), 12.20 (br. s., 1 H). | 493.2 | 493.2 |

†Compound 191-2 was produced as a by-product in the synthesis of Compound 195.

Example 45. Synthesis of (E)-1-[3-[[[4-[[5-chloro-4-(1H-indol-3-yl)pyrimidin-2-yl]amino]cyclohexyl]amino]methyl]-1-piperidyl]-4-(dimethylamino)but-2-en-1-one (Compound 193)

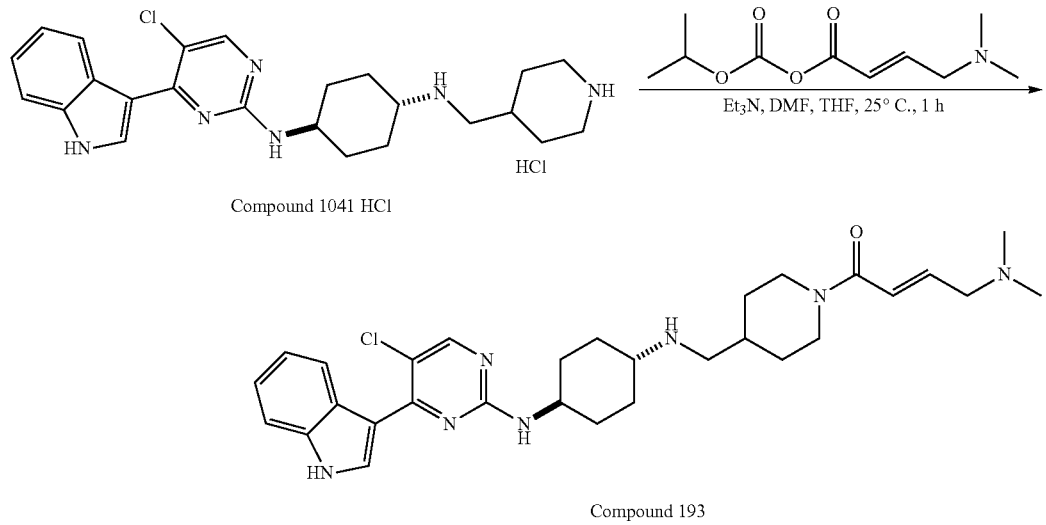

Compound 1041 HCl

Compound 193

To a solution of N4-[5-chloro-4-(1H-indol-3-yl)pyrimidin-2-yl]-N1-(3-piperidylmethyl)cyclohexane-1,4-diamine; hydrochloride (Compound 1041 HCl salt; 200 mg, 0.42 mmol) and Et₃N (106 mg, 1.05 mmol) in DMF (10 mL) was added isopropoxycarbonyl (E)-4-(dimethylamino)but-2-enoate (120 mg, 0.56 mmol) in THF (5 mL) at 25° C. and the mixture was stirred for 1 h. The mixture was concentrated under reduced pressure and purified by preparative HPLC to afford (E)-1-[3-[[[4-[[5-chloro-4-(1H-indol-3-yl)pyrimidin-2-yl]amino]cyclohexyl]amino]methyl]-1-piperidyl]-4-(dimethylamino)but-2-en-1-one, Compound 193, (68 mg, 27.5%) as a yellow solid.

LCMS: M+H⁺: 550.4@1.843 min (10-80 ACN in H₂O, 4.5 min). ¹H NMR: ET285-164-1 (MeOD, 400 MHz): δ 1.40-1.65 (m, 4H), 1.82 (d, J=10.58 Hz, 2H), 2.01-2.14 (m, 2H), 2.22-2.43 (m, 4H), 2.79 (t, J=11.25 Hz, 1H), 2.88-3.00 (m, 6H), 3.01-3.17 (m, 3H), 3.25 (t, J=10.58 Hz, 1H), 3.33-3.46 (m, 1H), 3.87-4.07 (m, 3H), 4.27-4.56 (m, 2H), 6.65-6.80 (m, 1H), 7.04 (d, J=14.99 Hz, 1H), 7.28-7.43 (m, 2H), 7.54 (d, J=7.94 Hz, 1H), 8.09 (s, 1H), 8.40 (br. s., 1H), 8.88 (br. s., 1H), 12.18 (br. s., 1H).

Following essentially the procedure described for Compound 193, the following compounds were prepared:

| Compound No. | ¹H NMR | Calcd. Mass | Found Mass (MH⁺) |
|---|---|---|---|
| 194 | (MeOD, 400 MHz): δ 1.19-1.72 (m, 2 H), 1.77-2.31 (m, 11 H), 2.69-2.86 (m, 1 H), 2.88-2.96 (m, 6 H), 2.99-3.20 (m, 3 H), 3.34-3.56 (m, 2 H), 3.83-4.20 (m, 3 H), 4.31-4.64 (m, 2 H), 6.63-6.83 (m, 1 H), 7.02 (d, J = 15.31 Hz, 1 H), 7.25-7.36 (m, 2 H), 7.55 (d, J = 7.78 Hz, 1 H), 8.25 (s, 1H), 8.49 (br. s., 1 H), 8.97 (br. s., 1 H), 12.23 (br. s., 1 H). | 550.3 | 550.3 |
| 196 | (MeOD, 400 MHz): δ 1.20-1.46 (m, 2 H), 1.61 (d, J = 9.54 Hz, 2 H), 1.81 (d, J = 11.29 Hz, 2 H), 1.98 (br. s., 2 H), 2.17 (br. s., 1 H), 2.34(br. s., 4 H), 2.82 (t, J = 12.67 Hz, 1 H), 2.92 (s, 6 H), 3.04 (d, J = 6.53 Hz, 2 H), 3.18-3.29 (m, 2 H), 3.98 (d, J = 6.78 Hz, 3 H), 4.21 (d, J = 13.05 Hz, 1 H), 4.61 (d, J = 12.30 Hz, 1 H), 6.69 (dt, J = 14.93, 7.34 Hz, 1 H), 7.04 (d, J = 15.06 Hz, 1 H), 7.31-7.49 (m, 2 H), 7.56 (d, J = 7.78 Hz, 1 H), 8.20 (s, 1 H), 8.55 (br. s., 1 H), 8.97 (br. s., 1 H), 12.23 (br. s., 1 H) | 550.3 | 550.3 |
| 197 | (MeOD, 400 MHz): δ 1.20-1.42 (m, 2 H), 1.87-2.31 (m, 11 H), 2.74-2.87 (m, 1 H), 2.91 (s, 6 H), 3.05 (d, J = 6.27 Hz, 2 H), 3.17-3.27(m, 1 H), 3.34-3.41 (m, 1 H), 3.96 (d, J = 7.28 Hz, 2 H), 4.19 (d, J = 12.80 Hz, 1 H), 4.43-4.66 (m, 2 H), 6.61-6.73 (m, 1 H), 7.02 (d, J = 15.06 Hz, 1 H), 7.28-7.39 (m, 2 H), 7.56 (d, J = 8.03 Hz, 1 H), 8.30 (s, 1 H), 8.56 (br. s., 1 H), 9.01 (br. s., 1 H), 12.24 (br. s., 1 H). | 550.3 | 550.3 |

Example 46. Synthesis of benzyl tert-butyl (1R,3S)-cyclohexane-1,3-diyldicarbamate (Compound 202-1)

(E)-4-bromobut-2-enoic acid

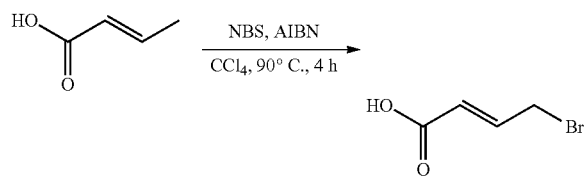

A mixture of (E)-but-2-enoic acid (10.00 g, 116.16 mmol), N-bromosuccinimide (NBS, 1.02 g, 118.48 mmol) and 2,2'-azobis(2-methylpropionitrile), (AIBN, 381.49 mg, 2.32 mmol) in $CCl_4$ (120 mL) was stirred at 90° C. for 4 h. The mixture was filtered and concentrated. The residue was re-crystallized with n-hexane to afford (E)-4-bromobut-2-enoic acid (19.17 g, 42.2%).

(E)-4-morpholinobut-2-enoic acid

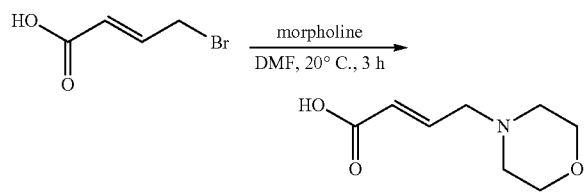

To a solution of (E)-4-bromobut-2-enoic acid (500 mg, 3.03 mmol) in DMF (8 mL) was added morpholine (792 mg, 9.09 mmol) at 20° C., and the mixture was stirred for 3 h. The mixture was evaporated, and purified by preparative HPLC to afford (E)-4-morpholinobut-2-enoic acid (260 mg, 50.1%).

N-((1S,3R)-3-(5-chloro-4-(1H-indol-3-yl)pyrimidin-2-yl)amino)cyclohexyl)-1-((E)-4-morpholinobut-2-enoyl)piperidine-4-carboxamide

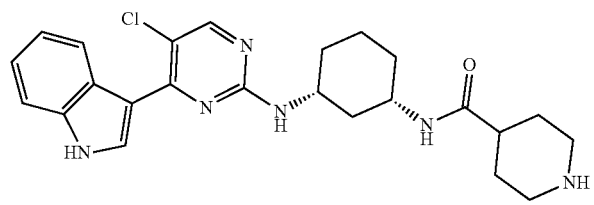

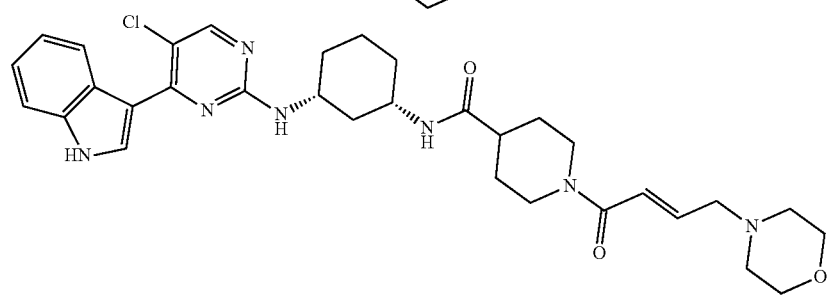

Compound 202-1

To a solution of (E)-4-morpholinobut-2-enoic acid (27 mg, 0.16 mmol) and TEA (31 mg, 0.31 mmol) in DCM (2 mL) was added isopropyl carbonochloridate (20 mg, 0.16 mmol) at 20° C. and the mixture was stirred for 3 h. The mixture was added into a solution of N-((1S,3R)-3-((5-chloro-4-(1H-indol-3-yl)pyrimidin-2-yl)amino)cyclohexyl) piperidine-4-carboxamide (Compound 1036; 70 mg, 0.15 mmol) and TEA (31 mg, 0.31 mmol) in DCM (3 mL) at 20° C. and stirred for 6 h. The final mixture was concentrated, and the residue was purified by preparative HPLC to afford N-((1S,3R)-3-((5-chloro-4-(1H-indol-3-yl)pyrimidin-2-yl) amino)cyclohexyl)-1-((E)-4-morpholinobut-2-enoyl)piperidine-4-carboxamide, Compound 202-1, (30 mg, 32%). LCMS: (M+H$^+$): 606.3@2.14 min (10-80% ACN in $H_2O$, 4.5 min). $^1$H NMR: (CDCl$_3$, 400 MHz): δ 8.88 (s, 1H), 8.57-8.56 (m, 1H), 8.41 (s, 1H), 8.24 (s, 1H), 7.46-7.44 (m, 1H), 7.31-7.30 (m, 2H), 6.85-6.81 (m, 1H), 6.44 (d, J=15.6 Hz, 1H), 5.39 (d, J=8.0 Hz, 1H), 5.04 (d, J=8.0 Hz, 1H), 4.61 (br. s., 1H), 4.01 (br.s., 3H), 3.75-3.72 (m, 4H), 3.15-3.14 (m, 3H), 2.75 (br.s., 1H), 2.48 (s, 5H), 2.30-2.21 (m, 2H), 2.08-2.05 (m, 1H), 1.87 (br.s., 3H), 1.58-1.53 (m, 2H), 1.28-1.09 (m, 4H).

N-((1R,3S)-3-((5-chloro-4-(1H-indol-3-yl)pyrimidin-2-yl)amino)cyclohexyl)-1-((E)-4-morpholinobut-2-enoyl)piperidine-4-carboxamide (Compound 202-2)

A similar process was used to produce N-((1R,3S)-3-((5-chloro-4-(1H-indol-3-yl)pyrimidin-2-yl)amino)cyclohexyl)-1-((E)-4-morpholinobut-2-enoyl)piperidine-4-carboxamide, Compound 202-2, utilizing N-((1R,3S)-3-((5-chloro-4-(1H-indol-3-yl)pyrimidin-2-yl)amino)cyclohexyl) piperidine-4-carboxamide (Compound 1044). Compound 1044 was prepared using an analogous process for producing Compound 1036 (see Examples 8 and 18) starting with the appropriate isomers. LCMS: (M+H$^+$): 606.3 @ 2.15 min (10-80% ACN in $H_2O$, 4.5 min). $^1$H NMR: (CDCl$_3$, 400 MHz): δ 8.99 (s, 1H), 8.57 (s, 1H), 8.38 (s, 1H), 8.22 (s, 1H), 7.44 (br.s., 1H), 7.29 (br.s., 1H), 6.85-6.79 (m, 1H), 6.43 (d, J=14.8 Hz, 1H), 5.39 (d, J=7.6 Hz, 1H), 5.08 (d, J=7.6 Hz, 1H), 4.61 (br.s., 1H), 4.01 (br.s., 3H), 3.73-3.72 (m, 4H), 3.13 (d, J=6 Hz, 2H), 2.46 (br.s., 5H), 2.82-2.19 (m, 3H), 2.05 (s, 3H), 1.84 (br.s., 4H), 1.66-1.53 (m, 6H), 1.26-1.06 (m, 19H), 0.89-0.86 (m, 9H).

Example 47. Synthesis of (S)-1-(4-(3-((5-chloro-4-(1H-indol-3-yl)pyrimidin-2-yl)amino)pyrrolidine-1-carbonyl)piperidin-1-yl)prop-2-en-1-one (Compound 210)

(S)-benzyl 4-(3-((tert-butoxycarbonyl)amino)pyrolidine-1-carbonyl)piperidine-1-carboxylate

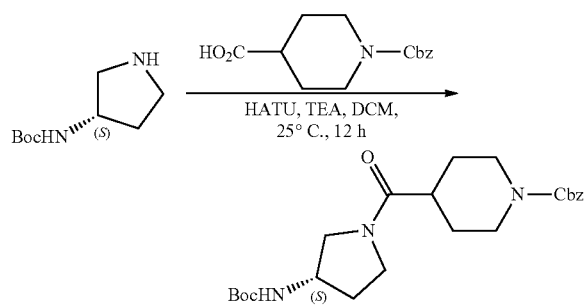

To a mixture of tert-butyl N-pyrrolidin-3-ylcarbamate (9 g, 48.32 mmol), TEA (9.8 g, 96.64 mmol), and 1-benzyloxycarbonylpiperidine-4-carboxylic acid (12.7 g, 48.32 mmol) in DCM (100 mL) was added HATU (27.6 g, 72.48 mmol) at 25° C. and was stirred for 12 h. The mixture was poured into water and extracted with EA. The combined organic phase was washed with saturated brine, dried with anhydrous Na$_2$SO$_4$, and concentrated. The residue was purified by silica gel (column height: 250 mm, diameter: 100 mm, 100-200 mesh silica gel, PE/EA=3/1, 1/1) to afford benzyl 4-[3-(tert-butoxycarbonylamino)pyrrolidine-1-carbonyl]piperidine-1-carboxylate (11 g, 52.8%) as a yellow oil.

(S)-benzyl 4-(3-aminopyrrolidine-1-carbonyl)piperidine-1-carboxylate

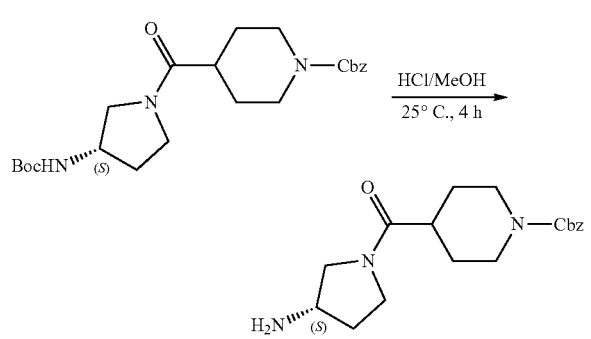

A mixture of benzyl 4-[3-(tert-butoxycarbonylamino)pyrrolidine-1-carbonyl]piperidine-1-carboxylate (7 g, 16.22 mmol) in HCl/MeOH (100 mL) was stirred at 25° C. for 4 h. The mixture was concentrated to afford benzyl 4-(3-aminopyrrolidine-1-carbonyl)piperidine-1-carboxylate (5.38 g, 93%) as a yellow oil.

(S)-benzyl 4-(3-((5-chloro-4-(1-(phenylsulfonyl)-1H-indol-3-yl)pyrimidin-2-yl)amino)pyrolidine-1-carbonyl)piperidine-1-carboxylate

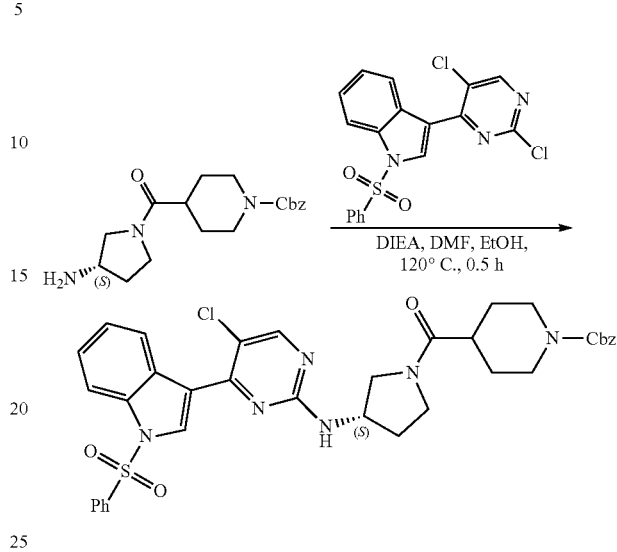

A mixture of 3-(2,5-dichloropyrimidin-4-yl)-1-(phenylsulfonyl)-1H-indole (1 g, 2.47 mmol), benzyl 4-(3-aminopyrrolidine-1-carbonyl)piperidine-1-carboxylate (0.8 g, 2.47 mmol) and DIPEA (0.96 g, 7.41 mmol) in DMF (4 mL) and EtOH (4 mL) was heated at 120° C. for 0.5 h by microwave. After cooling to 25° C., the mixture was diluted with EA, washed with water and brine, and the organic layer was dried over Na$_2$SO$_4$ and concentrated in vacuo. The residue was purified by silica gel chromatography (column height: 250 mm, diameter: 100 mm, 100-200 mesh silica gel, PE/EA=5/1, 0/1) to afford benzyl 4-[3-[[5-[1-(benzenesulfonyl)indol-3-1]-4-chloro-pyrimidin-2-yl]amino]pyrrolidine-1-carbonyl]piperidine-1-carboxylate (1 g, 57.9%) as a yellow oil.

(S)-benzyl 4-(3-((5-chloro-4-(1H-indol-3-yl)pyrimidin-2-yl)amino)pyrolidine-1-carbonyl)piperidine-1-carboxylate

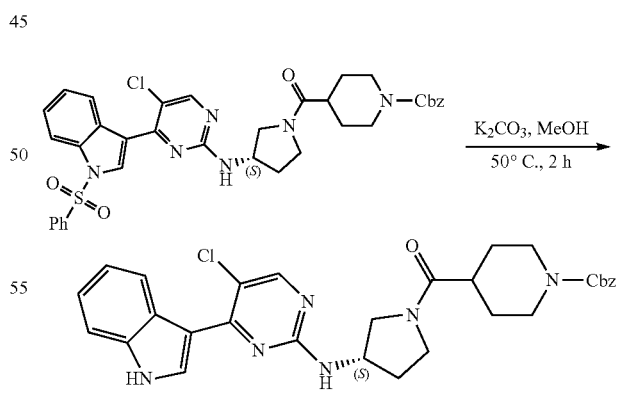

To a mixture of (S)-benzyl 4-(3-((5-chloro-4-(1-(phenylsulfonyl)-1H-indol-3-yl)pyrimidin-2-yl)amino)pyrrolidine-1-carbonyl)piperidine-1-carboxylate (0.75 g, 1.07 mmol) in MeOH (10 mL) was added K$_2$CO$_3$ (0.3 g, 2.14 mmol) under N$_2$ and the mixture was heated to 50° C. and stirred for 4 h. The mixture was poured into water and extracted with EA. The organic phase was washed with saturated brine, dried with anhydrous Na₂SO₄, and concentrated in vacuum to afford benzyl 4-[3-[[5-chloro-4-(1H-indol-3-yl)pyrimidin-2-yl]amino]pyrrolidine-1-carbonyl]piperidine-1-carboxylate (0.5 g, crude).

(S)-(3-((5-chloro-4-(1H-indol-3-yl)pyrimidin-2-yl)amino)pyrolidin-1-yl)(piperidin-4-yl)methanone (Compound 1042)

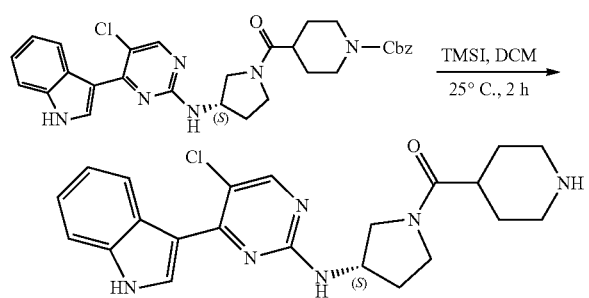

To a mixture of (S)-benzyl 4-(3-((5-chloro-4-(1H-indol-3-yl)pyrimidin-2-yl)amino) pyrrolidine-1-carbonyl)piperidine-1-carboxylate (0.4 g, 0.7 mmol) in DCM (10 mL) was added TMSI (0.72 g, 3.58 mmol) under N₂ at 25° C. and stirred for 2 h. The mixture was poured into water, extracted with DCM, the aqueous solution was concentrated under vacuum to afford [(3S)-3-[[5-chloro-4-(1H-indol-3-yl)pyrimidin-2-yl]amino]pyrolidin-1-yl]-(4-piperidyl)methanone (0.32 mg, crude) as a yellow solid. LCMS: (M+H⁺): 425.3@0.970 min (5-95% ACN in H₂O, 1.5 min)

(S)-1-(4-(3-((5-chloro-4-(1H-indol-3-yl)pyrimidin-2-yl)amino)pyrrolidine-1-carbonyl)piperidin-1-yl)prop-2-en-1-one (Compound 210)

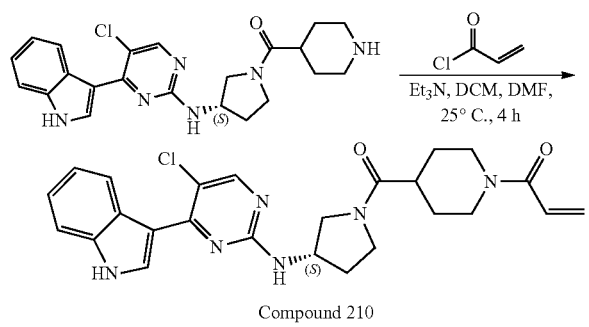

Compound 210

To a mixture of (S)-(3-((5-chloro-4-(1H-indol-3-yl)pyrimidin-2-yl)amino)pyrrolidin-1-yl)(piperidin-4-yl)methanone (200 mg, 0.47 mmol) and Et₃N (150 mg, 1.41 mmol) in DMF (10 mL) was added a solution of acryloyl chloride (42 mg, 0.47 mmol) in DCM (1 mL) at 25° C. and stirred for 4 h. The mixture was concentrated, and the residue was purified by preparative HPLC to afford (S)-1-(4-(3-((5-chloro-4-(1H-indol-3-yl)pyrimidin-2-yl)amino)pyrrolidine-1-carbonyl)piperidin-1-yl)prop-2-en-1-one (24 mg, 10.7%) as a yellow solid. LCMS: (M+H⁺): 479.2@2.368 min (10-80% ACN in H₂O, 4.5 min). ¹H NMR: (MeOD-d₆, 400 MHz): δ 1.64 (d, J=9.70 Hz, 2H), 1.77-1.96 (m, 2H), 2.15-2.36 (m, 1H), 2.38-2.60 (m, 1H), 2.70-2.98 (m, 2H), 3.14 (br. s., 1H), 3.66 (t, J=7.28 Hz, 1H), 3.71-3.84 (m, 1H), 3.85-3.93 (m, 1H), 3.98-4.30 (m, 2H), 4.52 (br. s., 1H), 4.60 (d, J=11.91 Hz, 1H), 5.68-5.78 (m, 1H), 6.18 (ddd, J=16.76, 8.82, 1.76 Hz, 1H), 6.76 (td, J=16.10, 11.03 Hz, 1H), 7.25-7.44 (m, 2H), 7.51-7.64 (m, 1H), 8.17-8.33 (m, 1H), 8.62 (br. s., 1H), 9.00 (d, J=7.06 Hz, 1H).

Example 48. Synthesis of (S,E)-1-(4-(3-((5-chloro-4-(1H-indol-3-yl)pyrimidin-2-yl)amino)pyrrolidine-1-carbonyl)piperidin-1-yl)-4-morpholinobut-2-en-1-one (Compound 211)

(Isopropyl carbonic) (E)-4-morpholinobut-2-enoic anhydride

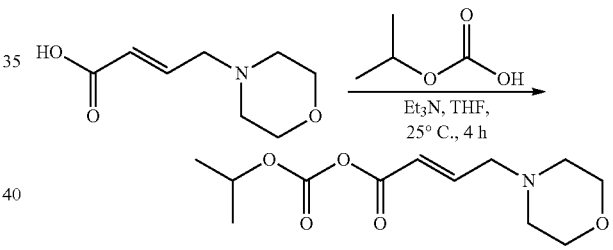

To a mixture of (E)-4-morpholinobut-2-enoic acid (100 mg, 0.58 mmol) and Et₃N (118 mg, 1.17 mmol) in THF (4 mL) was added isopropyl hydrogen carbonate (65 mg, 0.53 mmol) dropwise at 25° C. and stirred for 4 h. The mixture was concentrated to afford (E)-4-morpholinobut-2-enoic acid (100 mg, crude).

(S,E)-1-(4-(3-((5-chloro-4-(1H-indol-3-yl)pyrimidin-2-yl)amino)pyrolidine-1-carbonyl)piperidin-1-yl)-4-morpholinobut-2-en-1-one (Compound 211)

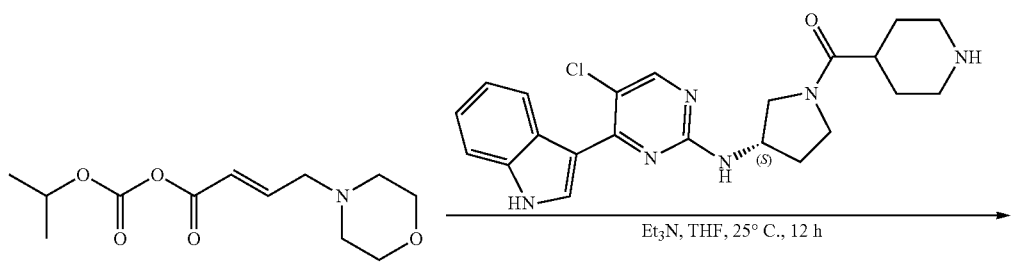

-continued

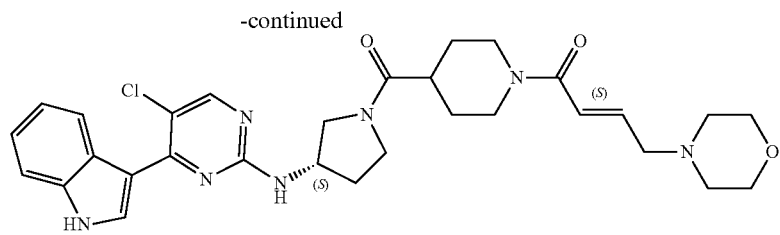

To a mixture of (S)-(3-((5-chloro-4-(1H-indol-3-yl)pyrimidin-2-yl)amino)pyrrolidin-1-yl) (piperidin-4-yl)methanone (Compound 1042; 100 mg, 0.24 mmol) and (isopropyl carbonic) (E)-4-morpholinobut-2-enoic anhydride (60 mg, 0.24 mmol) in THF (15 mL) was added Et$_3$N (72 mg, 0.71 mmol) at 25° C. and stirred for 12 h. The mixture was concentrated under vacuum and purified by preparative-HPLC to afford (S,E)-1-(4-(3-((5-chloro-4-(1H-indol-3-yl)pyrimidin-2-yl)amino)pyrrolidine-1-carbonyl)piperidin-1-yl)-4-morpholinobut-2-en-1-one, Compound 211, (15 mg, 11%) as yellow solid. LCMS: (M+H$^+$): 578.2@2.126 min (10-80% ACN in H$_2$O, 4.5 min). $^1$H NMR: (MeOD-d$_6$, 400 MHz): δ 1.66 (d, J=11.47 Hz, 2H), 1.86-1.93 (m, 2H), 2.22-2.33 (m, 1H), 2.52 (m, 1H), 2.89-2.96 (m, 3H), 3.18 (t, J=11.47 Hz, 2H), 3.46 (d, J=12.35 Hz, 2H), 3.66 (t, J=7.06 Hz, 1H), 3.65-3.79 (m, 3H), 3.82 (br. s., 2H), 3.90 (d, J=6.17 Hz, 2H), 4.07 (d, J=13.23 Hz, 2H), 4.13-4.25 (m, 1H), 4.57 (br. s., 1H), 4.60 (d, J=12.79 Hz, 1H), 6.68 (dq, J=15.05, 7.48 Hz, 1H), 7.01 (t, J=14.33 Hz, 1H), 7.33-7.37 (m, 2H), 7.55-7.58 (m, 1H), 8.18-8.27 (m, 1H), 8.61 (br. s., 1H), 8.99-9.01 (m, 1H).

Example 49. Synthesis of 1-[4-[[[(1S,3R)-3-[[5-chloro-4-(1H-indol-3-yl)pyrimidin-2-yl]amino]cyclohexyl]methyl]amino]-1-piperidyl]prop-2-en-1-one (Compound 127)

Benzyl4-[[(1S,3R)-3-(tert-butoxycarbonylamino)cyclohexanecarbonyl]amino]piperidine-1-carboxylate

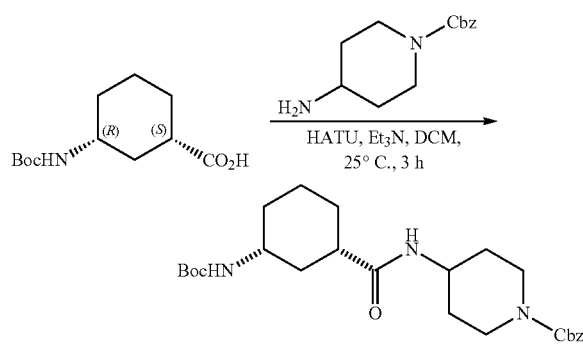

To a mixture of (1S,3R)-3-(tert-butoxycarbonylamino)cyclohexanecarboxylic acid (5 g, 20.55 mmol) and benzyl 4-aminopiperidine-1-carboxylate (5.3 g, 22.61 mmol) in DCM (200 mL) was added TEA (4.16 g, 41.10 mmol) and HATU (11.72 g, 30.83 mmol) under N$_2$ at 25° C. and stirred for 3 h. The mixture was diluted with DCM, washed with water and brine, and the organic phase wad concentrated under vacuum to afford benzyl4-[[[(1S,3R)-3-(tert-butoxycarbonylamino)cyclohexanecarbonyl]amino]piperidine-1-carboxylate (8 g, 84.6%) as a yellow solid.

Benzyl-4-[[[(1S,3R)-3-(tert-butoxycarbonylamino)cyclohexyl]methyl]amino]piperidine-1-carboxylate

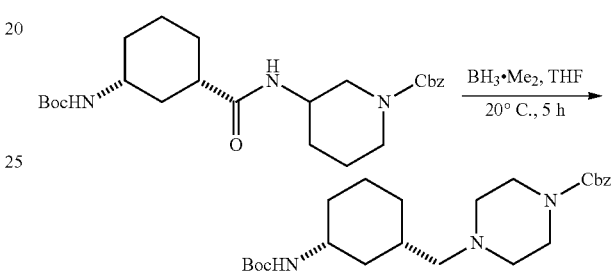

To a solution of benzyl4-[[(1S,3R)-3-(tert-butoxycarbonylamino)cyclohexanecarbonyl] amino]piperidine-1-carboxylate (8 g, 17.41 mmol) in THF (30 mL) was dropped BH$_3$·Me$_2$S (7.8 mL, 87.04 mmol) at 25° C. under N$_2$ and stirred for 12 h. The mixture was quenched with NaOH solution (1 M, 50 mL), extracted with EA, and the organic layer was dried over Na$_2$SO$_4$ and concentrated. The residue was purified by column to afford benzyl 4-[[[(1S,3R)-3-(tert-butoxycarbonylamino)cyclohexyl]methyl]amino]piperidine-1-carboxylate (5 g, 64.4%) as a white solid.

Benzyl-4-[[[(1S,3R)-3-aminocyclohexyl]methyl]amino]piperidine-1-carboxylate; hydrochloride

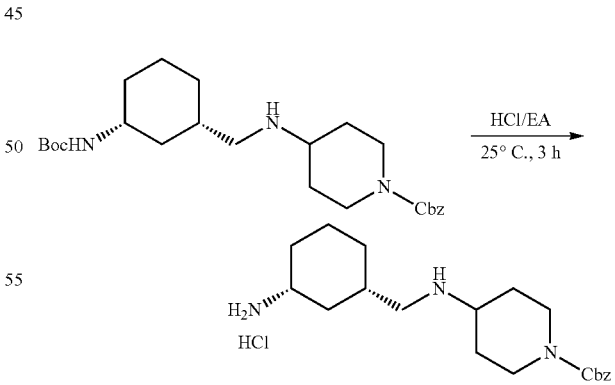

A solution of benzyl 4-[[[(1S,3R)-3-(tert-butoxycarbonylamino)cyclohexyl] methyl]amino]piperidine-1-carboxylate (5 g, 11.22 mmol) in HCl/EA (300 mL) was stirred for at 25° C. for 3 h. The mixture was concentrated under vacuum to afford benzyl-4-[[[(1S,3R)-3-aminocyclohexyl]methyl]amino]piperidine-1-carboxylate; hydrochloride (4 g, 93.2%), which was used for next step directly.

197

Benzyl-4-[[[(1S,3R)-3-[[4-[1-(benzenesulfonyl)indol-3-yl]-5-chloro-pyrimidin-2-yl]amino]cyclohexyl]methyl]amino]piperidine-1-carboxylate

To a solution of benzyl 4-[[[(1S,3R)-3-aminocyclohexyl]methyl]amino]piperidine-1-carboxylate hydrochloride (2.2 g, 5.76 mmol) and 1-(benzenesulfonyl)-3-(2,5-dichloropyrimidin-4-yl)indole (2.33 g, 5.76 mmol) in NMP (10 mL) was added DIPEA (3.72 g, 28.8 mmol).degassed, heated to 130° C., and stirred for 0.5 h by microwave. The mixture was poured into water, extracted with EA, and the organic layer was dried and concentrated. The residue was purified by column to afford the crude product (1 g), which was purified further by preparative HPLC to afford benzyl4-[[[(1S,3R)-3-[[4-[1-(benzenesulfonyl)indol-3-yl]-5-chloro-pyrimidin-2-yl]amino]cyclohexyl]methyl]amino]-piperidine-1-carboxylate (0.8 g, 19.5%) as a yellow solid.

Benzyl4-[[[(1R,3 S)-3-[[[5-chloro-4-(1H-indol-3-yl)pyrimidin-2-yl]amino]cyclohexyl]methyl]amino]piperidine-1-carboxylate and benzyl4-[[[(1S,3R)-3-[[5-chloro-4-(1H-indol-3-yl)pyrimidin-2-yl]amino]cyclohexyl]methyl]amino]piperidine-1-carboxylate

198

To a solution of benzyl 4-[[[(1S,3R)-3-[[[4-[1-(benzenesulfonyl)indol-3-yl]-5-chloro-pyrimidin-2-yl]amino]cyclohexyl]methyl]amino]piperidine-1-carboxylate (1.3 g, 1.82 mmol) in MeOH (50 mL) was added $K_2CO_3$ (0.5 g, 3.65 mmol). The mixture was heated to 50° C. and stirred for 2 h, then poured into water, extracted with EA, and the organic phase was concentrated. The residue was purified by column to afford the mixture of the desired product (800 mg) as a yellow solid. Then the mixture was separated by flash chromatography to afford benzyl 4-[[[(1R,3S)-3-[[[5-chloro-4-(1H-indol-3-yl)pyrimidin-2-yl]amino]cyclohexyl]methyl]amino]piperidine-1-carboxylate (0.24 g, 23.0%) and benzyl 4-[[[(1S,3R)-3-[[5-chloro-4-(1H-indol-3-yl)pyrimidin-2-yl]amino]cyclohexyl] methylamino]-piperidine-1-carboxylate (0.2 g, 19.1%).

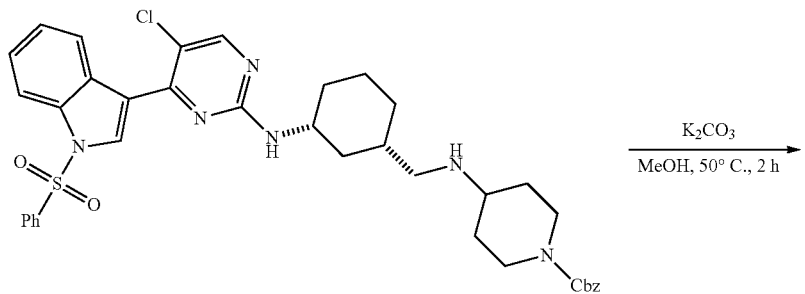

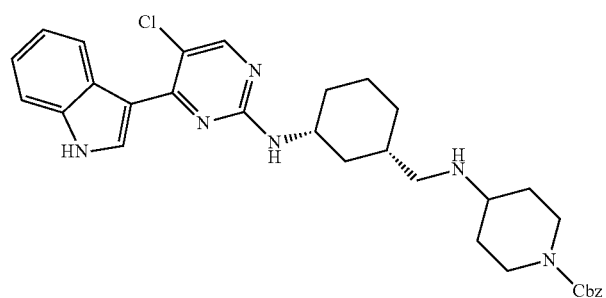

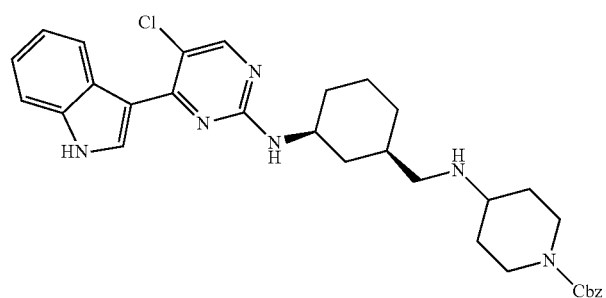

5-chloro-4-(1H-indol-3-yl)-N-[(1S,3R)-3-[(4-piperidylamino)methyl]cyclohexyl]-pyrimidin-2-amine (Compound 1043)

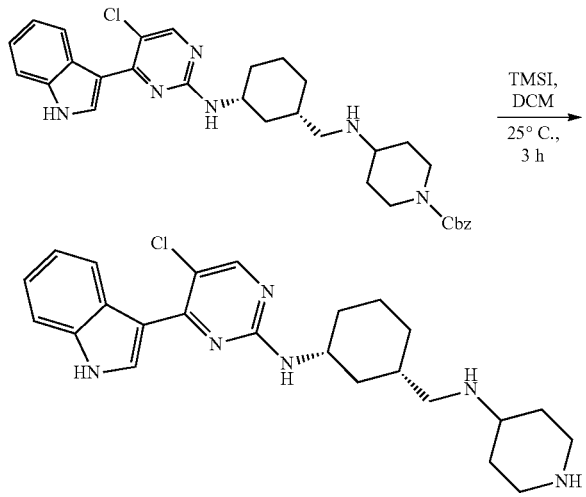

To a solution of benzyl 4-[[[(1S,3R)-3-[[5-chloro-4-(1H-indol-3-yl)pyrimidin-2-yl]amino]cyclohexyl]methyl]amino]piperidine-1-carboxylate (220 mg, 0.38 mmol) in DCM (10 mL) was added TMSI (384 mg, 1.92 mmol) at 25° C. and stirred for 3 h. Then the mixture was diluted with water, extracted with EtOAc, and the aqueous phase was concentrated under vacuum to afford 5-chloro-4-(1H-indol-3-yl)-N-[(1S,3R)-3-[(4-piperidylamino)methyl]cyclohexyl]pyrimidin-2-amine, Compound 1043 (200 mg, crude) as a yellow solid. LCMS: ET285-196-1 M+H$^+$: 439.3@0.734 min (5-95% ACN in H$_2$O, 1.5 min)

1-[4-[[(1S,3R)-3-[[5-chloro-4-(1H-indol-3-yl)pyrimidin-2-yl]amino]cyclohexyl]methylamino]-1-piperidyl]prop-2-en-1-one (Compound 127)

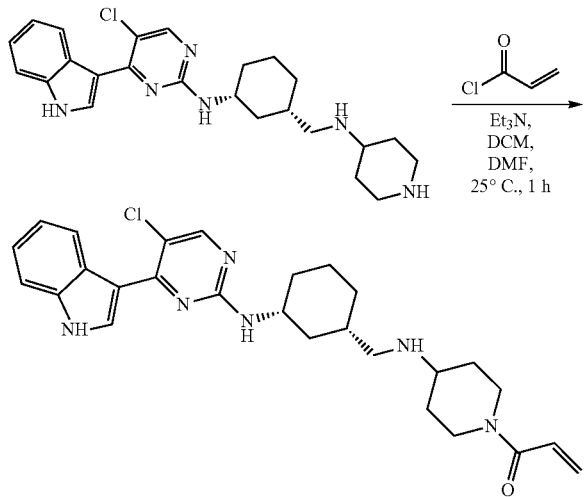

Compound 127

To a solution of 5-chloro-4-(1H-indol-3-yl)-N-[(1S,3R)-3-[(4-piperidylamino)methyl]-cyclohexyl]pyrimidin-2-amine (180 mg, 0.41 mmol) and TEA (83 mg, 0.82 mmol) in DMF (5 mL) was added a solution of prop-2-enoyl chloride (37 mg, 0.41 mmol) in DCM (1 mL) drop-wise at 25° C. under N$_2$ and stirred for 1 h. The mixture was concentrated under vacuum and purified by preparative HPLC to afford 1-[4-[[(1S,3R)-3-[[5-chloro-4-(1H-indol-3-yl)pyrimidin-2-yl]amino]cyclohexyl]methylamino]-1-piperidyl]prop-2-en-1-one, Compound 127 (15 mg, 6.9%), as a yellow solid.

LCMS: M+H$^+$: 493.2@2.187 min (10-80% ACN in H$_2$O, 4.5 min). $^1$HNMR: (MeOD, 400 MHz): δ 1.07-1.23 (m, 1H), 1.31 (q, J=11.80 Hz, 1H), 1.42-1.75 (m, 4H), 1.87-2.40 (m, 8H), 2.74 (d, J=14.05 Hz, 1H), 3.05 (d, J=7.03 Hz, 2H), 3.15 (br. s., 1H), 3.45 (br. s., 1H), 4.25 (br. s., 1H), 4.69 (br. s., 1H), 5.78 (dd, J=10.54, 1.76 Hz, 1H), 6.22 (dd, J=16.94, 1.88 Hz, 1H), 6.79 (dd, J=16.81, 10.79 Hz, 1H), 7.37 (d, J=8.78 Hz, 2H), 7.59 (d, J=5.52 Hz, 1H), 8.26 (s, 1H), 8.65 (br. s., 1H), 9.01 (br. s., 1H).

1-[4-[[(1R,3S)-3-[[5-chloro-4-(1H-indol-3-yl)pyrimidin-2-yl]amino]cyclohexyl]methylamino]-1-piperidyl]prop-2-en-1-one (Compound 212)

This compound was prepared in a similar manner to Compound 127 using benzyl 4-[[[(1R,3S)-3-[[5-chloro-4-(1H-indol-3-yl)pyrimidin-2-yl]amino]cyclohexyl]methyl]amino]piperidine-1-carboxylate.

Example 50. Synthesis of 1-(4-((4-((5-chloro-4-(1H-indol-3-yl)pyrimidin-2-yl) amino)piperidin-1-yl)methyl)piperidin-1-yl)prop-2-en-1-one (Compound 141)

tert-butyl 4-(iodomethyl)piperidine-1-carboxylate

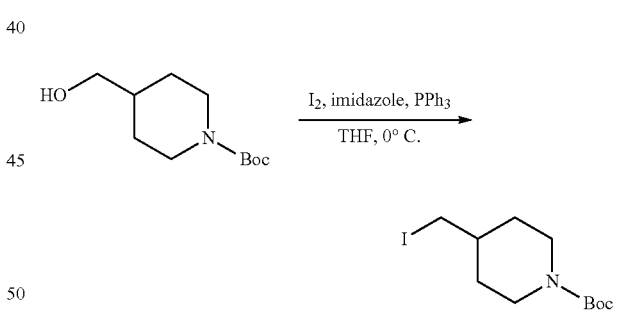

To a stirred solution of tert-butyl 4-(hydroxymethyl)piperidine-1-carboxylate (10.00 g, 46.45 mmol), PPh$_3$ (14.62 g, 55.74 mmol), and imidazole (3.79 g, 55.74 mmol) in THF (100 mL) at 0° C. was added I$_2$ (14.15 g, 55.74 mmol) in THF (50 mL) dropwise over 30 min. Then the reaction was allowed to warm to room temperature and stirred for 3 hr. The reaction was monitored by TLC, and the reaction was diluted with 20% ethyl acetate:hexane and filtered through a pad of silica. The filtrate was concentrated and purified by column to give the title compound (12.00 g, 36.90 mmol, 79.44% yield, purity: 90% on TLC) as a colorless oil.

201 tert-butyl 4-((4-((5-chloro-4-(1H-indol-3-yl) pyrimidin-2-yl)amino)piperidin-1-yl)methyl)piperidine-1-carboxylate

202

1-(4-((4-((5-chloro-4-(1H-indol-3-yl)pyrimidin-2-yl)amino)piperidin-1-yl)methyl)piperidin-1-yl)prop-2-en-1-one (Compound 141)

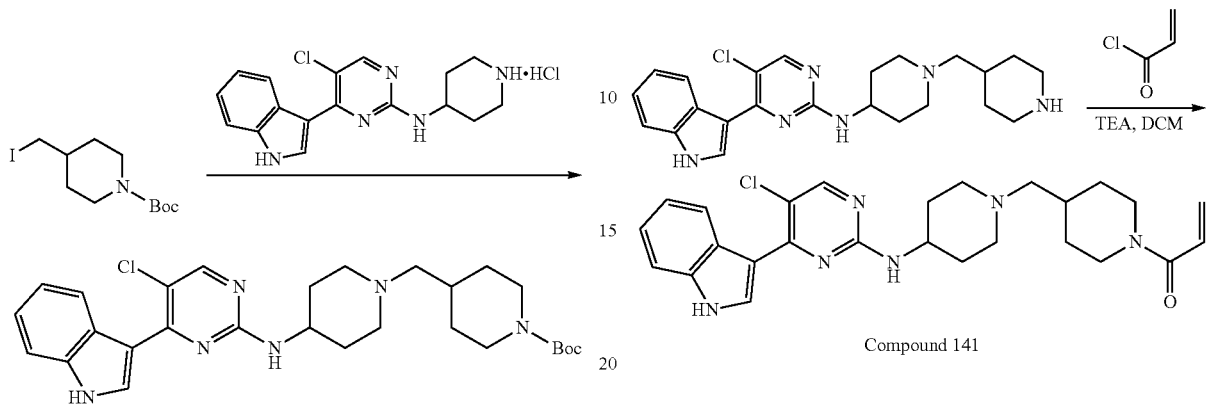

To a stirred solution of 5-chloro-4-(1H-indol-3-yl)-N-(piperidin-4-yl)pyrimidin-2-amine hydrochloride (0.32 g, 0.82 mmol) and K$_2$CO$_3$ (0.28 g, 2.06 mmol) in DMF (10 mL) was added tert-butyl 4-(iodomethyl)piperidine-1-carboxylate (0.32 g, 0.99 mmol). The reaction mixture was stirred at 80° C. for 24 hr, concentrated, and purified by column to give the title compound (0.35 g, 0.67 mmol, 80.94% yield).

5-chloro-4-(1H-indol-3-yl)-N-(1-(piperidin-4-ylmethyl) piperidin-4-yl)pyrimidin-2-amine (Compound 1048)

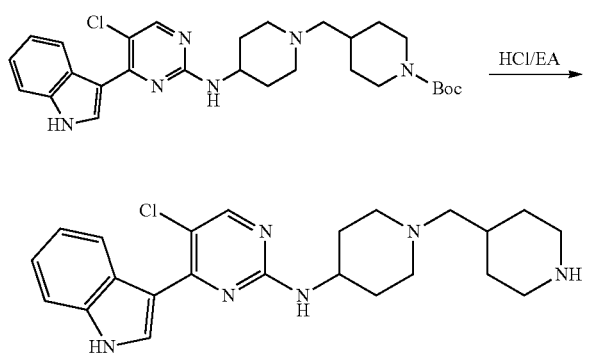

A mixture of tert-butyl 4-((4-((5-chloro-4-(1H-indol-3-yl) pyrimidin-2-yl)amino)piperidin-1-yl)methyl)piperidine-1-carboxylate (0.35 g, 0.67 mmol) in HCL/EA (10 mL) was stirred at 18° C. for 1 hr and then concentrated. The residue was dissolved in water and the solution was adjusted to pH 9 and extracted with DCM/isopropanol (4:1). The organic layer was washed with brine, dried over Na$_2$SO$_4$, and evaporated to give the title compound (0.15 g, 0.35 mmol, 52.95% yield).

To a stirred solution of 5-chloro-4-(1H-indol-3-yl)-N-[1-(4-piperidylmethyl)-4-piperidyl]pyrimidin-2-amine (150 mg, 0.35 mmol, 1.00 Eq) and TEA (71.43 mg, 0.70 mmol, 2.00 Eq) in THF (10 mL) was added dropwise prop-2-enoyl chloride (38.34 mg, 0.42 mmol, 1.20 Eq) at 0° C. The reaction mixture was allowed to come to room temperature and stirred for another 1 hr. The mixture was concentrated and purified by neutral preparative HPLC to yield after direct lyophilisation a white solid (40.00 mg, 0.08 mmol, 23.66% yield). LCMS: M–H$^+$=479.2. $^1$H NMR:_(400 MHz; MeOD) δ ppm 8.63 (s, d, J=7.6 Hz, 1H), 8.48 (s, 1H), 8.15 (s, 1H), 7.46 (d, J=8.0 Hz, 1H), 7.24-7.15 (m, 2H), 6.81-6.74 (m, 1H), 6.17 (d, J=15.2 Hz, 1H), 5.72 (d, J=10.4 Hz, 1H), 4.56 (d, J=12.4 Hz, 1H), 4.12 (d, J=12.8 Hz, 1H), 3.94 (brs, 1H), 3.17-3.10 (m, 2H), 2.98 (brs, 1H), 2.77-2.71 (m, 1H), 2.28-2.10 (m, 5H), 1.89-1.86 (m, 3H), 1.68-1.66 (m, 2H), 1.13 (brs, 2H).

Example 51. Synthesis of benzyl 4-(((1S,3R)-3-((5-chloro-4-(1H-indol-3-yl)pyrimidin-2-yl)amino)cyclohexyl)methyl)piperazine-1-carboxylate (Compound 129) and benzyl 4-(((1R,3S)-3-((5-chloro-4-(1H-indol-3-yl)pyrimidin-2-yl)amino)cyclohexyl)methyl)-piperazine-1-carboxylate (Compound 204)

Benzyl 4-(1S,3R)-3-((tert-butoxycarbonyl)amino) cyclohexanecarbonyl)piperazine-1-carboxylate and benzyl 4-(1R,3S)-3-((tert-butoxycarbonyl)amino) cyclohexane-1-carbonyl)piperazine-1-carboxylate

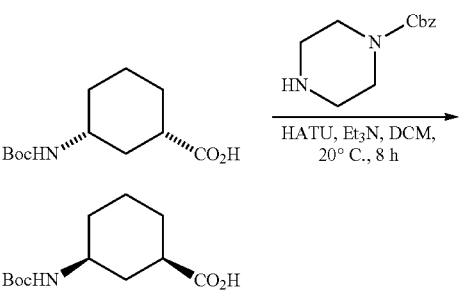

203

-continued

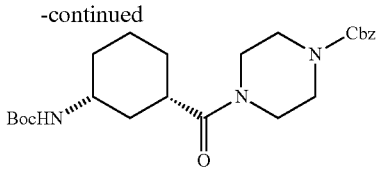

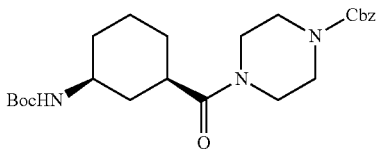

A mixture of (1S,3R)-3-(tert-butoxycarbonylamino)cyclohexanecarboxylic acid and (1R,3S)-3-(tert-butoxycarbonylamino)cyclohexanecarboxylic acid (3 g, 12.33 mmol), benzyl piperazine-1-carboxylate (3.26 g, 14.80 mmol), HATU (6.09 g, 16.03 mmol) and Et₃N (4.99 g, 49.32 mmol) in DCM (200 mL) was stirred at 25° C. for 12 h. The mixture was diluted with DCM, washed with water and brine, and the organic layer was dried over Na₂SO₄ and concentrated. The residue was purified by column to afford the benzyl title compounds (5 g, 91.01%) as a white oil.

Benzyl 4-(((1S,3R)-3-((tert-butoxycarbonyl)amino)cyclohexyl)methyl)piperazine-1-carboxylate and benzyl 4-(((1R,3S)-3-((tert-butoxycarbonyl)amino)cyclohexyl)methyl) piperazine-1-carboxylate

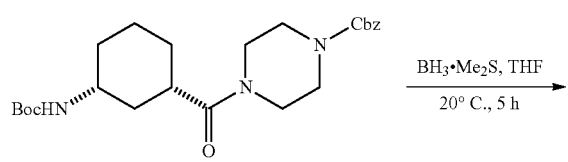

BH₃·Me₂S, THF
20° C., 5 h

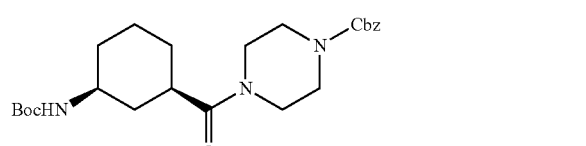

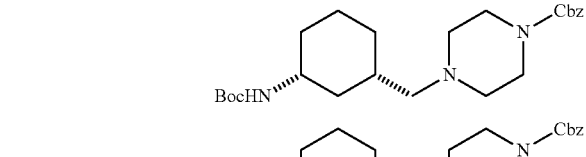

To benzyl 4-[(1S,3R)-3-(tert-butoxycarbonylamino)cyclohexanecarbonyl] piperazine-1-carboxylate and benzyl 4-[(1R,3S)-3-(tert-butoxycarbonylamino) cyclohexanecarbonyl]piperazine-1-carboxylate (5 g, 11.22 mmol) in THF (300 mL) was added BH₃·Me₂S (5.6 mL, 56.11 mmol) at 25° C., the mixture was heated to 50° C., and stirred for 4 h. The mixture was quenched with NaOH solution (1 M, 50 mL), extracted with EA, and the organic layer was dried over Na₂SO₄ and concentrated. The residue was purified by column to afford the benzyl title compounds (2.2 g, 36.3%) as a white solid.

204

Benzyl 4-[[(1S,3R)-3-aminocyclohexyl]methyl]piperazine-1-carboxylate hydrochloride and Benzyl 4-[[(1R,3S)-3-aminocyclohexyl]methyl]piperazine-1-carboxylate hydrochloride

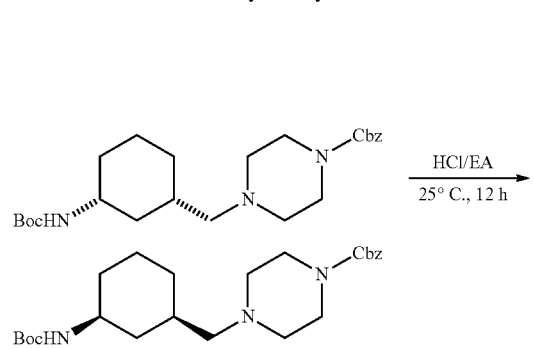

HCl/EA
25° C., 12 h

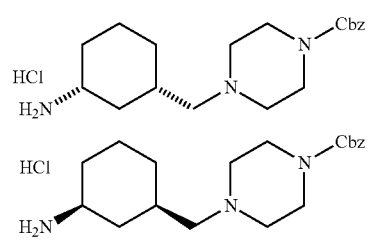

A mixture of benzyl 4-[[(1S,3R)-3-(tert-butoxycarbonylamino)cyclohexyl]methyl] piperazine-1-carboxylate and benzyl 4-[[(1R,3S)-3-(tert-butoxycarbonylamino) cyclohexyl]methyl]piperazine-1-carboxylate (2.20 g, 5.10 mmol) in HCl/EA (300 mL) was stirred at 25° C. for 12 h. The mixture was evaporated to give the title compounds (1.85 g, 69%) as a white solid.

Benzyl 4-(((1R,3S)-3-((5-chloro-4-(1-(phenylsulfonyl)-1H-indol-3-yl)pyrimidin-2-yl) amino)cyclohexyl)methyl)piperazine-1-carboxylate and benzyl 4-(((1S,3R)-3-((5-chloro-4-(1-(phenylsulfonyl)-1H-indol-3-yl)pyrimidin-2-yl)amino)cyclohexyl)methyl) piperazine-1-carboxylate

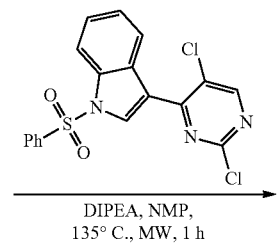

DIPEA, NMP,
135° C., MW, 1 h

-continued

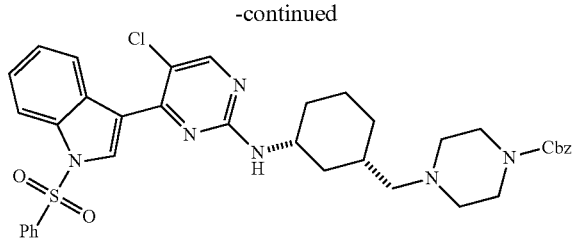

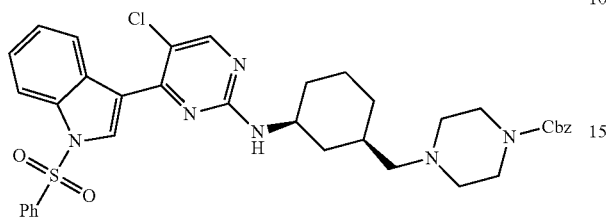

A mixture of 1-(benzenesulfonyl)-3-(2,5-dichloropyrimidin-4-yl)indole (0.9 g, 4.70 mmol), benzyl 4-[[(1S,3R)-3-aminocyclohexyl]methyl]piperazine-1-carboxylate; hydrochloride and benzyl 4-[[(1R,3S)-3-aminocyclohexyl]methyl]piperazine-1-carboxylate; hydrochloride (1.73 g, 4.70 mmol) and DIPEA (3.64 g, 28.20 mmol) in NMP (5 mL) was reacted at 135° C. for 1 h by microwave. The mixture was poured into water, extracted with EA, and organic layer was washed with water and brine, dried over $Na_2SO_4$ and concentrated. The residue was purified by column to afford the title compounds (1 g, 25.8%).

Benzyl 4-(((1S,3R)-3-((5-chloro-4-(1H-indol-3-yl)pyrimidin-2-yl)amino)cyclohexyl) methyl)piperazine-1-carboxylate and benzyl 4-(((1R,3S)-3-((5-chloro-4-(1H-indol-3-yl) pyrimidin-2-yl)amino)cyclohexyl)methyl)piperazine-1-carboxylate

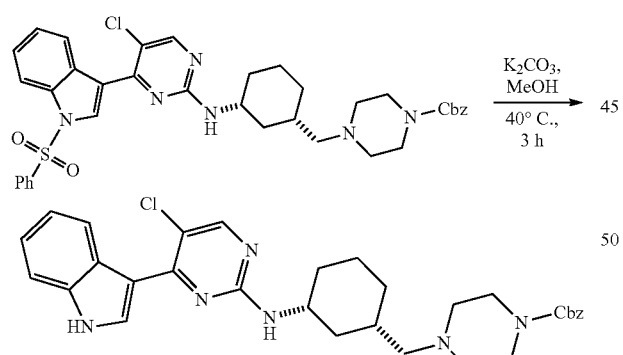

A mixture of benzyl 4-(((1R,3S)-3-((5-chloro-4-(1-(phenylsulfonyl)-1H-indol-3-yl)pyrimidin-2-yl)amino)cyclohexyl)methyl)piperazine-1-carboxylate and benzyl 4-(((1S,3R)-3-((5-chloro-4-(1-(phenylsulfonyl)-1H-indol-3-yl)pyrimidin-2-yl)amino)cyclohexyl)methyl) piperazine-1-carboxylate (1 g, 1.43 mmol) and $K_2CO_3$ (0.59 g, 4.29 mmol) in MeOH (50 mL) was heated to 50° C. for 3 h. The mixture was evaporated and the residue was purified by preparative HPLC to afford the title compounds (0.48 g, 60%).

Benzyl 4-(((1S,3R)-3-((5-chloro-4-(1H-indol-3-yl) pyrimidin-2-yl)amino)cyclohexyl) methyl)piperazine-1-carboxylate and benzyl 4-(((1R,3S)-3-((5-chloro-4-(1H-indol-3-yl) pyrimidin-2-yl)amino) cyclohexyl)methyl)piperazine-1-carboxylate

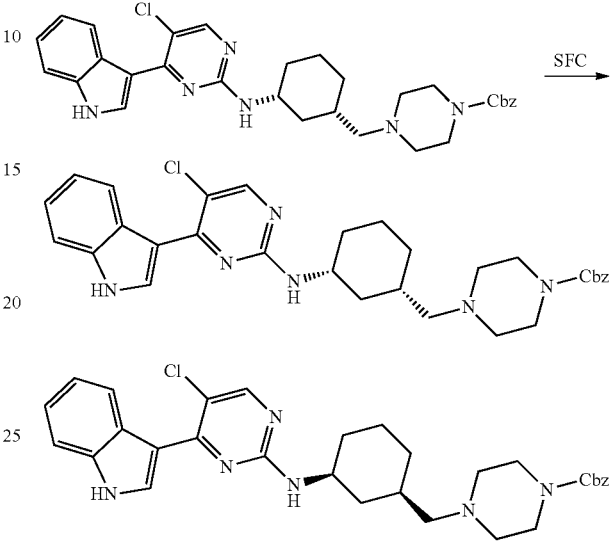

The mixture of benzyl 4-(((1S,3R)-3-((5-chloro-4-(1H-indol-3-yl)pyrimidin-2-yl) amino)cyclohexyl)methyl)piperazine-1-carboxylate (0.48 g, 0.8 mmol) was separated by silica flash chromatography to afford benzyl 4-(((1S,3R)-3-((5-chloro-4-(1H-indol-3-yl)pyrimidin-2-yl)amino)cyclohexyl)methyl)piperazine-1carboxylate (110 g, 229.%) and benzyl 4-(((1R,3S)-3-((5-chloro-4-(1H-indol-3-yl)pyrimidin-2-yl)amino)cyclohexyl)methyl)piperazine-1-carboxylate (180 mg, 37.5%).

5-chloro-4-(1H-indol-3-yl)-N-((1R,3S)-3-(piperazin-1-ylmethyl)cyclohexyl)pyrimidin-2-amine (Compound 1049)

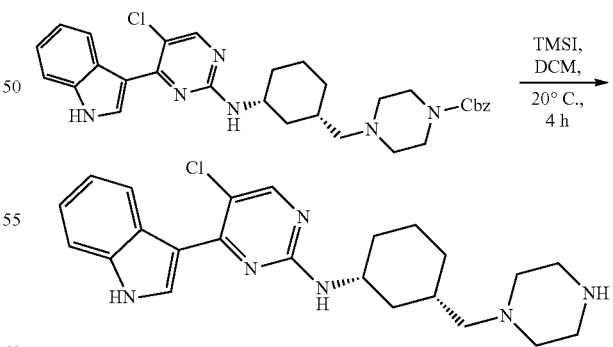

To a mixture of benzyl 4-(((1S,3R)-3-((5-chloro-4-(1H-indol-3-yl)pyrimidin-2-yl)amino) cyclohexyl)methyl)piperazine-1-carboxylate (110 mg, 0.196) in MeOH (10 mL) was added TMSI (196 mg, 0.983 mmol) at 20° C. and stirred for 4 h. The mixture was poured into water, extracted with EA, and the aqueous solution was evaporated to give 5-chloro-4-(1H-indol-3-yl)-N-((1R,3S)-3-(piperazin-1-ylmethyl)cyclohexyl)pyrimidin-2-amine (70 mg, 84.3%) as a yellow solid.

1-(4-(((1S,3R)-3-((5-chloro-4-(1H-indol-3-yl)pyrimidin-2-yl)amino)cyclohexyl)methyl)piperazin-1-yl)prop-2-en-1-one (Compound 129)

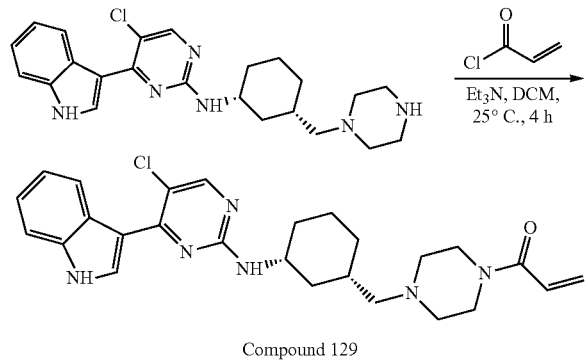

Compound 129

To a mixture of 5-chloro-4-(1H-indol-3-yl)-N-[(1R,3S)-3-(piperazin-1-ylmethyl)cyclohexyl]pyrimidin-2-amine (70 mg, 0.164 mmol) and Et₃N (41 mg, 0.411 mmol) in DCM (10 mL) and DMF (5 mL) was added a solution of prop-2-enoyl chloride (12 mg, 0.132 mmol) in DCM (2 mL) dropwise and at 25° C. for 3 h. The mixture was evaporated, and the residue was purified by preparative HPLC to afford 1-[4-[[(1S,3R)-3-[[5-chloro-4-(1H-indol-3-yl)pyrimidin-2-yl]amino]cyclohexyl]methyl]piperazin-1-yl]prop-2-en-1-one (5.8 mg, 7.35%) as a yellow solid. LCMS: M+H⁺: 479.2@2.186 min (10-80% ACN in H₂O, 4.5 min). ¹HNMR: (MeOD, 400 MHz): 1.16-1.28 (m, 2H), 1.50 (br. s., 1H), 1.68 (br. s., 1H), 1.94-2.04 (m, 2H), 2.20 (br. s., 2H), 2.41 (br. s., 1H), 3.14 (br. s., 4H), 3.63 (br. s., 4H), 4.26 (br. s., 1H), 4.59 (br. s., 1H), 5.83 (d, J=5.2 Hz, 1H), 6.26 (d, J=8.2 Hz, 1H), 6.72 (br. s., 1H), 7.39 (br. s., 2H), 7.60 (br. s., 1H), 8.28 (br. s., 1H), 8.66 (br. s., 1H), 9.00 (br. s., 1H).

1-(4-(((1R,3S)-3-((5-chloro-4-(1H-indol-3-yl)pyrimidin-2-yl)amino)cyclohexyl)methyl)-piperazin-1-yl)prop-2-en-1-one (Compound 1050 and Compound 204)

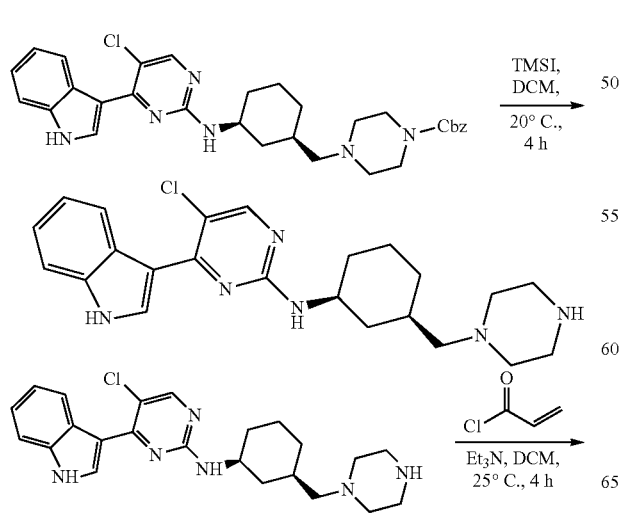

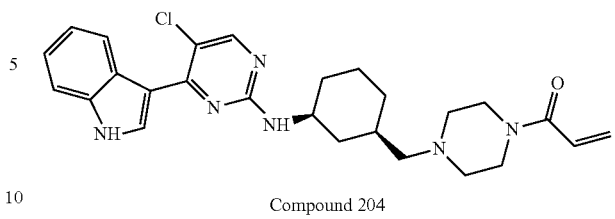

Compound 204

The title compound was prepared as above for Compound 129. LCMS: M+H⁺: 479.2@2.163 min (10-80% ACN in H₂O, 4.5 min). ¹H NMR: (MeOD, 400 MHz) 1.05-1.38 (m, 2H), 1.51 (br. s., 1H), 1.69 (br. s., 1H), 1.86-2.10 (m, 2H), 2.22 (br. s., 2H), 2.41 (br. s., 1H), 3.14 (br. s., 4H), 3.45-3.94 (m, 4H), 3.64-3.74 (m, 1H), 4.23 (br. s., 2H), 4.60 (br. s., 1H), 5.83 (d, J=9.79 Hz, 1H), 6.27 (d, J=16.44 Hz, 1H), 6.74 (br. s., 1H), 7.39 (br. s., 2H), 7.60 (br. s., 1H), 8.24 (br. s., 1H), 8.62 (br. s., 1H), 8.99 (br. s., 1H). 12.26 (br. s., 1H).

Example 52. Synthesis of (E)-1-[4-[(3R)-3-[[5-chloro-4-(1H-indol-3-yl)pyrimidin-2-yl]amino]pyrrolidine-1-carbonyl]-1-piperidyl]-4-(dimethylamino)but-2-en-1-one (Compound 213) and 1-[4-[(3R)-3-[[5-chloro-4-(1H-indol-3-yl)pyrimidin-2-yl]amino]pyrrolidine-1-carbonyl]-1-piperidyl]prop-2-en-1-one (Compound 214)

Benzyl 4-[(3R)-3-(tertbutoxycarbonylamino)pyrrolidine-1-carbonyl]piperidine-1-carboxylate

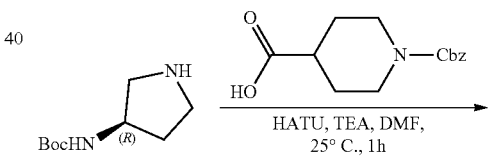

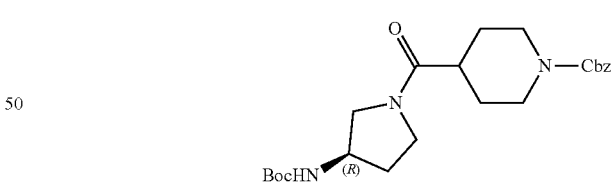

To a solution of tert-butyl N-[(3R)-pyrrolidin-3-yl]carbamate (10 g, 53.69 mmol) and 1-benzyloxycarbonylpiperidine-4-carboxylic acid (15.5 g, 59.06 mmol) in DCM (200 mL) was added TEA (10.87 g, 107.38 mmol) and HATU (30.62 g, 80.54 mmol) under N₂ protection at 25° C. and the mixture was stirred for 1 h. The mixture was diluted with DCM, washed with water and brine, and the organic phase was concentrated and purified by column to afford benzyl 4-[(3R)-3-(tertbutoxycarbonylamino)pyrrolidine-1-carbonyl]piperidine-1-carboxylate (15 g, 51.8%) as a colorless oil

209

Benzyl 4-[(3R)-3-aminopyrrolidine-1-carbonyl]piperidine-1-carboxylate hydrochloride

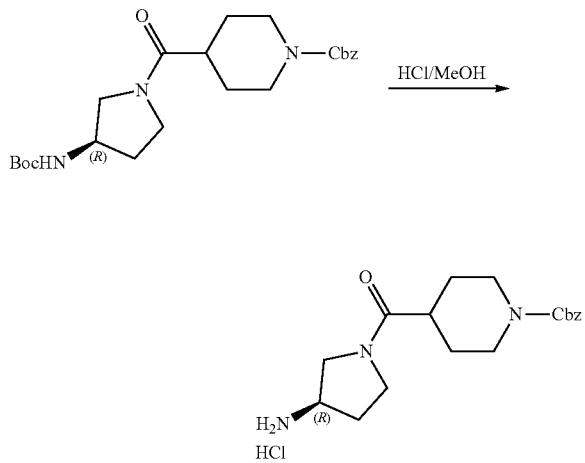

A solution of benzyl 4-[(3R)-3-(tert-butoxycarbonylamino)pyrrolidine-1-carbonyl]piperidine-1-carboxylate (10 g, 23.17 mmol) in HCl/MeOH (300 mL) was stirred at 25° C. for 3 h. The mixture was concentrated under vacuum to afford benzyl 4-[(3R)-3-aminopyrrolidine-1-carbonyl]piperidine-1-carboxylate; hydrochloride (6 g, 70.4%) as a white solid, which was directly used for next step.

Benzyl 4-[(3R)-3-[[4-[1-(benzenesulfonyl)indol-3-yl]-5-chloro-pyrimidin-2-yl]amino]pyrrolidine-1-carbonyl]piperidine-1-carboxylate

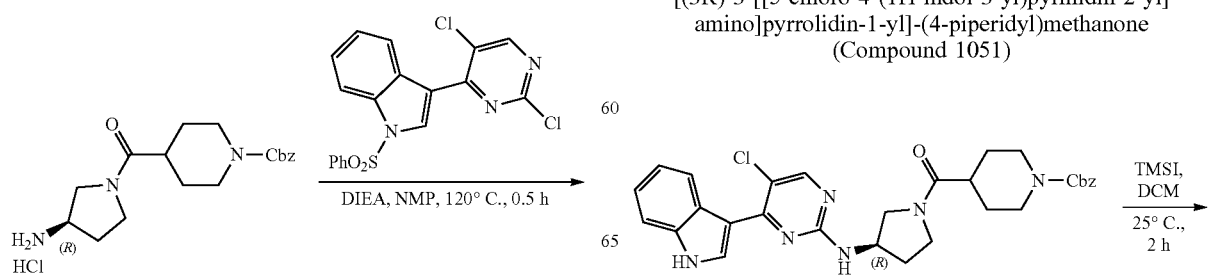

210

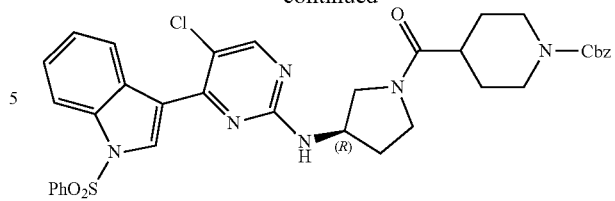

To a solution of benzyl 4-[(3R)-3-aminopyrrolidine-1-carbonyl]piperidine-1-carboxylate hydrochloride (1 g, 2.72 mmol) and 1-(benzenesulfonyl)-3-(2,5-dichloropyrimidin-4-yl)indole (1.1 g, 2.72 mmol) in DMF (8 mL) and EtOH (8 mL) was added DIPEA (1.76 g, 13.6 mmol). The reaction was degassed three times, then heated to 120° C. and stirred for 0.5 h by microwave. The mixture was poured into water, extracted with EA, and the organic phase was concentrated. The residue was purified by flash column to afford benzyl 4-[(3R)-3-[[4-[1-(benzenesulfonyl)indol-3-yl]-5-chloro-pyrimidin-2-yl]amino]pyrrolidine-1-carbonyl]piperidine-1-carboxylate (1.2 g, 63.1%) as a yellow liquid.

Benzyl 4-[(3R)-3-[[5-chloro-4-(1H-indol-3-yl)pyrmidin-2-yl]amino]pyrrolidine-1-carbonyl]piperidine-1-carboxylate

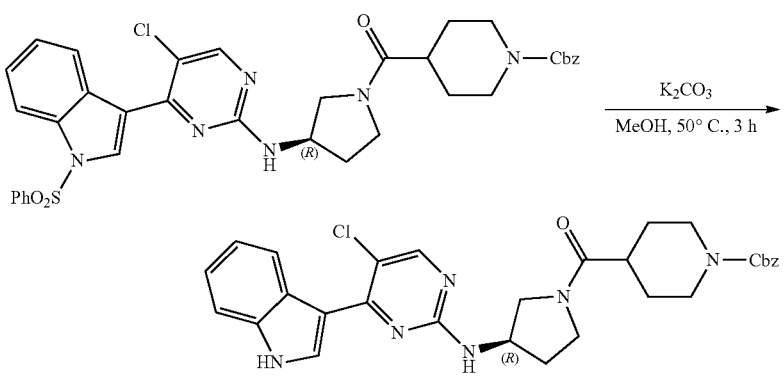

A mixture of benzyl 4-[(3R)-3-[[4-[1-(benzenesulfonyl)indol-3-yl]-5-chloro-pyrimidin-2-yl]amino]pyrrolidine-1-carbonyl]piperidine-1-carboxylate (1 g, 1.43 mmol) and K₂CO₃ (395 mg, 2.86 mmol) in MeOH (50 mL) was heated to 50° C. and stirred for 3 h. The mixture was poured into water, extracted with EA, and the organic phase was concentrated under vacuum to afford benzyl 4-[(3R)-3-[[5-chloro-4-(1H-indol-3-yl)pyrimidin-2-yl]amino]pyrrolidine-1-carbonyl]piperidine-1-carboxylate (600 mg, 75.0%) as a yellow solid.

[(3R)-3-[[5-chloro-4-(1H-indol-3-yl)pyrmidin-2-yl]amino]pyrrolidin-1-yl]-(4-piperidyl)methanone (Compound 1051)

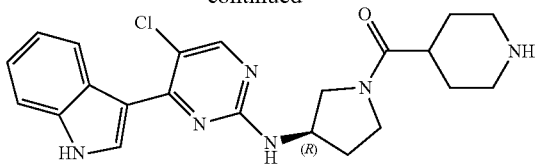

To a solution of benzyl 4-[(3R)-3-[[5-chloro-4-(1H-indol-3-yl)pyrimidin-2-yl]amino]pyrrolidine-1-carbonyl]piperidine-1-carboxylate (1 g, 1.79 mmol) in DCM (25 mL) was added TMSI (1.79 g, 8.95 mmol) at 25° C. and stirred for 2 h. The mixture was diluted with water, extracted with DCM, and the aqueous phase was concentrated under vacuum to afford [(3R)-3-[[5-chloro-4-(1H-indol-3-yl)pyrimidin-2-yl]amino]pyrrolidin-1-yl]-(4-piperidyl)methanone (600 mg, 78.9%) as a yellow solid.

(E)-1-[4-[(3R)-3-[[5-chloro-4-(1H-indol-3-yl)pyrimidin-2-yl]amino]pyrrolidine-1-carbonyl]-1-piperidyl]-4-(dimethylamino)but-2-en-1-one (Compound 213)

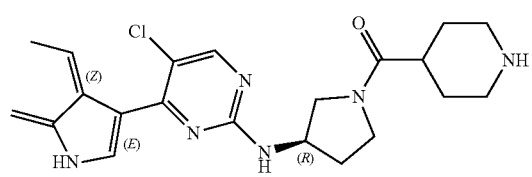

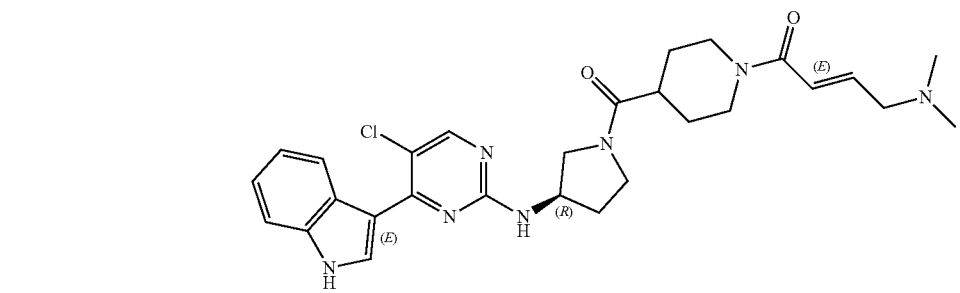

Compound 213

To a solution of [(3R)-3-[[5-chloro-4-(1H-indol-3-yl)pyrimidin-2-yl]amino]pyrrolidin-1-yl]-(4-piperidyl)methanone (150 mg, 0.35 mmol) and TEA (71 mg, 0.71 mmol) in DMF (3 mL) was added a solution of (E)-4-(dimethylamino)but-2-enoyl chloride (52 mg, 0.35 mmol) in DCM (1 mL) at 25° C. and stirred for 1 h. The reaction mixture was concentrated under vacuum and the residue was purified by preparative HPLC to afford (E)-1-[4-[(3R)-3-[[5-chloro-4-(1H-indol-3-yl)pyrimidin-2-yl]amino]pyrrolidine-1-carbonyl]-1-piperidyl]-4-(dimethylamino)but-2-en-1-one (30 mg, 15.8%) as a yellow solid. LCMS: M+H⁺: 536.2@2.113 min (10-80% ACN in H₂O, 4.5 min). ¹H NMR: (MeOD, 400 MHz): δ 1.57-1.72 (m, 2H), 1.83-1.97 (m, 2H), 2.15-2.32 (m, 1H), 2.37-2.54 (m, 1H), 2.73-3.04 (m, 8H), 3.20 (br.s., 1H), 3.65 (t, J=6.40 Hz, 1H), 3.73-3.87 (m, 2H), 3.88-4.01 (m, 4H), 4.05-4.29 (m, 2H), 4.43-4.67 (m, 2H), 6.62-6.73 (m, 1H), 7.01 (t, J=15.43 Hz, 1H), 7.27-7.38 (m, 2H), 7.53-7.59 (m, 1H), 7.97-8.24 (m, 1H), 8.43-8.58 (m, 1H), 8.90-9.00 (m, 1H).

1-[4-[(3R)-3-[[5-chloro-4-(1H-indol-3-yl)pyrimidin-2-yl]amino]pyrrolidine-1-carbonyl]-1-piperidyl]prop-2-en-1-one (Compound 214)

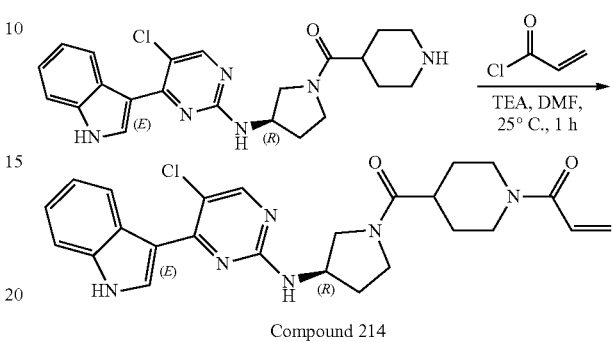

Compound 214

To a solution of [(3R)-3-[[5-chloro-4-(1H-indol-3-yl)pyrimidin-2-yl]amino]pyrrolidin-1-yl]-(4-piperidyl)methanone (200 mg, 0.47 mmol) and TEA (95 mg, 0.94 mmol) in DMF (3 mL) was added a solution of prop-2-enoyl chloride (43 mg, 0.47 mmol) in DCM (1 mL) at 25° C. and stirred for 1 h. The mixture was concentrated under vacuum and the residue was purified by preparative HPLC to afford 1-[4-[(3R)-3-[[5-chloro-4-(1H-indol-3-yl)pyrimidin-2-yl]amino]pyrrolidine-1-carbonyl]-1-piperidyl]prop-2-en-1-one (43 mg, 17.7%) as a yellow solid. LCMS: M+H⁺: 479.1@2.369 min (10-80% ACN in H₂O, 4.5 min). ¹HNMR: (MeOD, 400 MHz) δ 1.64 (br. s., 2H), 1.77-1.96 (m, 2H), 2.14-2.53 (m, 2H), 2.75-2.98 (m, 2H), 3.08-3.29 (m, 1H), 3.60-3.96 (m, 4H), 4.08-4.22 (m, 1H), 4.41-4.68 (m, 2H), 5.68-5.80 (m, 1H), 6.08-6.23 (m, 1H), 6.64-6.86 (m, 1H), 7.21-7.40 (m, 2H), 7.46-7.59 (m, 1H), 7.94 (br.s., 1H), 8.33-8.56 (m, 1H), 8.82-9.00 (m, 1H).

213

Example 53. Synthesis of N-((1S,3R)-3-((4-(1H-indol-3-yl)-5-(trifluoromethyl) pyrimidin-2-yl) amino)cyclohexyl)-5-((E)-4-(dimethylamino)but-2-enamido)picolinamide (Compound 248)

3-(2-chloro-5-(trifluoromethyl)pyrimidin-4-yl)-1H-indole

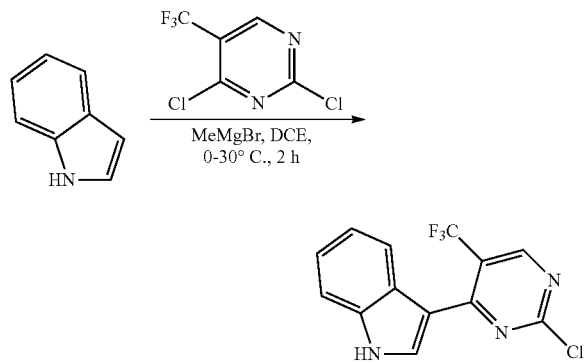

To a mixture of indole (3.0 g, 25.61 mmol) in DCE (40 mL) was added MeMgBr (38.4 mL, 38.42 mmol) at 0° C., the mixture was stirred at 0° C. for 0.5 h. Then 2,4-dichloro-5-(trifluoromethyl)pyrimidine (5.56 g, 25.61 mmol) was added at 0° C., the mixture was stirred at 30° C. for 1.5 h. The mixture was poured into water, extracted with EA, and the organic layer was dried over Na$_2$SO$_4$ and concentrated. The residue was purified by silica gel chromatography (Petroleum ether/Ethyl acetate=50:1-20:1) to afford title compound (5.4 g, 70.8%) as yellow solid.

Benzyl((1S,3R)-3-((4-(1H-indol-3-yl)-5-(trifluoromethyl)pyrimidin-2-yl)amino)cyclohexyl)carbamate

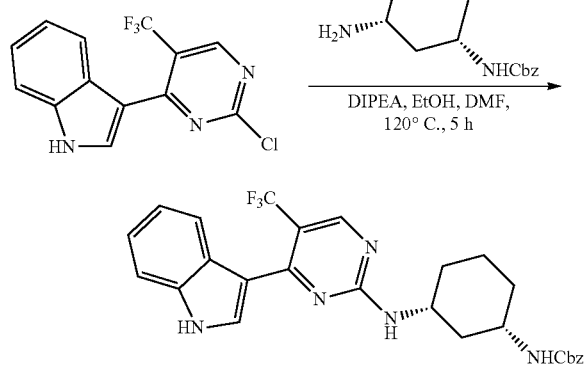

To a mixture of 3-[2-chloro-5-(trifluoromethyl)pyrimidin-4-yl]-1H-indole (1.0 g, 3.36 mmol) and benzyl ((1S,3R)-3-aminocyclohexyl)carbamate (1.0 g, 4.03 mmol) in DMF (10 mL) was added DIPEA (2.2 g, 16.8 mmol) at 25° C., the mixture was heated to 120° C. and stirred for 5 h. The mixture was poured into water (50 mL), extracted with EA (20 mL*2), and the organic layer was dried over Na$_2$SO$_4$ and concentrated. The residue was purified by flash column (DCM/MeOH=100:1~50:1) to afford title compound (1.3 g, 76.4%) as yellow solid.

214

(1R,3S)—N1-(4-(1H-indol-3-yl)-5-(trifluoromethyl) pyrmidin-2-yl)cyclohexane-1,3-diamine

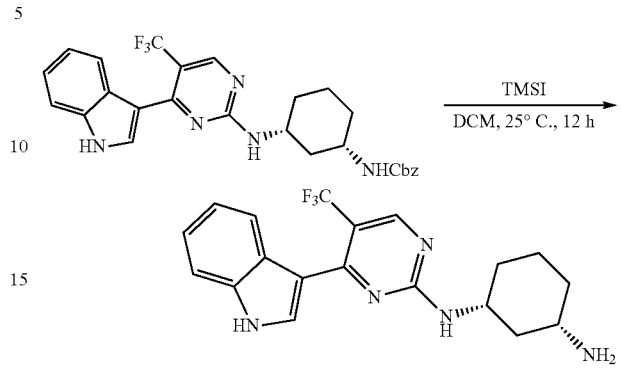

To a mixture of benzyl((1S,3R)-3-((4-(1H-indol-3-yl)-(trifluoromethyl) pyrimidin-2-yl) amino)cyclohexyl)carbamate (1.0 g, 2.1 mmol) in DCM (20 mL) was added TMSI (2.1 g, 10.5 mmol) at 30° C., the mixture was stirred for 12 h. The mixture was concentrated, and the residue was purified by flash column to afford title compound (600 mg, 90.9%) as a yellow solid.

N-((1S,3R)-3-((4-(1H-indol-3-yl)-5-(trifluoromethyl)pyrmidin-2-yl)amino)cyclohexyl)-5-aminopicolinamide (Compound 1052)

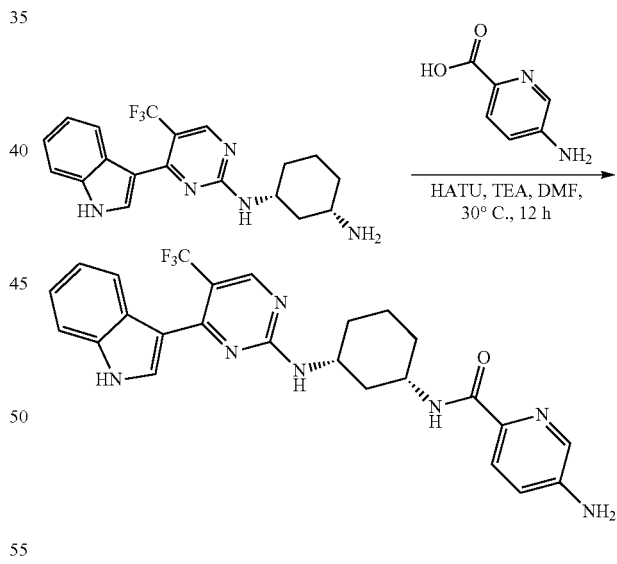

To a mixture of (1R,3S)—N1-[4-(1H-indol-3-yl)-5-(trifluoromethyl)pyrimidin-2-yl]cyclohexane-1,3-diamine (400 mg, 0.97 mmol) and 5-aminopyridine-2-carboxylic acid (147.6 mg, 1.07 mmol) in DMF (10 mL) was added TEA (196 mg, 1.96 mmol) and HATU (406.8 mg, 1.07 mmol) at 30° C. and the mixture was stirred for 12 h. The mixture poured into water, extracted with EA, and the organic layer was dried over Na$_2$SO$_4$ and concentrated. The residue was purified by silica gel chromatography to afford title compound (400 mg, 83.1%) as yellow solid. LCMS: (M+H$^+$): 496.3@0.813 min (5-95% ACN in H$_2$O, 1.5 min)

N-((1S,3R)-3-((4-(1H-indol-3-yl)-5-(trifluoromethyl)pyrimidin-2-yl)amino)cyclohexyl)-5-((E)-4-(dimethylamino)but-2-enamido)picolinamide

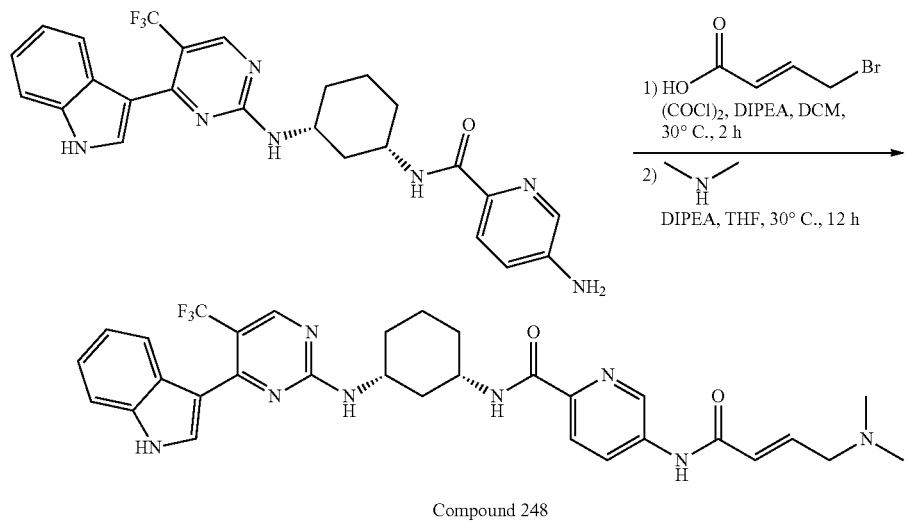

Compound 248

To a mixture of (E)-4-bromobut-2-enoic acid (99.9 mg, 0.6 mmol) in DCM (5 mL) was added (COCl)$_2$ (256.2 mg, 2.0 mmol) at 30° C. under N$_2$, the mixture was stirred for 1 h. Then this mixture was added to a solution of 5-amino-N-[(1S,3R)-3-[[4-(1H-indol-3-yl) -5-(trifluoromethyl)pyrimidin-2-yl]amino]cyclohexyl]pyridine-2-carboxamide (200 mg, 0.4 mmol) and DIPEA (156.4 mg, 1.2 mmol) in DCM (5 mL), the mixture was stirred at 30° C. for 1 h. Then dimethylamine (27.3 mg, 0.6 mmol) was added, the mixture was stirred for 12 h. The mixture was concentrated, and the residue was purified by pre-HPLC (HCl condition) to afford title compound (25 mg, 10.2%) as yellow solid.

LCMS: ET1741-66-P1A (M+H$^+$): 304.2@2.448 min (10-80% ACN in H$_2$O, 4.5 min).

$^1$H NMR: ET1741-66-P1A (MeOD, 400 MHz) δ 8.91 (br. s., 1H), 8.49 (br. s., 1H), 8.39 (br. s., 1H), 8.25 (d, J=8.28 Hz, 1H), 8.08 (d, J=8.78 Hz, 1H), 7.87 (br. s., 1H), 7.47 (br. s., 1H), 7.24 (br. s., 2H), 6.99 (d, J=15.31 Hz, 1H), 6.32 (d, J=15.56 Hz, 1H), 3.22 (d, J=5.77 Hz, 2H), 2.44-2.54 (m, 1H), 2.23-2.26 (m, 1H), 2.23-2.43 (m, 6H), 2.18 (br. s., 1H), 2.05 (br. s., 1H), 1.97 (d, J=11.54 Hz, 1H), 1.59 (br. s., 3H), 1.28-1.46 (m, 3H).

Example 54. Synthesis of 5-[[(E)-4-(dimethylamino)but-2-enoyl]amino]-N-[(1S,3R)-3-[[5-ethyl-4-(1H-indol-3-yl)pyrimidin-2-yl]amino]cyclohexyl]pyridine-2-carboxamide (Compound 262)

Benzyl N-[(1S,3R)-3-[[4-[1-(benzenesulfonyl)indol-3-yl]-5-chloro-pyrimidin-2-yl]amino]cyclohexyl]carbamate

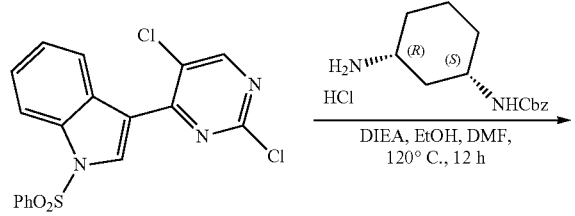

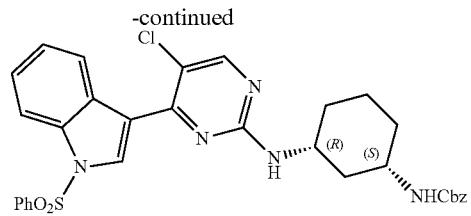

A mixture of benzyl N-[(1S,3R)-3-aminocyclohexyl]carbamate hydrochloride (5 g, 17.56 mmol), 1-(benzenesulfonyl)-3-(2,5-dichloropyrimidin-4-yl)indole (6.4 g, 15.80 mmol) and DIEA (11.4 g, 87.79 mmol) in DMF (50 mL) and EtOH (50 mL) was heated to 120° C. and stirred for 12 h under N$_2$. The mixture was poured into water (300 mL), extracted with EA (150 mL*3), and the organic phase was dried over Na$_2$SO$_4$ and concentrated under vacuum. The residue was purified by column to afford title compound (4 g, 37%) as yellow solid.

Benzyl N-[(1S,3R)-3-[[4-[1-(benzenesulfonyl)indol-3-yl]-5-vinyl-pyrimidin-2-yl]amino]cyclohexyl]carbamate

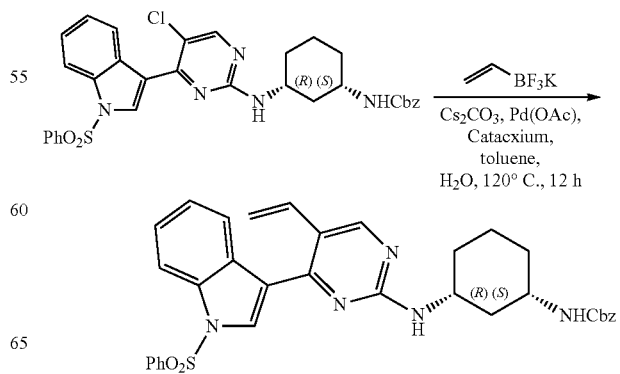

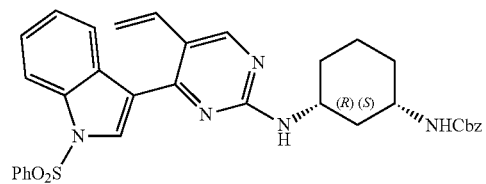

217

To a mixture of benzyl N-[(1S,3R)-3-[[4-[1-(benzenesulfonyl)indol-3-yl]-5-chloro-pyrimidin-2-yl]amino]cyclohexyl]carbamate (1.5 g, 2.43 mmol), potassium hydride trifluoro(vinyl) boron (1.63 g, 12.17 mmol) and Cs$_2$CO$_3$ (2.38 g, 7.30 mmol) in toluene (30 mL) and H$_2$O (6 mL) was added Catacxium (2.28 g, 2.43 mmol) and Pd(OAc)$_2$ (273.29 mg, 1.22 mmol) under N$_2$ protection, the mixture was heated to 120° C., and stirred for 12 h. The mixture was added water (50 mL), extracted with EA (50 mL*3), and the organic phase was dried over N$_2$SO$_4$ and concentrated. The residue was purified by column to afford title compound (1.60 g, 86.7%) as yellow solid.

(1R,3S)—N1-[4-[1-(benzenesulfonyl)indol-3-yl]-5-ethyl-pyrimidin-2-yl]cyclohexane-1,3-diamine

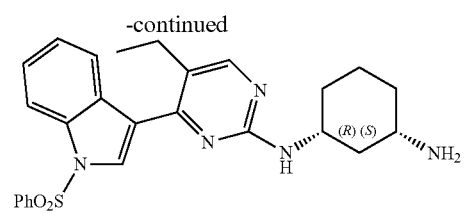

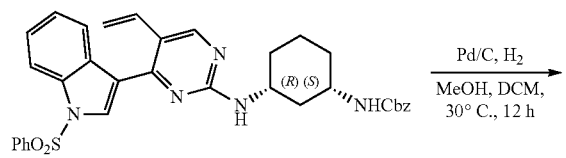

218

A solution of benzyl N-[(1S,3R)-3-[[4-[1-(benzenesulfonyl)indol-3-yl]-5-vinyl-pyrimidin-2-yl]amino]cyclohexyl]carbamate (1.5 g, 2.47 mmol) and Pd/C (1 g, 2.47 mmol) in MeOH (200 mL) and DCM (20 mL) was stirred at 30° C. for 12 h under H$_2$ (50 Psi) protection. The mixture was filtrated, and the filtrate was concentrated under vacuum to give title compound (1.2 g, 81.7%) as yellow solid.

5-amino-N-[(1S,3R)-3-[[4-[1-(benzenesulfonyl)indol-3-yl]-5-ethyl-pyrimidin-2-yl]amino]cyclohexyl]pyridine-2-carboxamide

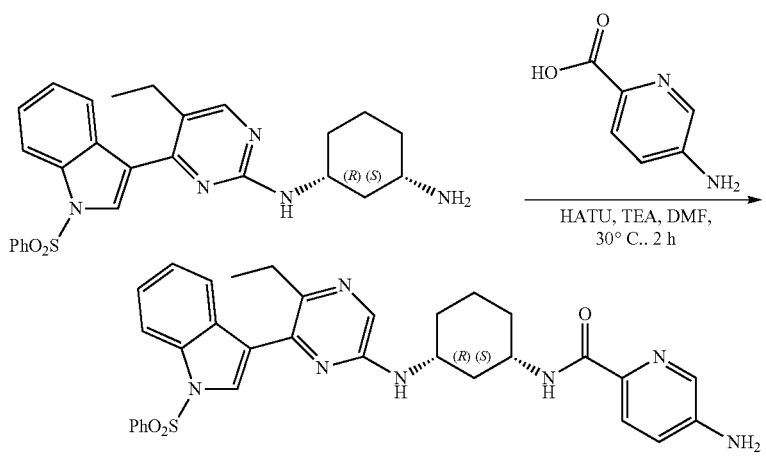

To a mixture of (1R,3S)—N1-[4-[1-(benzenesulfonyl)indol-3-yl]-5-ethyl-pyrimidin-2-yl]cyclohexane-1,3-diamine (400 mg, 0.84 mmol) and 5-aminopyridine-2-carboxylic acid (128 mg, 0.93 mmol) in DCM (20 mL) was added TEA (170 mg, 1.68 mmol) and HATU (480 mg, 1.26 mmol) at 30° C. and the mixture was stirred for 2 h. The mixture was poured into water (30 mL), extracted with EA (20 mL*3), the organic phase was concentrated, and the residue was purified by pre-HPLC to afford title compound (100 mg, 10%) as yellow solid.

5-amino-N-[(1S,3R)-3-[[5-ethyl-4-(1H-indol-3-yl)pyrimidin-2-yl]amino]cyclohexyl]pyridine-2-carboxamide (Compound 1053)

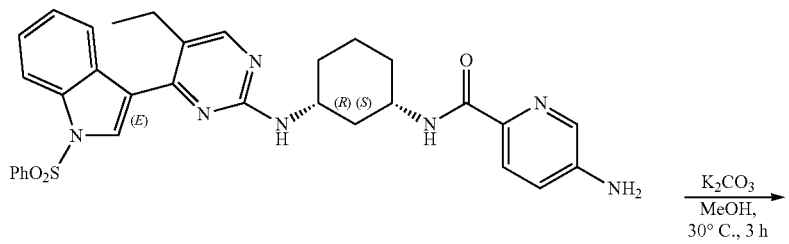

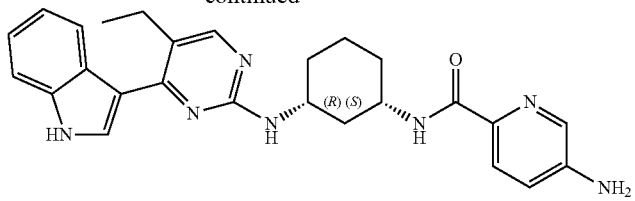

A solution of 5-amino-N-[(1S,3R)-3-[[4-[1-(benzenesulfonyl)indol-3-yl]-5-ethyl-pyrimidin-2-yl]amino]cyclohexyl]pyridine-2-carboxamide (120 mg, 0.2 mmol) and $K_2CO_3$ (56 mg, 0.40 mmol) in MeOH (10 mL) was stirred at 30° C. for 3 h. The mixture was poured into water (20 mL), extracted with EA (20 mL*2), and the organic phase was dried over $Na_2SO_4$ and concentrated to give title compound (90 mg, 78.5%) as white solid.

LCMS: (M+H$^+$): 456.2@0.743 min (5-95% ACN in $H_2O$, 1.5 min)

5-[[(E)-4-(dimethylamino)but-2-enoyl]amino]-N-[(1S,3R)-3-[[5-ethyl-4-(1H-indol-3-yl)pyrimidin-2-yl]amino]cyclohexyl]pyridine-2-carboxamide (Compound 262)

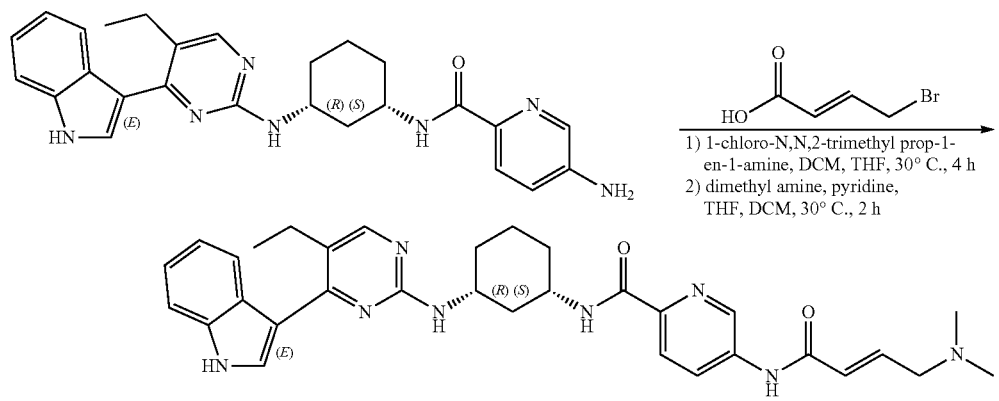

To a solution of (E)-4-bromobut-2-enoic acid (38 mg, 0.21 mmol) in DCM (5 mL) was added 1-chloro-N,N,2-trimethyl-prop-1-en-1-amine (35 mg, 0.26 mmol) at 0° C. and the mixture was stirred at 30° C. for 2 h. This mixture solution was added to a solution of 5-amino-N-[(1S,3R)-3-[[5-ethyl-4-(1H-indol-3-yl)pyrimidin-2-yl]amino]cyclohexyl]pyridine-2-carboxamide (80 mg, 0.175 mmol) and pyridine (21 mg, 0.26 mmol) in THF (5 mL) and the reaction mixture was stirred at 30° C. for 2 h. Then N-methylmethane amine (8 mg, 0.18 mmol) was added and the mixture was stirred at 30° C. for 2 h. The mixture was concentrated, and the residue mixture was purified by pre-HPLC to afford title compound (20 mg, 20%) as white solid.

LCMS: (M+H$^+$): 567.4@2.077 min (10-80% ACN in $H_2O$, 4.5 min). $^1$H NMR: (MeOD-d$_6$, 400 MHz) δ 8.86-8.89 (m, 1H), 8.27 (d, J=7.06 Hz, 1H), 8.23 (dd, J=8.60, 2.43 Hz, 1H), 8.10 (s, 1H), 8.03-8.07 (m, 1H), 7.73 (s, 1H), 7.43-7.46 (m, 1H), 7.18 (tt, J=7.44, 5.57 Hz, 2H), 6.93-6.99 (m, 1H), 6.28-6.32 (d, J=17.2 Hz, 1H), 4.04-4.12 (m, 2H), 3.20 (dd, J=6.39, 1.54 Hz, 2H), 2.73-2.79 (m, 2H), 2.40 (d, J=11.47 Hz, 1H), 2.30 (s, 6H), 2.15 (d, J=11.91 Hz, 1H), 2.03 (d, J=10.58 Hz, 1H), 1.91 (d, J=13.67 Hz, 1H), 1.58 (d, J=13.23 Hz, 1H), 1.45 (d, J=11.91 Hz, 1H), 1.28-1.39 (m, 2H), 1.20 (t, J=7.28 Hz, 3H).

Example 55. Synthesis of N-((1S,3R)-3-((5-chloro-4-(1H-indol-4-yl)pyrimidin-2-yl)amino)cyclohexyl)-5-(((E)-4-(dimethylamino)but-2-enamido)picolinamide (Compound 264)

4-(2,5-dichloropyrimidin-4-yl)-1H-indole

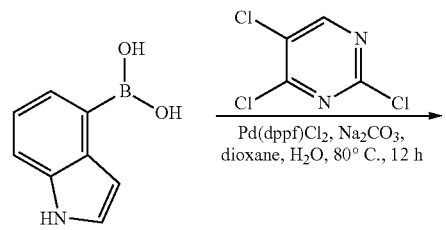

-continued

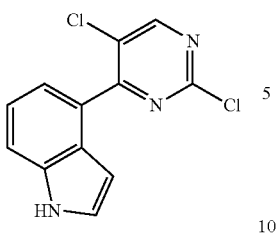

To a mixture of 1H-indol-4-ylboronic acid (20 g, 124.2 mmol) and 2,4,5-trichloropyrimidine (34.2 g, 186.4 mmol) in dioxane (400 mL) and H₂O (100 mL) was added Pd(dppf)Cl₂ (9.1 g, 12.4 mmol) and Na₂CO₃ (26.3 g, 248.5 mmol) under N₂, the mixture was heated to 80° C., and stirred for 12 h. The mixture was concentrated in vacuum, and the residue was purified by column (PE/EA=50/1, 10/1) to afford title compound (13.0 g, 39.6%).

tert-benzyl((1S,3R)-3-((5-chloro-4-(1H-indol-4-yl)pyrimidin-2-yl)amino)cyclohexyl)carbamate

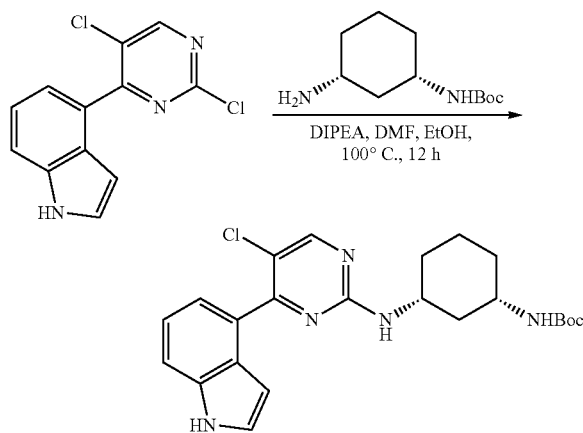

To a mixture of 4-(2,5-dichloropyrimidin-4-yl)-1H-indole (3 g, 11.3 mmol) and tert-butyl((1S,3R)-3-aminocyclohexyl)carbamate (3.6 g, 17.0 mmol) in DMF (20 mL) and EtOH (20 mL) was added DIPEA (2.9 g, 22.7 mmol) under N₂, the mixture was heated to 100° C., and stirred for 12 h. The mixture was purified by pre-HPLC (TFA condition) to afford title compound (2.8 g, 55.8%) as yellow solid.

(1R,3S)—N1-(5-chloro-4-(1H-indol-4-yl)pyrimidin-2-yl)cyclohexane-1,3-diamine

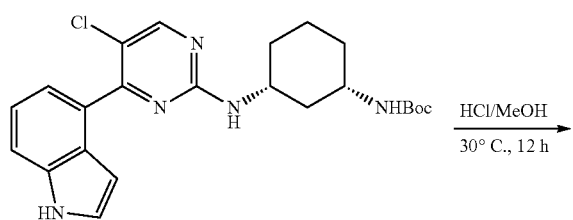

-continued

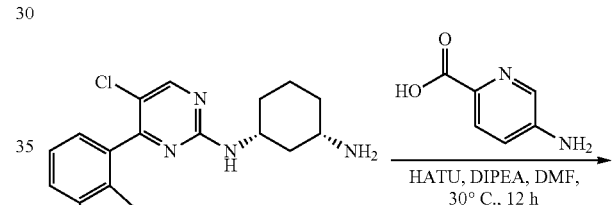

A mixture of tert-butyl N-[(1S,3R)-3-[[5-chloro-4-(1H-indol-4-yl)pyrimidin-2-yl]amino]cyclohexyl]carbamate (2 g, 4.5 mmol) was stirred at 30° C. for 12 h in 100 mL HCl in MeOH. The mixture was concentrated in vacuum to give title compound (1.5 g, crude) as a brown solid, which was used for next step directly.

5-amino-N-((1S,3R)-3-((5-chloro-4-(1H-indol-4-yl)pyrmidin-2-yl)amino)cyclohexyl)picolinamide
(Compound 1054)

To a mixture of (1R,3S)—N1-[5-chloro-4-(1H-indol-4-yl)pyrimidin-2-yl]cyclohexane-1,3-diamine (0.8 g, 2.3 mmol) and 5-aminopyridine-2-carboxylic acid (0.36 g, 2.6 mmol) in DMF (20 mL) was added HATU (1.1 g, 2.8 mmol) and DIPEA (0.45 g, 3.5 mmol) under N₂ and the mixture was stirred at 30° C. for 12 h. The mixture was poured into water (100 mL), extracted with EA (50 mL*3), and the organic layer was concentrated. The residue was purified by pre-HPLC (TFA condition) to afford title compound (0.3 g, 27.7%) as brown solid.

N-((1S,3R)-3-((5-chloro-4-(1H-indol-4-yl)pyrmidin-2-yl)amino)cyclohexyl)-5-((E)-4-(dimethylamino)but-2-enamido)picolinamide (Compound 264)

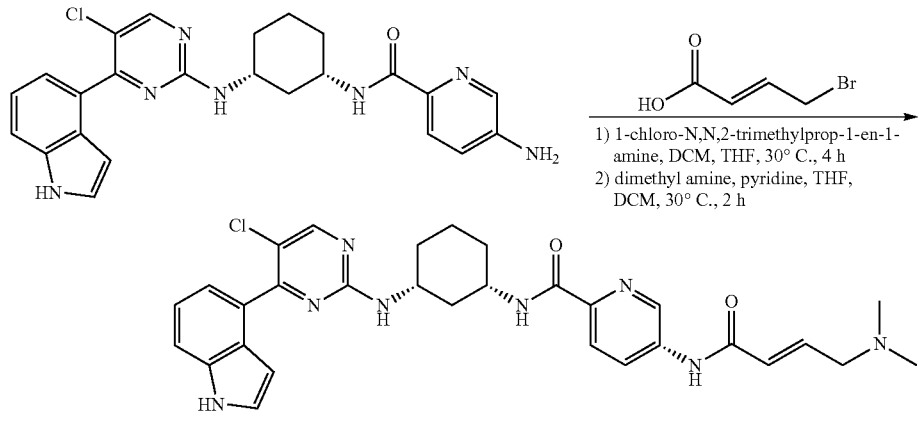

Compound 264

To a mixture of (E)-4-bromobut-2-enoic acid (35 mg, 0.22 mmol) in THF (3 mL) was added 1-chloro-N,N,2-trimethyl-prop-1-en-1-amine (29 mg, 0.22 mmol) at 30° C. and the mixture was stirred for 2 h. Then this solution was added to a solution of 5-amino-N-[(1S,3R)-3-[[5-chloro-4-(1H-indol-4-yl)pyrimidin-2-yl]amino]cyclohexyl]pyridine-2-carboxamide (100 mg, 0.22 mmol) and pyridine (25 mg, 0.32 mmol) in DCM (3 mL) and the mixture was stirred at 30° C. for 2 h. Finally, dimethyl amine (19 mg, 0.43 mmol) was added into the mixture and the mixture was stirred at 30° C. for 2 h. The mixture was concentrated, and the residue was purified by pre-HPLC to afford title compound (10 mg, 8.1%) as brown solid.

LCMS: M+H$^+$: 573.3@2.387 min (10-80% ACN in H$_2$O, 4.5 min). $^1$H NMR (MeOH, 400 MHz); δ 9.08 (br. s., 1H), 8.68 (br. s., 1H), 8.39 (br. s., 1H), 8.22 (br. s., 1H), 7.70 (d, J=8.03 Hz, 1H), 7.42-7.57 (m, 2H), 7.31 (br. s., 1H), 6.92-7.03 (m, 1H), 6.65 (d, J=14.81 Hz, 2H), 4.06 (d, J=6.53 Hz, 3H), 2.96 (s, 6H), 2.72 (br. s., 1H), 2.41 (br. s., 1H), 2.14 (br. s., 1H), 2.00 (br. s., 2H), 1.41-1.66 (m, 4H).

Example 56. Synthesis of N-((1S,3R)-3-((4-(1H-indol-3-yl)-5-methylpyrimidin-2-yl)amino)cyclohexyl)-5-((E)-4-(dimethylamino)but-2-enamido)picolinamide (Compound 265)

Benzyl-N-[(1S,3R)-3-[[4-[1-(benzenesulfonyl)indol-3-yl]-5-methyl-pyrimidin-2-yl]amino]cyclohexyl]carbamate

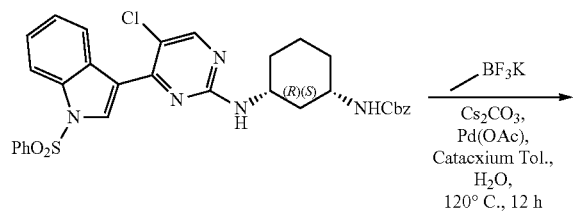

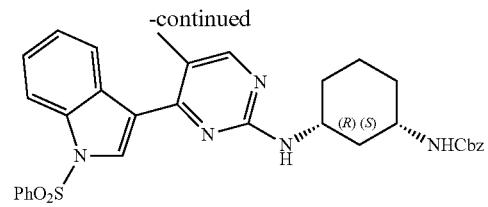

To a mixture of benzyl-N-[(1S,3R)-3-[[4-[1-(benzenesulfonyl)indol-3-yl]-5-chloro-pyrimidin-2-yl]amino]cyclohexyl]carbamate (1.5 g, 2.43 mmol), potassium hydride trifluoro(methyl) boron (1.48 g, 12.15 mmol), Cs$_2$CO$_3$ (2.38 g, 7.29 mmol) in toluene (50 mL) and H$_2$O (10 mL) was added Catacxium (2.28 g, 2.43 mmol) and Pd(OAc)$_2$ (273 mg, 1.22 mmol) under N$_2$ protection, the mixture was heated to 120° C., and stirred for 12 h. The mixture was concentrated, and the residue was purified by flash column to afford title compound (1.5 g, 92%) as yellow solid.

(1R,3S)—N1-[4-[1-(benzenesulfonyl)indol-3-yl]-5-methyl-pyrimidin-2-yl]cyclohexane-1,3-diamine

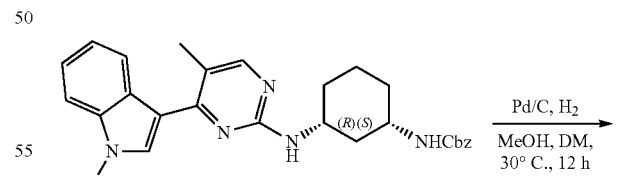

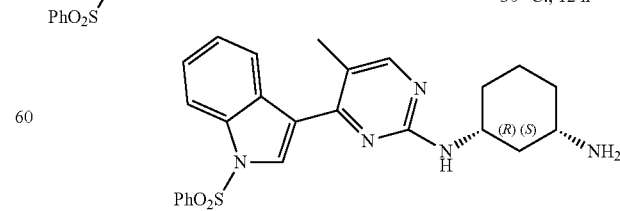

A mixture of benzyl N-[(1S,3R)-3-[[4-[1-(benzenesulfonyl)indol-3-yl]-5-methyl-pyrimidin-2-yl]amino]cyclohexyl]

carbamate (1.5 g, 2.52 mmol) and Pd/C (1 g, 2.52 mmol) in MeOH (200 mL) and DCM (20 mL) was stirred at 30° C. for 12 h under H$_2$ (50 Psi). The mixture was filtrated, and the filtrate was concentrated to give title compound (1.2 g, 86.7%) as yellow solid.

5-amino-N-[(1S,3R)-3-[[4-[1-(benzenesulfonyl)indol-3-yl]-5-methyl-pyrimidin-2-yl]amino]cyclohexyl]pyridine-2-carboxamide A mixture of 5-amino-N-[(1S,3R)-3-[[4-[1-(benzenesulfonyl)indol-3-yl]-5-methyl-pyrimidin-2-yl]amino]cyclohexyl]pyridine-2-carboxamide (300 mg, 0.51 mmol) in NaOH solution (2 mL) and MeOH (10 mL) was stirred at 25° C. for 5 h. The mixture was poured into water (20 mL), extracted with EA (30 mL*3), and the organic layer was dried over Na$_2$SO$_4$ and concentrated. The residue was purified by pre-HPLC (acid condition) to afford title compound (100 mg, 43.9%) as a white solid.

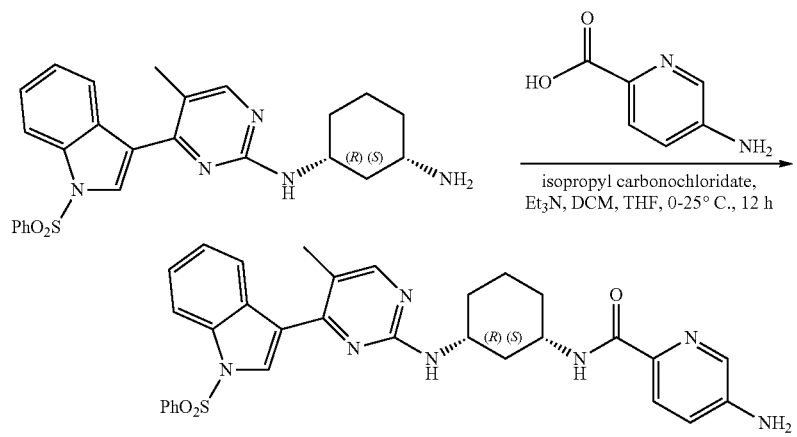

To a mixture of 5-aminopyridine-2-carboxylic acid (179 mg, 1.30 mmol) and Et$_3$N (131.54 mg, 1.30 mmol) in THF (2 mL) was added isopropyl carbonochloridate (159 mg, 1.30 mmol) at 0° C., the mixture was stirred at 0° C. for 0.5 h. Then the mixture solution was added to a solution of (1R,3S)—N1-[4-[1-(benzenesulfonyl)indol-3-yl]-5-methyl-pyrimidin-2-yl]cyclohexane-1,3-diamine (300 mg, 0.65 mmol) and Et$_3$N (131.54 mg, 1.30 mmol) in DCM (3 mL) at 25° C. and the mixture was stirred for 11.5 h. The mixture was poured into water (20 mL), extracted with EA (20 mL*3), and the organic layer was dried over Na$_2$SO$_4$ and concentrated to give title compound (300 mg, crude) as a yellow solid.

N-((1S,3R)-3-((4-(1H-indol-3-yl)-5-methylpyrimidin-2-yl)amino)cyclohexyl)-5-aminopicolinamide (Compound 1055)

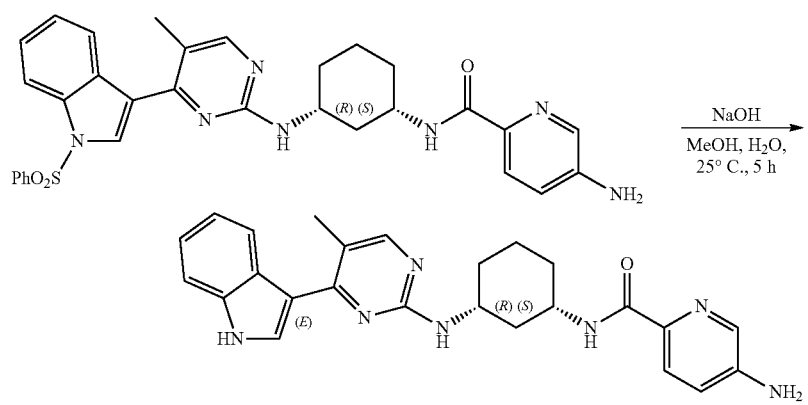

N-((1S,3R)-3-((4-(1H-indol-3-yl)-5-methylpyrimi-
din-2-yl)amino)cyclohexyl)-5-((E)-4-(dimethyl-
amino)but-2-enamido)picolinamide
(Compound 265)

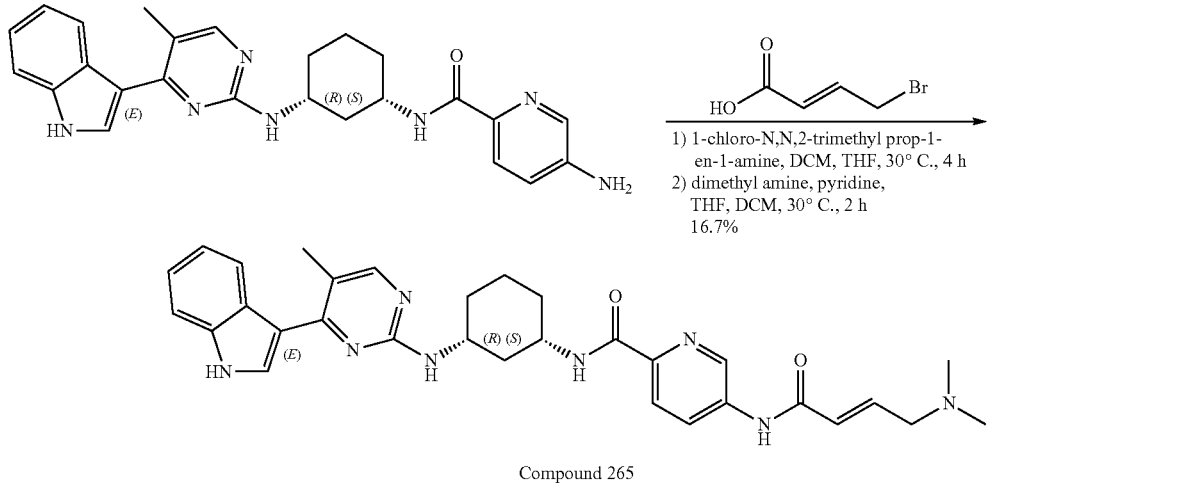

Compound 265

To a solution of (E)-4-bromobut-2-enoic acid (38 mg, 0.21 mmol) in DCM (5 mL) was added 1-chloro-N,N,2-trimethyl-prop-1-en-1-amine (35 mg, 0.26 mmol) at 0° C. and the mixture was stirred at 30° C. for 2 h. This mixture solution was added to a solution of 5-amino-N-[(1S,3R)-3-[[4-(1H-indol-3-yl)-5-methylpyrimidin-2-yl]amino]cyclohexyl]pyridine-2-carboxamide (50 mg, 0.11 mmol) and pyridine (21 mg, 0.26 mmol) in THF (5 mL) and the reaction mixture was stirred at 30° C. for 2 h. Then N-methylmethanamine (16 mg, 0.36 mmol, 0.36 ml, 1 mmol/L in THF) was added and the mixture was stirred at 30° C. for 2 h. The mixture was concentrated, and the residue mixture was purified by pre-HPLC to afford title compound (10.5 mg, 16.7%) as white solid.

LCMS: (M+H$^+$): 553.4@3.007 min (10-80% ACN in H$_2$O, 4.5 min). $^1$H NMR: (DMSO-d$_6$, 400 MHz), δ 8.88 (br. s., 1H), 8.61 (br. s., 1H), 8.47 (d, J=8.53 Hz, 1H), 8.24 (d, J=8.78 Hz, 1H), 8.07 (s, 1H), 8.02 (d, J=8.53 Hz, 1H), 7.94 (br. s., 1H), 7.46 (d, J=7.03 Hz, 1H), 7.19 (br. s., 2H), 6.82 (d, J=15.31 Hz, 1H), 6.70 (d, J=7.53 Hz, 1H), 6.30 (d, J=15.56 Hz, 1H), 3.95 (br. s., 3H), 3.08 (d, J=5.02 Hz, 2H), 2.30 (br. s., 3H), 2.19 (s, 6H), 2.02 (br. s., 1H), 1.84 (br. s., 2H), 1.35-1.59 (m, 3H), 1.26 (d, J=11.80 Hz, 1H).

Example 57. Synthesis of N-((1S,3R)-3-((5-chloro-
4-(1-methyl-1H-indol-4-yl) pyrimidin-2-yl)amino)
cyclohexyl)-5-((E)-4-(dimethylamino)but-2-ena-
mido)picolinamide (Compound 269)

4-(2,5-dichloropyrimidin-4-yl)-1-methyl-1H-indole

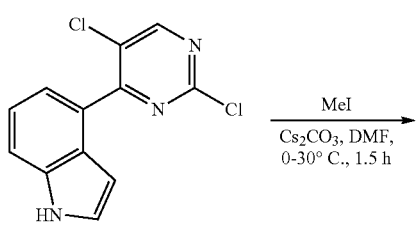

MeI
Cs$_2$CO$_3$, DMF,
0-30° C., 1.5 h

-continued

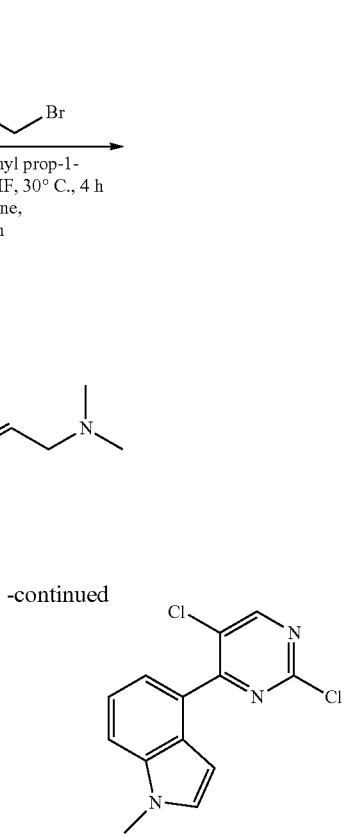

To a mixture of 4-(2,5-dichloropyrimidin-4-yl)-1H-indole (4.00 g, 15.15 mmol) in DMF (50 mL) was added Cs$_2$CO$_3$ (9.87 g, 30.29 mmol) at 0° C. under N$_2$ and the mixture was stirred for 0.5 h. Then iodomethane (2.15 g, 15.15 mmol) was added and the mixture was stirred for 1 h. The mixture was poured into water (100 mL), extracted with ethyl acetate (40 mL*3), and the combined organic phase was washed with saturated brine (40 mL*2), dried with anhydrous Na$_2$SO$_4$, filtered, and concentrated in vacuum. The residue was purified by silica gel chromatography (column height: 250 mm, diameter: 100 mm, 100-200 mesh silica gel, Petroleum ether/Ethyl acetate=40/1, 5/1) to afford title compound (3.10 g, 73.6%) as yellow solid.

Benzyl ((1S,3R)-3-((5-chloro-4-(1-methyl-1H-indol-
4-yl)pyrimidin-2-yl)amino) cyclohexyl)carbamate

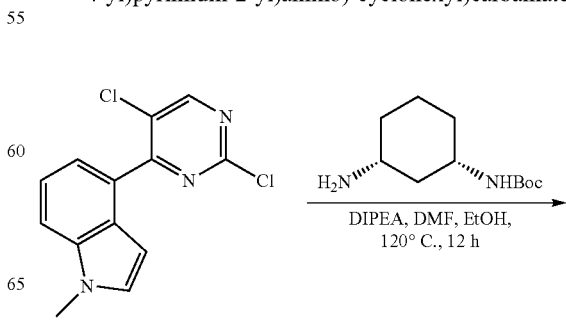

DIPEA, DMF, EtOH,
120° C., 12 h

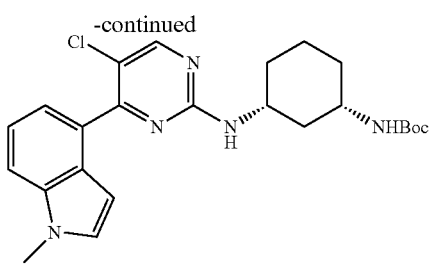

A mixture of 4-(2,5-dichloropyrimidin-4-yl)-1-methyl-indole (2.7 g, 9.71 mmol), tert-butyl N-[(1S,3R)-3-aminocyclohexyl]carbamate (2.08 g, 9.71 mmol) and DIPEA (3.75 g, 29.12 mmol) in DMF (20 mL) and EtOH (20 mL) was heated to 120° C. and stirred for 12 h. The mixture was poured into water (50 mL), extracted with ethyl acetate (50 mL*3), and the combined organic phase was washed with saturated brine (50 mL*2), dried over anhydrous Na₂SO₄, and filtered and concentrated in vacuum. The residue was purified by silica gel chromatography (column height: 250 mm, diameter: 100 mm, 100-200 mesh silica gel, Petroleum ether/Ethyl acetate=8/1, 1/1) to afford title compound (2.9 g, 65.5%) as yellow solid.

(1R,3S)—N1-(5-chloro-4-(1-methyl-1H-indol-4-yl)pyrimidin-2-yl)cyclohexane-1,3-diamine

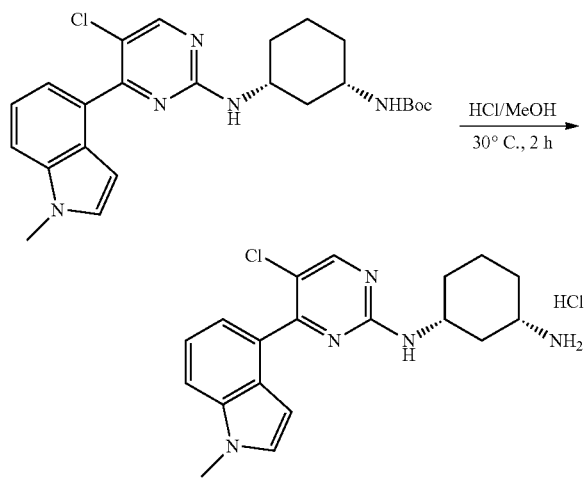

A mixture of tert-butyl N-[(1S,3R)-3-[[5-chloro-4-(1-methylindol-4-yl)pyrimidin-2-yl]amino]cyclohexyl]carbamate (2.9 g, 6.36 mmol) in HCl/MeOH (80 mL) was stirred at 30° C. for 2 h. The mixture was concentrated to give title compound (2.40 g, 96.2%).

5-amino-N-((1S,3R)-3-((5-chloro-4-(1-methyl-1H-indol-4-yl)pyrimidin-2-yl)amino)cyclohexyl)picolinamide (Compound 1056)

To a mixture of (1R,3S)—N1-(5-chloro-4-(1-methyl-1H-indol-4-yl)pyrimidin-2-yl) cyclohexane-1,3-diamine (1.00 g, 2.55 mmol), 5-aminopicolinic acid (0.39 g, 2.80 mmol) and Et₃N (0.77 g, 7.65 mmol) in DMF (10 mL) was added HATU (1.45 g, 3.82 mmol) at 30° C. under N₂ and the mixture was stirred for 4 h. The mixture was poured into water (50 mL), extracted with EA (20 mL*3), the combined organic phase was dried over anhydrous Na₂SO₄, and filtered and concentrated in vacuum. The residue was purified by pre-HPLC (TFA condition) to afford title compound (0.34 g, 18.2%) as yellow solid. LCMS: (M+H⁺): 476.0@0.800 min (5-95% ACN in H₂O, 1.5 min)

N-((1S,3R)-3-((5-chloro-4-(1-methyl-1H-indol-4-yl)pyrmidin-2-yl)amino)cyclohexyl)-5-((E)-4-(dimethylamino)but-2-enamido)picolinamide (Compound 269)

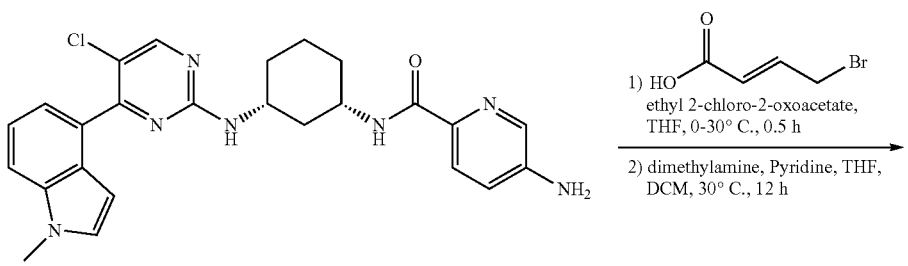

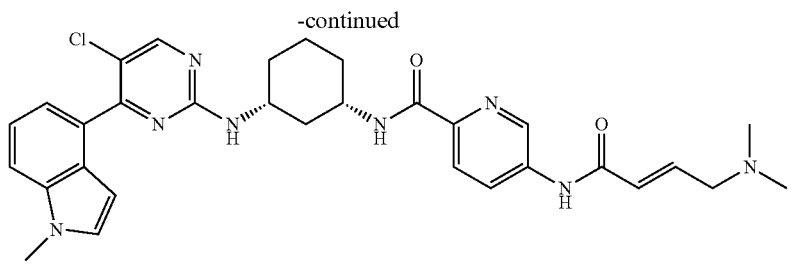

To a solution of (E)-4-bromobut-2-enoic acid (45.1 mg, 0.27 mmol) in DCM (5.0 mL) was added 1-chloro-N,N,2-trimethyl-prop-1-en-1-amine (42.1 mg, 0.32 mmol) and the mixture was stirred at 30° C. for 0.5 h. Then this mixture was added to a solution of 5-amino-N-(1S,3R)-3-[[5-chloro-4-(1-methylindol-4-yl)pyrimidin-2-yl]amino]cyclohexyl]pyridine-2-carboxamide (100.0 mg, 0.21 mmol) and pyridine (49.9 mg, 0.63 mmol) in THF (10.0 mL) and the mixture was stirred at 30° C. for 0.5 h. Then dimethylamine hydrochloride (47.4 mg, 1.05 mmol) was added and the mixture was stirred at 30° C. for 12 h. The mixture was concentrated in reduced pressure, and the residue was purified by pre-HPLC (basic condition) to afford title compound (4.0 mg, 3.24%) as white solid.

LCMS: (M+H$^+$): 587.3@2.531 min (10-80% ACN in H$_2$O, 4.5 min). $^1$H NMR: (MeOD, 400 MHz), δ 8.87 (d, J=2.01 Hz, 1H), 8.33 (s, 1H), 8.22 (dd, J=8.53, 2.26 Hz, 1H), 8.03 (d, J=8.66 Hz, 1H), 7.45-7.55 (m, 1H), 7.18-7.32 (m, 3H), 6.91-7.01 (m, 1H), 6.42 (d, J=2.89 Hz, 1H), 6.29 (d, J=15.43 Hz, 1H), 3.97 (br. s., 2H), 3.85 (s, 3H), 3.19 (d, J=6.53 Hz, 2H), 2.29 (s, 7H), 2.08 (d, J=12.30 Hz, 1H), 1.97 (d, J=10.04 Hz, 1H), 1.87 (d, J=13.18 Hz, 1H), 1.23-1.54 (m, 4H).

Example 58. Synthesis of (E)-N-(6-(((((1S,3R)-3-((5-chloro-4-(1H-indol-3-yl) pyrimidin-2-yl)amino)cyclohexyl)(methyl)amino)methyl)pyridin-3-yl)-4-(dimethylamino)but-2-enamide (Compound 377)

(1R,3S)—N1-[5-chloro-4-(1H-indol-3-yl)pyrimidin-2-yl]-N3-[(5-nitro-2-pyridyl)methyl]cyclohexane-1,3-diamine

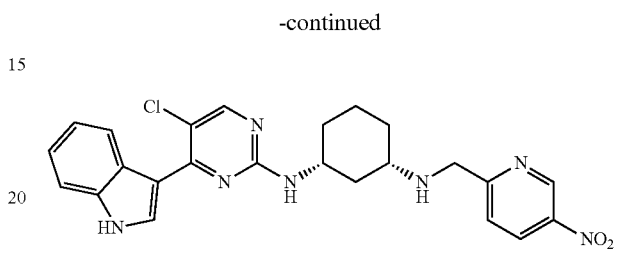

To a stirred solution of (1R,3S)—N1-[5-chloro-4-(1H-indol-3-yl)pyrimidin-2-yl]cyclohexane-1,3-diamine (2.5 g, 7.31 mmol) and 5-nitropyridine-2-carbaldehyde (1.22 g, 8.04 mmol) in DCE (30 mL) was added AcOH (0.44 g, 7.31 mmol) at 11° C. Then the mixture was stirred at 11° C. for 16 h. Then NaBH(OAc)$_3$ (2.32 g, 10.97 mmol) was added, the reaction mixture was stirred at 11° C. for 6 h. The mixture was added to NaHCO$_3$ solution (50 mL), extracted with DCM (50 mL % 5), and the organic layer was washed with brine (100 mL), dried over Na$_2$SO$_4$, filtered and evaporated. The residue was purified by silica gel chromatography (PE/EA=1:1 to DCM/MeOH=50:1) to give title compound (1.6 g, 46%) as brown solid.

(1S,3R)-N3-[5-chloro-4-(1H-indol-3-yl)pyrimidin-2-yl]-N1-methyl-N1-[(5-nitro-2-pyridyl)methyl]cyclohexane-1,3-diamine

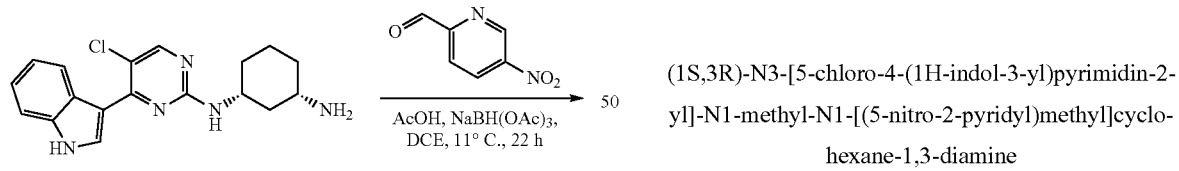

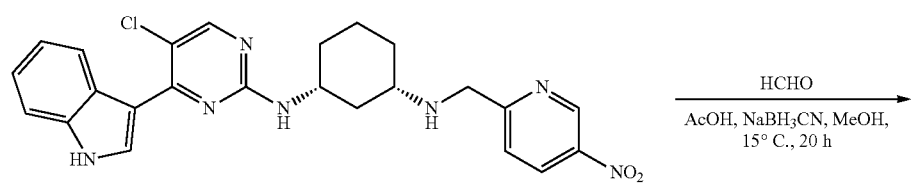

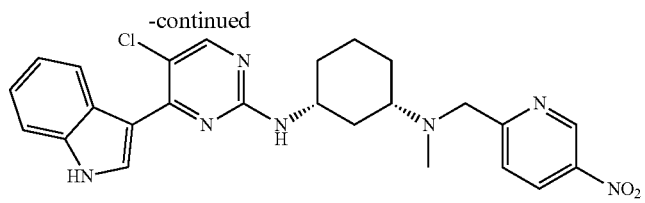

A mixture of (1R,3S)—N1-[5-chloro-4-(1H-indol-3-yl)pyrimidin-2-yl]-N3-[(5-nitro-2-pyridyl)methyl]cyclohexane-1,3-diamine (450 mg, 0.94 mmol), AcOH (56.54 mg, 0.94 mmol) and formaldehyde (76.42 mg, 0.94 mmol) in MeOH (10 mL) was stirred at 15° C. for 4 h. Then NaBH₃CN (88.75 mg, 1.41 mmol) was added and the mixture was stirred at 15° C. for 16 h. The mixture was added to NaHCO₃ solution (20 mL), extracted with DCM (40 mL*4), and the organic layer was washed with brine (100 mL), dried over Na₂SO₄, and evaporated. The residue was purified by silica gel column chromatography (DCM/MeOH=150:1 to 100:1 to 50:1) to give title compound (420 mg, 90.6%) as a yellow solid.

(1S,3R)-N1-[(5-amino-2-pyridyl)methyl]-N3-[5-chloro-4-(1H-indol-3-yl)pyrimidin-2-yl]-N1-methyl-cyclohexane-1,3-diamine (Compound 1057)

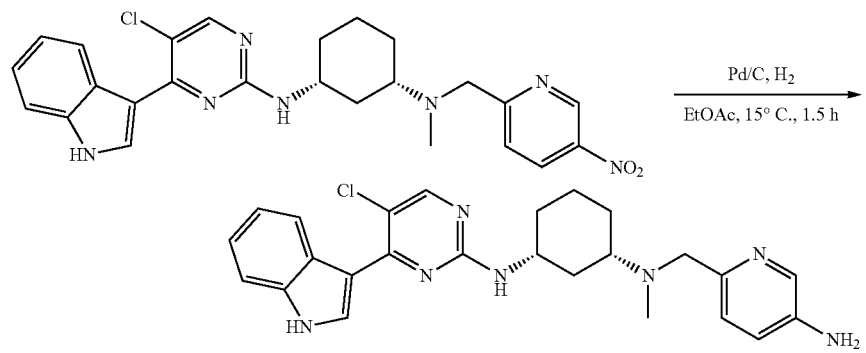

To a solution of (1S,3R)-N3-[5-chloro-4-(1H-indol-3-yl)pyrimidin-2-yl]-N1-methyl-N1-[(5-nitro-2-pyridyl)methyl]cyclohexane-1,3-diamine (370 mg, 752.08 umol) in EtOAc (5 mL) was added Pd/C (10%, 200 mg) under N₂. The suspension was degassed under vacuum and purged with H₂ three times. The mixture was stirred at 15° C. for 1.5 h under H₂ (15 psi). The reaction mixture was filtered through a pad of Celite filter cake which was washed with DCM (30 mL×4) and MeOH (10 mL×4). The filtrate was concentrated to give title compound (350 mg, crude) as a yellow solid.

LCMS: M+H⁺: 462.2@0.648 min (5-95% ACN in H₂O, 1.5 min)

(E)-N-[6-[[[(1S,3R)-3-[[5-chloro-4-(1H-indol-3-yl)pyrimidin-2-yl]amino]cyclohexyl]-methyl-amino]methyl]-3-pyridyl]-4-(dimethylamino)but-2-enamide (Compound 377)

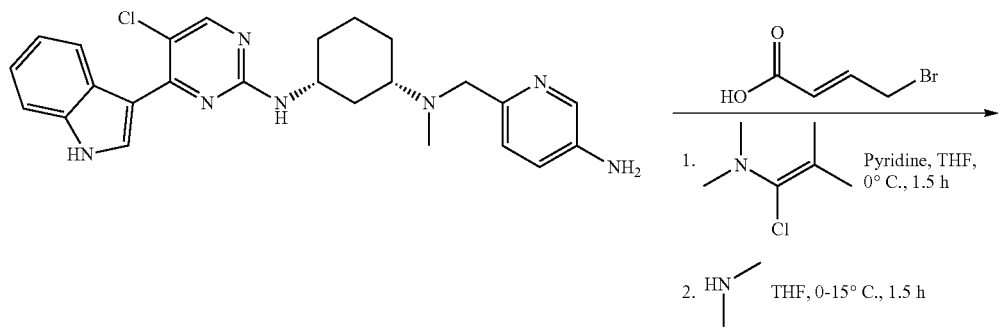

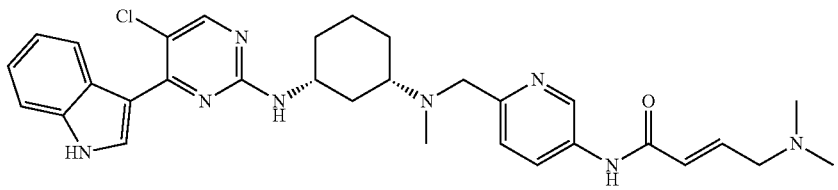

Compound 377

To a mixture of (E)-4-bromobut-2-enoic acid (64.28 mg, 389.62 umol) in DCM (5 mL) was added 1-chloro-N,N,2-trimethyl-prop-1-en-1-amine (52.06 mg, 389.62 umol) at 0° C. under N₂ and the mixture was stirred at 0° C. for 1 h. Then the mixture was added to a solution of (1S,3R)-N1-[(5-amino-2-pyridyl)methyl]-N3-[5-chloro-4-(1H-indol-3-yl)pyrimidin-2-yl]-N1-methyl-cyclohexane-1,3-diamine (150 mg, 324.68 umol) and pyridine (77.05 mg, 974.04 umol) in THF (5 mL) at 0° C. and the reaction mixture was stirred at 0° C. for 0.5 h. N-methylmethanamine (2 M, 1.62 mL, 3250 ummol) was added at 0° C. and the mixture was stirred at 15° C. for 1.5 h. The reaction mixture was concentrated, and the residue was purified by prep-HPLC (TFA). The solution of the prep-HPLC was adjusted with NaHCO₃ to pH=8, extracted with EtOAc/THF (2:1, 30 mL*3). The organic layer was dried over Na₂SO₄, filtered and the filtrate was concentrated to give title compound (31.2 mg, 16.7%) as white solid.

LCMS: ET3422-94-P1B M+H⁺: 573.3@1.977 min (10-80% ACN in H₂O, 4.5 min).

¹HNMR: ET3422-94-P1B (MeOD, 400 MHz), δ 8.72 (br. s., 1H), 8.60 (d, J=7.91 Hz, 1H), 8.47 (br. s., 1H), 8.15 (s, 1H), 8.08 (d, J=6.78 Hz, 1H), 7.45 (t, J=8.78 Hz, 2H), 7.19 (t, J=7.53 Hz, 1H), 7.08 (br. s., 1H), 6.86-6.99 (m, 1H), 6.28 (d, J=15.56 Hz, 1H), 3.97 (br. s., 1H), 3.69-3.90 (m, 2H), 3.21 (d, J=6.15 Hz, 2H), 2.79 (br. s., 1H), 2.39 (br. s., 2H), 2.32 (s, 6H), 2.11 (d, J=9.79 Hz, 1H), 1.89-2.05 (m, 2H), 1.36-1.51 (m, 3H), 1.29 (br. s., 2H), 0.89 (d, J=7.40 Hz, 1H).

Example 59. Synthesis of (E)-N-(6-((((1S,3R)-3-(5-chloro-4-(1H-indol-3-yl)pyrimidin-2-yl)amino)cyclohexyl)amino)methyl)pyridin-3-yl)-4-(dimethylamino)-N-methylbut-2-enamide (Compound 390)

(1R,3S)—N1-(5-chloro-4-(1H-indol-3-yl)pyrimidin-2-yl)-N3-((5-nitropyridin-2-yl)methyl)cyclohexane-1,3-diamine

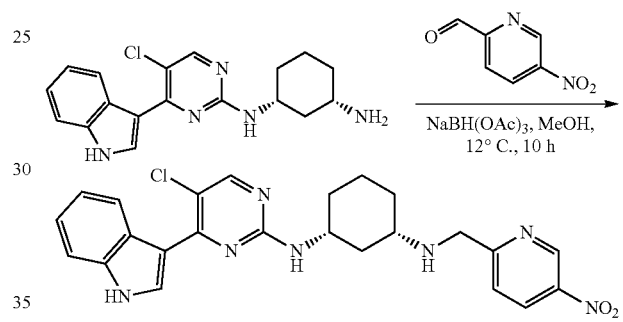

To a solution of (1R,3S)—N1-[5-chloro-4-(1H-indol-3-yl)pyrimidin-2-yl]cyclohexane-1,3-diamine (3.0 g, 8.78 mmol) and 5-nitropyridine-2-carbaldehyde (1.6 g, 10.53 mmol) in MeOH (15 mL) was stirred for 2 h. Then NaBH(OAc)₃ (3.7 g, 17.55 mmol) was added to the reaction. The mixture was stirred at 12° C. for 10 h. The mixture was concentrated under vacuum to afford a residue. The residue was purified by column chromatography to give title compound (3.0 g, 71.5%) as orange solid.

Tert-butyl((1S,3R)-3-((5-chloro-4-(1H-indol-3-yl)pyrimidin-2-yl)amino)cyclohexyl)((5-nitropyridin-2-yl)methyl)carbamate

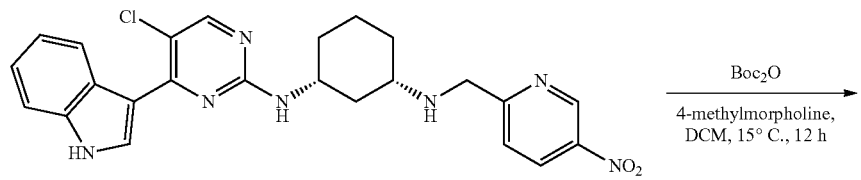

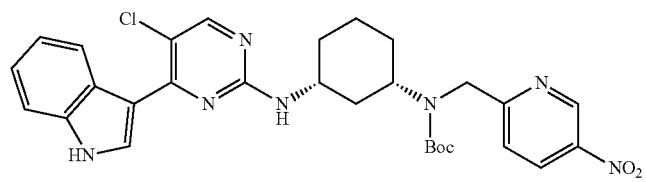

To a solution of (1R,3S)—N1-[5-chloro-4-(1H-indol-3-yl)pyrimidin-2-yl]-N3-[(5-nitro-2-pyridyl)methyl]cyclohexane-1,3-diamine (2.0 g, 4.18 mmol) and TEA (846.9 mg, 8.37 mmol) in DCM (20 mL) was added Boc₂O (1.1 g, 5.02 mmol). The mixture was stirred at 20° C. for 12 h. The mixture was concentrated to get the crude product. The crude product was purified by column to give title compound (1.5 g, 62.1%) as yellow solid.

Tert-butyl((5-aminopyridin-2-yl)methyl)((1S,3R)-3-((5-chloro-4-(1H-indol-3-yl)pyrimidin-2-yl)amino)cyclohexyl)carbamate

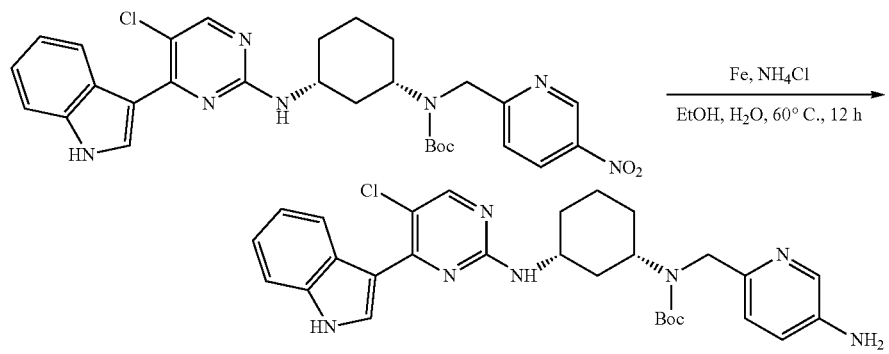

To a solution of tert-butyl N-[(1S,3R)-3-[[5-chloro-4-(1H-indol-3-yl)pyrimidin-2-yl]amino]cyclohexyl]-N-[(5-nitropyridin-2yl)methyl]carbamate (1.5 g, 2.59 mmol) in EtOH (20.0 mL) and H₂O (4.00 mL) was added Fe (723.3 mg, 12.95 mmol) and NH₄Cl (138.5 mg, 2.59 mmol). The reaction was stirred at 60° C. for 12 h. The suspension was filtered and the filtrate was concentrated to give title compound (1.0 g, 70.3%) as light yellow solid without further purification.

Tert-butyl ((1S,3R)-3-((5-chloro-4-(1H-indol-3-yl)pyrimidin-2-yl)amino)cyclohexyl)((5-(methylamino)pyridin-2-yl)methyl)carbamate

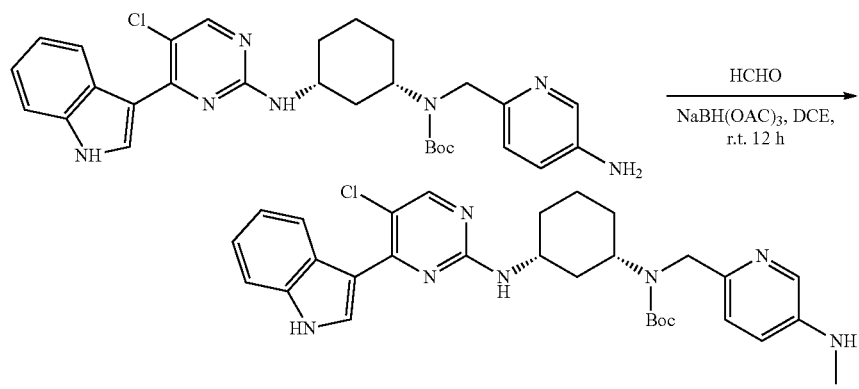

To a solution of tert-butyl((5-aminopyridin-2-yl)methyl)((1S,3R)-3-((5-chloro-4-(1H-indol-3-yl)pyrimidin-2-yl)amino)cyclohexyl)carbamate (500 mg, 0.91 mmol) and HCHO (88.9 mg, 1.1 mmol) in DCE (10 mL) was added NaBH(OAc)₃ (386.7 mg, 1.8 mmol). The reaction was stirred at 15° C. for 12 h. The reaction was concentrated to give the residue. The residue was purified by column to obtain title compound (150 mg, 27.8%) as light yellow solid.

Tert-butyl((1S,3R)-3-((5-chloro-4-(1H-indol-3-yl)pyrimidin-2-yl)amino)cyclohexyl)((5-((E)-4-(dimethylamino)-N-methylbut-2-enamido)pyridin-2-yl)methyl)carbamate

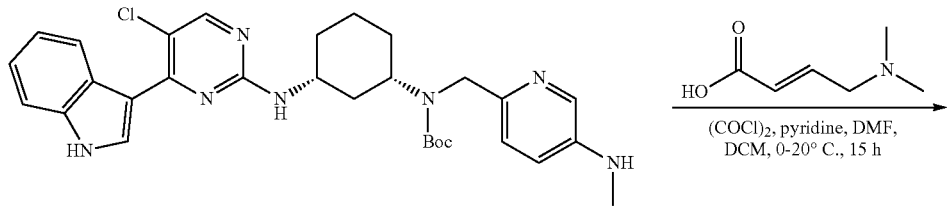

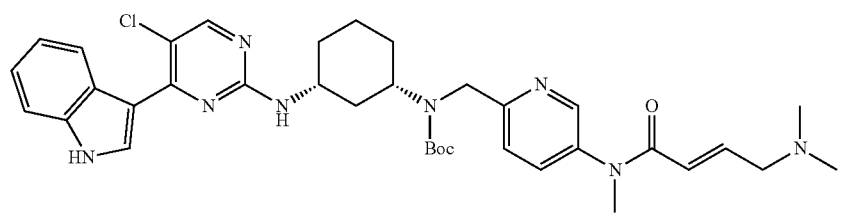

To a solution of (E)-4-(dimethylamino)but-2-enoic acid (66.3 mg, 0.4 mmol, HCl) in THF (5 mL) was added oxalyl dichloride (50.8 mg, 0.4 mmol) and DMF (1.03 uL, 0.013 mmol) at 0° C. The reaction mixture was stirred at 15° C. for 3 h. Then the mixture was added into a solution of tert-butyl ((1S,3R)-3-((5-chloro-4-(1H-indol-3-yl)pyrimidin-2-yl)amino) cyclohexyl)((5-(methylamino)pyridin-2-yl)methyl)carbamate (150 mg, 0.27 mmol) and pyridine (63.33 mg, 0.8 mmol) in DCM (5 mL) at 0° C. The reaction was stirred at 15° C. The reaction was concentrated. The residue was purified by the prep-TLC to give title compound (100 mg, 55.7%) as yellow solid.

(E)-N-(6-((((1S,3R)-3-((5-chloro-4-(1H-indol-3-yl)pyrimidin-2-yl)amino)cyclohexyl)amino)methyl)pyridin-3-yl)-4-(dimethylamino)-N-methylbut-2-enamide (Compound 390)

To a solution of tert-butyl((1S,3R)-3-((5-chloro-4-(1H-indol-3-yl) pyrimidin-2-yl)amino) cyclohexyl)((5-((E)-4-(dimethylamino)-N-methylbut-2-enamido)pyridin-2-yl) methyl)carbamate (100 mg, 0.15 mmol) in DCM (20 mL) was added TFA (4.0 mL) at 0° C. The reaction was stirred at 15° C. for 9 h. The mixture was concentrated to give a residue. The residue was purified by pre-HPLC (HCl condition) to give title compound (24.0 mg, 26%, HCl salt) as yellow solid.

LCMS: (M+H$^+$):573.4@1.959 min (10-80% ACN in H$_2$O, 4.5 min). $^1$H NMR (MeOD, 400 MHz), δ 8.98 (br. s., 1H), 8.56 (br. s., 2H), 8.22 (br. s., 1H), 7.85 (br. s., 1H), 7.58 (br. s., 2H), 7.34 (br. s., 2H), 6.79 (br. s., 1H), 6.43 (br. s., 1H), 4.53 (br. s., 2H), 3.88 (br. s., 2H), 3.57 (br. s., 1H), 3.40 (br. s., 3H), 3.01-2.62 (m, 8H), 2.38 (br. s., 1H), 2.26 (br. s., 1H), 2.09 (br. s., 1H), 1.78 (d, J=9.29 Hz, 1H), 1.70-1.52 (m, 3H).

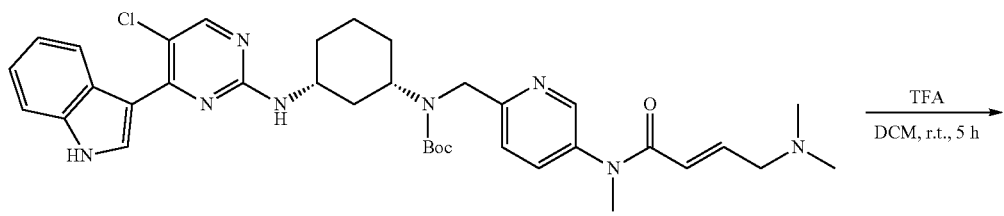

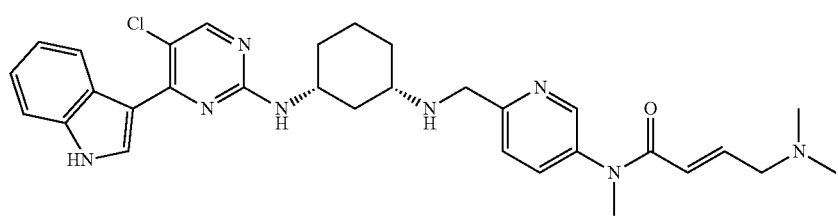

Example 60. Synthesis of 5-[[(E)-4-(dimethylamino)but-2-enoyl]amino]-N-[(1S,3R)-3-[[4-(1H-indol-3-yl)-5-(trifluoromethyl)pyrimidin-2-yl]amino]-1-methyl-cyclohexyl]pyridine-2-carboxamide (Compound 399)

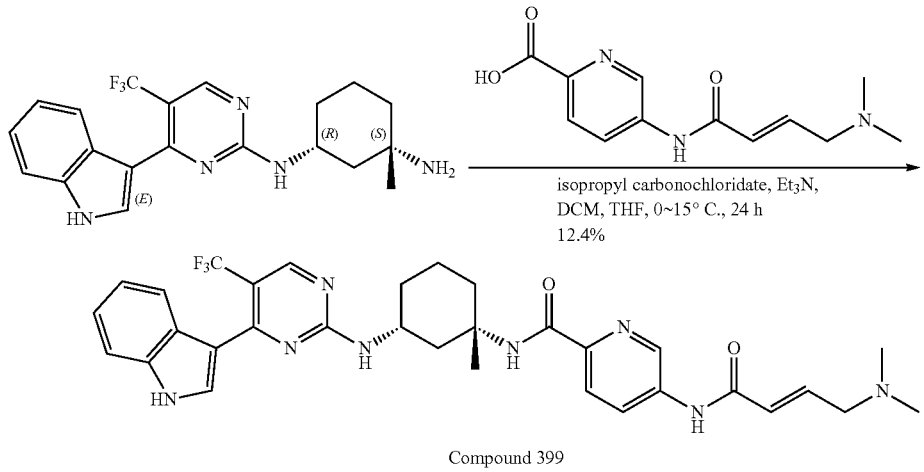

Compound 399

To a solution of 5-[[(E)-4-(dimethylamino)but-2-enoyl]amino]pyridine-2-carboxylic acid (192.03 mg, 528.99 umol, TFA salt) in THF (5 mL) and DCM (5 mL) was added Et₃N (129.92 mg, 1.28 mmol) and isopropyl carbonochloridate (94.41 mg, 770.37 umol) at 0° C. The reaction was stirred at 15° C. for 3 h. Then the mixture was added into (1S,3R)-N3-[4-(1H-indol-3-yl)-5-(trifluoromethyl)pyrimidin-2-yl]-1-methyl-cyclohexane-1,3-diamine (100 mg, 256.79 umol) in DCM (5 mL). The reaction was stirred at 15° C. for 21 h. The reaction was concentrated to give the residue. The residue was purified by prep-HPLC (HCl condition) to give title compound (22.0 mg, 12.4%, HCl salt) as a brown solid.

LCMS: (M+H$^+$): 621.4@2.457 min (10-80% ACN in H₂O, 4.5 min). $^1$H NMR: (MeOD, 400 MHz); δ 9.12 (br. s., 1H), 9.17-7.99 (m, 5H), 7.57 (br. s., 1H), 7.13-7.61 (m, 2H), 6.98 (dt, J=14.93, 7.34 Hz, 1H), 6.66 (d, J=14.56 Hz, 1H), 4.66-4.51 (m, 1H), 4.06 (br. s., 2H), 2.95 (br. s., 6H), 2.72-2.55 (m, 1H), 2.21 (d, J=11.29 Hz, 2H), 2.10-1.89 (m, 3H), 1.78 (br. s., 1H), 1.67 (d, J=6.78 Hz, 3H), 1.52 (d, J=8.03 Hz, 1H).

Example 61. Synthesis of (E)-4-(dimethylamino)-N-[6-[[[(1S,3R)-3-[[4-(1H-indol-3-yl)-5-(trifluoromethyl)pyrimidin-2-yl]amino]-1-methylcyclohexyl]amino]methyl]-3-pyridyl]but-2-enamide (Compound 403)

(1S,3R)-N3-[4-(1H-indol-3-yl)-5-(trifluoromethyl)pyrimidin-2-yl]-1-methyl-N1-[(5-nitro-2-pyridyl)methyl]cyclohexane-1,3-diamine

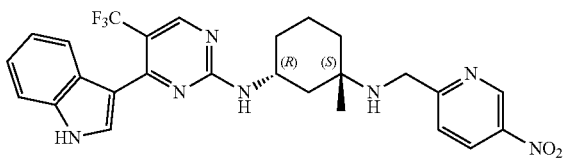

To a solution of (1S,3R)-N3-[4-(1H-indol-3-yl)-5-(trifluoromethyl)pyrimidin-2-yl]-1-methyl-cyclohexane-1,3-diamine (300 mg, 0.77 mmol) and 5-nitropyridine-2-carbaldehyde (152.34 mg, 1.0 mmol) in DCE (10 mL) was added HOAc (46.26 mg, 0.77 mmol) at 0° C. and the mixture was stirred at 15° C. for 1 h. Then NaBH(OAc)₃ (489.82 mg, 2.31 mmol) was added at 0° C. and the mixture was stirred at 15° C. for 1 h. The mixture was concentrated, and the residue was purified by column to give title compound (200 mg, 42%) as yellow solid.

(1S,3R)-N1-[(5-amino-2-pyridyl)methyl]-N3-[4-(1H-indol-3-yl)-5-(trifluoromethyl)pyrimidin-2-yl]-1-methyl-cyclohexane-1,3-diamine (Compound 1058)

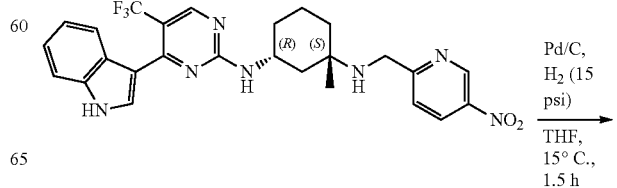

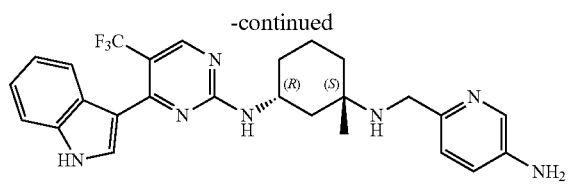

To a solution of (1S,3R)-N3-[4-(1H-indol-3-yl)-5-(trifluoromethyl)pyrimidin-2-yl]-1-methyl-N1-[(5-nitro-2-pyridyl)methyl]cyclohexane-1,3-diamine (100 mg, 190.29 umol) in THF (10 mL) was added Pd—C (5%, 100 mg) under $N_2$. The suspension was degassed under vacuum and purged with $H_2$ several times. The mixture was stirred at 15° C. for 1.5 h under $H_2$ (15 psi). The reaction mixture was filtered, and the filtrate was concentrated to give title compound (70 mg, 66.8%) was used into the next step without further purification as a yellow solid. LCMS: (M+H$^+$): 496.2@1.643 min (10-80% ACN in $H_2O$, 4.5 min)

(E)-4-(dimethylamino)-N-[6-[[[(1S,3R)-3-[[4-(1H-indol-3-yl)-5-(trifluoromethyl)pyrmidin-2-yl]amino]-1-methylcyclohexyl]amino]methyl]-3-pyridyl]but-2-enamide (Compound 403)

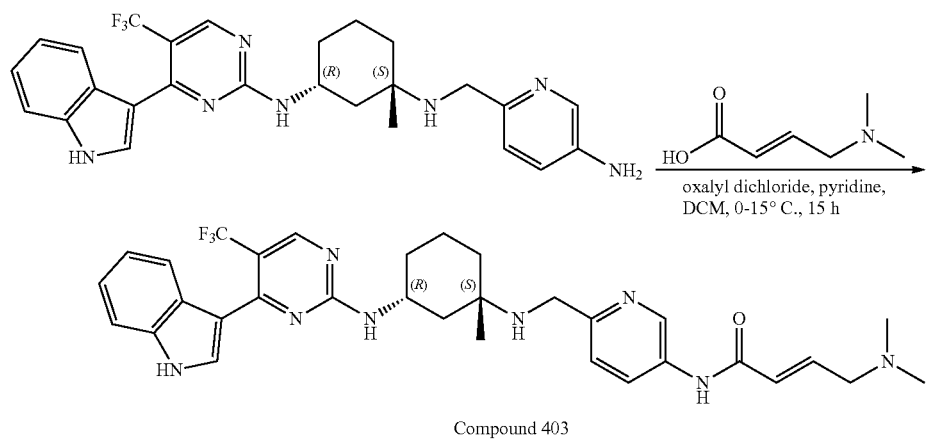

Compound 403

To a solution of (E)-4-(dimethylamino)but-2-enoic acid (46.79 mg, 282.52 umol) in DCM (5 mL) was added oxalyl dichloride (35.86 mg, 282.52 umol) and DMF (0.52 mg, 7.06 umol) at 0° C. for 3 h. Then the mixture was added to a solution of (1S,3R)-N1-[(5-amino-2-pyridyl)methyl]-N3-[4-(1H-indol-3-yl)-5-(trifluoromethyl)pyrimidin-2-yl]-1-methyl-cyclohexane-1,3-diamine (70 mg, 141.26 umol) in DCM (5 mL) at 0° C. and the reaction was stirred at 15° C. for 12 h. The mixture was concentrated under reduced pressure, and the residue was purified by prep-HPLC to give title compound (36.2 mg, 38%, HCl salt) as yellow solid. LCMS: (M+H$^+$): 607.4@2.148 min (10-80% ACN in $H_2O$, 4.5 min). $^1$H NMR: (MeOD, 400 MHz), δ 9.17 (br. s., 1H), 8.61-8.47 (m, 2H), 8.41-8.27 (m, 2H), 7.84 (d, J=8.28 Hz, 1H), 7.58 (br. s., 1H), 7.36 (d, J=3.51 Hz, 2H), 6.96 (dt, J=15.06, 7.28 Hz, 1H), 6.65 (d, J=15.31 Hz, 1H), 4.62 (br. s., 1H), 4.50 (br. s., 2H), 4.04 (d, J=7.03 Hz, 2H), 2.94 (s, 6H), 2.50 (d, J=10.29 Hz, 1H), 2.27 (d, J=11.54 Hz, 1H), 2.11-1.96 (m, 3H), 1.91-1.76 (m, 2H), 1.72-1.66 (m, 3H), 1.59 (d, J=10.79 Hz, 1H).

Example 62. Synthesis of 5-[[(E)-4-(dimethylamino)but-2-enoyl]amino]-N-[(1S,3R)-3-[[5-ethyl-4-(1H-indol-3-yl)pyrimidin-2-yl]amino]-1-methyl-cyclohexyl]pyridine-2-carboxamide (Compound 407)

BenzylN-[(1S,3R)-3-[[4-[1-(benzenesulfonyl)indol-3-yl]-5-vinyl-pyrimidin-2-yl]amino]-1-methyl-cyclohexyl]carbamate

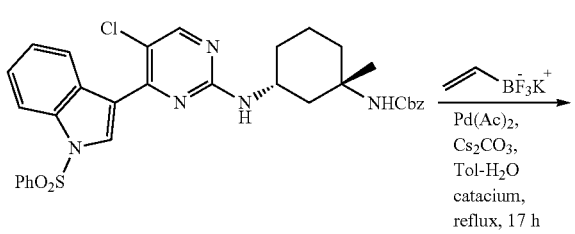

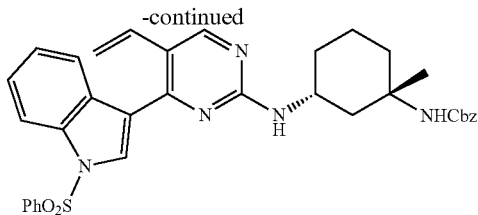

Benzyl-N-[(1S,3R)-3-[[4-[1-(benzenesulfonyl)indol-3-yl]-5-chloro-pyrimidin-2-yl]amino]-1-methyl-cyclohexyl]carbamate (11 g, 17.46 mmol), potassium trifluoro(vinyl)boranuide (11.69 g, 87.28 mmol), $Cs_2CO_3$ (17.06 g, 52.37 mmol), Pd(OAc)$_2$ (1.96 g, 8.73 mmol) and bis(1-adamantyl)-butyl-phosphane (6.26 g, 17.46 mmol) in toluene (100 mL) and $H_2O$ (20 mL) was degassed under vacuum and purged with $N_2$ three times. The reaction was heated to 120° C. and stirred for 17 h. The mixture was poured into water (100 mL), extracted with EtOAc (50 mL*3), and the organic layer was washed with brine (100 mL), dried over $Na_2SO_4$, concentrate. The residue was purified by silica gel chromatography (DCM/Ethyl acetate=80/1, 20/1) to give title compound (6 g, 55.2%) as brown solid.

(1S,3R)-N3-[4-[1-(benzenesulfonyl)indol-3-yl]-5-ethyl-pyrimidin-2-yl]-1-methyl-cyclohexane-1,3-diamine

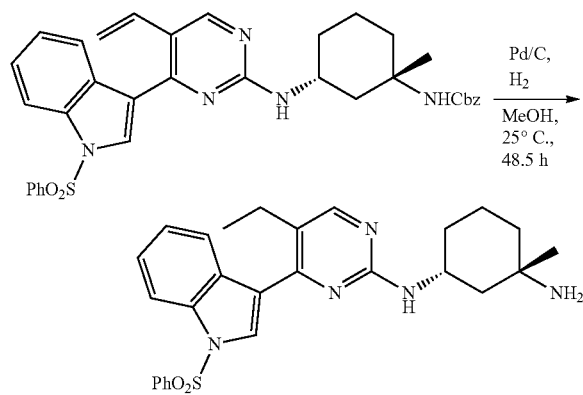

To a solution of benzyl N-[(1S,3R)-3-[[4-[1-(benzenesulfonyl)indol-3-yl]-5-vinyl-pyrimidin-2-yl]amino]-1-methyl-cyclohexyl]carbamate (6 g, 9.65 mmol) in MeOH (50 mL) and DCM (20 mL) was added Pd/C (3 g) under $N_2$. The suspension was degassed under vacuum and purged with $H_2$ three times. The mixture was stirred at 25° C. for 48.5 h under $H_2$ (50 psi). The mixture was filtered through a pad of Celite filter cake and the filtrate was concentrated to give title compound (4 g, crude) as brown solid.

(1S,3R)-N3-[5-ethyl-4-(1H-indol-3-yl)pyrimidin-2-yl]-1-methyl-cyclohexane-1,3-diamine

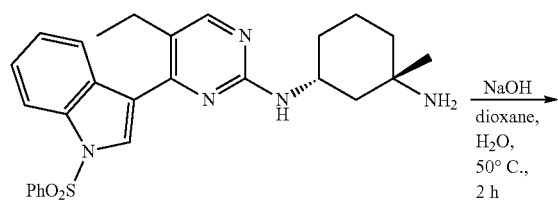

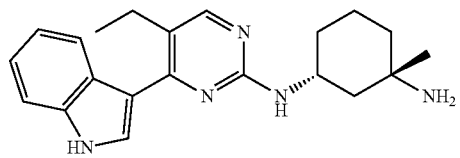

A mixture of (1S,3R)-N3-[4-[1-(benzenesulfonyl)indol-3-yl]-5-ethyl-pyrimidin-2-yl]-1-methyl-cyclohexane-1,3-diamine (1.00 g, 2.04 mmol) and NaOH (0.41 g, 10.2 mmol) in dioxane (10 mL) and $H_2O$ (1 mL) was stirred at 50° C. for 2 h. The reaction mixture was added to water (40 mL) and extracted with DCM (30 mL*5). The organic layer was wash with brine (50 mL), dried over $Na_2SO_4$, evaporated to give title compound (0.7 g, crude) as yellow solid.

5-[[(E)-4-(dimethylamino)but-2-enoyl]amino]-N-[(1S,3R)-3-[[5-ethyl-4-(1H-indol-3-yl)pyrimidin-2-yl]amino]-1-methyl-cyclohexyl]pyridine-2-carboxamide

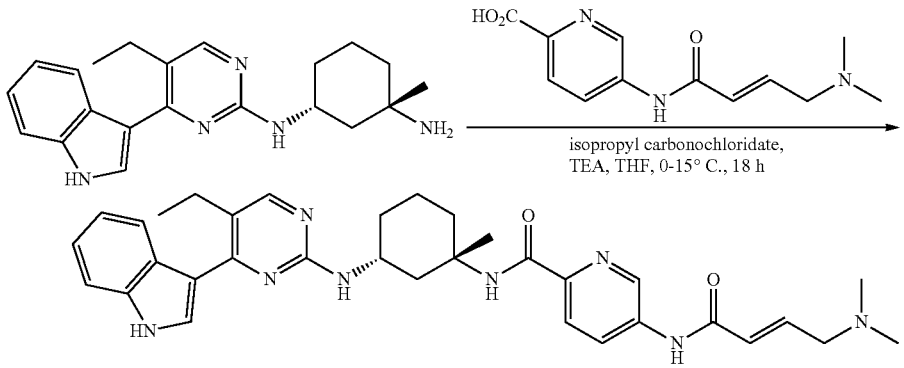

Compound 407

To a mixture of 5-[[(E)-4-(dimethylamino)but-2-enoyl]amino]pyridine-2-carboxylic acid (142.7 mg, 572.30 umol) and TEA (173.7 mg, 1720 umol) in THF (15 mL) was added isopropyl carbonochloridate (70.13 mg, 572.30 umol) at 0° C. and the mixture was stirred for 2 h. Then (1S,3R)-N3-[5-ethyl-4-(1H-indol-3-yl)pyrimidin-2-yl]-1-methyl-cyclohexane-1,3-diamine (200 mg, 572.30 umol) was added and the mixture was stirred at 15° C. for 16 h. The mixture was added to $H_2O$ (20 mL) and extract with EA:THF (3:1, 20 mL*3). The organic layer was combined and evaporated, and the residue was purified by prep-HPLC to afford title compound (87 mg, 26.1% yield) as yellow solid. LCMS: M+H$^+$: 581.4/291.4@2.174 min (10-80% ACN in $H_2O$, 4.5 min). $^1$H NMR: (MeOD, 400 MHz); δ 9.17 (br. s., 1H), 8.67-8.25 (m, 4H), 7.92 (s, 1H), 7.52 (br. s., 1H), 7.32 (br. s., 2H), 7.08-6.96 (m, 1H), 6.65 (d, J=15.31 Hz, 1H), 4.52 (br. s., 1H), 4.08 (d, J=7.03 Hz, 2H), 3.00-2.93 (m, 8H), 2.62 (br. s., 1H), 2.23-1.95 (m, 5H), 1.83-1.58 (m, 5H), 1.38 (t, J=7.28 Hz, 3H).

Example 63. Synthesis of (E)-4-(dimethylamino)-N-[6-[[[(1S,3R)-3-[[5-ethyl-4-(1H-indol-3-yl)pyrimidin-2-yl]amino]-1-methylcyclohexyl]amino]methyl]-3-pyridyl]but-2-enamide (Compound 411)

(1S,3R)-N3-[5-ethyl-4-(1H-indol-3-yl)pyrimidin-2-yl]-1-methyl-N1-[(5-nitro-2-pyridyl)methyl]cyclohexane-1,3-diamine

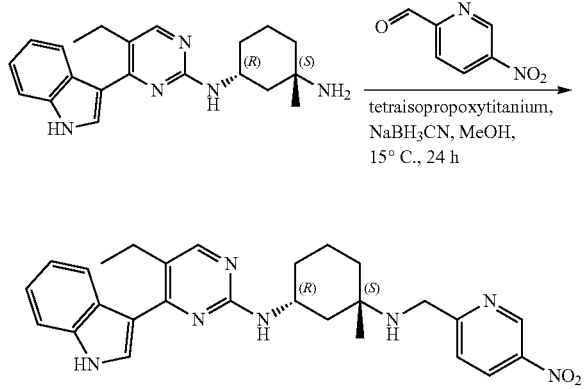

A mixture of (1S,3R)-N3-[5-ethyl-4-(1H-indol-3-yl)pyrimidin-2-yl]-1-methyl-cyclohexane-1,3-diamine (550 mg, 1.57 mmol), 5-nitropyridine-2-carbaldehyde (263.3 mg, 1.73 mmol) and tetraisopropoxytitanium (447.3 mg, 1.57 mmol) in MeOH (10 mL) was stirred at 15° C. for 17 h. Then NaBH₃CN (148.3 mg, 2.36 mmol) was added and the mixture was stirred at 15° C. for 7 h. The reaction mixture was poured into water (50 mL), extracted with DCM (20 mL*4), the organic layer was washed with brine (50 mL), dried over $Na_2SO_4$, and concentrated. The residue was purified by silica gel chromatography (DCM/MeOH=80/1-30/1) to give title compound (320 mg, 41.9%) as yellow solid.

(1S,3R)-N1-[(5-amino-2-pyridyl)methyl]-N3-[5-ethyl-4-(1H-indol-3-yl)pyrimidin-2-yl]-1-methylcyclohexane-1,3-diamine (Compound 1059)

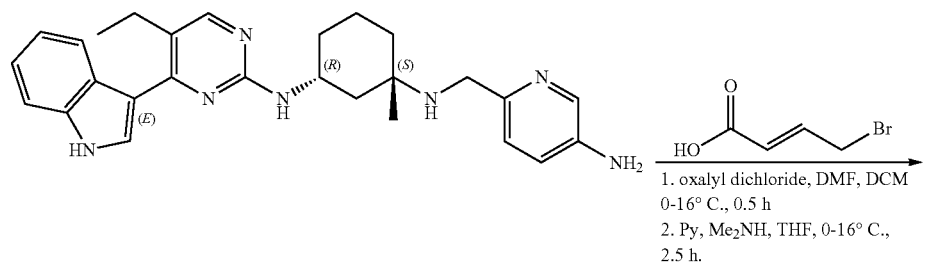

To a mixture of (1S,3R)-N3-[5-ethyl-4-(1H-indol-3-yl)pyrimidin-2-yl]-1-methyl-N1-[(5-nitro-2-pyridyl)methyl]cyclohexane-1,3-diamine (300 mg, 617.82 umol) in EtOAc (20 mL) was added Pd/C (200 mg) under $N_2$. The suspension was degassed under vacuum and purged with $H_2$ several times. The mixture was stirred at 15° C. for 2 h under $H_2$ ball (15 psi). The reaction solution was filtered and the filter was concentrated to give title compound (280 mg, 99.4%) as light yellow solid. LCMS: M+H⁺: 456.1@0.739 min (5-95% ACN in $H_2O$, 1.5 min).

(E)-4-(dimethylamino)-N-[6-[[[1S,3R)-3-[[5-ethyl-4-(1H-indol-3-yl)pyrimidin-2-yl]amino]-1-methylcyclohexyl]amino]methyl]-3-pyridyl]but-2-enamide (Compound 411)

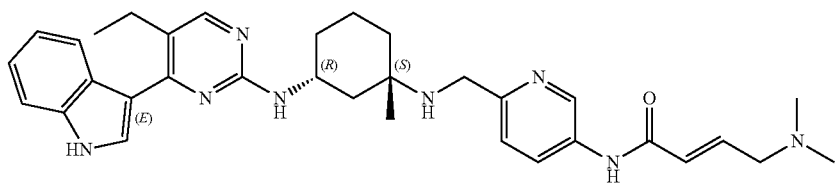

Compound 411

To a stirred solution of (E)-4-bromobut-2-enoic acid (36.21 mg, 219.49 umol) in DCM (5 mL) was added oxalyldichloride (27.86 mg, 219.49 umol) dropwise at 0° C., followed by DMF (1.60 mg, 21.95 umol), and the mixture was stirred at 16° C. for 0.5 h. This mixture was added to a solution of 1S,3R)-N1-[(5-amino-2-pyridyl)methyl]-N3-[5-ethyl-4-(1H-indol-3-yl)

pyrimidin-2-yl]-1-methyl-cyclohexane-1,3-diamine (100 mg, 219.49 umol) and pyridine (52.1 mg, 658.47 umol) in DCM (5 mL) at 0° C. dropwise and the mixture was stirred at 0° C. for 0.5 h. Then N-methylmethanamine (98.95 mg, 2.19 mmol) was added at 0° C., the reaction mixture was allowed to warm to 16° C., and stirred for 2 h. The mixture was concentrated, and the residue was purified by acidic prep-HPLC (HCl) to afford title compound (15.70 mg, 11.8%, HCl) as dark yellow solid. LCMS: M+H$^+$: 567.4@1.860 min (10-80% ACN in H$_2$O, 4.5 min).

$^1$HNMR: (MeOD, 400 MHz); δ 9.10 (br. s., 1H), 8.59 (d, J=7.28 Hz, 1H), 8.38-8.25 (m, 2H), 7.99 (s, 1H), 7.72 (d, J=8.28 Hz, 1H), 7.56 (d, J=7.53 Hz, 1H), 7.38-7.23 (m, 2H), 6.94 (dt, J=15.00, 7.18 Hz, 1H), 6.63 (d, J=15.06 Hz, 1H), 4.46 (br. s., 3H), 4.03 (d, J=7.03 Hz, 2H), 3.03-2.88 (m, 8H), 2.49 (d, J=11.29 Hz, 1H), 2.26 (d, J=11.04 Hz, 1H), 2.06 (br. s., 2H), 1.96-1.77 (m, 3H), 1.68 (s, 3H), 1.54 (d, J=12.80 Hz, 1H), 1.36 (t, J=7.28 Hz, 3H).

Example 64. Synthesis of 5-[[(E)-4-(dimethylamino)but-2-enoyl]amino]-N-[(1S,3R)-3-[[5-ethyl-4-(2-methyl-1H-indol-3-yl)pyrimidin-2-yl]amino]-1-methyl-cyclohexyl]pyridine-2-carboxamide (Compound 412)

1-(benzenesulfonyl)-3-(2,5-dichloropyrimidin-4-yl)-2-methyl-indole

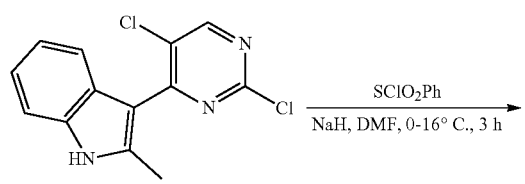

To a stirred solution of 3-(2,5-dichloropyrimidin-4-yl)-2-methyl-1H-indole (5.00 g, 17.98 mmol) in DMF (50 mL) was added NaH (1.44 g, 35.96 mmol) at 0° C. under N$_2$ and the mixture was stirred at 0° C. for 0.5 h. Then benzenesulfonyl chloride (4.76 g, 26.97 mmol) was added at 0° C. and the mixture was allowed to warm to 16° C. and stirred for 3 h. The mixture was poured into water (100 mL), extracted by EtOAc (40 mL*3), and the organic layer was washed with water (100 mL*2) and brine (100 mL), dried over Na$_2$SO$_4$ and concentrated. The residue was purified by silica gel chromatography (column height: 250 mm, diameter: 100 mm, 100-200 mesh silica gel, Petroleum ether/Ethyl acetate=8/1, 5/1) to give title compound (6.50 g, 86.4%) as light yellow solid.

Benzyl N-[(1S,3R)-3-[[4-[1-(benzenesulfonyl)-2-methyl-indol-3-yl]-5-chloro-pyrimidin-2-yl]amino]-1-methyl-cyclohexyl]carbamate

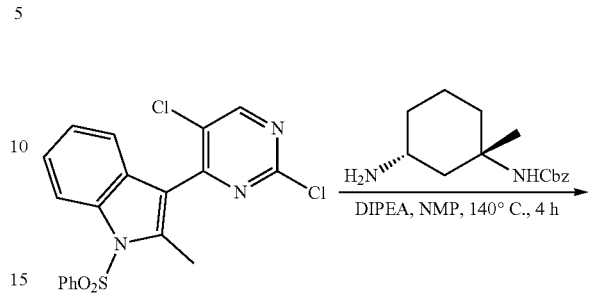

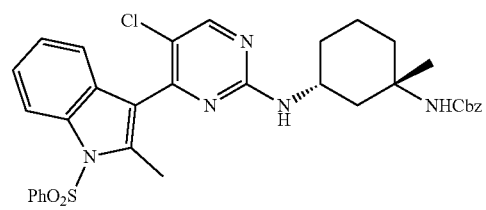

A mixture of 1-(benzenesulfonyl)-3-(2,5-dichloropyrimidin-4-yl)-2-methyl-indole (6.50 g, 15.54 mmol), benzyl N-[(1S,3R)-3-amino-1-methyl-cyclohexyl]carbamate (4.89 g, 18.65 mmol) and DIPEA (6.02 g, 46.62 mmol) in NMP (80 mL) was heated to 140° C. and stirred for 4 h. The reaction mixture was cooled to r.t., diluted with EtOAc (80 mL), washed with water (100 mL*3) and brine (100 mL), dried over Na$_2$SO$_4$, filtered, and concentrated. The residue was purified by silica gel chromatography eluted with Petroleum ether/Ethyl acetate=8:1-4:1) to give title compound (9.00 g, 89.9%) as light yellow solid.

Benzyl N-[(1S,3R)-3-[[4-[1-(benzenesulfonyl)-2-methyl-indol-3-yl]-5-vinyl-pyrimidin-2-yl]amino]-1-methylcyclohexyl]carbamate

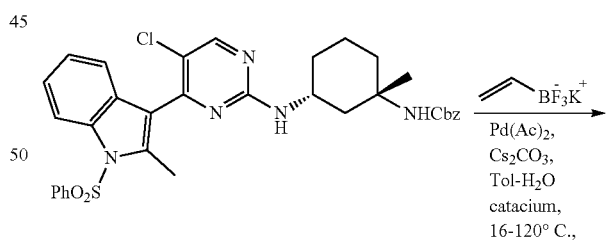

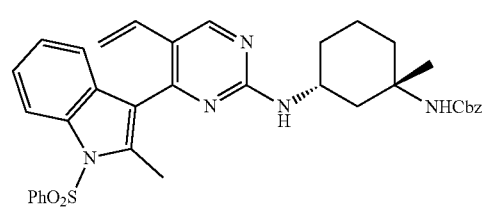

A mixture of benzyl N-[(1S,3R)-3-[[4-[1-(benzenesulfonyl)-2-methyl-indol-3-yl]-5-chloro-pyrimidin-2-yl]amino]-1-methylcyclohexyl]carbamate (4.00 g, 6.21 mmol), potassium trifluoro(vinyl)boranuide (4.16 g, 31.05 mmol), Cs$_2$CO$_3$ (6.07 g, 18.63 mmol) and Pd(OAc)$_2$ (697.04 mg, 3.11 mmol), bis(1-adamantyl)-butyl-phosphane (2.23 g, 6.21 mmol) in toluene (40 mL) and H$_2$O (8 mL) was degassed under vacuum and purged with N$_2$ three times at 16° C. Then the mixture was stirred at 120° C. under N$_2$ for 12 h. The reaction mixture was poured into water (100 mL), extracted with EtOAc (40 mL*4), and the organic layer was dried over Na$_2$SO$_4$, and evaporated. The residue was purified by silica gel chromatography (100-200 mesh silica gel, Petroleum ether/Ethyl acetate=6/1, 3/1) to give title compound (560.00 mg, 14.1%) as brown solid.

Benzyl N-[(1S,3R)-3-[[4-[1-(benzenesulfonyl)-2-methyl-indol-3-yl]-5-vinyl-pyrimidin-2-yl]amino]-1-methylcyclohexyl]carbamate

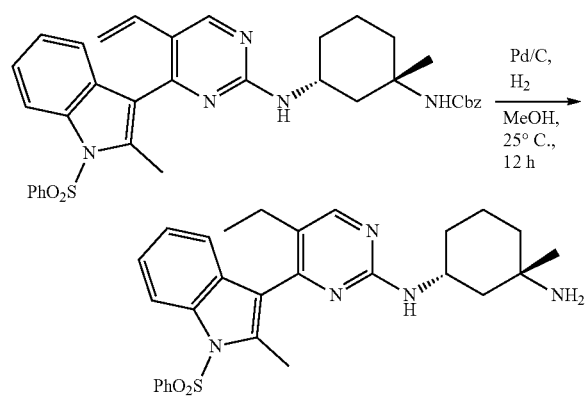

To a solution of benzyl N-[(1S,3R)-3-[[4-[1-(benzenesulfonyl)-2-methyl-indol-3-yl]-5-vinyl-pyrimidin-2-yl]amino]-1-methylcyclohexyl]carbamate (730 mg, 1.15 mmol) in MeOH (10 mL) and DCM (2 mL) was added Pd/C (500 mg) under N$_2$. The suspension was degassed under vacuum and purged with H$_2$ three times. The mixture was stirred at 25° C. for 24 h under H$_2$ (50 psi). The reaction mixture was filtered through a pad of Celite. The filter cake was washed with MeOH (10 mL×2) and DCM (10 mL×4), and the filtrate was concentrated to give title compound (250 mg, crude) as brown solid.

(1S,3R)-N3-[5-ethyl-4-(2-methyl-1H-indol-3-yl)pyrimidin-2-yl]-1-methyl-cyclohexane-1,3-diamine

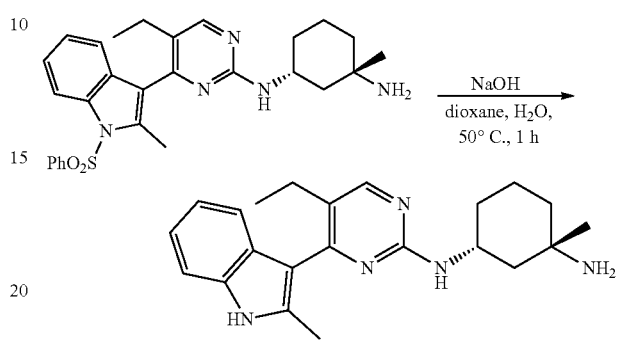

A mixture of (1S,3R)-N3-[4-[1-(benzenesulfonyl)-2-methyl-indol-3-yl]-5-ethyl-pyrimidin-2-yl]-1-methyl-cyclohexane-1,3-diamine (260 mg, 516.22 umol) and NaOH (62.4 mg, 1.56 mmol) in MeOH (5 mL) and H$_2$O (1 mL) was heated to 70° C. and stirred for 1 h. The mixture was poured into water (30 mL), extracted with DCM (10 mL*5), and the organic layer was washed with brine (30 mL), dried over Na$_2$SO$_4$, filtered and concentrated to give title compound (160 mg, crude) as light yellow solid.

5-[[(E)-4-(dimethylamino)but-2-enoyl]amino]-N-[(1S,3R)-3-[[5-ethyl-4-(2-methyl-1H-indol-3-yl)pyrimidin-2-yl]amino]-1-methyl-cyclohexyl]pyridine-2-carboxamide (Compound 412)

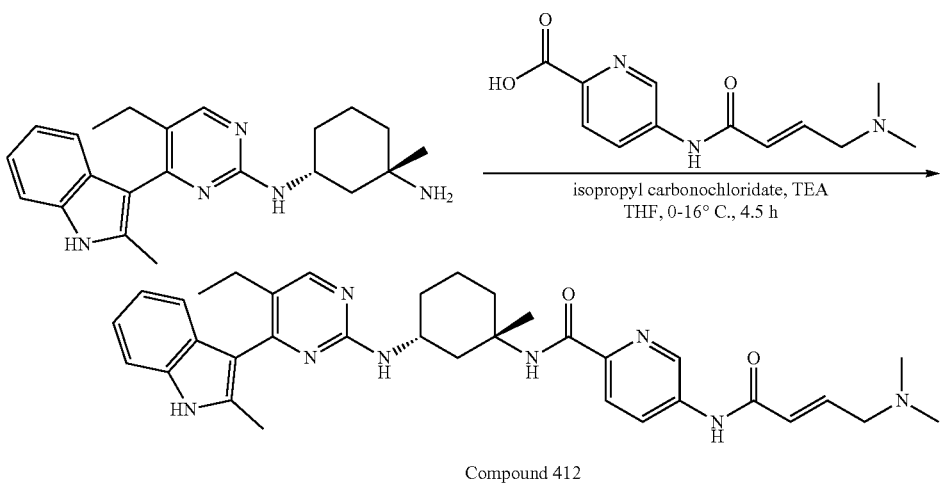

Compound 412

To a stirred solution of 5-[[(E)-4-(dimethylamino)but-2-enoyl]amino]pyridine-2-carboxylic acid (68.5 mg, 275.10 umol) and TEA (83.5 mg, 825.3 umol) in THF (3 mL) was added isopropyl carbonochloridate (33.7 mg, 275.10 umol) at 0° C. slowly. The reaction mixture was stirred at 16° C. for 3 h. Then this mixture was added to a stirred solution of (1S,3R)-N3-[5-ethyl-4-(2-methyl-1H-indol-3-yl)pyrimidin-2-yl]-1-methyl-cyclohexane-1,3-diamine (100 mg, 275.10 umol) and TEA (55.6 mg, 550.20 umol) in THF (5 mL) at 0° C. and the mixture was allowed to warm to 16° C. and stirred for 1.5 h. The reaction mixture was concentrated, the residue was purified by acidic prep-HPLC (HCl) to give title compound (72.70 mg, 41.8%, HCl) as dark yellow solid. LCMS: M+H+: 595.4@2.216 min (10-80% ACN in H₂O, 4.5 min).

¹HNMR (MeOD, 400 MHz); δ 9.17 (br. s., 1H), 8.61-8.20 (m, 3H), 7.40 (d, J=7.78 Hz, 2H), 7.23-7.10 (m, 2H), 7.05-6.94 (m, 1H), 6.65 (d, J=15.31 Hz, 1H), 4.29 (t, J=6.53 Hz, 1H), 4.06 (d, J=7.03 Hz, 2H), 2.95 (s, 6H), 2.66 (d, J=6.27 Hz, 2H), 2.55 (br. s., 4H), 2.14-2.05 (m, 1H), 1.95 (br. s., 3H), 1.79-1.61 (m, 2H), 1.57 (s, 3H), 1.46 (dd, J=14.93, 7.40 Hz, 1H), 1.07-0.95 (m, 3H).

Example 65. Synthesis of (E)-4-(dimethylamino)-N-[6-[[[(1S,3R)-3-[[5-ethyl-4-(1H-indazol-3-yl)pyrimidin-2-yl]amino]-1-methyl-cyclohexyl]amino]methyl]-3-pyridyl]but-2-enamide (Compound 413)

Benzyl N-[(1S,3R)-3-[[5-chloro-4-[2-(2-trimethylsilylethoxymethyl)indazol-3-yl]pyrimidin-2-yl]amino]-1-methyl-cyclohexyl]carbamate A solution of 2-[[3-(2,5-dichloropyrimidin-4-yl)indazol-2-yl]methoxy]ethyl-trimethyl-silane (5 g, 12.65 mmol), Benzyl N-[(1S,3R)-3-amino-1-methyl-cyclohexyl]carbamate (3.98 g, 15.18 mmol) and DIEA (8.17 g, 63.25 mmol) in DMF (20 mL) and EtOH (20 mL) was added and stirred at 120° C. for 4 h. The mixture was washed with water (30 mL) and extracted by EA (50 mL*3). The organic layer was combined, dried over Na₂SO₄, and evaporated under reduced pressure to dryness. The residue was purified by column PE/EA=(10:1-8:1-5:1-4:1) to give title compound (7 g, 89.07%) as yellow solid.

Benzyl N-[(1S,3R)-1-methyl-3-[[4-[2-(2-trimethylsilylethoxymethyl)indazol-3-yl]-5-vinyl-pyrimidin-2-yl]amino]cyclohexyl]carbamat

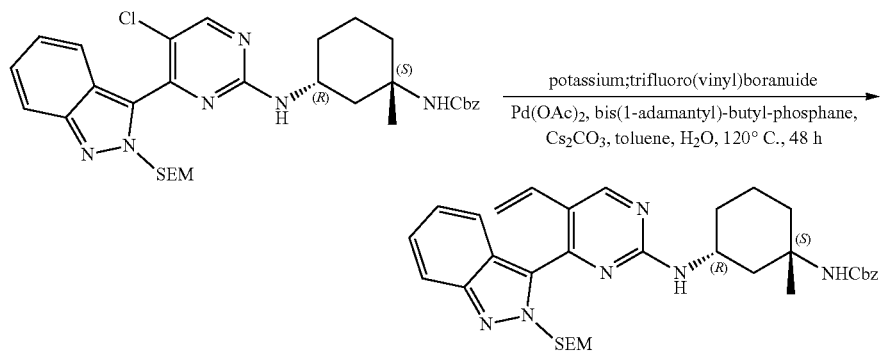

A flask was fitted with benzyl N-[(1S,3R)-3-[[5-chloro-4-[2-(2-trimethylsilylethoxymethyl)indazol-3-yl]pyrimidin-2-yl]amino]-1-methyl-cyclohexyl]carbamate (2 g, 3.22 mmol), potassium trifluoro(vinyl)boranuide (2.16 g, 16.10 mmol), Pd(OAc)₂ (361.39 mg, 1.61 mmol), Cs₂CO₃ (3.15 g, 9.66 mmol) and bis(1-adamantyl)-butyl-phosphane (1.15 g, 3.22 mmol) in toluene (30 mL) and H₂O (6 mL). The reaction mixture was stirred at 120° C. under N₂ for 48 h. The mixture was filtered and extracted by EA (50 mL*3). The organic layer was combined, dried over Na₂SO₄ and evaporated under reduce pressure to dryness. The residue was purified by column PE/EA=(10:1-5:1-3:1) to give title compound (700 mg, 35.47%) as brown solid.

(1S,3R)-N3-[5-ethyl-4-[2-(2-trimethylsilylethoxymethyl)indazol-3-yl]pyrimidin-2-yl]-1-methyl-cyclohexane-1,3-diamine

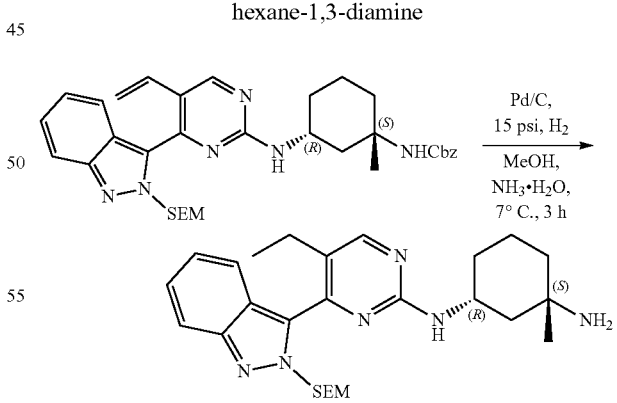

To a solution of benzyl N-[(1S,3R)-1-methyl-3-[[4-[2-(2-trimethylsilylethoxymethyl)indazol-3-yl]-5-vinyl-pyrimidin-2-yl]amino]cyclohexyl]carbamate (500 mg, 815.87 umol) in MeOH (30 mL) and NH₃.H₂O (3 mL) was added Pd/C (200 mg, 10%). The mixture was stirred at 7° C. under H₂ (15 psi) for 3 h. The mixture was filtered and the filtrate was evaporated to give title compound (400 mg, crude) as brown oil.

255

(1S,3R)-N3-[5-ethyl-4-[2-(2-trimethylsilylethoxymethyl)indazol-3-yl]pyrimidin-2-yl]-1-methyl-N1-[(5-nitro-2-pyridyl)methyl]cyclohexane-1,3-diamine

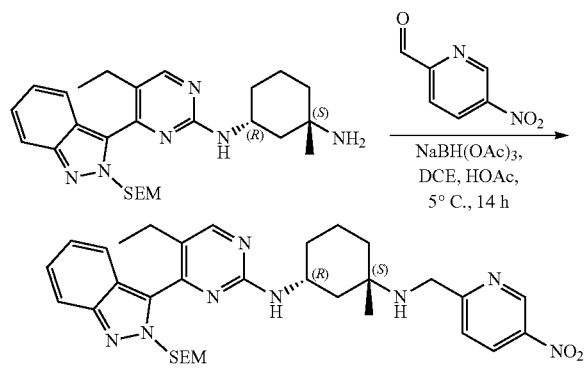

256

A solution of (1S,3R)-N3-[5-ethyl-4-[2-(2-trimethylsilylethoxymethyl)indazol-3-yl]pyrimidin-2-yl]-1-methyl-cyclohexane-1,3-diamine (500 mg, 1.04 mmol) in DCE (30 mL) was added 5-nitropyridine-2-carbaldehyde (158.21 mg, 1.04 mmol) and HOAc (62.46 mg, 1.04 mmol). The reaction mixture was stirred at 5° C. for 12 h. Then NaBH(OAc)$_3$ (440.88 mg, 2.08 mmol) was added and the mixture was stirred at 5° C. for another 2 h. The mixture was evaporated and the residue was purified by column (DCM/MeOH=80:1-60:1-50:1) to give title compound (200 mg, 31.18%) as yellow oil.

1-[(1S,3R)-3-[[5-chloro-4-(1H-indol-3-yl)pyrimidin-2-yl]amino]cyclohexyl]-4-prop-2-enoyl-piperazin-2-one

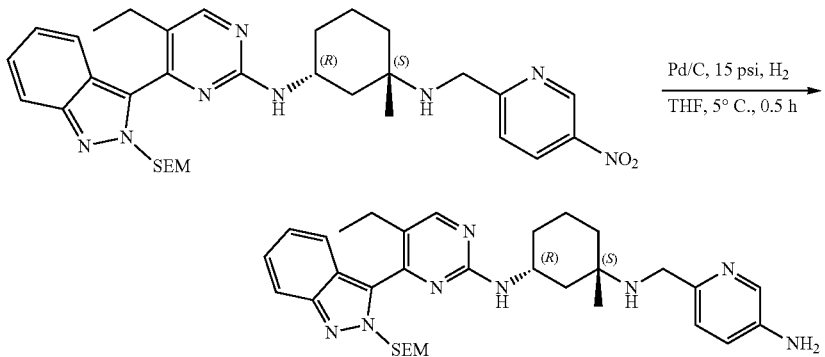

To a solution of (1S,3R)-N3-[5-ethyl-4-[2-(2-trimethylsilylethoxymethyl)indazol-3-yl]pyrimidin-2-yl]-1-methyl-N1-[(5-nitro-2-pyridyl)methyl]cyclohexane-1,3-diamine (170 mg, 275.60 umol) in THF (30 mL) was added Pd/C (10%, 70 mg) and the mixture was stirred at 5° C. under H$_2$ (15 psi) for 0.5 h. The mixture was filtered and the solvent was evaporated under reduced pressure to dryness to give title compound (170 mg, crude) as brown solid.

(E)-4-(dimethylamino)-N-[6-[[[(1S,3R)-3-[[5-ethyl-4-(1H-indazol-3-yl)pyrimidin-2-yl]amino]-1-methyl-cyclohexyl]amino]methyl]-3-pyridyl]but-2-enamide

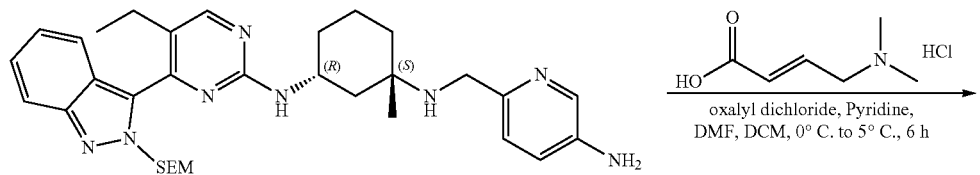

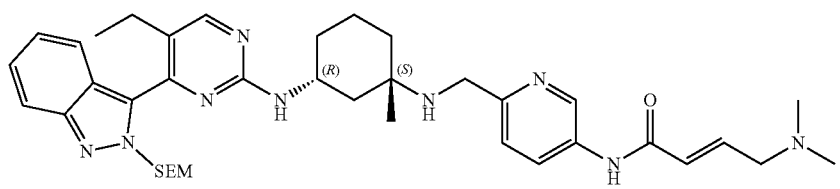

To a solution of (E)-4-(dimethylamino)but-2-enoic acid (47.98 mg, 289.69 umol, HCl salt) in DCM (1 mL) was added oxalyl dichloride (36.77 mg, 289.69 umol) and DMF (10.59 mg, 144.85 umol), the mixture was stirred at 0° C. for 2 h. Then the mixture was added to a solution of (1S,3R)-N1-[(5-amino-2-pyridyl)methyl]-N3-[5-ethyl-4-[2-(2-trimethylsilylethoxymethyl)indazol-3-yl]pyrimidin-2-yl]-1-methyl-cyclohexane-1,3-diamine (170 mg, 289.69 umol) and pyridine (45.83 mg, 579.38 umol) in DCM (14 mL) at 0° C. The mixture was then slowly warmed to 5° C. for 12 h. The mixture was evaporated and the residue was purified by column (DCM/MeOH=70:1-50:1-30:1-10:1) to afford title compound (100 mg, 34.4%).

(E)-4-(dimethylamino)-N-[6-[[[(1S,3R)-3-[[5-ethyl-4-(1H-indazol-3-yl)pyrimidin-2-yl]amino]-1-methyl-cyclohexyl]amino]methyl]-3-pyridyl]but-2-enamide (Compound 413)

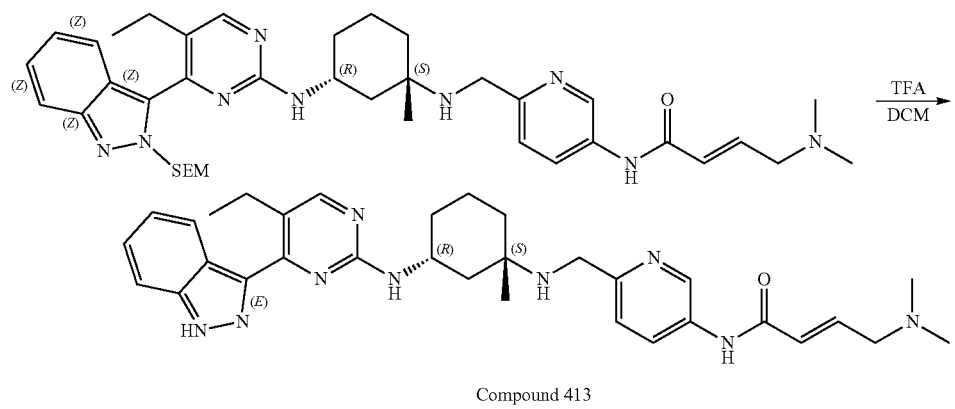

Compound 413

(E)-4-(dimethylamino)-N-[6-[[[(1S,3R)-3-[[5-ethyl-4-(1H-indazol-3-yl)pyrimidin-2-yl]amino]-1-methyl-cyclohexyl]amino]methyl]-3-pyridyl]but-2-enamide (100 mg, 123.3 umol) was purified by prep-HPLC(TFA) to give (E)-4-(dimethylamino)-N-[6-[[[(1S,3R)-3-[[5-ethyl-4-(1H-indazol-3-yl)pyrimidin-2-yl]amino]-1-methyl-cyclohexyl]amino]methyl]-3-pyridyl]but-2-enamide (30 mg, TFA salt). Then the final product was purified by prep-HPLC (Neutral) to give title compound (4.4 mg, 4.4%). LCMS: M+H$^+$: 568.5@1.947 min (10-80% ACN in H$_2$O, 4.5 min). $^1$H NMR (MeOD, 400 MHz); δ 8.76 (s, 1H), 8.45 (d, J=7.6 Hz, 1H), 8.19 (s, 1H), 8.07 (d, J=8.4 Hz, 1H), 7.58 (d, J=8.4 Hz, 1H), 7.45-7.39 (m, 2H), 7.22-7.18 (m, 1H), 6.95-6.91 (m, 1H), 6.27 (d, J=15.2 Hz, 1H), 4.22 (s, 1H), 3.96 (s, 2H), 3.19 (d, J=5.2 Hz, 2H), 3.04-2.99 (m, 2H), 2.30 (s, 6H), 2.17-2.15 (m, 2H), 1.84-1.77 (m, 1H), 1.74-1.66 (m, 1H), 1.63-1.57 (m, 1H), 1.54-1.51 (m, 2H), 1.37 (s, 4H), 1.20-1.16 (m, 3H).

Example 66. Synthesis of 1-[4-[(1S,3R)-3-[(5-chloro-4-imidazo[1,2-a]pyridin-3-yl-pyrimidin-2-yl)amino]cyclohexyl]piperazin-1-yl]prop-2-en-1-one (Compound 414)

Tert-butyl N-[(1R,3S)-3-(benzyloxycarbonylamino)cyclohexyl]carbamate

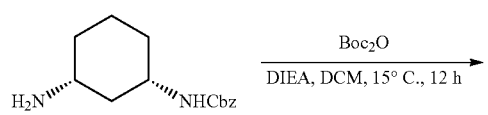

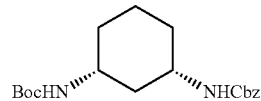

To a mixture of benzyl N-[(1S,3R)-3-aminocyclohexyl]carbamate (15 g, 60.4 mmol) and DIEA (19.5 g, 151 mmol) in DCM (300 mL) was added (Boc)$_2$O (17.1 g, 78.5 mmol). Then the mixture was stirred at 15° C. for 12 h. The solution was washed with 0.5 N aq of HCl (500 ml), extracted with DCM (500 ml). The organic layer was separated, dried and concentrated. The residue was purified by silica gel chromatography (PE/EA=5/1) to afford title compound (18 g, 86%) as a white solid.

Tert-butyl N-[(1R,3S)-3-aminocyclohexyl]carbamate

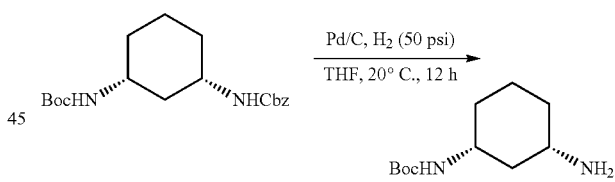

To a solution of tert-butyl N-[(1R,3S)-3-(benzyloxycarbonylamino)cyclohexyl]carbamate (8 g, 23 mmol) in EtOH (100 mL) was added Pd/C (10%, 5 g) under N$_2$. The suspension was degassed under vacuum and purged with H$_2$ 3 times. The mixture was stirred under H$_2$ (50 psi) at 20° C. for 12 h. The reaction mixture was filtered and the filtrate was concentrated. The crude product was used into the next step without purification. Title compound (5.1 g, crude) was obtained as a white solid.

Tert-butyl N-[(1R,3S)-3-(4-benzylpiperazin-1-yl)cyclohexyl]carbamate

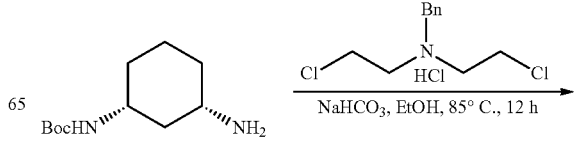

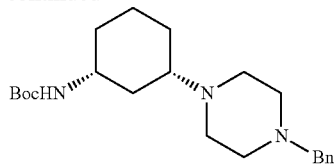

To a mixture of tert-butyl N-[(1R,3S)-3-aminocyclohexyl]carbamate (9.5 g, 44.33 mmol) and N-benzyl-2-chloro-N-(2-chloroethyl)ethanamine (10.3 g, 44.33 mmol) in EtOH (100 mL) was added NaHCO₃ (14.9 g, 177.3 mmol). The mixture was heated to 85° C. and stirred for 12 h. The reaction mixture was quenched by addition NH₃.H₂O 50 mL and concentrated under reduced pressure to give a residue. The residue was diluted with water 100 mL and extracted with DCM 150 mL* 3. The combined organic layers were washed with brine 400 mL, dried over Na₂SO₄, filtered and concentrated under reduced pressure to give a residue. The residue was purified by column chromatography (SiO₂, DCM/MeOH=100/1 to 30/1). Title compound (8 g, 48%) was obtained as a white solid.

Tert-butyl N-[(1R,3S)-3-piperazin-1-ylcyclohexyl]carbamate

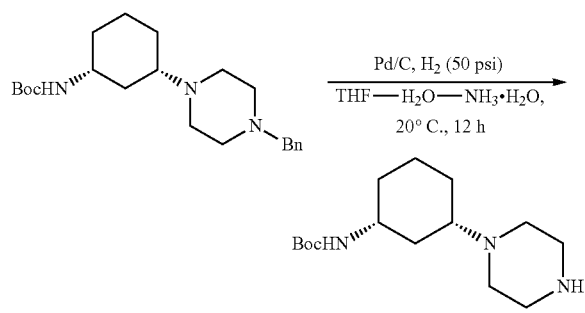

To a solution of tert-butyl N-[(1R,3S)-3-(4-benzylpiperazin-1-yl)cyclohexyl]carbamate (5 g, 13.4 mmol) in THF (120 mL), H₂O (40 mL) and NH₃.H₂O (20 mL) was added Pd/C (5 g). The suspension was degassed under vacuum and purged with H₂ 3 times. The mixture was stirred under H₂ (50 psi) at 20° C. for 12 h. The reaction mixture was filtered and the filtrate was concentrated. Title compound (3.8 g, crude) was obtained as a light yellow oil.

Benzyl 4-[(1S,3R)-3-(tert-butoxycarbonylamino)cyclohexyl]piperazine-1-carboxylate

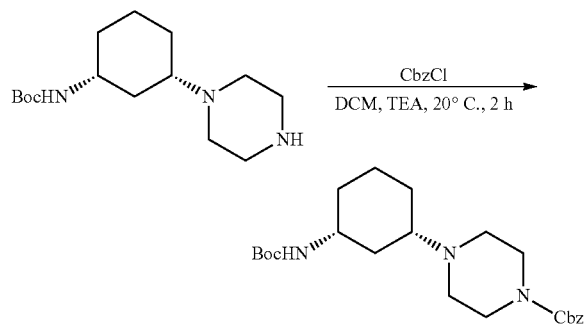

To a solution of tert-butyl N-[(1R,3S)-3-piperazin-1-ylcyclohexyl]carbamate (3.8 g, 13.4 mmol) and DIEA (3.5 g, 26.82 mmol) in DCM (50 mL) was added benzyl carbonochloridate (3 g, 17.4 mmol). Then the reaction was stirred at 20° C. for 2 h. The reaction mixture was diluted with H₂O 30 mL and extracted with DCM 30 mL*3. The combined organic layers were washed with brine 60 mL, dried over Na₂SO₄, filtered and concentrated under reduced pressure to give a residue. The residue was purified by column chromatography (PE/EA=2/1). Title compound (5.6 g, 90%) was obtained as a light oil.

Benzyl 4-[(1S,3R)-3-aminocyclohexyl]piperazine-1-carboxylate

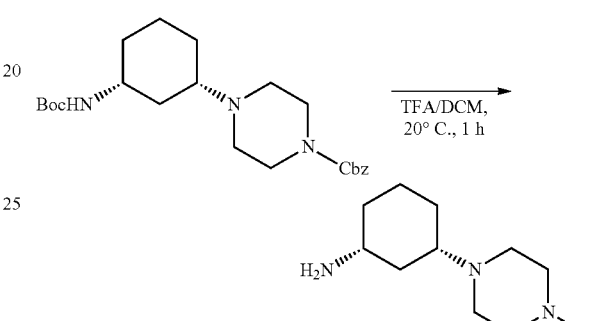

The reaction of benzyl-4-[(1S,3R)-3-(tert-butoxycarbonylamino)cyclohexyl]piperazine-1-carboxylate (2.5 g, 6 mmol) in DCM (50 mL) and TFA (5 mL) was stirred at 20° C. for 1 h. The reaction mixture was concentrated. The residue was diluted with MeOH 50 mL and basic resin was added to the liquid to pH=9. Then the mixture was filtered and the filtrate was concentrated to give a residue. Title compound (2.2 g, crude) was obtained as a yellow gum.

4-[(Z)-2-butoxyvinyl]-2,5-dichloro-pyrimidine

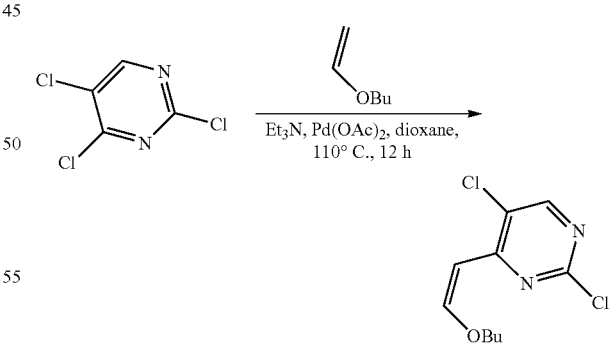

To a solution of 2,4,5-trichloropyrimidine (50 g, 272.6 mmol), 1-vinyloxybutane (54.6 g, 545.2 mmol) and TEA (67 g, 681.5 mmol) in dioxane (400 mL) was added Pd(OAc)₂ (1.7 g, 27.3 mmol). Then the reaction was heated to 110° C. and stirred for 12 h. The mixture was concentrated. The crude product dissolved by DCM (500 mL) and filtered. The filtrate was concentrated and purified by MPLC to afford title compound (15 g, 20%) as a yellow oil.

261

3-(2,5-dichloropyrimidin-4-yl)imidazo[1,2-a]pyridine

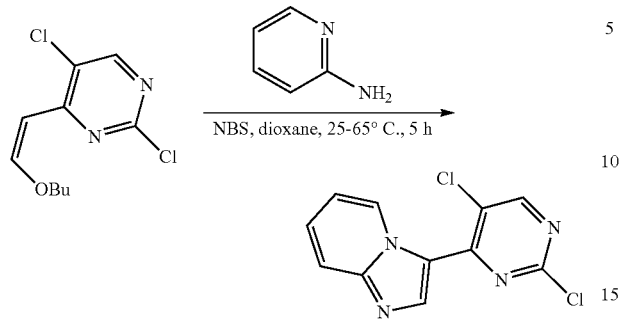

NBS (4.32 g, 24.28 mmol) was added to a solution of 4-[(Z)-2-butoxyvinyl]-2,5-dichloro-pyrimidine (6 g, 24.28 mmol) in dioxane (130 mL) and $H_2O$ (50 mL) at 25° C. The mixture was stirred at 25° C. for 1 h and then pyridin-2-amine (2.28 g, 24.28 mmol) was added to the reaction and the reaction was heated at 65° C. for 4 h. The mixture was concentrated and extracted with DCM (200 ml) and water (200 mL). The organic layer was washed with brine (200 mL), dried with $Na_2SO_4$, and concentrated. The crude was purified by column (PE/EA=2/1) to afford title compound (4.5 g, 63%) as a yellow solid.

Benzyl-4-[(1S,3R)-3-[(5-chloro-4-imidazo]1,2-a]pyridin-3-yl-pyrimidin-2-yl)amino]cyclohexyl]piperazine-1-carboxylate

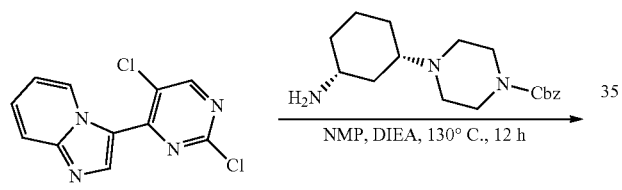

262

-continued

To a solution of 3-(2,5-dichloropyrimidin-4-yl)imidazo[1,2-a]pyridine (500 mg, 1.89 mmol) and benzyl 4-[(1S,3R)-3-aminocyclohexyl]piperazine-1-carboxylate (599 mg, 1.89 mmol) in NMP (20 mL) was added DIEA (975 mg, 7.54 mmol). Then the reaction was heated to 130° C. and stirred for 12 h. The reaction mixture was concentrated under reduced pressure. The residue was diluted with $H_2O$ 30 mL and extracted with DCM 30 mL*3. The combined organic layer was washed with brine 50 mL, dried over $Na_2SO_4$, filtered and concentrated under reduced pressure to give a residue. The residue was purified by column (DCM/MeOH=50/1) to afford title compound (300 mg, 26%) as a brown solid.

5-chloro-4-imidazo[1,2-a]pyridin-3-yl-N-[(1R,3S)-3-piperazin-1-yl]cyclohexyl]pyrimidin-2-amine (Compound 1060)

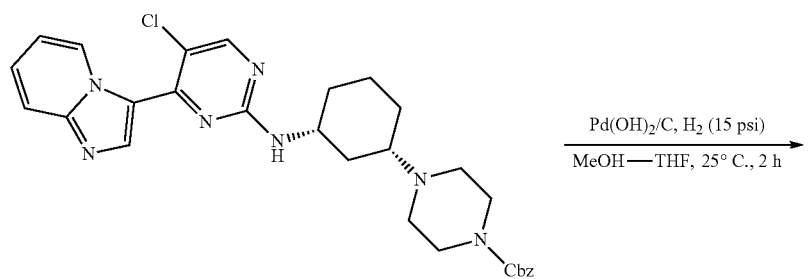

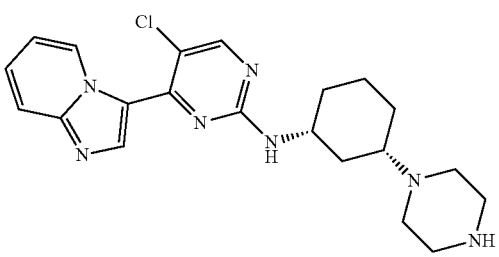

To a solution of benzyl 4-[(1S,3R)-3-[(5-chloro-4-imidazo[1,2-a]pyridin-3-yl-pyrimidin-2-yl)amino]cyclohexyl]piperazine-1-carboxylate (300 mg, 549 umol) in MeOH (5 mL) and THF (5 mL) was added Pd(OH)$_2$/C (200 mg) at 25° C. and the reaction was stirred under H$_2$ (15 psi) at 25° C. for 2 h. The reaction mixture was filtered and concentrated. Title compound (200 mg, crude) was obtained as a black brown solid.

LCMS: (M+H$^+$): 412.0@0.681 min (5-95% ACN in H$_2$O, 1.5 min)

1-[4-[(1S,3R)-3-[(5-chloro-4-imidazo[1,2-a]pyridin-3-yl-pyrimidin-2-yl)amino]cyclohexyl]piperazin-1-yl]prop-2-en-1-one (Compound 414)

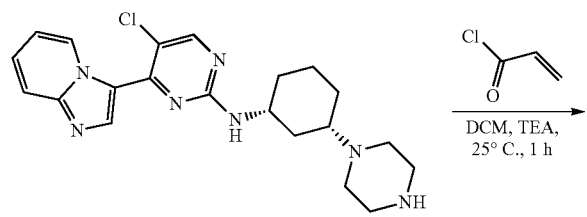

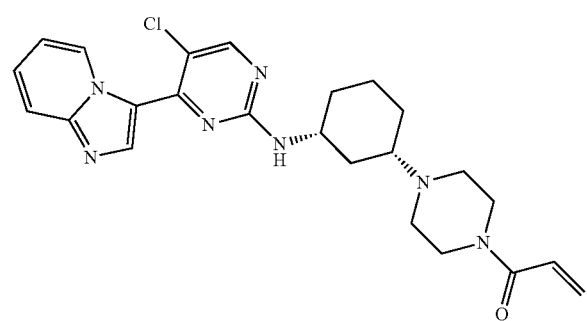

To a mixture of 5-chloro-4-imidazo[1,2-a]pyridin-3-yl-N-[(1R,3S)-3-piperazin-1-ylcyclohexyl]pyrimidin-2-amine (200 mg, 485.5 umol) and TEA (147 mg, 1.46 mmol) in DCM (10 mL) was added prop-2-enoyl chloride (53 mg, 583 umol) in one portion at 25° C. under N$_2$. The mixture was stirred at 25° C. for 1 h. The mixture was concentrated. The residue was purified by prep-HPLC (HCl). Then the product was washed with MTBE. Title compound (45 mg, 16%, HCl) was obtained as a yellow solid. LCMS: (M+H$^+$): 466.3@1.676 min (10-80% ACN in H$_2$O, 4.5 min). $^1$H NMR: ET3417-146-P1B (MeOD, 400 MHz); δ 10.36-10.09 (m, 1H), 9.16-8.95 (m, 1H), 8.65-8.48 (m, 1H), 8.24-8.05 (m, 2H), 7.77-7.62 (m, 1H), 6.87-6.71 (m, 1H), 6.37-6.21 (m, 1H), 5.92-5.76 (m, 1H), 4.80-4.67 (m, 1H), 4.51-4.34 (m, 1H), 4.07-3.95 (m, 1H), 3.78-3.54 (m, 3H), 3.50-3.41 (m, 1H), 3.26-3.11 (m, 2H), 2.72-2.60 (m, 1H), 2.30-2.00 (m, 3H), 1.75-1.27 (m, 5H).

Example 67. Synthesis of (R,E)-1-(3-((4-((5-chloro-4-(1H-indol-3-yl)pyrimidin-2-yl) amino)benzyl)amino)piperidin-1-yl)-4-(dimethylamino)but-2-en-1-one (Compound 415)

(R)-benzyl 3-((4-nitrobenzyl)amino)piperidine-1-carboxylate

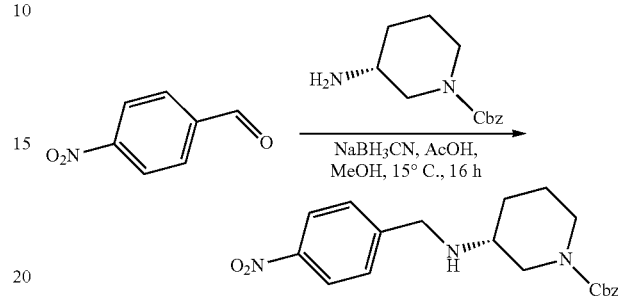

To a mixture of 4-nitrobenzaldehyde (8.0 g, 52.94 mmol) and (R)-benzyl 3-aminopiperidine-1-carboxylate (12.4 g, 52.94 mmol) in MeOH (100 mL) was added AcOH (1.59 g, 26.47 mmol) at 15° C. and the mixture was stirred for 4 h. Then NaBH$_3$CN (4.99 g, 79.41 mmol) was added and the mixture was stirred at 15° C. for 12 h. The mixture was poured into water (200 mL), extracted with EA (100 mL*3), and the organic layer was dried over Na$_2$SO$_4$ and concentrated. The residue was purified by column (EA:PE=10:1) to give title compound (14.5 g, 74%) as a yellow oil.

(R)-benzyl 3-((tert-butoxycarbonyl)(4-nitrobenzyl)amino)piperidine-1-carboxylate

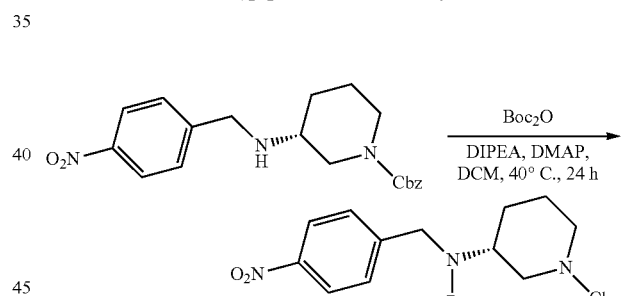

A mixture of benzyl (3R)-3-[(4-nitrophenyl)methylamino]piperidine-1-carboxylate (4.10 g, 11.10 mmol), Boc$_2$O (3.15 g, 14.43 mmol), DIPEA (4.30 g, 33.30 mmol) and DMAP (1.36 g, 11.10 mmol) in DCM (100 mL) was heated to 40° C. and stirred for 24 h. The mixture was diluted with DCM (200 mL) and washed with HCl solution (200 mL) and brine (300 mL). The organic layer was dried over Na$_2$SO$_4$ and concentrated. The residue was purified by column (SiO$_2$, EA: PE=1:10-1:0) to give title compound (1.80 g, 31.0%).

(R)-benzyl 3-((4-aminobenzyl)(tert-butoxycarbonyl)amino)piperidine-1-carboxylate

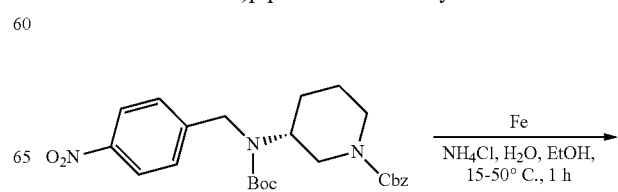

-continued

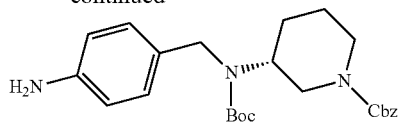

To a mixture of (R)-benzyl 3-((tert-butoxycarbonyl)(4-nitrobenzyl)amino)piperidine-1-carboxylate (400 mg, 0.85 mmol) in EtOH (20 mL) and NH₄Cl solution (5 mL) was added Fe (237.90 mg, 4.26 mmol) at 15° C., the mixture was heated to 60° C. and stirred for 1 h. The mixture was filtered by silica gel and the filtrate was concentrated. The residue was diluted with EA (100 mL), washed with water (100 mL*3) and brine (200 mL), dried over Na₂SO₄, filtered, and concentrated to give title compound (250 mg, 66.7%) as a yellow solid.

LCMS: (M+H⁺): 440.3@0.765 min (5-95% ACN in H₂O, 1.5 min)

(R)-benzyl 3-((tert-butoxycarbonyl)(4-((5-chloro-4-(1-(phenylsulfonyl)-1H-indol-3-yl)pyrimidin-2-yl)amino)benzyl)amino)piperidine-1-carboxylate

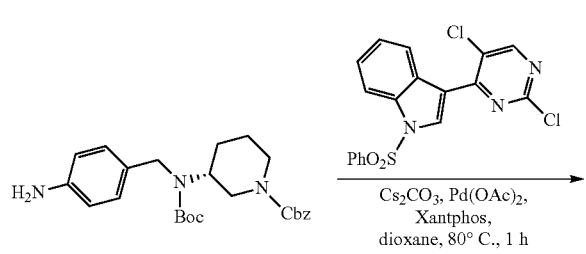

-continued

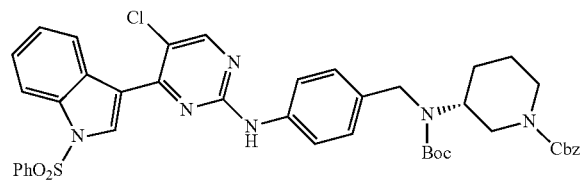

A mixture of 1-(benzenesulfonyl)-3-(2,5-dichloropyrimidin-4-yl)indole (250 mg, 0.62 mmol), (R)-benzyl 3-((4-aminobenzyl)(tert-butoxycarbonyl)amino)piperidine-1-carboxylate (272 mg, 0.62 mmol), Cs₂CO₃ (604 mg, 1.86 mmol), Pd(OAc)₂ (41.6 mg, 0.18 mmol) and Xantphos (161.0 mg, 0.28 mmol) in dioxane (10 mL) was degassed for three times, heated to 80° C., and stirred for 1 h. The mixture was poured into water (100 mL) and extracted with EA (50 mL*3). The organic layer was dried over Na₂SO₄, filtered and concentrated. The residue was purified by column (SiO₂, EA:DCM=0:1-1:1) to give title compound (250 mg, 42.5%, 85% purity) as a yellow oil.

(R)-benzyl 3-((tert-butoxycarbonyl)(4-((5-chloro-4-(1H-indol-3-yl)pyrimidin-2-yl)amino)benzyl)amino)piperidine-1-carboxylate

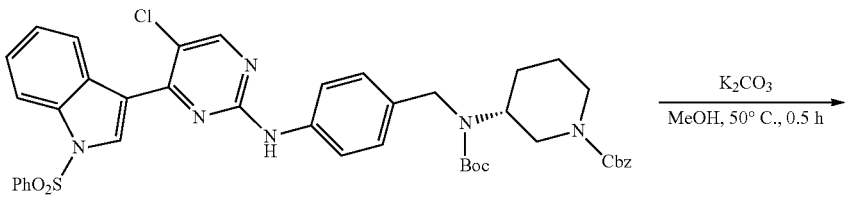

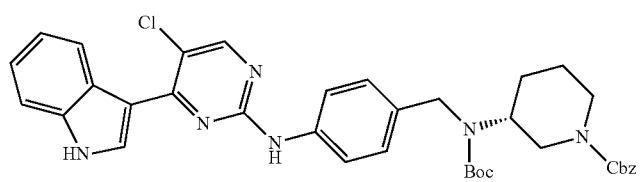

A mixture of (R)-benzyl 3-((tert-butoxycarbonyl)(4-((5-chloro-4-(1-(phenylsulfonyl)-1H-indol-3-yl)pyrimidin-2-yl)amino)benzyl)amino)piperidine-1-carboxylate (220 mg, 0.28 mmol) and K₂CO₃ (113 mg, 0.82 mmol) in MeOH (5 mL) was heated to 50° C. and stirred for 0.5 h. The mixture was poured into water (100 mL), extracted with EA (50 mL*3), and the organic layer was dried over Na₂SO₄, filtered, and concentrated to give title compound (200 mg, crude) as a yellow solid, which was used into the next step without further purification.

(R)-tert-butyl 4-((5-chloro-4-(1H-indol-3-yl)pyrimidin-2-yl)amino)benzyl(piperidin-3-yl)carbamate

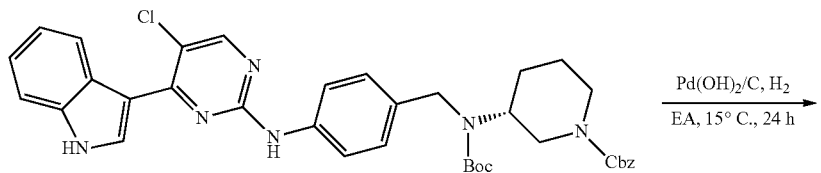

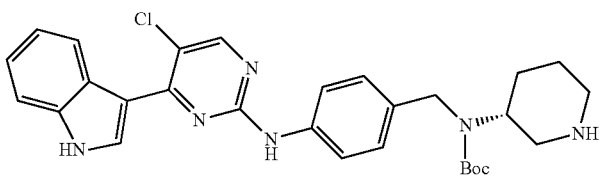

To a solution of (R)-benzyl 3-((tert-butoxycarbonyl)(4-((5-chloro-4-(1H-indol-3-yl)pyrimidin-2-yl)amino)benzyl)amino)piperidine-1-carboxylate (200 mg, 0.30 mmol) in EA (20 mL) was Pd(OH)$_2$/C (10%, 100 mg) under N$_2$. The suspension was degassed under vacuum and purged with H$_2$ several times. The mixture was stirred at 15° C. for 24 h under H$_2$ (15 psi). The mixture was filtered, and the filtrate was concentrated. The residue was purified by prep-HPLC (TFA) to give title compound (60 mg, 33.8%) as a yellow solid.

(R)-tert-butyl(1-acryloylpiperidin-3-yl)(4-((5-chloro-4-(1H-indol-3-yl)pyrimidin-2-yl)amino)benzyl)carbamate

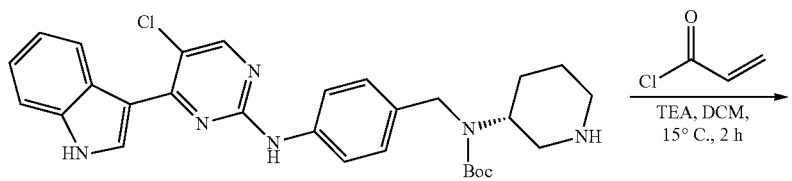

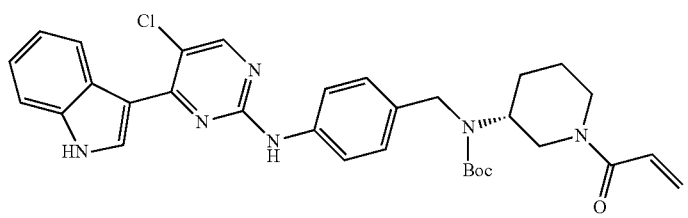

To a mixture of (R)-tert-butyl 4-((5-chloro-4-(1H-indol-3-yl)pyrimidin-2-yl)amino)benzyl(piperidin-3-yl)carbamate (50 mg, 93.80 umol) and Et$_3$N (28.5 mg, 281.40 umol) in DCM (5 mL) was added prop-2-enoyl chloride (8.5 mg, 93.80 umol) at 15° C. and the mixture was stirred for 2 h. The mixture was concentrated to give title compound (50 mg, 30% LCMS purity, crude) as a yellow oil, which was used into the next step without further purification.

(R,E)-tert-butyl 4-((5-chloro-4-(1H-indol-3-yl)py-rimidin-2-yl)amino)benzyl(1-(4-(dimethylamino)but-2-enoyl)piperidin-3-yl)carbamate LCMS: (M+H⁺): 544.3@0.764 min (10-80% ACN in H₂O, 4.5 min). ¹H NMR: (MeOD, 400 MHz); δ 8.83 (br. s., 1H), 8.47 (d, J=8.03 Hz, 1H), 8.39 (s, 1H), 7.80 (d, J=8.03

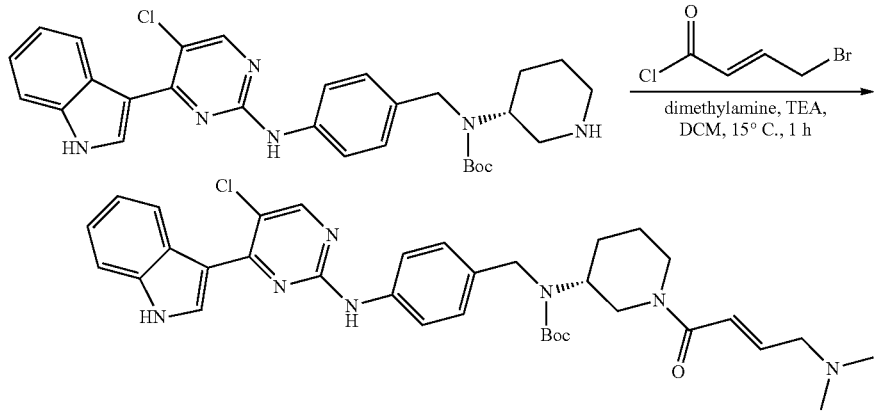

To a mixture of (R)-tert-butyl 4-((5-chloro-4-(1H-indol-3-yl)pyrimidin-2-yl)amino)benzyl(piperidin-3-yl)carbamate (40 mg, 75.04 umol) and Et₃N (30.4 mg, 300.16 umol) in DCM (10 mL) was added (E)-4-bromobut-2-enoyl chloride (41.3 mg, 225.12 umol) at 15° C. and the mixture was stirred for 0.5 h. Then dimethylamine (10.1 mg, 225.1 mmol) was added and the mixture was stirred at 15° C. for 0.5 h. The mixture was concentrated to give title compound (80 mg, crude) as a yellow solid, which was used into the next step without further purification.

(R,E)-1-(3-((4-((5-chloro-4-(1H-indol-3-yl)pyrimi-din-2-yl)amino)benzyl)amino)piperidin-1-yl)-4-(dimethylamino)but-2-en-1-one (Compound 415)

Hz, 2H), 7.75-7.62 (m, 2H), 7.53 (d, J=8.28 Hz, 1H), 7.30 (t, J=7.53 Hz, 1H), 7.18 (d, J=8.03 Hz, 1H), 7.03 (d, J=15.06 Hz, 1H), 6.81-6.68 (m, 1H), 4.52 (d, J=12.80 Hz, 1H), 4.42 (d, J=6.27 Hz, 2H), 3.99 (d, J=6.53 Hz, 2H), 3.93 (d, J=13.30 Hz, 1H), 3.46 (br. s., 2H), 3.07-2.81 (m, 6H), 2.50-2.12 (m, 2H), 2.05-1.84 (m, 2H), 1.67 (br. s., 1H).

Example 68. Synthesis of N-((1S,3R)-3-(5-chloro-4-(1H-indol-3-yl)pyrimidin-2-ylamino)-1-methylcy-clohexyl)-5-(E)-4-(dimethylamino)but-2-enamido) picolinamide (Compound 267)

(+/−) Benzyl tert-butyl ((1S,3R)-1-methylcyclohexane-1,3-diyl)dicarbamate

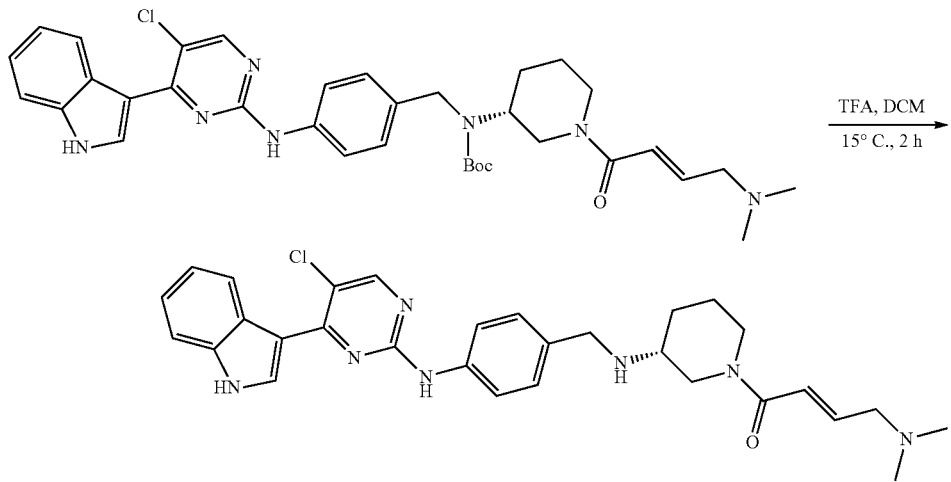

Compound 415

A mixture of (R,E)-tert-butyl 4-((5-chloro-4-(1H-indol-3-yl)pyrimidin-2-yl)amino)benzyl(1-(4-(dimethylamino)but-2-enoyl)piperidin-3-yl)carbamate (80 mg, 124.19 umol) in DCM (5 mL) and TFA (1 mL) was stirred at 15° C. for 2 h. The mixture was concentrated, and the residue was purified by prep-HPLC (HCl) to afford title compound (6.70 mg, 8.4%, 85% purity) as a yellow solid.

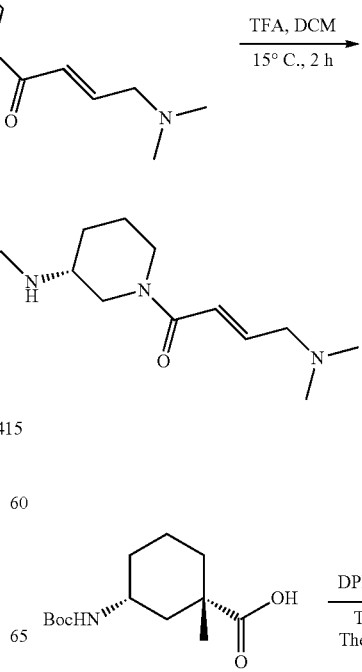

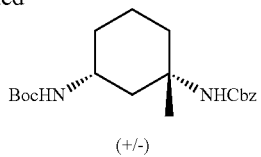

(+/-)

A solution of (+/−)-(1S,3R)-3-((tert-butoxycarbonyl)amino)-1-methylcyclohexanecarboxylic acid prepared as in WO2010/148197 (4.00 g, 15.5 mmol) in toluene (155 mL) was treated with Et$_3$N (2.4 mL, 17.1 mmol) and DPPA (3.68 mL, 17.1 mmol) and heated at reflux for 1 h. Benzyl alcohol (8.0 mL, 77.7 mmol) and Et$_3$N (4.4 mL, 31.4 mmol) were added to the reaction mixture and the solution was heated at 100° C. for 72 h. The mixture was cooled to room temperature and then diluted with EtOAc (300 mL) and H$_2$O (300 mL). The layers were separated and the aqueous layer was extracted with EtOAc (3×200 mL). The combined organics layers were washed with brine (100 mL), filtered and evaporated to dryness. The residue was purified by SiO$_2$ chromatography (EtOAc in hexanes, 0 to 50% gradient) and afforded the title compound (3.40 g, 9.38 mmol, 60%) as a white solid.

Benzyl tert-butyl ((1S,3R)-1-methylcyclohexane-1,3-diyl)dicarbamate and benzyl tert-butyl ((1R,3S)-1-methylcyclohexane-1,3-diyl)dicarbamate

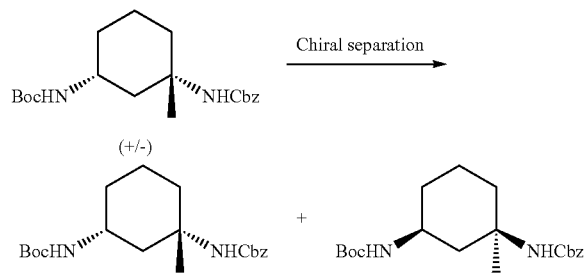

Both enantiomers of (+/−)-Benzyl tert-butyl ((1S,3R)-1-methylcyclohexane-1,3-diyl)dicarbamate (3.40 g, 9.38 mmol) were separated using preparative chiral HPLC (Chiralpak IA, 5 um, 20×250 mm; hex/MeOH/DCM=90/5/5) to yield both compounds benzyl tert-butyl ((1S,3R)-1-methylcyclohexane-1,3-diyl)dicarbamate (1.20 g, 3.31 mmol) and benzyl tert-butyl ((1R,3S)-1-methylcyclohexane-1,3-diyl)dicarbamate (1.15 g, 3.17 mmol) as white solids.

Benzyl ((1S,3R)-3-amino-1-methylcyclohexyl)carbamate hydrochloride

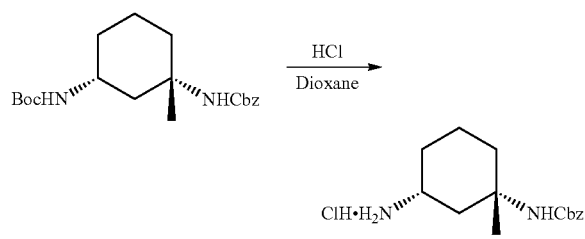

A solution of benzyl tert-butyl ((1S,3R)-1-methylcyclohexane-1,3-diyl)dicarbamate (700 mg, 1.93 mmol) in DCM (19 mL) was treated with a 4M solution of HCl in dioxane (9.66 mL, 38.6 mmol) and stirred 16 h at rt. The mixture was evaporated to dryness and afforded the title compound (577 mg, 1.93 mmol, 100%) as a white solid which was used in the next step without further purification.

(1S,3R)-Benzyl-3-(5-chloro-4-(1-(phenylsulfonyl)-1H-indol-3-yl)pyrimidin-2-ylamino)-1-methylcyclohexylcarbamate

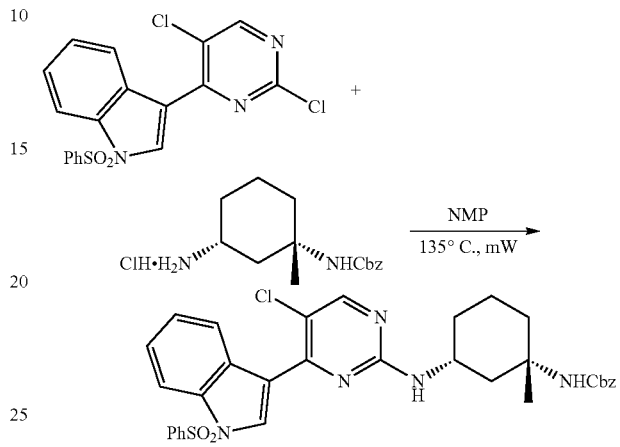

A solution of 3-(2,5-dichloropyrimidin-4-yl)-1-(phenylsulfonyl)-1H-indole (1.02 g, 2.53 mmol), benzyl ((1S,3R)-3-amino-1-methylcyclohexyl)carbamate hydrochloride (577 mg, 1.93 mmol) and DIPEA (1.15 mL, 6.60 mmol) in NMP (11 mL) was heated at 135° C. (microwave) for 60 min. The cooled mixture was diluted with EtOAc (250 mL), washed with H$_2$O (100 mL), brine (100 mL), dried over MgSO$_4$, filtered and evaporated to dryness. The residue was purified by SiO$_2$ chromatography (EtOAc in DCM, 0 to 50% gradient) and afforded the title compound (747 mg, 1.19 mmol, 54%) as a yellow foam.

(1S,3R)—N-(5-chloro-4-(1-(phenylsulfonyl)-1H-indol-3-yl)pyrmidin-2-yl)-3-methylcyclohexane-1,3-diamine

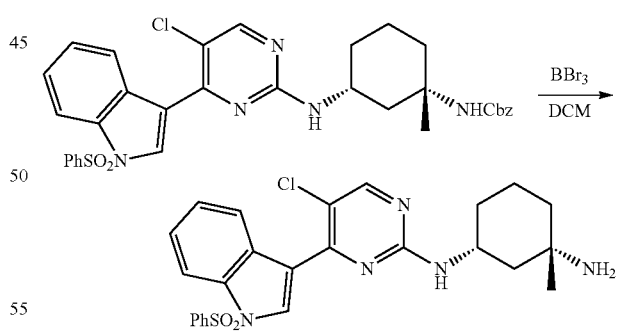

A cooled (−78° C.) solution of 1S,3R)-benzyl-3-(5-chloro-4-(1-(phenylsulfonyl)-1H-indol-3-yl)pyrimidin-2-ylamino)-1-methylcyclohexylcarbamate (747 mg, 1.19 mmol) in DCM (39 mL) was treated with a 1M solution of BBr$_3$ in DCM (2.83 mL, 2.83 mmol) and was slowly warmed up to rt. MeOH (10 mL) was added to the mixture was the resulting solution was stirred 1 h at rt. The resulting mixture was evaporated to dryness. The residue was purified by reverse phase chromatography (C$_{18}$, H$_2$O/ACN+0.1% HCO$_2$H, 0 to 60% gradient) and afforded the title compound (485 mg, 0.978 mmol, 83%) as a yellow solid.

273

5-amino-N-((1S,3R)-3-(5-chloro-4-(1-(phenylsulfo-nyl)-1H-indol-3-yl)pyrmidin-2-ylamino)-1-methyl-cyclohexyl)picolinamide

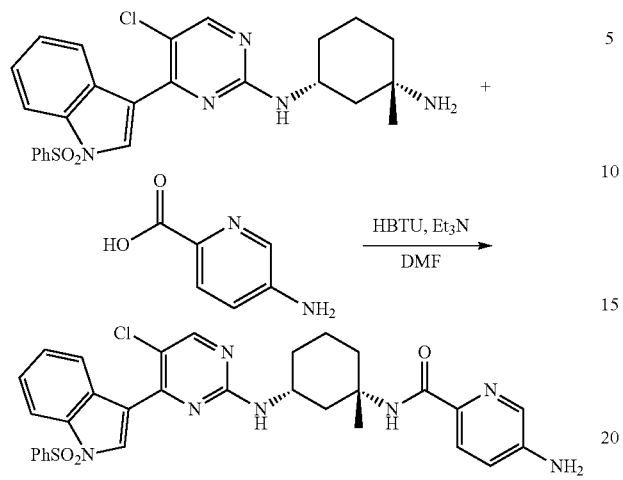

274

A solution of (1R,3S)—N-(5-chloro-4-(1-(phenylsulfo-nyl)-1H-indol-3-yl)pyrimidin-2-yl)-3-methylcyclohexane-1,3-diamine (75.0 mg, 0.150 mmol) and 5-aminopicolinic acid (25.0 mg, 0.180 mmol) in DMF (5.0 mL) was treated with HBTU (86.0 mg, 0.230 mmol) and DIPEA (79 μL, 0.45 mmol). The resulting mixture was stirred 5 h at rt and diluted with MeTHF (50 mL) and saturated NaHCO₃ (50 mL). The layers were separated and the aqueous layer was extracted with MeTHF (2×50 mL). The combined organic layers were dried over MgSO₄, filtered and evaporated to dryness. The residue was purified by SiO₂ chromatography (EtOAc in DCM, 0 to 50% gradient) and afforded the title compound (74.0 mg, 0.120 mmol, 79%) as a light yellow oil.

5-amino-N-((1S,3R)-3-(5-chloro-4-(1H-indol-3-yl)pyrmidin-2-ylamino)-1-methylcyclohexyl)picolina-mide (Compound 1061)

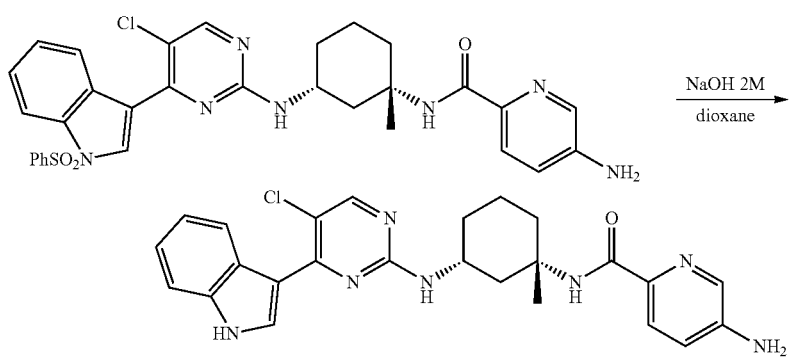

A solution of 5-amino-N-((1S,3R)-3-(5-chloro-4-(1-(phe-nylsulfonyl)-1H-indol-3-yl)pyrimidin-2-ylamino)-1-meth-ylcyclohexyl)picolinamide (74.0 mg, 0.120 mmol) in 1,4-dioxane (4.0 mL) was treated with a 2M solution of NaOH in H₂O (960 μL, 4.78 mmol) and heated at 60° C. for 1 h. The cooled mixture was diluted with MeTHF (30 mL) and H₂O (30 mL). The layers were separated and the aqueous layer was extracted with MeTHF (3×30 mL). The combined organic layers were dried over MgSO₄, filtered and evaporated to dryness affording the title compound (57.0 mg, 0.120 mmol, 100%) as a light yellow oil which was used in the next step without further purification.

N-((1S,3R)-3-(5-chloro-4-(1H-indol-3-yl)pyrmidin-2-ylamino)-1-methylcyclohexyl)-5-((E)-4-(dimethyl-amino)but-2-enamido)picolinamide
(Compound 267)

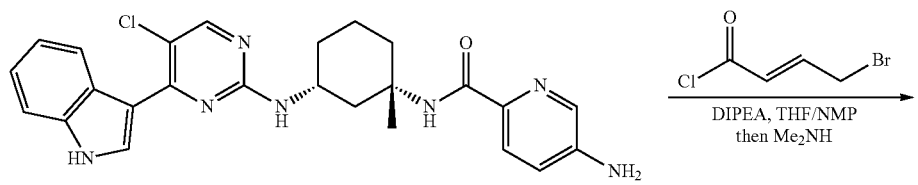

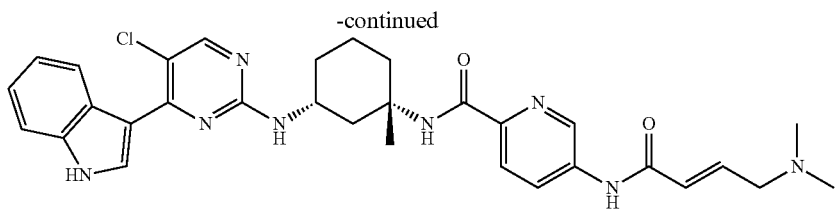

A cooled (−78° C.) solution of 5-amino-N-((1S,3R)-3-(5-chloro-4-(1H-indol-3-yl)pyrimidin-2-ylamino)-1-methylcyclohexyl)picolinamide (57.0 mg, 0.120 mmol) and DIPEA (104 μL, 0.598 mmol) in THF/NMP (4.0 mL/1.0 mL) was treated with a 54.2 mg/mL solution of (E)-4-bromobut-2-enoyl chloride in DCM (104 μL, 0.598 mmol). The resulting mixture was stirred 4 h at −78° C. before addition of a 2M solution of dimethylamine in THF (359 μL, 0.717 mmol). The resulting mixture was warmed up to rt and stirred 45 min at this temperature before being evaporated to dryness. The residue was purified by reverse phase chromatography (C$_{18}$, H$_2$O/ACN+0.1% HCO$_2$H, 0 to 50% gradient) and afforded the title compound (15.0 mg, 0.026 mmol, 22%) as a white solid after lyophilization. LCMS: Calculated: 587.12; Found (M+H$^+$): 587.39. $^1$H NMR (500 MHz, DMSO) δ 11.84 (s, 1H), 10.54 (s, 1H), 8.82 (d, J=2.3 Hz, 1H), 8.64 (s, 1H), 8.47 (s, 1H), 8.25 (dd, J=8.6, 2.4 Hz, 2H), 7.98 (d, J=8.9 Hz, 2H), 7.50 (d, J=7.7 Hz, 1H), 7.25-7.07 (m, 3H), 6.81 (dt, J=15.5, 5.8 Hz, 1H), 6.29 (d, J=15.4 Hz, 1H), 4.23-4.08 (m, 1H), 3.08 (dd, J=5.7, 1.1 Hz, 2H), 2.46-2.37 (m, 1H), 2.18 (s, 6H), 2.04-1.95 (m, 2H), 1.87-1.70 (m, 3H), 1.63-1.46 (m, 4H), 1.39-1.26 (m, 1H).

Example 69. Synthesis of N-(6-(((1S,3R)-3-(5-chloro-4-(1H-indol-3-yl)pyrimidin-2-ylamino)cyclohexylamino)methyl)pyridin-3-yl)acrylamide (Compound 261)

(1S,3R)-3-(Benzyloxycarbonylamino)cyclohexylamino-2,2-dimethylpropionate

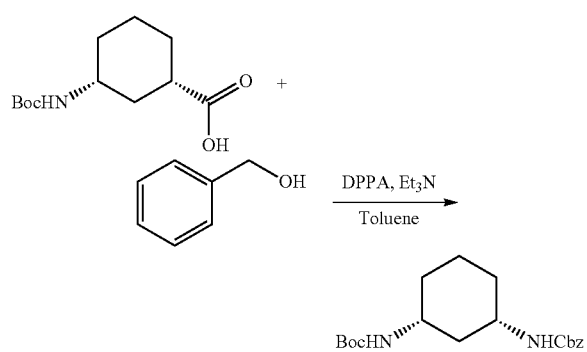

To a solution of (1S,3R)-3-(tert-butoxycarbonylamino)cyclohexanecarboxylic acid (8.77 g, 36.1 mmol) (prepared following Tetrahedron: *Asymmetry* 2010 (21), 864-866) in toluene (145 mL) was added Et$_3$N (5.53 mL, 39.7 mmol) and DPPA (7.7 mL, 36.1 mmol). The resulting solution was stirred for 2 h at 110° C. and cooled down to 80° C. Benzyl alcohol (4.66 mL, 45.1 mmol) and triethylamine (5.53 mL, 39.7 mmol) were added, and the mixture was stirred for 20 h at 80° C. The cooled solution was diluted with EtOAc (100 mL) and water (50 mL). The layers were separated, and the aqueous layer was extracted with EtOAc (2×50 mL). The combined organic layers were dried over MgSO$_4$, filtered, and concentrated under reduced pressure. The residue was purified by SiO$_2$ chromatography (EtOAc in hexanes, 1 to 100% gradient) to afford the title compound (9.89 g, 28.4 mmol, 79% yield) as a white solid.

Benzyl (1S,3R)-3-aminocyclohexylcarbamate hydrochloride

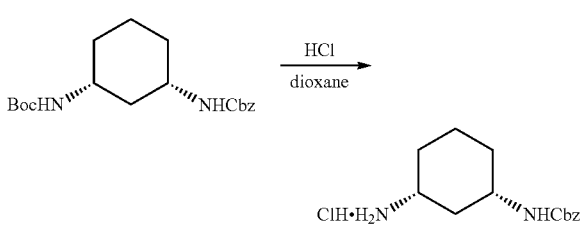

A solution of (1S,3R)-3-(benzyloxycarbonylamino)cyclohexylamino-2,2-dimethylpropionate (1.50 g, 4.31 mmol) in DCM (43 mL) was treated with a 4M solution of HCl in dioxane (16.0 mL, 64.6 mmol) and stirred for 2 h at rt. The resulting solution was evaporated to dryness and afforded the title compound (1.23 g, 4.31 mmol, 100%) as a white solid which was used in the next step without further purification.

Benzyl (1S,3R)-3-(5-chloro-4-(1-(phenylsulfonyl)-1H-indol-3-yl)pyrimidin-2-ylamino)cyclohexylcarbamate

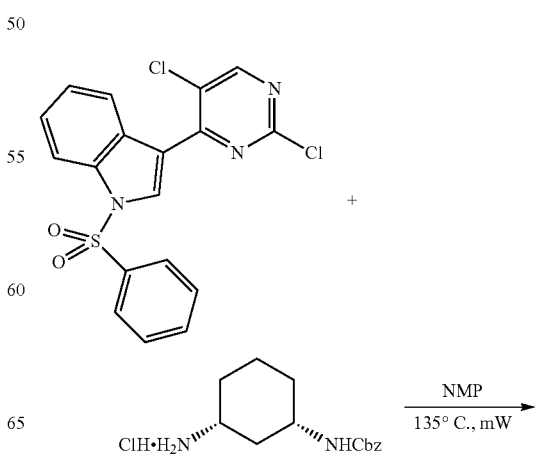

277

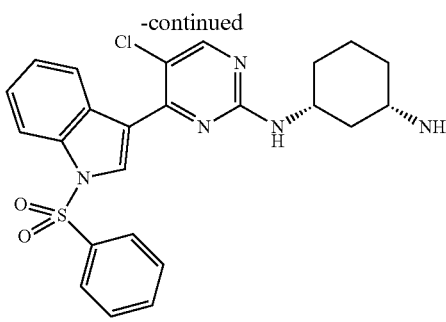

A solution of 3-(2,5-dichloropyrimidin-4-yl)-1-(phenylsulfonyl)-1H-indole (791 mg, 1.96 mmol), benzyl (1S,3R)-3-aminocyclohexylcarbamate hydrochloride (613 mg, 2.15 mmol) and diisopropylethylamine (0.75 mL, 4.31 mmol) in NMP (20 mL) was heated 30 min at 135° C. (microwave). The mixture was diluted with EtOAc (100 mL), washed with H₂O (50 mL), brine (50 mL), dried (MgSO₄), filtered and evaporated to dryness. The residue was purified by SiO₂ chromatography (EtOAc in hexanes, 5 to 70% gradient), and afforded the title compound (1.04 g, 1.69 mmol, 40%) as a yellow solid.

(1R,3S)—N-(5-chloro-4-(1-(phenylsulfonyl)-1H-indol-3-yl)pyrimidin-2-yl)cyclohexane-1,3-diamine

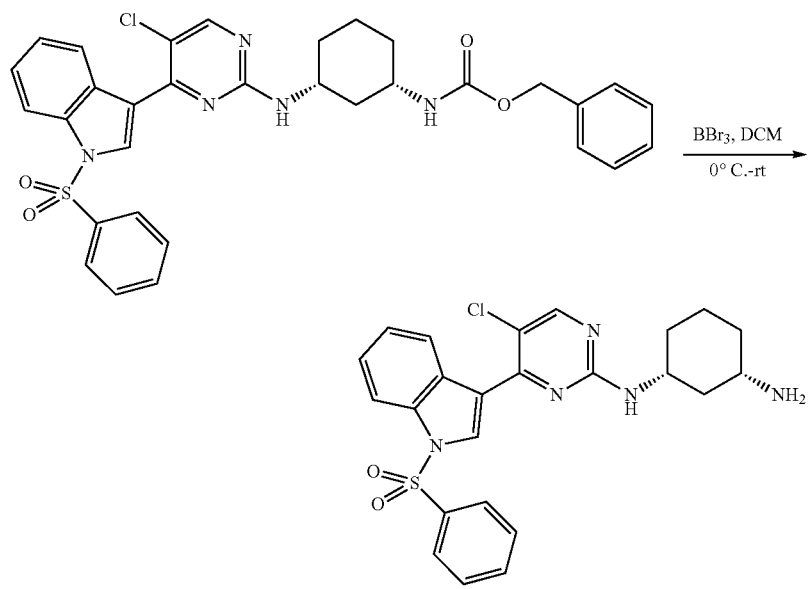

A solution of 1M BBr₃ in DCM (1.97 mL, 1.97 mmol) was added to a stirring solution of benzyl (1S,3R)-3-(5-chloro-4-(1-(phenylsulfonyl)-1H-indol-3-yl)pyrimidin-2-ylamino)cyclohexylcarbamate (971 mg, 1.58 mmol) at 0° C. The reaction mixture was allowed to stir 30 min at this temperature and then allowed to stir at room temperature overnight. The solution was then re-cooled to 0° C. and quenched with MeOH (10 mL). The solution was allowed to stir 30 min and was then concentrated under reduced pressure to a light yellow oil. The oil was purified by reverse phase column (C₁₈, H₂O/ACN+0.1% HCO₂H, 5 to 100% gradient) to yield the title compound as a light yellow solid (762 mg, 1.58 mmol, 100%).

278

5-Amino-N-methoxy-N-methylpicolinamide

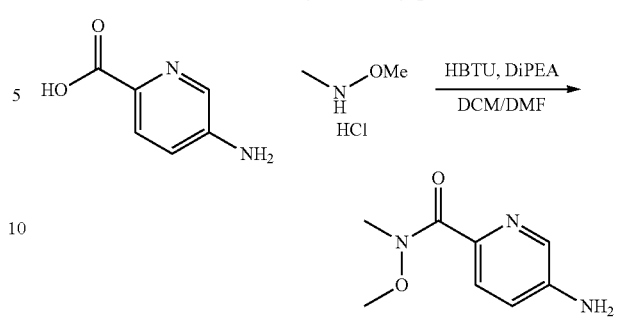

N,O-dimethylhydroxylamine hydrochloride (520 mg, 5.33 mmol), 5-aminopyridine-2-carboxylic acid (491 mg, 3.55 mmol), HBTU (2.02 g, 5.33 mmol) and diisopropylethylamine (2.48 mL, 14.2 mmol) were stirred in a mixture of DCM/DMF (5/1, 23.7 mL) at room temperature overnight. The reaction mixture was poured into a saturated solution of NaHCO₃ (50 mL) and the product extracted 4 times with 2-methyltetrahydrofuran (50 mL). Organics were combined, washed with water, brine, dried over MgSO₄, filtered and concentrated under reduced pressure to afford the title compound as an orange foamy solid (643 mg, 3.55 mmol, 100%).

Benzyl 6-(methoxy(methyl)carbamoyl)pyridin-3-ylcarbamate

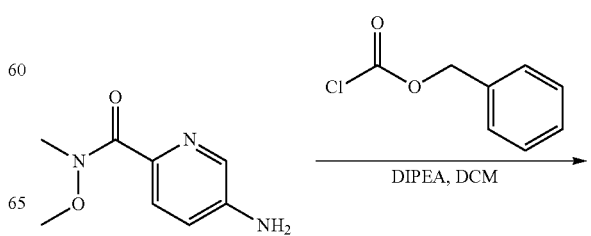

-continued

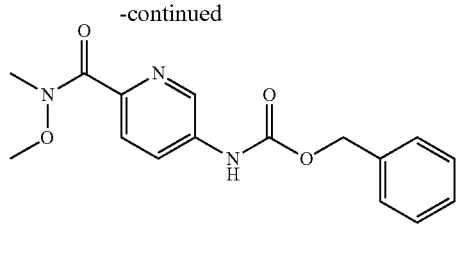

Diisopropylethylamine (1.9 mL, 10.7 mmol) was added to a stirring solution of 5-amino-N-methoxy-N-methylpicolinamide (643 mg, 3.55 mmol) in DCM (24 mL) and cooled to 0° C. Benzylchloroformate (0.76 mL, 5.3 mmol) was then added to the solution and the reaction mixture stirred from 0° C. to room temperature overnight. Aqueous sodium bicarbonate (100 mL) was added and the phases were separated. The aqueous phase was extracted twice with dichloromethane (50 mL). Organics were combined, washed with brine, dried over MgSO$_4$, filtered and concentrated to afford the title compound as a yellow oil (391 mg, 1.24 mmol, 35%).

Benzyl 6-formylpyridin-3-ylcarbamate

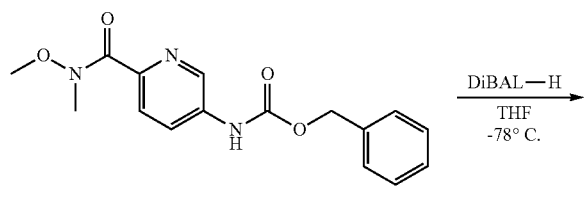

-continued

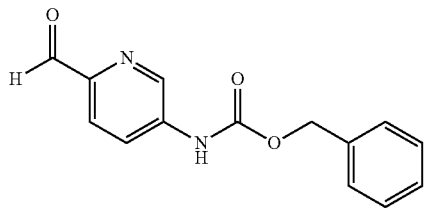

Diisobutylaluminium hydride 1M in DCM (1.90 mL, 1.90 mmol) was added dropwise to a stirring solution of benzyl 6-(methoxy(methyl)carbamoyl)pyridin-3-ylcarbamate (391 mg, 1.24 mmol) in tetrahydrofuran (5 mL) at −78° C. The resulting solution was allowed to stir at this temperature for 1 h 30 min. The solution was then quenched at −78° C. with 1M HCl (10 mL) and temperature was slowly raised to 0° C. A saturated aqueous solution of NaHCO$_3$ (50 mL) was added to the reaction mixture and the solution was extracted 3 times with EtOAc (50 mL). The combined organic layers were dried over MgSO$_4$, filtered and evaporated to dryness. The residue was purified by SiO$_2$ chromatography (EtOAc in hexanes, 0 to 100% gradient) and afforded the title compound as a white solid (69 mg, 0.27 mmol, 22%).

Benzyl 6-((((1S,3R)-3-(5-chloro-4-(1-(phenylsulfonyl)-1H-indol-3-yl)pyrimidin-2-ylamino)cyclohexylamino)methyl)pyridin-3-ylcarbamate

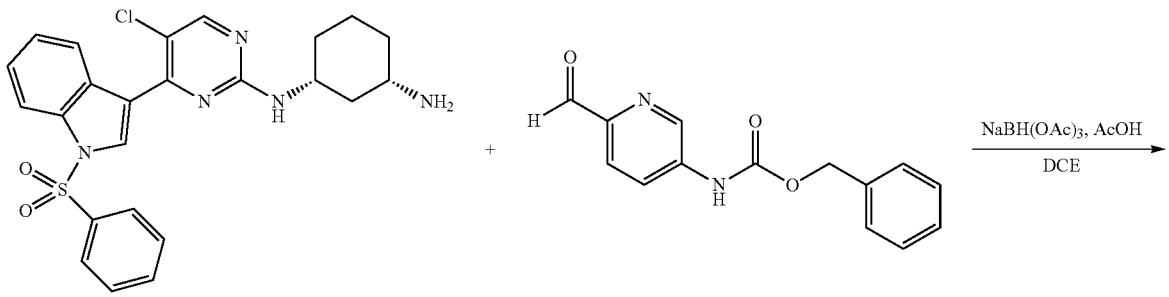

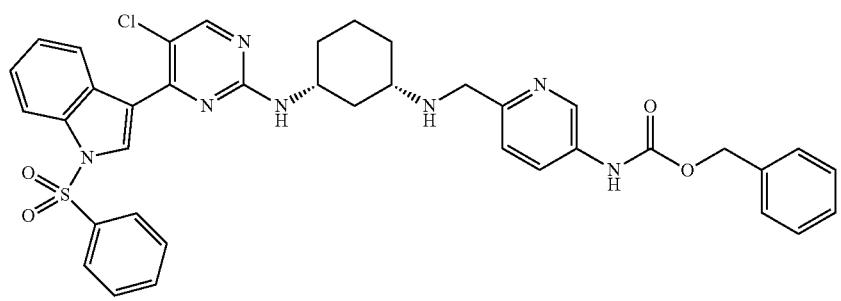

To a DCE solution (3.1 mL) of (1R,3S)—N-(5-chloro-4-(1-(phenylsulfonyl)-1H-indol-3-yl)pyrimidin-2-yl)cyclohexane-1,3-diamine (120 mg, 0.25 mmol) was added acetic acid (7.0 μL, 0.12 mmol) followed by the addition of benzyl 6-formylpyridin-3-ylcarbamate (69 mg, 0.27 mmol). The reaction mixture was stirred at room temperature for 10 minutes. Sodium triacetoxyborohydride (106 mg, 0.50 mmol) was then added in one portion and the resulting mixture was stirred at room temperature overnight. The reaction mixture was diluted with dichloromethane (50 mL) and the organic phase was washed with saturated solution of NaHCO₃ (50 mL) and brine (50 mL). The organic layer was dried over MgSO₄, filtered and concentrated under reduced pressure to afford the title compound as a pale yellow solid (167 mg, 0.231 mmol, 93%).

Benzyl 6-((((1S,3R)-3-(5-chloro-4-(1-(phenylsulfonyl)-1H-indol-3-yl)pyrimidin-2-ylamino)cyclohexyl)(Boc)amino)methyl) pyridin-3-ylcarbamate (167 mg, 0.231 mmol) was dissolved in DCM (2 mL) and triethylamine (64 μL, 0.46 mmol) was added. The solution was cooled to 0° C. and di-tert-butyl dicarbonate (53 mg, 0.240 mmol) was added. The reaction mixture was stirred from 0° C. to room temperature overnight. The reaction mixture was then quenched with a saturated solution of NaHCO₃ (50 mL) and extracted 3 times with DCM (50 mL). The combined organic layers were dried over MgSO₄, filtered and evaporated to dryness. The residue was purified by SiO₂ chromatography (EtOAc in DCM, 10 to 100% gradient) and afforded the title compound as a white solid (139 mg, 0.169 mmol, 73%).

tert-Butyl (5-aminopyridin-2-yl)methyl((1S,3R)-3-(5-chloro-4-(1H-indol-3-yl)pyrimidin-2-ylamino)cyclohexyl)carbamate

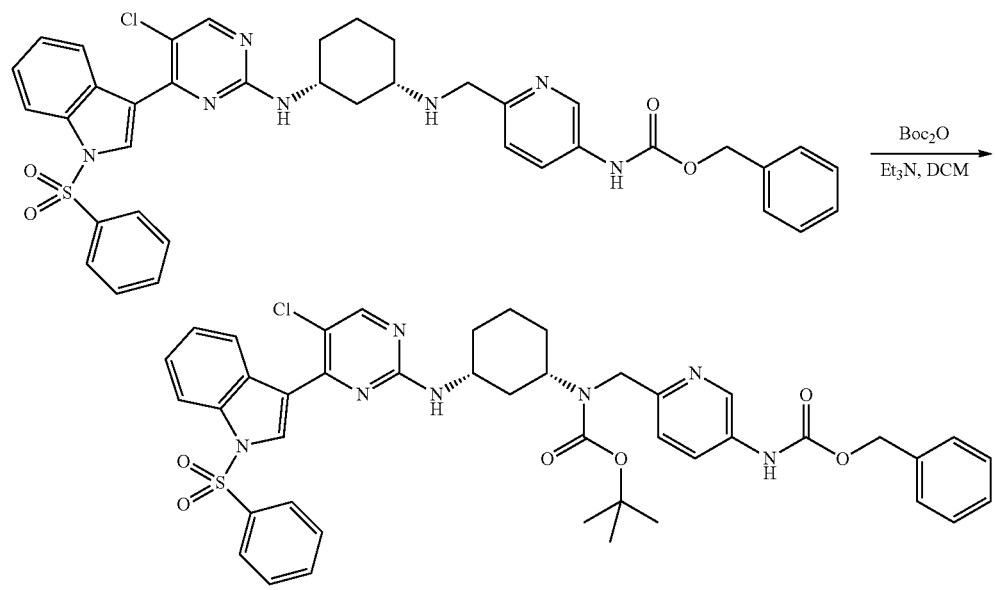

Benzyl 6-(((1S,3R)-3-(5-chloro-4-(1-(phenylsulfonyl)-1H-indol-3-yl)pyrimidin-2-ylamino)cyclohexylamino)

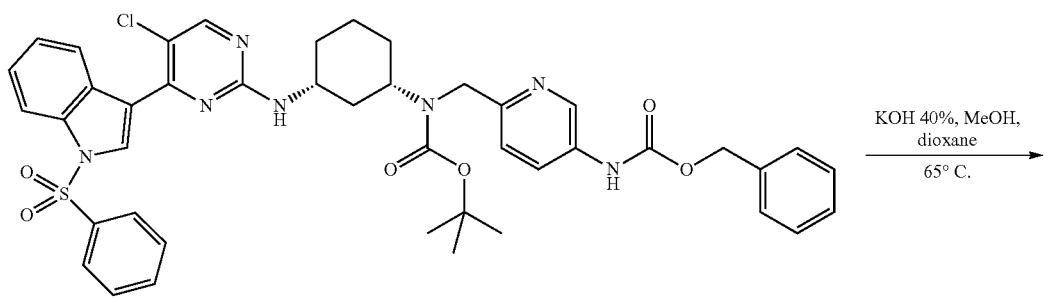

-continued

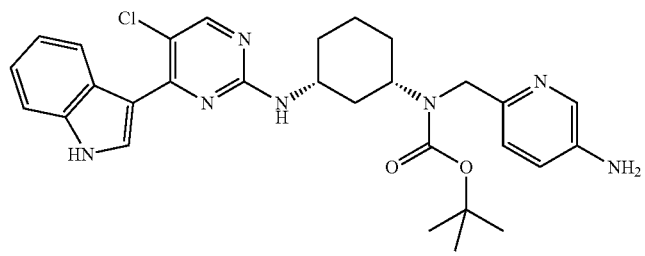

Benzyl 6-((((1S,3R)-3-(5-chloro-4-(1-(phenylsulfonyl)-1H-indol-3-yl)pyrimidin-2-ylamino)cyclohexyl)(Boc)amino)methyl) pyridin-3-ylcarbamate (139 mg, 0.169 mmol) was dissolved in 1,4-dioxane (1.1 mL) and KOH 40% in water (474 uL, 3.38 mmol) was added. The reaction mixture was stirred at 65° C. overnight. The reaction mixture was then diluted with water (50 mL) and extracted 3 times with EtOAc (50 mL) and 2-methyltetrahydrofuran (50 mL). The combined organic layers were washed with brine, dried over MgSO$_4$, filtered and concentrated under reduced pressure. The residue was purified by SiO$_2$ chromatography (THF in DCM, 0 to 100% gradient) and afforded the title compound as a pale yellow solid (45 mg, 0.082 mmol, 49%).

tert-Butyl (1S,3R)-3-(5-chloro-4-(1H-indol-3-yl)pyrimidin-2-ylamino)cyclohexyl((5-((E)-4-(dimethylamino)but-2-enamido)pyridin-2-yl)methyl)carbamate

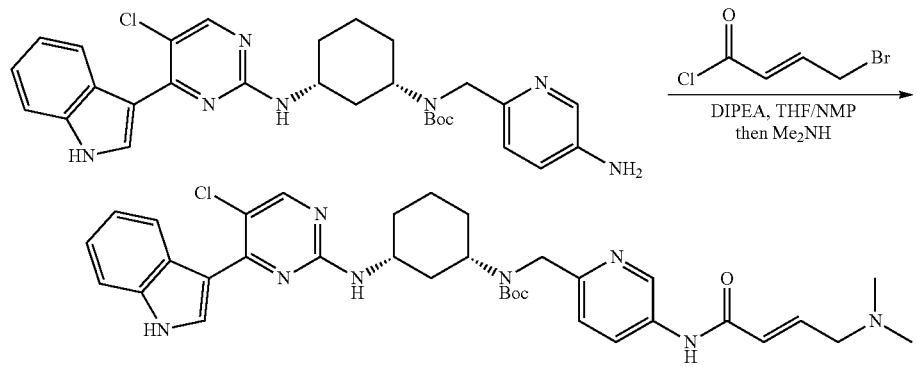

A cooled (−78° C.) solution of tert-butyl (5-aminopyridin-2-yl)methyl((1S,3R)-3-(5-chloro-4-(1H-indol-3-yl)pyrimidin-2-ylamino)cyclohexyl)carbamate (45 mg, 0.082 mmol) and DIPEA (43 µL, 0.25 mmol) in NMP/THF (0.3 mL/1.2 mL) was treated with a 54.2 mg/mL solution of (E)-4-bromobut-2-enoyl chloride in DCM (278 µL, 0.08 mmol). The resulting mixture was stirred 1 h under inert atmosphere at −78° C. before addition of a 2M solution of dimethylamine in THF (246 µL, 0.49 mmol). The resulting mixture was warmed up to rt and stirred 1 h at this temperature before being concentrated. The residue was then re-dissolved in MeTHF (20 mL) and washed twice with water (10 mL). The aqueous layers were extracted twice with MeTHF (20 mL). Organic extracts were combined, washed with brine, dried over MgSO$_4$, filtered, concentrated, providing the title compound as a brown oil (54 mg, 0.082 mmol, 100%).

(E)-N-(6-(((1S,3R)-3-(5-chloro-4-(1H-indol-3-yl)pyrimidin-2-ylamino)cyclohexylamino)methyl)pyridin-3-yl)-4-(dimethylamino)but-2-enamide

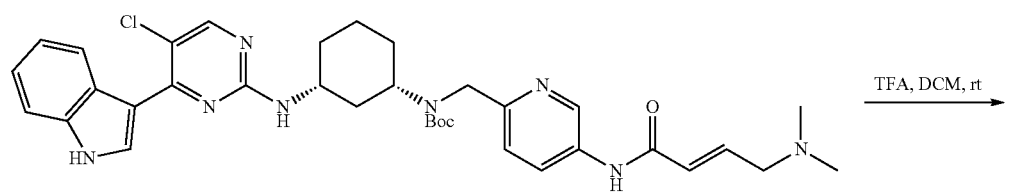

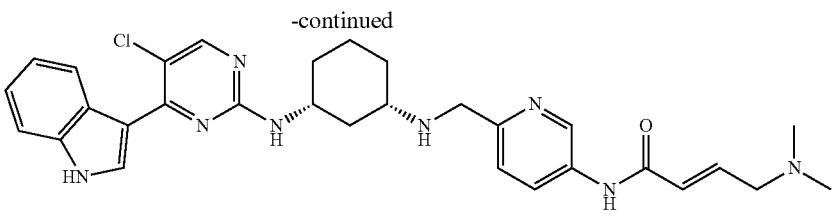

tert-Butyl (1S,3R)-3-(5-chloro-4-(1H-indol-3-yl)pyrimidin-2-ylamino)cyclohexyl((5-((E)-4-(dimethylamino)but-2-enamido)pyridin-2-yl)methyl)carbamate (54 mg, 0.082 mmol) was dissolved in DCM (1 mL) and trifluoroacetic acid (83 µL, 1.23 mmol, 15 eq) was added. The reaction mixture was stirred at room temperature for 5 h. The reaction mixture was then concentrated to remove DCM and excess TFA. Excess triethylamine was added and the residual oil was purified by reverse phase flash chromatography ($C_{18}$, $H_2O$/ACN+0.1% $HCO_2H$, 0 to 50% gradient). Pure fractions were directly lyophilized and afforded the title compound as a white solid (21 mg, 0.038 mmol, 46%). LCMS: Calculated: 559.1; Found (M+H$^+$): 559.37.

1H NMR (500 MHz, DMSO) δ 11.83 (br s, 1H), 10.26 (s, 1H), 8.74 (br s, 1H), 8.55 (br s, 1H), 8.47 (d, J=2.8 Hz, 1H), 8.24 (s, 1H), 8.19 (s, 1H), 8.04 (d, J=6.7 Hz, 1H), 7.48 (d, J=8.2 Hz, 1H), 7.40 (d, J=9.0 Hz, 1H), 7.26 (s, 1H), 7.18 (t, J=7.4 Hz, 1H), 7.05 (br s, 1H), 6.76 (dt, J=15.4, 5.9 Hz, 1H), 6.27 (dt, J=15.4, 1.6 Hz, 1H), 3.93 (br s, 3H), 3.07 (dd, J=5.9, 1.5 Hz, 2H), 2.73 (br s, 1H), 2.35 (br s, 1H), 2.18 (s, 6H), 2.01 (br s, 2H), 1.79 (brs, 1H), 1.40-1.20 (m, 3H), 1.15-1.05 (m, 1H).

Example 70. Synthesis of (E)-N-(6-(((1S,3R)-3-(5-chloro-4-(1H-indol-3-yl)pyrimidin-2-ylamino)-1-methylcyclohexylamino)methyl)pyridin-3-yl)-4-(dimethylamino)but-2-enamide (Compound 294)

(+/−) Benzyl tert-butyl ((1S,3R)-1-methylcyclohexane-1,3-diyl)dicarbamate

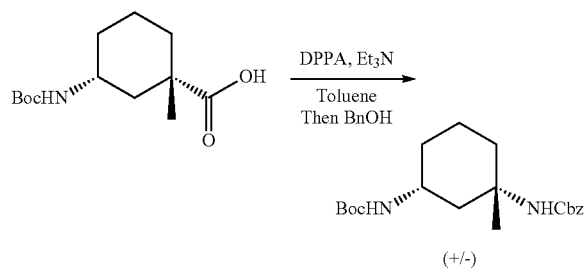

A solution of (+/−)-(1S,3R)-3-((tert-butoxycarbonyl)amino)-1-methylcyclohexanecarboxylic acid prepared as in WO2010/148197 (4.00 g, 15.5 mmol) in toluene (155 mL) was treated with Et$_3$N (2.4 mL, 17.1 mmol) and DPPA (3.68 mL, 17.1 mind) and heated at reflux for 1 h. Benzyl alcohol (8.0 mL, 77.7 mmol) and Et$_3$N (4.4 mL, 31.4 mmol) were added to the reaction mixture and the solution was heated at 100° C. for 72 h. The mixture was cooled to room temperature and then diluted with EtOAc (300 mL) and H$_2$O (300 mL). The layers were separated and the aqueous layer was extracted with EtOAc (3×200 mL). The combined organics layers were washed with brine (100 mL), filtered and evaporated to dryness. The residue was purified by SiO$_2$ chromatography (EtOAc in hexanes, 0 to 50% gradient) and afforded the title compound (3.40 g, 9.38 mmol, 60%) as a white solid.

Benzyl tert-butyl ((1S,3R)-1-methylcyclohexane-1,3-diyl)dicarbamate and benzyl tert-butyl ((1R,3S)-1-methylcyclohexane-1,3-diyl)dicarbamate

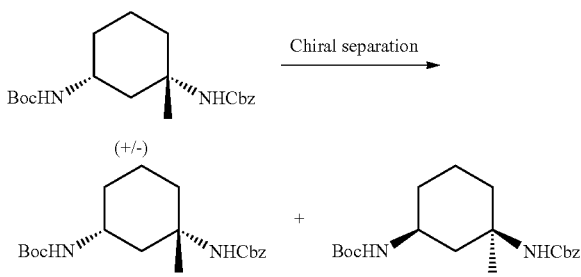

Both enantiomers of (+/−)-Benzyl tert-butyl ((1S,3R)-1-methylcyclohexane-1,3-diyl)dicarbamate (3.40 g, 9.38 mmol) were separated using preparative chiral HPLC (Chiralpak IA, 5 um, 20×250 mm; hex/MeOH/DCM=90/5/5) to yield both compounds benzyl tert-butyl ((1S,3R)-1-methylcyclohexane-1,3-diyl)dicarbamate (1.20 g, 3.31 mmol) and benzyl tert-butyl ((1R,3S)-1-methylcyclohexane-1,3-diyl)dicarbamate (1.15 g, 3.17 mmol) as white solids.

Benzyl ((1S,3R)-3-amino-1-methylcyclohexyl)carbamate hydrochloride

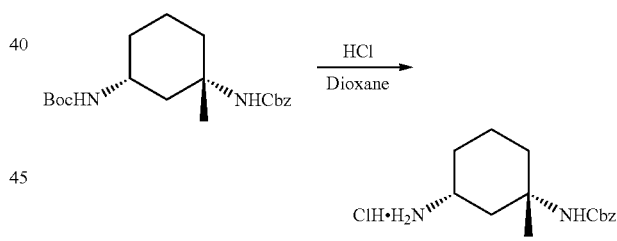

A solution of benzyl tert-butyl ((1S,3R)-1-methylcyclohexane-1,3-diyl)dicarbamate (700 mg, 1.93 mmol) in DCM (19 mL) was treated with a 4M solution of HCl in dioxane (9.66 mL, 38.6 mmol) and stirred 16 h at rt. The mixture was evaporated to dryness and afforded the title compound (577 mg, 1.93 mmol, 100%) as a white solid which was used in the next step without further purification.

(1S,3R)-Benzyl-3-(5-chloro-4-(1-(phenylsulfonyl)-1H-indol-3-yl)pyrimidin-2-ylamino)-1-methylcyclohexylcarbamate

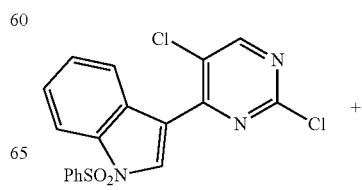

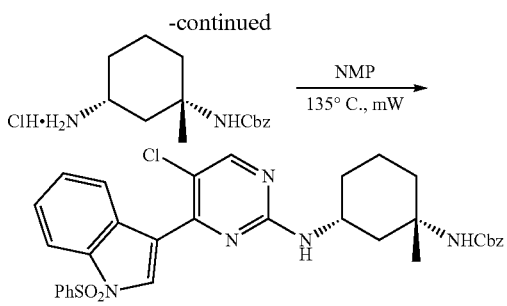

A solution of 3-(2,5-dichloropyrimidin-4-yl)-1-(phenylsulfonyl)-1H-indole (1.02 g, 2.53 mmol), benzyl ((1S,3R)-3-amino-1-methylcyclohexyl)carbamate hydrochloride (577 mg, 1.93 mmol) and DIPEA (1.15 mL, 6.60 mmol) in NMP (11 mL) was heated at 135° C. (microwave) for 60 min. The cooled mixture was diluted with EtOAc (250 mL), washed with H₂O (100 mL), brine (100 mL), dried over MgSO₄, filtered and evaporated to dryness. The residue was purified by SiO₂ chromatography (EtOAc in DCM, 0 to 50% gradient) and afforded the title compound (747 mg, 1.19 mmol, 54%) as a yellow foam.

(1S,3R)—N-(5-chloro-4-(1-(phenylsulfonyl)-1H-indol-3-yl)pyrimidin-2-yl)-3-methylcyclohexane-1,3-diamine

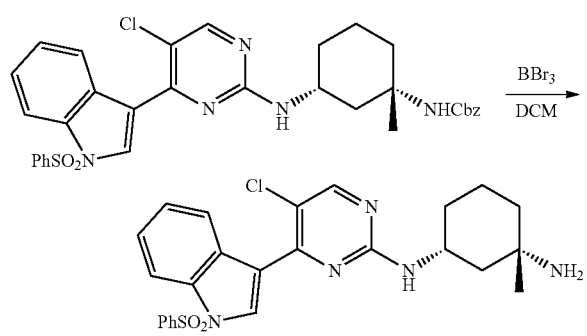

A cooled (−78° C.) solution of (1S,3R)-benzyl-3-(5-chloro-4-(1-(phenylsulfonyl)-1H-indol-3-yl)pyrimidin-2-ylamino)-1-methylcyclohexylcarbamate (747 mg, 1.19 mmol) in DCM (39 mL) was treated with a 1M solution of BBr₃ in DCM (2.83 mL, 2.83 mmol) and was slowly warmed up to rt. MeOH (10 mL) was added to the mixture was the resulting solution was stirred 1 h at rt. The resulting mixture was evaporated to dryness. The residue was purified by reverse phase chromatography (C₁₈, H₂O/ACN+0.1% HCO₂H, 0 to 60% gradient) and afforded the title compound (485 mg, 0.978 mmol, 83%) as a yellow solid.

5-Amino-N-methoxy-N-methylpicolinamide

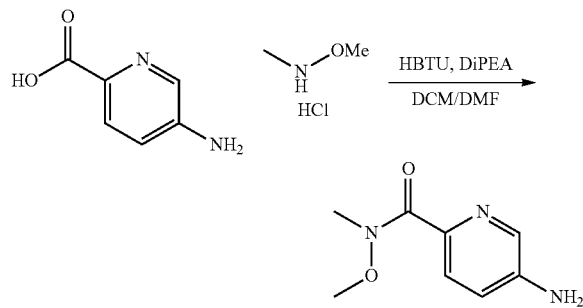

N,O-dimethylhydroxylamine hydrochloride (520 mg, 5.33 mmol), 5-aminopyridine-2-carboxylic acid (491 mg, 3.55 mmol), HBTU (2.02 g, 5.33 mmol) and diisopropylethylamine (2.48 mL, 14.2 mmol) were stirred in a mixture of DCM/DMF (5/1, 23.7 mL) at room temperature overnight. The reaction mixture was poured into a saturated solution of NaHCO₃ (50 mL) and the product extracted 4 times with 2-methyltetrahydrofuran (50 mL). Organics were combined, washed with water, brine, dried over MgSO₄, filtered and concentrated under reduced pressure to afford the title compound as an orange foamy solid (643 mg, 3.55 mmol, 100%).

Benzyl 6-(methoxy(methyl)carbamoyl)pyridin-3-ylcarbamate

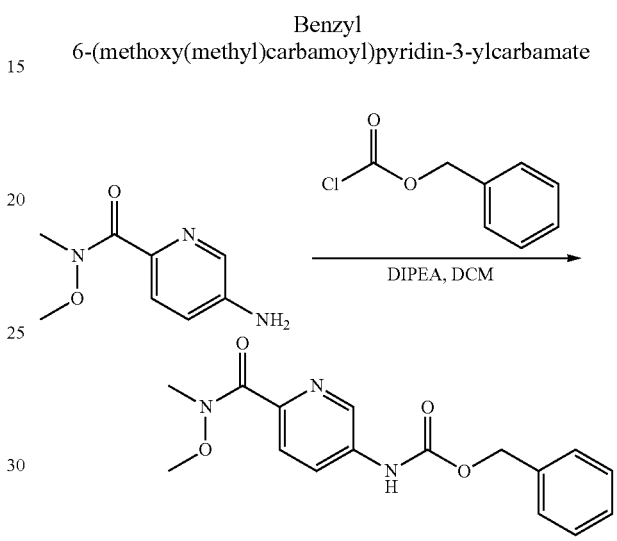

Diisopropylethylamine (1.9 mL, 10.7 mmol) was added to a stirring solution of 5-amino-N-methoxy-N-methylpicolinamide (643 mg, 3.55 mmol) in DCM (24 mL) and cooled to 0° C. Benzylchloroformate (0.76 mL, 5.3 mmol) was then added to the solution and the reaction mixture stirred from 0° C. to room temperature overnight. Aqueous sodium bicarbonate (100 mL) was added and the phases were separated. The aqueous phase was extracted twice with dichloromethane (50 mL). Organics were combined, washed with brine, dried over MgSO₄, filtered and concentrated to afford the title compound as a yellow oil (391 mg, 1.24 mmol, 35%).

Benzyl 6-formylpyridin-3-ylcarbamate

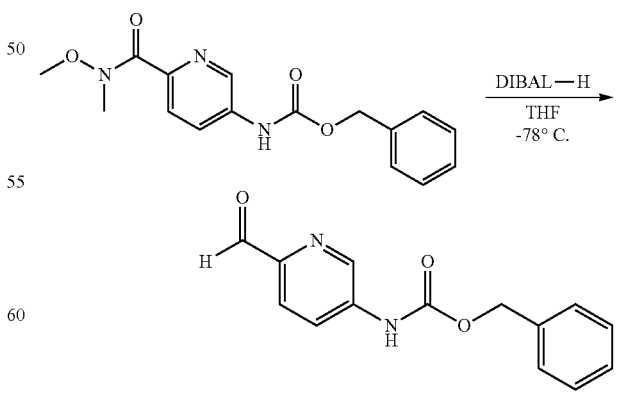

Diisobutylaluminium hydride 1M in DCM (1.90 mL, 1.90 mmol) was added dropwise to a stirring solution of benzyl 6-(methoxy(methyl)carbamoyl)pyridin-3-ylcarbamate (391 mg, 1.24 mmol) in tetrahydrofuran (5 mL) at −78° C. The resulting solution was allowed to stir at this temperature for 1 h 30 min. The solution was then quenched at −78° C. with 1M HCl (10 mL) and temperature was slowly raised to 0° C. A saturated aqueous solution of NaHCO$_3$ (50 mL) was added to the reaction mixture and the solution was extracted 3 times with EtOAc (50 mL). The combined organic layers were dried over MgSO$_4$, filtered and evaporated to dryness. The residue was purified by SiO$_2$ chromatography (EtOAc in hexanes, 0 to 100% gradient) and afforded the title compound as a white solid (69 mg, 0.27 mmol, 22%).

Benzyl 6-(((1S,3R)-3-(5-chloro-4-(1-(phenylsulfonyl)-1H-indol-3-yl)pyrimidin-2-ylamino)-1-methylcyclohexylamino)methyl)pyridin-3-ylcarbamate mixture was stirred at room temperature overnight. NaBH(OAc)$_3$ (71 mg, 0.33 mmol) was then added in one portion and the resulting mixture was stirred at room temperature for 5 h. Titanium isopropoxide (49 uL, 0.17 mmol) and NaBH(OAc)$_3$ (36 mg, 0.17 mmol) were added and the reaction was heated to 50° C. overnight. A saturated solution of NaHCO$_3$ (50 mL) was added and the mixture was stirred for 15 minutes and was then filtrated over Celite and washed with EtOAc (100 mL). The phases were separated and the aqueous phase extracted 2 more times with EtOAc (100 mL). The organic layers were combined, dried over MgSO$_4$, filtered and evaporated to dryness affording the title compound as a pale yellow solid (82 mg, 0.11 mmol, 100%). Product was used crude for next step.

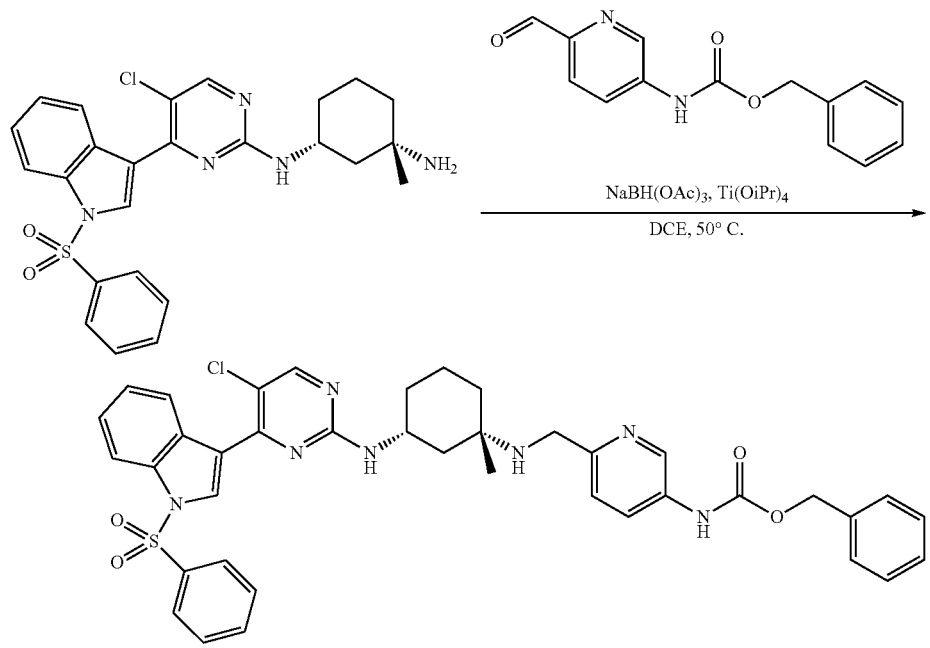

To a DCE (3.7 mL) solution of (1S,3R)—N-(5-chloro-4-(1-(phenylsulfonyl)-1H-indol-3-yl)pyrimidin-2-yl)-3-methylcyclohexane-1,3-diamine (55 mg, 0.11 mmol) was added benzyl 6-formylpyridin-3-ylcarbamate (31 mg, 0.12 mmol) and titanium isopropoxide (98 uL, 0.33 mmol). The reaction (1S,3R)—N$^1$-((5-Aminopyridin-2-yl)methyl)-N$^3$-(5-chloro-4-(1H-indol-3-yl)pyrimidin-2-yl)-1-methylcyclohexane-1,3-diamine (Compound 1062)

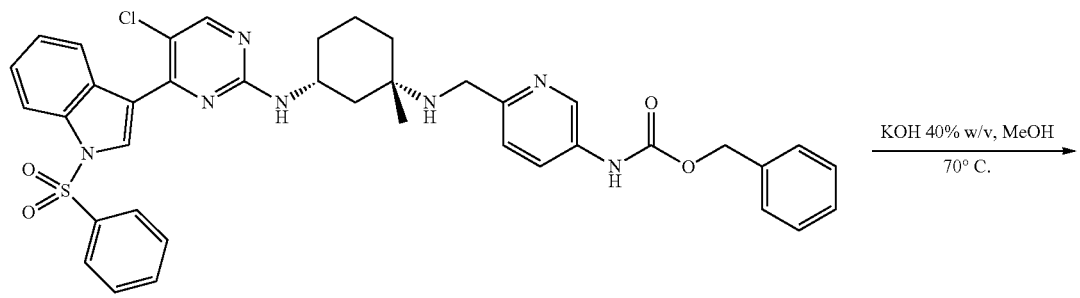

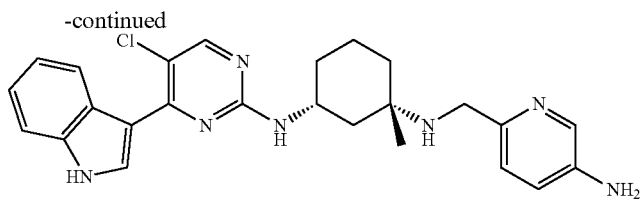

Benzyl 6-(((1S,3R)-3-(5-chloro-4-(1-(phenylsulfonyl)-1H-indol-3-yl)pyrimidin-2-ylamino)-1-methylcyclohexylamino) methyl)pyridin-3-ylcarbamate (82 mg, 0.11 mmol) was dissolved in methanol (2.2 mL) and KOH 40% w/v (0.23 mL, 1.7 mmol) was added. The reaction mixture was stirred at 70° C. for 3 days. The reaction mixture was then diluted with water (50 mL) and extracted 3 times with EtOAc (50 mL) and 2-methyltetrahydrofuran (50 mL). The organic layers were combined, washed with brine (50 mL), dried over MgSO$_4$, filtered and evaporated to dryness. The residue was purified by SiO$_2$ chromatography (MeOH in DCM, 0 to 10% gradient) and afforded the title compound as a pale yellow solid (46 mg, 0.099 mmol, 89% over 2 steps).

(E)-N-(6-(((1S,3R)-3-(5-chloro-4-(1H-indol-3-yl)pyrimidin-2-ylamino)-1-methylcyclohexylamino)methyl)pyridin-3-yl)-4-(dimethylamino)but-2-enamide (Compound 294)

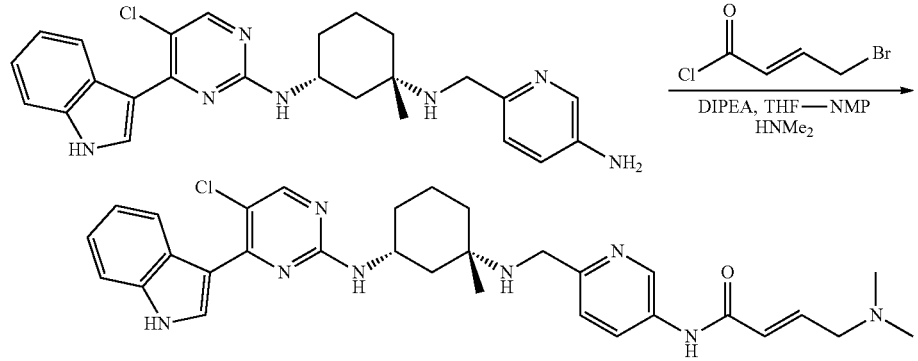

A cooled (−78° C.) solution of 5(1S,3R)—N$^1$-(5-aminopyridin-2-yl)methyl)-N$^3$-(5-chloro-4-(1H-indol-3-yl)pyrimidin-2-yl)-1-methylcyclohexane-1,3-diamine (30 mg, 0.065 mmol), and DIPEA (34 μL, 0.195 mmol) in THF/NMP (1.0 mL/0.3 mL) was treated with a 54.2 mg/mL solution of (E)-4-bromobut-2-enoyl chloride in DCM (220 μL, 0.065 mmol). The resulting mixture was stirred 4 h at −78° C. before addition of a 2M solution of dimethylamine in THF (97 μL, 0.195 mmol). The resulting mixture was warmed up to −20° C. for 2 h and then evaporated to dryness. The residue was purified by reverse phase chromatography (C$_{18}$, H$_2$O/ACN+0.1% HCO$_2$H, 5 to 70% gradient) and afforded the title compound (5.7 mg, 0.0099 mmol, 15%) as a white solid after lyophilization. LCMS: Calculated: 573.13, Found (M+H$^+$): 573.34. $^1$H NMR (500 MHz, DMSO) δ 11.84 (s, 1H), 10.25 (s, 1H), 8.74 (s, 1H), 8.59 (br d, J=9.5 Hz, 1H), 8.50-8.41 (m, 1H), 8.28-8.16 (m, 2H), 8.03 (dd, J=8.8, 2.3 Hz, 1H), 7.54-7.46 (m, 1H), 7.44 (d, J=8.3 Hz, 1H), 7.36-7.27 (m, 1H), 7.20 (dd, J=13.3, 7.0 Hz, 1H), 7.16-7.04 (m, 1H), 6.76 (dt, J=15.5, 5.9 Hz, 1H), 6.27 (dt, J=15.3, 1.6 Hz, 1H), 4.22-4.07 (m, 1H), 3.88 (s, 2H), 3.06 (dd, J=5.8, 1.4 Hz, 2H), 2.18 (s, 6H), 2.01-1.85 (m, 2H), 1.77-1.68 (m, 1H), 1.64-1.42 (m, 4H), 1.37-1.28 (m, 1H), 1.26 (br s, 3H).

Example 71. Synthesis of 3-(5-chloro-2-(((1R,3S)-3-(4-((E)-4-(dimethylamino)but-2-enoyl)piperazin-1-yl)cyclohexyl)amino)pyrimidin-4-yl)indolin-2-one (Compound 293)

3-(2,5-Dichloropyrimidin-4-yl)-3H-indol-2-ol

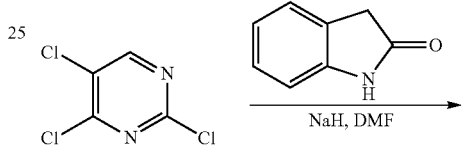

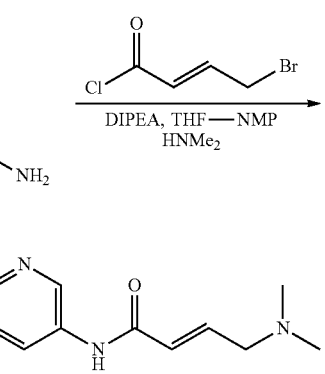

2-Oxindole (239 mg, 1.79 mmol) was dissolved in DMF (15 mL) at room temperature and sodium hydride (144 mg, 3.60 mmol) was added. The reaction mixture stirred at room temperature for 15 minutes. 2,4,5-Trichloropyrimidine (300 mg, 1.63 mmol) was then added dropwise and the resulting solution was stirred at room temperature for 30 minutes. The solution was then quenched a saturated aqueous solution of NH$_4$Cl (100 mL) and extracted 3 times with DCM (100 mL). The organic layers were combined, washed with water (50 mL), brine (50 mL), dried over MgSO$_4$, filtered and evaporated to dryness. The crude residue was stirred in EtOH (20 mL), filtered, washed with EtOH (5 mL) and hexanes (5 mL) to yield the title compound (379 mg, 1.35 mmol, 83%) as an orange solid.

3-(2,5-Dichloropyrimidin-4-yl)-3H-indol-2-ol was then used in the synthetic procedure described in Example 33 to produce Compound 1045 and then subjected to the last step in Example 70 to produce 3-(5-chloro-2-(((1R,3S)-3-(4-((E)-4-(dimethylamino)but-2-enoyl)piperazin-1-yl)cyclohexyl)amino)pyrimidin-4-yl)indolin-2-one (Compound 293).

LCMS: Calculated: 538.08, Found (M+H$^+$): 538.33. $^1$H NMR (500 MHz, DMSO) δ 10.62 (s, 1H), 8.40-8.28 (m, 1H), 8.14 (s, 1H), 7.41 (br d, J=5.7 Hz, 1H), 7.20 (dt, J=7.7, 3.9 Hz, 1H), 7.02 (d, J=7.3 Hz, 1H), 6.91 (t, J=7.5 Hz, 1H), 6.86 (d, J=7.8 Hz, 1H), 6.65-6.51 (m, 2H), 5.02 (br s, 1H), 3.71-3.58 (m, 1H), 3.53-3.42 (m, 4H), 3.17-3.10 (m, 2H), 2.48-2.37 (m, 4H), 2.34-2.26 (m, 1H), 2.23 (s, 3H), 2.22 (s, 3H), 2.02-1.87 (m, 1H), 1.81-1.66 (m, 3H), 1.26-1.17 (m, 1H), 1.13-1.02 (m, 2H).

Example 72. Synthesis of 1-(4-((1S,3R)-3-((4-([1,2,4]triazolo[4,3-a]pyridin-3-yl)-5-chloropyrimidin-2-yl)amino)cyclohexyl)piperazin-1-yl)prop-2-en-1-one (Compound 344)

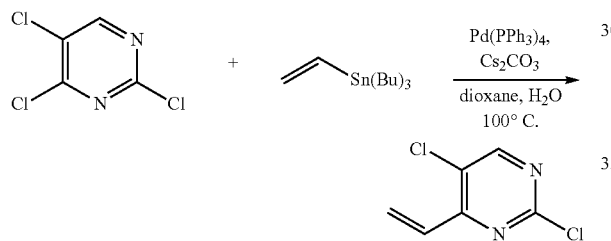

Tributyl (vinyl)tin (908 mg, 2.86 mmol) was mixed with 2,4,5-trichloropyrimidine (500 mg, 2.73 mmol) in toluene (6.8 mL) and the solution was degassed with nitrogen prior to the addition of tetrakistriphenylphosphine palladium (158 mg, 0.140 mmol). The reaction mixture was stirred at 110° C. for 1 h 30 min. The reaction mixture was cooled to room temperature, diluted with a saturated aqueous solution of NaHCO$_3$ (100 mL) and extracted three times with EtOAc (100 mL). The organics were combined, washed with brine (50 mL), dried over MgSO$_4$ and evaporated to dryness. The residue was purified by SiO$_2$ chromatography containing 10% w/w of K$_2$CO$_3$ (EtOAc in hexanes, 0 to 30% gradient) and afforded the title compound (395 mg, 2.26 mmol, 83%) as a clear oil.

2,5-Dichloropyrimidine-4-carbaldehyde

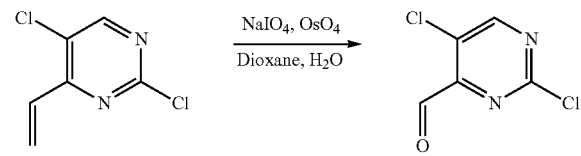

2,5-Dichloro-4-vinylpyrimidine (200 mg, 1.14 mmol) was dissolved in a 4:1 mixture of 1,4-dioxane/water (46 mL) and sodium periodate (745 mg, 3.50 mmol) was added. Osmium tetraoxide (0.25 mL, 4 wt % in water, 0.04 mmol) was added dropwise and the reaction mixture stirred at room temperature for 15 h. The reaction mixture was then diluted with water (50 mL) and extracted three times with EtOAc (100 mL). The organics were combined, dried over MgSO$_4$, filtered and evaporated to dryness affording the title compound (202 mg, 1.14 mmol, 100%) as a pale yellow oil which was used without further purification.

3-(2,5-Dichloropyrimidin-4-yl)-[1,2,4]triazolo[4,3-a]pyridine

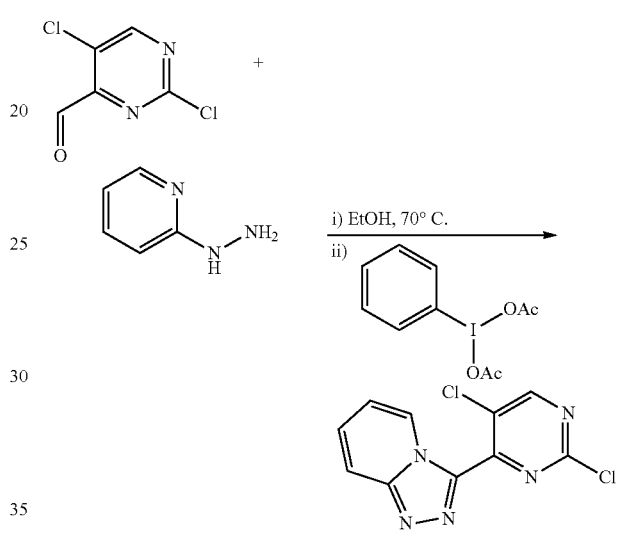

2,5-Dichloropyrimidine-4-carbaldehyde (202 mg, 1.14 mmol) was dissolved in ethanol (4 mL) and 2-hydrazinylpyridine (125 mg, 1.14 mmol) was added. The reaction mixture was heated at 70° C. for 2 h 30 min. The reaction mixture was then cooled to room temperature and iodobenzene diacetate (478 mg, 1.48 mmol) was added. The reaction mixture was stirred at room temperature for 1 h, evaporated to dryness and filtered through a silica gel pad eluting with 20% EtOAc in DCM (500 mL). The filtrate was evaporated to dryness and the obtained residue was stirred in Et$_2$O (30 mL) for 10 minutes, filtered, washed with Et$_2$O (5 mL) and dried under vacuum to afford the title compound (88 mg, 0.33 mmol, 29% over 3 steps) as a beige solid.

3-(2,5-Dichloropyrimidin-4-yl)-[1,2,4]triazolo[4,3-a]pyridine was then subjected to the synthesis scheme described below for Compound 375 to produce 1-(4-((1S,3R)-3-((4-([1,2,4]triazolo[4,3-a]pyridin-3-yl)-5-chloropyrimidin-2-yl)amino)cyclohexyl)piperazin-1-yl)prop-2-en-1-one.

LCMS: Calculated: 466.97, Found (M+H$^+$): 467.33. $^1$H NMR (500 MHz, DMSO) δ 9.53 (s, 1H, rotomer A), 9.24 (s, 1H, rotomer B), 8.58 (s, 1H), 8.00 (d, J=9.2 Hz, 1H), 7.78 (d, J=7.9 Hz, 1H), 7.59 (ddd, J=9.1, 6.6, 0.8 Hz, 1H), 7.17 (t, J=6.5 Hz, 1H), 6.77 (dd, J=16.7, 10.4 Hz, 1H), 6.08 (dd, J=16.7, 2.4 Hz, 1H), 5.65 (dd, J=10.5, 2.3 Hz, 1H), 3.80-3.67 (m, 2H), 3.54-3.46 (m, 4H), 2.49-2.39 (m, 4H), 2.12 (br d, J=9.5 Hz, 1H), 1.94 (br d, J=10.9 Hz, 1H), 1.84-1.71 (m, 2H), 1.36-1.11 (m, 4H).

Example 73. Synthesis of (1R,3S)—N1-(4-([1,2,4]triazolo[4,3-a]pyridin-3-yl)-5-chloropyrimidin-2-yl)-3-methylcyclohexane-1,3-diamine Benzyl (1S,3R)-3-(4-([1,2,4]triazolo[4,3-a]pyridin-3-yl)-5-chloropyrimidin-2-ylamino)-1-methylcyclohexylcarbamate

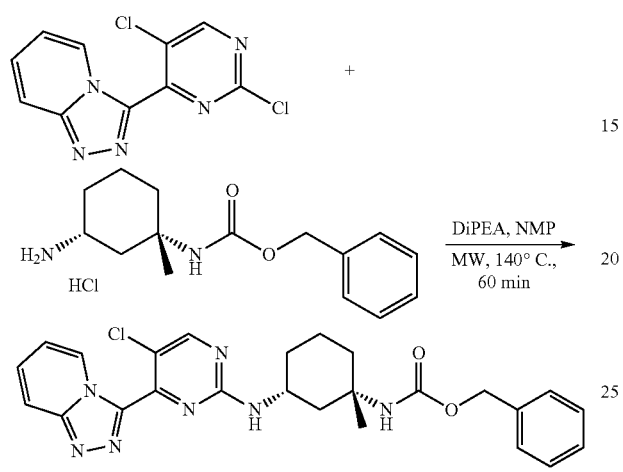

A solution of 3-(2,5-Dichloropyrimidin-4-yl)-[1,2,4]triazolo[4,3-a]pyridine (169 mg, 0.64 mmol), (1S,3R)-Benzyl-3-amino-1-methylcyclohexylcarbamate hydrochloride (190 mg, 0.64 mmol) and diisopropylethylamine (442 µL, 2.54 mmol) in NMP (2.5 mL) was heated at 140° C. (microwave) for 60 min. The cooled mixture was diluted with MeTHF (100 mL), washed with H₂O (100 mL), brine (100 mL), dried over MgSO₄, filtered and evaporated to dryness. The residue was purified by SiO₂ chromatography (EtOAc in DCM, 50 to 100% gradient) and afforded the title compound (220 mg, 0.45 mmol, 70%) as a yellow solid.

(1R,3S)—N1-(4-([1,2,4]triazolo[4,3-a]pyridin-3-yl)-5-chloropyrimidin-2-yl)-3-methylcyclohexane-1,3-diamine

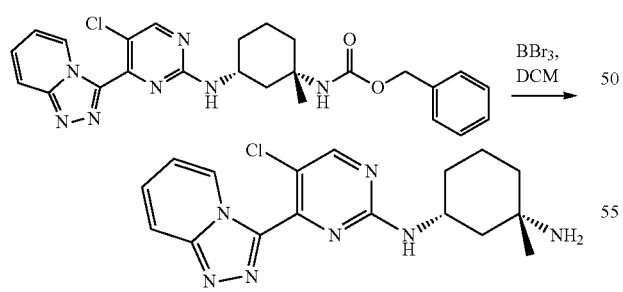

A solution of 1M BBr₃ in DCM (0.55 mL, 0.55 mmol) was added to a stirring solution of benzyl (1S,3R)-3-(4-([1,2,4]triazolo[4,3-a]pyridin-3-yl)-5-chloropyrimidin-2-ylamino)-1-methylcyclohexylcarbamate (218 mg, 0.44 mmol) at 0° C. The reaction mixture was allowed to stir 30 min at this temperature and then allowed to stir at room temperature overnight. The solution was then cooled back to 0° C. and quenched with MeOH (10 mL). The solution was allowed to stir 30 min and was then evaporated to dryness. The obtained residue was then stirred in Et₂O (20 mL) with a minimal amount of DCM, filtered, washed with Et₂O (5 mL) to afford the title compound (250 mg, 0.699 mmol, 158%) as a yellow solid. Inorganic borane salts were present with the compound. The solid was used for next step without further purification, considering 100% yield.

Example 74. Synthesis of 1-(4-((1S,3R)-3-(5-chloro-4-(5-methoxy-1H-indol-3-yl)pyrimidin-2-ylamino)cyclohexyl)piperazin-1-yl)prop-2-en-1-one (Compound 375)

3-(2,5-dichloropyrimidin-4-yl)-5-methoxy-1H-indole

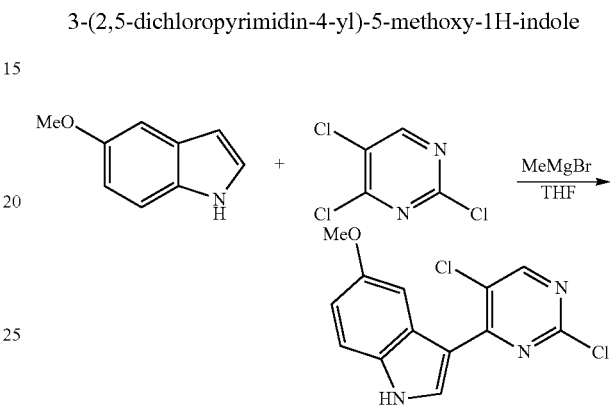

To an ice-cold solution of 5-methoxyindole (525 mg, 3.57 mmol) in THF (2.0 mL) was added dropwise a solution of methylmagnesium bromide (1.30 mL, 3.0 M in Et₂O, 3.90 mmol). The resulting solution was stirred at this temperature for 1 h, then 2,4,5-trichloropyrimidine (0.21 mL, 1.83 mmol) was added dropwise to the reaction mixture at 0° C. The resulting solution was stirred at room temperature for 1 h and 60° C. for 1.5 hour. The reaction was then allowed to cool to room temperature and acetic acid (0.21 mL, 3.66 mmol) was added dropwise followed by water (3.2 mL) and THF (0.64 mL). This mixture was stirred at 60° C. for 20 min. The reaction was allowed to cool to room temperature and partitioned between EtOAc (200 mL) and H₂O (60 mL). The organic layer was dried over Na₂SO₄ and evaporated to dryness. The crude material was purified by SiO₂ chromatography (EtOAc in hexanes 5 to 100% gradient) and afforded the title compound as a light yellow solid (207 mg, 0.704 mmol, 38%).

Benzyl 4-((1S,3R)-3-(5-chloro-4-(5-methoxy-1H-indol-3-yl)pyrimidin-2-ylamino)cyclohexyl)piperazine-1-carboxylate

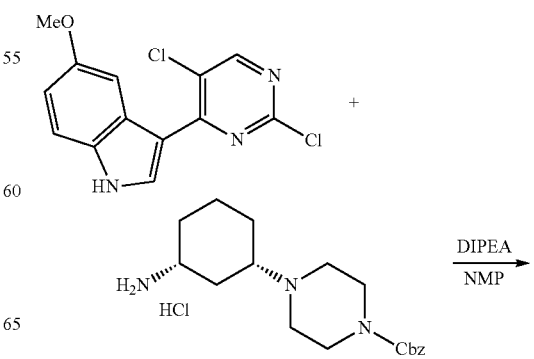

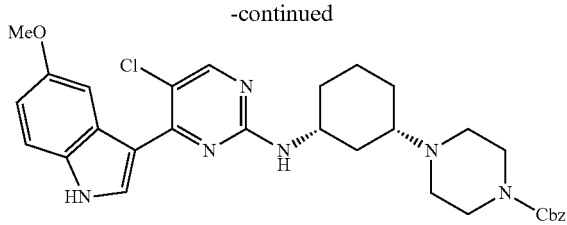

A solution of 3-(2,5-dichloropyrimidin-4-yl)-5-methoxy-1H-indole (107 mg, 0.364 mmol), benzyl 4-((1S,3R)-3-aminocyclohexyl)piperazine-1-carboxylate hydrochloride (101 mg, 0.285 mmol) and DIPEA (0.25 mL, 1.44 mmol) in NMP (2.0 mL) was heated at 145° C. (microwave) for 120 min. The cooled mixture was diluted with EtOAc (100 mL), washed with H₂O (50 mL), dried over Na₂SO₄, filtered and evaporated to dryness. The residue was purified by reverse phase chromatography (C₁₈, H₂O/ACN+0.1% HCO₂H, 0 to 100% gradient). Fractions containing product were concentrated under reduced pressure to remove ACN. Aqueous NaHCO₃ (100 mL) and MeTHF (100 mL) were added, the phases were separated and the aqueous was extracted twice more with MeTHF (100 mL). The combined organic layers were dried over Na₂SO₄, filtered and evaporated to dryness to afford the title compound (29 mg, 0.050 mmol, 18%) as a yellow oil.

5-Chloro-4-(5-methoxy-1H-indol-3-yl)-N-((1R,3S)-3-(piperazin-1-yl)cyclohexyl)pyrmidin-2-amine (Compound 1063)

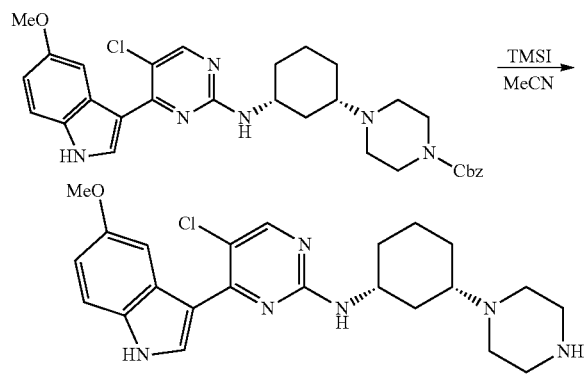

To an ice-cold solution of benzyl 4-((1S,3R)-3-(5-chloro-4-(5-methoxy-1H-indol-3-yl)pyrimidin-2-ylamino)cyclohexyl)piperazine-1-carboxylate (29 mg, 0.052 mmol) in ACN (1.0 mL) was added dropwise iodotrimethylsilane (70 μL, 0.260 mmol). The resulting solution was stirred and allowed to go up to room temperature over 1 h The reaction was partitioned between EtOAc (100 mL) and a saturated aqueous solution of NaHCO₃ (50 mL). The organic layer was dried over Na₂SO₄, concentrated under reduced pressure and purified by reverse phase chromatography (C₁₈, H₂O/ACN+0.1% HCO₂H, 0 to 80% gradient). Fractions containing product were concentrated under reduced pressure to remove ACN. Aqueous NaHCO₃ (100 mL) and MeTHF (100 mL) were added, the phases were separated and the aqueous was extracted twice more with MeTHF (100 mL). The combined organic layers were dried over Na₂SO₄, filtered and evaporated to dryness to afford the title compound (8.0 mg, 0.019 mmol, 36%) as a yellow oil.

1-(4-((1S,3R)-3-(5-chloro-4-(5-methoxy-1H-indol-3-yl)pyrmidin-2-ylamino)cyclohexyl)piperazin-1-yl)prop-2-en-1-one (Compound 375)

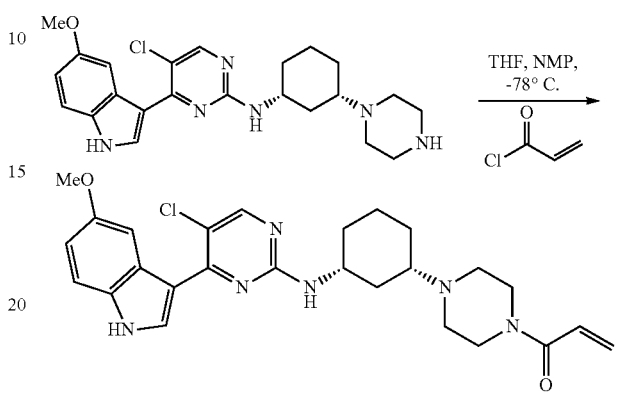

A cooled (−78° C.) solution of 5-chloro-4-(5-methoxy-1H-indol-3-yl)-N-((1R,3S)-3-(piperazin-1-yl)cyclohexyl)pyrimidin-2-amine (30 mg, 0.070 mmol) in THF (0.8 mL) and NMP (0.2 mL) was treated with DIPEA (60 μL, 0.344 mmol) and acryloyl chloride (1.10 μL, 0.074 mmol). After 60 min at this temperature the reaction was allowed to warm up to room temperature and evaporated to dryness. The residue was purified by reverse phase chromatography (C₁₈, H₂O/ACN+0.1% HCO₂H 0 to 80% gradient) and afforded the title compound (11.5 mg, 0.024 mmol, 34%) as a white powder.

LCMS: Calculated: 495.02, Found (M+H⁺): 495.37. ¹H NMR (500 MHz, DMSO) δ 11.75 (s, 1H), 8.40 (d, J=3.1 Hz, 1H), 8.33 (s, 1H), 8.01 (d, J=7.8 Hz, 1H), 7.99 (d, J=2.5 Hz, 1H), 7.39 (d, J=8.8 Hz, 1H), 6.84 (dd, J=8.8, 2.5 Hz, 1H), 6.18 (dd, J=17.1, 10.1 Hz, 1H), 6.06 (dd, J=17.1, 2.3 Hz, 1H), 5.55 (dd, J=10.1, 2.3 Hz, 1H), 3.82 (br s, 4H), 3.78 (s, 3H), 3.68-3.57 (m, 1H), 3.49-3.43 (m, 1H), 2.66-2.56 (m, 4H), 2.45 (t, J=11.5 Hz, 1H), 1.96 (br d, J=11.6 Hz, 1H), 1.79-1.72 (m, 3H), 1.33-0.98 (m, 3H).

Example 75. Synthesis of 1-(4-((1S,3R)-3-(5-chloro-4-(5-methyl-1H-indol-3-yl)pyrimidin-2-ylamino)cyclohexyl)piperazin-1-yl)prop-2-en-1-one (Compound 340)

3-(2,5-Dichloropyrimidin-4-yl)-5-methyl-1H-indole

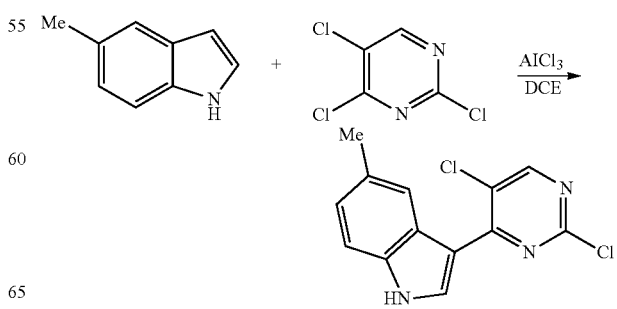

To a solution of 2,4,5-trichloropyrimidine (150 μL, 1.31 mmol) in CH₂Cl₂ (10 mL) was added aluminum chloride (191 mg, 1.43 mmol). The resulting suspension was stirred at 75° C. for 10 min. Then, 5-methylindole (178 mg, 1.36 mmol) was added in three portions and stirred at 80° C. overnight. The reaction was cooled to room temperature, ice (30 mL) was added and the solution vigorously stirred for 1 h. The mixture was extracted then with EtOAc (150 mL), the organic layer was washed with water (30 mL), dried over Na₂SO₄ and evaporated to dryness. The residue was purified by SiO₂ chromatography (EtOAc in hexanes 0 to 100% gradient) and afforded the title compound as a beige solid (204 mg, 0.733 mmol, 56%).

This intermediate was then used in place of 3-(2,5-dichloropyrimidin-4-yl)-5-methoxy-1H-indole and synthesis was carried out as described in the prior example to produce the title compound 1-(4-((1S,3R)-3-(5-chloro-4-(5-methyl-1H-indol-3-yl)pyrimidin-2-ylamino)cyclohexyl)piperazin-1-yl)prop-2-en-1-one (Compound 340).

LCMS: Calculated: 479.02; Found (M+H⁺): 479.30. 1H NMR (500 MHz, DMSO) δ 11.66 (br s, 1H), 8.38-8.28 (m, 2H), 8.15 (br s, 1H), 7.30 (d, J=8.2 Hz, 1H), 7.09 (d, J=7.6 Hz, 1H), 6.97 (d, J=8.2 Hz, 1H), 6.69 (dd, J=16.6, 10.5 Hz, 1H), 6.01 (dd, J=16.7, 2.4 Hz, 1H), 5.58 (dd, J=10.5, 2.3 Hz, 1H), 3.94-3.83 (m, 1H), 3.78-3.58 (m, 1H), 3.45-3.38 (m, 4H), 2.42-2.39 (m, 3H), 2.39-2.37 (m, 3H), 2.08-2.00 (m, 1H), 1.98-1.87 (m, 1H), 1.82-1.57 (m, 3H), 1.35-1.20 (m, 2H), 1.18-1.05 (m, 2H).

Example 76. Synthesis of N—((S)-1-((1S,3R)-3-((5-chloro-4-(1H-indol-3-yl)pyrimidin-2-yl)amino)cyclohexyl)pyrrolidin-3-yl)acrylamide (Compound 370)

(1R,3R)-3-(5-Chloro-4-(1-(phenylsulfonyl)-1H-indol-3-yl)pyrimidin-2-ylamino)cyclohexanol

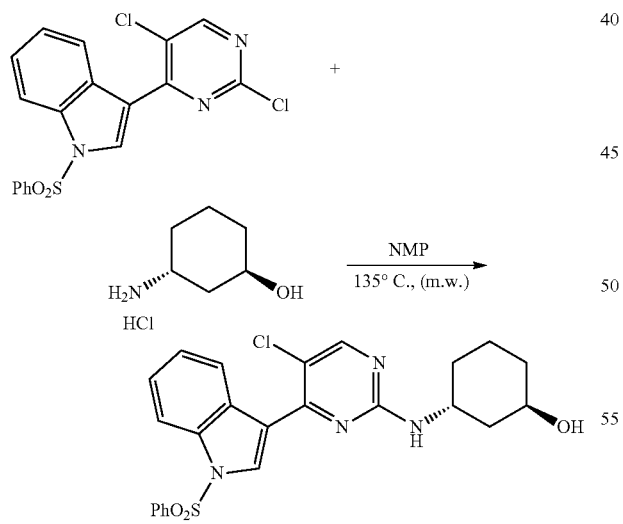

A solution of 3-(2,5-dichloropyrimidin-4-yl)-1-(phenylsulfonyl)-1H-indole (2.30 g, 2.69 mmol), (1R,3R)-3-aminocyclohexanol hydrochloride (750 mg, 4.95 mmol) and diisopropylethylamine (4.3 mL, 6.51 mmol) in NMP (18 mL) was heated 45 min at 135° C. (m.W) three times. The cooled mixture was then diluted with EtOAc (500 mL) and water (200 mL). The layers were separated and the organic layer was washed twice more with H₂O (100 mL) and brine (100 mL). The organics were combined, dried over Na₂SO₄, filtered and evaporated to dryness. The residue was purified by SiO₂ column (DCM/MeOH 0 to 20% gradient) and afforded the title compound (1.65 g, 3.42 mmol, 69%) as a yellow oil.

(3R)-3-(5-chloro-4-(1-(phenylsulfonyl)-1H-indol-3-yl)pyrimidin-2-ylamino)cyclohexanone

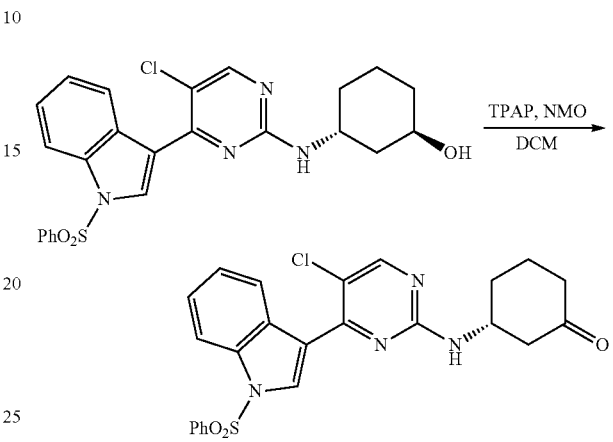

(1R,3R)-3-(5-chloro-4-(1-(phenylsulfonyl)-1H-indol-3-yl)pyrimidin-2-ylamino)cyclohexanol (1.05 g, 2.17 mmol) was dissolved in DCM (22 mL) and 4 Å molecular sieve (500 mg/mmol, 1.09 g) was added along with NMO (382 mg, 3.26 mmol). The suspension was cooled to 0° C. Then, TPAP (60 mg, 0.17 mmol) was added and the reaction mixture stirred from 0° C. to room temperature for 16 h. The solution was filtered through a pad of silica gel, rinsed with 40% EtOAc in DCM (1.5 L). The resulting filtrated was evaporated to dryness. The mixture was purified by SiO₂ column (DCM/EtOAc 0 to 50% gradient) and afforded the title compound as a grey solid (667 mg, 1.39 mmol, 64%).

tert-Butyl (S)-1-((1S,3R)-3-(5-chloro-4-(1-(phenylsulfonyl)-1H-indol-3-yl)pyrimidin-2-ylamino)cyclohexyl)pyrolidin-3-ylcarbamate

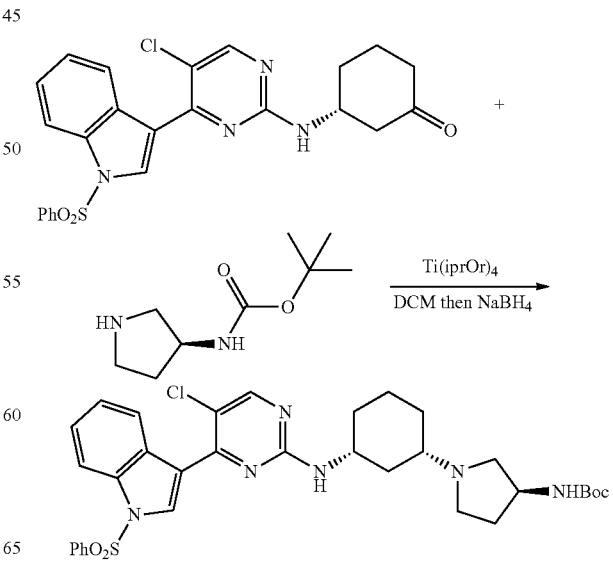

Titanium isopropoxide (0.77 mL, 2.60 mmol) was added to a stirring solution of (3R)-3-(5-chloro-4-(1-(phenylsulfonyl)-1H-indol-3-yl)pyrimidin-2-ylamino)cyclohexanone (250 mg, 0.520 mmol) and (S)-tert-butyl pyrrolidin-3-ylcarbamate (145 mg, 0.780 mmol) at room temperature. The reaction mixture was allowed to stir for 15 h at room temperature. NaBH₄ (59.0 mg, 1.56 mmol) was then added and the reaction mixture was cooled to −78° C. whereupon MeOH (5 mL) was added dropwise. The reaction mixture was then allowed to warm up to rt, was diluted with DCM (150 mL) and NaHCO₃ (sat) (30 mL) and filtered through Celite. The phases were then separated, dried with MgSO₄, filtered and evaporated to dryness. The residue was purified by SiO₂ chromatography (DCM/THF 0 to 70% gradient) and afforded the title compound as a yellow oil (153 mg, 0.235 mmol, 45%).

Tert-Butyl (S)-1-((1S,3R)-3-(5-chloro-4-(1-(phenylsulfonyl)-1H-indol-3-yl)pyrimidin-2-ylamino)cyclohexyl)pyrrolidin-3-ylcarbamate was then subjected to the same synthetic sequence as Example 33 to produce N—((S)-1-((1S,3R)-3-((5-chloro-4-(1H-indol-3-yl)pyrimidin-2-yl)amino)cyclohexyl)pyrrolidin-3-yl)acrylamide (Compound 370).

LCMS: Calculated: 446.99; Found (M+H⁺): 465.36. ¹H NMR (500 MHz, DMSO) δ 11.83 (s, 1H), 8.57 (br s, 1H), 8.47 (s, 1H), 8.23 (s, 1H), 8.20 (d, J=7.0 Hz, 1H), 7.49 (d, J=7.5 Hz, 1H), 7.21 (t, J=7.4 Hz, 1H), 7.21 (br s, 1H), 7.15 (t, J=7.5 Hz, 1H), 6.21 (dd, J=17.1, 10.2 Hz, 1H), 6.04 (dd, J=17.1, 2.0 Hz, 1H), 5.54 (dd, J=10.1, 2.2 Hz, 1H), 4.26-4.12 (m, 1H), 3.96-3.73 (m, 2H), 2.77-2.69 (m, 2H), 2.48-2.37 (m, 2H), 2.35-2.16 (m, 1H), 2.12-2.02 (m, 1H), 2.00-1.85 (m, 2H), 1.85-1.72 (m, 1H), 1.59-1.49 (m, 1H), 1.44-1.30 (m, 1H), 1.31-1.18 (m, 2H), 1.17-1.06 (m, 1H).

Example 77. Synthesis of 1-(4-((1S,5R)-5-(5-chloro-4-(1H-indol-3-yl)pyrimidin-2-ylamino)bicyclo[3.2.1]octan-1-yl)piperazin-1-yl)prop-2-en-1-one (Compound 409) and 1-(4-((1R,5S)-5-(5-chloro-4-(1H-indol-3-yl)pyrimidin-2-ylamino)bicyclo[3.2.1]octan-1-yl)piperazin-1-yl)prop-2-en-1-one (Compound 408)

Bicyclo[3.2.1]octane-1,5-dicarboxylic acid

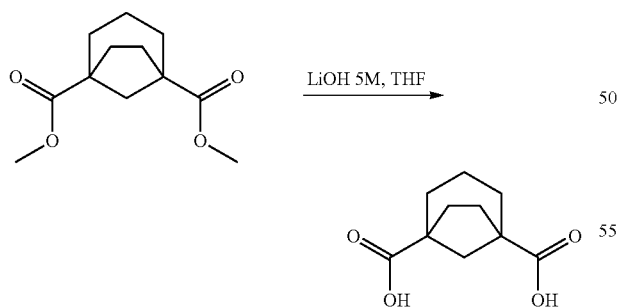

An aqueous LiOH solution (4.4 mL, 5 M, 22.00 mmol) was added to a stirring solution of dimethyl bicyclo[3.2.1]octane-1,5-dicarboxylate (prepared following WO 2006/012395) (1.25 g, 5.52 mmol) in THF (40 mL). The reaction mixture was stirred overnight at room temperature. The THF of the reaction mixture was evaporated and the aqueous solution was extracted twice with ether (50 mL) to remove organic impurities. The aqueous layer was then acidified with concentrated HCl until a pH of 3 was obtained and extracted three times with EtOAc (50 mL). The organics were combined, dried over Na₂SO₄ and evaporated to dryness affording the title compound (0.98 g, 4.94 mmol, 90%) as a white solid.

Dibenzyl bicyclo[3.2.1]octane-1,5-diyldicarbamate

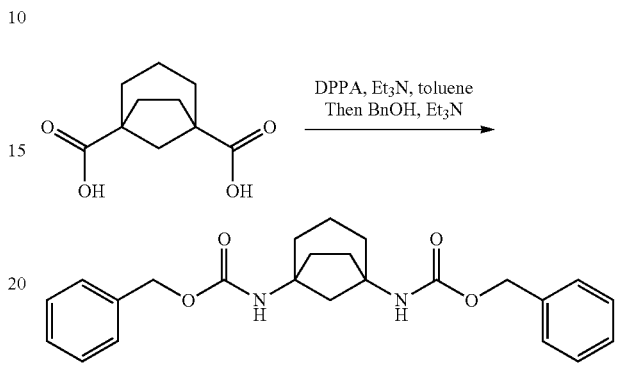

To a stirring solution of bicyclo[3.2.1]octane-1,5-dicarboxylic acid (0.98 g, 4.94 mmol) in toluene (50 mL), Et₃N (1.5 mL, 10.9 mmol) and DPPA (2.3 mL, 10.9 mmol) were added. The resulting mixture was stirred at 100° C. for 1 h. Then, benzyl alcohol (2.6 mL, 24.7 mmol) and triethylamine (1.5 mL, 10.9 mmol) were added to the reaction mixture and the solution was then stirred at 100° C. for 48 hrs. The reaction mixture was then concentrated, poured into water (100 mL) and EtOAc (100 mL) and the phases were separated. The aqueous phase was extracted twice with EtOAc (100 mL). The organics were combined, washed twice with brine (50 mL), dried over Na₂SO₄, filtered and evaporated to dryness. The residue was purified by SiO₂ chromatography (EtOAc in hexanes, 0 to 50% gradient) and afforded the title compound (1.3 g, 3.18 mmol, 64%) as an off-white solid.

Bicyclo[3.2.1]octane-1,5-diamine

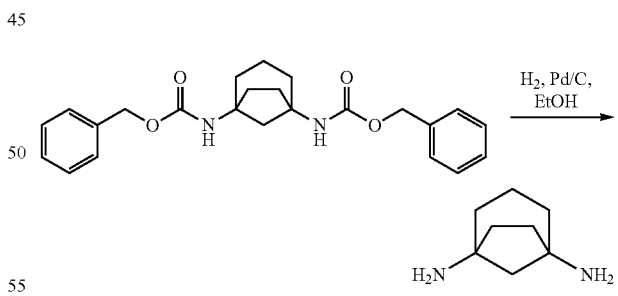

To a stirring solution of dibenzyl bicyclo[3.2.1]octane-1,5-diyldicarbamate (1.30 g, 3.19 mmol) in ethanol (53 mL) was added Pd/C (10% w/w on activated carbon). The reaction mixture was then allowed to stir under a positive pressure of hydrogen (1 atm) at room temperature for 16 h. The reaction mixture was filtered through a pad of Celite eluting with MeOH, then the filtrate was evaporated to dryness and afforded the title compound as a clear oil (448 mg, 3.19 mmol, 100%), that was used for the next step without further purification.

303

N[1]-(5-Chloro-4-(1H-indol-3-yl)pyrimidin-2-yl)bicyclo[3.2.1]octane-1,5-diamine

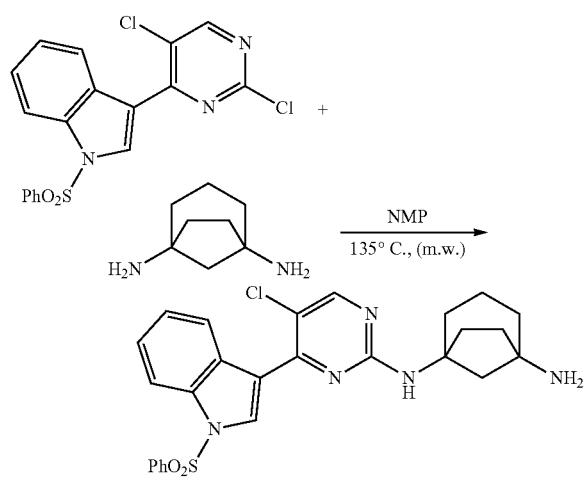

A solution of 3-(2,5-dichloropyrimidin-4-yl)-1-(phenylsulfonyl)-1H-indole (1.36 g, 3.35 mmol), bicyclo[3.2.1]octane-1,5-diamine (448 mg, 3.20 mmol) and diisopropylethylamine (1.67 mL, 9.58 mmol) in NMP (13 mL) was heated 45 min at 135° C. (mW) two times. The cooled mixture was then diluted with EtOAc (200 mL) and water (100 mL). The layers were separated and the organic layer was washed twice more with H₂O (100 mL) and brine (100 mL). The organics were combined, dried over Na₂SO₄, filtered and evaporated to dryness. The mixture was purified by SiO₂ column (DCM/MeOH 0 to 20% gradient) and afforded the title compound (335 mg, 0.659 mmol, 21%) as a light yellow oil.

5-Chloro-4-(1-(phenylsulfonyl)-1H-indol-3-yl)-N-(5-(4-tosylpiperazin-1-yl)bicyclo[3.2.1]octan-1-yl)pyrimidin-2-amine

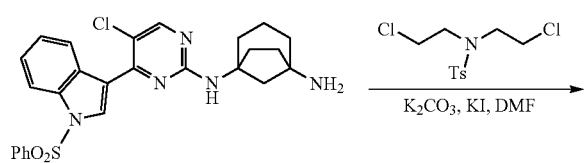

304

-continued

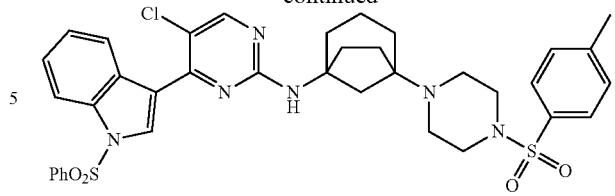

N,N-Bis(2-chloroethyl)-p-toluenesulfonamide (171 mg, 0.576 mmol), potassium iodide (191 mg, 1.15 mmol) and K₂CO₃ (159 mg, 1.15 mmol) were added to a stirring solution of N[1]-(5-chloro-4-(1H-indol-3-yl)pyrimidin-2-yl)bicyclo[3.2.1]octane-1,5-diamine (195 mg, 0.384 mmol). The resulting mixture was then heated at 130° C. for 16 h. The solution was cooled to room temperature, diluted with EtOAc (100 mL) and washed with H₂O three times (50 mL). The organics were combined, dried over Na₂SO₄, filtered and evaporated to dryness. The mixture was purified by SiO₂ column (DCM/EtOAc 0 to 60% gradient) and afforded the title compound (133 mg, 0.182 mmol, 47%) as an off white solid.

5-Chloro-4-(1-(phenylsulfonyl)-1H-indol-3-yl)-N-(5-(piperazin-1-yl)bicyclo[3.2.1]octan-1-yl)pyrimidin-2-amine

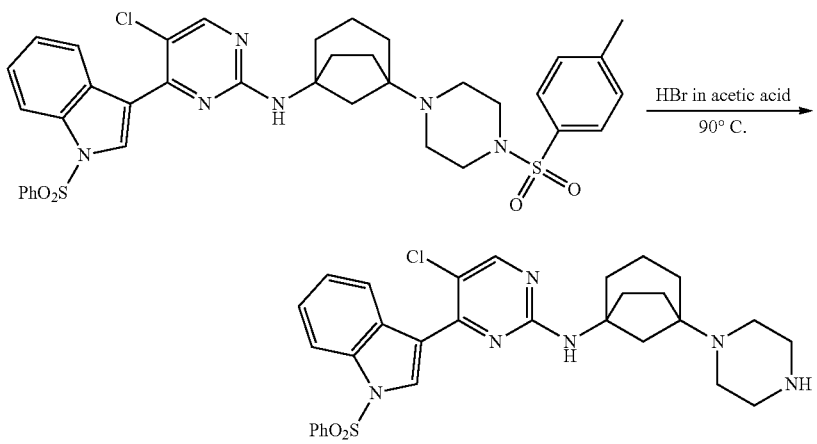

4-Hydroxybenzoic acid (125 mg, 0.902 mmol) was added to a stirring solution of 5-chloro-4-(1-(phenylsulfonyl)-1H-indol-3-yl)-N-(5-(4-tosylpiperazin-1-yl)bicyclo[3.2.1]octan-1-yl)pyrimidin-2-amine (200 mg, 0.274 mmol) in HBr in acetic acid (33%, 5.5 mL) at room temperature. The resulting solution was stirred at 90° C. for 1 h. The solution was then cool to rt and NaOH (5M) was added until a pH of 10 was obtained. The resulting mixture was extracted three times into DCM (50 mL). The organics were combined, dried over Na₂SO₄, filtered and evaporated to dryness. The residue was purified by reverse phase chromatography (C₁₈, H₂O/ACN+0.1% HCO₂H 0 to 55% gradient) and afforded the title compound (99.5 mg, 0.172 mmol, 63%) as a white solid after lyophilization.

5-Chloro-4-(1H-indol-3-yl)-N-(5-(piperazin-1-yl)bicyclo[3.2.1]octan-1-yl)pyrimidin-2-amine (Compound 1064)

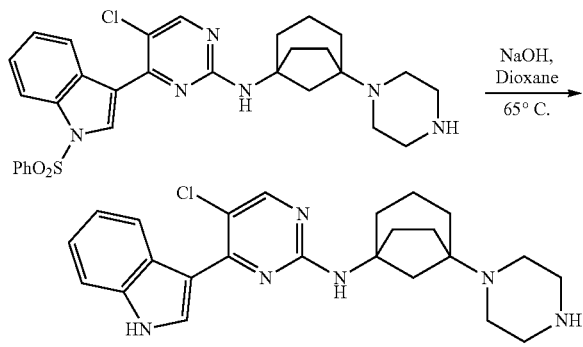

A solution of 5-chloro-4-(1-(phenylsulfonyl)-1H-indol-3-yl)-N-(5-(piperazin-1-yl)bicyclo[3.2.1]octan-1-yl)pyrimidin-2-amine (100 mg, 0.172 mmol) in dioxane (4.3 mL) was treated with a 2M solution of NaOH in H$_2$O (1.03 mL, 5.17 mmol) and heated at 60° C. for 16 h. The cooled mixture was diluted with MeTHF (30 mL) and H$_2$O (30 mL). The layers were separated and the aqueous layer was extracted three times with MeTHF (30 mL). The organics were combined, dried over Na$_2$SO$_4$, filtered and evaporated to dryness affording the title compound (75.3 mg, 0.172 mmol, 100%) as a light yellow oil which was used in the next step without further purification.

1-(4-(5-(5-Chloro-4-(1H-indol-3-yl)pyrimidin-2-ylamino)bicyclo[3.2.1]octan-1-yl)piperazin-1-yl)prop-2-en-1-one

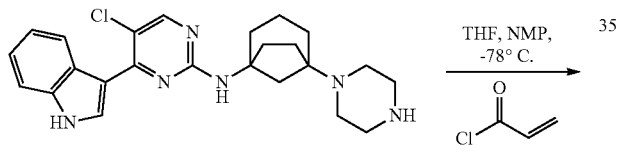

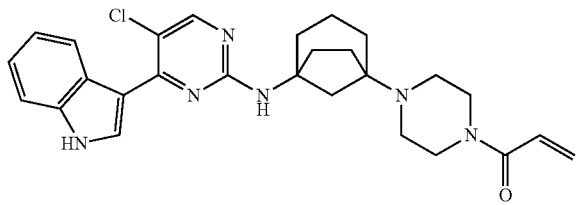

To a −78° C. solution of 5-Chloro-4-(1H-indol-3-yl)-N-(5-(piperazin-1-yl)bicyclo[3.2.1]octan-1-yl)pyrimidin-2-amine (75.3 mg, 0.172 mmol) and DIPEA (150 µL, 0.862 mmol) in THF/NMP (4.3 mL/1.0 mL) was added slowly a solution of acryloyl chloride (14.8 µL, 0.181 mmol). After 30 min at this temperature the reaction was allowed to warm up to room temperature and evaporated to dryness. The residue was purified by reverse phase chromatography (C$_{18}$, H$_2$O/ACN+0.1% HCO$_2$H 0 to 55% gradient) and afforded the title compound (45.5 mg, 0.093 mmol, 54%) as a light yellow solid after lyophilization.

LCMS: Calculated: 491.03, Found (M+H$^+$): 491.46. $^1$H NMR (500 MHz, DMSO) δ 11.79 (s, 1H), 8.58 (br s, 1H), 8.38 (s, 1H), 8.25 (s, 1H), 7.48 (d, J=8.0 Hz, 1H), 7.25-7.10 (m, 3H), 6.77 (dd, J=16.7, 10.5 Hz, 1H), 6.09 (dd, J=16.7, 2.4 Hz, 1H), 5.66 (dd, J=10.5, 2.4 Hz, 1H), 3.55-3.52 (m, 4H), 2.54-2.43 (m, 4H), 2.14-1.98 (m, 4H), 1.87 (d, J=10.1 Hz, 1H), 1.78-1.60 (m, 4H), 1.60-1.47 (m, 2H), 1.38-1.27 (m, 1H).

1-(4-((1R,5S)-5-(5-Chloro-4-(1H-indol-3-yl)pyrmidin-2-ylamino)bicyclo[3.2.1]octan-1-yl)piperazin-1-yl)prop-2-en-1-one (Compound 408) and 1-(4-((1S,5R)-5-(5-chloro-4-(1H-indol-3-yl)pyrimidin-2-ylamino)bicyclo[3.2.1]octan-1-yl)piperazin-1-yl)prop-2-en-1-one (Compound 409)

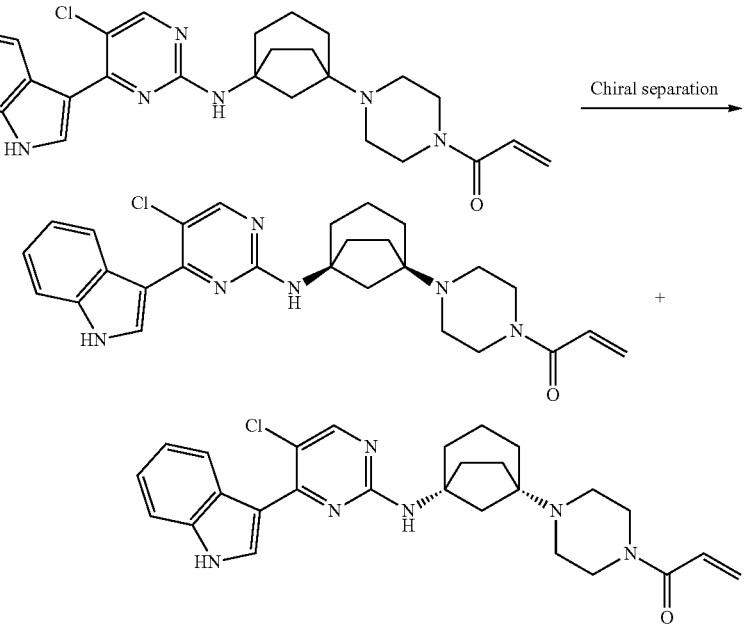

Both enantiomers of 1-(4-(5-(5-Chloro-4-(1H-indol-3-yl)pyrimidin-2-ylamino)bicyclo[3.2.1]octan-1-yl)piperazin-1-yl)prop-2-en-1-one (45.5 mg, 0.093 mmol) were separated using preparative chiral HPLC (Chiralpak IA, 5 um, 20×250 mm; hex/MeOH/DCM=80/5/15) to yield both compounds 1-(4-((1R,5S)-5-(5-Chloro-4-(1H-indol-3-yl)pyrimidin-2-ylamino)bicyclo[3.2.1]octan-1-yl)piperazin-1-yl)prop-2-en-1-one (3.1 mg, 0.0063 mmol, 12%) and 1-(4-((1S,5R)-5-(5-chloro-4-(1H-indol-3-yl)pyrimidin-2-ylamino)bicyclo[3.2.1]octan-1-yl)piperazin-1-yl)prop-2-en-1-one (3.8 mg, 0.0077 mmol, 15%) as white solids.

Example 78. Synthesis of N-((1S,3R)-3-(5-chloro-4-(2-oxoindolin-3-yl)pyrimidin-2-ylamino)cyclohexyl)-5-((E)-4-(dimethylamino)but-2-enamido)picolinamide (Compound 282)

3-(2,5-Dichloropyrimidin-4-yl)-3H-indol-2-ol

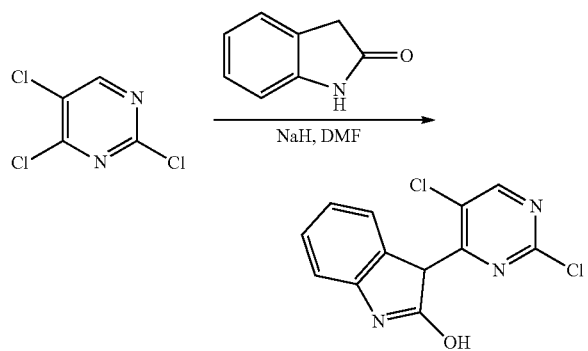

2-Oxindole (239 mg, 1.79 mmol) was dissolved in DMF (15 mL) at room temperature and sodium hydride (144 mg, 3.60 mmol) was added. The reaction mixture stirred at room temperature for 15 minutes. 2,4,5-Trichloropyrimidine (300 mg, 1.63 mmol) was then added dropwise and the resulting solution was stirred at room temperature for 30 minutes. The solution was then quenched with a saturated aqueous solution of $NH_4Cl$ (100 mL) and extracted 3 times with DCM (100 mL). The organic layers were combined, washed with water (50 mL), brine (50 mL), dried over $MgSO_4$, filtered and evaporated to dryness. The crude residue was stirred in EtOH (20 mL), filtered, washed with EtOH (5 mL) and hexanes (5 mL) to yield the title compound (379 mg, 1.35 mmol, 83%) as an orange solid.

(1S,3R)-3-(Benzyloxycarbonylamino)cyclohexylamino-2,2-dimethylpropionate

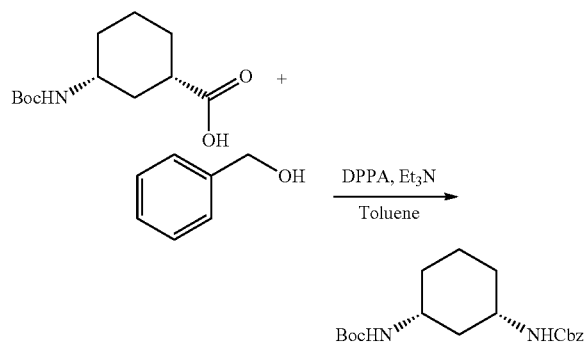

To a solution of (1S,3R)-3-(tert-butoxycarbonylamino)cyclohexanecarboxylic acid (8.77 g, 36.1 mmol) (prepared following Tetrahedron: Asymmetry 2010 (21), 864-866) in toluene (145 mL) was added $Et_3N$ (5.53 mL, 39.7 mmol) and DPPA (7.7 mL, 36.1 mmol). The resulting solution was stirred for 2 h at 110° C. and cooled down to 80° C. Benzyl alcohol (4.66 mL, 45.1 mmol) and triethylamine (5.53 mL, 39.7 mmol) were added, and the mixture was stirred for 20 h at 80° C. The cooled solution was diluted with EtOAc (100 mL) and water (50 mL). The layers were separated, and the aqueous layer was extracted twice with EtOAc (50 mL). The combined organic layers were dried over $MgSO_4$, filtered, and concentrated under reduced pressure. The residue was purified by $SiO_2$ chromatography (EtOAc in hexanes, 1 to 100% gradient) to afford the title compound (9.89 g, 28.4 mmol, 79%) as a white solid.

Benzyl (1S,3R)-3-aminocyclohexylcarbamate hydrochloride

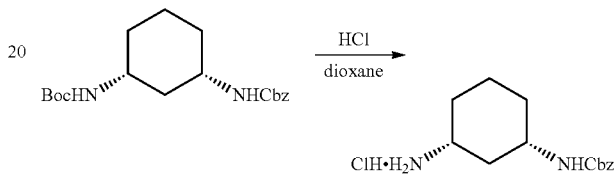

A solution of (1S,3R)-3-(benzyloxycarbonylamino)cyclohexylamino-2,2-dimethylpropionate (1.50 g, 4.31 mmol) in DCM (43 mL) was treated with a 4M solution of HCl in dioxane (16.0 mL, 64.6 mmol) and stirred for 2 h at rt. The resulting solution was evaporated to dryness and afforded the title compound (1.23 g, 4.31 mmol, 100%) as a white solid which was used in the next step without further purification.

Benzyl (1S,3R)-3-(5-chloro-4-(2-hydroxy-3H-indol-3-yl)pyrimidin-2-ylamino)cyclohexylcarbamate

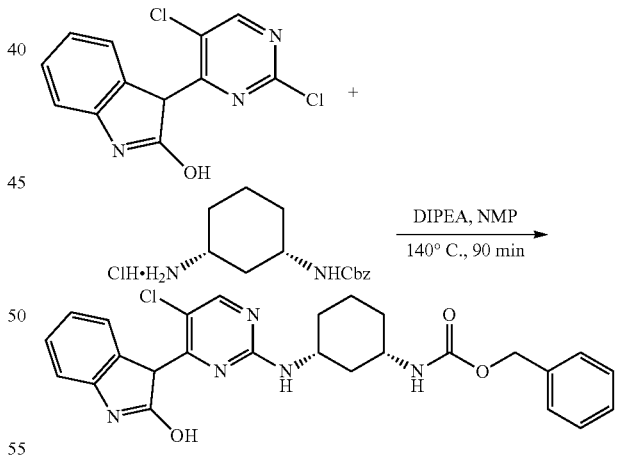

3-(2,5-Dichloropyrimidin-4-yl)-3H-indol-2-ol (79 mg, 0.28 mmol), benzyl (1S,3R)-3-aminocyclohexylcarbamate hydrochloride (88 mg, 0.31 mmol) and diisopropylethylamine (246 μL, 1.41 mmol) were dissolved in NMP (1.9 mL) in a microwave vial. The vial was heated to 140° C. under microwave irradiation and stirred for 90 min. The reaction mixture was poured into water (30 mL) and extracted with dichloromethane (50 mL). The organics were combined, washed with water (50 mL), brine (50 mL), dried with $MgSO_4$ filtered and concentrated. The residue was purified by $SiO_2$ chromatography (EtOAc in hexanes:DCM (9:1), 40 to 100% gradient) to afford the title compound (61.3 mg, 0.125 mmol, 48% yield) as a yellow solid.

3-(2-((1R,3S)-3-Aminocyclohexylamino)-5-chloro-pyrimidin-4-yl)-3H-indol-2-ol

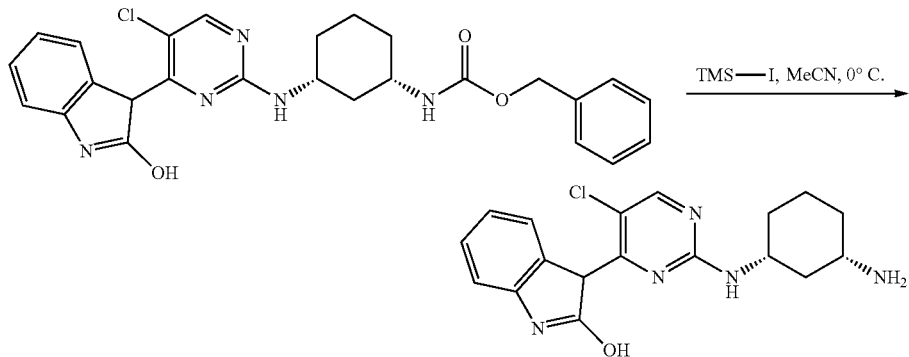

Benzyl (1S,3R)-3-(5-chloro-4-(2-hydroxy-3H-indol-3-yl)pyrimidin-2-ylamino)cyclohexylcarbamate (60.0 mg, 0.122 mmol) was dissolved in acetonitrile (2.4 mL) and the solution was cooled to 0° C. Iodotrimethylsilane (174 μL, 1.22 mmol) was added dropwise at 0° C., and the mixture was then stirred for 3 h. MeOH (3 mL) was added dropwise at 0° C., the solution was then slowed to warm to room temperature and was concentrated to dryness. The crude residue was purified by reverse phase flash chromatography (from 5 to 70% MeCN—H₂O-0.1% HCOOH buffer). Fractions containing product were concentrated to dryness and the residue was dissolved with 2-methyltetrahydrofuran (20 mL) and stirred for 10 minutes with excess powdered potassium carbonate. The mixture was filtered, washed with 2-methyltetrahydrofuran (30 mL) and evaporated to dryness affording the title compound (22 mg, 0.061 mmol, 50%) as a yellow solid.

5-Amino-N-((1S,3R)-3-(5-chloro-4-(2-hydroxy-3H-indol-3-yl)pyrimidin-2-ylamino)cyclohexyl)picolinamide (Compound 1065)

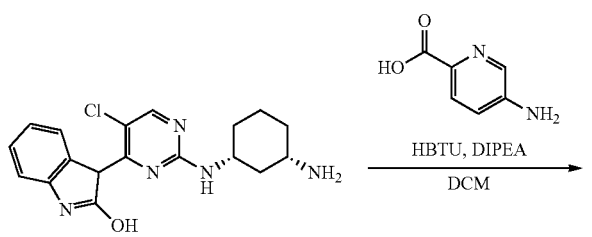

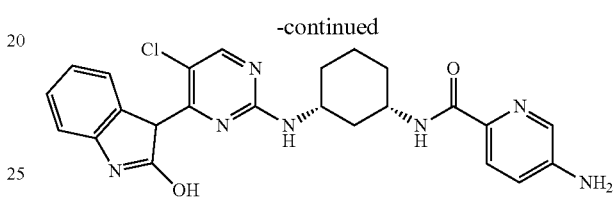

3-(2-((1R,3S)-3-Aminocyclohexylamino)-5-chloropyrimidin-4-yl)-3H-indol-2-ol (22 mg, 0.061 mmol), the 5-amino-2-pyridinecarboxylic acid (8.3 mg, 0.060 mmol), the coupling agent HBTU (34 mg, 0.090 mmol), diisopropylethylamine (42 uL, 0.24 mmol) were mixed in DCM (0.40 mL) and stirred at room temperature overnight. The reaction mixture was poured into a saturated aqueous solution of NaHCO₃ (30 mL) and the product extracted 4 times with 2-methyltetrahydrofuran (30 mL). The organics were combined, washed with water (30 mL), brine (30 mL), dried over MgSO₄, filtered and evaporated to dryness. The residue was purified by SiO₂ chromatography (MeOH in DCM, 0 to 10% gradient) to afford the title compound (15.5 mg, 0.032 mmol, 54%) as a yellow solid.

N-((1S,3R)-3-(5-Chloro-4-(2-oxoindolin-3-yl)pyrimidin-2-ylamino)cyclohexyl)-5-((E)-4-(dimethylamino)but-2-enamido)picolinamide (Compound 282)

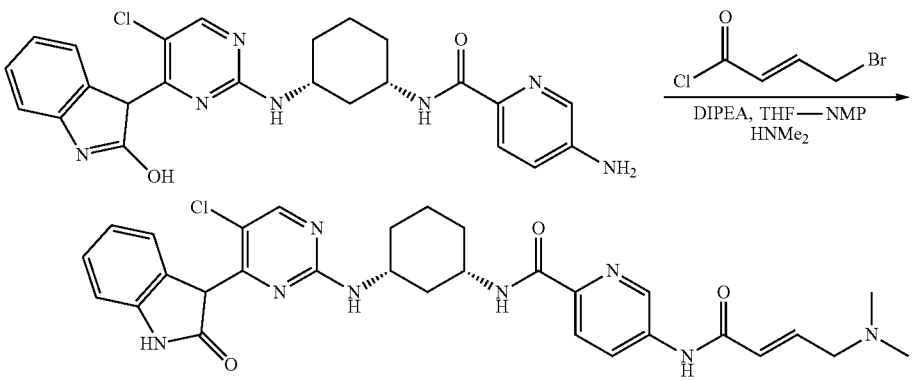

A cooled (−78° C.) solution of 5-Amino-N-((1S,3R)-3-(5-chloro-4-(2-hydroxy-3H-indol-3-yl)pyrimidin-2-ylamino)cyclohexyl)picolinamide (15.5 mg, 0.032 mmol), and DIPEA (17.0 µL, 0.097 mmol) in THF/NMP (0.5 mL/0.2 mL) was treated with a 54.2 mg/mL solution of (E)-4-bromobut-2-enoyl chloride in DCM (115 µL, 0.034 mmol). The resulting mixture was stirred 8 h at −78° C. before addition of a 2M solution of dimethylamine in THF (49 µL, 0.097 mmol). The resulting mixture was warmed up to −20° C., stirred overnight and then evaporated to dryness. The residue was purified by reverse phase chromatography ($C_{18}$, $H_2O$/ACN+0.1% $HCO_2H$, 5 to 70% gradient) and afforded the title compound (4.3 mg, 0.007 mmol, 23%) as a light yellow solid after lyophilization. LCMS: Calculated=589.09; Found [M+1$^+$]=589.30. $^1$H NMR (500 MHz, DMSO) Mixture of 2 diastereoisomers δ 10.62 (s, 1H), 10.53 (s, 1H), 8.87 (d, J=2.9 Hz, 1H), 8.40 (d, J=7.9 Hz, 1H), 8.24-8.19 (m, 1H), 8.02-7.94 (m, 1H), 7.48 (d, J=7.3 Hz, 1H), 7.21 (t, J=7.3 Hz, 1H), 7.02 (d, J=7.0 Hz, 1H), 6.91 (td, J=7.7, 1.0 Hz, 1H), 6.89-6.84 (m, 1H), 6.81 (dtd, J=15.3, 5.7, 1.1 Hz, 1H), 6.54 (br s, 1H), 6.29 (dd, J=15.4, 1.6 Hz, 1H), 5.07-4.96 (m, 1H), 3.86-3.77 (m, 1H), 3.75-3.64 (m, 1H), 3.17 (d, J=5.0 Hz, 1H), 3.08 (d, J=5.7 Hz, 2H), 2.18 (s, 6H), 2.08 (d, J=6.3 Hz, 1H), 1.84-1.69 (m, 2H), 1.45-1.26 (m, 3H), 1.19-1.09 (m, 1H).

Example 79. CDK7 Kinase Activity

Compounds of the invention were assayed for CDK7 activity at Life Technologies™ (Grand Island, New York) using their commercially available Adapta® kinase assay services. Compounds were tested at concentrations ranging from 10 µM down to 0.514 nM in a series of 3-fold serial dilutions. Details of these assays, including substrates used, are available on the Life Technologies web site (http://www.lifetechnologies.com/us/en/home/life-science/drug-discovery/target-and-lead-identification-and-validation/kinasebiology/kinase-activity-assays.html). The results of the assay are shown below in Table 3 where "A" represents a calculated $IC_{50}$ of less than 100 nM; "B" represents a calculated $IC_{50}$ of between 100 nM and 1 µM; and "C" represents a calculated $IC_{50}$ of greater than 1 µM.

TABLE 3

CDK7 Inhibitory Activity of Selected Compounds of the Invention.

| Compound No. | CDK7 Inhibition ($IC_{50}$) |
|---|---|
| 100 | A |
| 101 | A |
| 102 | A |
| 103 | A |
| 104 | A |
| 105 | A |
| 106 | A |
| 107 | A |
| 108 | C |
| 109 | C |
| 110 | A |
| 111 | A |
| 112 | A |
| 113 | A |
| 114 | A |
| 115 | A |
| 116 | A |
| 117 | A |
| 118 | A |
| 124 | A |
| 127 | A |
| 129 | A |
| 141 | A |
| 153 | A |
| 158 | A |
| 163 | A |
| 165 | A |
| 167 | A |
| 168 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | B |
| 181 | A |
| 182 | A |
| 183 | A |
| 184 | B |
| 185 | C |
| 186 | A |
| 187 | A |
| 188 | A |
| 189 | B |
| 190 | A |
| 191-1 | A |
| 191-2 | C |
| 192 | A |
| 193 | A |
| 194 | B |
| 195 | B |
| 196 | A |
| 197 | A |
| 198 | A |
| 199 | B |
| 200 | B |
| 201 | A |
| 202-1 | C |
| 202-2 | A |
| 203-1 | A |
| 203-2 | B |
| 203-3 | B |
| 203-4 | B |
| 203-5 | B |
| 203-6 | A |
| 203-7 | B |
| 203-8 | A |
| 204 | A |
| 205 | B |
| 206 | B |
| 207 | A |
| 208 | B |
| 209 | B |
| 210 | B |
| 211 | B |
| 212 | A |
| 213 | A |
| 214 | B |
| 215 | B |
| 216 | B |
| 217 | A |
| 218 | A |
| 219 | A |
| 220 | A |
| 221 | B |
| 222 | A |
| 223 | A |
| 224 | A |
| 225 | B |

TABLE 3-continued

CDK7 Inhibitory Activity of Selected Compounds of the Invention.

| Compound No. | CDK7 Inhibition (IC$_{50}$) |
|---|---|
| 226 | B |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | B |
| 244 | A |
| 245 | B |
| 246 | B |
| 247 | B |
| 248 | A |
| 249 | B |
| 250 | A |
| 251 | B |
| 252 | A |
| 1000 | A |
| 1002 | A |
| 1003 | A |
| 1004 | A |
| 1005 | A |
| 1006 | A |
| 1007 | A |
| 1009 | A |
| 1010 | A |
| 1022 | A |

Compounds of the invention were further assayed for CDK7 activity at Biortus Biosciences (Jiangyin, Jiangsu Province, P.R. of China) using a CDK7 kinase assay developed with a Caliper/LabChip EZ Reader (Perkin Elmer, Waltham, Mass.). This assay measures the amount of phosphorylated peptide substrate produced as a fraction of the total peptide following an incubation period (30 min.) with the following components: test compounds (variable concentrations from 10 µM down to 0.514 nM in a series of 3-fold serial dilutions), CDK7/Cyclin H/MAT1 trimeric complex (10 nM), ATP (2 mM), and "FAM-CDK7tide" peptide substrate (2 µM, synthesized fluorophore-labeled peptide with the following sequence: 5-FAM-YSPTSPSYS-PTSPSYSPTSPSKKKK) in the following buffer: 20 mM MES, pH 6.75, 6 mM MgCl2, 0.01% Tween 20, 0.05 mg/mL BSA. The incubation period was chosen such that the total fraction of phosphorylated peptide product produced was 20% for the uninhibited kinase. CDK7 kinase inhibition IC50 values were recorded for selected test compounds reported in Table 4, where "A" represents a calculated IC$_{50}$ of less than 100 nM; "B" represents a calculated IC$_{50}$ of between 100 nM and 1 µM; and "C" represents a calculated IC$_{50}$ of greater than 1 µM.

TABLE 4

CDK7 Inhibitory Activity of Selected Compounds of the Invention.

| Compound No. | CDK7 Inhibition (IC$_{50}$) |
|---|---|
| 106 | A |
| 110 | A |
| 112 | B |
| 113 | A |
| 115 | A |
| 116 | A |
| 117 | A |
| 118 | A |
| 124 | A |
| 127 | A |
| 158 | A |
| 168 | A |
| 173 | A |
| 174 | A |
| 179 | A |
| 181 | A |
| 182 | A |
| 186 | A |
| 188 | A |
| 198 | A |
| 203-1 | A |
| 207 | A |
| 212 | A |
| 213 | A |
| 217 | A |
| 219 | A |
| 220 | A |
| 221 | A |
| 222 | A |
| 223 | A |
| 224 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | B |
| 244 | A |
| 245 | A |
| 246 | A |
| 248 | A |
| 249 | A |
| 255 | A |
| 256 | A |
| 257 | B |
| 258 | A |
| 259 | B |
| 260 | A |
| 261 | A |
| 262 | A |
| 263 | B |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |

TABLE 4-continued

CDK7 Inhibitory Activity of Selected Compounds of the Invention.

| Compound No. | CDK7 Inhibition (IC$_{50}$) |
|---|---|
| 278 | A |
| 279 | A |
| 280 | A |
| 281 | A |
| 282 | B |
| 283 | B |
| 284 | B |
| 285 | A |
| 286 | A |
| 287 | A |
| 288 | A |
| 289 | A |
| 290 | A |
| 291 | A |
| 292 | C |
| 293 | B |
| 294 | A |
| 295 | A |
| 296 | B |
| 297 | A |
| 298 | A |
| 299 | A |
| 300 | A |
| 301 | B |
| 302 | B |
| 303 | A |
| 304 | B |
| 305 | A |
| 306 | A |
| 307 | A |
| 308 | B |
| 309 | B |
| 310 | B |
| 311 | A |
| 312 | B |
| 313 | A |
| 314 | B |
| 315 | B |
| 316 | B |
| 317 | B |
| 318 | B |
| 319 | A |
| 320 | B |
| 321 | A |
| 322 | A |
| 323 | A |
| 324 | A |
| 325 | B |
| 326 | A |
| 327 | A |
| 328 | B |
| 329 | A |
| 330 | A |
| 331 | A |
| 332 | A |
| 333 | A |
| 334 | B |
| 335 | B |
| 336 | A |
| 337 | B |
| 338 | A |
| 339 | B |
| 340 | A |
| 341 | A |
| 342 | A |
| 343 | A |
| 344 | A |
| 345 | A |
| 346 | B |
| 347 | A |
| 348 | A |
| 349 | B |
| 350 | B |
| 351 | A |

TABLE 4-continued

CDK7 Inhibitory Activity of Selected Compounds of the Invention.

| Compound No. | CDK7 Inhibition (IC$_{50}$) |
|---|---|
| 352 | A |
| 353 | B |
| 354 | A |
| 355 | C |
| 356 | B |
| 357 | A |
| 358 | A |
| 359 | A |
| 360 | A |
| 361 | B |
| 362 | A |
| 363 | B |
| 364 | B |
| 365 | A |
| 366 | A |
| 367 | A |
| 368 | B |
| 369 | B |
| 370 | A |
| 371 | B |
| 372 | A |
| 373 | C |
| 374 | A |
| 375 | C |
| 376 | A |
| 377 | A |
| 378 | A |
| 379 | B |
| 380 | A |
| 381 | C |
| 382 | B |
| 383 | B |
| 384 | A |
| 385 | A |
| 386 | A |
| 387 | B |
| 388 | B |
| 389 | C |
| 390 | A |
| 391 | A |
| 392 | A |
| 393 | A |
| 394 | A |
| 395 | B |
| 396 | A |
| 397 | A |
| 398 | A |
| 399 | A |
| 400 | A |
| 401 | A |
| 402 | B |
| 403 | A |
| 404 | A |
| 405 | A |
| 406 | A |
| 407 | A |
| 408 | A |
| 409 | A |
| 410 | A |
| 411 | A |
| 412 | B |
| 413 | A |
| 414 | B |
| 415 | A |

Example 80. Inhibition of Cell Proliferation

Jurkat Cells. Jurkat cells are a cell line established from a human T cell leukemia. Representative compounds of the invention were tested at different concentrations (from 10 μM to 316 pM; 0.5 log serial dilutions) for their ability to inhibit the proliferation of Jurkat cells. Known CDK inhibitors flavopiridol and triptolide were used as positive controls. Cells were grown in RPMI 1640+10% FBS+1% Glutamax. The cells were supplemented with FBS (Life Technologies) and 100 U·mL$^{-1}$ penicillin, 100 μL$^{-1}$ streptomycin (Invitrogen) and cultured at 37° C. in a humidified chamber in the presence of 5% $CO_2$. Proliferation assays were conducted over a 72 hour time period. CellTiter-Glo® (Promega Corporation, Madison, Wis. USA) was used to assess the anti-proliferative effects of the compounds following manufacturer's directions and utilizing the reagents supplied with the CellTiter-Glo® kit. In this table, "A" represents an $IC_{50}$ of less than 500 nM; "B" an $IC_{50}$ of between 500 nM and 5 μM; and "C" an $IC_{50}$ of greater than 5 μM.

TABLE 5

Inhibition of Proliferation of Jurkat Cells by Compounds of the Invention.

| Compound No. | Jurkat $IC_{50}$ |
|---|---|
| 100 | B |
| 101 | C |
| 102 | B |
| 103 | B |
| 104 | B |
| 105 | B |
| 107 | B |
| 109 | A |
| 110 | A |
| 111 | A |
| 112 | C |
| 113 | A |
| 114 | C |
| 115 | A |
| 117 | A |
| 118 | A |
| 124 | C |
| 127 | C |
| 141 | A |
| 153 | A |
| 158 | B |
| 163 | A |
| 165 | B |
| 167 | A |
| 170 | B |
| 171 | A |
| 172 | A |
| 173 | B |
| 174 | A |
| 175 | A |
| 176 | B |
| 177 | C |
| 178 | A |
| 180 | A |
| 181 | B |
| 182 | B |
| 183 | A |
| 184 | C |
| 185 | A |
| 186 | B |
| 187 | A |
| 188 | A |
| 189 | A |
| 190 | B |
| 191-1 | A |
| 191-2 | C |
| 192 | A |
| 193 | B |
| 194 | A |
| 195 | A |
| 196 | B |
| 197 | B |
| 198 | B |
| 199 | B |
| 200 | A |
| 201 | B |
| 202-1 | B |
| 202-2 | A |
| 203-1 | B |
| 203-2 | C |
| 203-3 | C |
| 203-4 | C |
| 203-5 | C |
| 203-6 | C |
| 203-7 | C |
| 203-8 | B |
| 204 | A |
| 205 | B |
| 206 | B |
| 207 | A |
| 208 | A |
| 209 | B |
| 210 | B |
| 211 | C |
| 212 | C |
| 213 | C |
| 214 | C |
| 215 | B |
| 216 | A |
| 217 | B |
| 218 | B |
| 219 | A |
| 220 | B |
| 221 | B |
| 222 | B |
| 223 | C |
| 224 | C |
| 225 | C |
| 226 | B |
| 227 | C |
| 228 | B |
| 229 | B |
| 230 | B |
| 232 | A |
| 233 | A |
| 234 | A |
| 235 | A |
| 236 | A |
| 237 | A |
| 238 | A |
| 239 | B |
| 240 | A |
| 241 | A |
| 243 | A |
| 244 | A |
| 252 | B |
| 1000 | B |
| 1002 | B |
| 1003 | B |
| 1004 | B |
| 1005 | B |
| 1006 | B |
| 1007 | B |
| 1022 | C |
| 1023 | B |
| 1024 | B |
| 1025 | B |
| 1026 | B |
| 1027 | B |
| 1028 | B |
| 1029 | B |

A673 Cells.

A673 cells are a cell line derived from human muscle Ewing's sarcoma. Representative compounds of the invention were tested at different concentrations (from 4 μM to 126.4 pM; 0.5 log serial dilutions) for their ability to inhibit the proliferation of A673 cells. Known CDK inhibitors flavopiridol and triptolide were used as positive controls. Cells were grown in Dulbecco's Modified Eagle's Medium, +10% FBS+1 mM Sodium Pyruvate. The cells were cultured at 37° C. in a humidified chamber in the presence of 5% $CO_2$. Proliferation assays were conducted over a 72 hour time period. CyQUANT® (Life Technologies, Chicago, Ill. USA) was used to assess the anti-proliferative effects of the compounds following manufacturer's directions and utilizing the reagents supplied with the CyQUANT® kit. In this table, "A" represents an $IC_{50}$ of less than 500 nM; "B" an $IC_{50}$ of between 500 nM and 5 µM; and "C" an $IC_{50}$ of greater than 5 µM.

TABLE 6

Inhibition of Proliferation of A673 Cells by Compounds of the Invention.

| Compound No. | A673 $IC_{50}$ (nM) |
|---|---|
| 106 | A |
| 109 | A |
| 110 | A |
| 112 | A |
| 113 | A |
| 114 | C |
| 115 | A |
| 116 | A |
| 117 | A |
| 118 | A |
| 127 | A |
| 129 | A |
| 153 | A |
| 163 | A |
| 165 | A |
| 167 | A |
| 168 | A |
| 174 | A |
| 180 | A |
| 181 | A |
| 182 | A |
| 183 | A |
| 184 | C |
| 185 | A |
| 186 | A |
| 187 | A |
| 188 | A |
| 189 | A |
| 190 | A |
| 191-1 | B |
| 203-1 | B |
| 203-3 | B |
| 203-4 | A |
| 203-5 | A |
| 203-7 | A |
| 205 | A |
| 206 | A |
| 207 | A |
| 208 | B |
| 209 | A |
| 211 | A |
| 212 | A |
| 213 | A |
| 214 | A |
| 226 | A |
| 227 | A |
| 228 | A |
| 229 | A |
| 230 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | C |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | A |
| 311 | A |
| 312 | A |
| 313 | A |
| 314 | A |
| 315 | A |
| 316 | A |
| 317 | A |
| 318 | A |

TABLE 6-continued

Inhibition of Proliferation of A673 Cells by Compounds of the Invention.

| Compound No. | A673 IC$_{50}$ (nM) |
|---|---|
| 319 | A |
| 320 | A |
| 321 | A |
| 322 | A |
| 323 | A |
| 324 | A |
| 325 | A |
| 326 | A |
| 327 | A |
| 328 | A |
| 329 | A |
| 330 | A |
| 331 | A |
| 332 | A |
| 333 | A |
| 334 | C |
| 335 | A |
| 336 | B |
| 337 | A |
| 338 | A |
| 339 | A |
| 340 | A |
| 341 | A |
| 342 | A |
| 343 | A |
| 344 | A |
| 345 | A |
| 346 | A |
| 347 | A |
| 348 | A |
| 349 | A |
| 350 | A |
| 351 | A |
| 352 | A |
| 353 | A |
| 354 | A |
| 355 | A |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | A |
| 369 | A |
| 370 | A |
| 371 | A |
| 372 | B |
| 373 | A |
| 374 | A |
| 375 | A |
| 376 | A |
| 377 | A |
| 378 | B |
| 379 | A |
| 380 | A |
| 381 | A |
| 382 | A |
| 383 | A |
| 384 | A |
| 385 | A |
| 386 | B |
| 387 | B |
| 388 | A |
| 389 | A |
| 390 | A |
| 391 | A |
| 392 | A |
| 393 | A |
| 394 | A |
| 395 | A |
| 396 | A |
| 397 | A |
| 398 | A |
| 399 | A |
| 400 | A |
| 401 | A |
| 402 | A |
| 403 | A |
| 404 | A |
| 405 | A |
| 406 | A |
| 407 | A |
| 408 | A |
| 409 | A |
| 410 | A |
| 411 | A |
| 412 | A |
| 413 | A |
| 414 | A |
| 415 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising a compound of the formula

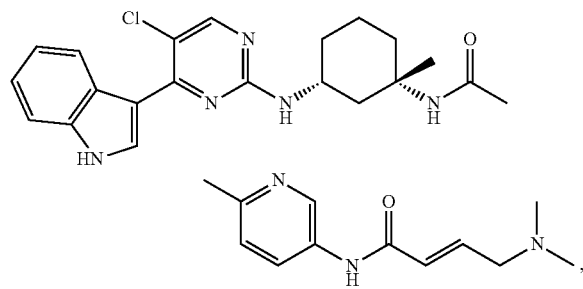

or a stereoisomer thereof, and a pharmaceutically acceptable excipient.

2. A pharmaceutical composition comprising a pharmaceutically acceptable salt of a compound of the formula

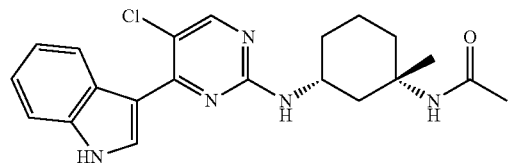

-continued

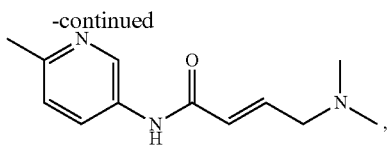

or a stereoisomer thereof, and a pharmaceutically acceptable excipient.

3. The pharmaceutical composition of claim 2, wherein the pharmaceutically acceptable salt is a hydrochloric acid salt.

4. The pharmaceutical composition of claim 1, wherein the composition is an aqueous solution.

5. The pharmaceutical composition of claim 1, wherein the composition is formulated for parenteral administration.

6. The pharmaceutical composition of claim 5, wherein the composition is formulated for intravenous or intralesional injection or infusion.

7. The pharmaceutical composition of claim 1, wherein the composition is in a single unit dosage form or packaged as a plurality of single unit dosages.

8. The pharmaceutical composition of claim 2, wherein the composition is an aqueous solution.

9. The pharmaceutical composition of claim 2, wherein the composition is formulated for parenteral administration.

10. The pharmaceutical composition of claim 9, wherein the composition is formulated for intravenous or intralesional injection or infusion.

11. The pharmaceutical composition of claim 2, wherein the composition is in a single unit dosage form or packaged as a plurality of single unit dosages.

12. The pharmaceutical composition of claim 3, wherein the composition is an aqueous solution.

13. The pharmaceutical composition of claim 3, wherein the composition is formulated for parenteral administration.

14. The pharmaceutical composition of claim 13, wherein the composition is formulated for intravenous or intralesional injection or infusion.

15. The pharmaceutical composition of claim 3, wherein the composition is in a single unit dosage form or packaged as a plurality of single unit dosages.

16. The pharmaceutical composition of claim 1, wherein the composition comprises the stereoisomer of the compound.

17. The pharmaceutical composition of claim 2, wherein the composition comprises the stereoisomer of the salt of the compound.

18. The pharmaceutical composition of claim 3, wherein the composition comprises the stereoisomer of the salt of the compound.

* * * * *